US012606563B2

(12) United States Patent
Heo et al.

(10) Patent No.: US 12,606,563 B2
(45) Date of Patent: Apr. 21, 2026

(54) ORGANIC LIGHT-EMITTING DEVICE

(71) Applicant: LG CHEM, LTD., Seoul (KR)

(72) Inventors: Dong Uk Heo, Daejeon (KR); Sujeong Geum, Daejeon (KR); Jaegoo Lee, Daejeon (KR); Sung Kil Hong, Daejeon (KR); Woochul Lee, Daejeon (KR); Jae Tak Lee, Daejeon (KR); Jung Min Yoon, Daejeon (KR)

(73) Assignee: LG CHEM, LTD., Seoul (KR)

( * ) Notice: Subject to any disclaimer, the term of this patent is extended or adjusted under 35 U.S.C. 154(b) by 981 days.

(21) Appl. No.: 17/629,926

(22) PCT Filed: Nov. 27, 2020

(86) PCT No.: PCT/KR2020/017129
§ 371 (c)(1),
(2) Date: Jan. 25, 2022

(87) PCT Pub. No.: WO2021/107699
PCT Pub. Date: Jun. 3, 2021

(65) Prior Publication Data
US 2022/0271226 A1 Aug. 25, 2022

(30) Foreign Application Priority Data
Nov. 29, 2019 (KR) ........................ 10-2019-0157080

(51) Int. Cl.
*C07D 487/04* (2006.01)
*C07D 239/26* (2006.01)
(Continued)

(52) U.S. Cl.
CPC ......... *C07D 487/04* (2013.01); *C07D 239/26* (2013.01); *C07D 251/24* (2013.01);
(Continued)

(58) Field of Classification Search
CPC ... H10K 85/654; H10K 85/658; C07D 251/24
See application file for complete search history.

(56) References Cited

U.S. PATENT DOCUMENTS

2007/0231503 A1* 10/2007 Hwang .................. C09K 11/06
428/411.1
2015/0236274 A1 8/2015 Hatakeyama et al.
(Continued)

FOREIGN PATENT DOCUMENTS

CN 108727358 A * 11/2018 ........... C07D 213/06
KR 10-2006-0051622 5/2006
(Continued)

OTHER PUBLICATIONS

Machine-generated English-language translation of CN-108727358-A.*
(Continued)

*Primary Examiner* — Vu A Nguyen
(74) *Attorney, Agent, or Firm* — Bryan Cave Leighton Paisner LLP

(57) ABSTRACT

Provided is an organic light-emitting device including an anode, a cathode, a light-emitting layer including a compound of Formula 1 between the anode and cathode, and a first organic material layer including a compound of Chemical Formula 2 between the light-emitting layer and the cathode:
(Continued)

<Chemical Formula 1>

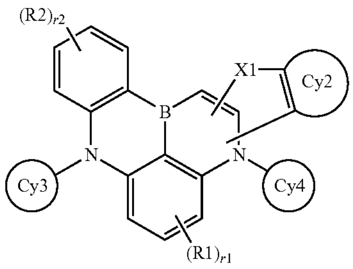

wherein:

X1 is O or S;

Cy2 is one selected from among a substituted or unsubstituted aromatic hydrocarbon ring and a substituted or unsubstituted aliphatic hydrocarbon ring, or is a fused ring of two or more rings selected from this group; and Cy3 and Cy4 are each independently one selected from among a substituted or unsubstituted: aromatic hydrocarbon ring, aliphatic hydrocarbon ring, and aromatic heteroring, or each independently is a fused ring of two or more rings selected from this group;

<Chemical Formula 2>

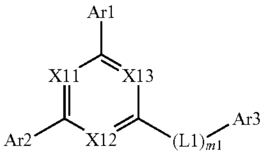

wherein:

X11 to X13 are N or CR', and at least one of X11 to X13 is N.

10 Claims, 1 Drawing Sheet

(51) Int. Cl.

| | |
|---|---|
| ***C07D 251/24*** | (2006.01) |
| ***C07F 5/02*** | (2006.01) |
| ***C07F 7/08*** | (2006.01) |
| ***C09K 11/06*** | (2006.01) |
| ***H10K 50/11*** | (2023.01) |
| ***H10K 50/18*** | (2023.01) |
| ***H10K 85/40*** | (2023.01) |
| ***H10K 85/60*** | (2023.01) |
| ***H10K 101/10*** | (2023.01) |
| ***H10K 101/30*** | (2023.01) |

(52) U.S. Cl.

CPC ............ *C07F 5/027* (2013.01); *C07F 7/0812* (2013.01); *C09K 11/06* (2013.01); *H10K 85/40* (2023.02); *H10K 85/615* (2023.02); *H10K 85/654* (2023.02); *H10K 85/6572* (2023.02); *H10K 85/658* (2023.02); *C07B 2200/05* (2013.01); *C09K 2211/1018* (2013.01); *H10K 50/11* (2023.02); *H10K 50/18* (2023.02); *H10K 2101/10* (2023.02); *H10K 2101/30* (2023.02)

(56) References Cited

U.S. PATENT DOCUMENTS

| | | | | |
|---|---|---|---|---|
| 2016/0322583 | A1* | 11/2016 | Kim | C09K 11/06 |
| 2016/0351825 | A1* | 12/2016 | Kim | H10K 85/6572 |
| 2018/0301629 | A1 | 10/2018 | Hatakeyama et al. | |
| 2019/0058124 | A1 | 2/2019 | Hatakeyama et al. | |
| 2020/0172558 | A1* | 6/2020 | Joo | C07F 5/02 |
| 2021/0151683 | A1 | 5/2021 | Sakaino et al. | |
| 2021/0184121 | A1 | 6/2021 | Suh et al. | |

FOREIGN PATENT DOCUMENTS

| | | |
|---|---|---|
| KR | 10-2016-0085603 | 7/2016 |
| KR | 10-2016-0119683 | 10/2016 |
| KR | 10-2017-0130434 | 11/2017 |
| KR | 10-2018-0072245 | 6/2018 |
| KR | 10-2019-0101900 | 9/2019 |
| KR | 10-2020-0132752 | 11/2020 |
| WO | 2006-033563 | 3/2006 |
| WO | 2015-102118 | 7/2015 |
| WO | 2019-013063 | 1/2019 |
| WO | 2020-231214 | 11/2020 |

OTHER PUBLICATIONS

Hatakeyama et al., Adv. Mater. 2016, 28, 2777-2781.*

Office Action of Korean Patent Office in Appl'n No. 10-2020-0162739, dated Feb. 19, 2022.

International Search Report and the Written Opinion of PCT/KR2020/017129, mailed Apr. 2, 2021.

* cited by examiner

【FIG. 1】
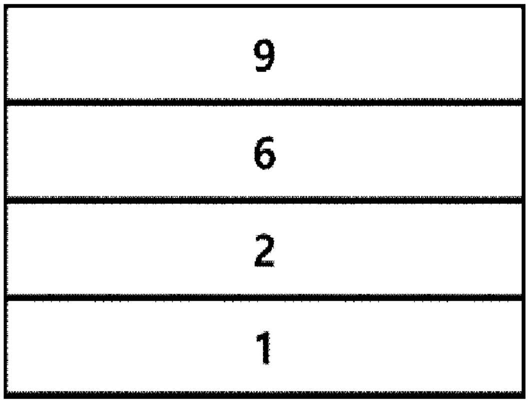
【FIG. 2】
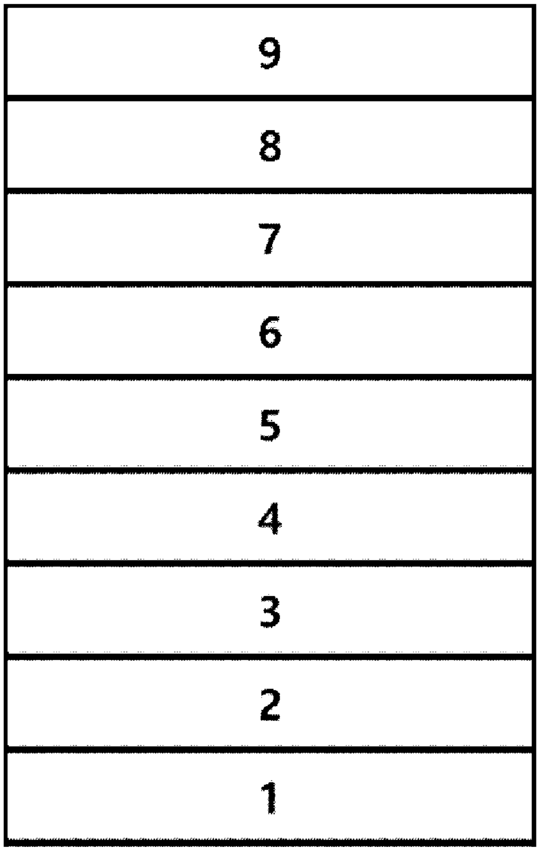

ORGANIC LIGHT-EMITTING DEVICE

CROSS-REFERENCE TO RELATED APPLICATION(S)

This application is a National Stage Application of International Application No. PCT/KR2020/017129 filed on Nov. 27, 2020, which claims priority to and the benefits of Korean Patent Application No. 10-2019-0157080, filed with the Korean Intellectual Property Office on Nov. 29, 2019, the entire contents of which are incorporated herein by reference.

TECHNICAL FIELD

The present specification relates to an organic light emitting device.

BACKGROUND

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, can be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS (Patent Document 1) KR 10-2006-0051622 A

BRIEF DESCRIPTION

Technical Problem

The present specification provides an organic light emitting device.

Technical Solution

One embodiment of the present specification provides an organic light emitting device including an anode; a cathode; a light emitting layer provided between the anode and the cathode; and a first organic material layer provided between the light emitting layer and the cathode, wherein the light emitting layer includes a compound of the following Chemical Formula 1, and the first organic material layer includes a compound of the following Chemical Formula 2:

<Chemical Formula 1>

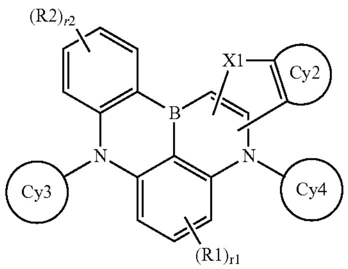

wherein in Chemical Formula 1:

X1 is O or S,

Cy2 is one selected from the group consisting of a substituted or unsubstituted aromatic hydrocarbon ring and a substituted or unsubstituted aliphatic hydrocarbon ring, or a fused ring of two or more rings selected from the above-described group;

Cy3 and Cy4 are the same as or different from each other, and each independently is one selected from the group consisting of a substituted or unsubstituted aromatic hydrocarbon ring, a substituted or unsubstituted aliphatic hydrocarbon ring, and a substituted or unsubstituted aromatic heteroring, or a fused ring of two or more rings selected from the above-described group;

R1 and R2 are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r1 is an integer of 0 to 3, and when r1 is 2 or greater, the R1s are the same as or different from each other; and r2 is an integer of 0 to 4, and when r2 is 2 or greater, the R2s are the same as or different from each other;

<Chemical Formula 2>

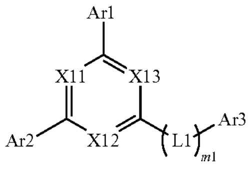

wherein in Chemical Formula 2:

X11 to X13 are N or CR', and at least one of X11 to X13 is N;

R' is hydrogen, deuterium, a cyano group, a halogen group, a substituted or unsubstituted alkyl group, a substituted or unsubstituted alkenyl group, a substituted or unsubstituted alkoxy group, a substituted or unsubstituted alkylthio group; a substituted or unsubstituted cycloalkyl group, a substituted or unsubstituted silyl group, a substituted or unsubstituted aryl group, a substituted or unsubstituted aryloxy group, a substituted or unsubstituted arylthio group, or a substituted or unsubstituted heterocyclic group;

L1 is a direct bond, a substituted or unsubstituted arylene group, or a substituted or unsubstituted divalent heterocyclic group;

m1 is an integer of 1 to 3, and when m1 is 2 or greater, the L1s are the same as or different from each other;

Ar1 and Ar2 are the same as or different from each other, and each independently is a substituted or unsubstituted aryl group or a substituted or unsubstituted heterocyclic group; and Ar3 is any one of the following Chemical Formulae 2-A to 2-C:

<Chemical Formula 2-A>

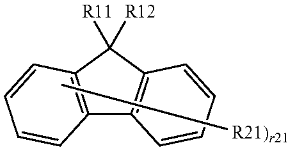

<Chemical Formula 2-B>

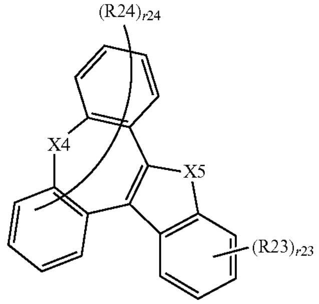

<Chemical Formula 2-C>

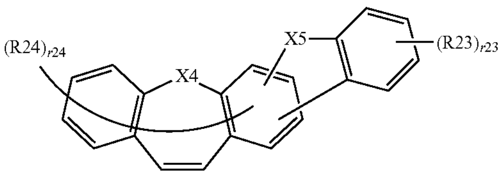

wherein in Chemical Formulae 2-A to 2-C:

R11 and R12 are a substituted or unsubstituted alkyl group or a substituted or unsubstituted aryl group, or bond to adjacent groups to form a substituted or unsubstituted ring;

X4 is O, S, or NR25;

X5 is O, S, or NR22;

any one of R21 to R25 is linked to Chemical Formula 2, and the rest are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r21 is an integer of 0 to 7, r23 is an integer of 0 to 4, and r24 is an integer of 0 to 8; and when r21, r23 and r24 are each 2 or greater, substituents in the parentheses are the same as or different from each other.

Advantageous Effects

By including a compound of Chemical Formula 1 in a light emitting layer and a compound of Chemical Formula 2 in a first organic material layer, an organic light emitting device described in the present specification has low driving voltage, excellent efficiency properties and/or excellent lifetime. Specifically, low driving voltage, high efficiency and improved lifetime can be obtained by controlling a degree of hole and/or electron transfer through properly adjusting HOMO energy level and LUMO energy level.

DESCRIPTION OF THE DRAWINGS

FIG. 1 illustrates an example of an organic light emitting device in which a substrate (1), an anode (2), a light emitting layer (6), a hole blocking layer (7) and a cathode (9) are consecutively laminated.

FIG. 2 illustrates an example of an organic light emitting device in which a substrate (1), an anode (2), a hole injection layer (3), a first hole transfer layer (4), a second hole transfer layer (5), a light emitting layer (6), a hole blocking layer (7), an electron transfer and injection layer (8) and a cathode (9) are consecutively laminated.

REFERENCE NUMERALS

1: Substrate
2: Anode
3: Hole Injection Layer
4: First Hole Transfer Layer
5: Second Hole Transfer Layer
6: Light Emitting Layer
7: Hole Blocking Layer
8: Electron Transfer and Injection Layer
9: Cathode

DETAILED DESCRIPTION

Hereinafter, the present specification will be described in more detail.

Chemical Formula 1 of the present disclosure includes a 5-membered heteroring including an oxygen or sulfur atom, and is capable of securing structural stability and superior electrochemical properties of the compound using sufficient electrons. Specifically, first triplet excitation energy of Chemical Formula 1 is lowered, and a difference between first singlet excitation energy and the first triplet excitation energy increases. Accordingly, triplet quenching is suppressed, and as a result, voltage, efficiency and/or lifetime of an organic light emitting device including the same are enhanced.

Chemical Formula 2 of the present disclosure enhances electron migration properties by including a monocyclic ring including N, and, by including a fluorene group or a fused cyclic ring group containing N, O or S, enhances effects of hole blocking and electron transfer by forming a wide band gap of the molecule, and as a result, effects of enhancing voltage, efficiency and/or lifetime of an organic light emitting device including the same are obtained.

Herein, when using the compound of Chemical Formula 1 in a light emitting layer and using the compound of Chemical Formula 2 in a first organic material layer (specifically, electron transfer area), properties of long lifetime, low voltage and/or high efficiency of the device are strengthened due to a synergy effect in the organic light emitting device.

Accordingly, an organic light emitting device having properties of high efficiency, low voltage and/or long lifetime can be obtained when using the compound of Chemical Formula 1 and the compound of Chemical Formula 2 described above in the organic light emitting device.

In the present specification, a description of a certain part "including" certain constituents means capable of further including other constituents, and does not exclude other constituents unless particularly stated on the contrary.

In the present specification, a description of one member being placed "on" another member includes not only a case of the one member being in contact with the another member but a case of still another member being present between the two members.

In the present specification,

" 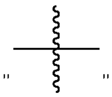 "

or a dotted line means a position bonding to a chemical formula or a compound.

Examples of substituents in the present specification are described below, however, the substituents are not limited thereto.

The term "substitution" means a hydrogen atom bonding to a carbon atom of a compound being changed to another substituent, and the position of substitution is not limited as long as it is a position at which a hydrogen atom is substituted, that is, a position at which a substituent can substitute, and when two or more substituents substitute, the two or more substituents can be the same as or different from each other.

In the present specification, a term "substituted or unsubstituted" means being substituted with one, two or more substituents selected from the group consisting of deuterium, a halogen group, a cyano group, a nitro group, a hydroxyl group, an alkyl group, a cycloalkyl group, an alkoxy group, a phosphine oxide group, an aryloxy group, an alkylthio group, an arylthio group, an alkylthioxy group, an arylthioxy group, an alkylsulfoxy group, an arylsulfoxy group, an alkenyl group; a silyl group, a boron group, an amine group, an aryl group, or a heterocyclic group, or being substituted with a substituent linking two or more substituents among the substituents previously recited, or having no substituents. For example, "a substituent linking two or more substituents" can include a biphenyl group. In other words, a biphenyl group can be an aryl group, or interpreted as a substituent linking two phenyl groups.

In the present specification, a term "substituted or unsubstituted" means being substituted with one, two or more substituents selected from the group consisting of deuterium, a halogen group, a cyano group, a nitro group, a hydroxyl group, an amine group, a silyl group, a boron group, an alkoxy group, an aryloxy group, an alkyl group, a cycloalkyl group, an aryl group, and a heterocyclic group, or being substituted with a substituent linking two or more substituents among the substituents illustrated above, or having no substituents.

In the present specification, a term "substituted or unsubstituted" means being substituted with one, two or more substituents selected from the group consisting of deuterium, a cyano group, a halogen group, an alkyl group, an alkoxy group, a cycloalkyl group, a silyl group, an aryl group, an aryloxy group, a heterocyclic group, or an amine group, or being substituted with a substituent linking two or more substituents among the substituents illustrated above, or having no substituents.

In the present specification, linking two or more substituents refers to replacing hydrogen of any one substituent with another substituent. For example, an isopropyl group and a phenyl group can be linked to become a substituent of

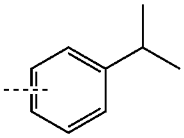

or

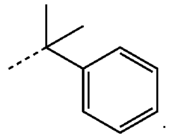

.

In the present specification, linking three substituents includes not only continuously linking (substituent 1)-(substituent 2)-(substituent 3), but also linking (substituent 2) and (substituent 3) to (substituent 1). For example, two phenyl groups and an isopropyl group can be linked to become a substituent of

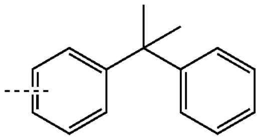

or

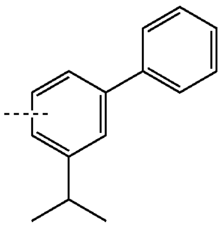

.

The same rule described above also applies to linking four or more substituents.

In the present specification, "substituted with A or B" includes not only a case of being substituted only with A or substituted with only B, but also a case of being substituted with A and B.

Examples of the substituents are described below, however, the substituents are not limited thereto.

In the present specification, examples of the halogen group can include fluorine (—F), chlorine (—Cl), bromine (—Br) or iodine (—I).

In the present specification, the silyl group can have a chemical formula of $—SiY_aY_bY_c$, and $Y_a$, $Y_b$ and $Y_c$ can each be hydrogen, a substituted or unsubstituted alkyl group, or a substituted or unsubstituted aryl group. Specific examples of the silyl group can include a trimethylsilyl group, a triethylsilyl group, a t-butyl-dimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group can have a chemical formula of $—BY_dY_e$, and $Y_d$ and $Y_e$ can each be hydrogen, a substituted or unsubstituted alkyl group, or a substituted or unsubstituted aryl group. Specific examples of the boron group can include a trimethylboron group, a triethylboron group, a t-butyl-dimethylboron group, a triphenylboron group, a phenylboron group and the like, but are not limited thereto.

In the present specification, the alkyl group can be linear or branched, and although not particularly limited thereto, the number of carbon atoms is preferably from 1 to 60. According to one embodiment, the number of carbon atoms of the alkyl group is from 1 to 30. According to another embodiment, the number of carbon atoms of the alkyl group is from 1 to 20. According to another embodiment, the number of carbon atoms of the alkyl group is from 1 to 10. Specific examples of the alkyl group can include a methyl group, an ethyl group, a propyl group, an n-propyl group, an isopropyl group, a butyl group, an n-butyl group, an isobutyl group, a tert-butyl group, a pentyl group, an n-pentyl group, a hexyl group, an n-hexyl group, a heptyl group, an n-heptyl group, an octyl group, an n-octyl group and the like, but are not limited thereto.

In the present specification, the descriptions on the alkyl group provided above can be applied to the arylalkyl group except for being substituted with an aryl group.

In the present specification, the alkoxy group can be linear, branched or cyclic. The number of carbon atoms of the alkoxy group is not particularly limited, but is preferably from 1 to 20. Specific examples thereof can include methoxy, ethoxy, n-propoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy and the like, but are not limited thereto.

Substituents including the alkyl group, the alkoxy group and other alkyl group parts described in the present specification include both linear or branched forms.

In the present specification, the alkenyl group can be linear or branched, and although not particularly limited thereto, the number of carbon atoms is preferably from 2 to 40. According to one embodiment, the number of carbon atoms of the alkenyl group is from 2 to 20. According to another embodiment, the number of carbon atoms of the alkenyl group is from 2 to 10. According to another embodiment, the number of carbon atoms of the alkenyl group is from 2 to 6. Specific examples thereof can include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, the alkynyl group is a substituent including a triple bond between a carbon atom and a carbon atom, can be linear or branched, and although not particularly limited thereto, the number of carbon atoms is preferably from 2 to 40. According to one embodiment, the number of carbon atoms of the alkynyl group is from 2 to 20. According to another embodiment, the number of carbon atoms of the alkynyl group is from 2 to 10.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. Specific examples thereof can include a cyclopropyl group, a cyclobutyl group, a cyclopentyl group, a cyclohexyl group, a cycloheptyl group, a cyclooctyl group and the like, but are not limited thereto.

In the present specification, the amine group can be selected from the group consisting of —$NH_2$, an alkylamine group, an alkylarylamine group, an arylamine group, an arylheteroarylamine group, an alkylheteroarylamine group, and a heteroarylamine group, and although not particularly limited thereto, the number of carbon atoms is preferably from 1 to 60. In the arylamine group, the number of carbon atoms is from 6 to 60. According to another embodiment, the number of carbon atoms of the arylamine group is from 6 to 40. Specific examples of the amine group can include a methylamine group, a dimethylamine group, an ethylamine group, a diethylamine group, a phenylamine group, a naphthylamine group, a biphenylamine group, an anthracenylamine group, a 9-methylanthracenylamine group, a diphenylamine group, an N-phenylnaphthylamine group, a ditolylamine group, an N-phenyltolylamine group, a triphenylamine group, an N-phenylbiphenylamine group, an N-phenylnaphthylamine group, an N-biphenylnaphthylamine group, an N-naphthylfluorenylamine group, an N-phenylphenanthrenylamine group, an N-biphenylphenanthrenylamine group, an N-phenylfluorenylamine group, an N-phenylterphenylamine group, an N-phenanthrenylfluorenylamine group, an N-biphenylfluorenylamine group, an N-(4-(tert-butyl)phenyl)-N-phenylamine group, an N,N-bis(4-(tert-butyl)phenyl)amine group, an N,N-bis(3-(tert-butyl)phenyl)amine group, and the like, but are not limited thereto.

In the present specification, the alkylarylamine group means an amine group in which N of the amine group is substituted with an alkyl group and an aryl group.

In the present specification, the arylheteroarylamine group means an amine group in which N of the amine group is substituted with an aryl group and a heteroaryl group.

In the present specification, the alkylheteroarylamine group means an amine group in which N of the amine group is substituted with an alkyl group and a heteroaryl group.

In the present specification, the alkyl group in the alkylamine group, the arylalkylamine group, the alkylthioxy group, the alkylsulfoxy group and the alkylheteroarylamine group is the same as the examples of the alkyl group. Specific examples of the alkylthioxy group can include a methylthioxy group, an ethylthioxy group, a tert-butylthioxy group, a hexylthioxy group, an octylthioxy group, and the like, and specific examples of the alkylsulfoxy group can include mesyl, an ethylsulfoxy group, a propylsulfoxy group, a butylsulfoxy group, and the like, however, the alkylthioxy group and the alkylsulfoxy group are not limited thereto.

In the present specification, the cycloalkyl group is not particularly limited, but preferably has 3 to 60 carbon atoms, and according to one embodiment, the number of carbon atoms of the cycloalkyl group is from 3 to 30. According to another embodiment, the number of carbon atoms of the cycloalkyl group is from 3 to 20. According to another embodiment, the number of carbon atoms of the cycloalkyl group is from 3 to 6. The cycloalkyl group includes not only a monocyclic group, but also a bicyclic group such as a bridgehead, a fused ring or a spiro ring. Specific examples thereof can include a cyclopropyl group, a cyclobutyl group, a cyclopentyl group, a cyclohexyl group, a cycloheptyl group, a cyclooctyl group, an adamantyl group and the like, but are not limited thereto.

In the present specification, the cycloalkene is a cyclic group that has a double bond present in the hydrocarbon ring but is not aromatic, and although not particularly limited thereto, the number of carbon atoms can be from 3 to 60, and according to one embodiment, the number of carbon atoms can be from 3 to 30. The cycloalkene includes not only a monocyclic group, but also a bicyclic group such as a bridgehead, a fused ring or a spiro ring. Examples of the cycloalkene can include cyclopropene, cyclobutene, cyclopentene, cyclohexene and the like, but are not limited thereto.

In the present specification, the aryl group is not particularly limited, but preferably has 6 to 60 carbon atoms, and can be a monocyclic aryl group or a polycyclic aryl group. According to one embodiment, the number of carbon atoms of the aryl group is from 6 to 30. According to one embodiment, the number of carbon atoms of the aryl group is from 6 to 20. When the aryl group is a monocyclic aryl group, examples thereof can include a phenyl group, a biphenyl group, a terphenyl group, a quaterphenyl group and the like, but are not limited thereto. Examples of the polycyclic aryl group can include a naphthyl group, an anthracenyl group, a phenanthrenyl group, a pyrenyl group, a perylenyl group, a triphenyl group, a chrysenyl group, a fluorenyl group, a triphenylenyl group and the like, but are not limited thereto.

In the present specification, the fluorenyl group can be substituted, and two substituents can bond to each other to form a spiro structure. Herein, the spiro structure can be an aromatic hydrocarbon ring or an aliphatic hydrocarbon ring.

When the fluorenyl group is substituted, a spirofluorenyl group such as

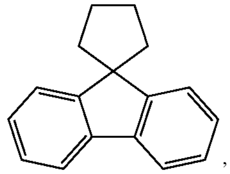
,
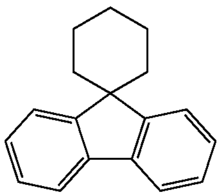
and
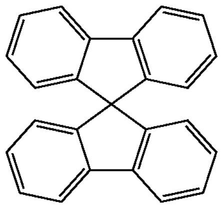
, or a substituted fluorenyl group such as

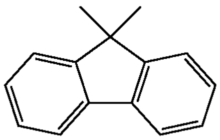

(9,9-dimethylfluorenyl group) and

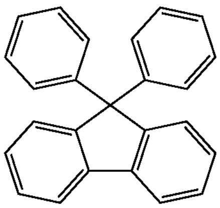 [SMILES: c1ccc(C2(c3ccccc3)c3ccccc3-c3ccccc32)cc1]

(9,9-diphenylfluorenyl group) can be included. However, the structure is not limited thereto.

In the present specification, the substituted aryl group can also include a form in which an aliphatic ring is fused to the aryl group. For example, a tetrahydronaphthalene group or a dihydroindene group of the following structures is included in the substituted aryl group. In the following structures, one of the carbons of the benzene ring can be linked to other positions:

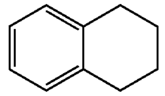
tetrahydronaphthalene
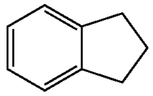
dihydroindene
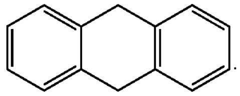
dihydroanthracene In the present specification, the alkylaryl group means an aryl group substituted with an alkyl group, and can have substituents other than the alkyl group additionally linked thereto.

In the present specification, the arylalkyl group means an alkyl group substituted with an aryl group, and can have substituents other than the aryl group additionally linked thereto.

In the present specification, the aryloxy group means linking an aryl group to an oxygen atom, and the arylthio group means linking an aryl group to a sulfur atom, and as the aryl group in the aryloxy group and the arylthio group, the descriptions on the aryl group provided above can be applied. The aryl group in the aryloxy group is the same as the examples of the aryl group described above. Specific examples of the aryloxy group can include a phenoxy group, a p-tolyloxy group, an m-tolyloxy group, a 3,5-dimethylphenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and examples of the arylthioxy group can include a phenylthioxy group, a 2-methylphenylthioxy group, a 4-tert-butylphenylthioxy group and the like, however, the aryloxy group and the arylthioxy group are not limited thereto.

In the present specification, the heterocyclic group is a cyclic group including one or more of N, O, P, S, Si and Se as a heteroatom, and although not particularly limited thereto, the number of carbon atoms is preferably from 2 to 60. According to one embodiment, the number of carbon atoms of the heterocyclic group is from 2 to 30. According to one embodiment, the number of carbon atoms of the heterocyclic group is from 2 to 20. Examples of the heterocyclic group can include a pyridyl group, a quinoline group, a thiophene group, a dibenzothiophene group, a furan group, a dibenzofuran group, a naphthobenzofuran group, a carbazole group, a benzocarbazole group, a naphthobenzothiophene group, a dibenzosilole group, a naphthobenzosilole group, a hexahydrocarbazole group, a dihydroacridine group, a dihydrodibenzoazasiline group, a phenoxazine group, a phenothiazine group, a dihydrodibenzoazasiline group, a spiro(dibenzosilole-dibenzoazasiline) group, a spiro(acridine-fluorene) group, and the like, but are not limited thereto:

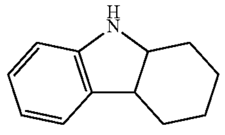

hexahydrocarbazole

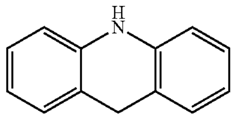

dihydroacridine

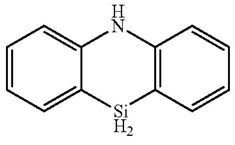

dihydrodibenzooazasiline

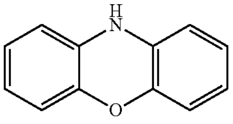

phenoxazine

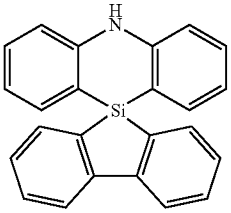

spiro[dibenzosilole-dibenzoazasiline]

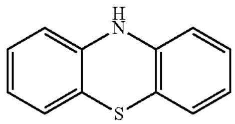

phenothiazine

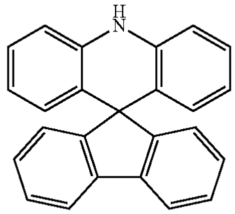

spiro[acridine-fluorene] .

In the present specification, the descriptions on the heterocyclic group provided above can be applied to the heteroaryl group except for being aromatic.

In the present specification, the descriptions on the aryl group can be applied to the arylene group except for being divalent.

In the present specification, the descriptions on the heterocyclic group can be applied to the divalent heteroring except for being divalent.

In the present specification, the hydrocarbon ring group can be an aromatic hydrocarbon ring group; an aliphatic hydrocarbon ring group; or a fused ring group of aromatic hydrocarbon ring and aliphatic hydrocarbon ring, and the descriptions on the aryl group provided above can be applied to the aromatic hydrocarbon ring group, and the descriptions on the cycloalkyl group provided above can be applied to the aliphatic hydrocarbon ring group.

In the present specification, the “ring” in the substituted or unsubstituted ring formed by bonding to adjacent groups means a hydrocarbon ring; or a heteroring.

The hydrocarbon ring can be aromatic, aliphatic or a fused ring of aromatic and aliphatic, and can be selected from among the examples of the cycloalkyl group or the aryl group.

In the present specification, the meaning of bonding to adjacent groups to form a ring means bonding to adjacent groups to form a substituted or unsubstituted aliphatic hydrocarbon ring, a substituted or unsubstituted aromatic hydrocarbon ring, a substituted or unsubstituted aliphatic heteroring, a substituted or unsubstituted aromatic heteroring, or a fused ring thereof. The hydrocarbon ring means a ring formed only with carbon and hydrogen atoms. The heteroring means a ring including one or more selected from among elements such as N, O, P, S, Si and Se. In the present specification, the aliphatic hydrocarbon ring, the aromatic hydrocarbon ring, the aliphatic heteroring and the aromatic heteroring can be monocyclic or polycyclic.

In the present specification, the aliphatic hydrocarbon ring means, as a ring that is not aromatic, a ring formed only with carbon and hydrogen atoms. Examples of the aliphatic hydrocarbon ring can include cyclopropane, cyclobutane, cyclobutene, cyclopentane, cyclopentene, cyclohexane, cyclohexene, 1,4-cyclohexadiene, cycloheptane, cycloheptene, cyclooctane, cyclooctene, bicyclooctene and the like, but are not limited thereto.

In the present specification, the aromatic hydrocarbon ring means an aromatic ring formed only with carbon and hydrogen atoms. Examples of the aromatic hydrocarbon ring can include benzene, naphthalene, anthracene, phenanthrene, perylene, fluoranthene, triphenylene, phenalene, pyrene, tetracene, chrysene, pentacene, fluorene, indene, acenaphthylene, benzofluorene, spirofluorene and the like, but are not limited thereto. In the present specification, the aromatic hydrocarbon ring can be interpreted to have the same meaning as the aryl group.

In the present specification, the aliphatic heteroring means an aliphatic ring including one or more of heteroatoms. Examples of the aliphatic heteroring can include oxirane, tetrahydrofuran, 1,4-dioxane, pyrrolidine, piperidine, morpholine, oxepane, azokane, thiokane and the like, but are not limited thereto.

In the present specification, the aromatic heteroring means an aromatic ring including one or more of heteroatoms. Examples of the aromatic heteroring can include pyridine, pyrrole, pyrimidine, pyridazine, furan, thiophene, imidazole, parazole, oxazole, isoxazole, thiazole, isothiazole, triazole, oxadiazole, thiadiazole, dithiazole, tetrazole, pyran, thiopyran, diazine, oxazine, thiazine, dioxin, triazine, tetrazine, isoquinoline, quinoline, quinone, quinazoline, quinoxaline, naphthyridine, acridine, phenanthridine, diazanaphthalene, triazaindene, indole, indolizine, benzothiazole, benzoxazole, benzimidazole, benzothiophene, benzofuran, dibenzothiophene, dibenzofuran, carbazole, benzocarbazole, dibenzocarbazole, phenazine, imidazopyridine, phenoxazine, indolocarbazole, indenocarbazole and the like, but are not limited thereto.

In the present specification, the fused ring of aromatic hydrocarbon ring and aliphatic hydrocarbon ring means the aromatic hydrocarbon ring and the aliphatic hydrocarbon ring forming a fused ring. Examples of the fused ring of aromatic and aliphatic can include a 1,2,3,4-tetrahydronaphthalene group, a 2,3-dihydro-1H-indene group and the like, but are not limited thereto.

In the present specification, the “adjacent” group can mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring can be interpreted as groups “adjacent” to each other. In addition, substituents linked to consecutive two carbons in the aliphatic ring (total of 4) can also be interpreted as groups “adjacent” to each other.

In the present specification, the meaning of “adjacent groups bonding to each other to form a ring” among the substituents is bonding to adjacent groups to form a substituted or unsubstituted hydrocarbon ring; or a substituted or unsubstituted heteroring.

In the present specification, a "5-membered or 6-membered ring formed by adjacent groups bonding to each other" means a ring including substituents participating in the ring formation being 5-membered or 6-membered. It includes an additional ring being fused to the ring including substituents participating in the ring formation.

In the present specification, when substituents of an aromatic hydrocarbon ring or an aryl group bond to adjacent substituents to form an aliphatic hydrocarbon ring, the aliphatic hydrocarbon ring includes two pi electrons (carbon-carbon double bond) of the aromatic hydrocarbon ring or the aryl group even when the double bond is not specified.

Hereinafter, preferred embodiments of the present disclosure will be described in detail. However, embodiments of the present disclosure can be modified to various forms, and the scope of the present disclosure is not limited to the embodiments described below.

Hereinafter, Chemical Formula 1 will be described in detail.

<Chemical Formula 1>

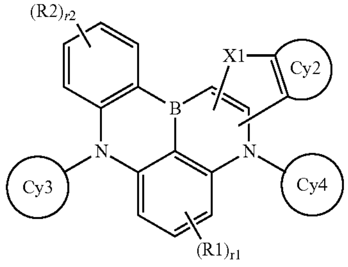

In Chemical Formula 1:

X1 is O or S;

Cy2 is one selected from the group consisting of a substituted or unsubstituted aromatic hydrocarbon ring and a substituted or unsubstituted aliphatic hydrocarbon ring, or a fused ring of two or more rings selected from the above-described group;

Cy3 and Cy4 are the same as or different from each other, and each independently is one selected from the group consisting of a substituted or unsubstituted aromatic hydrocarbon ring, a substituted or unsubstituted aliphatic hydrocarbon ring, and a substituted or unsubstituted aromatic heteroring, or a fused ring of two or more rings selected from the above-described group;

R1 and R2 are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r1 is an integer of 0 to 3, and when r1 is 2 or greater, the R1s are the same as or different from each other; and r2 is an integer of 0 to 4, and when r2 is 2 or greater, the R2s are the same as or different from each other.

In one embodiment of the present specification, Chemical Formula 1 is one of the following Chemical Formula 101 or 102:

<Chemical Formula 101>

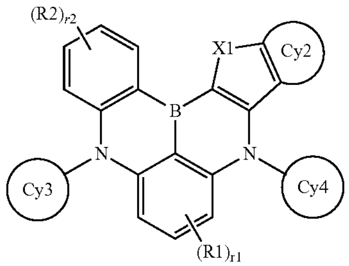

<Chemical Formula 102>

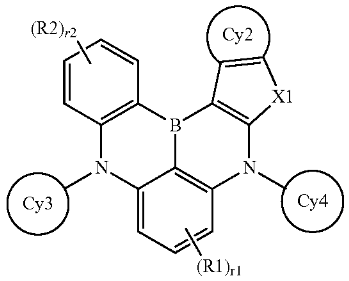

wherein in Chemical Formulae 101 and 102:

X1, Cy2 to Cy4, R1, R2, r1 and r2 have the same definitions as in Chemical Formula 1.

In one embodiment of the present specification, Cy2 is one selected from the group consisting of a substituted or unsubstituted aromatic hydrocarbon ring and a substituted or unsubstituted aliphatic hydrocarbon ring, or a fused ring of two or more rings selected from the above-described group.

In one embodiment of the present specification, Cy2 is a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring.

In one embodiment of the present specification, Cy2 is a substituted or unsubstituted C6-C60 aromatic hydrocarbon ring, a substituted or unsubstituted C5-C60 aliphatic hydrocarbon ring, or a substituted or unsubstituted fused ring of a C6-C60 aromatic hydrocarbon ring and a C5-C60 aliphatic hydrocarbon ring.

In one embodiment of the present specification, Cy2 is a substituted or unsubstituted C6-C30 aromatic hydrocarbon ring, a substituted or unsubstituted C5-C30 aliphatic hydrocarbon ring, or a substituted or unsubstituted fused ring of a C6-C30 aromatic hydrocarbon ring and a C5-C30 aliphatic hydrocarbon ring.

In one embodiment of the present specification, Cy2 is a substituted or unsubstituted C6-C20 aromatic hydrocarbon ring, a substituted or unsubstituted C5-C20 aliphatic hydrocarbon ring, or a substituted or unsubstituted fused ring of a C6-C20 aromatic hydrocarbon ring and a C5-C20 aliphatic hydrocarbon ring.

In one embodiment of the present specification, Cy2 is one selected from the group consisting of a substituted or unsubstituted benzene ring, a substituted or unsubstituted naphthalene ring, a substituted or unsubstituted fluorene ring, a substituted or unsubstituted benzofluorene ring, a substituted or unsubstituted cyclohexene ring, a substituted or unsubstituted cyclopentene ring, and a substituted or unsubstituted bicyclooctene ring, or a fused ring of two or more rings selected from the above-described group.

In one embodiment of the present specification, Cy2 is one selected from the group consisting of a benzene ring, a naphthalene ring, a fluorene ring, a benzofluorene ring, a cyclohexene ring, a cyclopentene ring, and a bicyclooctene ring, or a fused ring of two or more rings selected from the above-described group, and the ring is unsubstituted or substituted with one or more groups selected from the group consisting of deuterium, an alkyl group having 1 to 10 carbon atoms, a cycloalkyl group having 3 to 20 carbon atoms and an aryl group having 6 to 20 carbon atoms, or a group linking two or more groups selected from the above-described group.

In one embodiment of the present specification, Cy2 is one selected from the group consisting of a substituted or unsubstituted benzene ring, a substituted or unsubstituted naphthalene ring, a substituted or unsubstituted cyclohexene ring, a substituted or unsubstituted cyclopentene ring, and a substituted or unsubstituted bicyclooctene ring, or a fused ring of two or more rings selected from the above-described group.

In one embodiment of the present specification, Cy2 is one selected from the group consisting of a benzene ring, a naphthalene ring, a cyclohexene ring, a cyclopentene ring, and a bicyclooctene ring, or a fused ring of two or more rings selected from the above-described group, and the ring is unsubstituted or substituted with one or more groups selected from the group consisting of deuterium, an alkyl group having 1 to 10 carbon atoms, a cycloalkyl group having 3 to 20 carbon atoms and an aryl group having 6 to 20 carbon atoms, or a group linking two or more groups selected from the above-described group.

In one embodiment of the present specification, Cy2 is a substituted or unsubstituted benzene ring, a substituted or unsubstituted cyclohexene ring, a substituted or unsubstituted tetrahydronaphthalene ring, or a substituted or unsubstituted 1,2,3,4-tetrahydro-1,4-ethanonaphthalene ring.

In one embodiment of the present specification, Cy2 is a benzene ring, a cyclohexene ring, a tetrahydronaphthalene ring, or a 1,2,3,4-tetrahydro-1,4-ethanonaphthalene ring, and the ring is unsubstituted or substituted with one or more groups selected from the group consisting of deuterium, an alkyl group having 1 to 10 carbon atoms, a cycloalkyl group having 3 to 20 carbon atoms and an aryl group having 6 to 20 carbon atoms, or a group linking two or more groups selected from the above-described group.

In one embodiment of the present specification, Cy2 is a benzene ring that is unsubstituted or substituted with deuterium, a methyl group, $CD_3$, an i-propyl group, a t-butyl group, an adamantyl group or a phenyl group; a cyclohexene ring that is unsubstituted or substituted with a methyl group; a tetrahydronaphthalene ring that is unsubstituted or substituted with deuterium, a methyl group, $CD_3$, an i-propyl group or a t-butyl group; or a 1,2,3,4-tetrahydro-1,4-ethanonaphthalene ring that is unsubstituted or substituted with deuterium, a methyl group, $CD_3$, an i-propyl group or a t-butyl group.

In one embodiment of the present specification, Cy2 is a benzene ring that is unsubstituted or substituted with deuterium, a methyl group, $CD_3$, an i-propyl group, a t-butyl group, an adamantyl group or a phenyl group; a cyclohexene ring that is unsubstituted or substituted with a methyl group; a tetrahydronaphthalene ring that is unsubstituted or substituted with deuterium, a methyl group or $CD_3$; or a 1,2,3,4-tetrahydro-1,4-ethanonaphthalene ring

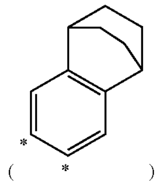 [SMILES: c1ccc2c(c1)C1CCC2CC1]

that is unsubstituted or substituted with a methyl group, and * means a position fused to Chemical Formula 1.

In one embodiment of the present specification, Cy2 is a benzene ring that is unsubstituted or substituted with R3; a cyclohexene ring that is unsubstituted or substituted with R3; a tetrahydronaphthalene ring that is unsubstituted or substituted with R3; or a 1,2,3,4-tetrahydro-1,4-ethanonaphthalene ring that is unsubstituted or substituted with R3.

In one embodiment of the present specification, Cy2 is a benzene ring that is unsubstituted or substituted with deuterium or a C1-C10 alkyl group that is unsubstituted or substituted with deuterium; a tetrahydronaphthalene ring substituted with a C1-C10 alkyl group; or a 1,2,3,4-tetrahydro-1,4-ethanonaphthalene ring substituted with a C1-C10 alkyl group.

In one embodiment of the present specification, Cy2 is a benzene ring that is unsubstituted or substituted with a methyl group, $CD_3$ or a t-butyl group; a tetrahydronaphthalene ring substituted with a methyl group; or a 1,2,3,4-tetrahydro-1,4-ethanonaphthalene ring substituted with a methyl group.

In one embodiment of the present specification, Cy2 is any one of the following structural formulae, and the following structural formulae are unsubstituted or substituted with a methyl group, $CD_3$ or a t-butyl group:

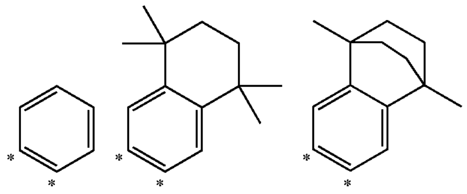

wherein in the structural formulae, * means a fused position.

In one embodiment of the present specification, Cy2 is the following Chemical Formula Cy2-1 or Cy2-2:

<Chemical Formula Cy2-1>

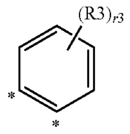

<Chemical Formula Cy2-2>

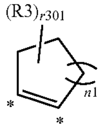

wherein in Chemical Formulae Cy2-1 and Cy2-2:

R3 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bonds to adjacent substituents to form a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring;

n1 is 1 or 2;

r3 is an integer of 0 to 4, and r301 is an integer of 0 to 8;

when r3 and r301 are each 2 or greater, the two or more R3s are the same as or different from each other; and

* means a position fused to Chemical Formula 1.

In one embodiment of the present specification, R3 is hydrogen, deuterium, a cyano group, a halogen group, a substituted or unsubstituted alkyl group, a substituted or unsubstituted cycloalkyl group, a substituted or unsubstituted silyl group, a substituted or unsubstituted aryl group, a substituted or unsubstituted heterocyclic group, or a substituted or unsubstituted amine group, or bonds to adjacent substituents to form a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring.

In one embodiment of the present specification, R3 is hydrogen, deuterium, a cyano group, a halogen group, a substituted or unsubstituted C1-C60 alkyl group, a substituted or unsubstituted C3-C60 cycloalkyl group, a substituted or unsubstituted silyl group, a substituted or unsubstituted C6-C60 aryl group, a substituted or unsubstituted C2-C60 heterocyclic group, or a substituted or unsubstituted amine group, or bonds to adjacent substituents to form a substituted or unsubstituted C6-C60 aromatic hydrocarbon ring, a substituted or unsubstituted C5-C60 aliphatic hydrocarbon ring, or a substituted or unsubstituted fused ring of C6-C60 aromatic hydrocarbon ring and C5-C60 aliphatic hydrocarbon ring.

In one embodiment of the present specification, R3 is hydrogen, deuterium, a cyano group, a halogen group, a substituted or unsubstituted C1-C30 alkyl group, a substituted or unsubstituted C3-C30 cycloalkyl group, a substituted or unsubstituted silyl group, a substituted or unsubstituted C6-C30 aryl group, a substituted or unsubstituted C2-C30 heterocyclic group, or a substituted or unsubstituted amine group, or bonds to adjacent substituents to form a substituted or unsubstituted C6-C30 aromatic hydrocarbon ring, a substituted or unsubstituted C5-C30 aliphatic hydrocarbon ring, or a substituted or unsubstituted fused ring of C6-C30 aromatic hydrocarbon ring and C5-C30 aliphatic hydrocarbon ring.

In one embodiment of the present specification, R3 is hydrogen, deuterium, a cyano group, a halogen group, a substituted or unsubstituted C1-C20 alkyl group, a substituted or unsubstituted C3-C20 cycloalkyl group, a substituted or unsubstituted silyl group, a substituted or unsubstituted C6-C20 aryl group, a substituted or unsubstituted C2-C20 heterocyclic group, or a substituted or unsubstituted amine group, or bonds to adjacent substituents to form a substituted or unsubstituted C6-C20 aromatic hydrocarbon ring, a substituted or unsubstituted C5-C20 aliphatic hydrocarbon ring, or a substituted or unsubstituted fused ring of C6-C20 aromatic hydrocarbon ring and C5-C20 aliphatic hydrocarbon ring.

In one embodiment of the present specification, R3 is hydrogen, deuterium, a substituted or unsubstituted C1-C20 alkyl group, a substituted or unsubstituted C3-C20 cycloalkyl group, a substituted or unsubstituted C6-C20 aryl group, or a substituted or unsubstituted C2-C20 heterocyclic group, or bonds to adjacent substituents to form a substituted or unsubstituted C6-C20 aromatic hydrocarbon ring or a substituted or unsubstituted C5-C20 aliphatic hydrocarbon ring.

In one embodiment of the present specification, R3 is hydrogen; deuterium; a C1-C20 alkyl group that is unsubstituted or substituted with deuterium; a C3-C20 cycloalkyl group that is unsubstituted or substituted with deuterium; a C6-C20 aryl group that is unsubstituted or substituted with deuterium; or a C2-C20 heterocyclic group that is unsubstituted or substituted with deuterium, or bonds to adjacent substituents to form a C6-C20 aromatic hydrocarbon ring that is unsubstituted or substituted with deuterium or an alkyl group that is unsubstituted or substituted with deuterium; or a C5-C20 aliphatic hydrocarbon ring that is unsubstituted or substituted with deuterium or an alkyl group that is unsubstituted or substituted with deuterium.

In one embodiment of the present specification, R3 is hydrogen, deuterium, a substituted or unsubstituted methyl group, a substituted or unsubstituted propyl group, a substituted or unsubstituted butyl group, a substituted or unsubstituted adamantyl group, or a substituted or unsubstituted phenyl group, or bonds to adjacent substituents to form a substituted or unsubstituted cyclohexene ring or a substituted or unsubstituted bicyclooctene ring.

In one embodiment of the present specification, R3 is hydrogen; deuterium; a methyl group that is unsubstituted or substituted with deuterium; a propyl group that is unsubstituted or substituted with deuterium; a butyl group that is unsubstituted or substituted with deuterium; an adamantyl group that is unsubstituted or substituted with deuterium or an alkyl group that is unsubstituted or substituted with deuterium; or a phenyl group that is unsubstituted or substituted with deuterium or an alkyl group that is unsubstituted or substituted with deuterium, or bonds to adjacent substituents to form a cyclohexene ring that is unsubstituted or substituted with deuterium or an alkyl group that is unsubstituted or substituted with deuterium; or a bicyclooctene ring that is unsubstituted or substituted with deuterium or an alkyl group that is unsubstituted or substituted with deuterium.

In one embodiment of the present specification, R3 is hydrogen, deuterium, a methyl group, a propyl group, a butyl group, an adamantyl group, or a phenyl group, or bonds to adjacent substituents to form a cyclohexene ring or a bicyclooctene ring, and the group or the ring is unsubstituted or substituted with deuterium or an alkyl group that is unsubstituted or substituted with deuterium.

In one embodiment of the present specification, R3 is hydrogen; deuterium; a methyl group that is unsubstituted or substituted with deuterium; a propyl group that is unsubstituted or substituted with deuterium; a butyl group that is unsubstituted or substituted with deuterium; an adamantyl group that is unsubstituted or substituted with deuterium; or a phenyl group that is unsubstituted or substituted with deuterium, or bonds to adjacent substituents to form a cyclohexene ring that is unsubstituted or substituted with deuterium, a methyl group or $CD_3$; or a bicyclooctene ring that is unsubstituted or substituted with deuterium, a methyl group or $CD_3$.

In one embodiment of the present specification, R3 is hydrogen, deuterium, a methyl group, $CD_3$, an i-propyl group, a t-butyl group, an adamantyl group, or a phenyl group, or bonds to adjacent substituents to form a cyclohexene ring that is unsubstituted or substituted with deuterium, a methyl group or $CD_3$; or a bicyclo[2.2.2]oct-2-ene

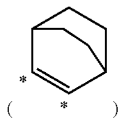

ring that is unsubstituted or substituted with a methyl group, and * means a position fused to Chemical Formula Cy2-1 or Cy2-2.

In one embodiment of the present specification, R3 is hydrogen, deuterium, or a C1-C10 alkyl group that is unsubstituted or substituted with deuterium, or bonds to adjacent substituents to form a cyclohexene ring substituted with a C1-C10 alkyl group or a bicyclo[2.2.2]oct-2-ene ring substituted with a C1-C10 alkyl group.

In one embodiment of the present specification, R3 is hydrogen, deuterium, a methyl group, $CD_3$, or a t-butyl group, or bonds to adjacent substituents to form a cyclohexene ring substituted with a methyl group, or a bicyclo [2.2.2]oct-2-ene ring substituted with a methyl group.

In one embodiment of the present specification, when R3 forms a ring, Cy2-1 is any one of the following structural formulae:

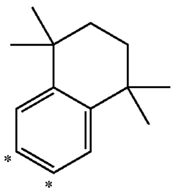

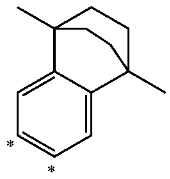

wherein in the structural formulae, * means a position fused to Chemical Formula 1, and the structural formulae are unsubstituted or substituted with deuterium or an alkyl group that is unsubstituted or substituted with deuterium.

In one embodiment of the present specification, the structural formulae are unsubstituted or substituted with deuterium, a methyl group or $CD_3$.

In one embodiment of the present specification, Cy2-2 is the following structural formula:

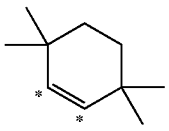

wherein in the structural formula, * means a position fused to Chemical Formula 1.

In one embodiment of the present specification, n1 is 2.

In one embodiment of the present specification, r3 is an integer of 0 to 4.

In one embodiment of the present specification, r3 is an integer of 1 to 4.

In one embodiment of the present specification, r301 is an integer of 0 to 8.

In one embodiment of the present specification, r301 is an integer of 1 to 8.

In one embodiment of the present specification, Cy3 and Cy4 are the same as or different from each other, and each independently is one selected from the group consisting of a substituted or unsubstituted aromatic hydrocarbon ring, a substituted or unsubstituted aliphatic hydrocarbon ring, and a substituted or unsubstituted aromatic heteroring, or a fused ring of two or more rings selected from the above-described group.

In one embodiment of the present specification, Cy3 and Cy4 are the same as or different from each other, and each independently is one selected from the group consisting of a substituted or unsubstituted C6-C60 aromatic hydrocarbon ring, a substituted or unsubstituted C5-C60 aliphatic hydrocarbon ring, and a substituted or unsubstituted C2-C60 aromatic heteroring, or a fused C9-C60 ring of two or more rings selected from the above-described group.

In one embodiment of the present specification, Cy3 and Cy4 are the same as or different from each other, and each independently is one selected from the group consisting of a substituted or unsubstituted C6-C30 aromatic hydrocarbon ring, a substituted or unsubstituted C5-C30 aliphatic hydrocarbon ring, and a substituted or unsubstituted C2-C30 aromatic heteroring, or a substituted or unsubstituted fused C9-C30 ring of two or more rings selected from the above-described group.

In one embodiment of the present specification, Cy3 and Cy4 are the same as or different from each other, and each independently is one selected from the group consisting of a substituted or unsubstituted C6-C20 aromatic hydrocarbon ring, a substituted or unsubstituted C5-C20 aliphatic hydrocarbon ring, and a substituted or unsubstituted C2-C20 aromatic heteroring, or a substituted or unsubstituted fused C9-C20 ring of two or more rings selected from the above-described group.

In one embodiment of the present specification, Cy3 and Cy4 are the same as or different from each other, and each independently is one selected from the group consisting of a substituted or unsubstituted C6-C20 aromatic hydrocarbon ring and a substituted or unsubstituted C5-C20 aliphatic hydrocarbon ring, or a substituted or unsubstituted fused C9-C20 ring of two or more rings selected from the above-described group.

In one embodiment of the present specification, Cy3 and Cy4 are the same as or different from each other, and each independently is one selected from the group consisting of a substituted or unsubstituted benzene ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted cyclohexene ring, a substituted or unsubstituted cyclopentene ring, a substituted or unsubstituted tetrahydronaphthalene ring, a substituted or unsubstituted dibenzofuran ring, a substituted or unsubstituted dibenzothiophene ring, a substituted or unsubstituted dibenzosilole ring, a substituted or unsubstituted naphthobenzofuran ring, a substituted or unsubstituted naphthobenzothiophene ring, and a substituted or unsubstituted naphthobenzosilole ring, or a fused ring of two or more rings selected from the above-described group.

In one embodiment of the present specification, Cy3 and Cy4 are the same as or different from each other, and each independently is a substituted or unsubstituted benzene ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted tetrahydronaphthalene ring, a substituted or unsubstituted dibenzofuran ring, a substituted or unsubstituted dibenzothiophene ring, a substituted or unsubstituted dibenzosilole ring, a substituted or unsubstituted naphthobenzofuran ring, a substituted or unsubstituted naphthobenzothiophene ring, or a substituted or unsubstituted naphthobenzosilole ring.

In one embodiment of the present specification, Cy3 and Cy4 are the same as or different from each other, and each independently is a substituted or unsubstituted benzene ring, a substituted or unsubstituted naphthalene ring, a substituted or unsubstituted phenanthrene ring, a substituted or unsubstituted fluorene ring, a substituted or unsubstituted benzofluorene ring, a substituted or unsubstituted tetrahydronaphthalene ring, a substituted or unsubstituted dibenzofuran ring, a substituted or unsubstituted dibenzothiophene ring, a substituted or unsubstituted dibenzosilole ring, or a substituted or unsubstituted naphthobenzofuran ring.

In one embodiment of the present specification, Cy3 and Cy4 are the same as or different from each other, and each independently is a benzene ring that is unsubstituted or substituted with deuterium, a halogen group, a C1-C10 alkyl group, a silyl group or a C6-C20 aryl group; a fluorene ring that is unsubstituted or substituted with a C1-C10 alkyl group or a C6-C20 aryl group; a tetrahydronaphthalene ring substituted with a C1-C10 alkyl group or a C6-C20 aryl group; or a dibenzofuran ring.

In one embodiment of the present specification, Cy3 and Cy4 are the same as or different from each other, and each independently is a benzene ring that is unsubstituted or substituted with deuterium, a fluoro group, a methyl group, a t-butyl group, a trimethylsilyl group or a phenyl group; a dimethylfluorene ring; a tetrahydronaphthalene ring substituted with a methyl group or a phenyl group; or a dibenzofuran ring.

In one embodiment of the present specification, Cy3 is a benzene ring that is unsubstituted or substituted with R4; a naphthalene ring that is unsubstituted or substituted with R4; a phenanthrene ring that is unsubstituted or substituted with R4; a fluorene ring that is unsubstituted or substituted with R4; a benzofluorene ring that is unsubstituted or substituted with R4; a tetrahydronaphthalene ring that is unsubstituted or substituted with R4; a dibenzofuran ring that is unsubstituted or substituted with R4; a dibenzothiophene ring that is unsubstituted or substituted with R4; a dibenzosilole ring that is unsubstituted or substituted with R4; a naphthobenzofuran ring that is unsubstituted or substituted with R4; a naphthobenzothiophene ring that is unsubstituted or substituted with R4; or a naphthobenzosilole ring that is unsubstituted or substituted with R4.

In one embodiment of the present specification, Cy4 is a benzene ring that is unsubstituted or substituted with R5; a naphthalene ring that is unsubstituted or substituted with R5; a phenanthrene ring that is unsubstituted or substituted with R5; a fluorene ring that is unsubstituted or substituted with R5; a benzofluorene ring that is unsubstituted or substituted with R5; a tetrahydronaphthalene ring that is unsubstituted or substituted with R5; a dibenzofuran ring that is unsubstituted or substituted with R5; a dibenzothiophene ring that is unsubstituted or substituted with R5; a dibenzosilole ring that is unsubstituted or substituted with R5; a naphthobenzofuran ring that is unsubstituted or substituted with R5; a naphthobenzothiophene ring that is unsubstituted or substituted with R5; or a naphthobenzosilole ring that is unsubstituted or substituted with R5.

In one embodiment of the present specification, Cy2 to Cy4 are each unsubstituted or substituted with substituents of R3 to R5 described below.

In one embodiment of the present specification, descriptions of R5 provided below can be applied to R4.

In one embodiment of the present specification, Cy3 and Cy4 are the same as or different from each other, and each independently is the following Chemical Formula 1-A:

<Chemical Formula 1-A>

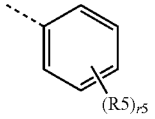

wherein in Chemical Formula 1-A:

a dotted line is a position linked to Chemical Formula 1;

R5 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group; a substituted or unsubstituted aryl group, a substituted or unsubstituted aryloxy group, a substituted or unsubstituted arylthio group, a substituted or unsubstituted heterocyclic group, or a substituted or unsubstituted amine group, or bonds to adjacent substituents to form a substituted or unsubstituted ring; and r5 is an integer of 0 to 5, and when r5 is 2 or greater, the R5s are the same as or different from each other.

In one embodiment of the present specification, R5 is hydrogen, deuterium, a cyano group, a halogen group, a substituted or unsubstituted alkyl group, a substituted or unsubstituted cycloalkyl group, a substituted or unsubstituted silyl group, a substituted or unsubstituted aryl group, a substituted or unsubstituted heterocyclic group, or a substituted or unsubstituted amine group, or bonds to adjacent substituents to form a substituted or unsubstituted ring.

In one embodiment of the present specification, R5 is hydrogen, deuterium, a cyano group, a halogen group, a substituted or unsubstituted C1-C60 alkyl group, a substituted or unsubstituted C3-C60 cycloalkyl group, a substituted or unsubstituted silyl group, a substituted or unsubstituted C6-C60 aryl group, a substituted or unsubstituted C2-C60 heterocyclic group, or a substituted or unsubstituted amine group, or bonds to adjacent substituents to form a substituted or unsubstituted C2-C60 ring.

In one embodiment of the present specification, R5 is hydrogen, deuterium, a cyano group, a halogen group, a substituted or unsubstituted C1-C30 alkyl group, a substituted or unsubstituted C3-C30 cycloalkyl group, a substituted or unsubstituted silyl group, a substituted or unsubstituted C6-C30 aryl group, a substituted or unsubstituted C2-C30 heterocyclic group, or a substituted or unsubstituted amine group, or bonds to adjacent substituents to form a substituted or unsubstituted C2-C30 ring.

In one embodiment of the present specification, R5 is hydrogen, deuterium, a cyano group, a halogen group, a substituted or unsubstituted C1-C20 alkyl group, a substituted or unsubstituted C3-C20 cycloalkyl group, a substituted or unsubstituted silyl group, a substituted or unsubstituted C6-C20 aryl group, a substituted or unsubstituted C2-C20 heterocyclic group, or a substituted or unsubstituted amine group, or bonds to adjacent substituents to form a substituted or unsubstituted C2-C20 ring.

In one embodiment of the present specification, R5 is hydrogen; deuterium; a cyano group; a halogen group; a C1-C20 alkyl group that is unsubstituted or substituted with deuterium; a C6-C20 arylalkyl group that is unsubstituted or substituted with deuterium; a C3-C20 cycloalkyl group that is unsubstituted or substituted with deuterium; a silyl group that is unsubstituted or substituted with a C1-C20 alkyl group or a C6-C20 aryl group; a C6-C20 aryl group that is unsubstituted or substituted with one or more groups selected from the group consisting of deuterium, a cyano group, a halogen group, a C1-C20 alkyl group, a silyl group and a C6-C20 aryl group, or a group linking two or more selected from the above-described group; or an amine group that is unsubstituted or substituted with a C6-C20 aryl group, or bonds to adjacent substituents to form a C2-C30 ring that is unsubstituted or substituted with one or more groups selected from the group consisting of deuterium, a cyano group, a halogen group, a C1-C20 alkyl group, a silyl group and a C6-C20 aryl group, or a group linking two or more selected from the above-described group.

In one embodiment of the present specification, R5 is hydrogen, deuterium, a cyano group, a fluoro group, a substituted or unsubstituted methyl group, a substituted or unsubstituted propyl group, a substituted or unsubstituted butyl group, a substituted or unsubstituted phenylpropyl group, a substituted or unsubstituted cyclohexyl group, a substituted or unsubstituted silyl group, a substituted or unsubstituted phenyl group, a substituted or unsubstituted biphenyl group, a substituted or unsubstituted naphthyl group, a substituted or unsubstituted tetrahydronaphthalene group, or a substituted or unsubstituted amine group, or two or more R5s bond to a benzene ring to form a substituted or unsubstituted naphthalene ring, a substituted or unsubstituted phenanthrene ring, a substituted or unsubstituted fluorene ring, a substituted or unsubstituted benzofluorene ring, a substituted or unsubstituted tetrahydronaphthalene ring, a substituted or unsubstituted dibenzofuran ring, a substituted or unsubstituted dibenzothiophene ring, a substituted or unsubstituted dibenzosilole ring, a substituted or unsubstituted naphthobenzofuran ring, a substituted or unsubstituted naphthobenzothiophene ring, or a substituted or unsubstituted naphthobenzosilole ring.

In one embodiment of the present specification, R5 is hydrogen, deuterium, a cyano group, a fluoro group, a substituted or unsubstituted methyl group, a substituted or unsubstituted propyl group, a substituted or unsubstituted butyl group, a substituted or unsubstituted phenylpropyl group, a substituted or unsubstituted cyclohexyl group, a substituted or unsubstituted silyl group, a substituted or unsubstituted phenyl group, a substituted or unsubstituted biphenyl group, a substituted or unsubstituted naphthyl group, a substituted or unsubstituted tetrahydronaphthalene group, or a substituted or unsubstituted amine group, or two or more R5s bond to a benzene ring to form a substituted or unsubstituted naphthalene ring, a substituted or unsubstituted phenanthrene ring, a substituted or unsubstituted fluorene ring, a substituted or unsubstituted benzofluorene ring, a substituted or unsubstituted tetrahydronaphthalene ring, a substituted or unsubstituted dibenzofuran ring, a substituted or unsubstituted dibenzothiophene ring, a substituted or unsubstituted dibenzosilole ring, or a substituted or unsubstituted naphthobenzofuran ring.

In one embodiment of the present specification, R5 is hydrogen; deuterium; a cyano group; a fluoro group; a methyl group that is unsubstituted or substituted with deuterium; a propyl group that is unsubstituted or substituted with deuterium; a butyl group that is unsubstituted or substituted with deuterium; a phenylpropyl group that is unsubstituted or substituted with deuterium; a cyclohexyl group that is unsubstituted or substituted with deuterium; a silyl group that is unsubstituted or substituted with a methyl group or a phenyl group; a phenyl group that is unsubstituted or substituted with one or more groups selected from the group consisting of deuterium, a cyano group, a fluoro group, a methyl group, a t-butyl group, a silyl group, a phenyl group, a biphenyl group and a naphthyl group, or a group linking two or more selected from the above-described group; a biphenyl group that is unsubstituted or substituted with one or more groups selected from the group consisting of deuterium, a cyano group, a fluoro group, a methyl group, a t-butyl group, a silyl group, a phenyl group, a biphenyl group and a naphthyl group, or a group linking two or more selected from the above-described group; a naphthyl group that is unsubstituted or substituted with one or more groups selected from the group consisting of deuterium, a cyano group, a fluoro group, a methyl group, a t-butyl group, a silyl group, a phenyl group, a biphenyl group and a naphthyl group, or a group linking two or more selected from the above-described group; a tetrahydronaphthalene group that is unsubstituted or substituted with a methyl group; or an amine group that is unsubstituted or substituted with a phenyl group, or two or more R5s bond to a benzene ring to form a naphthalene ring; a phenanthrene ring; a dimethylfluorene ring; a diphenylfluorene ring; a benzofluorene ring; a tetrahydronaphthalene ring; a dibenzofuran ring; a dibenzothiophene ring; a dibenzosilole ring; or a naphthobenzofuran ring, and the ring is unsubstituted or substituted with one or more groups selected from the group consisting of deuterium, a cyano group, a fluoro group, a methyl group, a t-butyl group, a silyl group, a phenyl group, a biphenyl group and a naphthyl group, or a group linking two or more selected from the above-described group.

In one embodiment of the present specification, R5 is hydrogen; deuterium; a cyano group; a fluoro group; a methyl group; $CD_3$; an i-propyl group; a t-butyl group; a sec-butyl group; a phenylpropyl group; a cyclohexyl group; a trimethylsilyl group; a triphenylsilyl group; a phenyl group that is unsubstituted or substituted with deuterium, a cyano group, a fluoro group, a methyl group, $CD_3$, $CF_3$, a t-butyl group, a trimethylsilyl group, a phenyl group, a biphenyl group or a naphthyl group; a biphenyl group; a naphthyl group; a tetrahydronaphthalene group substituted with a methyl group; or a diphenylamine group, or two or more R5s bond to a benzene ring to form a naphthalene ring that is unsubstituted or substituted with a phenyl group; a phenanthrene ring; a dimethylfluorene ring that is unsubstituted or substituted with a t-butyl group; a diphenylfluorene ring that is unsubstituted or substituted with a t-butyl group; a benzofluorene ring that is unsubstituted or substituted with a methyl group; a tetrahydronaphthalene ring substituted with a methyl group; a dibenzofuran ring that is unsubstituted or substituted with a t-butyl group; a dibenzothiophene ring that is unsubstituted or substituted with a t-butyl group; a dibenzosilole ring that is unsubstituted or substituted with a phenyl group; or a naphthobenzofuran ring. Herein, the tetrahydronaphthalene ring substituted with a methyl group is unsubstituted or substituted with a phenyl group that is unsubstituted or substituted with deuterium, a methyl group, $CD_3$, $CF_3$, a t-butyl group, a trimethylsilyl group, a phenyl group, a biphenyl group or a naphthyl group.

In one embodiment of the present specification, R5 is hydrogen; deuterium; a halogen group; a C1-C10 alkyl group; a silyl group that is unsubstituted or substituted with a C1-C10 alkyl group or a C6-C20 aryl group; or a phenyl group that is unsubstituted or substituted with deuterium, a halogen group or a C1-C10 alkyl group, or two or more R5s bond to a benzene ring to form a fluorene ring unsubstituted or substituted with a C1-C10 alkyl group or a C6-C20 aryl group; a tetrahydronaphthalene ring substituted with a C1-C10 alkyl group or a C6-C20 aryl group; or a dibenzofuran ring.

In one embodiment of the present specification, R5 is hydrogen; deuterium; a fluoro group; a methyl group; a t-butyl group; a trimethylsilyl group; or a phenyl group that is unsubstituted or substituted with deuterium, a fluoro group or a t-butyl group, or two or more R5s bond to a benzene ring to form a dimethylfluorene ring; a tetrahydronaphthalene ring substituted with a methyl group or a phenyl group; or a dibenzofuran ring.

In one embodiment of the present specification, a substituent (R5) that is not hydrogen is linked to an ortho position with respect to the dotted line of Chemical Formula 1-A.

In one embodiment of the present specification, Chemical Formula 1-A is any one of the following Chemical Formulae 1-A-1 to 1-A-3:

<Chemical Formula 1-A-1>

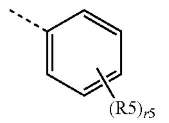

<Chemical Formula 1-A-2>

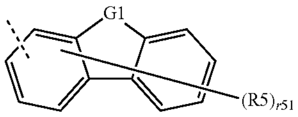

<Chemical Formula 1-A-3>

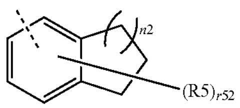

wherein in Chemical Formulae 1-A-1 to 1-A-3:

a dotted line, R5 and r5 have the same definitions as in Chemical Formula 1-A;

G1 is —O—, —S—, —NG2-, —CG2G3-, or —SiG2G3-;

G2 and G3 are the same as or different from each other, and each independently hydrogen, deuterium, a substituted or unsubstituted alkyl group, or a substituted or unsubstituted aryl group, or bond to adjacent substituents to form a substituted or unsubstituted ring;

n2 is 1 or 2; and r51 is an integer of 0 to 7, r52 is an integer of 0 to 11, and when r51 and r52 are each 2 or greater, the R5s are the same as or different from each other.

In one embodiment of the present specification, n2 is 2.

In one embodiment of the present specification, G1 is —O—, —S—, or —CG2G3-.

In one embodiment of the present specification, G2 and G3 are the same as or different from each other, and each independently is hydrogen, deuterium, a substituted or unsubstituted alkyl group, or a substituted or unsubstituted aryl group, or bond to adjacent substituents to form a substituted or unsubstituted ring.

In one embodiment of the present specification, G2 and G3 are the same as or different from each other, and each independently is hydrogen, deuterium, a substituted or unsubstituted C1-C10 alkyl group, or a substituted or unsubstituted C6-C30 aryl group, or bond to adjacent substituents to form a substituted or unsubstituted C6-C30 aromatic hydrocarbon ring.

In one embodiment of the present specification, G2 and G3 are the same as or different from each other, and each independently is hydrogen; deuterium; a C1-C6 alkyl group that is unsubstituted or substituted with deuterium; or a C6-C30 aryl group that is unsubstituted or substituted with deuterium or a C1-C6 alkyl group, or bond to adjacent substituents to form a C6-C20 aromatic hydrocarbon ring.

In one embodiment of the present specification, G2 and G3 are the same as or different from each other, and each independently is hydrogen, deuterium, a methyl group, or a phenyl group, or bond to each other to form a fluorene ring.

In one embodiment of the present specification, G2 and G3 are the same as or different from each other, and each independently is hydrogen, deuterium, a methyl group, or a phenyl group.

In one embodiment of the present specification, Chemical Formula 1-A-1 is selected from among the following structures:

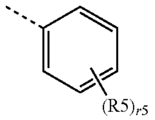

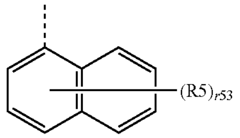

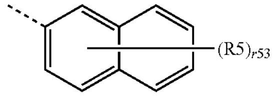

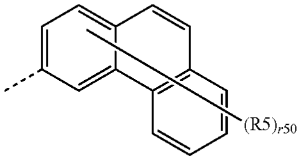

wherein in the structures, a dotted line, R5 and r5 have the same definitions as in Chemical Formula 1-A-1; and r50 is an integer of 0 to 9, r53 is an integer of 0 to 7, and when r50 and r53 are each 2 or greater, the R5s are the same as or different from each other.

In one embodiment of the present specification, Chemical Formula 1-A-2 is selected from among the following structures:

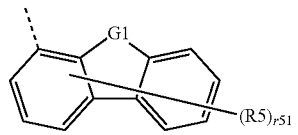

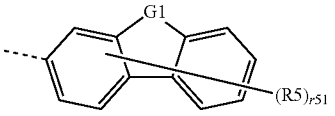

-continued

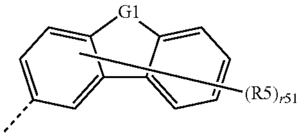

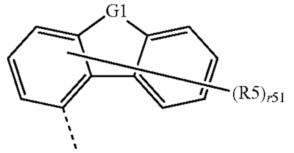

wherein in the structures, a dotted line, G1, R5 and r51 have the same definitions as in Chemical Formula 1-A-2.

In one embodiment of the present specification, Chemical Formula 1-A-3 is selected from among the following structures:

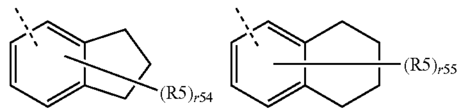

wherein in the structures, a dotted line and R5 have the same definitions as in Chemical Formula 1-A-3;

r54 is an integer of 0 to 9, and r55 is an integer of 0 to 11; and when r54 and r55 are each 2 or greater, the R5s are the same as or different from each other.

In one embodiment of the present specification, Chemical Formula 1-A-3 is selected from among the following structures:

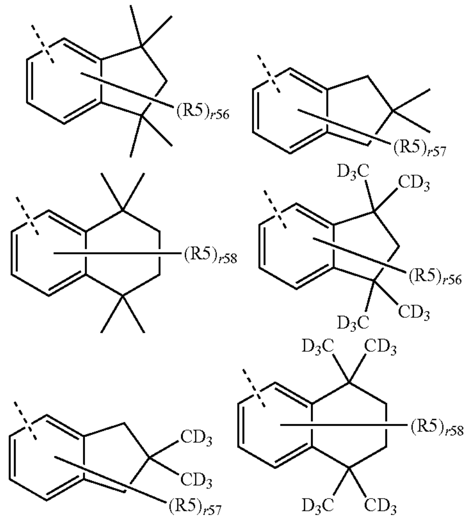

wherein in the structures, a dotted line and R5 have the same definitions as in Chemical Formula 1-A-3;

r56 is an integer of 0 to 5, r57 is an integer of 0 to 7, and r58 is an integer of 0 to 7; and when r56 to r58 are each 2 or greater, the R5s are the same as or different from each other.

In one embodiment of the present specification, Chemical Formula 1-A-3 is selected from among the following structures:

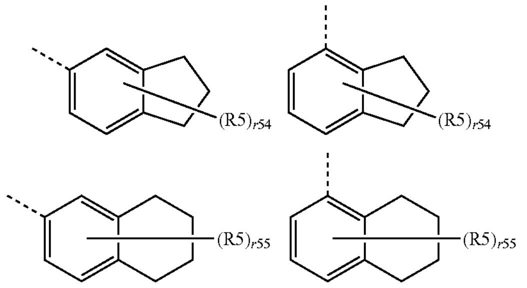

wherein in the structures, a dotted line and R5 have the same definitions as in Chemical Formula 1-A-3;

r54 is an integer of 0 to 9, and r55 is an integer of 0 to 11; and when r54 and r55 are each 2 or greater, the R5s are the same as or different from each other.

In one embodiment of the present specification, Chemical Formula 1-A-3 is selected from among the following structures:

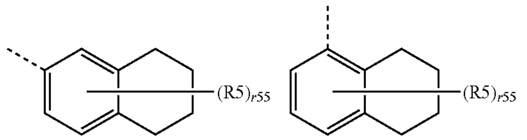

wherein in the structures, a dotted line and R5 have the same definitions as in Chemical Formula 1-A-3;

r55 is an integer of 0 to 11, and when r55 is 2 or greater, the R5s are the same as or different from each other.

In one embodiment of the present specification, Cy3 and Cy4 are the same as or different from each other, and each independently is any one of the following structural formulae:

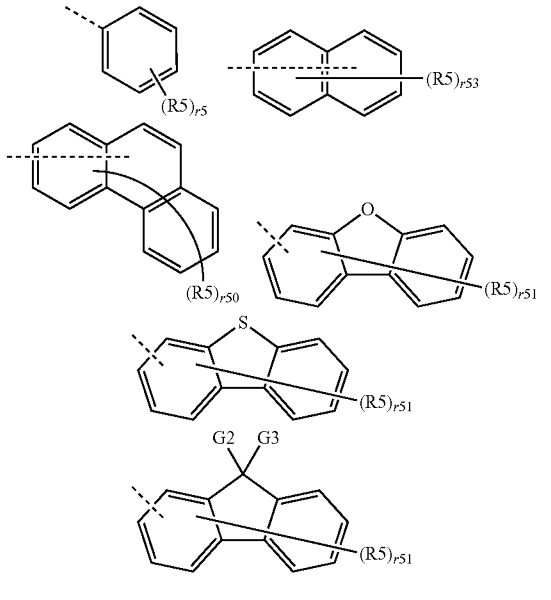

-continued

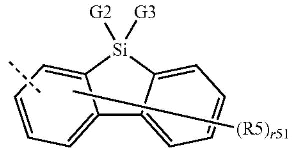

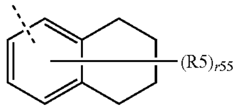

wherein in the structural formulae:

R5 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bonds to adjacent substituents to form a substituted or unsubstituted ring;

G2 and G3 are the same as or different from each other, and each independently is hydrogen, deuterium, a substituted or unsubstituted alkyl group, or a substituted or unsubstituted aryl group, or bond to adjacent substituents to form a substituted or unsubstituted ring;

r5 is an integer of 0 to 5, r50 is an integer of 0 to 9, r51 is an integer of 0 to 7, r53 is an integer of 0 to 7, and r55 is an integer of 0 to 11;

when r5, r50, r51, r53 and r55 are each 2 or greater, the R5s are the same as or different from each other; and a dotted line means a position linked to Chemical Formula 1.

In one embodiment of the present specification, at least one of Cy3 and Cy4 is a substituted or unsubstituted tetrahydronaphthalene ring.

In one embodiment of the present specification, at least one of Cy3 and Cy4 is Chemical Formula 1-A-3.

In one embodiment of the present specification, Chemical Formula 1 is any one of the following Chemical Formulae 103 to 106:

<Chemical Formula 103>

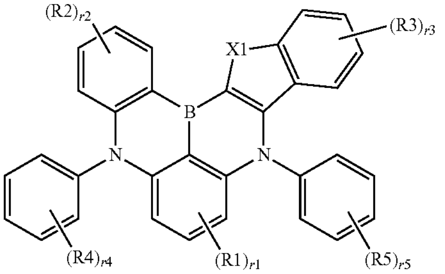

-continued

<Chemical Formula 104>

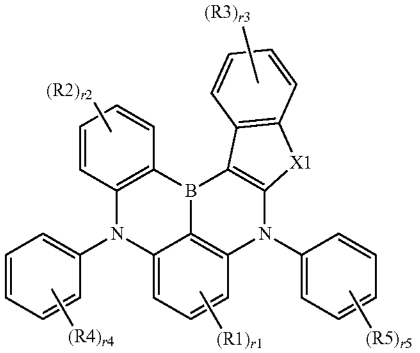

<Chemical Formula 105>

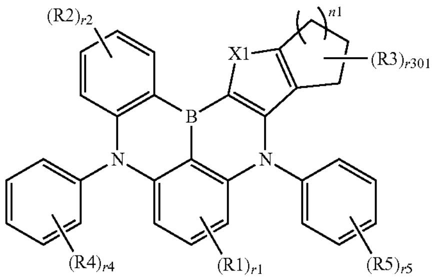

<Chemical Formula 106>

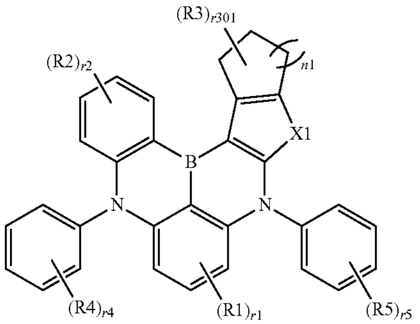

wherein in Chemical Formulae 103 to 106:

X1, R1, R2, r1 and r2 have the same definitions as in Chemical Formula 1;

R3 to R5 are the same as or different from each other, and each independently hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group;

R3 can bond to adjacent substituents to form a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring;

R4 and R5 can each bond to adjacent substituents to form a substituted or unsubstituted ring;

n1 is 1 or 2;

r3 is an integer of 0 to 4, r4 and r5 are each an integer of 0 to 5, and r301 is an integer of 0 to 8; and when r3 to r5 and r301 are each 2 or greater, substituents in the parentheses are the same as or different from each other.

In one embodiment of the present specification, the definitions on R5 described above can be applied to R4.

In one embodiment of the present specification, R1 and R2 are the same as or different from each other, and each independently is hydrogen, deuterium, a cyano group, a halogen group, a substituted or unsubstituted C1-C30 alkyl group, a substituted or unsubstituted C1-C30 alkoxy group, a substituted or unsubstituted C1-C30 alkylthio group, a substituted or unsubstituted C3-C60 cycloalkyl group, a substituted or unsubstituted silyl group, a substituted or unsubstituted C6-C60 aryl group, a substituted or unsubstituted C6-C60 aryloxy group, a substituted or unsubstituted C6-C60 arylthio group, a substituted or unsubstituted C2-C60 heterocyclic group, or a substituted or unsubstituted amine group, or bond to adjacent substituents to form a substituted or unsubstituted C2-C30 ring.

In one embodiment of the present specification, R1 and R2 are the same as or different from each other, and each independently is hydrogen, deuterium, a cyano group, a halogen group, a substituted or unsubstituted C1-C10 alkyl group, a substituted or unsubstituted C1-C10 alkoxy group, a substituted or unsubstituted C1-C10 alkylthio group, a substituted or unsubstituted C3-C30 cycloalkyl group, a substituted or unsubstituted silyl group, a substituted or unsubstituted C6-C30 aryl group, a substituted or unsubstituted C6-C30 aryloxy group, a substituted or unsubstituted C6-C30 arylthio group, a substituted or unsubstituted C2-C30 heterocyclic group, or a substituted or unsubstituted amine group, or bond to adjacent substituents to form a substituted or unsubstituted C2-C30 ring.

In one embodiment of the present specification, R1 and R2 are the same as or different from each other, and each independently is hydrogen, deuterium, a cyano group, a halogen group, a substituted or unsubstituted C1-C10 alkyl group, a substituted or unsubstituted C1-C10 alkoxy group, a substituted or unsubstituted C1-C10 alkylthio group, a substituted or unsubstituted C3-C30 cycloalkyl group, a substituted or unsubstituted C1-C30 alkylsilyl group, a substituted or unsubstituted C6-C90 arylsilyl group, a substituted or unsubstituted C6-C30 aryl group, a substituted or unsubstituted C6-C30 aryloxy group, a substituted or unsubstituted C6-C30 arylthio group, a substituted or unsubstituted C2-C30 heterocyclic group, a substituted or unsubstituted C6-C30 arylamine group, or a substituted or unsubstituted C2-C30 heteroarylamine group, or bond to adjacent substituents to form a substituted or unsubstituted C2-C30 ring.

In one embodiment of the present specification, R3 to R5 are the same as or different from each other, and each independently is hydrogen, deuterium, a cyano group, a halogen group, a substituted or unsubstituted C1-C30 alkyl group, a substituted or unsubstituted C1-C30 alkoxy group, a substituted or unsubstituted C1-C30 alkylthio group, a substituted or unsubstituted C3-C60 cycloalkyl group, a substituted or unsubstituted silyl group, a substituted or unsubstituted C6-C60 aryl group, a substituted or unsubstituted C6-C60 aryloxy group, a substituted or unsubstituted C6-C60 arylthio group, a substituted or unsubstituted C2-C60 heterocyclic group, or a substituted or unsubstituted amine group.

In one embodiment of the present specification, R3 to R5 are the same as or different from each other, and each independently is hydrogen, deuterium, a cyano group, a halogen group, a substituted or unsubstituted C1-C10 alkyl group, a substituted or unsubstituted C1-C10 alkoxy group, a substituted or unsubstituted C1-C10 alkylthio group, a substituted or unsubstituted C3-C30 cycloalkyl group, a substituted or unsubstituted silyl group, a substituted or unsubstituted C6-C30 aryl group, a substituted or unsubstituted C6-C30 aryloxy group, a substituted or unsubstituted C6-C30 arylthio group, a substituted or unsubstituted C2-C30 heterocyclic group, or a substituted or unsubstituted amine group.

In one embodiment of the present specification, R3 to R5 are the same as or different from each other, and each independently is hydrogen, deuterium, a cyano group, a halogen group, a substituted or unsubstituted C1-C10 alkyl group, a substituted or unsubstituted C1-C10 alkoxy group, a substituted or unsubstituted C1-C10 alkylthio group, a substituted or unsubstituted C3-C30 cycloalkyl group, a substituted or unsubstituted C1-C30 alkylsilyl group, a substituted or unsubstituted C6-C90 arylsilyl group, a substituted or unsubstituted C6-C30 aryl group, a substituted or unsubstituted C6-C30 aryloxy group, a substituted or unsubstituted C6-C30 arylthio group, a substituted or unsubstituted C2-C30 heterocyclic group, a substituted or unsubstituted C6-C30 arylamine group, or a substituted or unsubstituted C2-C30 heteroarylamine group.

In one embodiment of the present specification, R3 can bond to adjacent substituents to form a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring.

In one embodiment of the present specification, R3 can bond to adjacent substituents to form a substituted or unsubstituted C6-C60 aromatic hydrocarbon ring, a substituted or unsubstituted C3-C60 aliphatic hydrocarbon ring, or a substituted or unsubstituted fused ring of C6-C60 aromatic hydrocarbon ring and C3-C60 aliphatic hydrocarbon ring.

In one embodiment of the present specification, R3 can bond to adjacent substituents to form a substituted or unsubstituted C6-C30 aromatic hydrocarbon ring, a substituted or unsubstituted C3-C30 aliphatic hydrocarbon ring, or a substituted or unsubstituted fused ring of C6-C30 aromatic hydrocarbon ring and C3-C30 aliphatic hydrocarbon ring.

In one embodiment of the present specification, R4 and R5 can each bond to adjacent substituents to form a substituted or unsubstituted ring.

In one embodiment of the present specification, R4 and R5 can each bond to adjacent substituents to form a substituted or unsubstituted C2-C60 ring.

In one embodiment of the present specification, R4 and R5 can each bond to adjacent substituents to form a substituted or unsubstituted C2-C30 ring.

In one embodiment of the present specification, R1 is hydrogen, deuterium, a substituted or unsubstituted alkyl group, a substituted or unsubstituted cycloalkyl group, a substituted or unsubstituted aryl group, a substituted or unsubstituted heterocyclic group, or a substituted or unsubstituted amine group.

In one embodiment of the present specification, R1 is hydrogen, deuterium, a substituted or unsubstituted methyl group, a substituted or unsubstituted ethyl group, a substituted or unsubstituted propyl group, a substituted or unsubstituted butyl group, a substituted or unsubstituted cyclohexyl group, a substituted or unsubstituted adamantyl group, a substituted or unsubstituted phenyl group, a substituted or unsubstituted biphenyl group, a substituted or unsubstituted naphthyl group, a substituted or unsubstituted fluorenyl group, a substituted or unsubstituted tetrahydronaphthalene group, a substituted or unsubstituted dibenzofuran group, a substituted or unsubstituted dibenzothiophene group, a substituted or unsubstituted carbazole group, a substituted or unsubstituted hexahydrocarbazole group, a substituted or unsubstituted cyclohexene-fused hexahydrocarbazole group, a substituted or unsubstituted phenoxazine group

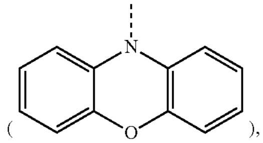, a substituted or unsubstituted phenothiazine group

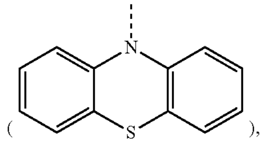, a substituted or unsubstituted amine group, a substituted or unsubstituted dihydroacridine group

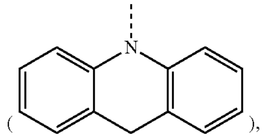, or a substituted or unsubstituted dihydrodibenzoazasiline group

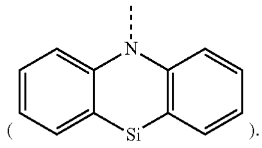.

In one embodiment of the present specification, R1 is hydrogen; deuterium; a C1-C10 alkyl group; a phenyl group that is unsubstituted or substituted with a cyano group; a hexahydrocarbazole group that is unsubstituted or substituted with a C1-C10 alkyl group; a phenoxazine group; or a diphenylamine group that is unsubstituted or substituted with a C1-C10 alkylsilyl group.

In one embodiment of the present specification, R1 is hydrogen; deuterium; a methyl group; a t-butyl group; a phenyl group that is unsubstituted or substituted with a cyano group; a hexahydrocarbazole group that is unsubstituted or substituted with a methyl group or a t-butyl group; a phenoxazine group; or a diphenylamine group that is unsubstituted or substituted with a trimethylsilyl group.

In one embodiment of the present specification, R1 is unsubstituted or substituted with one or more groups selected from the group consisting of deuterium, a cyano group, a halogen group, an alkyl group, an alkoxy group, a silyl group and an aryl group, or a group linking two or more selected from the above-described group.

In one embodiment of the present specification, R1 is any one of the following Chemical Formulae 1-B-1 to 1-B-4:

<Chemical Formula 1-B-1>

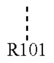

<Chemical Formula 1-B-2>

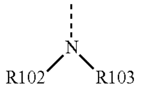

<Chemical Formula 1-B-3>

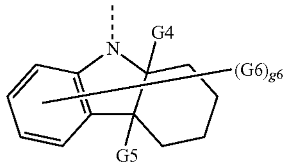

<Chemical Formula 1-B-4>

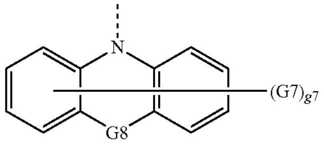

wherein in Chemical Formulae 1-B-1 to 1-B-4:

G8 is a direct bond, —O—, —S—, —CG9G10-, or —SiG9G10-;

R101 to R103 and G4 to G7 are the same as or different from each other, and each independently hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

G9 and G10 are the same as or different from each other, and each independently hydrogen, deuterium, a substituted or unsubstituted alkyl group, or a substituted or unsubstituted aryl group, or bond to adjacent substituents to form a substituted or unsubstituted ring;

g6 is an integer of 0 to 12, and g7 is an integer of 0 to 8;

when g6 and g7 are each 2 or greater, substituents in the parentheses are the same as or different from each other; and a dotted line means a position bonding to Chemical Formula 1.

In one embodiment of the present specification, G8 is a direct bond.

In one embodiment of the present specification, G8 is —O—; or —S—.

In one embodiment of the present specification, G8 is —CG9G10- or —SiG9G10-.

In one embodiment of the present specification, G9 and G10 are the same as or different from each other, and each independently is hydrogen, deuterium, a substituted or unsubstituted alkyl group, or a substituted or unsubstituted aryl group.

In one embodiment of the present specification, G9 and G10 are the same as or different from each other, and each independently is a substituted or unsubstituted C1-C10 alkyl group or a substituted or unsubstituted C6-C30 aryl group.

In one embodiment of the present specification, G9 and G10 are the same as or different from each other, and each independently is a substituted or unsubstituted methyl group or a substituted or unsubstituted phenyl group.

In one embodiment of the present specification, G9 and G10 are the same as or different from each other, and each independently is a methyl group or a phenyl group.

In one embodiment of the present specification, R101 to R103 and G4 to G7 are the same as or different from each other, and each independently is hydrogen, deuterium, a substituted or unsubstituted alkyl group, a substituted or unsubstituted cycloalkyl group, a substituted or unsubstituted silyl group, a substituted or unsubstituted aryl group, or a substituted or unsubstituted heterocyclic group, or bond to adjacent substituents to form a substituted or unsubstituted ring.

In one embodiment of the present specification, R101 to R103 and G4 to G7 are the same as or different from each other, and each independently is hydrogen, deuterium, a substituted or unsubstituted C1-C60 alkyl group, a substituted or unsubstituted C3-C60 cycloalkyl group, a substituted or unsubstituted silyl group, a substituted or unsubstituted C6-C60 aryl group, or a substituted or unsubstituted C2-C60 heterocyclic group, or bond to adjacent substituents to form a substituted or unsubstituted C2-C60 ring.

In one embodiment of the present specification, R101 to R103 and G4 to G7 are the same as or different from each other, and each independently is hydrogen, deuterium, a substituted or unsubstituted C1-C30 alkyl group, a substituted or unsubstituted C3-C30 cycloalkyl group, a substituted or unsubstituted silyl group, a substituted or unsubstituted C6-C30 aryl group, or a substituted or unsubstituted C2-C30 heterocyclic group, or bond to adjacent substituents to form a substituted or unsubstituted C2-C30 ring.

In one embodiment of the present specification, R101 to R103 and G4 to G7 are the same as or different from each other, and each independently is hydrogen, deuterium, a substituted or unsubstituted C1-C20 alkyl group, a substituted or unsubstituted C3-C20 cycloalkyl group, a substituted or unsubstituted silyl group, a substituted or unsubstituted C6-C20 aryl group, or a substituted or unsubstituted C2-C20 heterocyclic group, or bond to adjacent substituents to form a substituted or unsubstituted C2-C20 ring.

In one embodiment of the present specification, R101 to R103 and G4 to G7 are the same as or different from each other, and each independently is hydrogen; deuterium; a C1-C30 alkyl group that is unsubstituted or substituted with one or more groups selected from the group consisting of deuterium, a cyano group, a halogen group, a C1-C20 alkyl group, a C1-C20 alkoxy group, a silyl group and a C6-C20 aryl group, or a group linking two or more selected from the above-described group; a C3-C30 cycloalkyl group that is unsubstituted or substituted with one or more groups selected from the group consisting of deuterium, a cyano group, a halogen group, a C1-C20 alkyl group, a C1-C20 alkoxy group, a silyl group and a C6-C20 aryl group, or a group linking two or more selected from the above-described group; a silyl group that is unsubstituted or substituted with one or more groups selected from the group consisting of deuterium, a cyano group, a halogen group, a C1-C20 alkyl group, a C1-C20 alkoxy group, a silyl group and a C6-C20 aryl group, or a group linking two or more selected from the above-described group; a C6-C30 aryl group that is unsubstituted or substituted with one or more groups selected from the group consisting of deuterium, a cyano group, a halogen group, a C1-C20 alkyl group, a C1-C20 alkoxy group, a silyl group and a C6-C20 aryl group, or a group linking two or more selected from the above-described group; or a C2-C30 heterocyclic group that is unsubstituted or substituted with one or more groups selected from the group consisting of deuterium, a cyano group, a halogen group, a C1-C20 alkyl group, a C1-C20 alkoxy group, a silyl group and a C6-C20 aryl group, or a group linking two or more selected from the above-described group, or bond to adjacent substituents to form a C2-C30 ring unsubstituted or substituted with one or more groups selected from the group consisting of deuterium, a cyano group, a halogen group, a C1-C20 alkyl group, a C1-C20 alkoxy group, a silyl group and a C6-C20 aryl group, or a group linking two or more selected from the above-described group.

In one embodiment of the present specification, R101 is hydrogen, deuterium, a substituted or unsubstituted alkyl group, a substituted or unsubstituted cycloalkyl group, a substituted or unsubstituted aryl group, or a substituted or unsubstituted heterocyclic group.

In one embodiment of the present specification, R101 is hydrogen, deuterium, a substituted or unsubstituted methyl group, a substituted or unsubstituted ethyl group, a substituted or unsubstituted propyl group, a substituted or unsubstituted butyl group, a substituted or unsubstituted cyclohexyl group, a substituted or unsubstituted adamantyl group, a substituted or unsubstituted phenyl group, a substituted or unsubstituted biphenyl group, a substituted or unsubstituted naphthyl group, a substituted or unsubstituted fluorenyl group, a substituted or unsubstituted tetrahydronaphthalene group, a substituted or unsubstituted dibenzofuran group, or a substituted or unsubstituted dibenzothiophene group.

In one embodiment of the present specification, R101 is hydrogen; deuterium; a methyl group that is unsubstituted or substituted with deuterium; an ethyl group that is unsubstituted or substituted with deuterium; a propyl group that is unsubstituted or substituted with deuterium; a butyl group that is unsubstituted or substituted with deuterium; a cyclohexyl group that is unsubstituted or substituted with deuterium; an adamantyl group that is unsubstituted or substituted with deuterium; a phenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a biphenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a naphthyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a fluorenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a tetrahydronaphthalene group that is unsubstituted or substituted with deuterium, a methyl group or a butyl group; a dibenzofuran group that is unsubstituted or substituted with deuterium, a methyl group or a butyl group; or a dibenzothiophene group that is unsubstituted or substituted with deuterium, a methyl group or a butyl group.

In one embodiment of the present specification, R101 is hydrogen; deuterium; a methyl group; $CD_3$; an ethyl group; an i-propyl group; a t-butyl group; a cyclohexyl group; an adamantyl group; a phenyl group that is unsubstituted or substituted with one or more groups selected from the group consisting of deuterium, a cyano group, a fluoro group, a methyl group, a t-butyl group, —$OCF_3$, a trimethylsilyl group, a triphenylsilyl group and a phenyl group, or a group linking two or more selected from the above-described group; a biphenyl group; a naphthyl group that is unsubstituted or substituted with deuterium; a fluorenyl group that is unsubstituted or substituted with a methyl group or a phenyl group; a tetrahydronaphthalene group that is unsubstituted or substituted with a methyl group; a dibenzofuran group; or a dibenzothiophene group.

In one embodiment of the present specification, R101 is hydrogen; deuterium; a methyl group; $CD_3$; an ethyl group; an i-propyl group; a t-butyl group; a cyclohexyl group; an adamantyl group; a phenyl group that is unsubstituted or substituted with deuterium, a cyano group, a fluoro group, a methyl group, a t-butyl group, —$OCF_3$, a trimethylsilyl group, a triphenylsilyl group or a phenyl group; a biphenyl group; a naphthyl group that is unsubstituted or substituted with deuterium; a dimethylfluorenyl group; a tetrahydronaphthalene group that is unsubstituted or substituted with a methyl group; a dibenzofuran group; or a dibenzothiophene group.

In one embodiment of the present specification, R101 is hydrogen, deuterium, a methyl group, a t-butyl group, or a phenyl group that is unsubstituted or substituted with a cyano group.

In one embodiment of the present specification, R102 and R103 are the same as or different from each other, and each independently is hydrogen, deuterium, a substituted or unsubstituted aryl group, or a substituted or unsubstituted heterocyclic group.

In one embodiment of the present specification, R102 and R103 are the same as or different from each other, and each independently a substituted or unsubstituted phenyl group, a substituted or unsubstituted biphenyl group, a substituted or unsubstituted naphthyl group, a substituted or unsubstituted fluorenyl group, a substituted or unsubstituted tetrahydronaphthalene group, a substituted or unsubstituted dibenzofuran group, or a substituted or unsubstituted dibenzothiophene group.

In one embodiment of the present specification, R102 and R103 are the same as or different from each other, and each independently is a phenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a biphenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a naphthyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a fluorenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a tetrahydronaphthalene group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a dibenzofuran group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; or a dibenzothiophene group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group.

In one embodiment of the present specification, R102 and R103 are the same as or different from each other, and each independently is a phenyl group that is unsubstituted or substituted with one or more groups selected from the group consisting of deuterium, a cyano group, a fluoro group, a methyl group, a propyl group, a butyl group, a methoxy group, a silyl group and a phenyl group, or a group linking two or more selected from the above-described group; a biphenyl group that is unsubstituted or substituted with deuterium; a naphthyl group that is unsubstituted or substituted with deuterium; a fluorenyl group that is unsubstituted or substituted with a methyl group or a phenyl group; a tetrahydronaphthalene group that is unsubstituted or substituted with a methyl group; a dibenzofuran group; or a dibenzothiophene group.

In one embodiment of the present specification, R102 and R103 are the same as or different from each other, and each independently is a phenyl group that is unsubstituted or substituted with deuterium, a cyano group, a fluoro group, a methyl group, $CD_3$, $CF_3$, an i-propyl group, a t-butyl group, a trimethylsilyl group, a triphenylsilyl group or a phenylpropyl group; a biphenyl group that is unsubstituted or substituted with deuterium; a naphthyl group; a dimethylfluorenyl group; a tetrahydronaphthalene group that is unsubstituted or substituted with a methyl group; a dibenzofuran group; or a dibenzothiophene group.

In one embodiment of the present specification, R102 and R103 are the same as or different from each other, and each independently is a phenyl group that is unsubstituted or substituted with a C1-C10 alkylsilyl group.

In one embodiment of the present specification, R102 and R103 are the same as or different from each other, and each independently is a phenyl group that is unsubstituted or substituted with a trimethylsilyl group.

In one embodiment of the present specification, G4 to G7 are the same as or different from each other, and each independently is hydrogen, deuterium, a substituted or unsubstituted alkyl group, a substituted or unsubstituted silyl group, or a substituted or unsubstituted aryl group, or bond to adjacent substituents to form a substituted or unsubstituted ring.

In one embodiment of the present specification, G4 to G7 are the same as or different from each other, and each independently is hydrogen, deuterium, a substituted or unsubstituted C1-C10 alkyl group, a substituted or unsubstituted C1-C30 alkylsilyl group, a substituted or unsubstituted C6-C30 arylsilyl group, or a substituted or unsubstituted C6-C30 aryl group, or bond to adjacent substituents to form a substituted or unsubstituted C3-C30 aliphatic hydrocarbon ring, or a substituted or unsubstituted C6-C30 aromatic hydrocarbon ring.

In one embodiment of the present specification, G4 to G7 are the same as or different from each other, and each independently is hydrogen; deuterium; a C1-C6 alkyl group that is unsubstituted or substituted with deuterium; a C1-C18 alkylsilyl group; a C6-C60 arylsilyl group; or a C6-C30 aryl group that is unsubstituted or substituted with deuterium or a C1-C6 alkyl group, or bond to adjacent substituents to form a C3-C20 aliphatic hydrocarbon ring unsubstituted or substituted with deuterium or an alkyl group; or a C6-C20 aromatic hydrocarbon ring unsubstituted or substituted with deuterium or an alkyl group.

In one embodiment of the present specification, G4 and G5 are the same as or different from each other, and each independently is a methyl group that is unsubstituted or substituted with deuterium.

In one embodiment of the present specification, G4 and G5 are a methyl group.

In one embodiment of the present specification, G6 and G7 are the same as or different from each other, and each independently is hydrogen, deuterium, a substituted or unsubstituted methyl group, a substituted or unsubstituted tert-butyl group, a substituted or unsubstituted trimethylsilyl group, or a substituted or unsubstituted phenyl group, or bond to adjacent substituents to form a substituted or unsubstituted cyclohexene ring, or a substituted or unsubstituted benzene ring.

In one embodiment of the present specification, G6 and G7 are the same as or different from each other, and each independently is hydrogen, deuterium, a methyl group, a tert-butyl group, a trimethylsilyl group, or a phenyl group, or bond to adjacent substituents to form a cyclohexene ring unsubstituted or substituted with a methyl group.

In one embodiment of the present specification, G6 is hydrogen, deuterium, a methyl group, a t-butyl group, a trimethylsilyl group, or a phenyl group, or bonds to adjacent substituents to form a cyclohexene ring unsubstituted or substituted with a methyl group.

In one embodiment of the present specification, G6 is hydrogen, deuterium, or a t-butyl group.

In one embodiment of the present specification, G7 is hydrogen or deuterium.

In one embodiment of the present specification, G7 is hydrogen.

In one embodiment of the present specification, Chemical Formula 1-B-3 is any one of the following structural formulae:

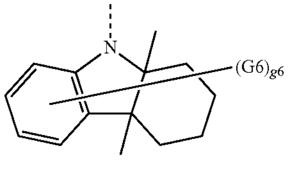

-continued

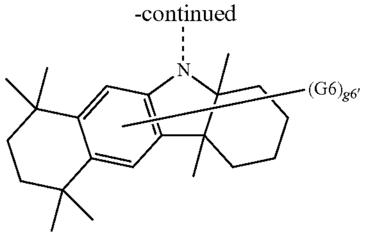

wherein in the structural formulae, a dotted line, G6 and g6 have the same definitions as in Chemical Formula 1-B-3; and g6' is an integer of 0 to 10, and when g6' is 2 or greater, the two or more G6s are the same as or different from each other.

In one embodiment of the present specification, Chemical Formula 1-B-4 is any one of the following structural formulae:

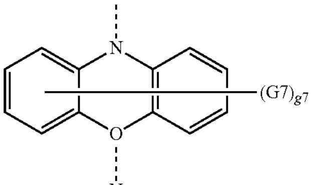

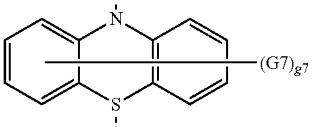

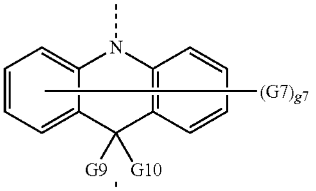

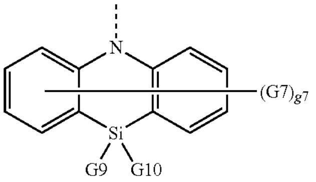

In the structural formulae, a dotted line, G7, G9, G10 and g7 have the same definitions as in Chemical Formula 1-B-4.

In one embodiment of the present specification, R2 is hydrogen, deuterium, a substituted or unsubstituted alkyl group, a substituted or unsubstituted silyl group, a substituted or unsubstituted alkylaryl group, a substituted or unsubstituted cycloalkyl group, a substituted or unsubstituted aryl group, a substituted or unsubstituted heterocyclic group, or a substituted or unsubstituted amine group, or bonds to adjacent substituents to form a substituted or unsubstituted aliphatic hydrocarbon ring, a substituted or unsubstituted aromatic hydrocarbon ring, or a substituted or unsubstituted heteroring.

In one embodiment of the present specification, R2 is unsubstituted or substituted with one or more groups selected from the group consisting of deuterium, a cyano group, a halogen group, an alkyl group, a silyl group and an aryl group, or a group linking two or more selected from the above-described group.

In one embodiment of the present specification, R2 is hydrogen, deuterium, a substituted or unsubstituted methyl group, a substituted or unsubstituted propyl group, a substituted or unsubstituted butyl group, a substituted or unsubstituted silyl group, a substituted or unsubstituted phenylpropyl group, a substituted or unsubstituted cyclohexyl group, a substituted or unsubstituted phenyl group, a substituted or unsubstituted hexahydrocarbazole group, a substituted or unsubstituted carbazole group, or a substituted or unsubstituted amine group, or bonds to adjacent substituents to form a substituted or unsubstituted cyclohexene ring, a substituted or unsubstituted benzene ring, a substituted or unsubstituted benzofuran ring, a substituted or unsubstituted benzothiophene ring, a substituted or unsubstituted indene ring, or a substituted or unsubstituted benzopyran ring.

In one embodiment of the present specification, R2 is hydrogen, deuterium, a methyl group, a propyl group, a butyl group, a silyl group, a phenylpropyl group, a cyclohexyl group, a phenyl group, a hexahydrocarbazole group, a carbazole group, or an amine group, or bonds to adjacent substituents to form a cyclohexene ring, a benzene ring, a benzofuran ring, a benzothiophene ring, an indene ring, or a benzopyran ring, and the substituent or the ring is unsubstituted or substituted with one or more groups selected from the group consisting of deuterium, a cyano group, a halogen group, an alkyl group, a silyl group and an aryl group, or a group linking two or more selected from the above-described group.

In one embodiment of the present specification, R2 is hydrogen; deuterium; a methyl group that is unsubstituted or substituted with deuterium; a propyl group that is unsubstituted or substituted with deuterium; a butyl group that is unsubstituted or substituted with deuterium; a silyl group that is unsubstituted or substituted with a methyl group or a phenyl group; a phenylpropyl group that is unsubstituted or substituted with deuterium; a cyclohexyl group that is unsubstituted or substituted with deuterium; a phenyl group that is unsubstituted or substituted with one or more groups selected from the group consisting of deuterium, a cyano group, a fluoro group, a methyl group, a propyl group, a butyl group and a silyl group, or a group linking two or more selected from the above-described group; a hexahydrocarbazole group that is unsubstituted or substituted with a methyl group, a propyl group, a butyl group or a phenyl group; a carbazole group; an amine group that is unsubstituted or substituted with one or more groups selected from the group consisting of deuterium, a methyl group, a propyl group, a butyl group, a silyl group and a phenyl group, or a group linking two or more selected from the above-described group; or an amine group substituted with a tetrahydronaphthalene group that is unsubstituted or substituted with a methyl group, or bonds to adjacent substituents to form a cyclohexene ring unsubstituted or substituted with a methyl group; a benzene ring; a benzofuran ring unsubstituted or substituted with a butyl group; a benzothiophene ring unsubstituted or substituted with a butyl group; an indene ring unsubstituted or substituted with a methyl group; or a benzopyran ring unsubstituted or substituted with a methyl group.

In one embodiment of the present specification, R2 is hydrogen; deuterium; a methyl group; an i-propyl group; a t-butyl group; a trimethylsilyl group; a phenylpropyl group that is unsubstituted or substituted with deuterium; a cyclohexyl group; a phenyl group that is unsubstituted or substituted with deuterium, a cyano group, a fluoro group, a methyl group, an i-propyl group, a t-butyl group or a trimethylsilyl group; a hexahydrocarbazole group that is unsubstituted or substituted with a methyl group, a t-butyl group or a phenyl group; a carbazole group; a diphenylamine group that is unsubstituted or substituted with deuterium, a methyl group, an i-propyl group, a t-butyl group or a trimethylsilyl group; or an amine group substituted with a tetrahydronaphthalene group that is unsubstituted or substituted with a methyl group, or bonds to adjacent substituents to form a cyclohexene ring unsubstituted or substituted with a methyl group; a benzene ring; a benzofuran ring unsubstituted or substituted with a t-butyl group; a benzothiophene ring unsubstituted or substituted with a t-butyl group; an indene ring unsubstituted or substituted with a methyl group; or a benzopyran

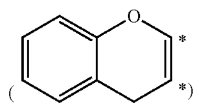

ring unsubstituted or substituted with a methyl group, and * means a fused position.

In one embodiment of the present specification, R2 is hydrogen; deuterium; a C1-C10 alkyl group; a phenyl group that is unsubstituted or substituted with deuterium, a halogen group or a C1-C10 alkyl group; a hexahydrocarbazole group substituted with a C1-C10 alkyl group; or a diphenylamine group that is unsubstituted or substituted with a C1-C10 alkyl group, or bonds to adjacent substituents to form a cyclohexene ring substituted with a methyl group.

In one embodiment of the present specification, R2 is hydrogen; deuterium; a methyl group; a t-butyl group; a phenyl group that is unsubstituted or substituted with deuterium, a fluoro group or a methyl group; a hexahydrocarbazole group substituted with a methyl group; or a diphenylamine group that is unsubstituted or substituted with an i-propyl group, or bonds to adjacent substituents to form a cyclohexene ring substituted with a methyl group.

In one embodiment of the present specification, when R2 forms a ring, it is any one of the following structural formulae:

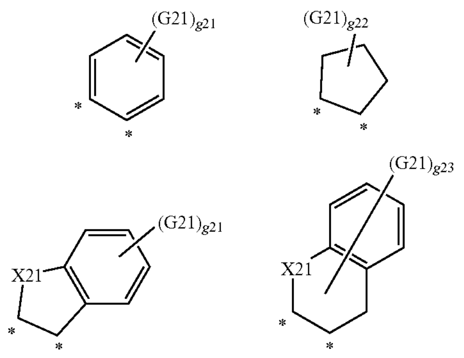

wherein in the structural formulae:

X21 is O, S, or CG201G202;

G21, G201 and G202 are the same as or different from each other, and each independently is hydrogen, deuterium, a substituted or unsubstituted alkyl group, or a substituted or unsubstituted aryl group;

n21 is 1 or 2, g21 is an integer of 0 to 4, g22 is an integer of 0 to 8, and g23 is an integer of 0 to 6;

when n21, g21, g22 and g23 are each 2 or greater, the two or more G21s are the same as or different from each other; and

* means a position fused to Chemical Formula 1.

In one embodiment of the present specification, G21, G201 and G202 are the same as or different from each other, and are hydrogen, deuterium, or a substituted or unsubstituted alkyl group.

In one embodiment of the present specification, G21, G201 and G202 are the same as or different from each other, and are hydrogen, deuterium, or a substituted or unsubstituted C1-C30 alkyl group.

In one embodiment of the present specification, G21, G201 and G202 are the same as or different from each other, and are hydrogen, deuterium, or a substituted or unsubstituted C1-C20 alkyl group.

In one embodiment of the present specification, G21, G201 and G202 are the same as or different from each other, and are hydrogen, deuterium, or a substituted or unsubstituted methyl group.

In one embodiment of the present specification, G21, G201 and G202 are the same as or different from each other, and are hydrogen, deuterium, or a methyl group that is unsubstituted or substituted with deuterium.

In one embodiment of the present specification, G21, G201 and G202 are the same as or different from each other, and are hydrogen, deuterium, or a methyl group.

In one embodiment of the present specification, n21 is 2.

In one embodiment of the present specification, g21 is an integer of 1 to 4.

In one embodiment of the present specification, g22 is an integer of 1 to 4.

In one embodiment of the present specification, g23 is an integer of 1 to 4.

In one embodiment of the present specification, when R2 forms a ring, it is any one of the following structural formulae:

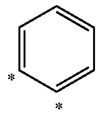
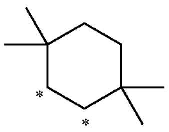
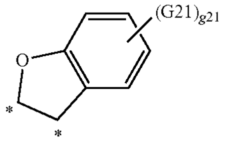
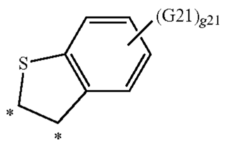
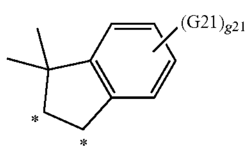
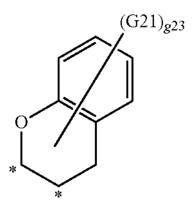
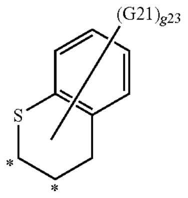

wherein in the structural formulae, the substituents have the same definitions as above.

In one embodiment of the present specification, R3 has the same definition as in Chemical Formulae Cy2-1 and Cy2-2.

In one embodiment of the present specification, R4 has the same definition as R5 in Chemical Formula 1-A.

In one embodiment of the present specification, R5 has the same definition as in Chemical Formula 1-A.

In one embodiment of the present specification, in Chemical Formula 1, at least one of

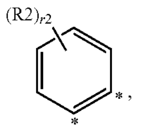

Cy2 to Cy4 and R1 includes a ring to which a substituted or unsubstituted aliphatic hydrocarbon ring is fused, and * means a position fused to Chemical Formula 1.

In one embodiment of the present specification, in Chemical Formula 1, at least one of

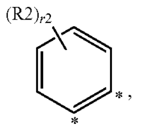

Cy2 to Cy4 and R1 includes a ring to which a C6 to C30 aliphatic hydrocarbon ring unsubstituted or substituted with a C1-C20 alkyl group is fused, and * means a position fused to Chemical Formula 1.

In one embodiment of the present specification, the aliphatic hydrocarbon ring can be hexagonal ring.

In one embodiment of the present specification, in Chemical Formula 1, at least one of

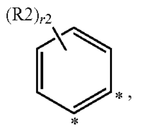

Cy2 to Cy4 and R1 includes a ring to which a substituted or unsubstituted cyclohexene ring or a substituted or unsubstituted bicyclooctene ring is fused, and * means a position fused to Chemical Formula 1.

In one embodiment of the present specification, in Chemical Formula 1, at least one of

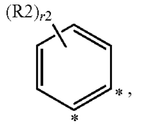

Cy2 to Cy4 and R1 includes a ring to which a cyclohexene ring that is unsubstituted or substituted with a methyl group, or a bicyclooctene ring that is unsubstituted or substituted with a methyl group, is fused, and * means a position fused to Chemical Formula 1.

In one embodiment of the present specification, Chemical Formula 1 is any one of the following Chemical Formulae 107 to 109:

<Chemical Formula 107>

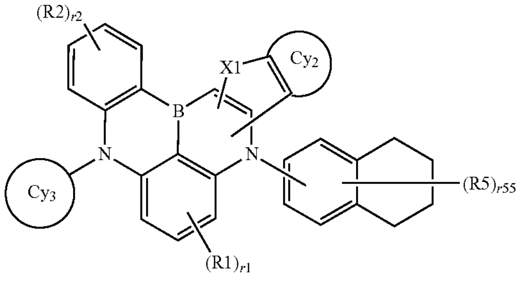

<Chemical Formula 108>

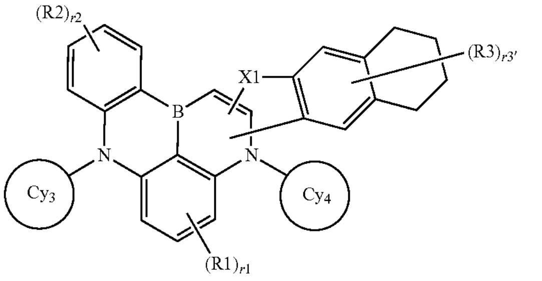

<Chemical Formula 109>

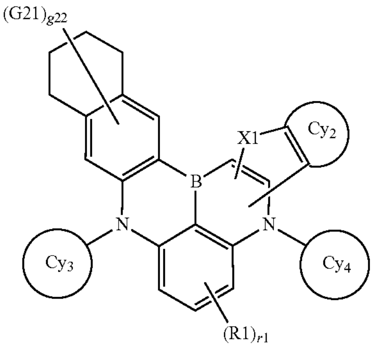

In Chemical Formulae 107 to 109, substituents have the same definitions as above, r3' is an integer of 0 to 10, and when r3' is 2 or greater, the two or more R3s are the same as or different from each other.

In one embodiment of the present specification, the compound of Chemical Formula 1 is any one of the following compounds:

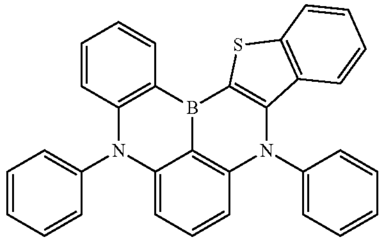

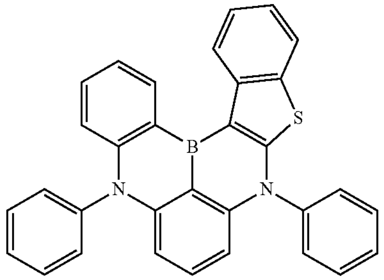

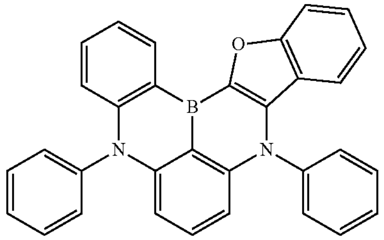

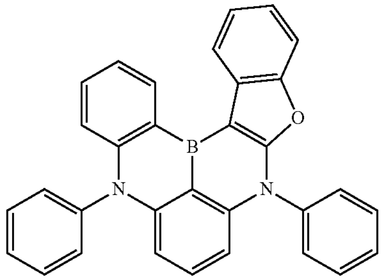

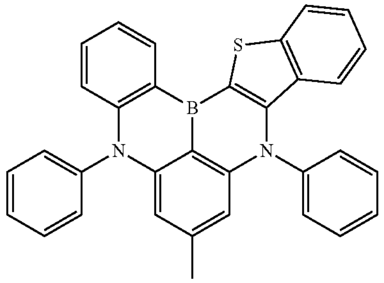

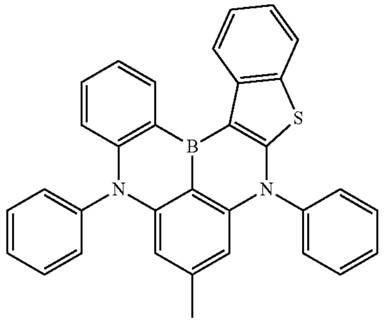

-continued
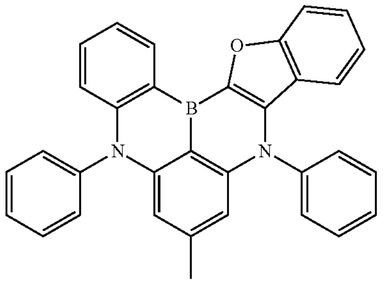
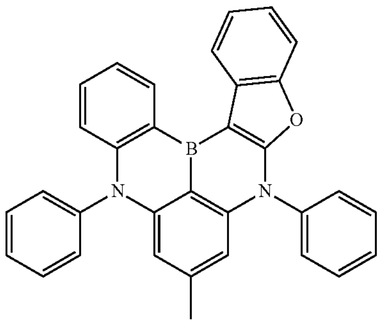
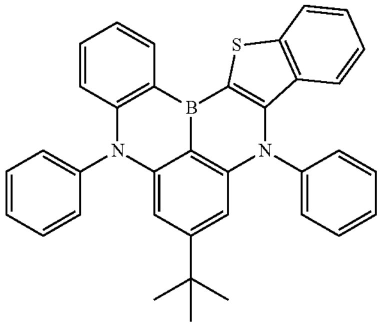
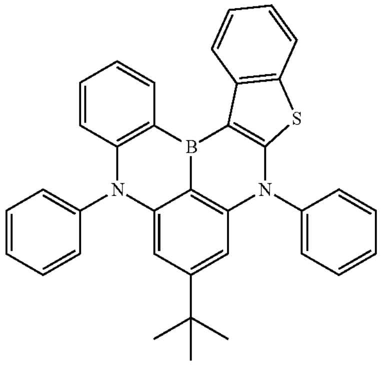
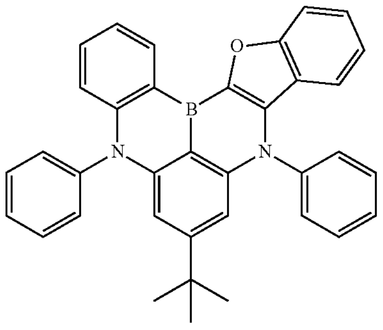
-continued
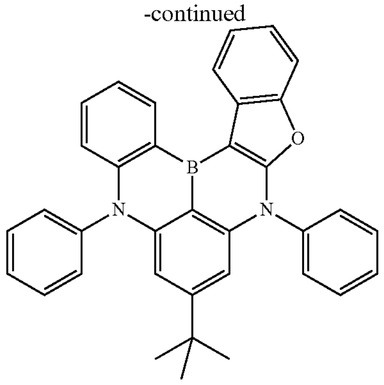
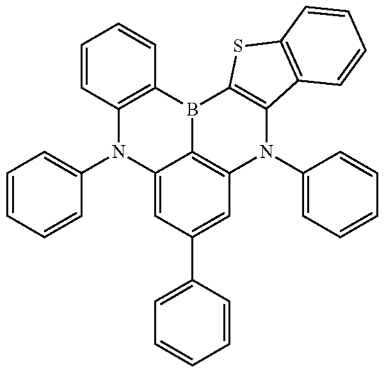
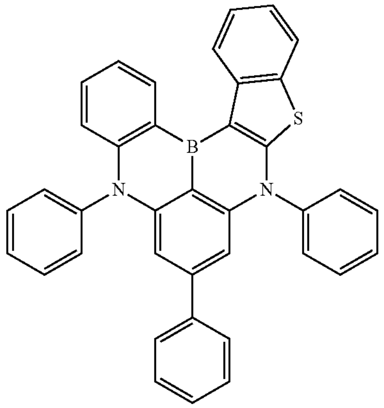
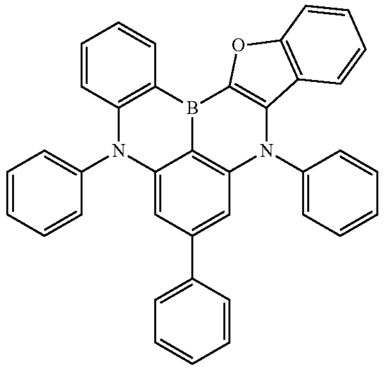

-continued
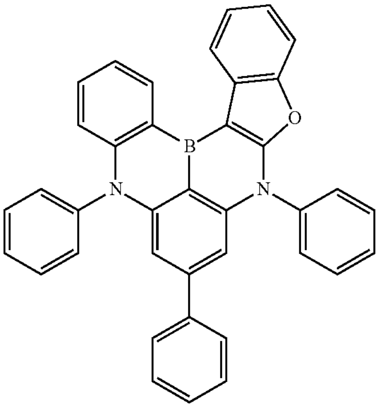
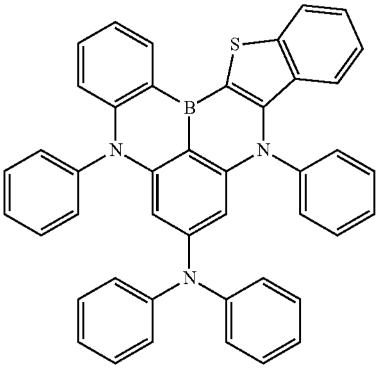
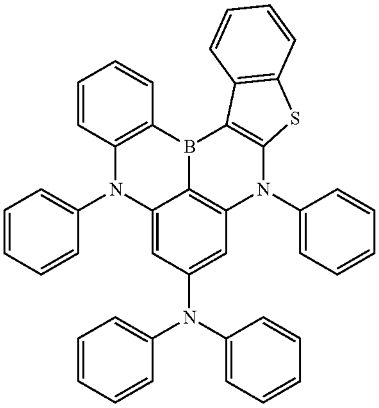
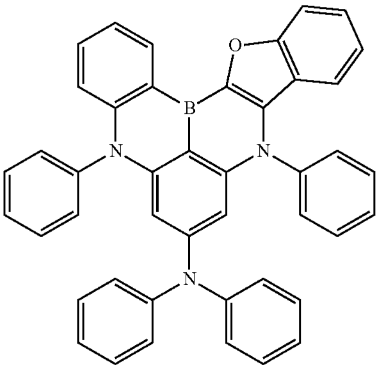
-continued
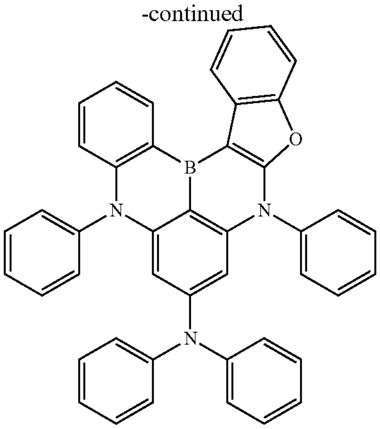
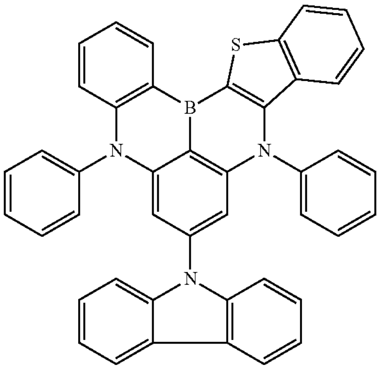
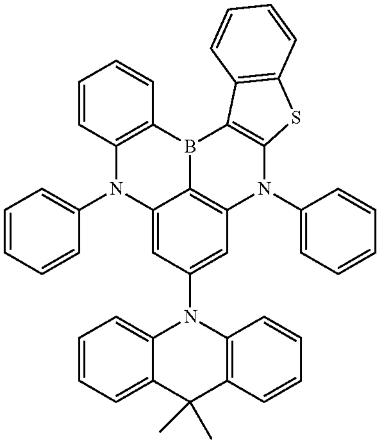
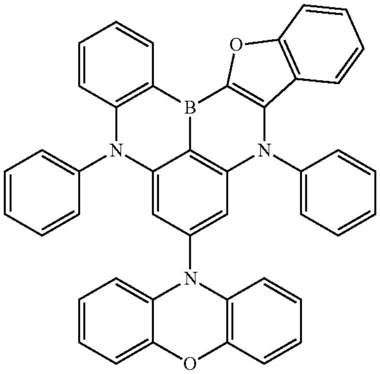

-continued
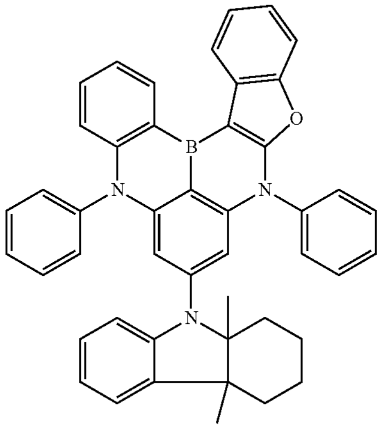
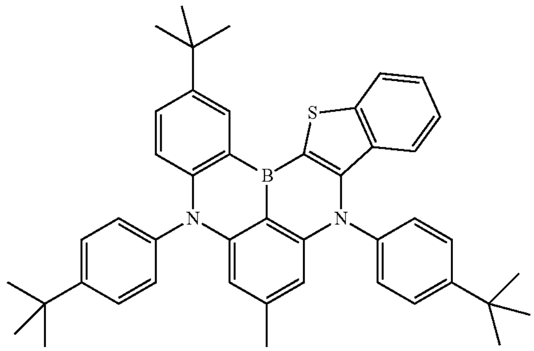
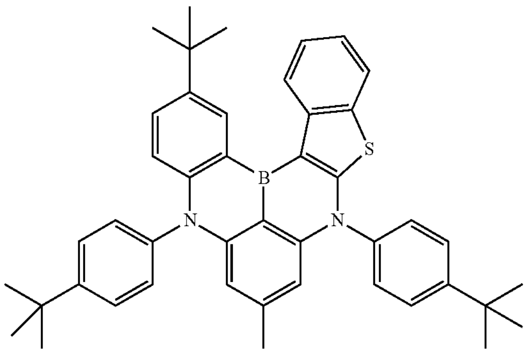
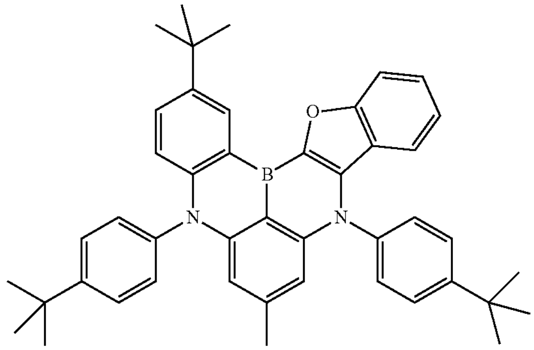
-continued
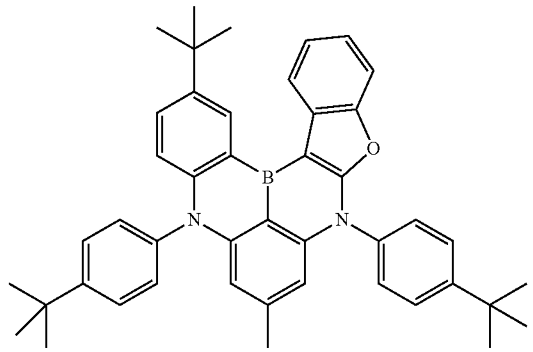
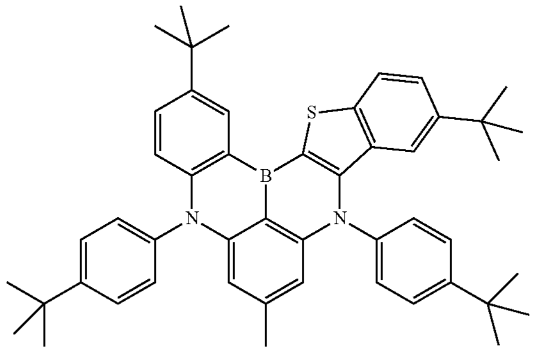
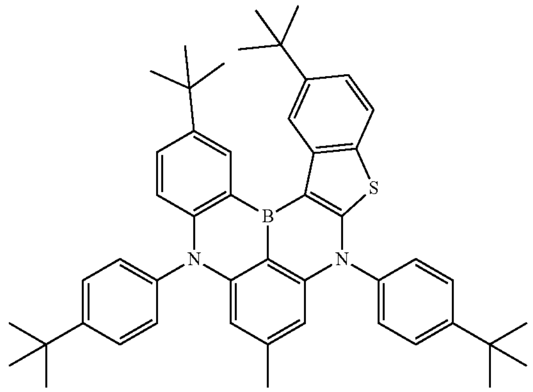
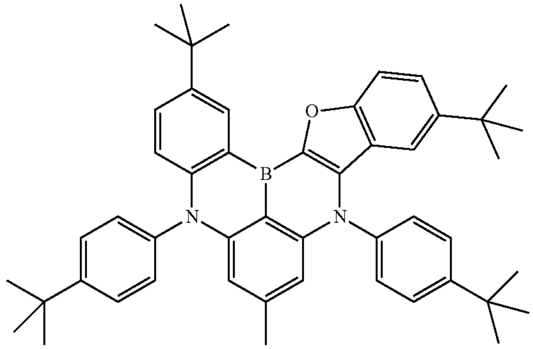

-continued
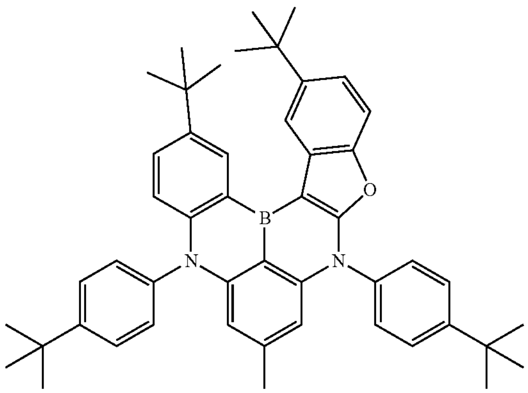
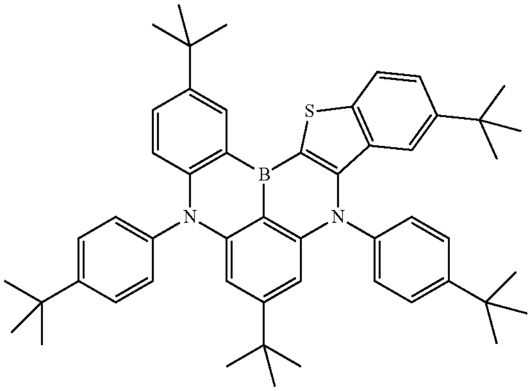
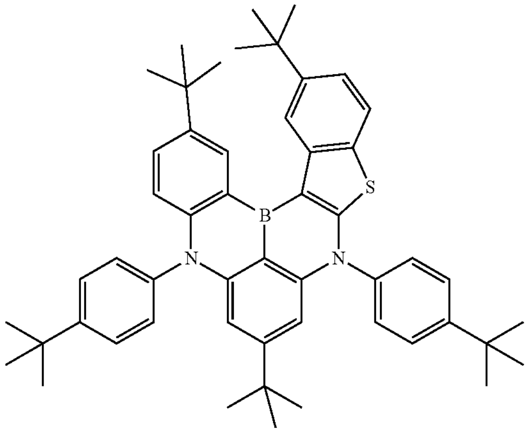
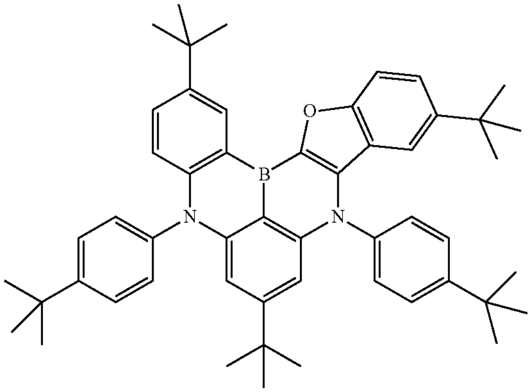
-continued
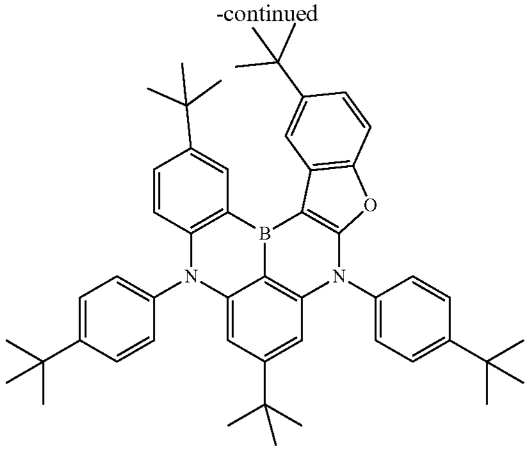
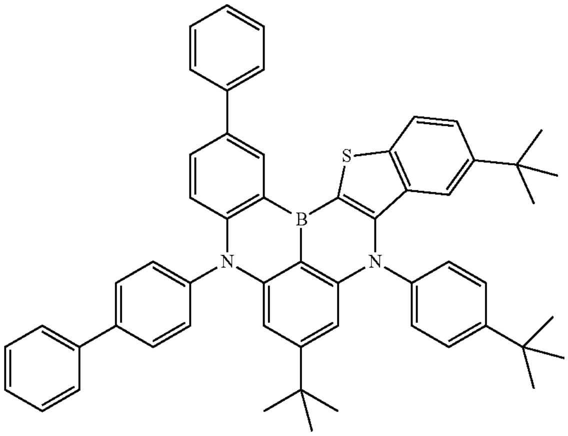
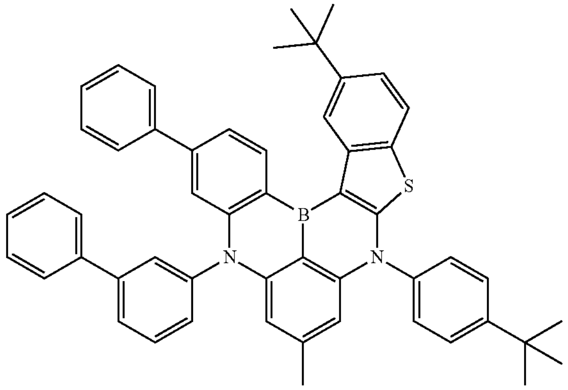
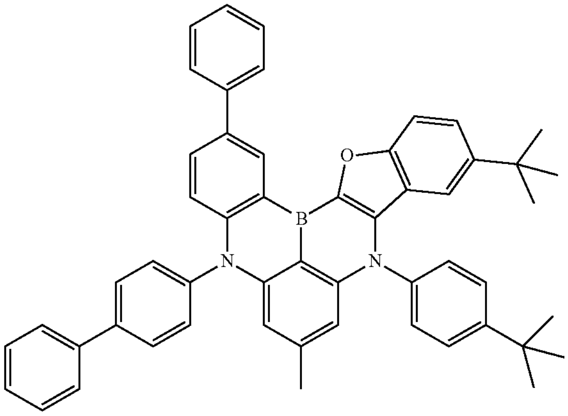

-continued
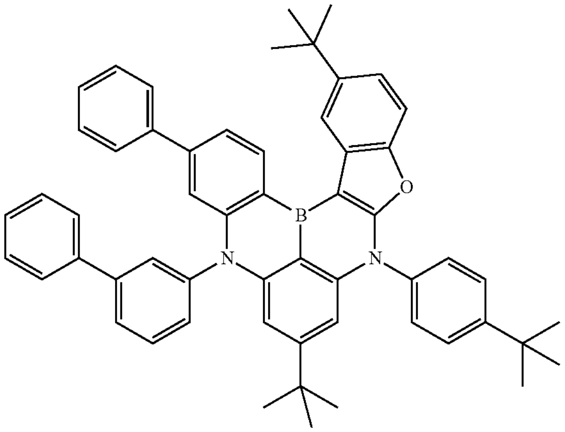
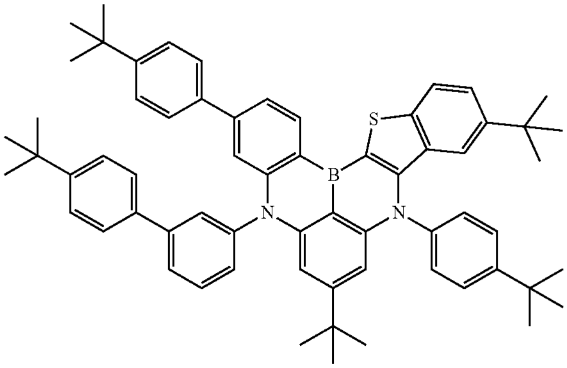
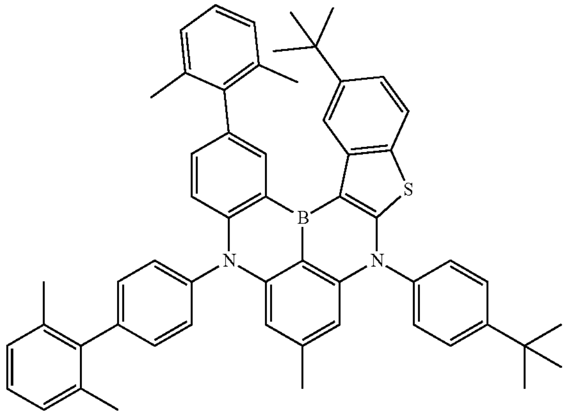
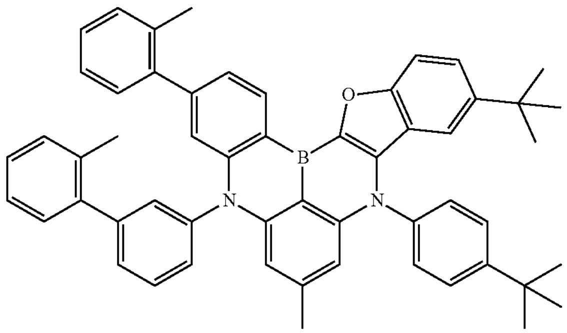
-continued
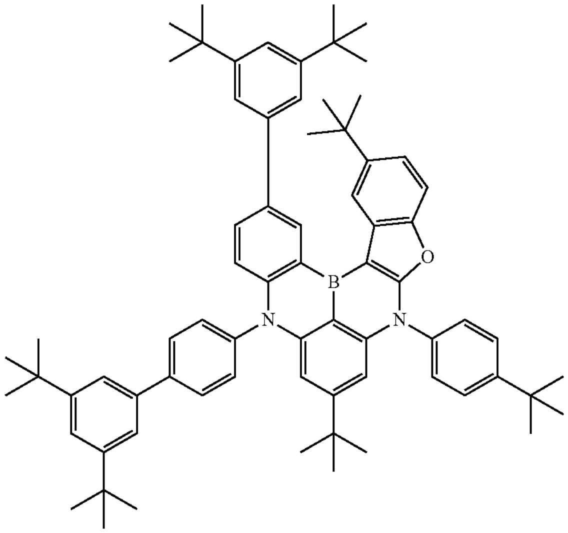
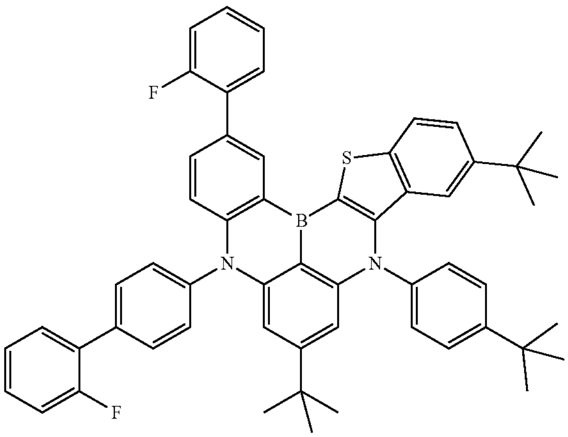
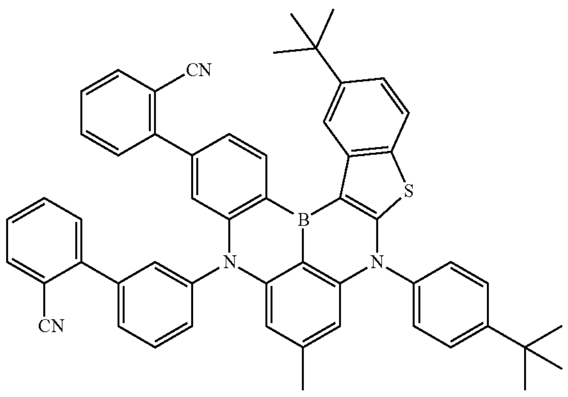

-continued
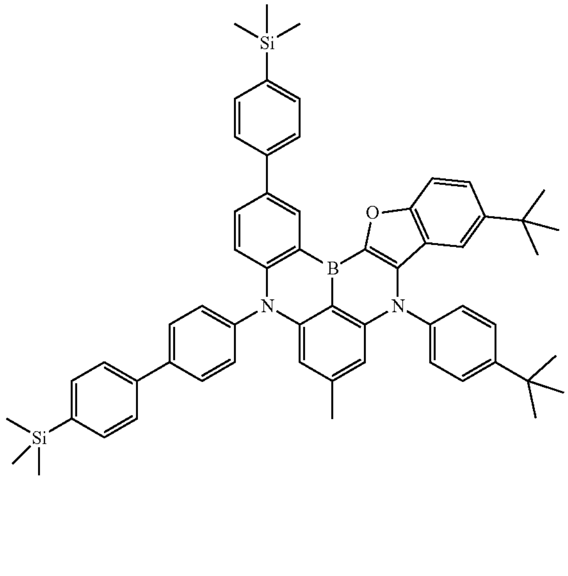
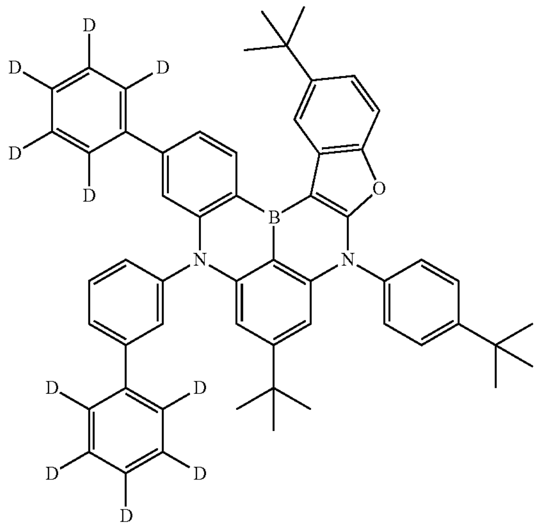
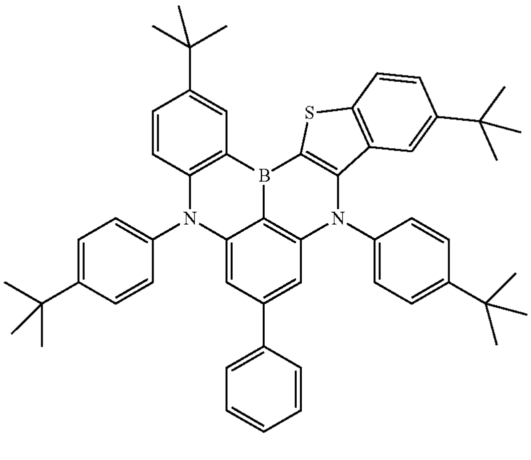
-continued
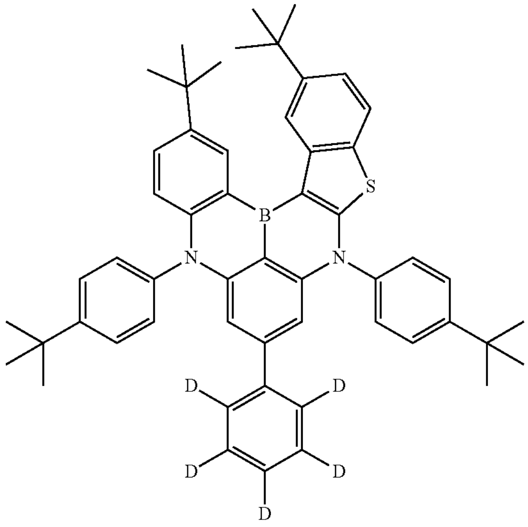
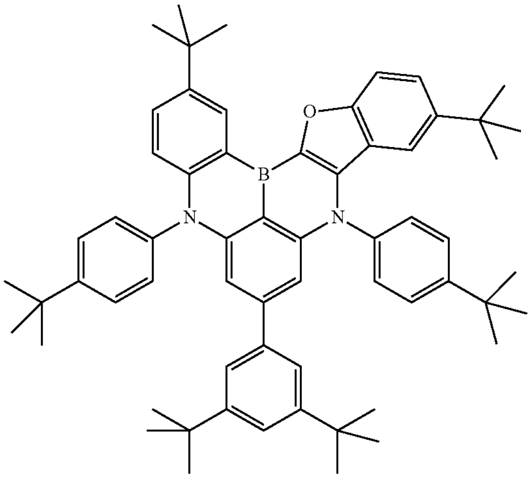
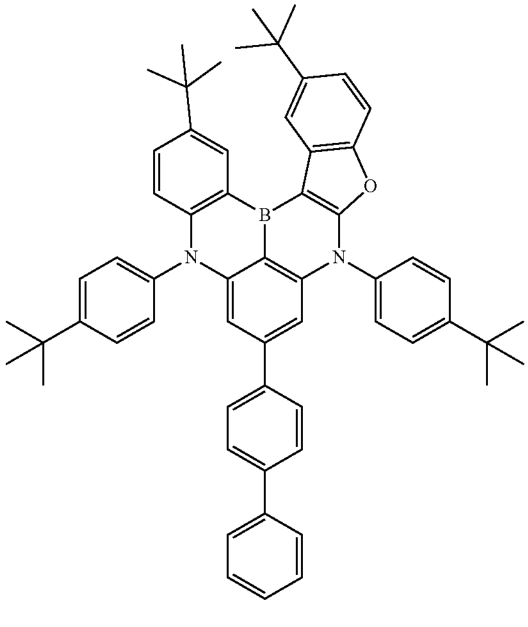 [SMILES: CC(C)(C)c1ccc(N2c3ccc(C(C)(C)C)cc3B3c4c2cc(-c2ccc(-c5ccccc5)cc2)cc4N(c2ccc(C(C)(C)C)cc2)c2oc4ccc(C(C)(C)C)cc4c23)cc1]

-continued
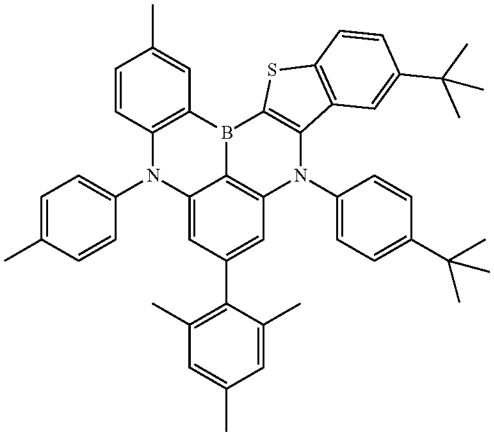
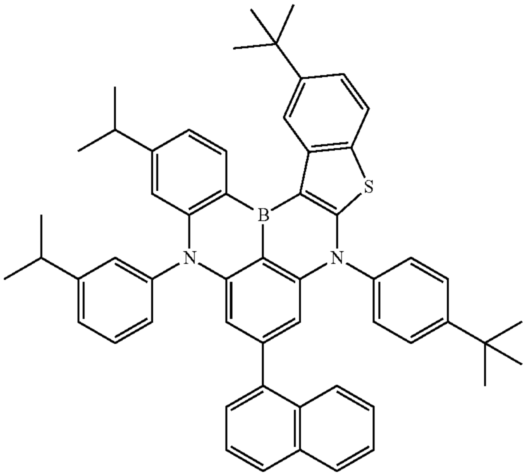
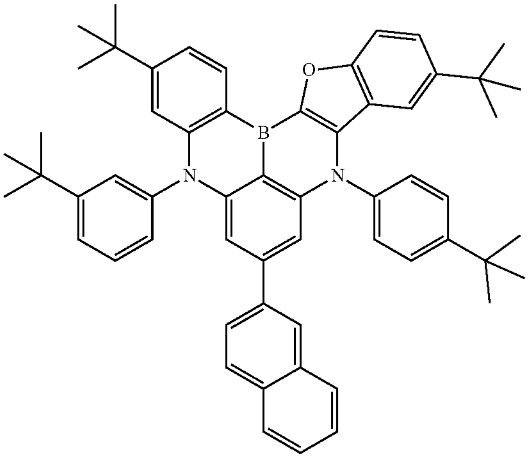
-continued
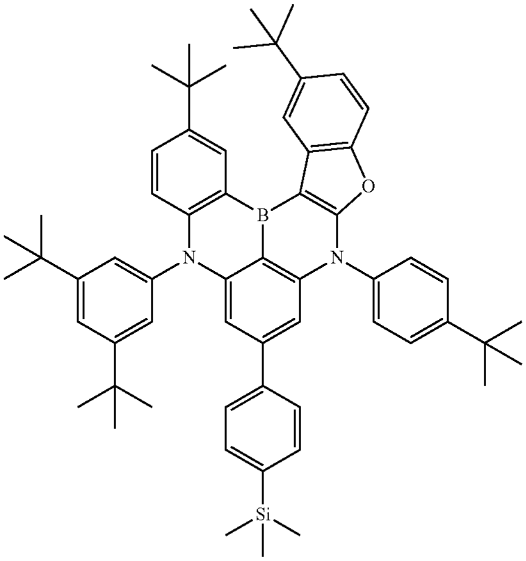
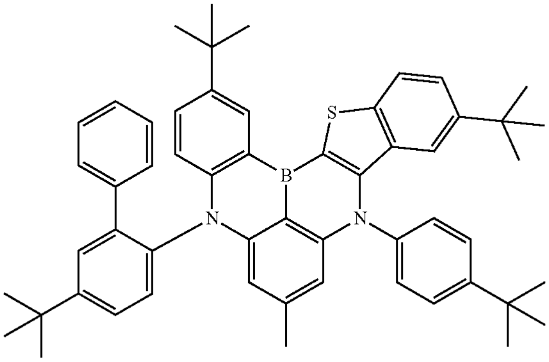
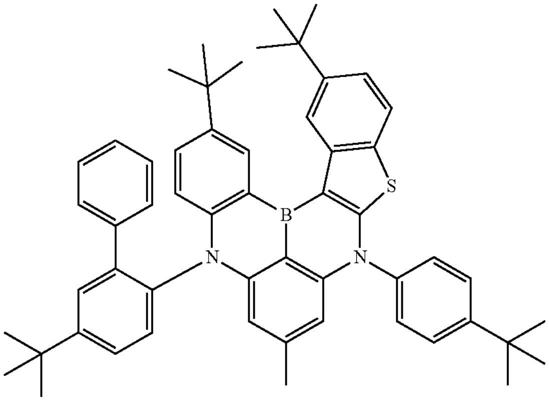
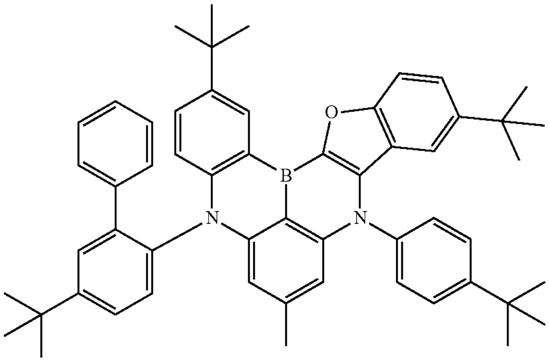

-continued
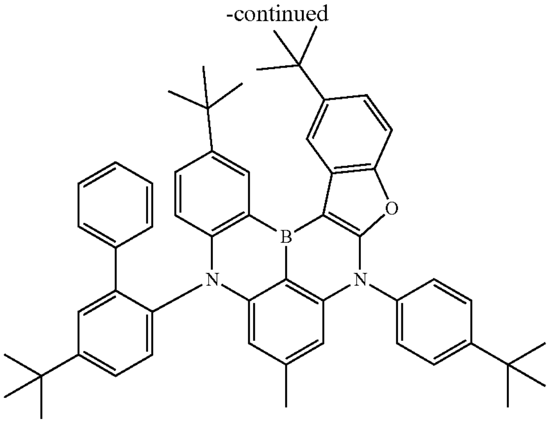
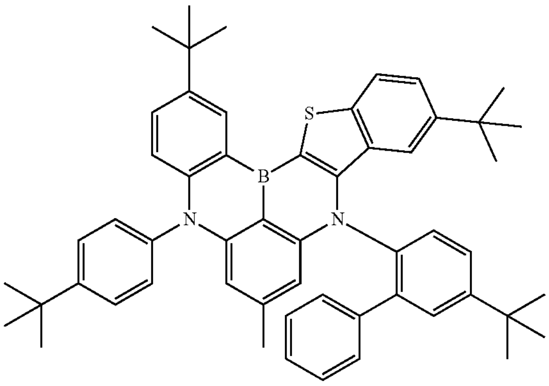
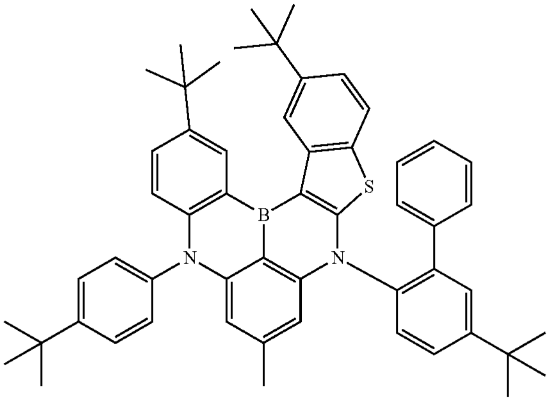
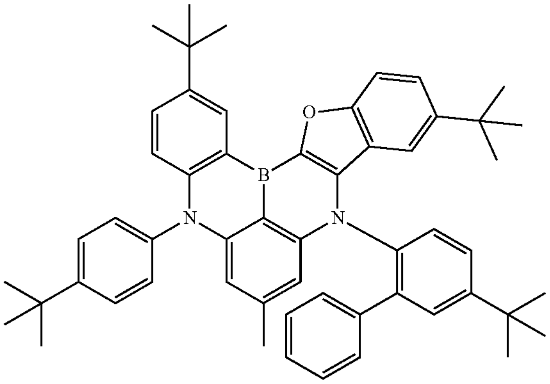
-continued
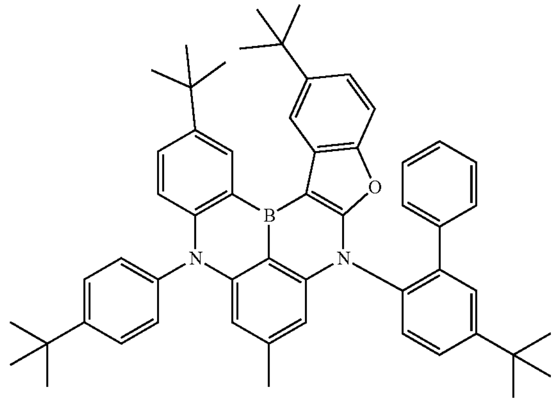
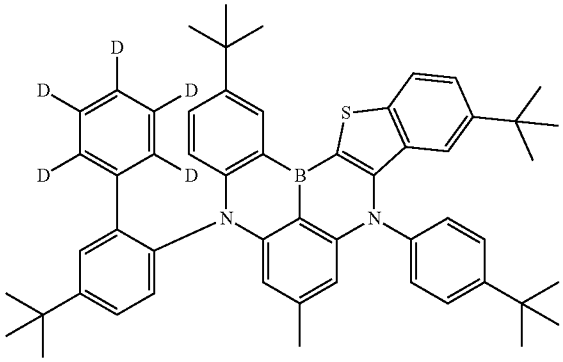
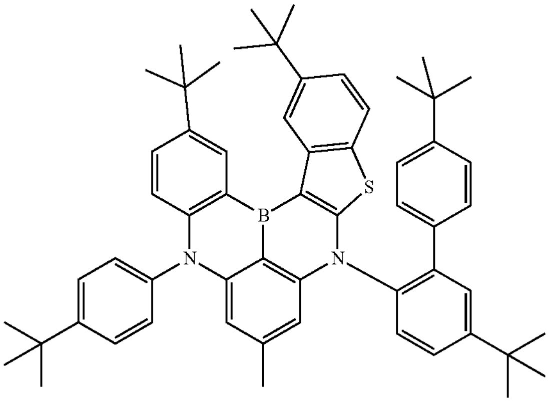
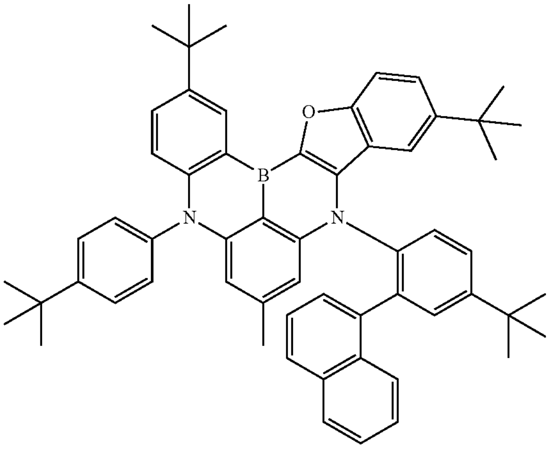

-continued
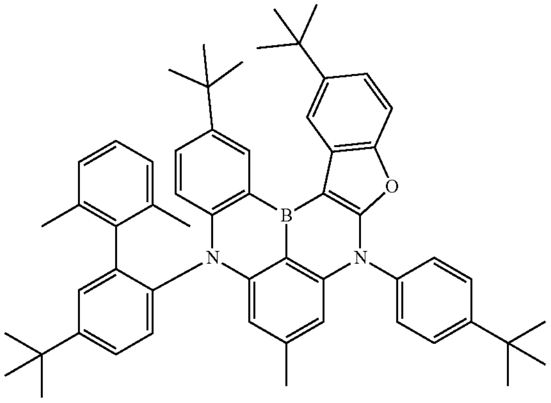
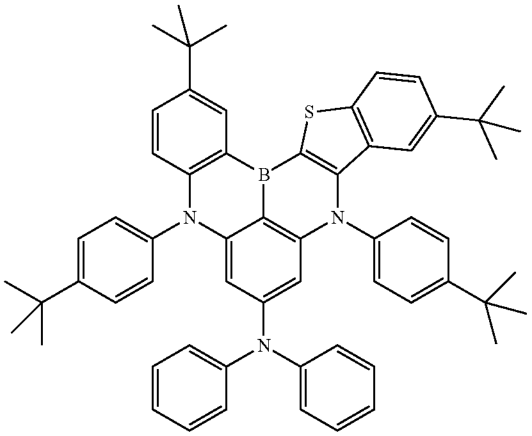
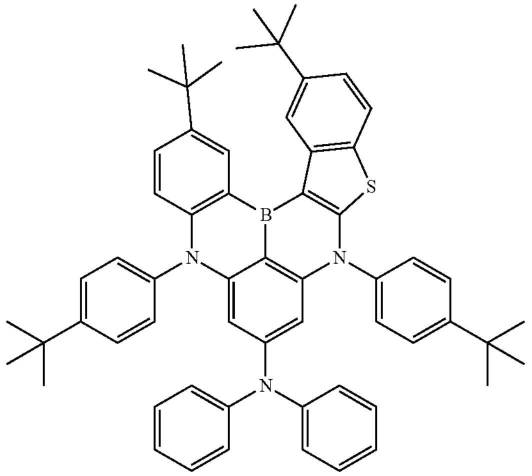
-continued
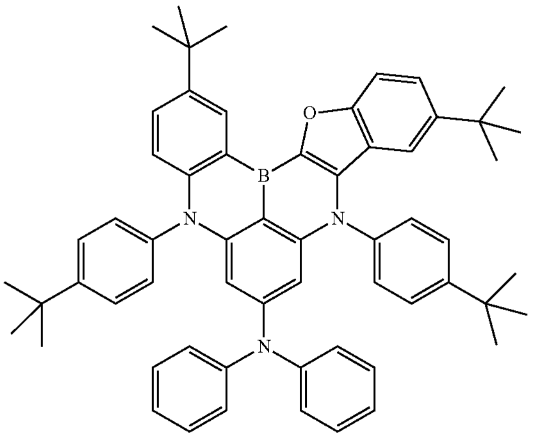
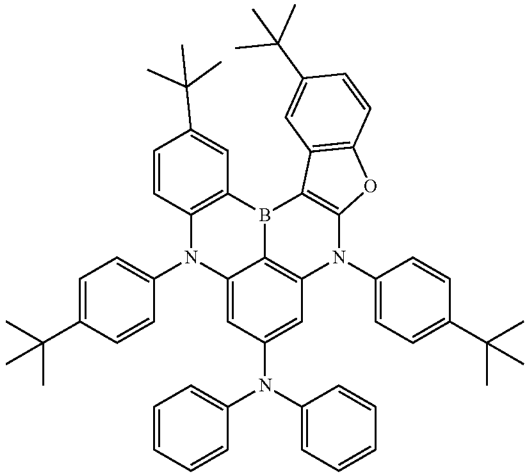
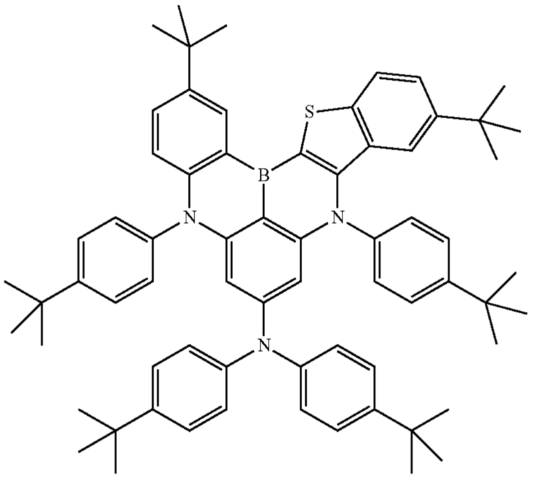

65
-continued
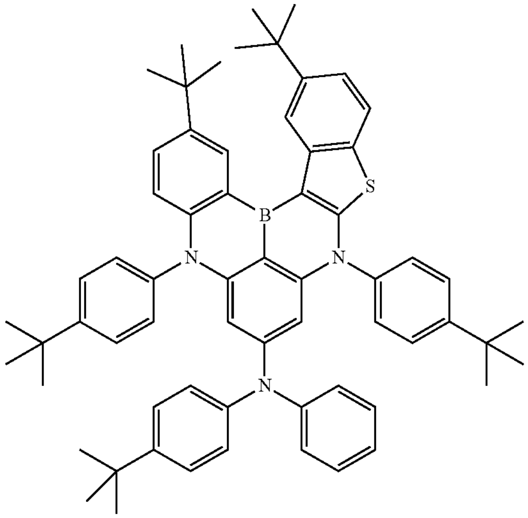
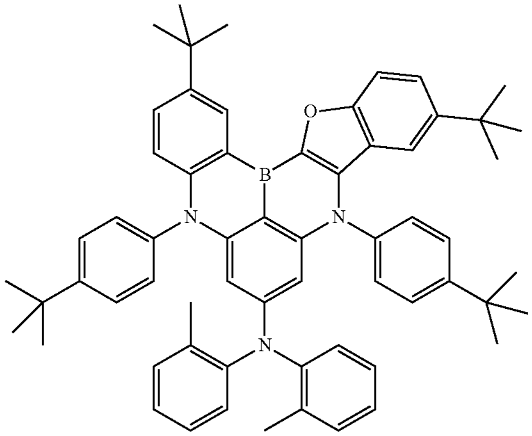
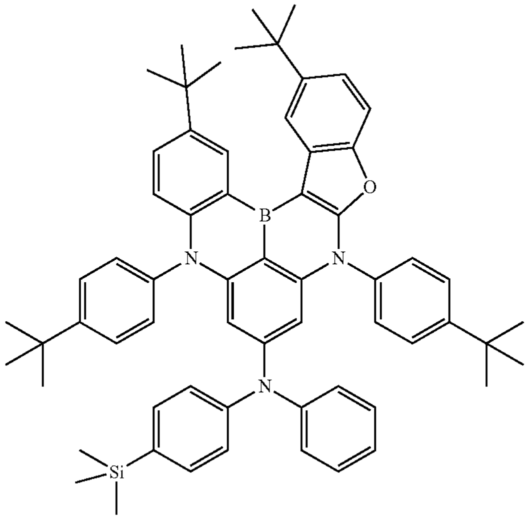 [SMILES: CC(C)(C)c1ccc(N2c3ccc(C(C)(C)C)cc3B3c4c2cc(N(c2ccccc2)c2ccc([Si](C)(C)C)cc2)cc4N(c2ccc(C(C)(C)C)cc2)c2oc4ccc(C(C)(C)C)cc4c23)cc1]
66
-continued
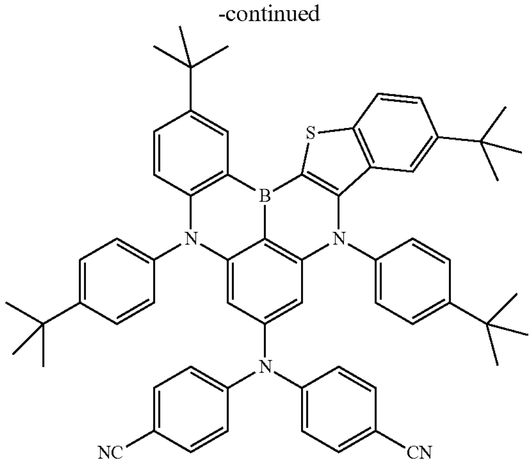
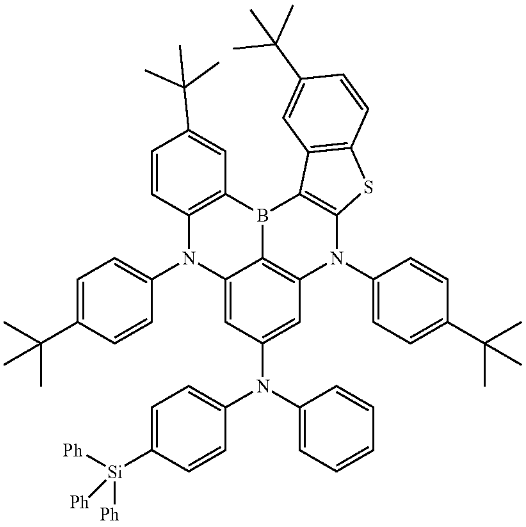
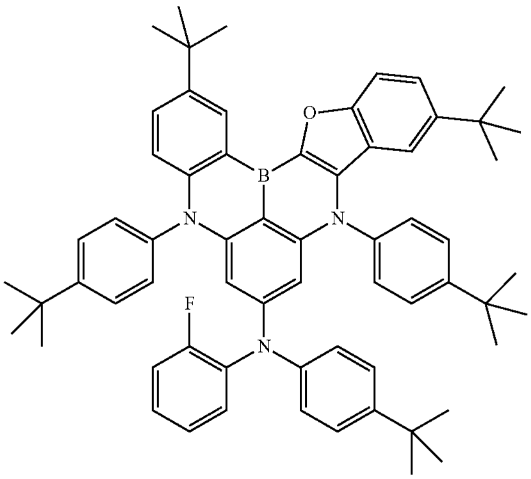

-continued
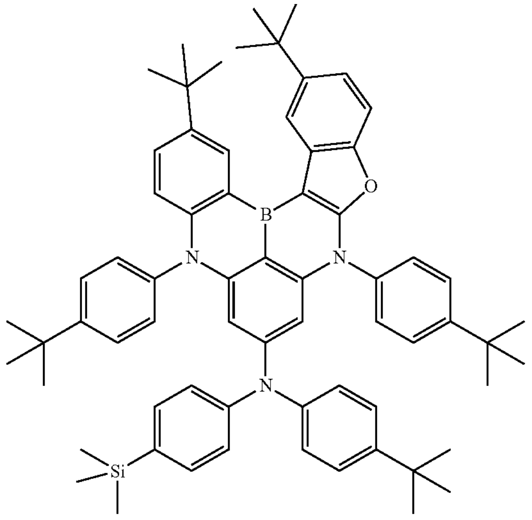 [SMILES: CC(C)(C)c1ccc(N(c2ccc([Si](C)(C)C)cc2)c2cc3c4c(c2)N(c2ccc(C(C)(C)C)cc2)c2oc5ccc(C(C)(C)C)cc5c2B4c2cc(C(C)(C)C)ccc2N3c2ccc(C(C)(C)C)cc2)cc1]
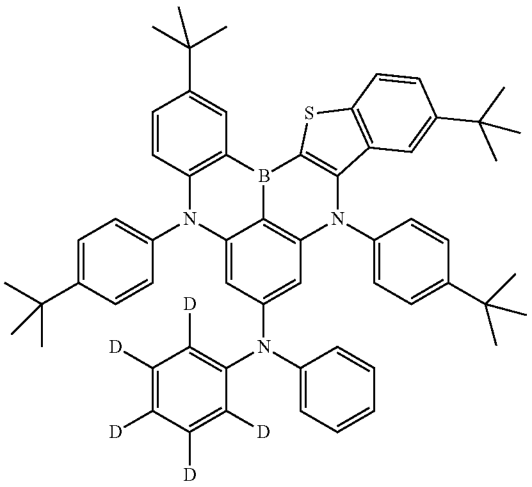
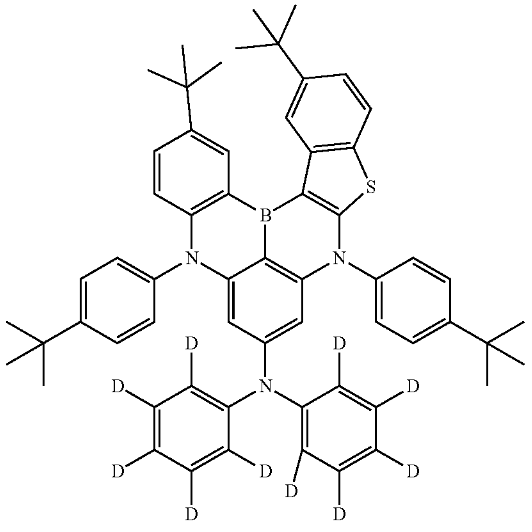
-continued
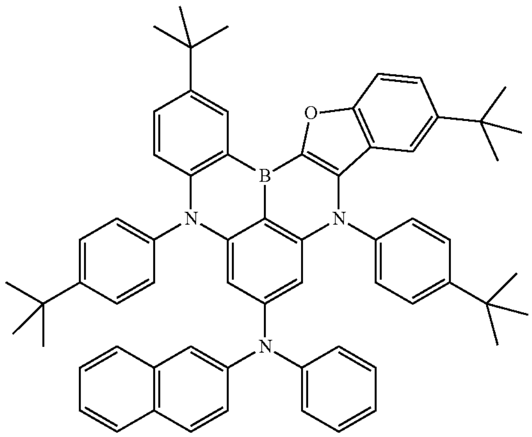
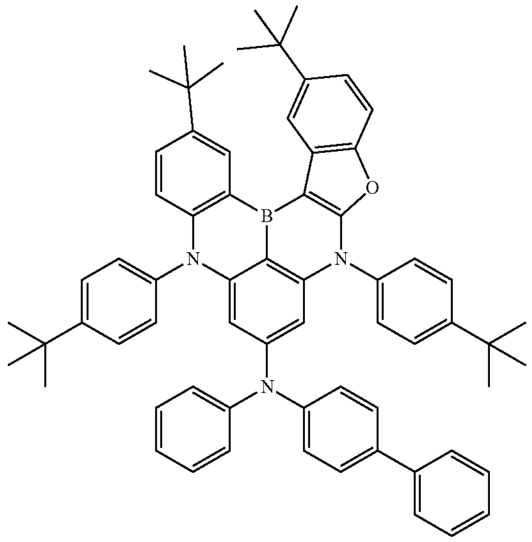 [SMILES: CC(C)(C)c1ccc(N2c3ccc(C(C)(C)C)cc3B3c4c2cc(N(c2ccccc2)c2ccc(-c5ccccc5)cc2)cc4N(c2ccc(C(C)(C)C)cc2)c2oc4ccc(C(C)(C)C)cc4c23)cc1]
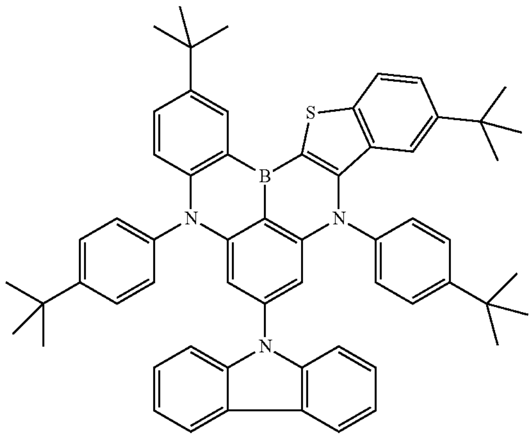

-continued
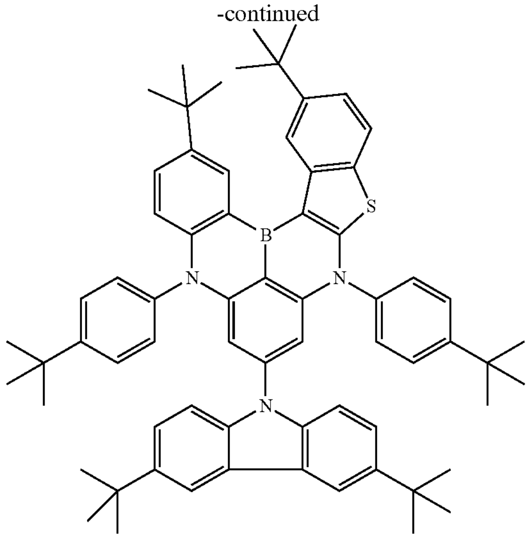
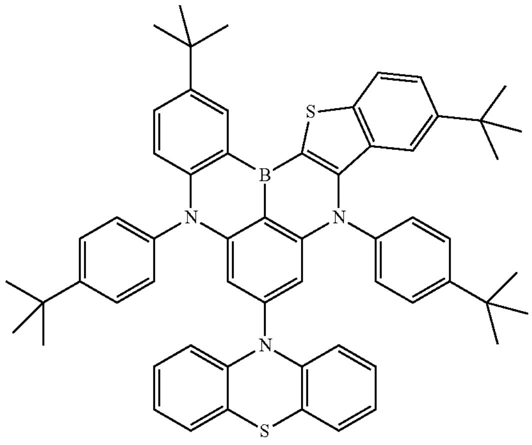
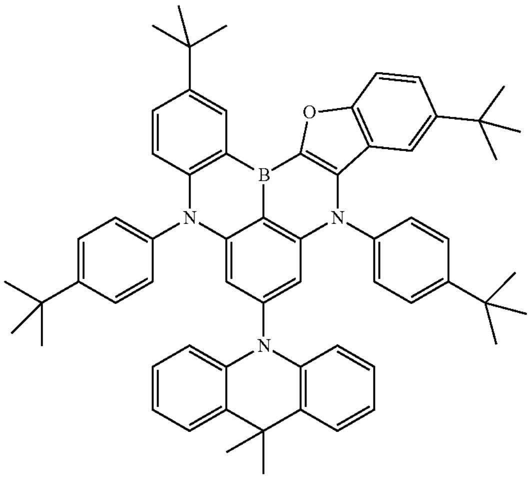
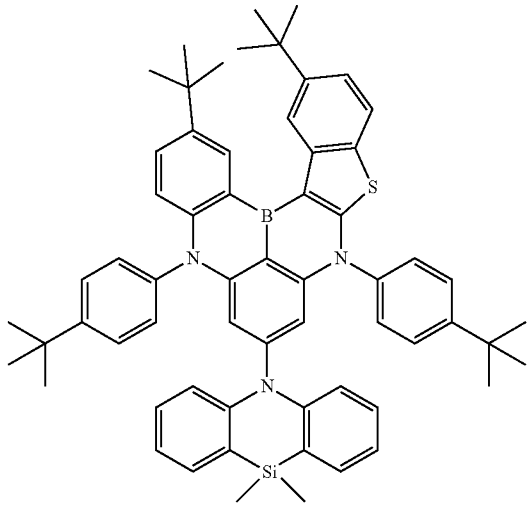
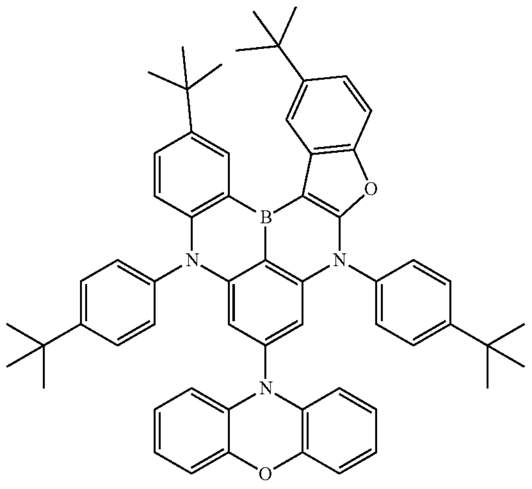
-continued
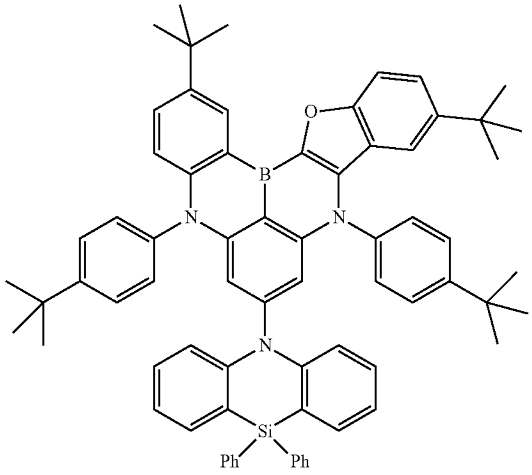

-continued
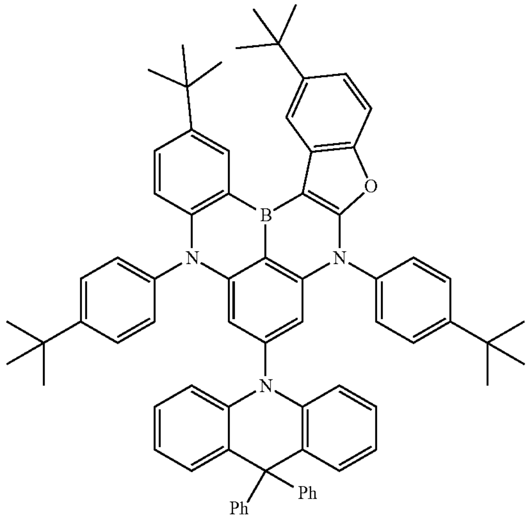 [SMILES: CC(C)(C)c1ccc(N2c3ccc(C(C)(C)C)cc3B3c4c2cc(N2c5ccccc5C(c5ccccc5)(c5ccccc5)c5ccccc52)cc4N(c2ccc(C(C)(C)C)cc2)c2oc4ccc(C(C)(C)C)cc4c23)cc1]
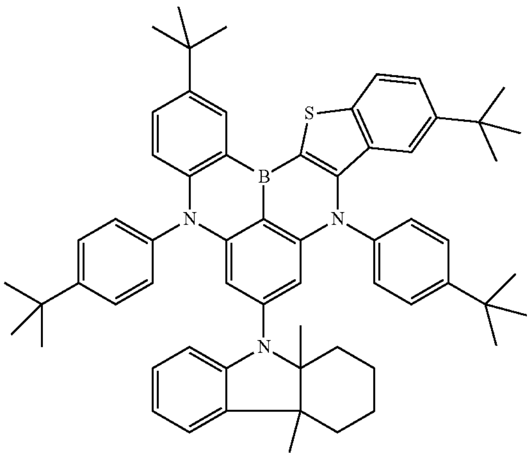
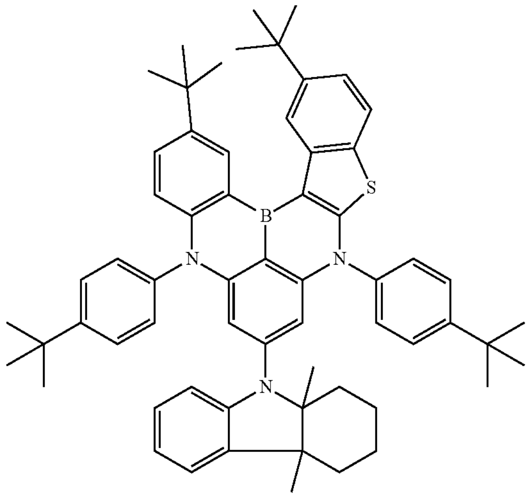
-continued
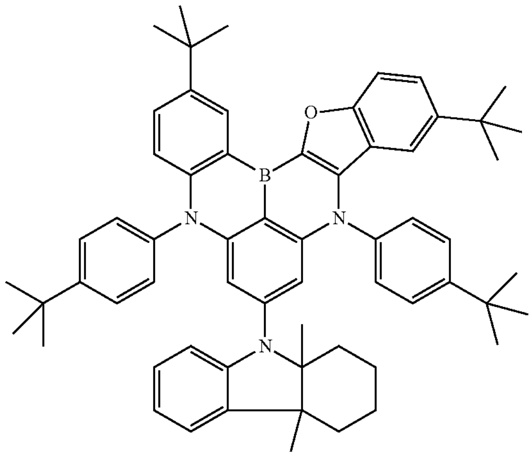
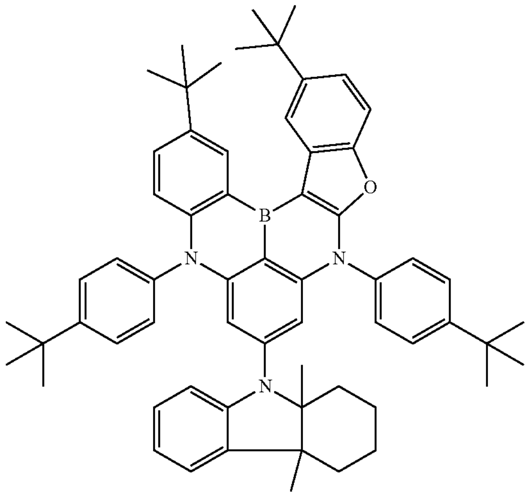
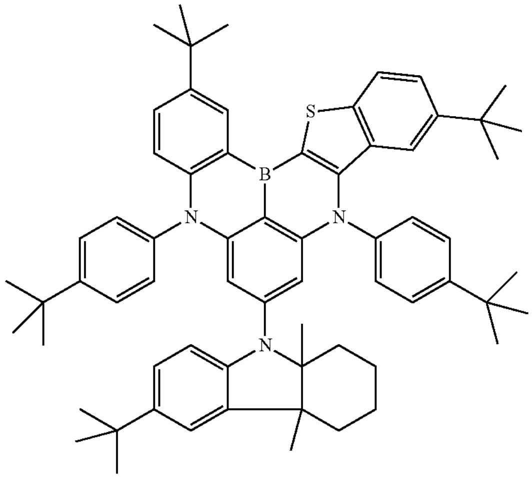

-continued
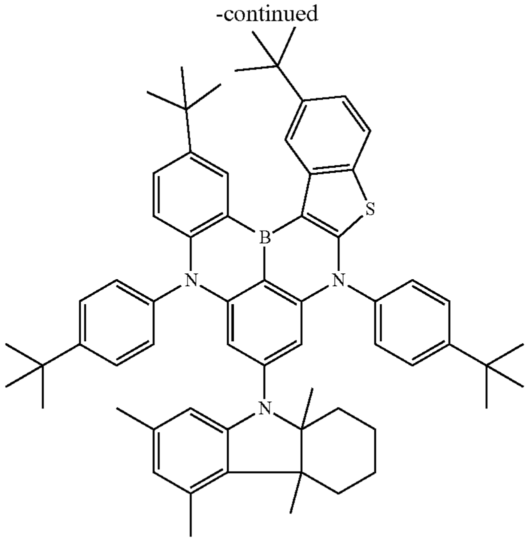
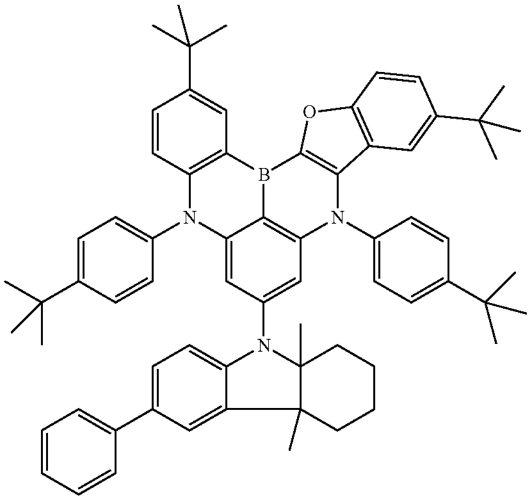
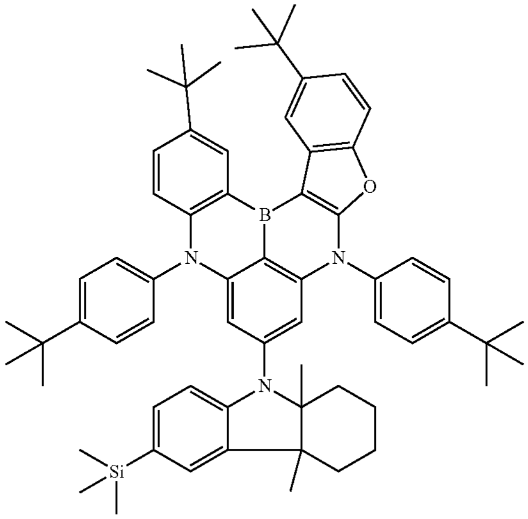 [SMILES: CC(C)(C)c1ccc(N2c3ccc(C(C)(C)C)cc3B3c4c2cc(N2c5ccc([Si](C)(C)C)cc5C5(C)CCCCC25C)cc4N(c2ccc(C(C)(C)C)cc2)c2oc4ccc(C(C)(C)C)cc4c23)cc1]
-continued
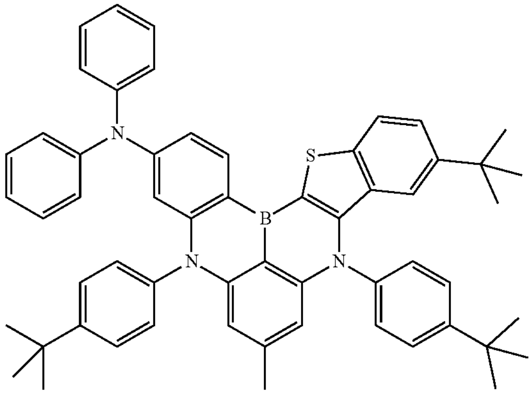
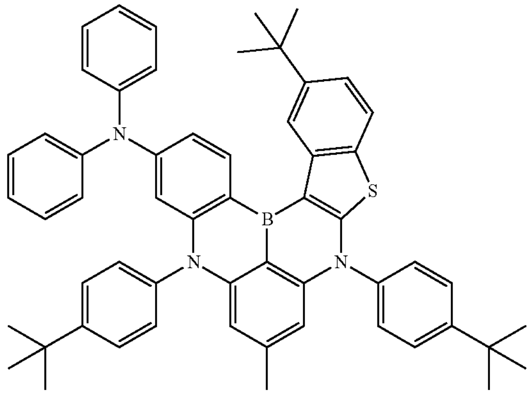
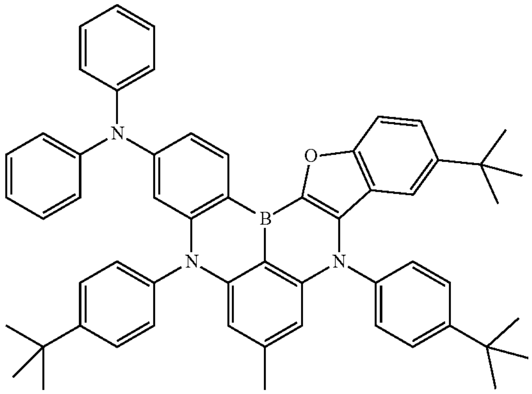
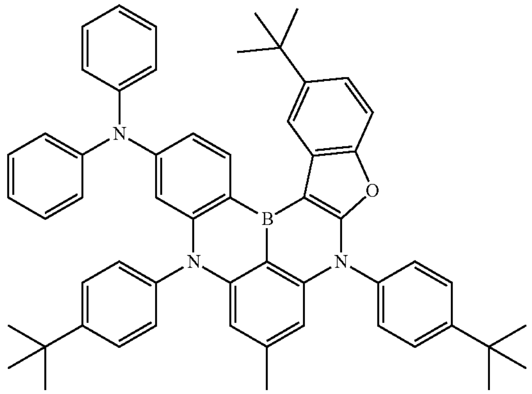

-continued
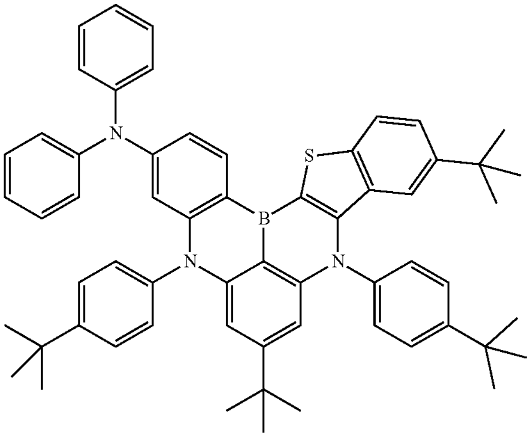
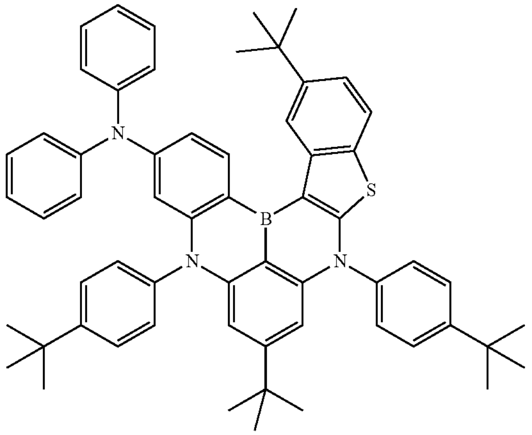
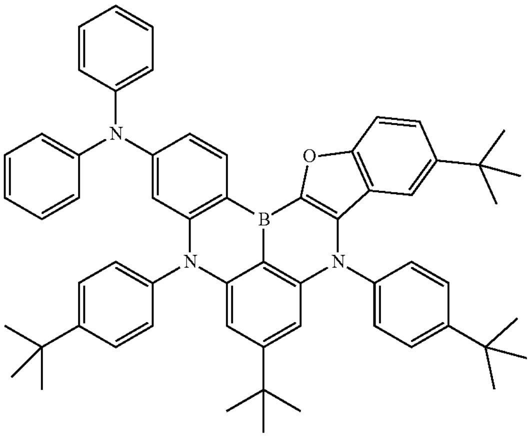
-continued
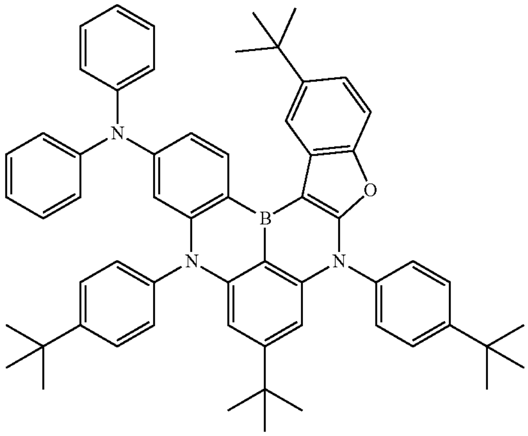
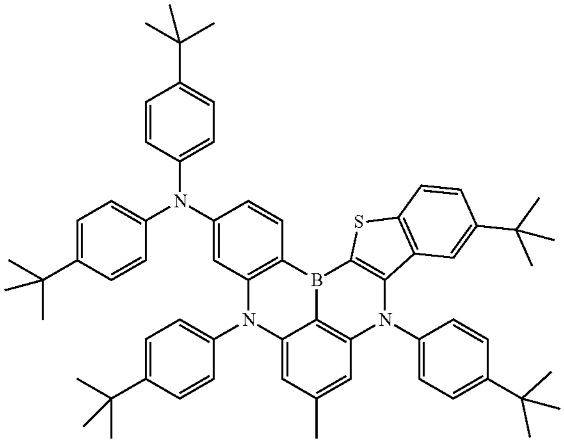
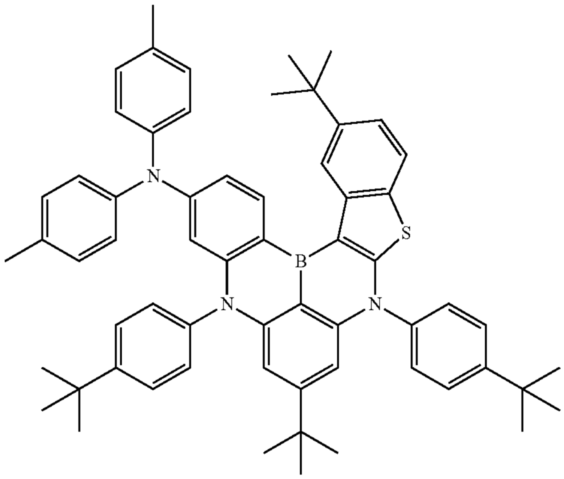

-continued
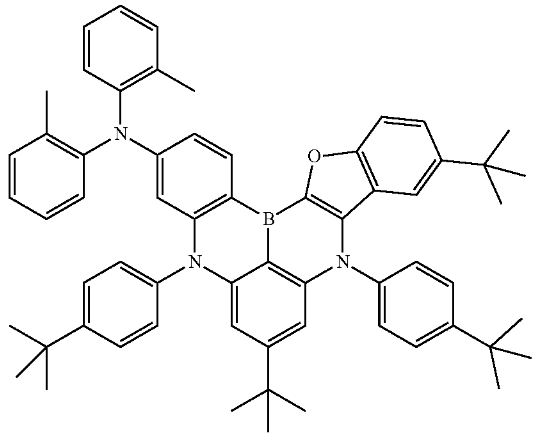
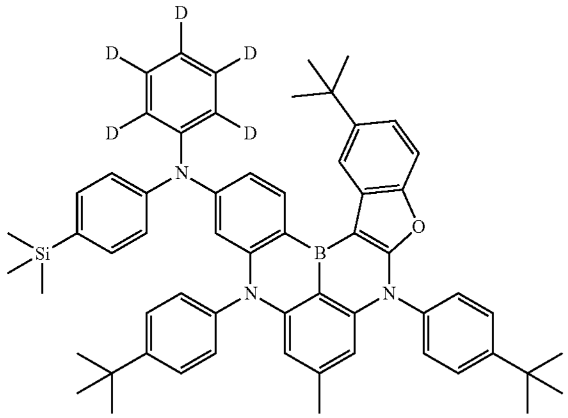
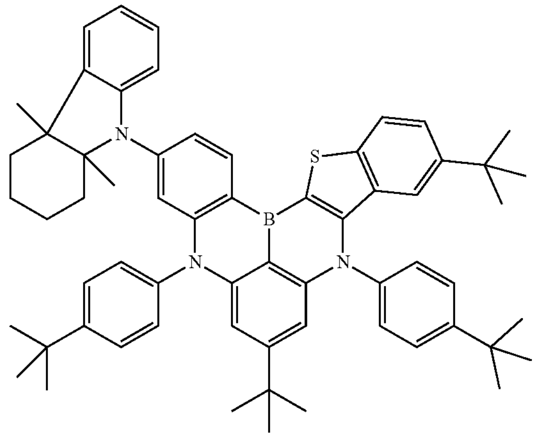
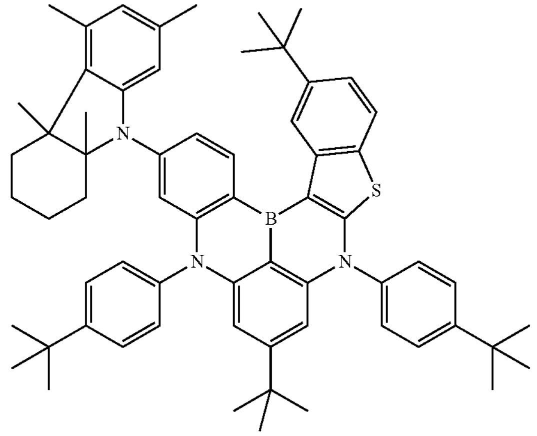
-continued
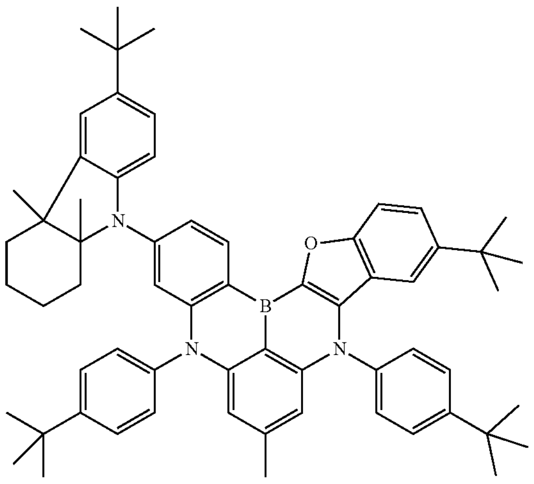
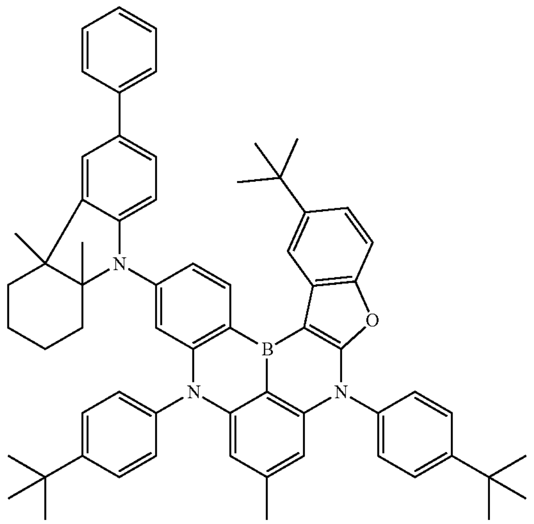
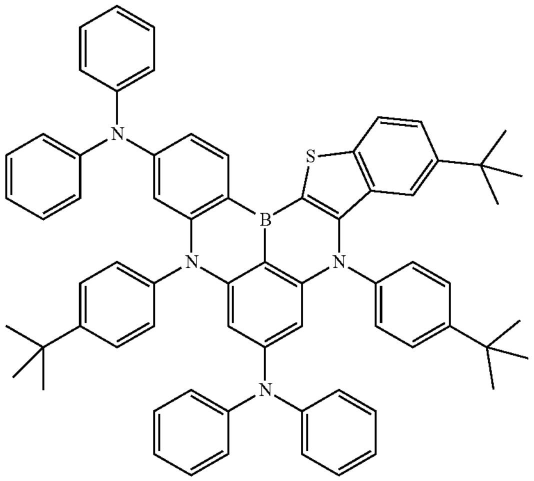

-continued
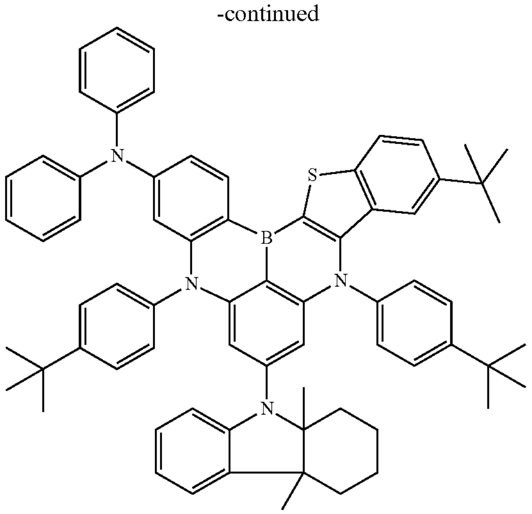
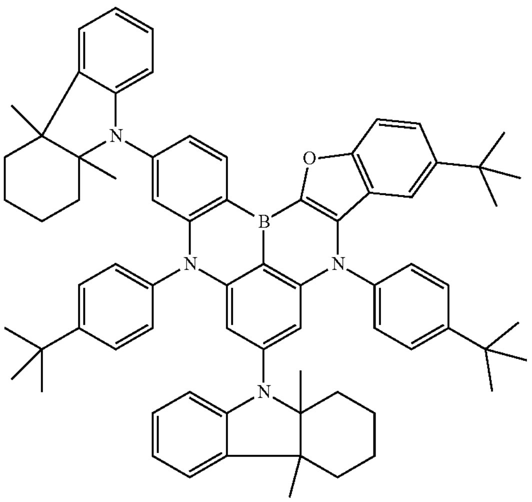
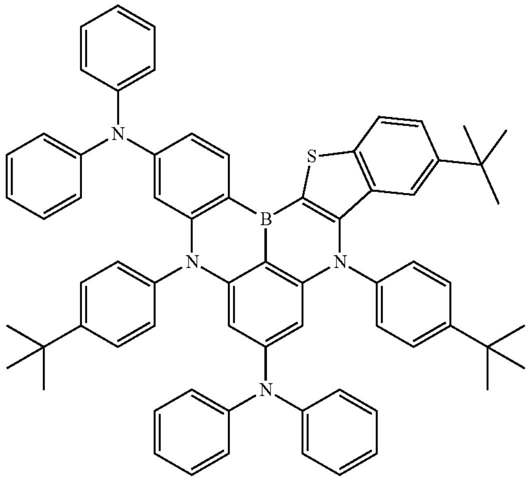 [SMILES: CC(C)(C)c1ccc(N2c3cc(N(c4ccccc4)c4ccccc4)ccc3B3c4sc5ccc(C(C)(C)C)cc5c4N(c4ccc(C(C)(C)C)cc4)c4cc(N(c5ccccc5)c5ccccc5)cc2c43)cc1]
-continued
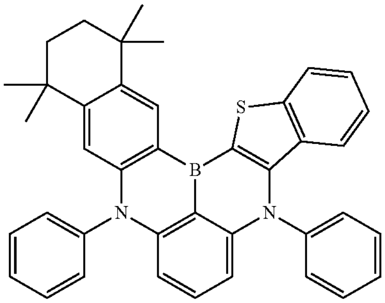
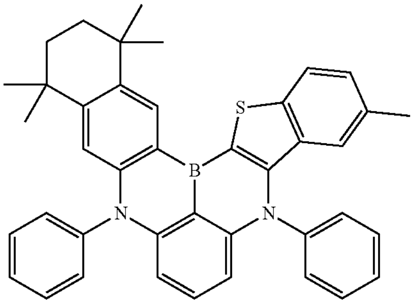
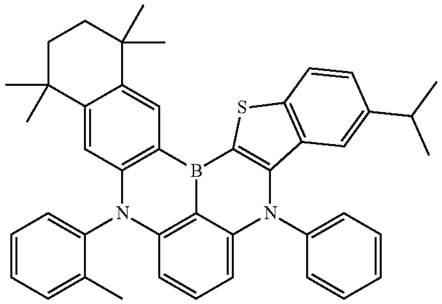
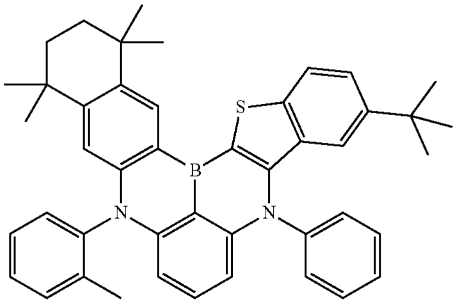
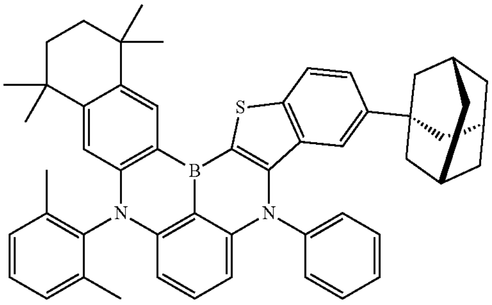

-continued
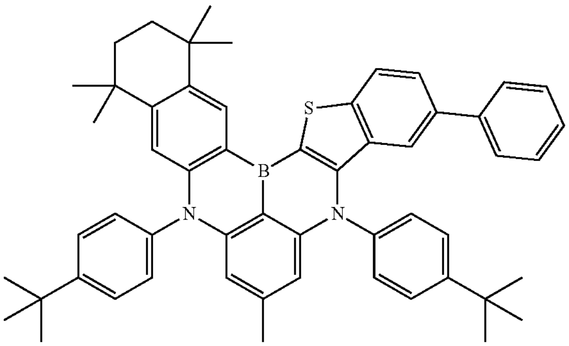
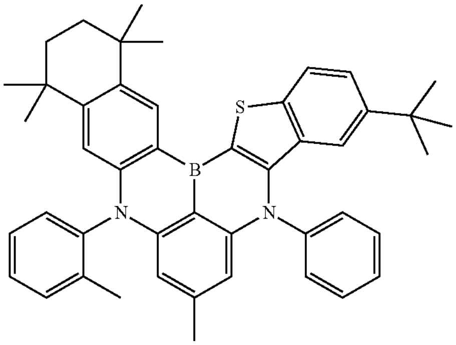
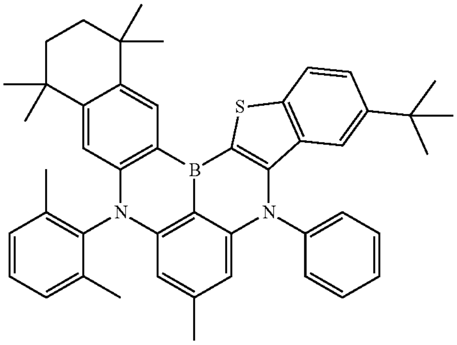
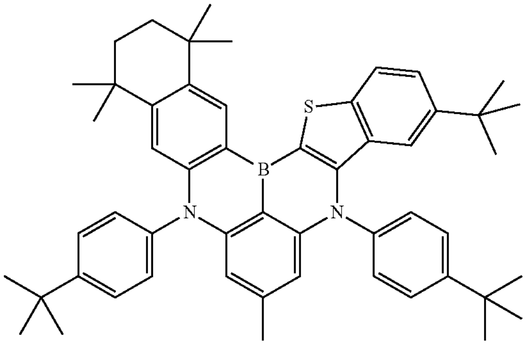
-continued
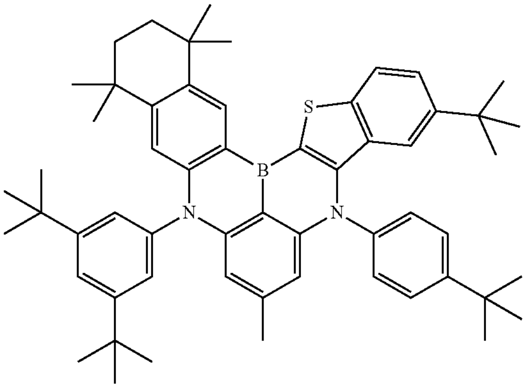
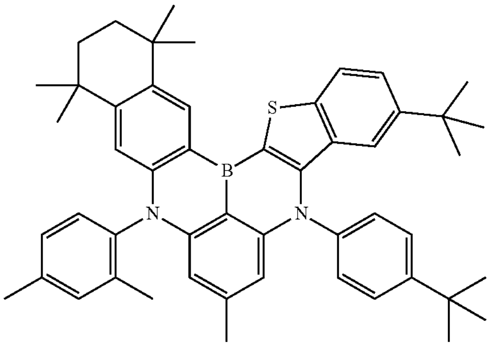
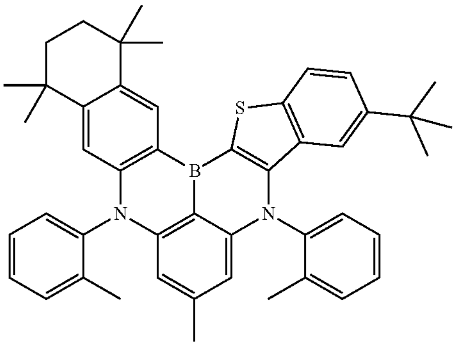
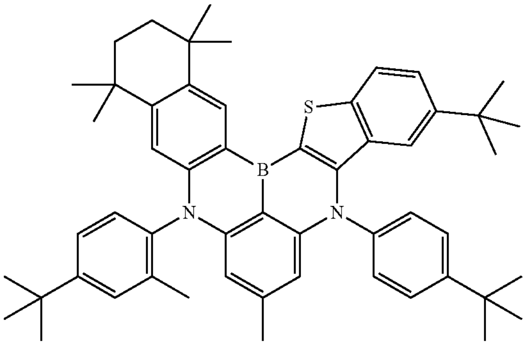

-continued
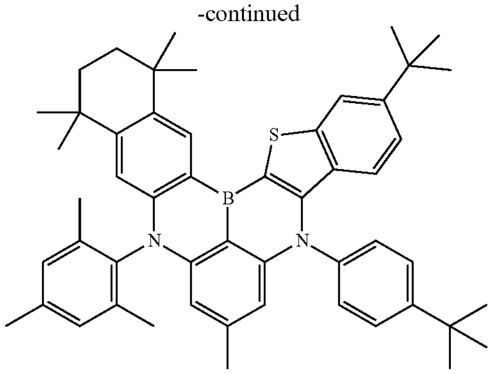
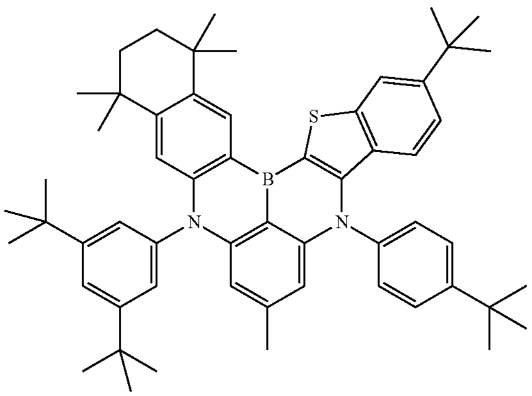
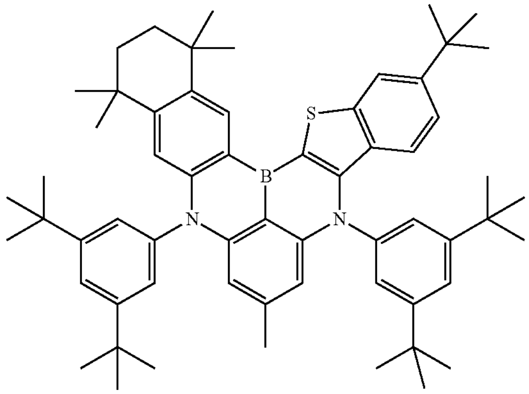
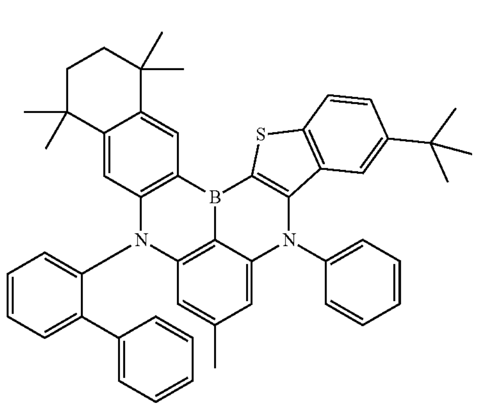
-continued
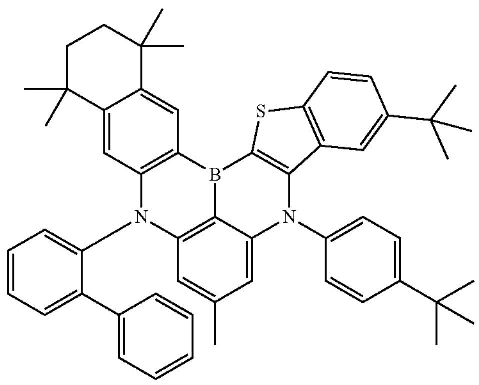
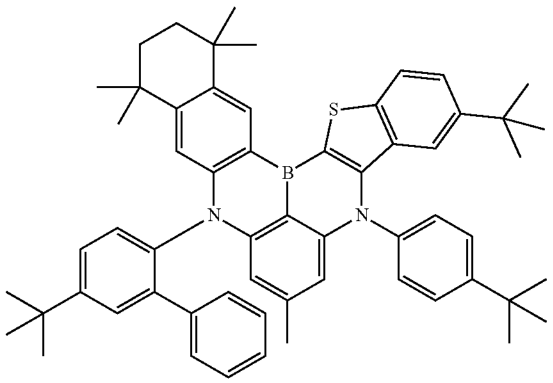
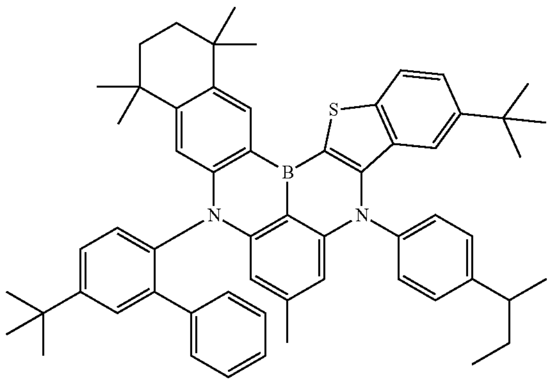
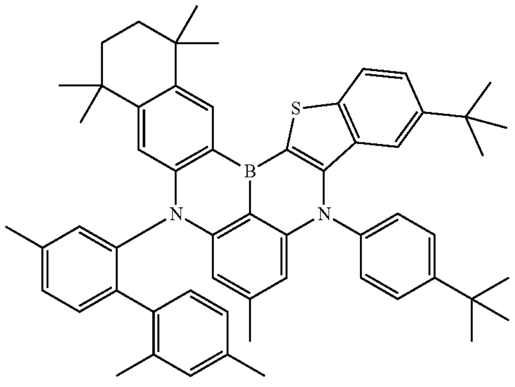

-continued
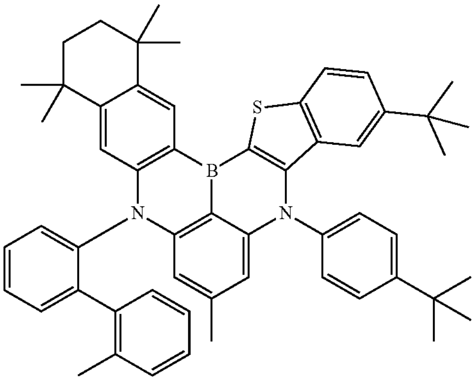
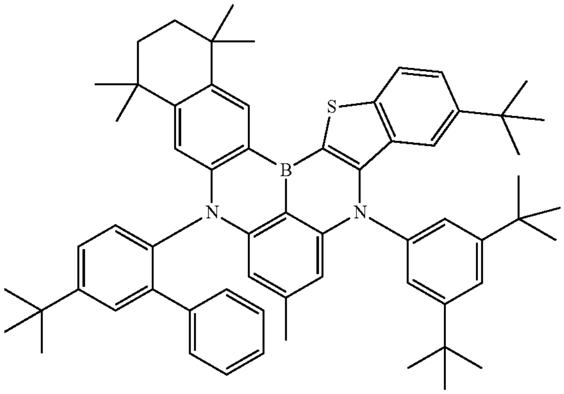
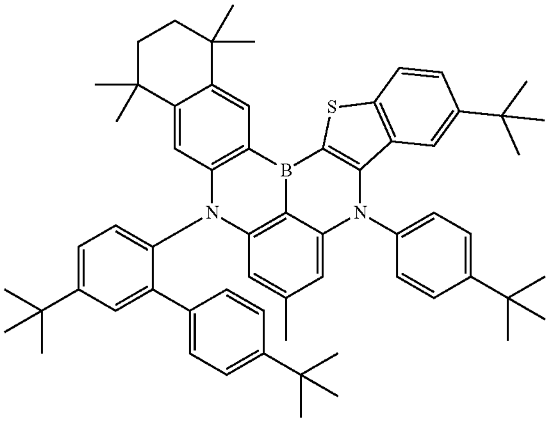
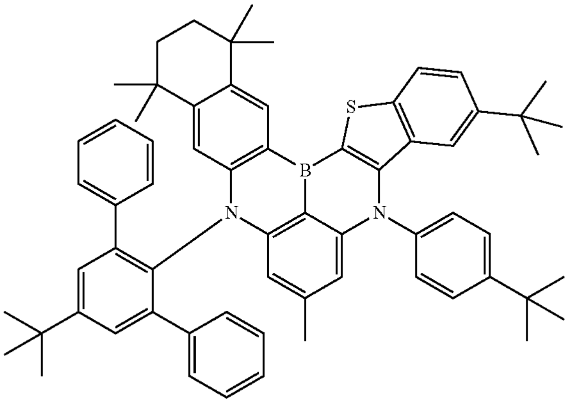
-continued
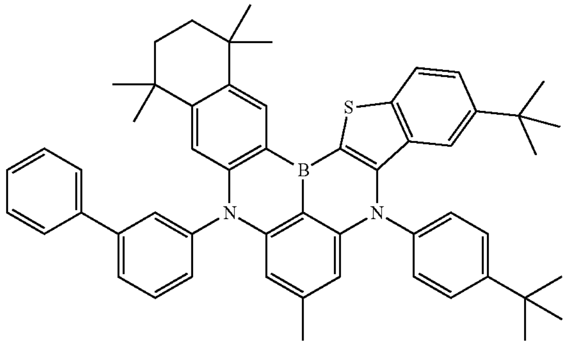
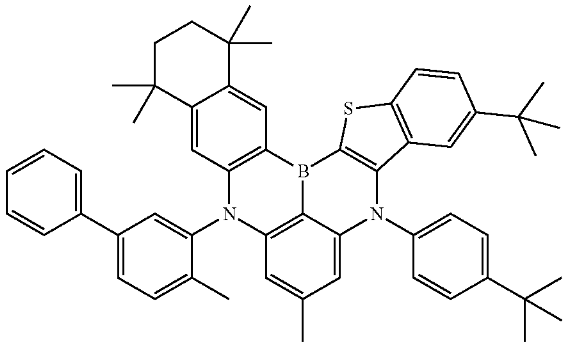
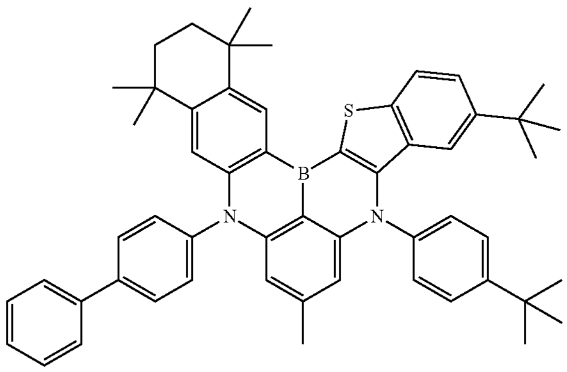
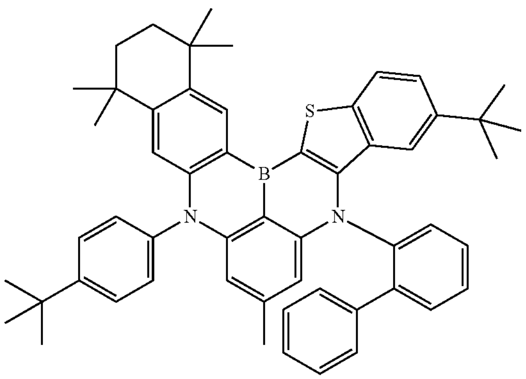

-continued
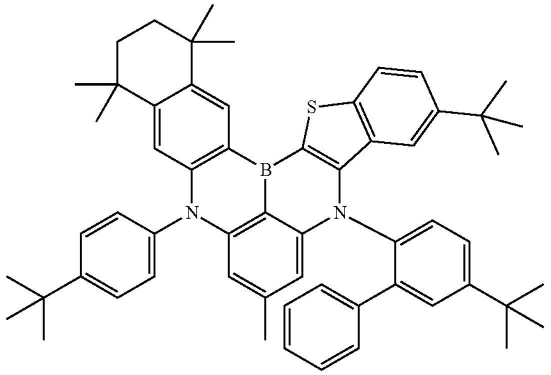
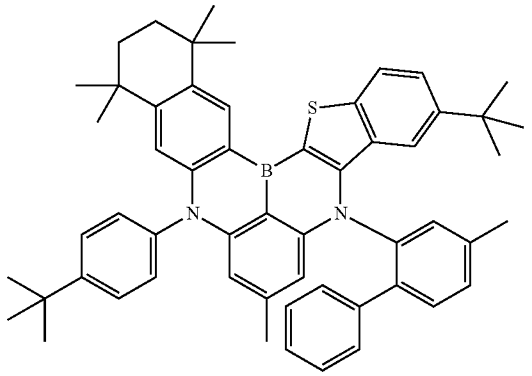
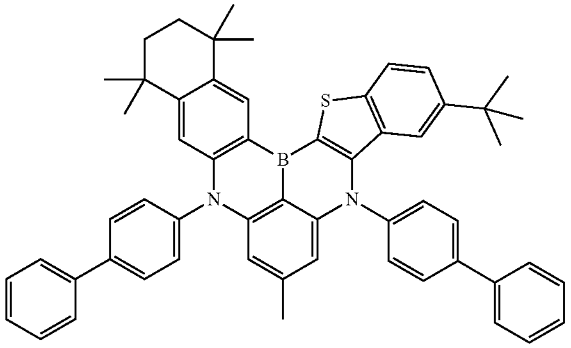
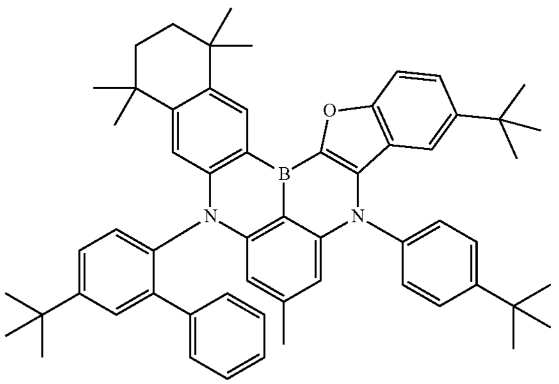
-continued
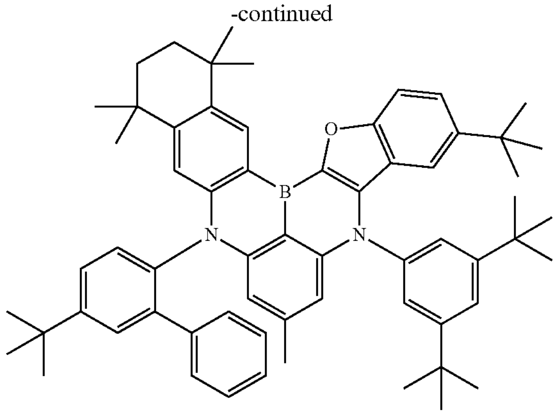
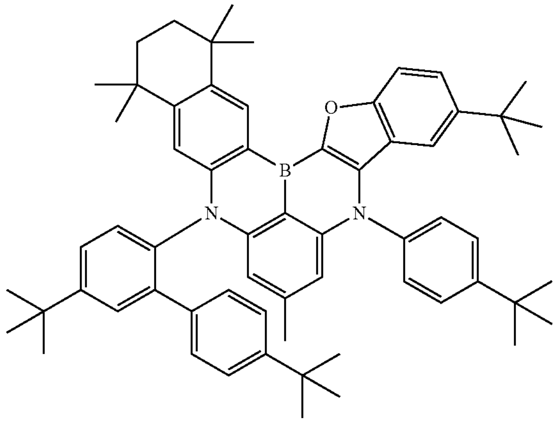
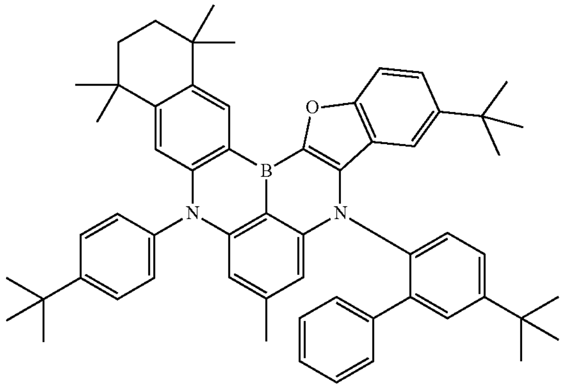
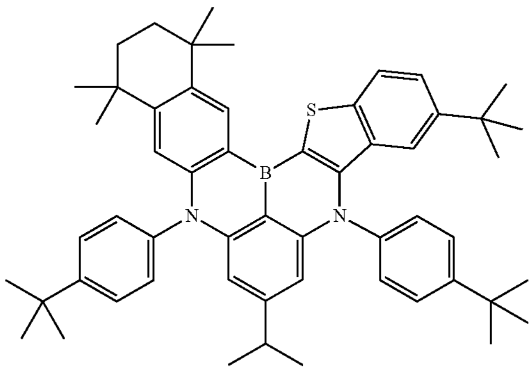

-continued
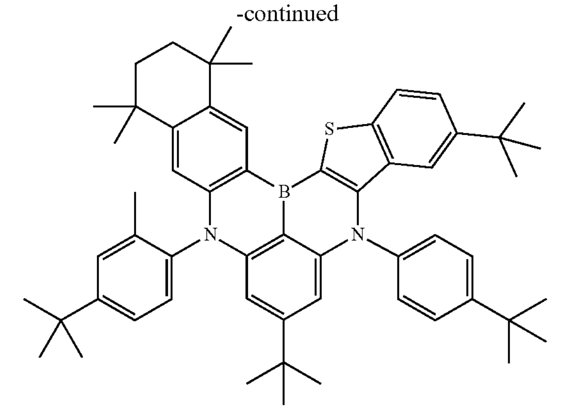
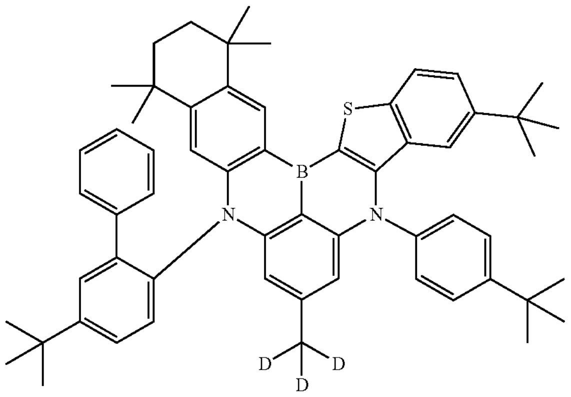
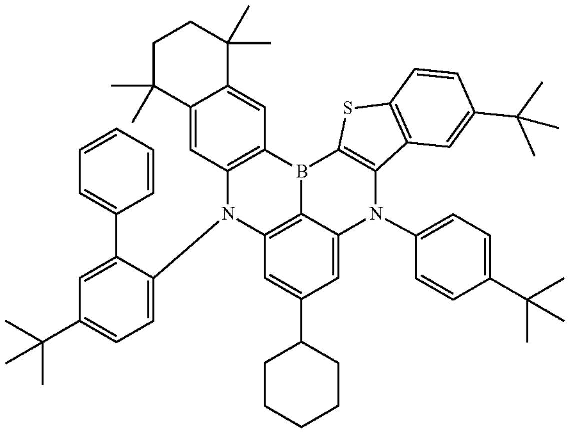
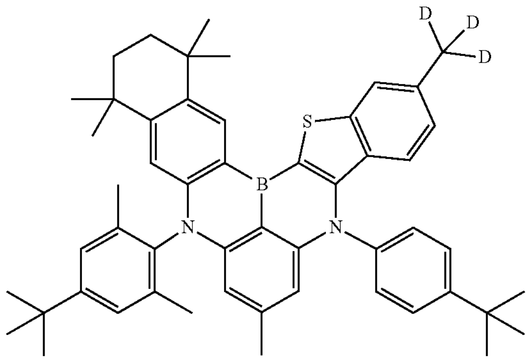
-continued
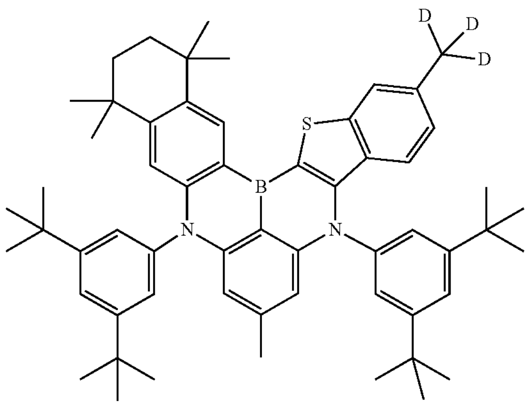
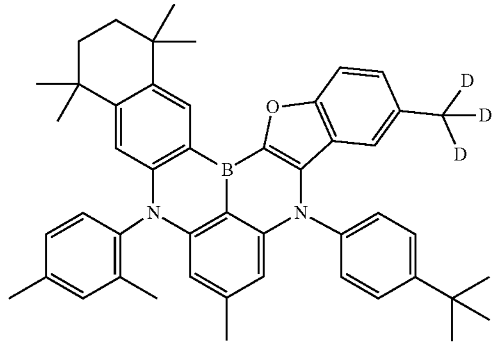
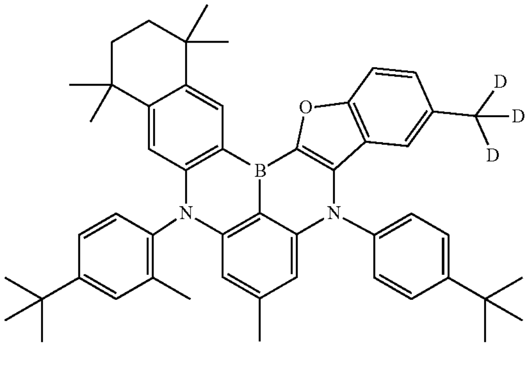
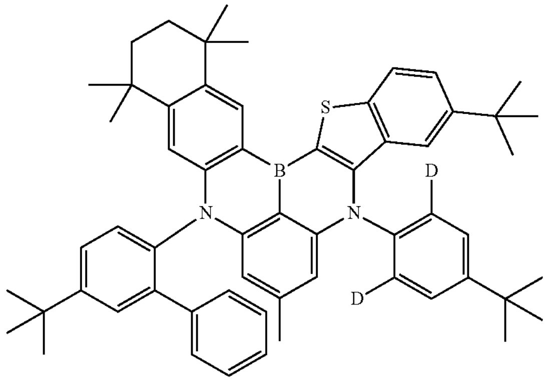

-continued
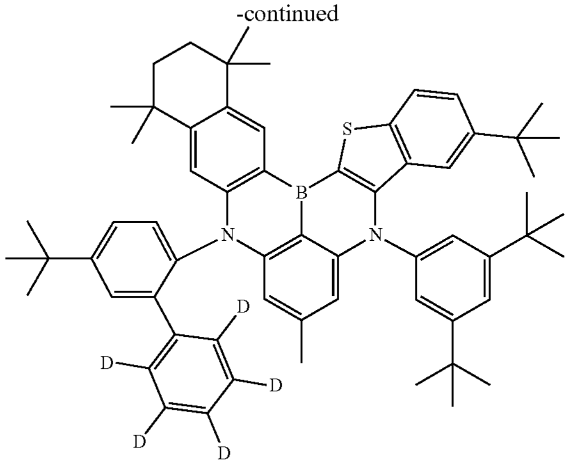
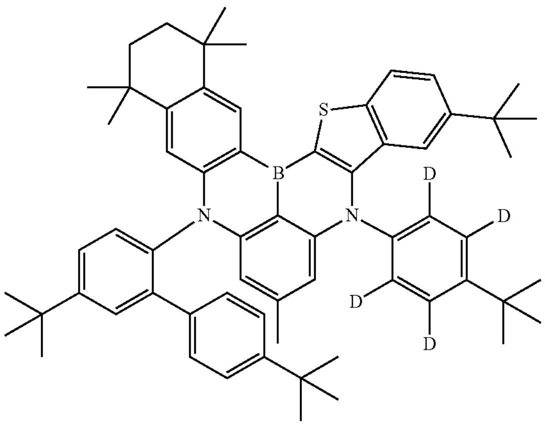
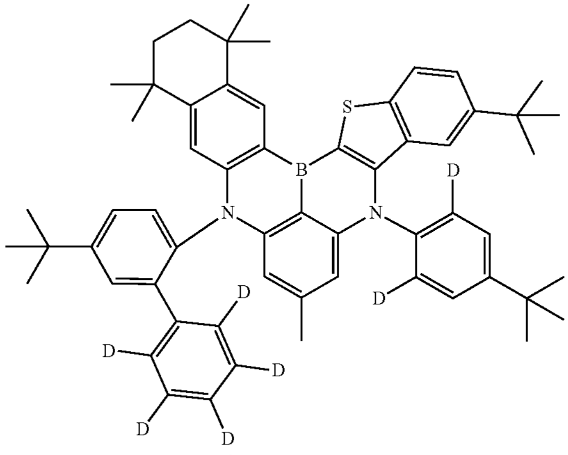
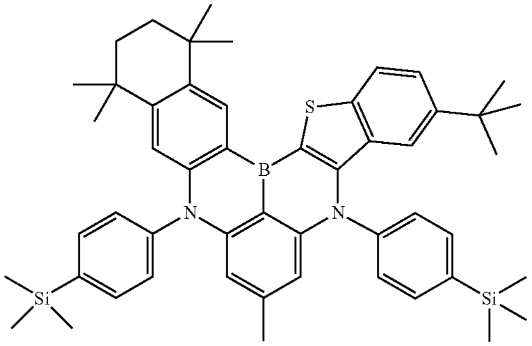
-continued
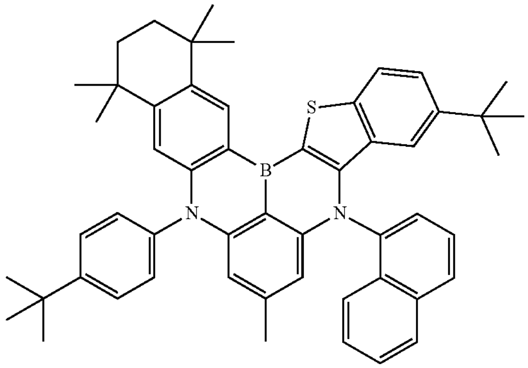
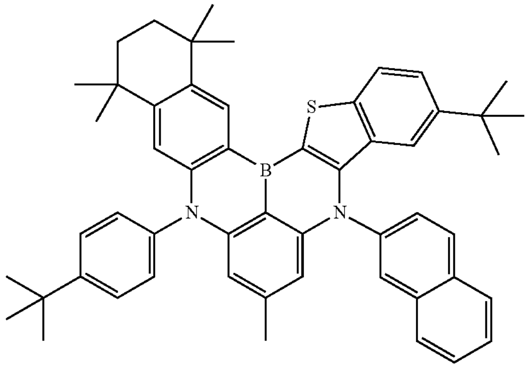
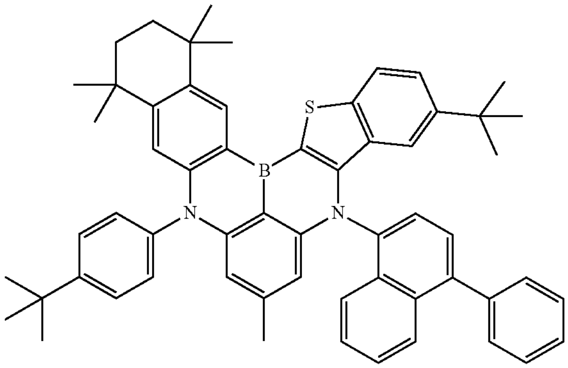
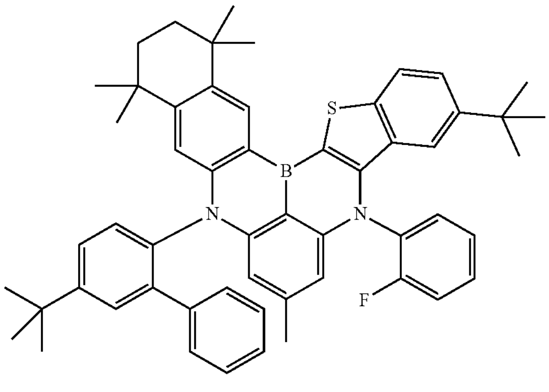

-continued
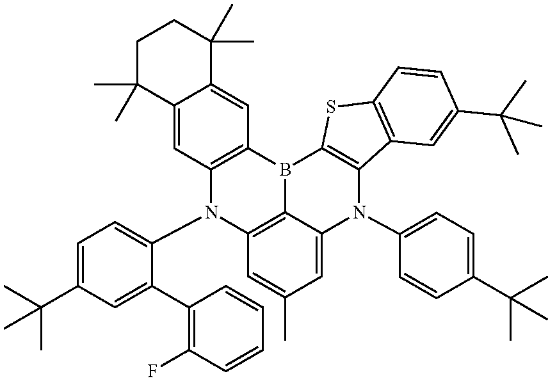
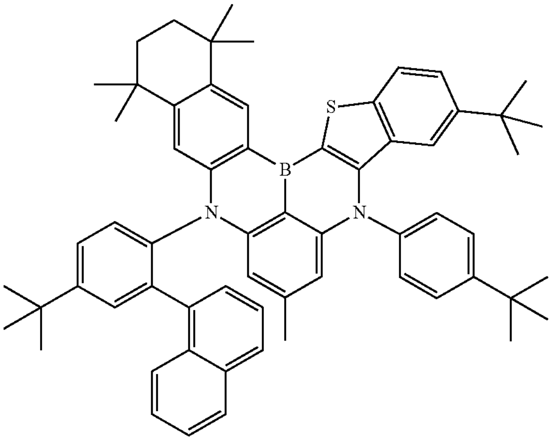
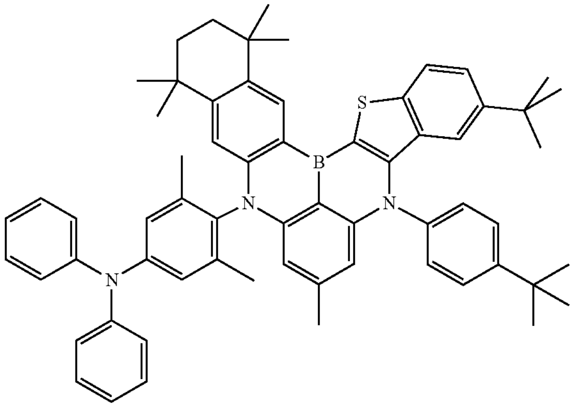
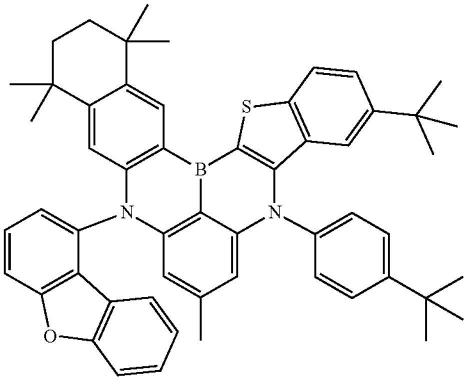
-continued
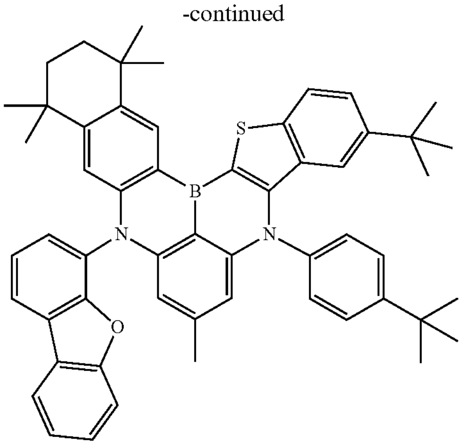
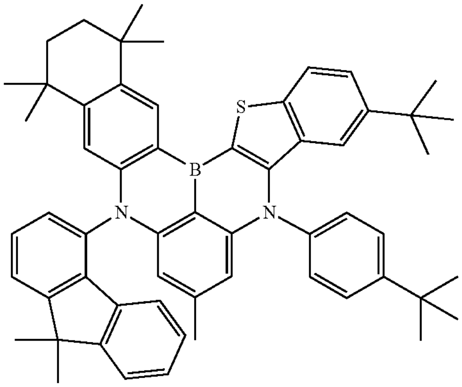
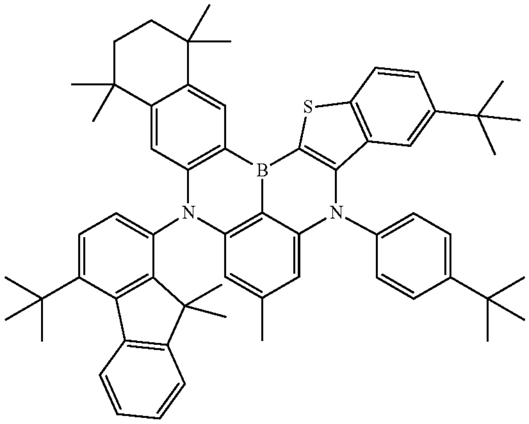
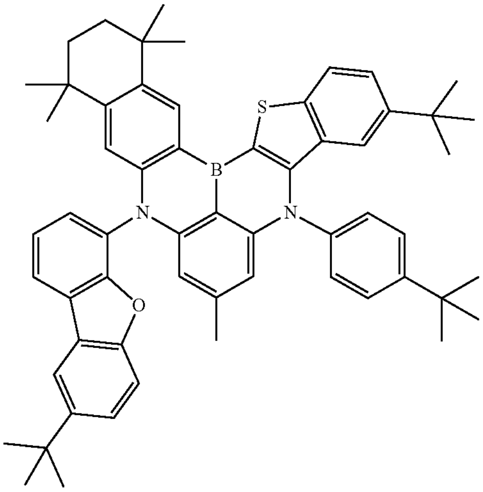

-continued
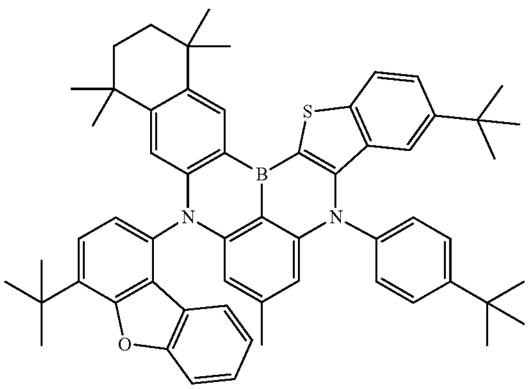
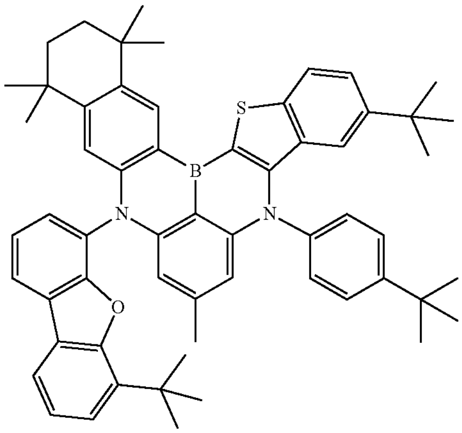
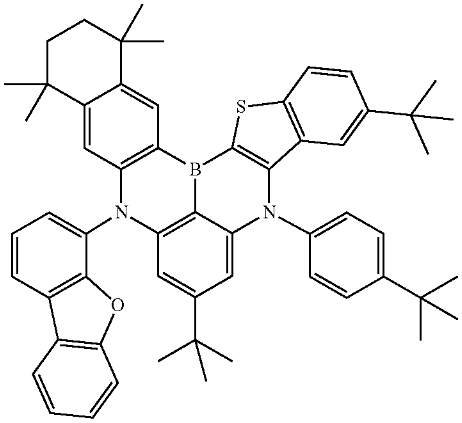
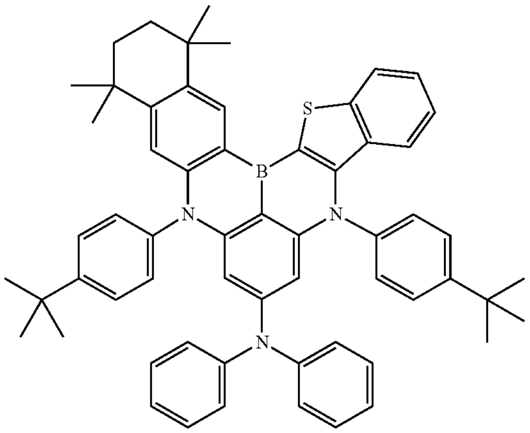
-continued
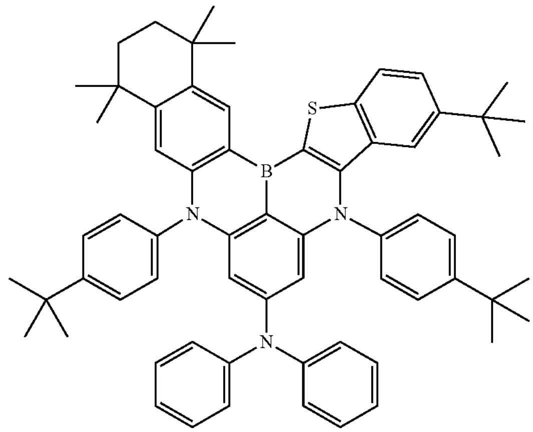
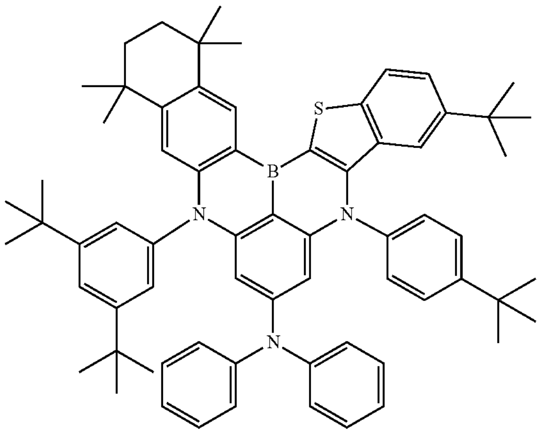
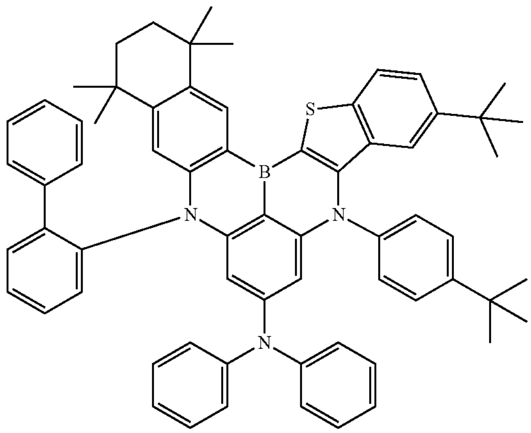

-continued
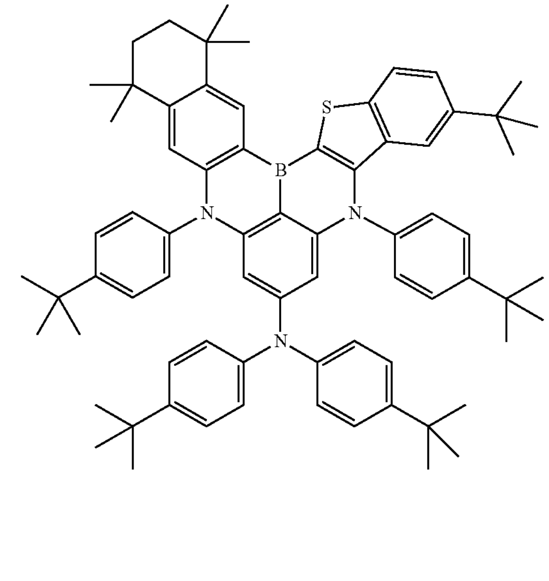
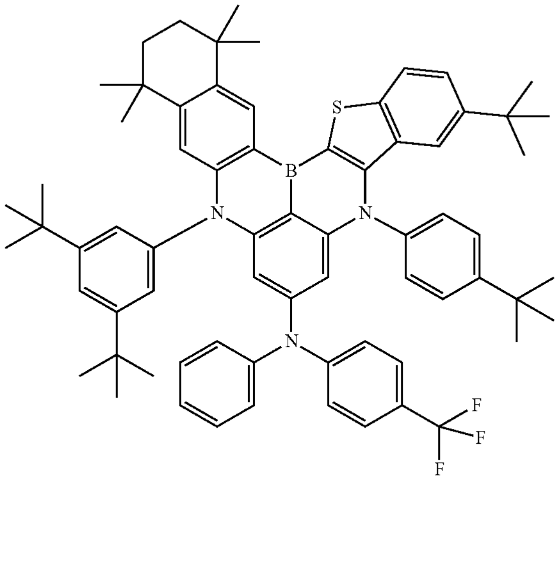
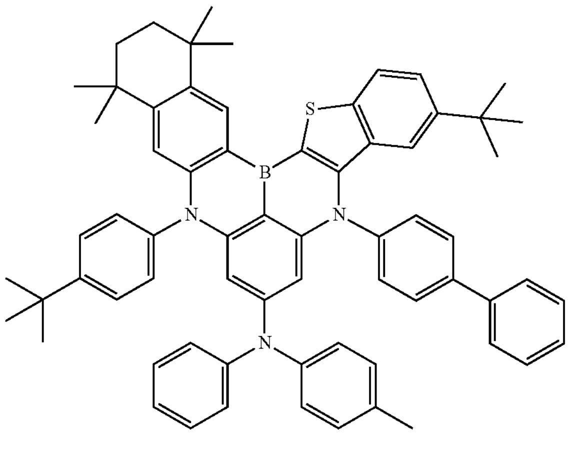
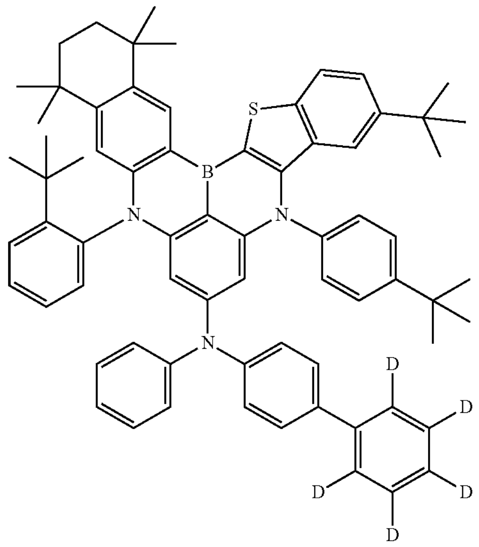
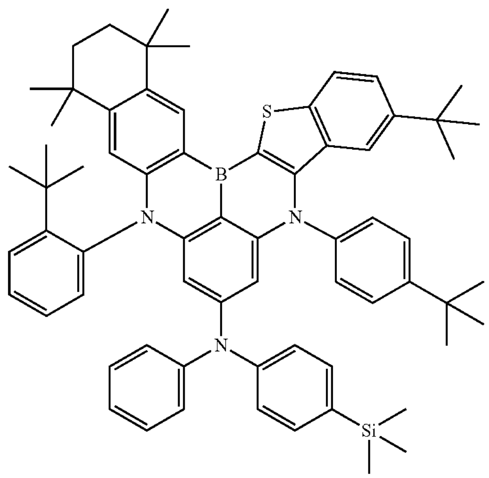
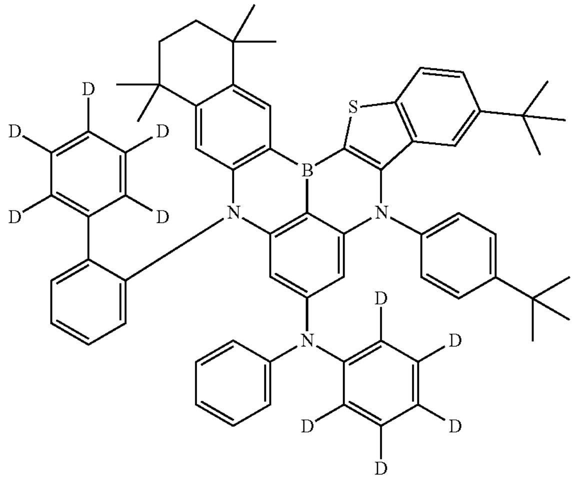
-continued -continued
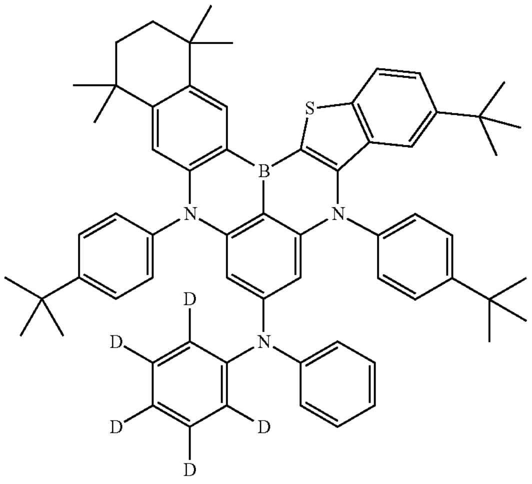
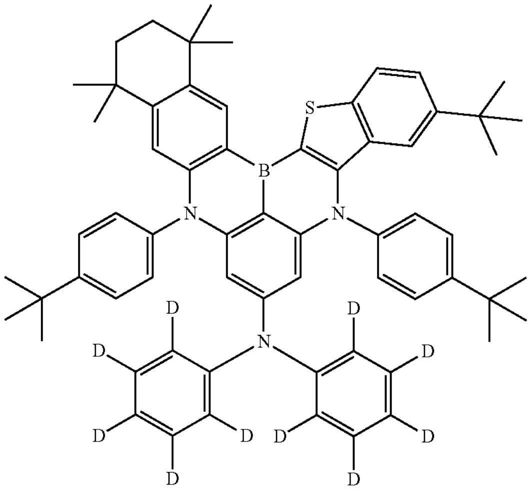
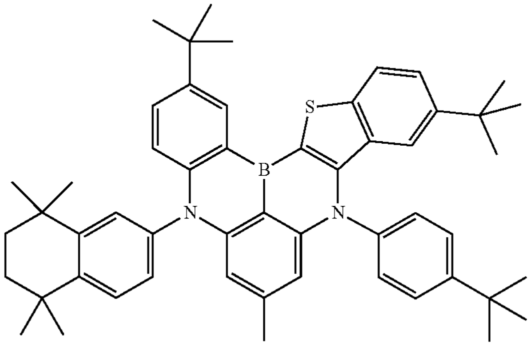
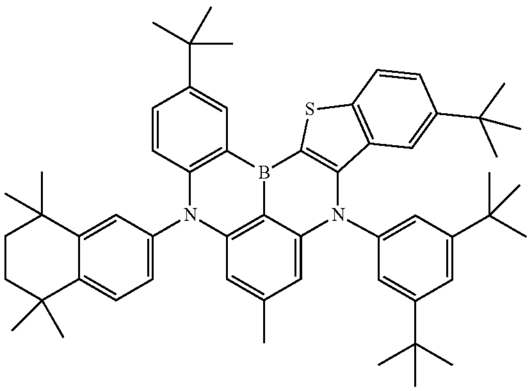
-continued
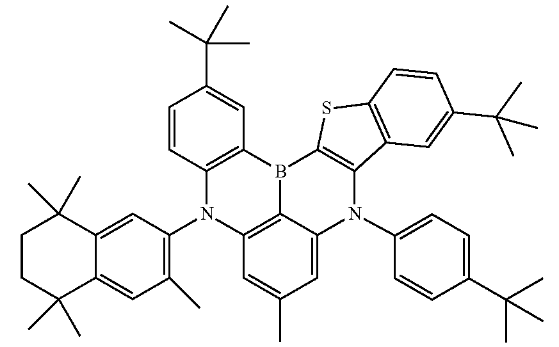
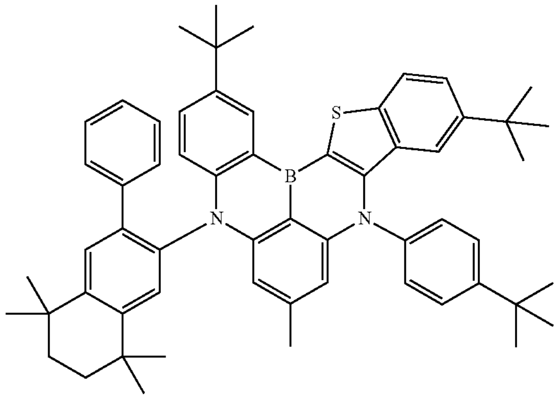
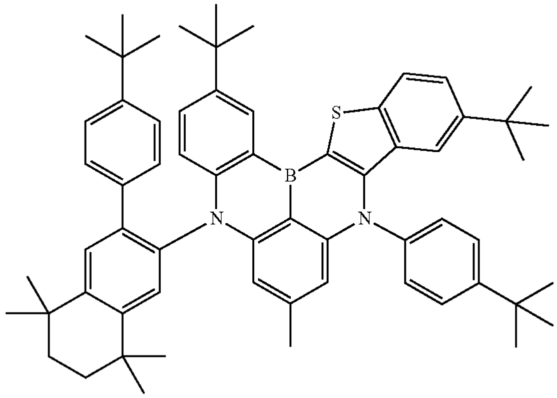
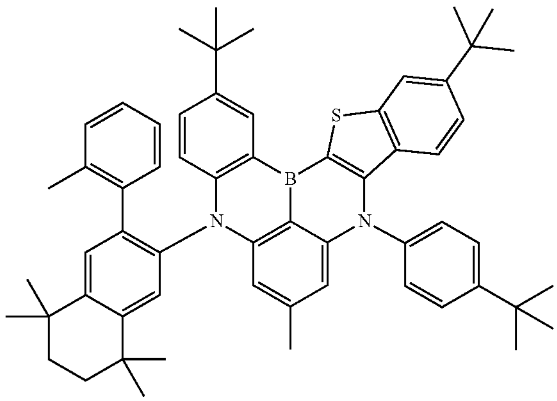

-continued
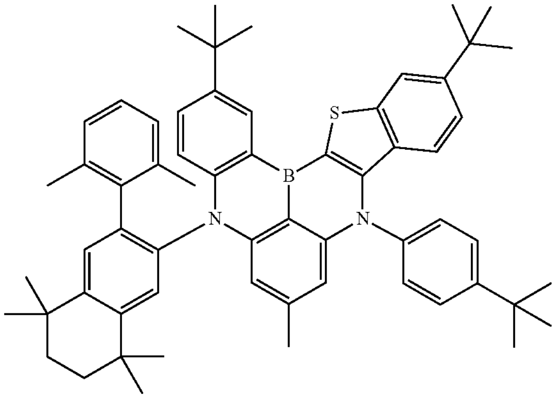
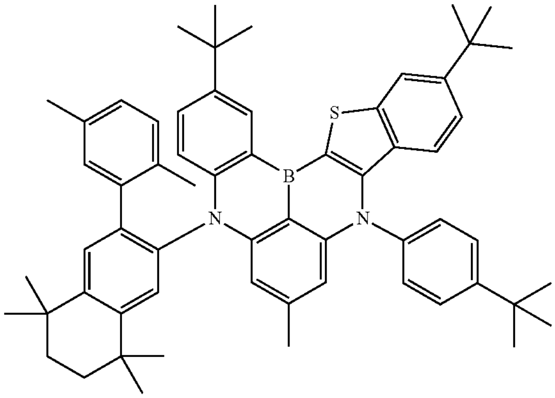
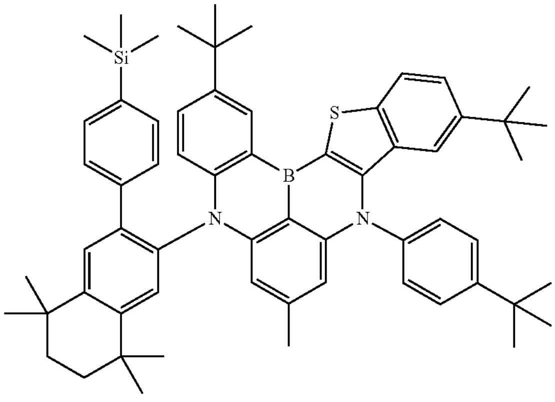
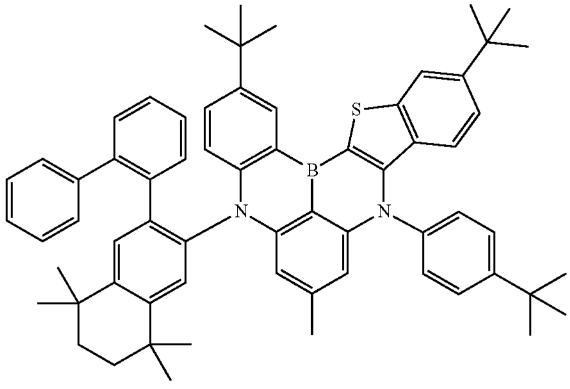
-continued
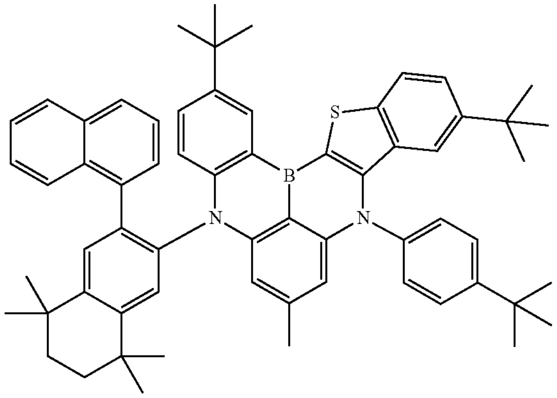
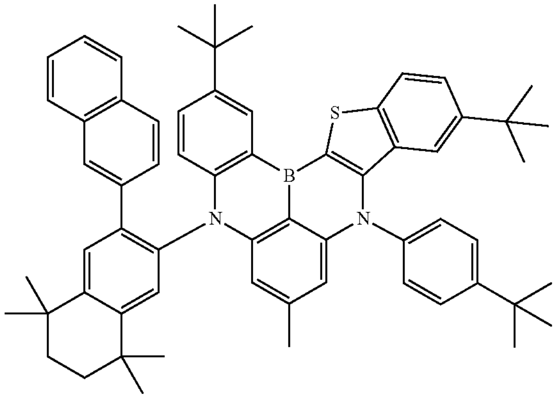
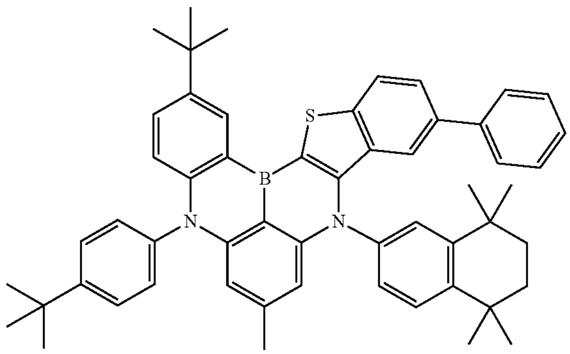
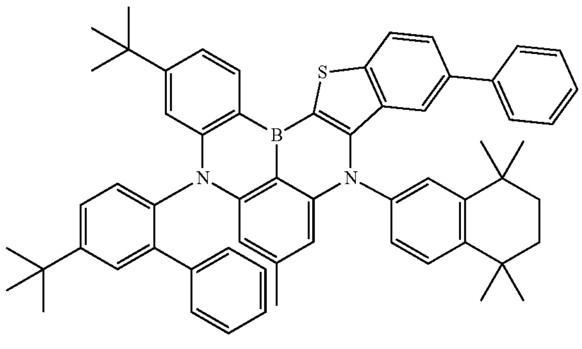

-continued
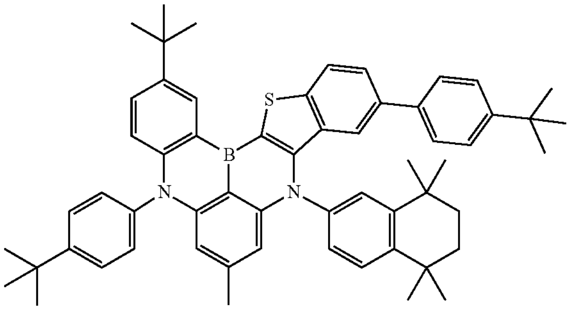
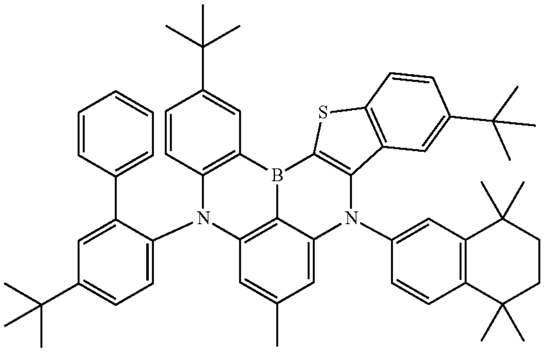
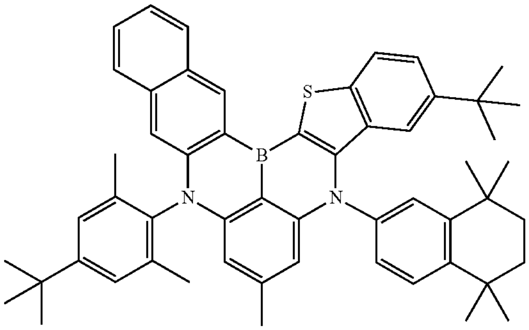
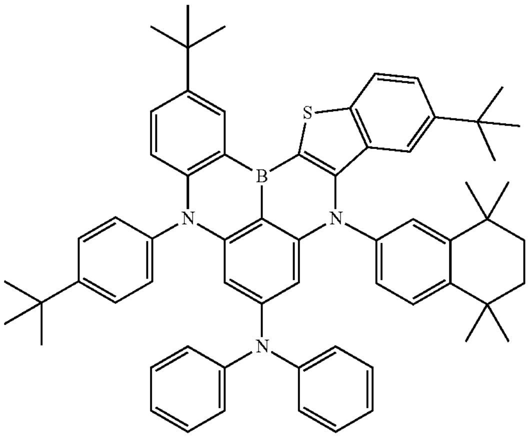
-continued
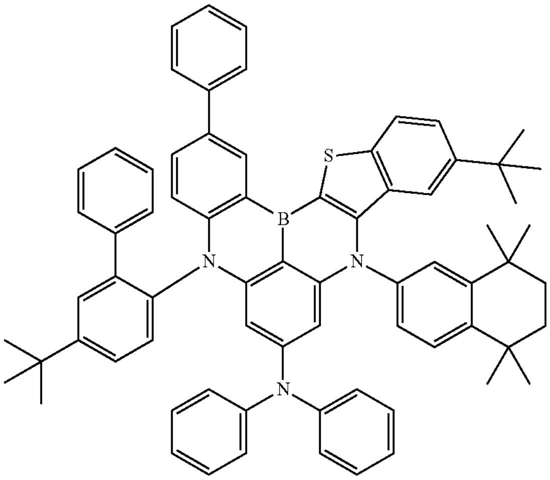
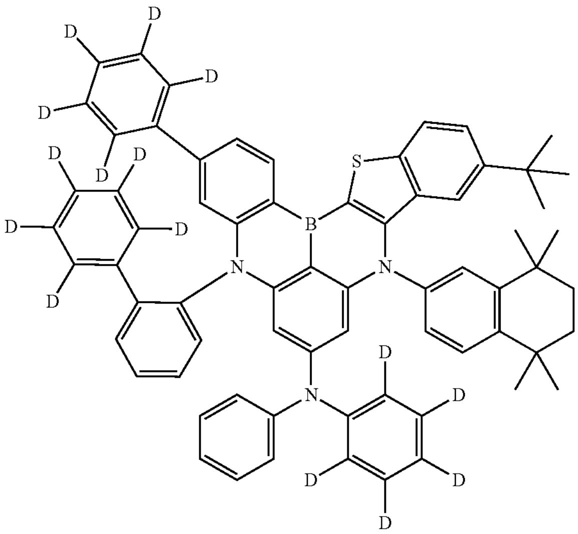
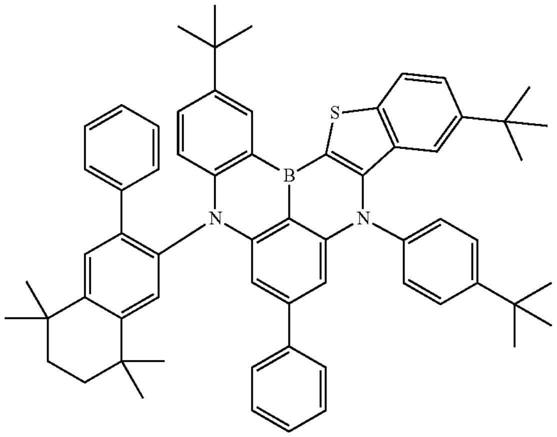

-continued
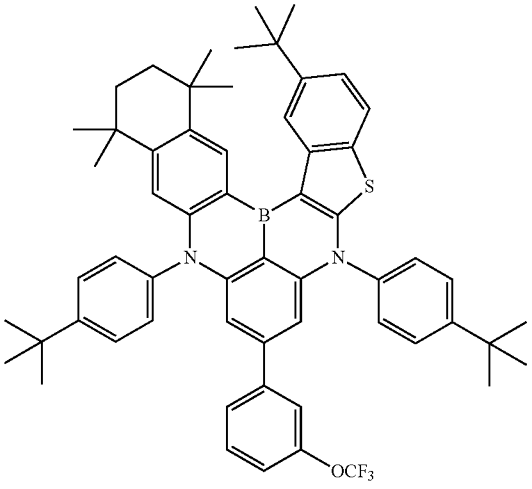
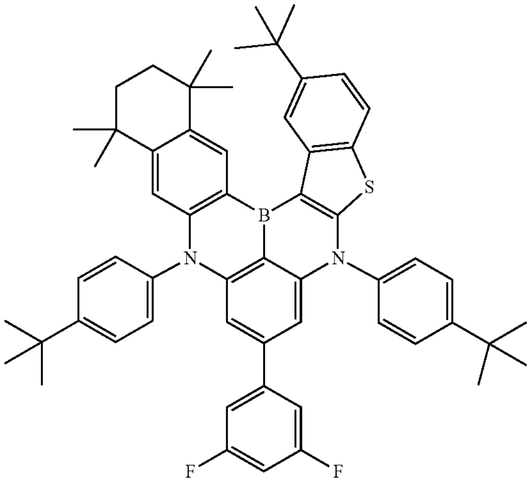
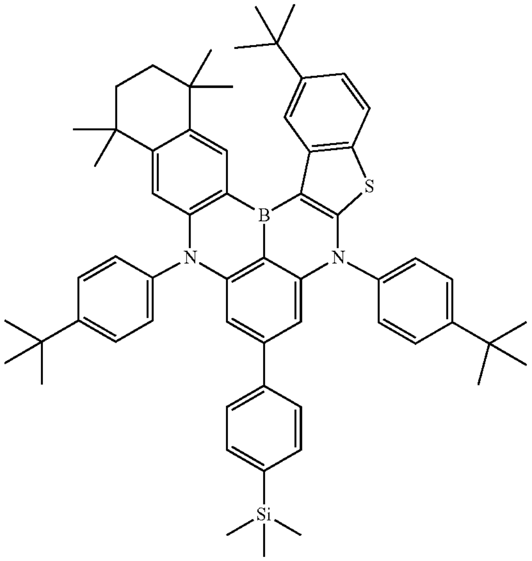
-continued
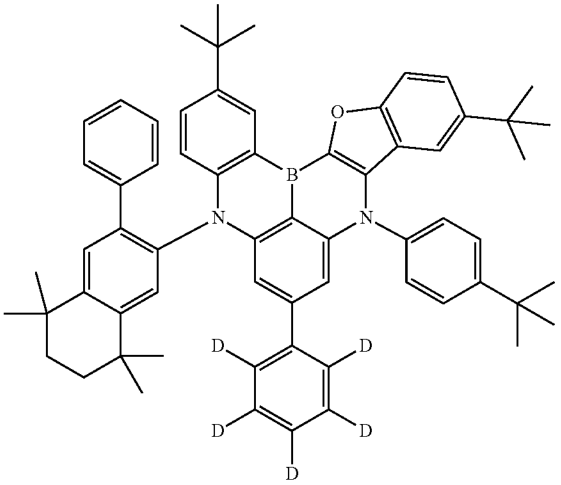
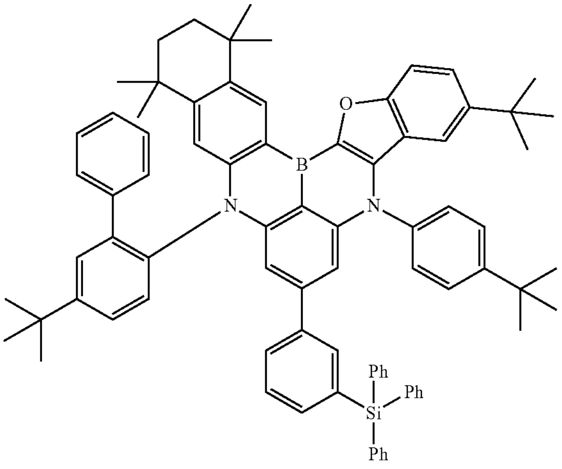
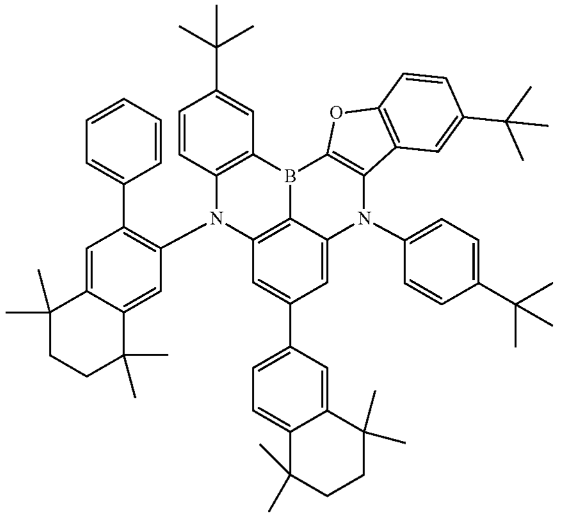

-continued
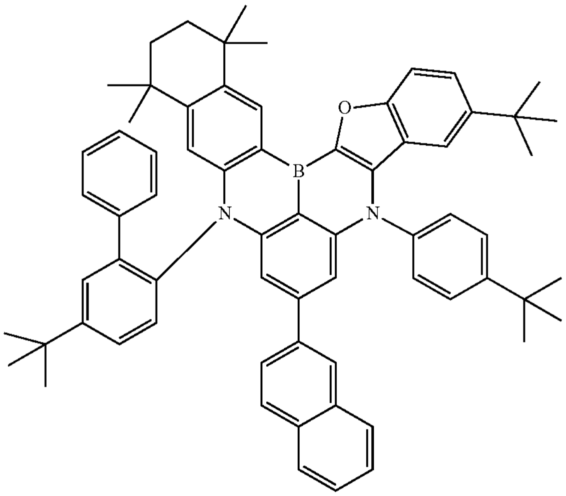
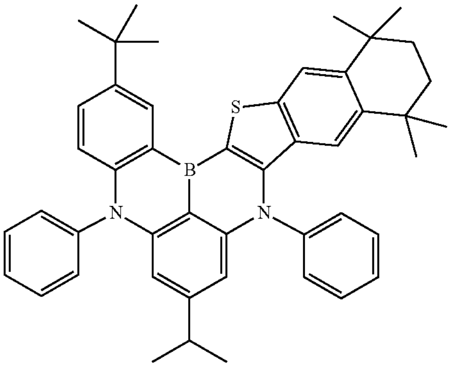
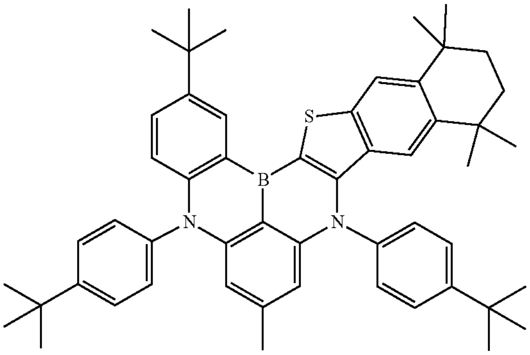
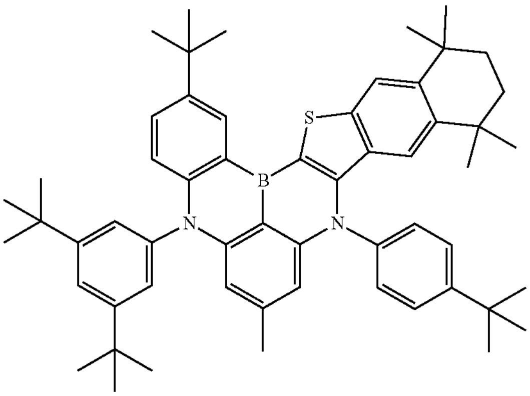
-continued
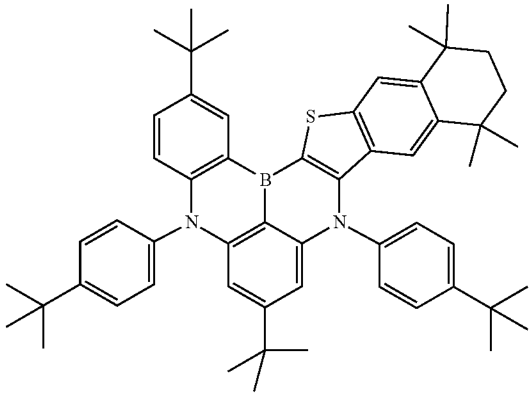
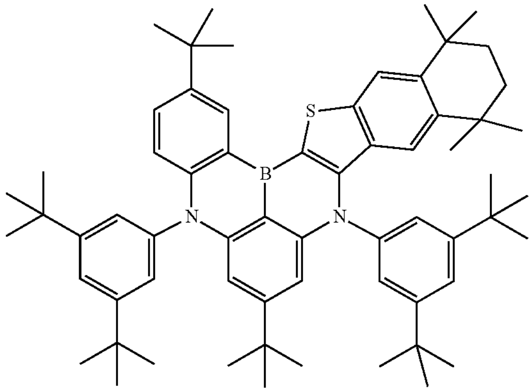
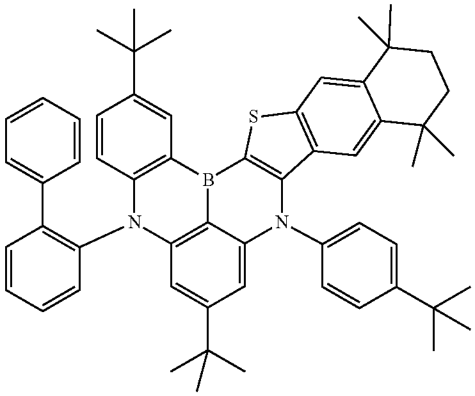
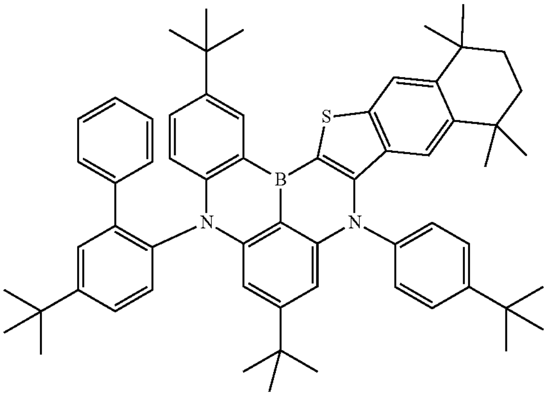

-continued
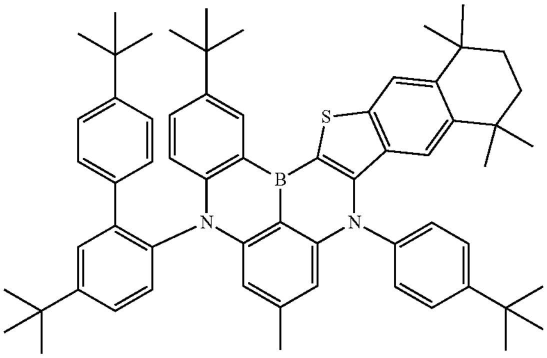
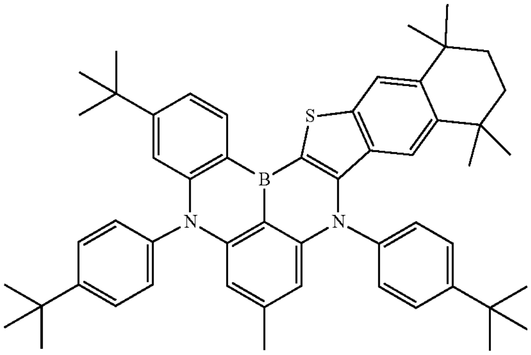
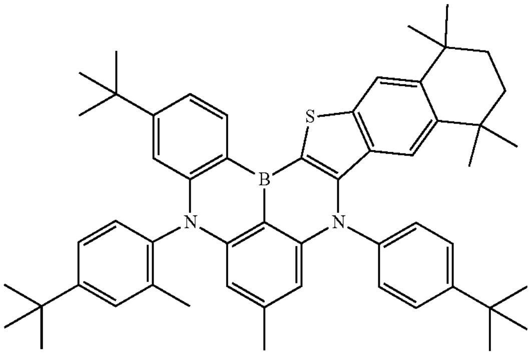
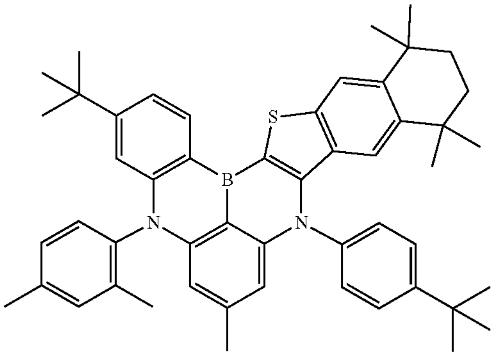
-continued
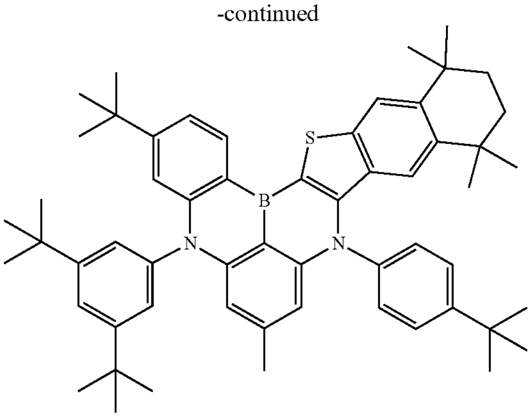
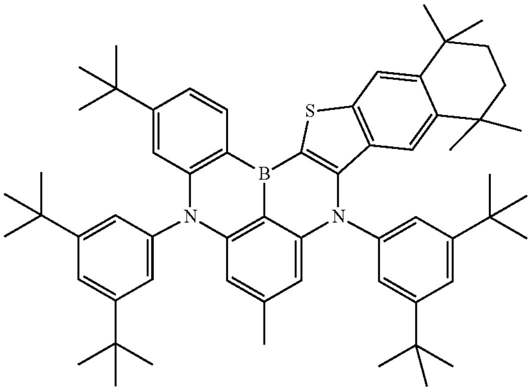
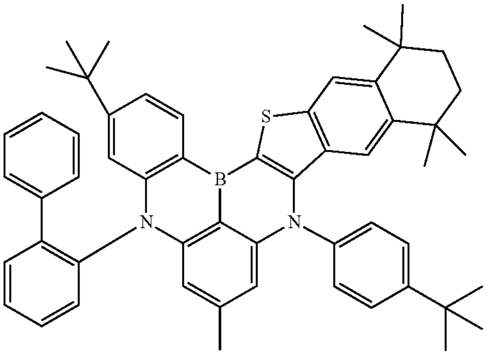
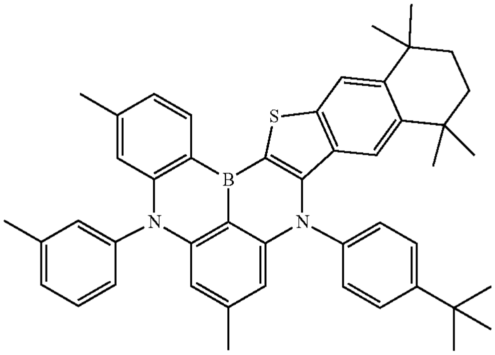

-continued
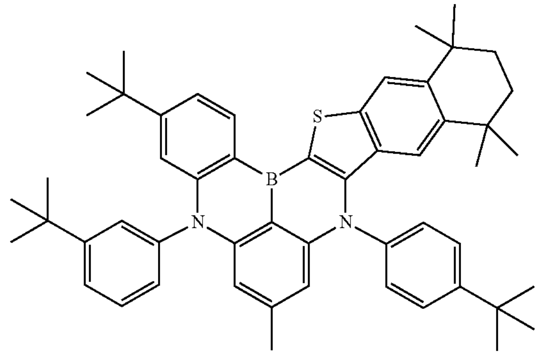
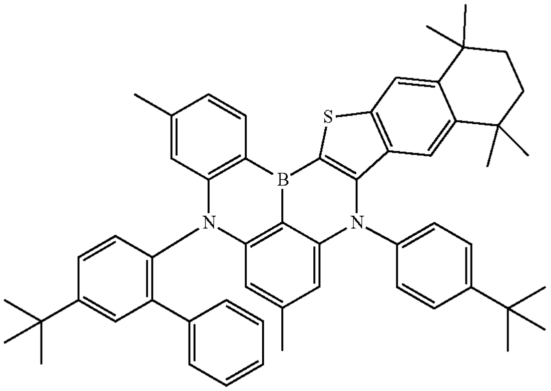
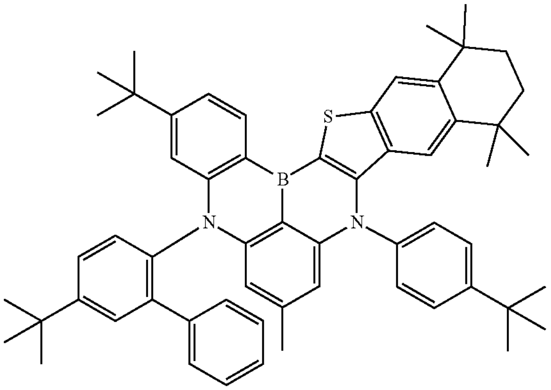
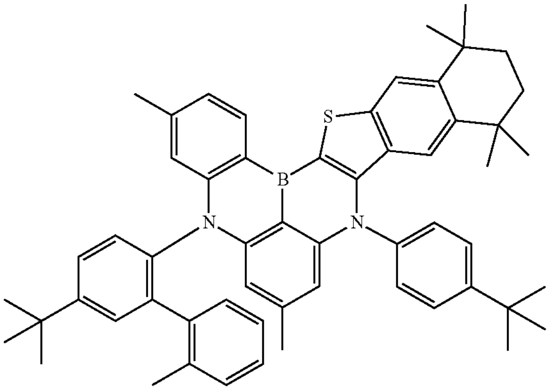
-continued
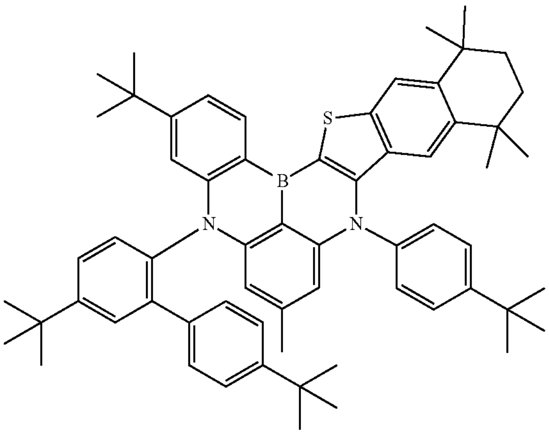
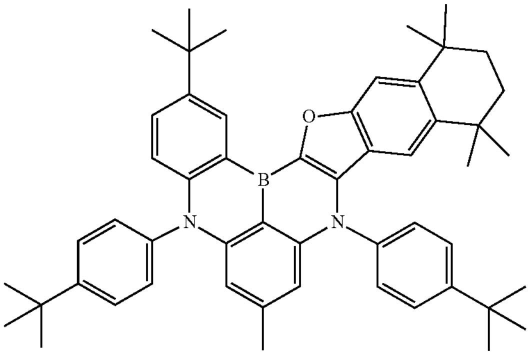
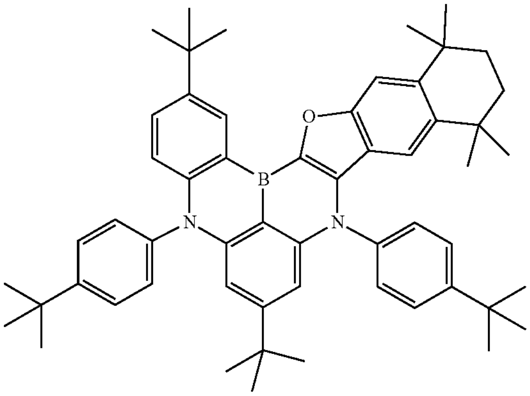
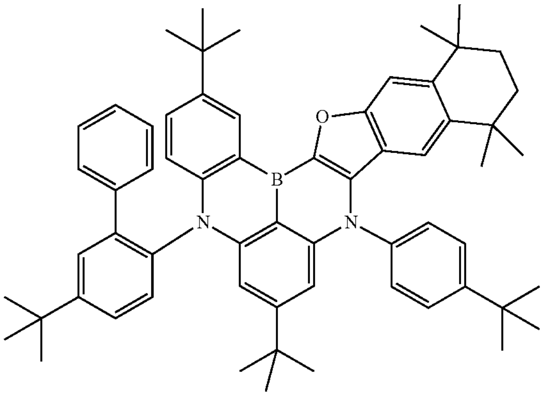

-continued
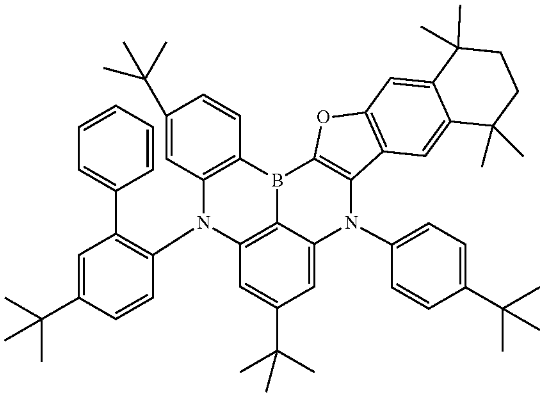
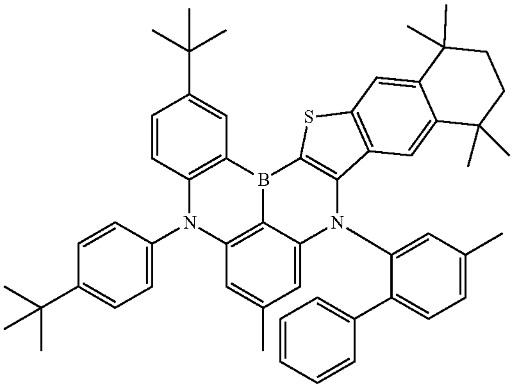
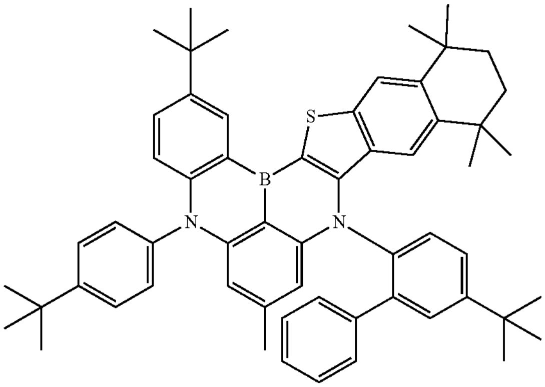
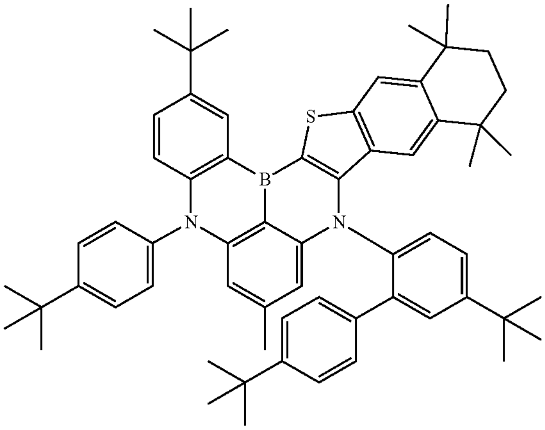
-continued
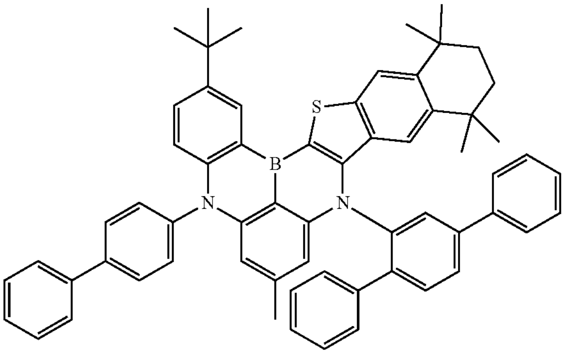
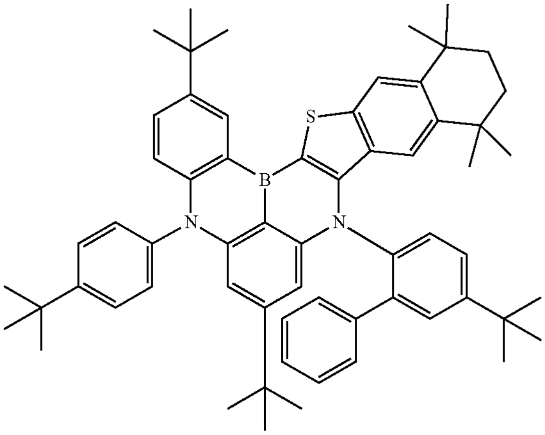
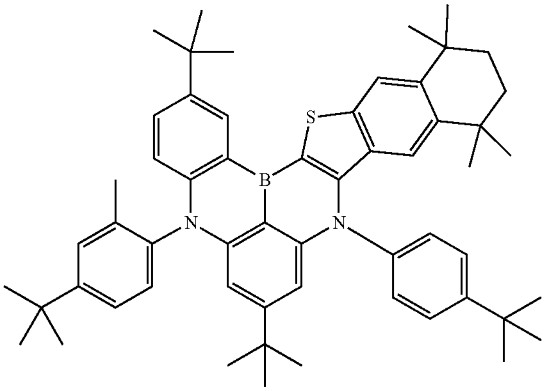
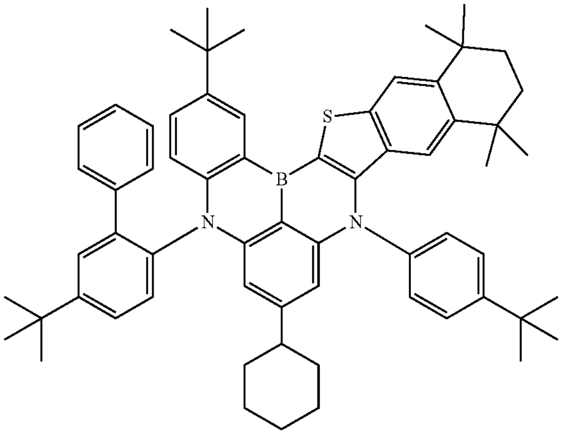

-continued
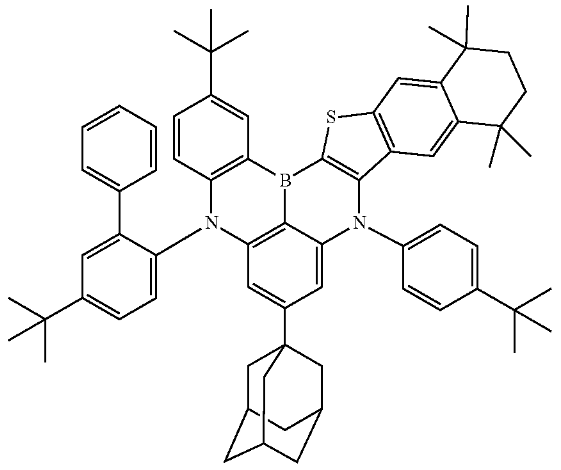
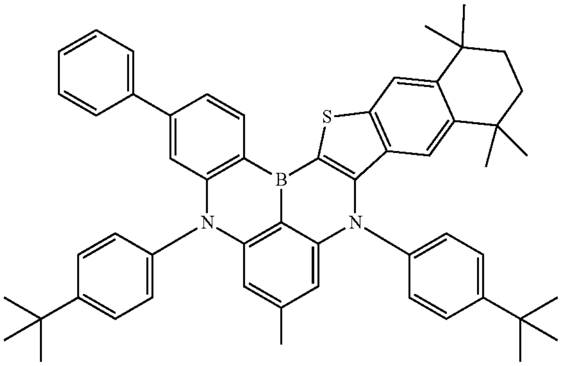
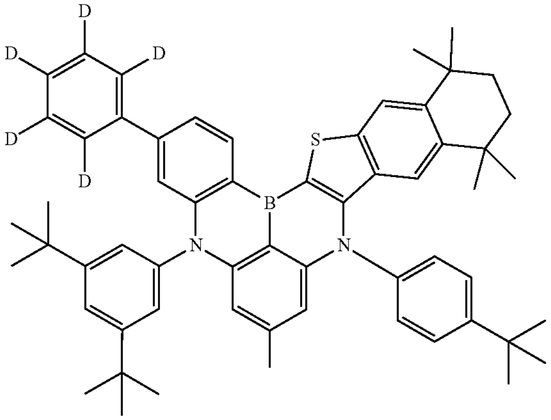
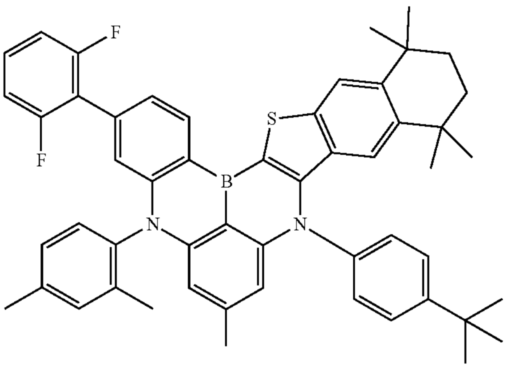
-continued
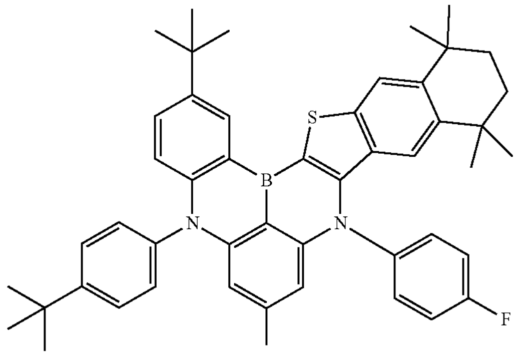
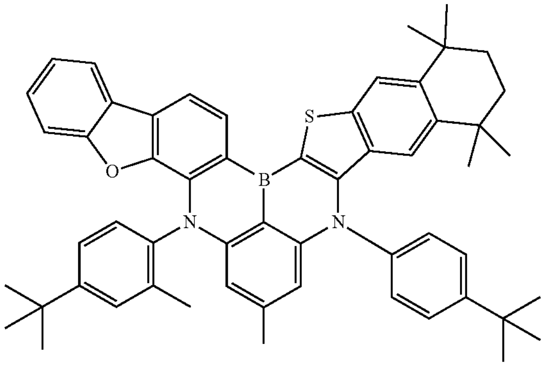
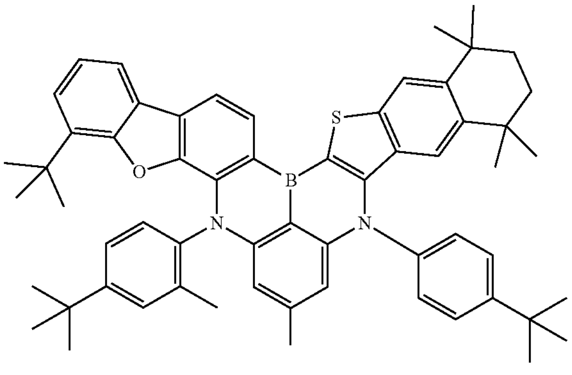
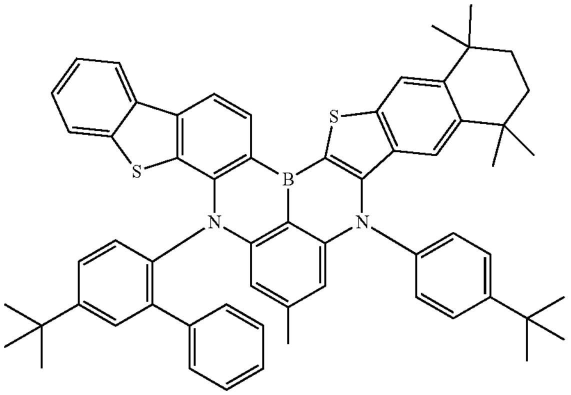

-continued
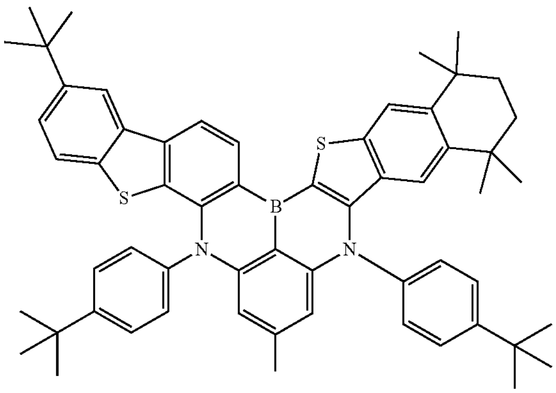
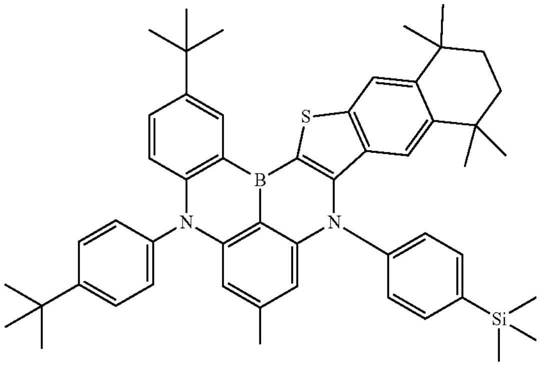
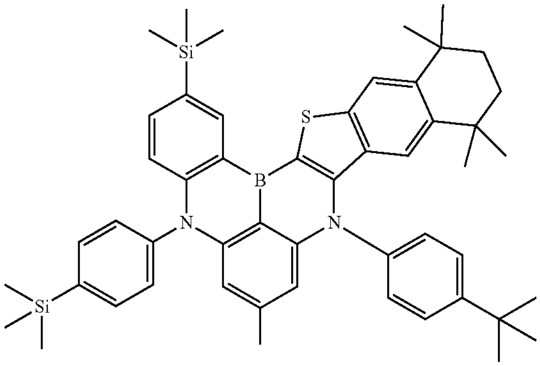
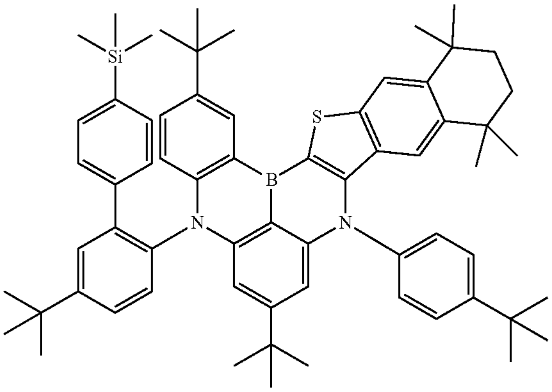
-continued
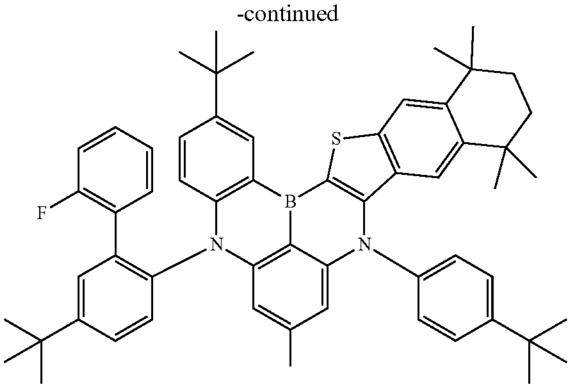
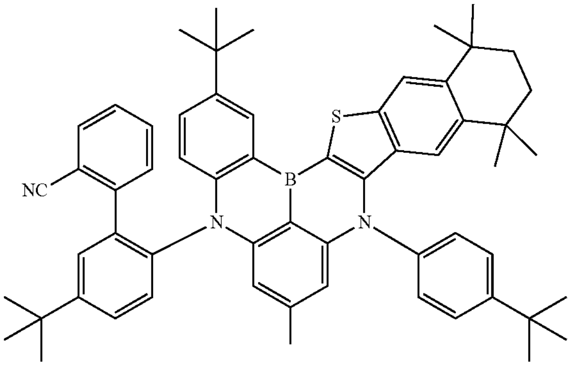
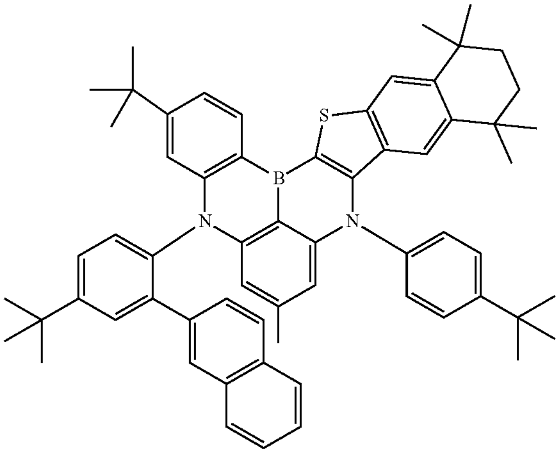
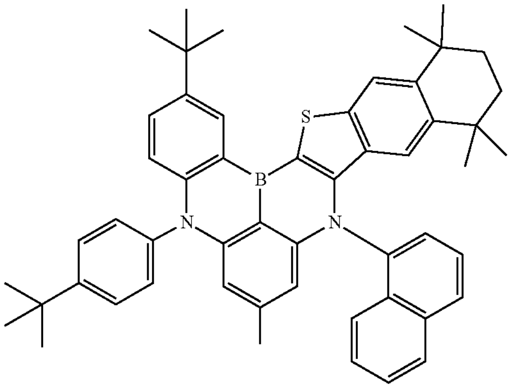

-continued
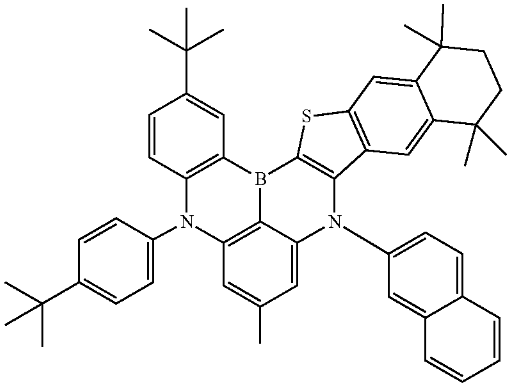
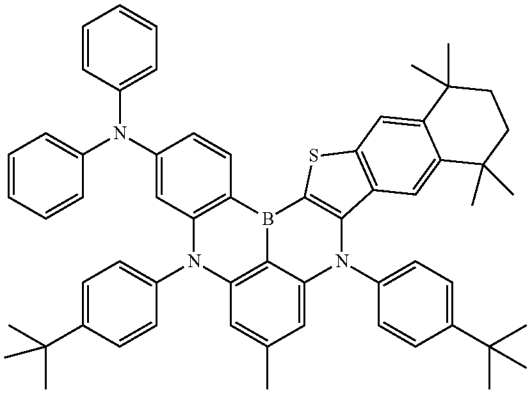
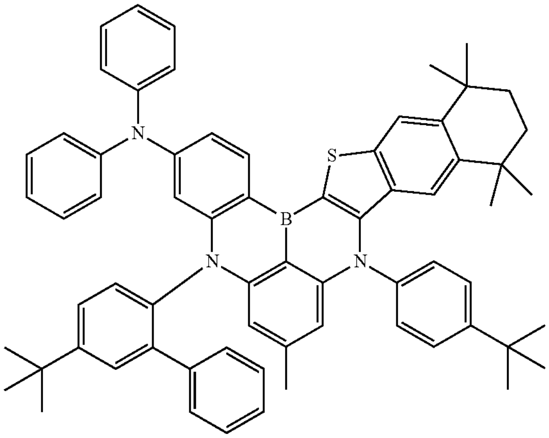
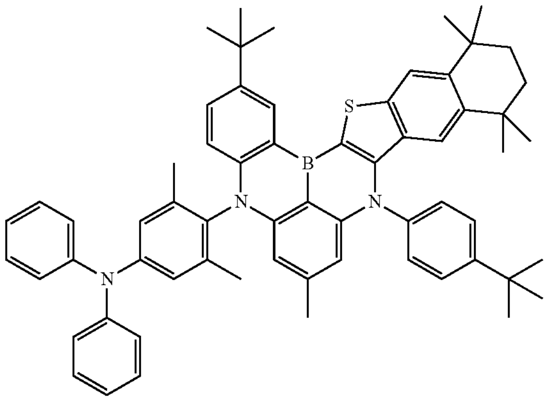
-continued
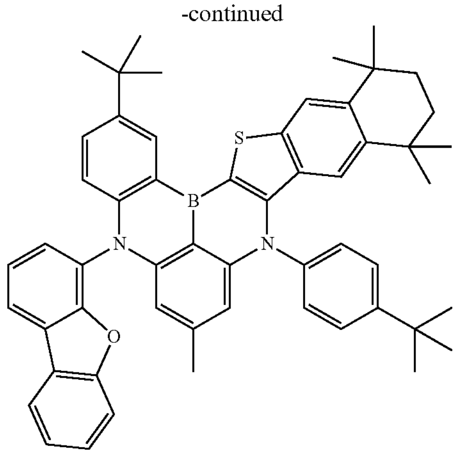
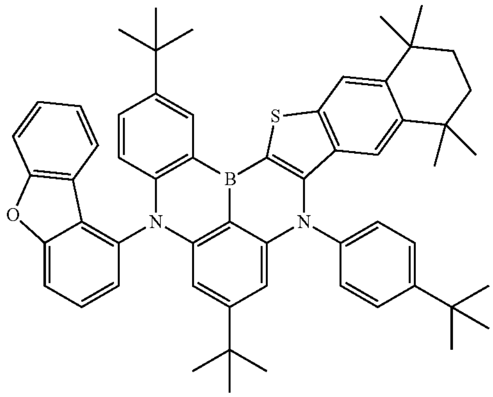
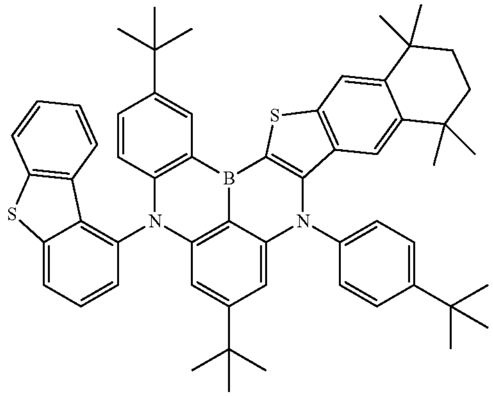
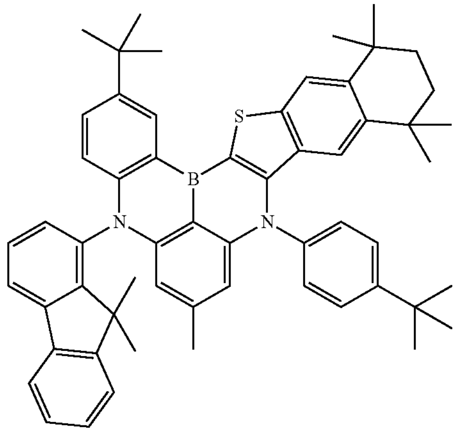

-continued
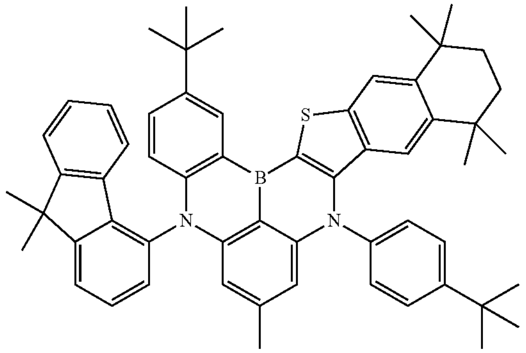
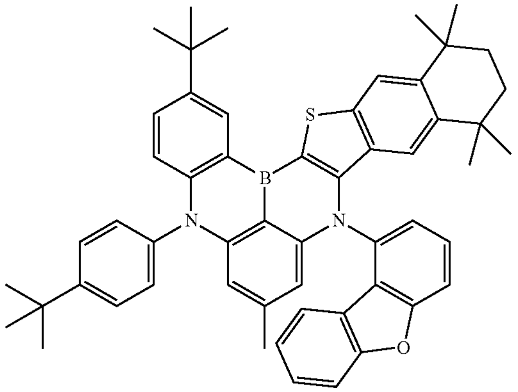
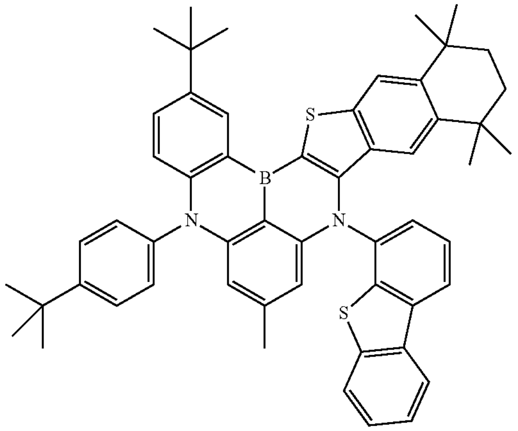
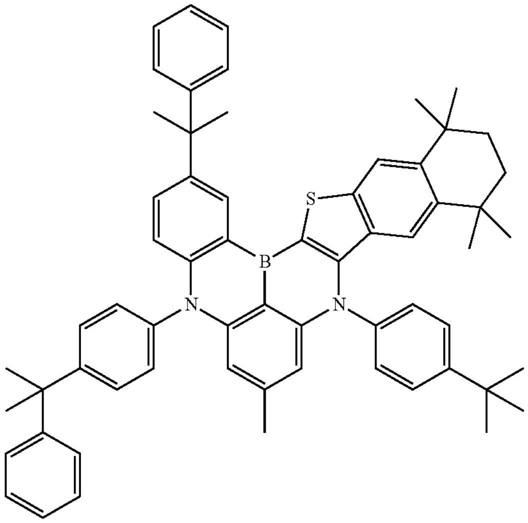
-continued
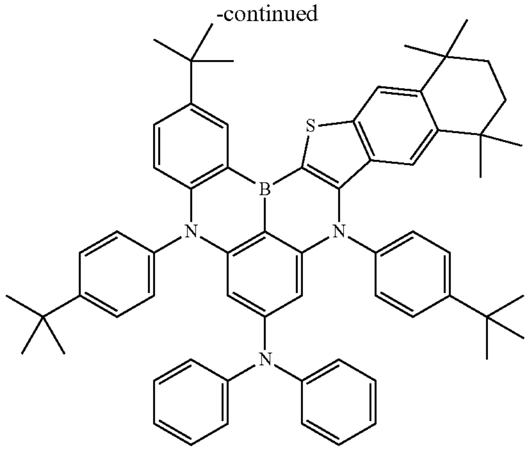
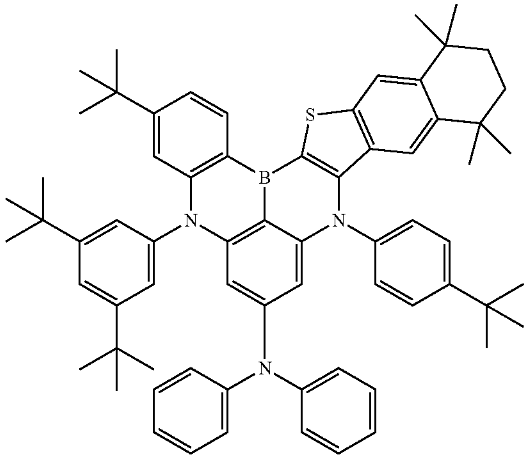
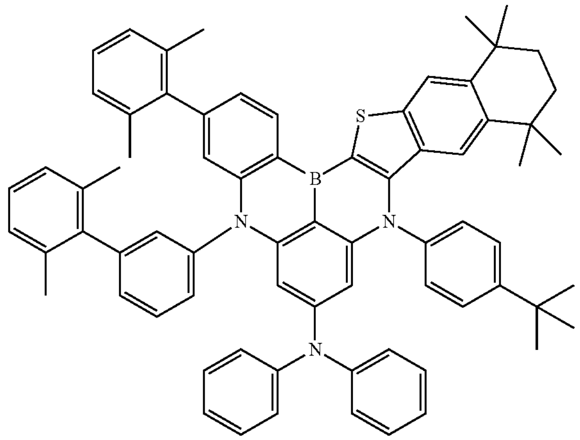

-continued
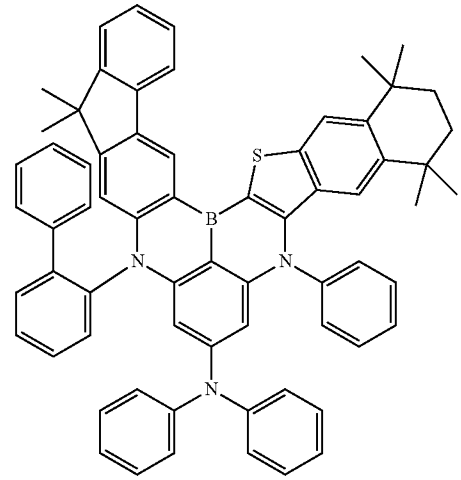
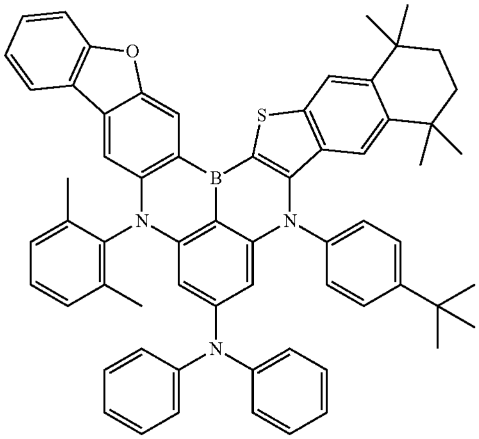
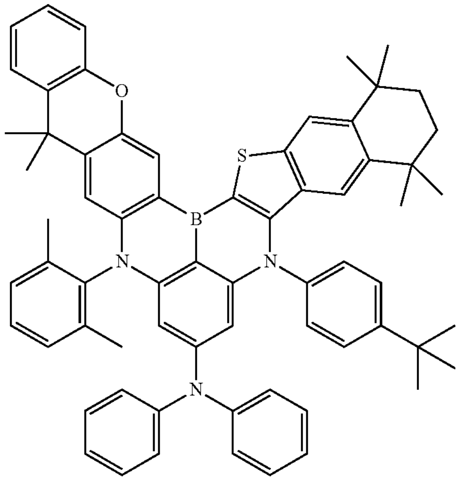
-continued
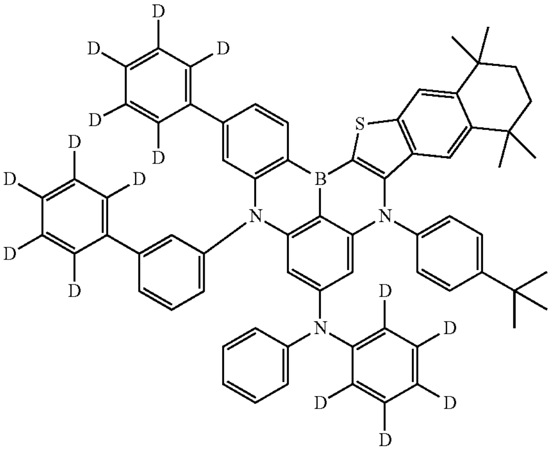
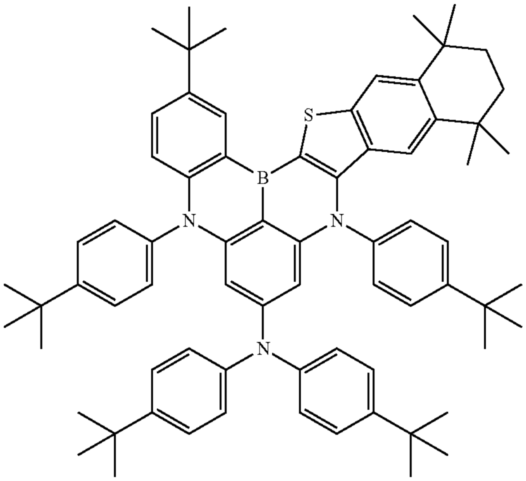
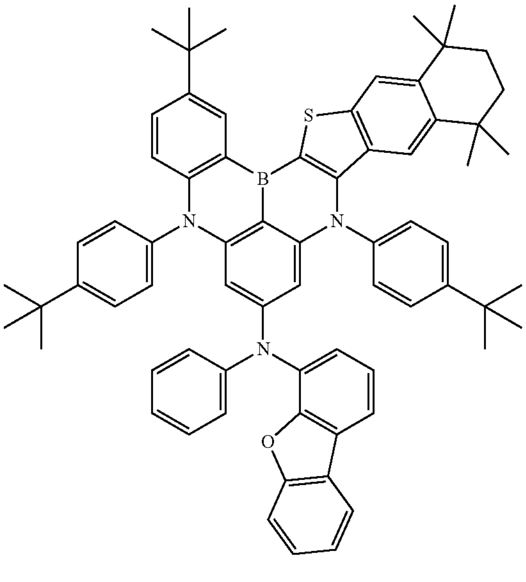

-continued
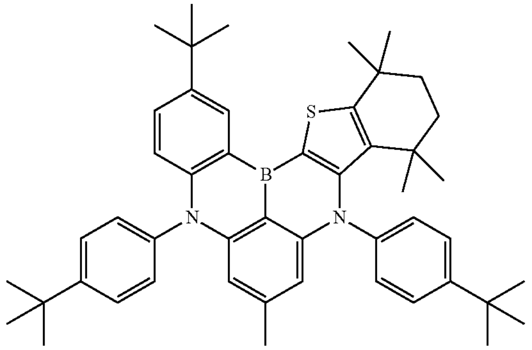
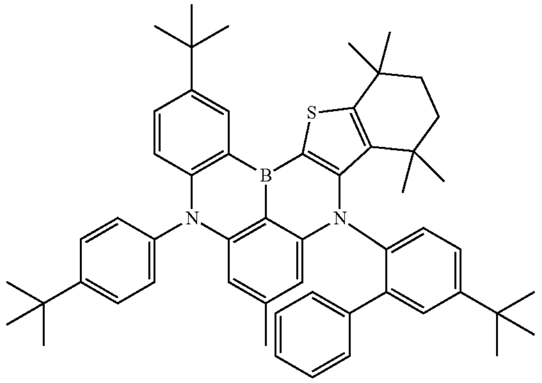
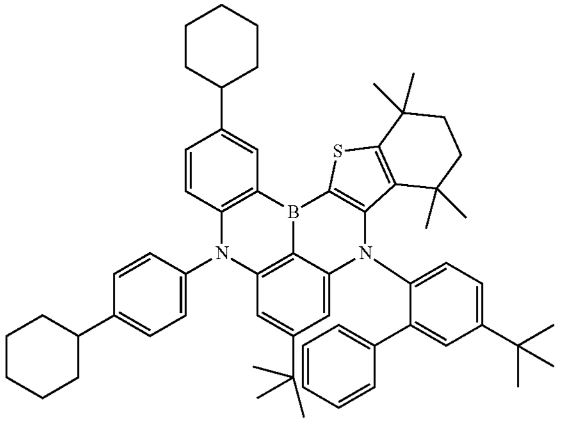
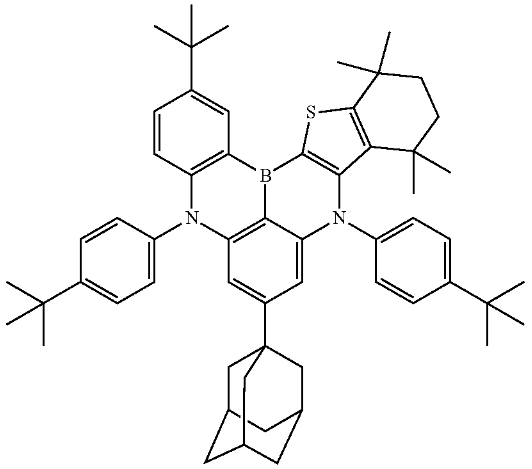
-continued
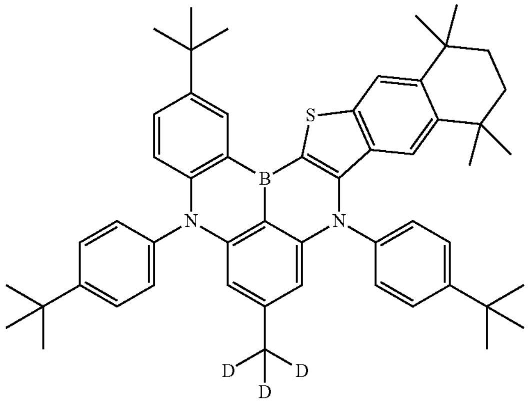
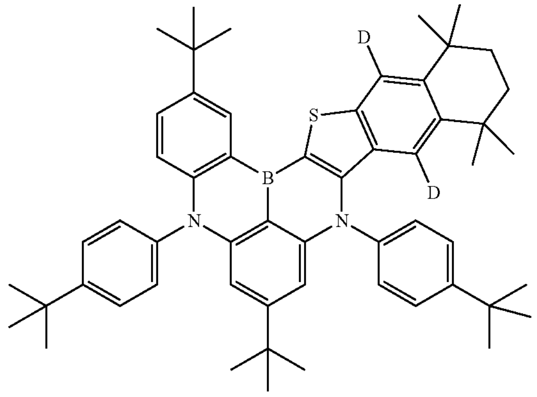
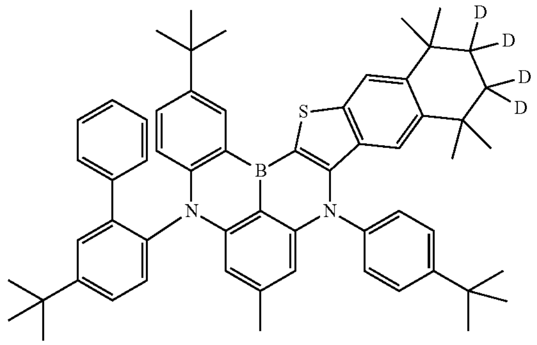
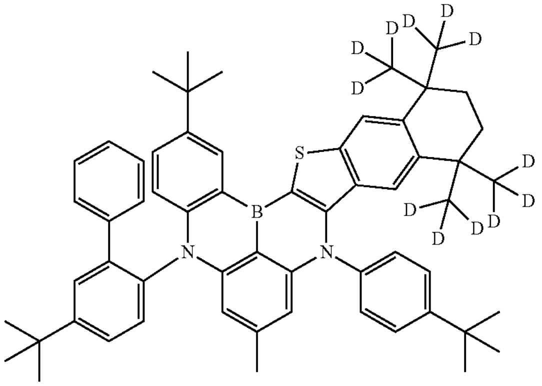

-continued
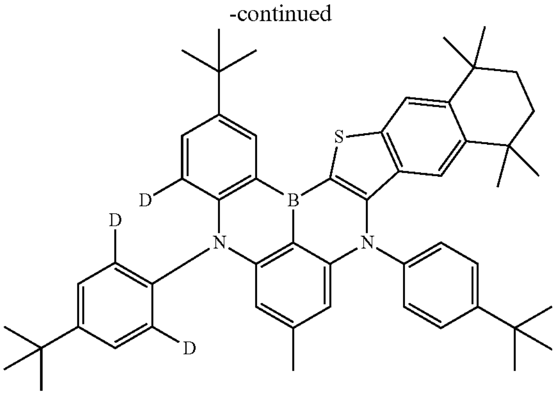
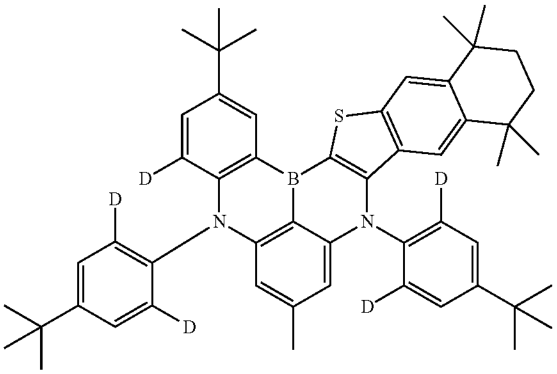
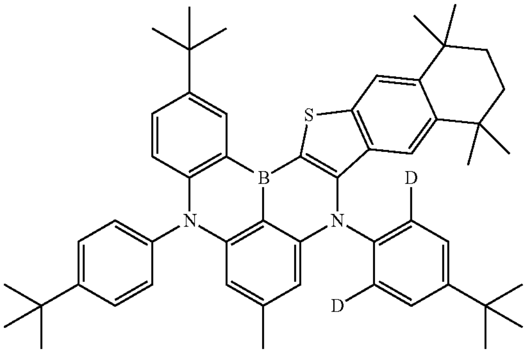
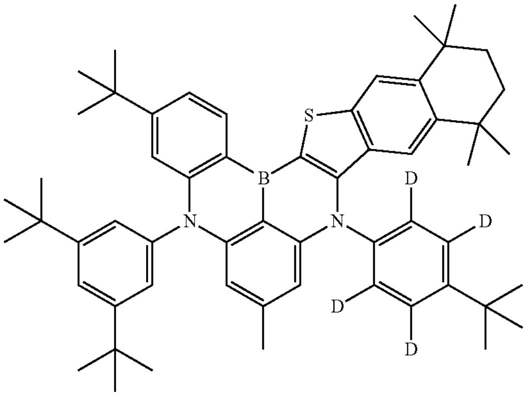
-continued
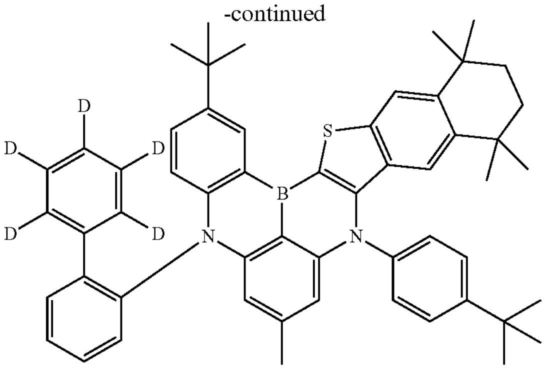
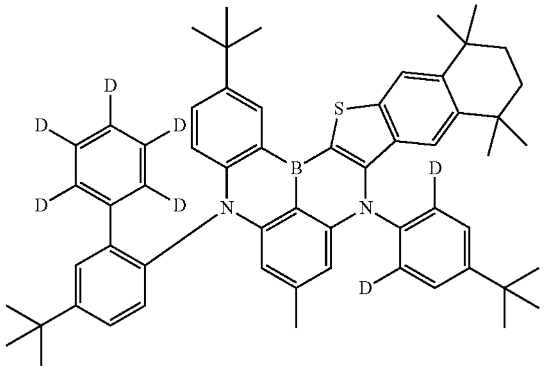
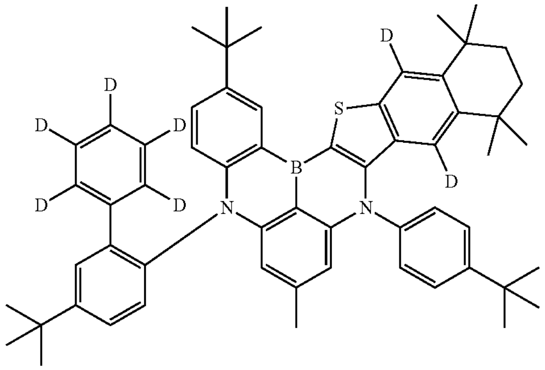
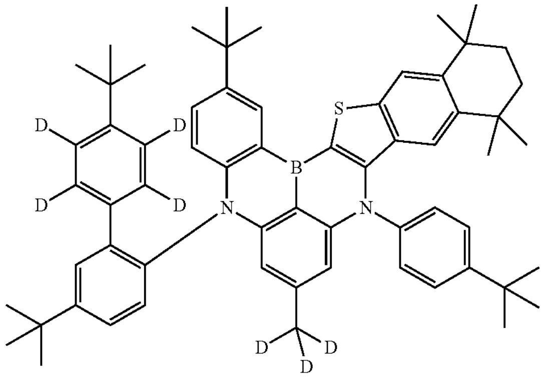

-continued
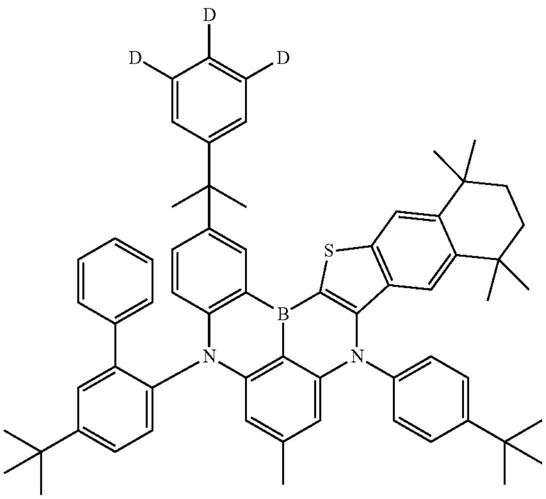
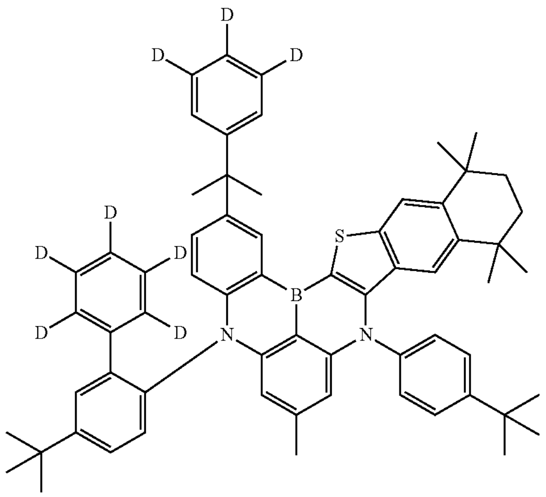
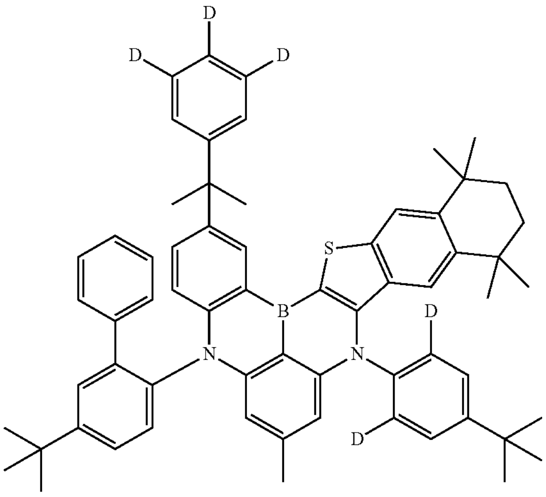
-continued
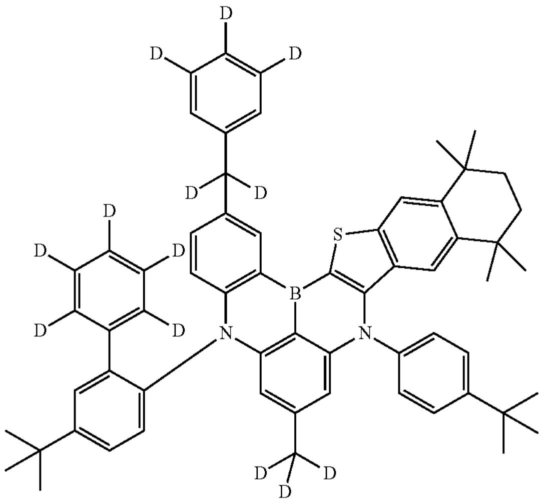
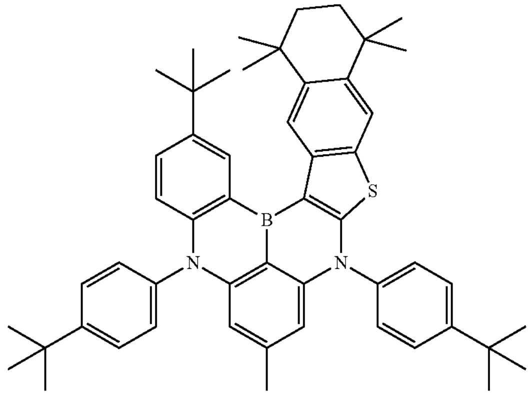
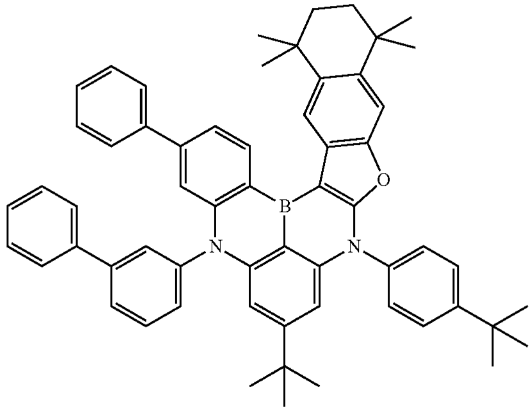
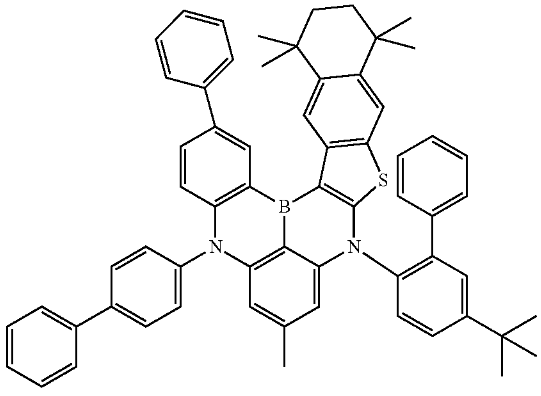

-continued
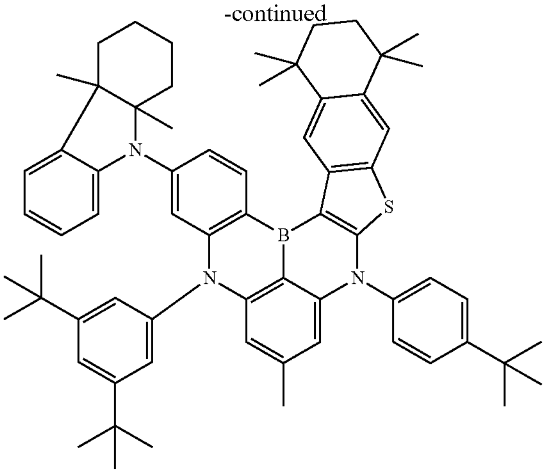
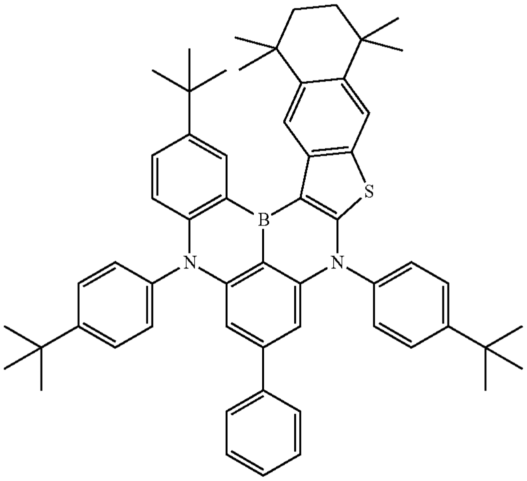
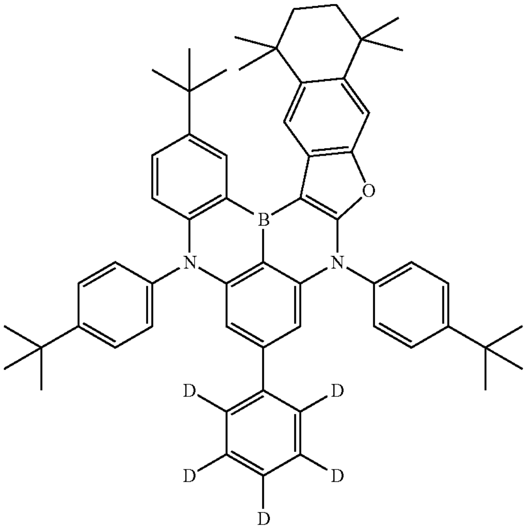
-continued
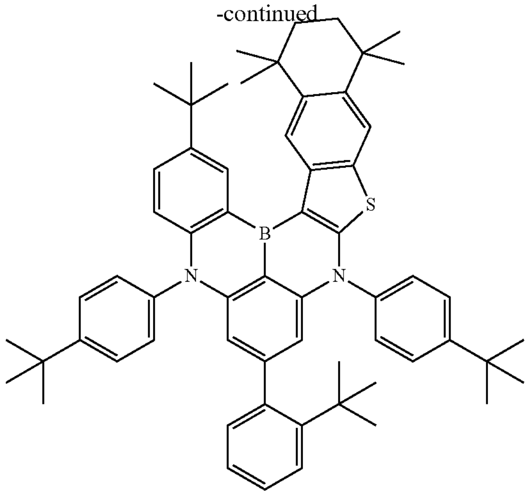
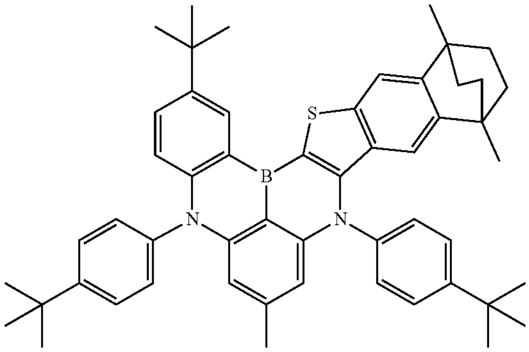
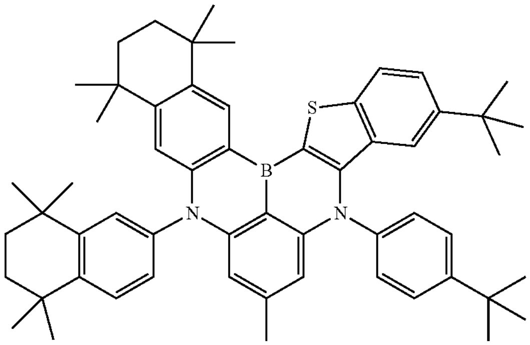
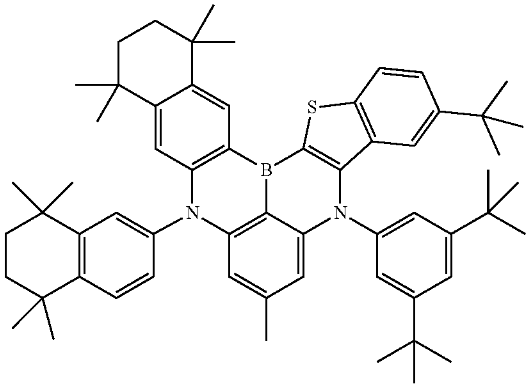

-continued
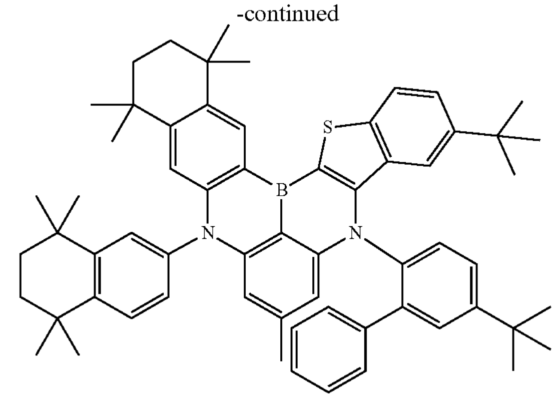
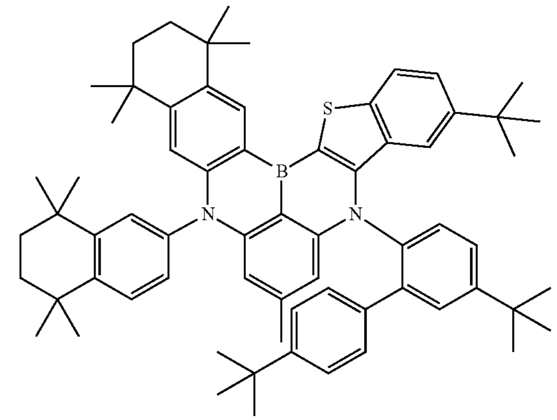
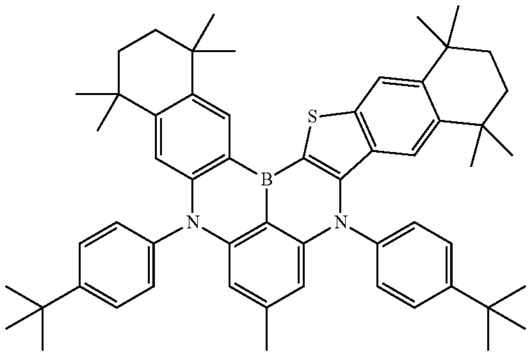
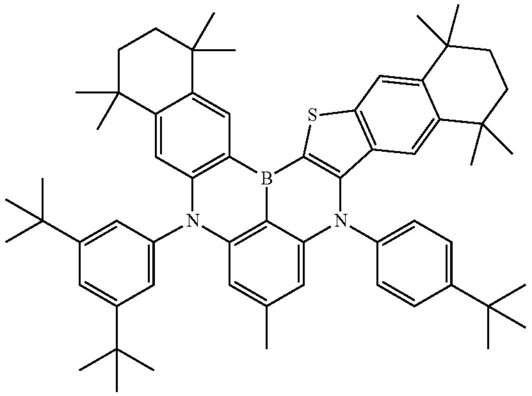
-continued
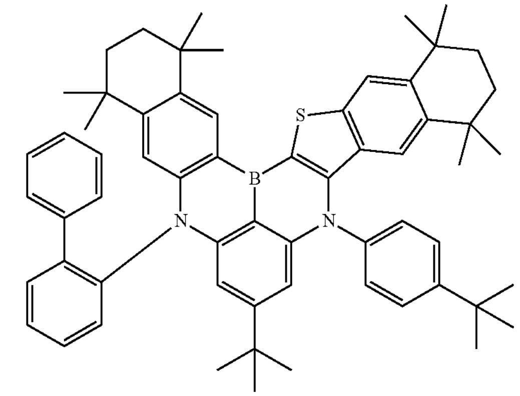
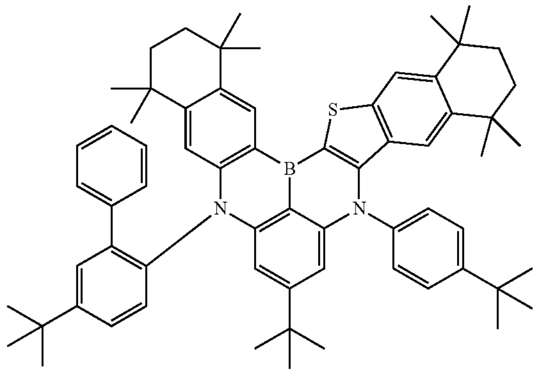
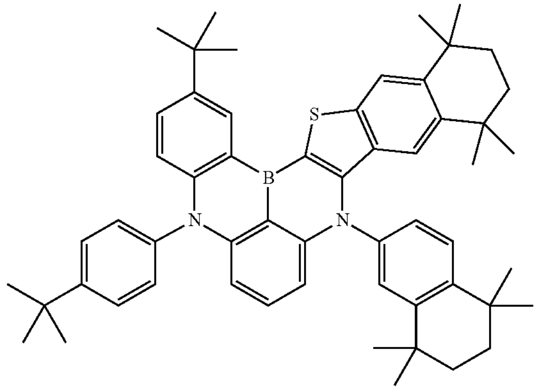
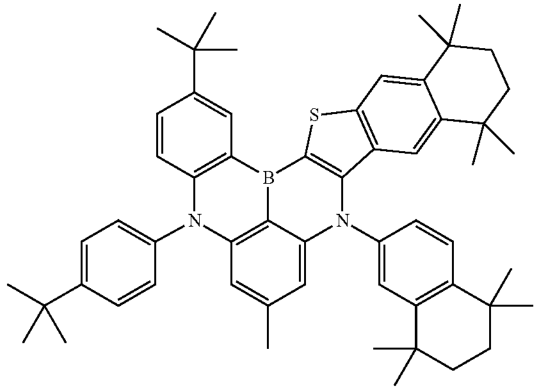

-continued
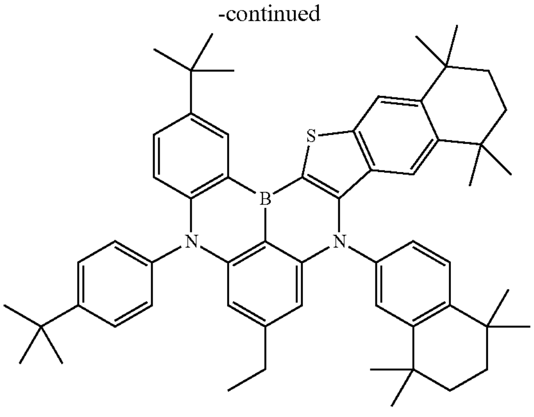
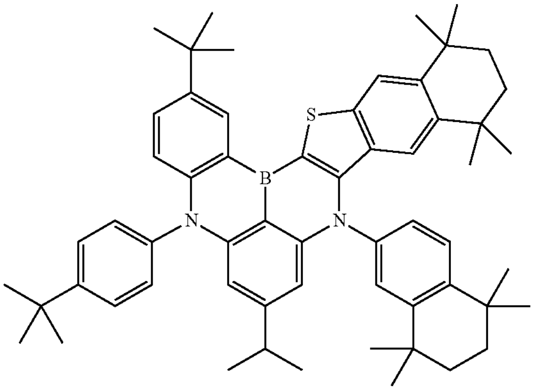
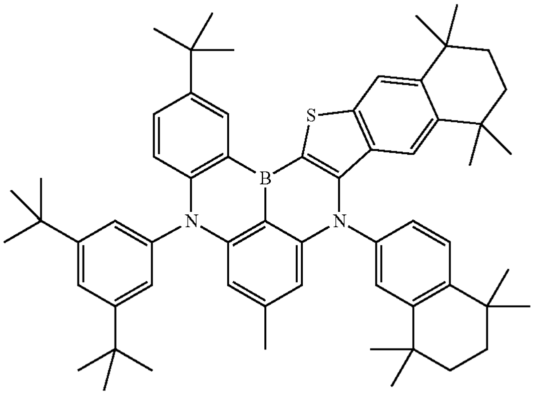
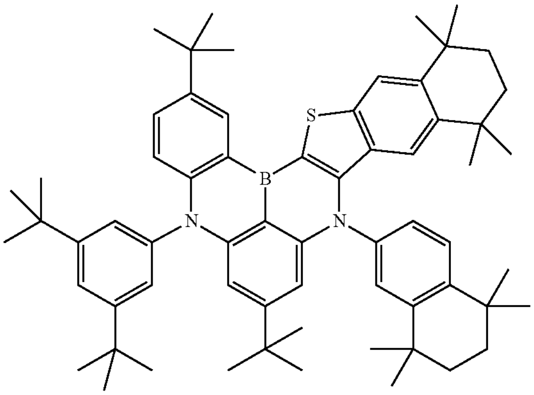
-continued
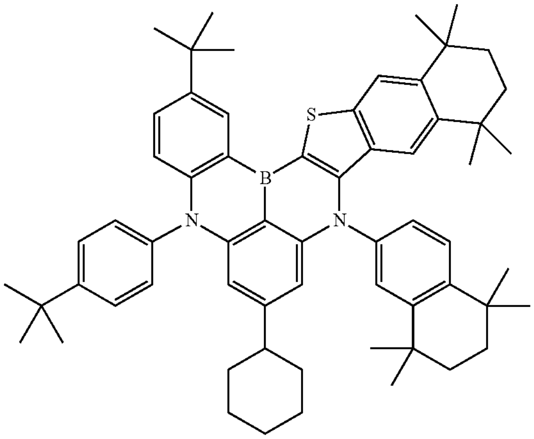
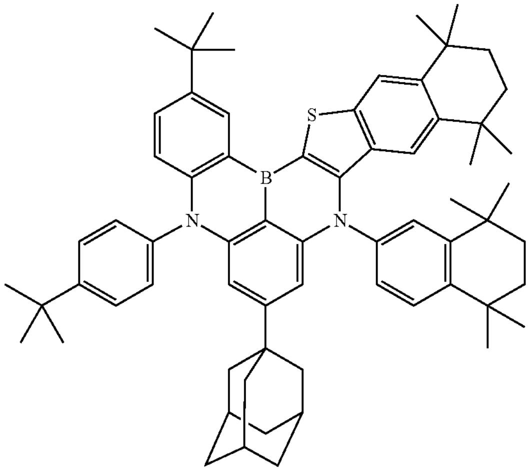
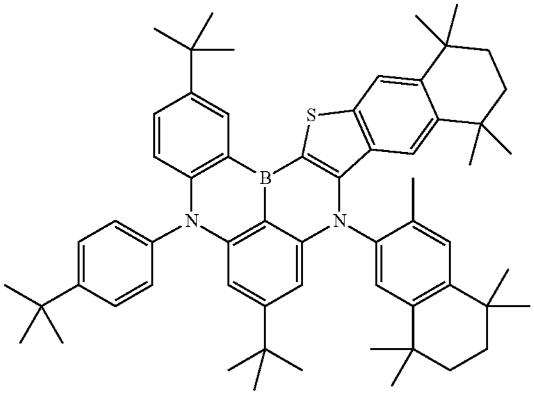

-continued
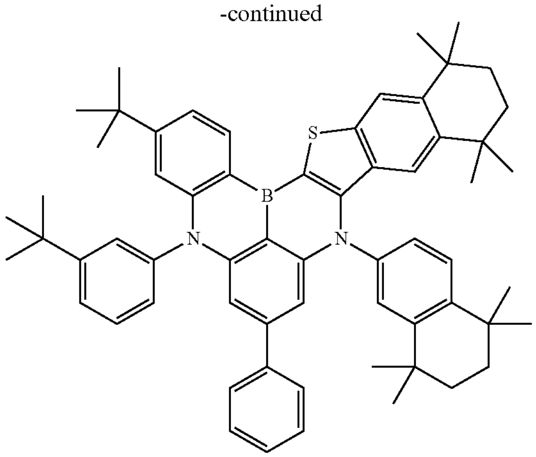
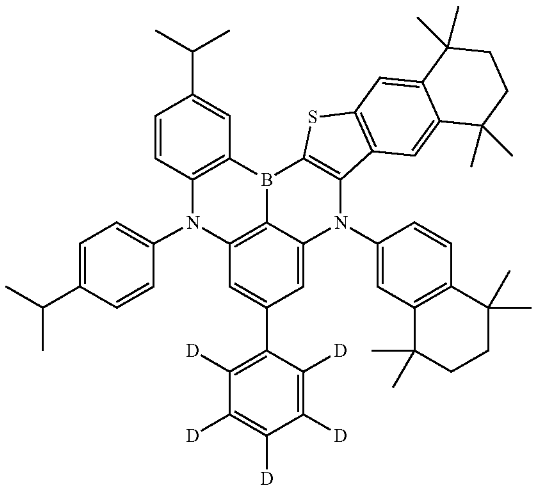
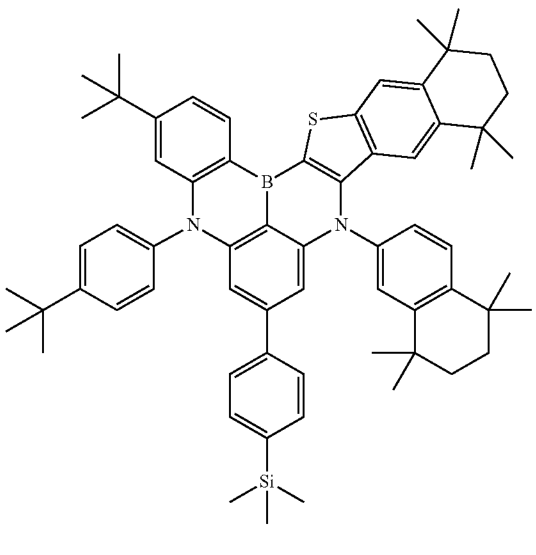
-continued
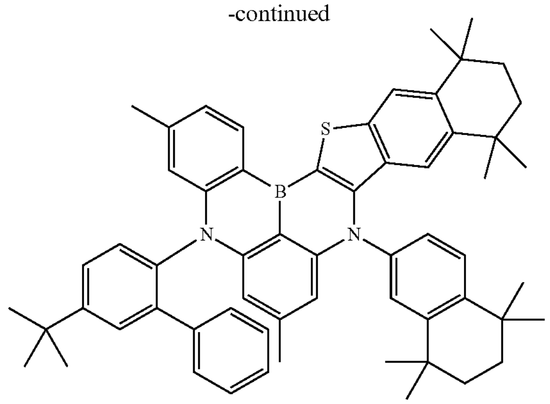
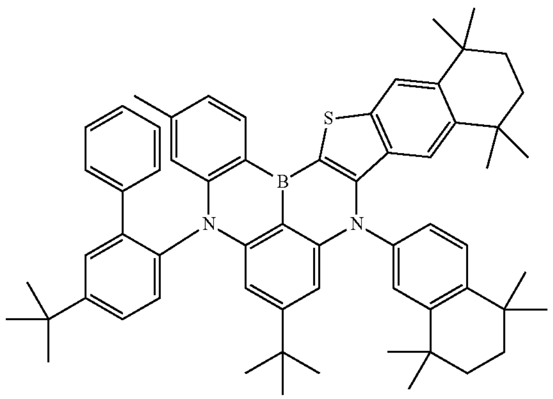
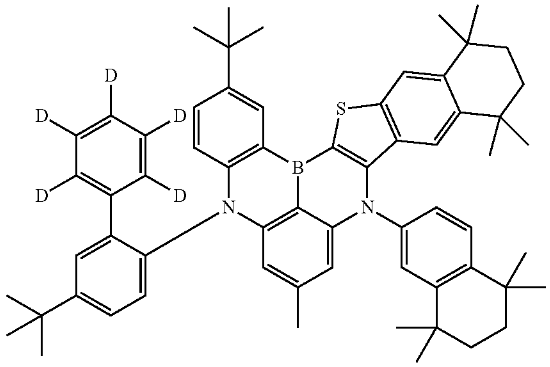
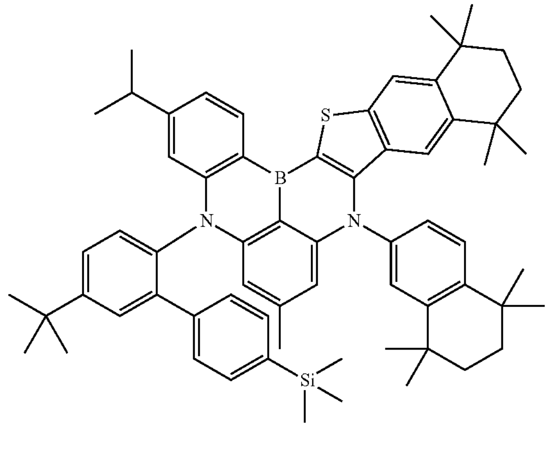

-continued
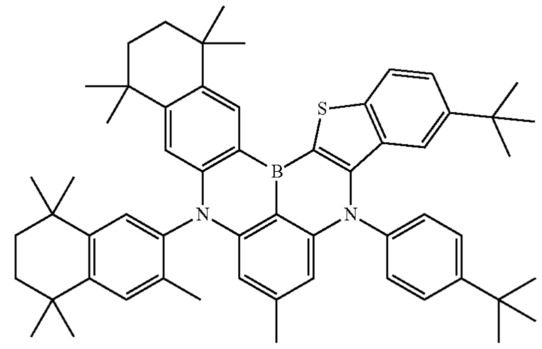
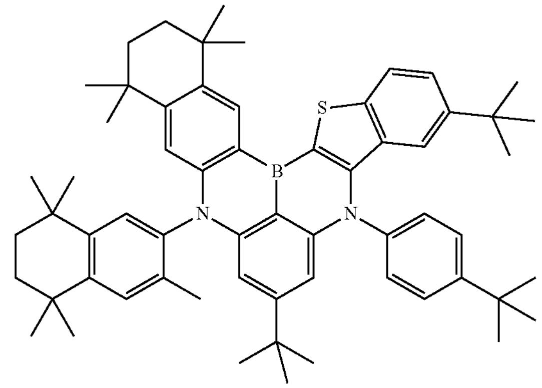
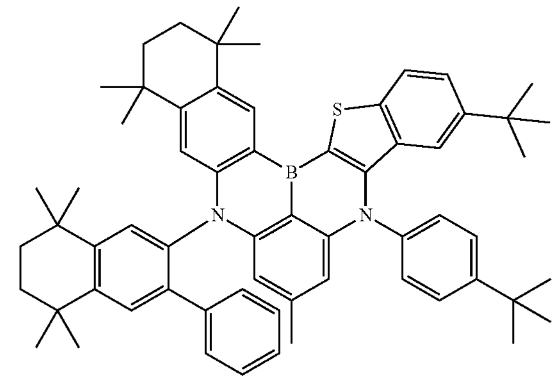
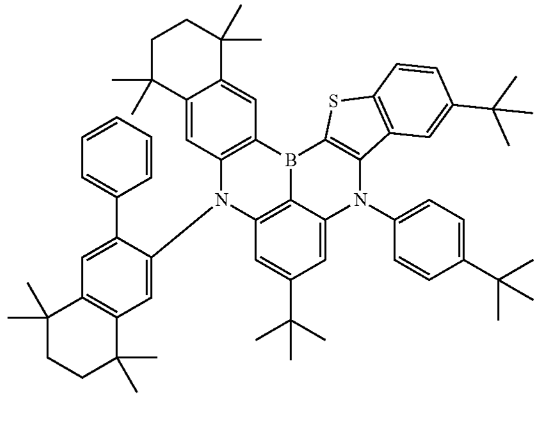
-continued
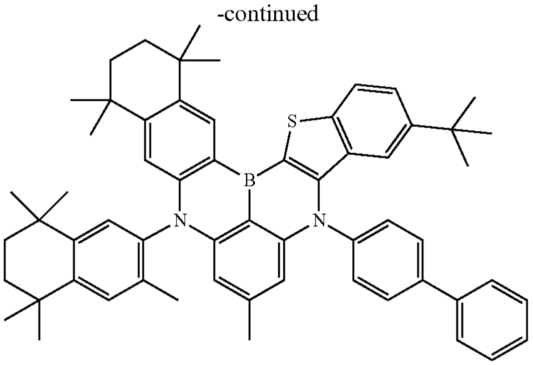
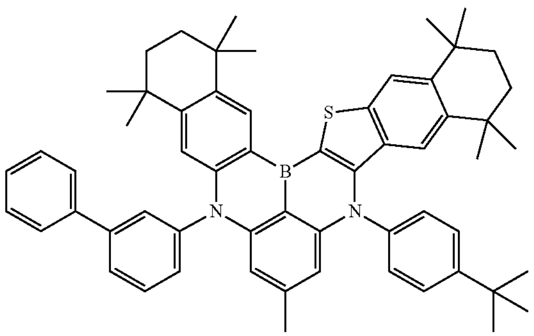
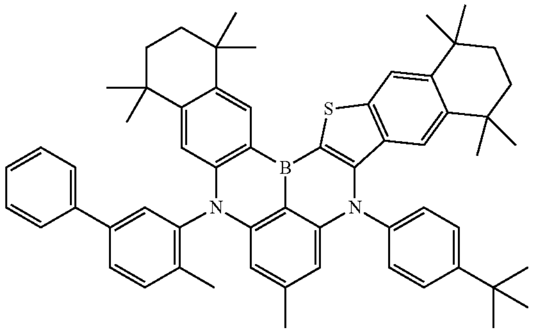
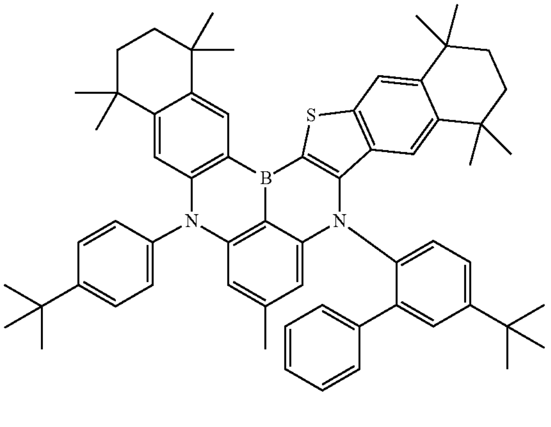

-continued
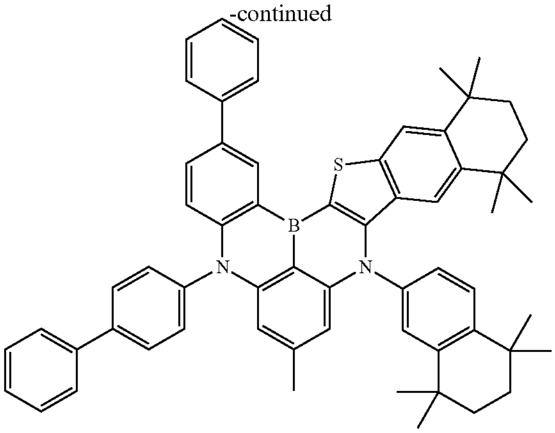
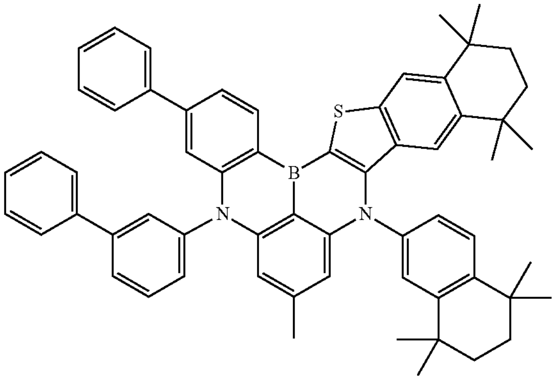
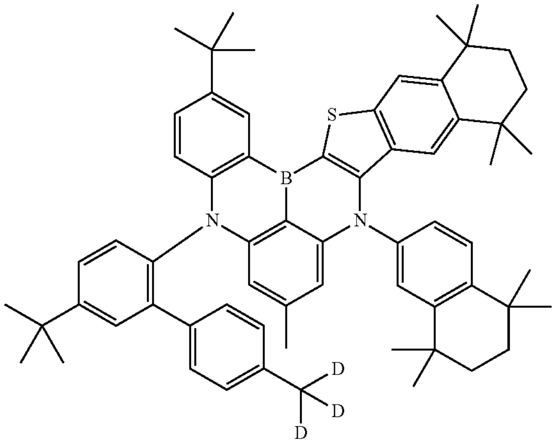
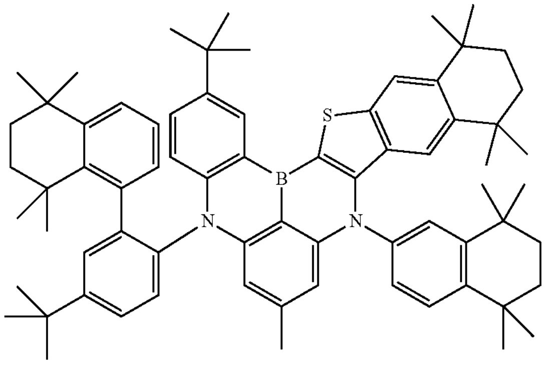
-continued
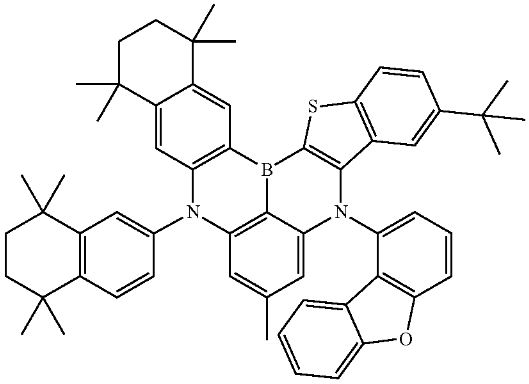
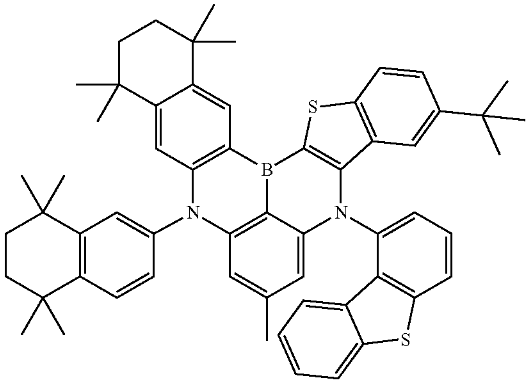
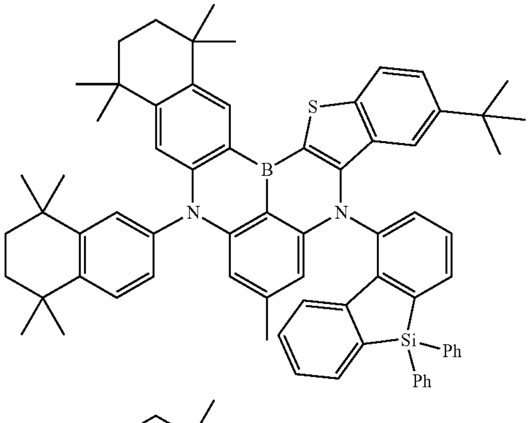
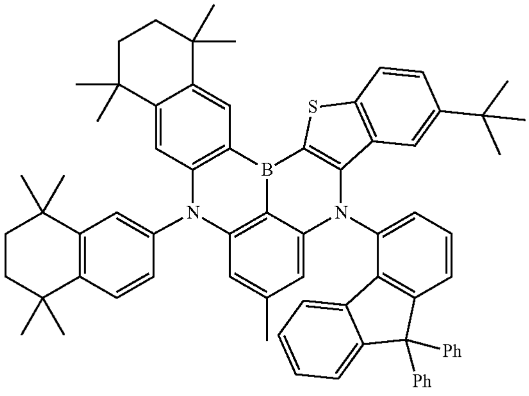

-continued
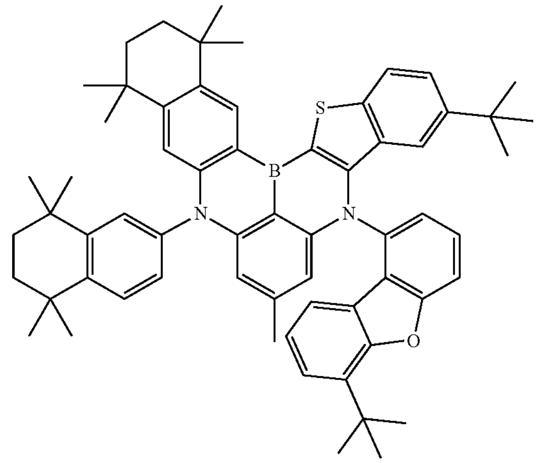
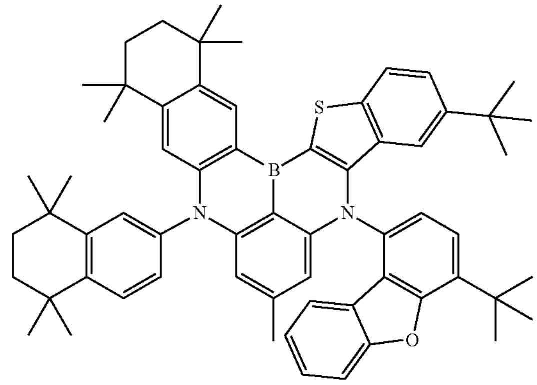
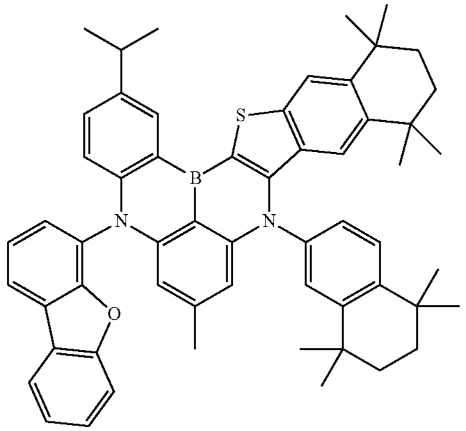
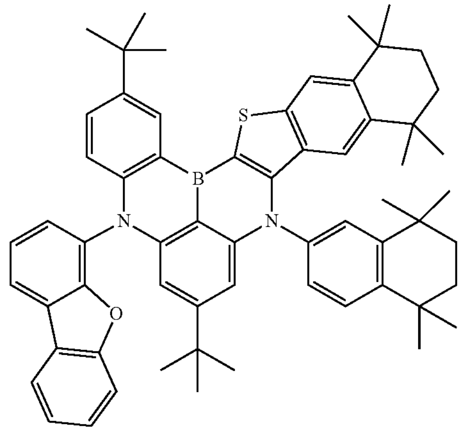
-continued
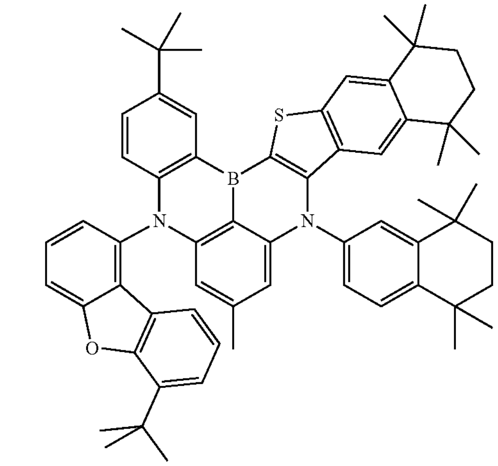
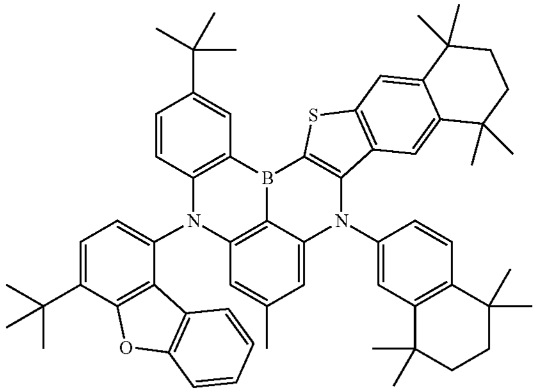
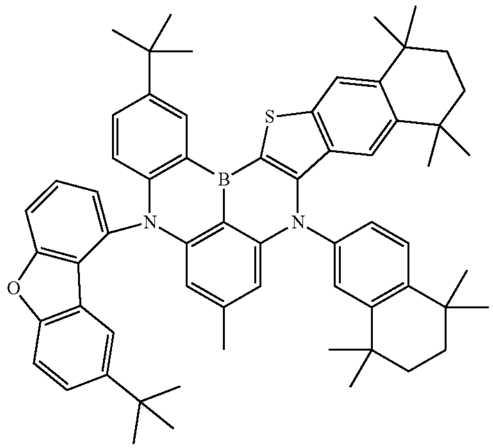
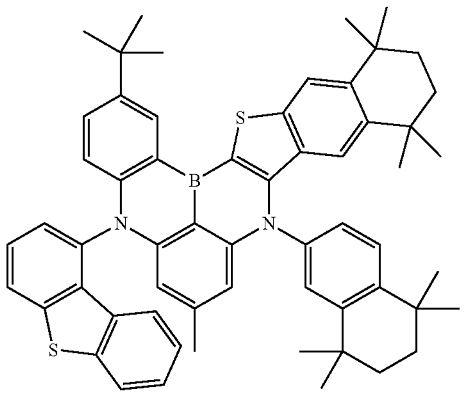

-continued
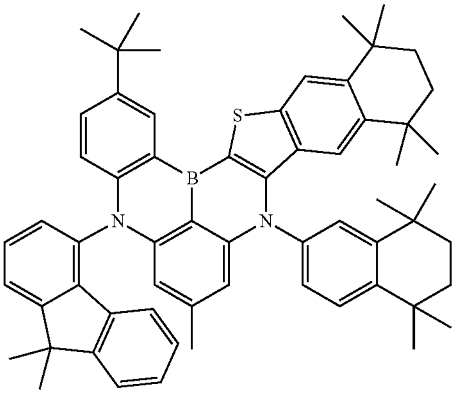
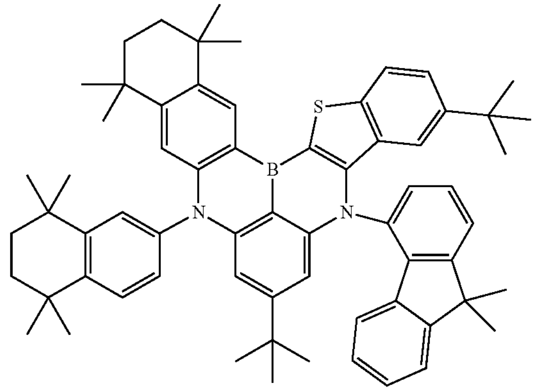
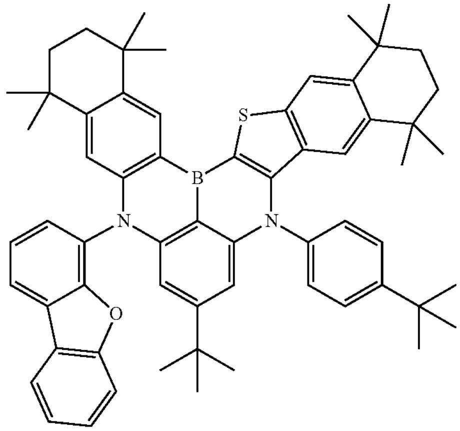
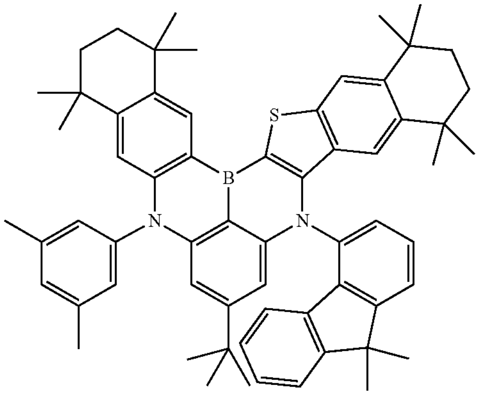
-continued
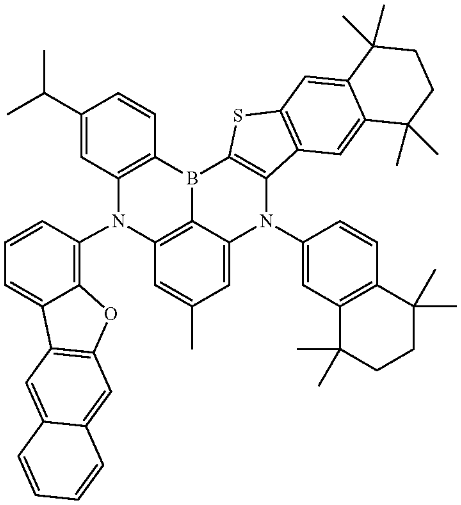
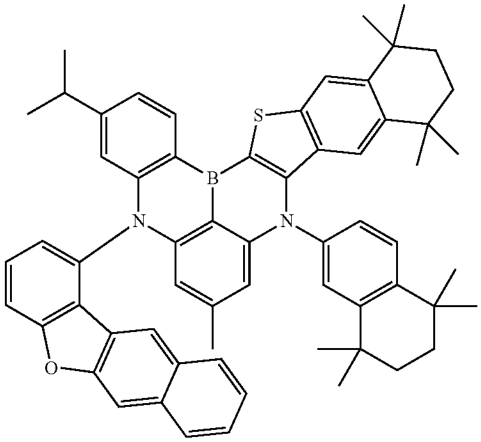
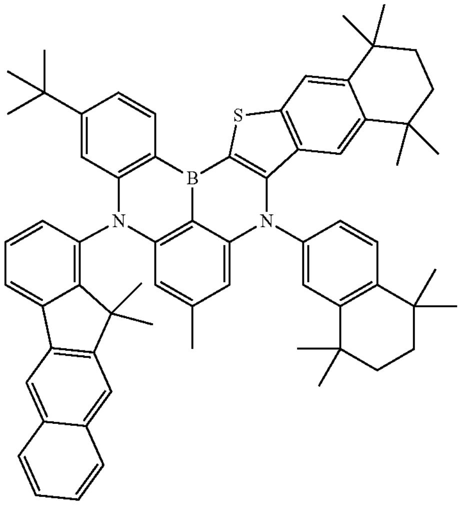

-continued
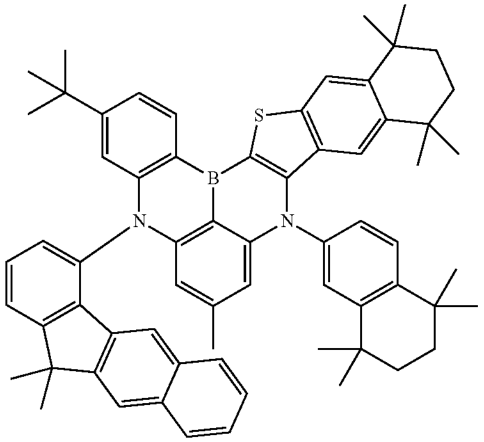
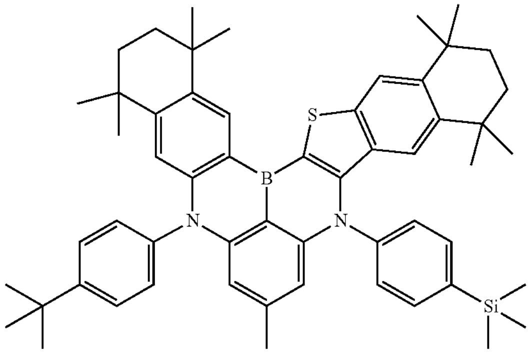
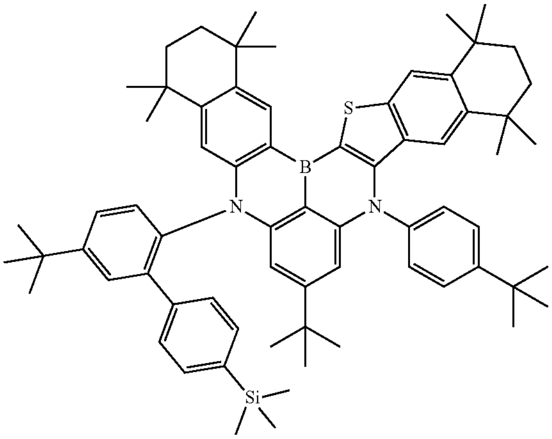
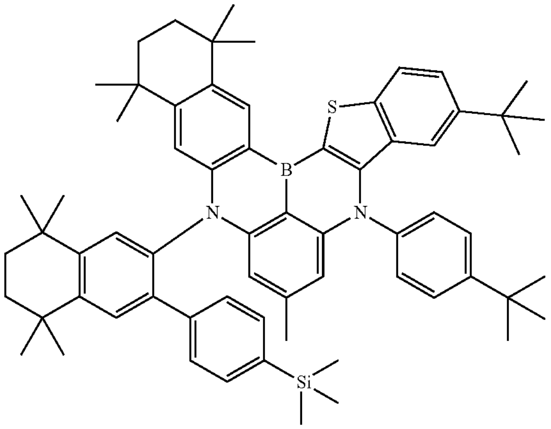
-continued
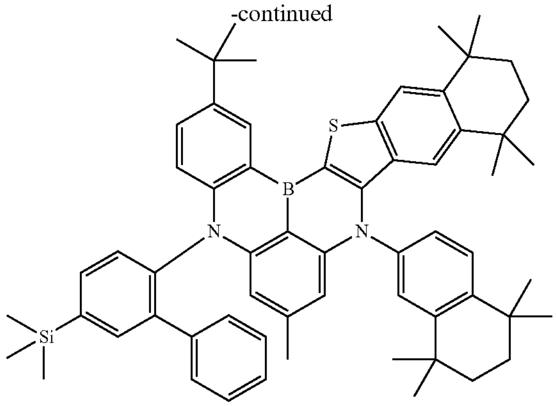
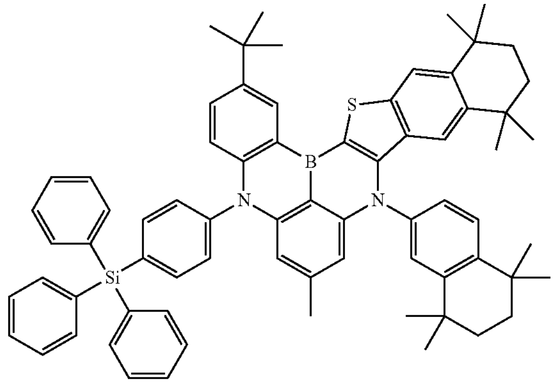
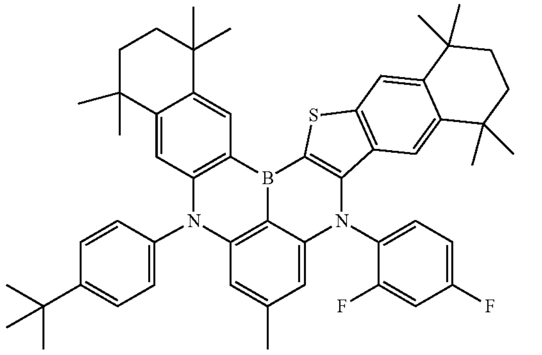
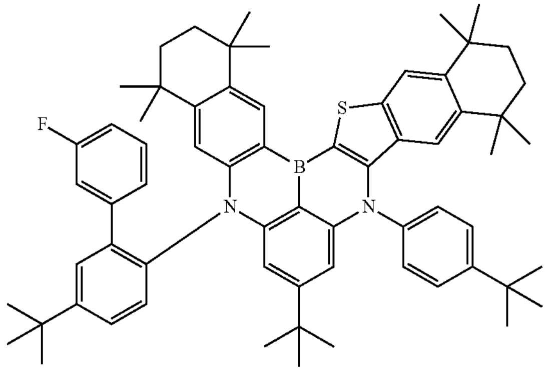

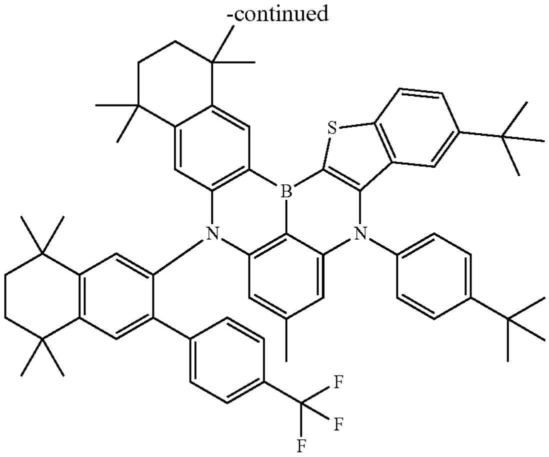
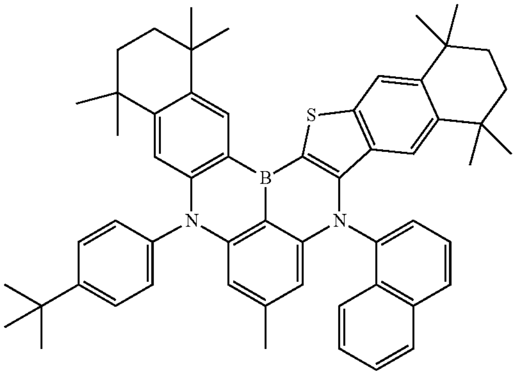
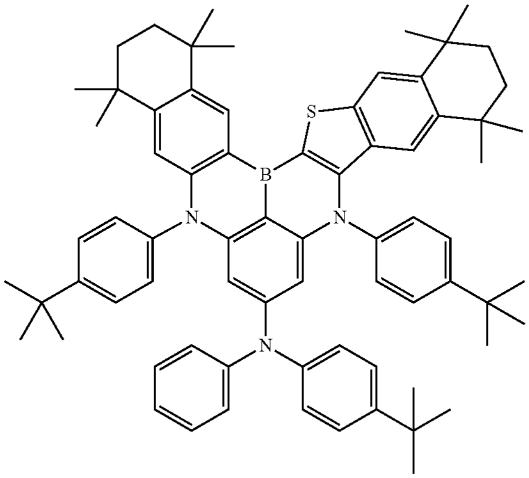
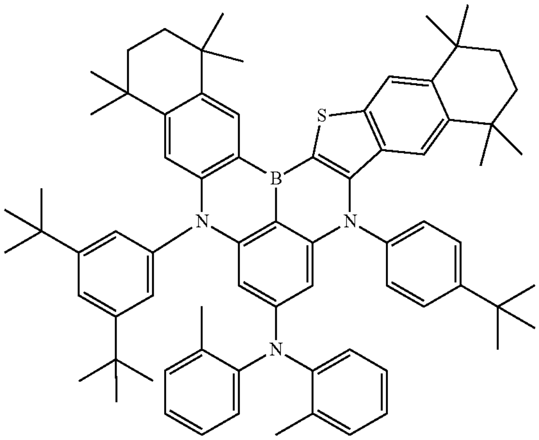
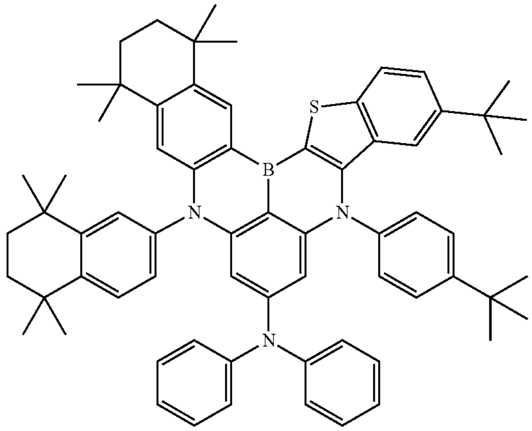
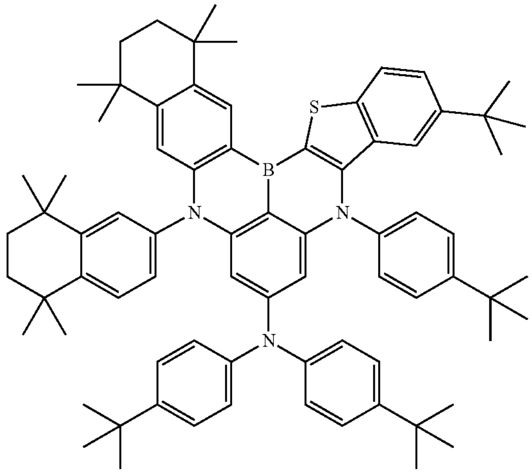
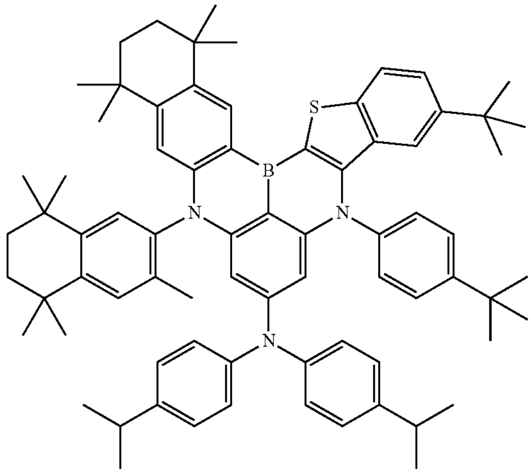

-continued
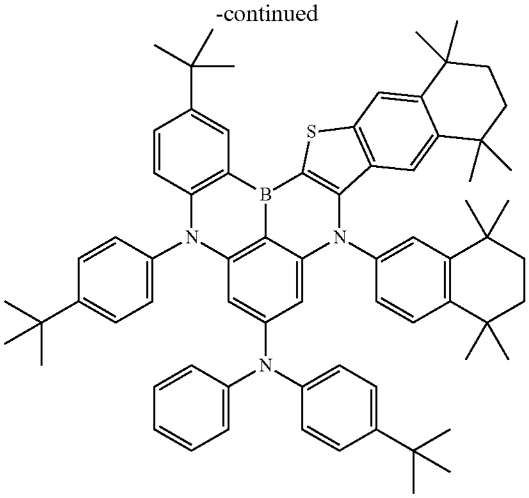
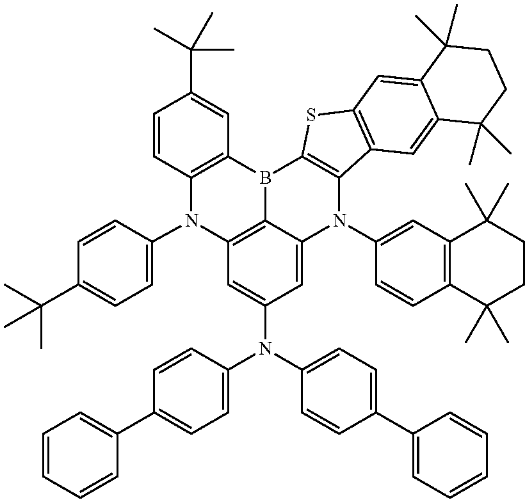
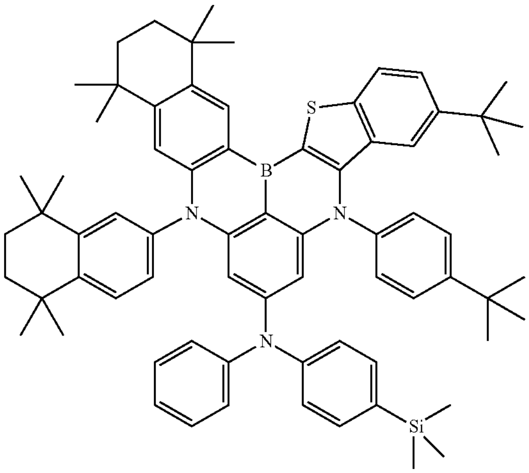
-continued
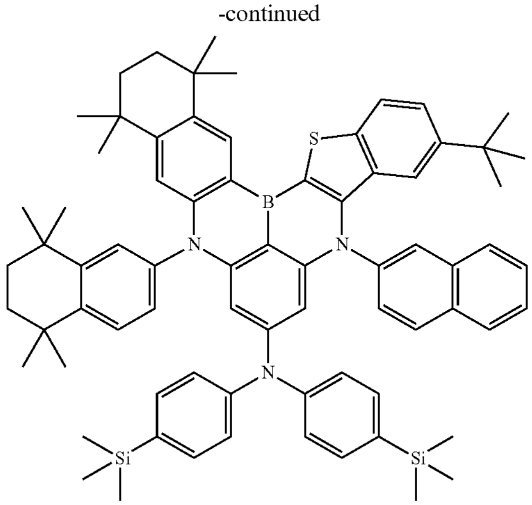
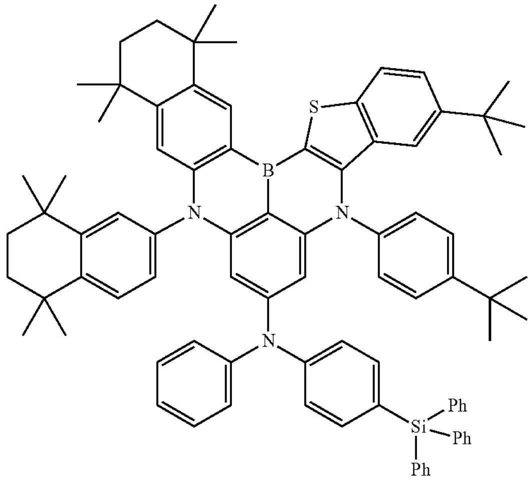
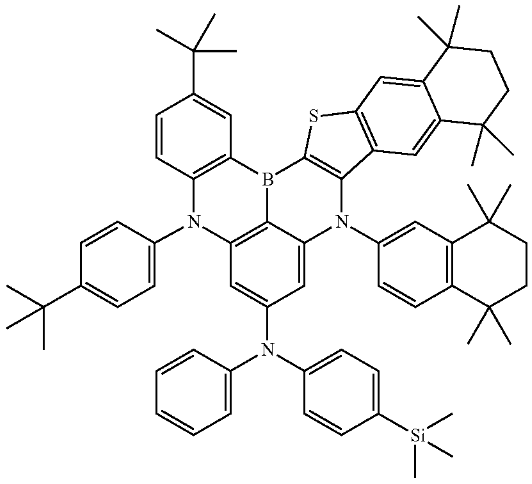

-continued
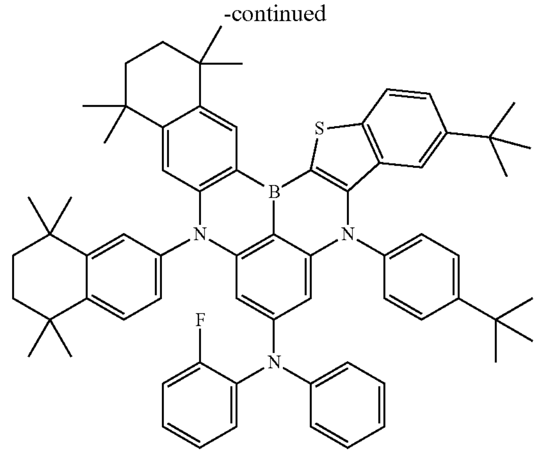
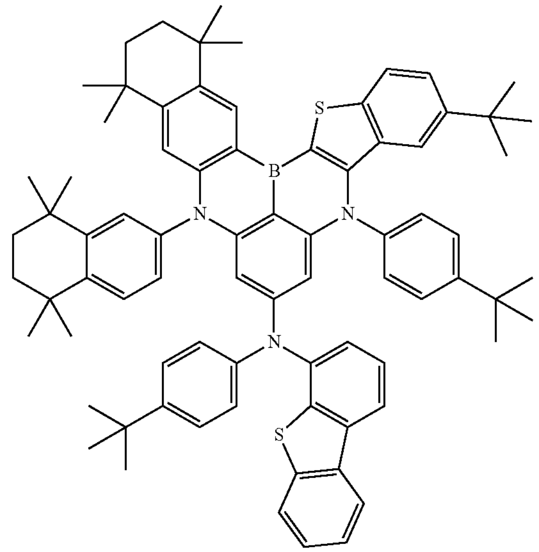
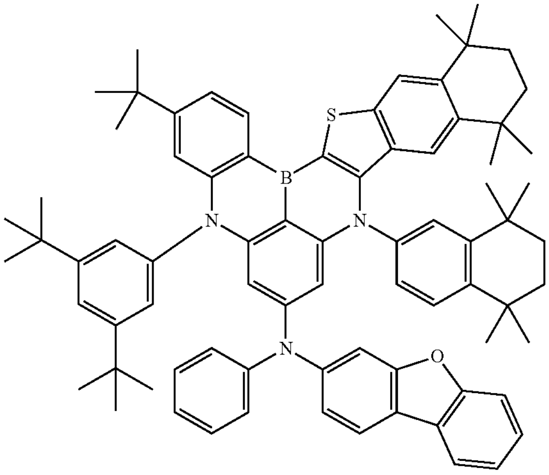
-continued
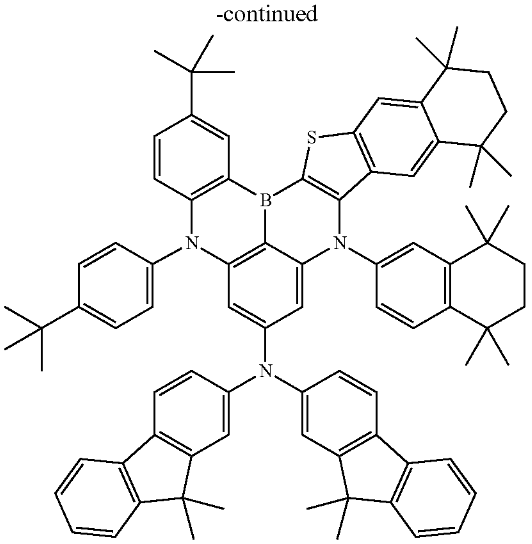
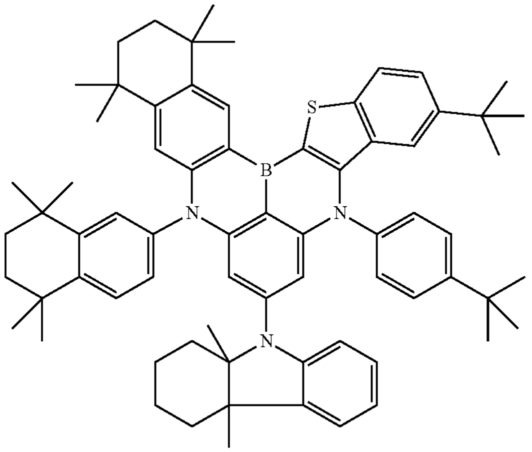
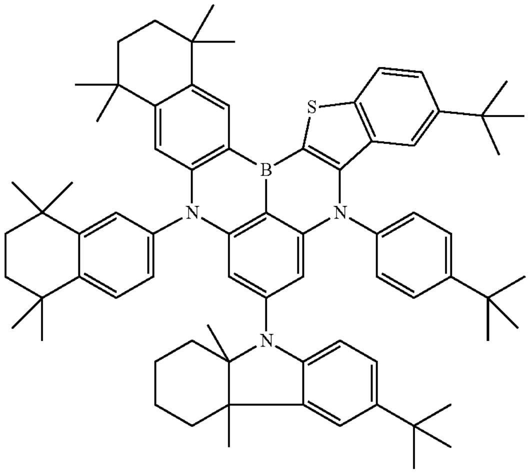

-continued
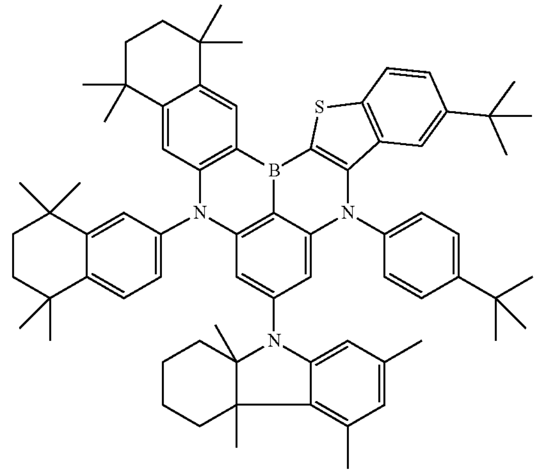
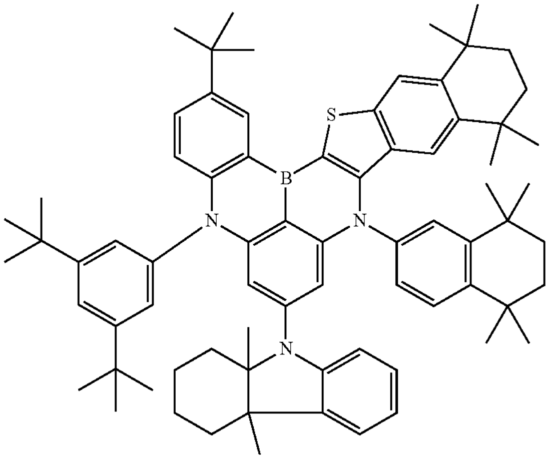
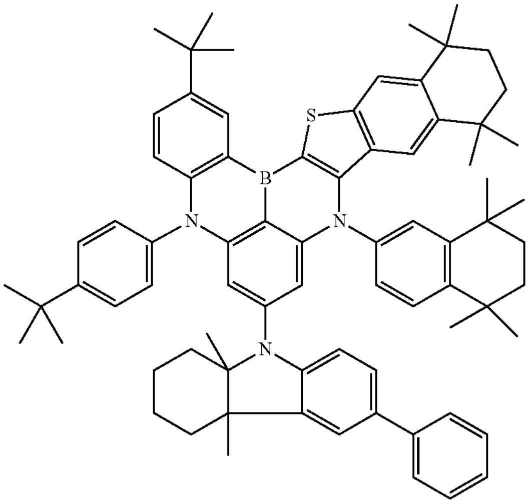
-continued
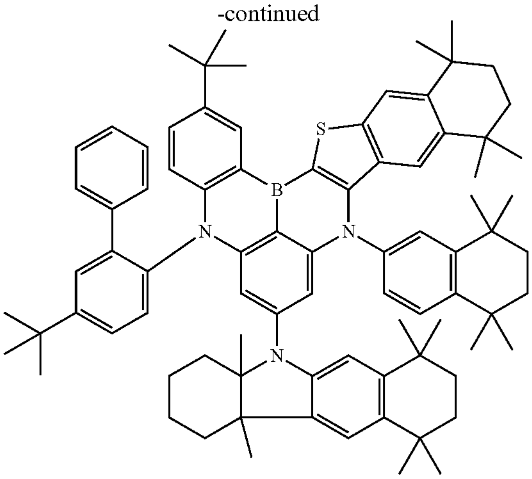
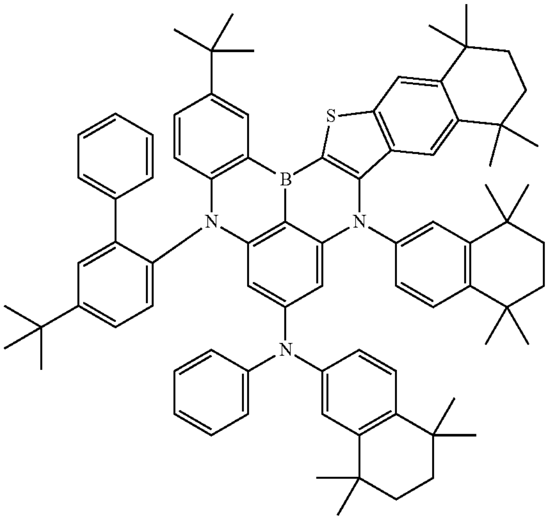
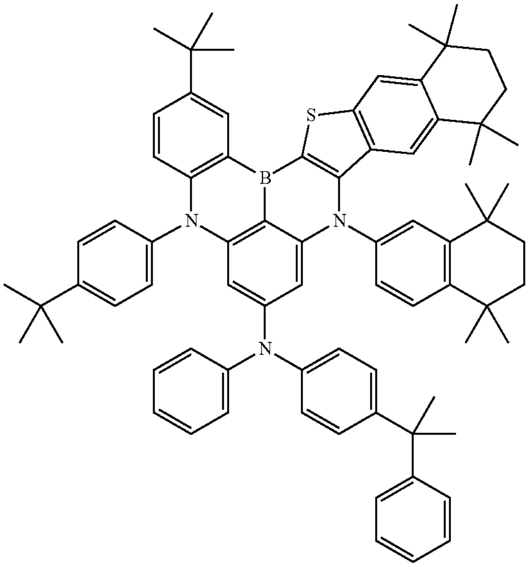

-continued
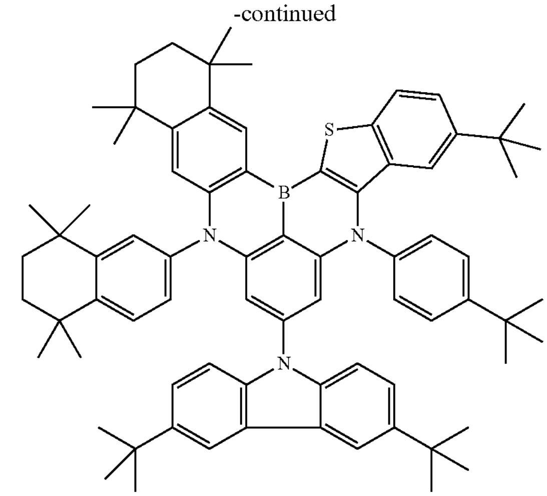
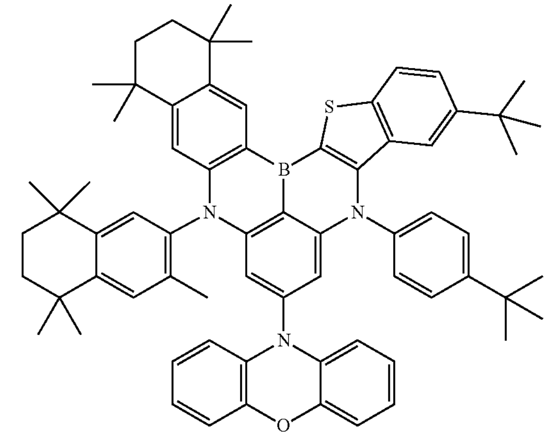
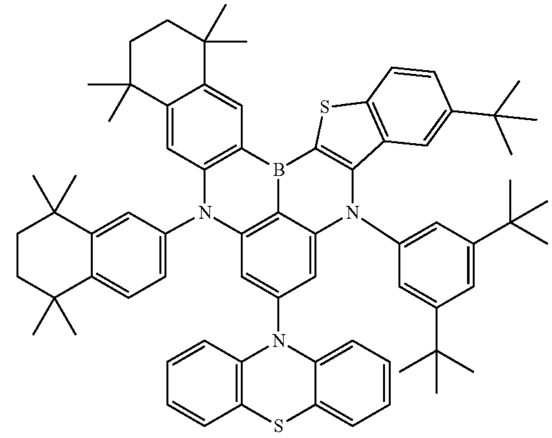
-continued
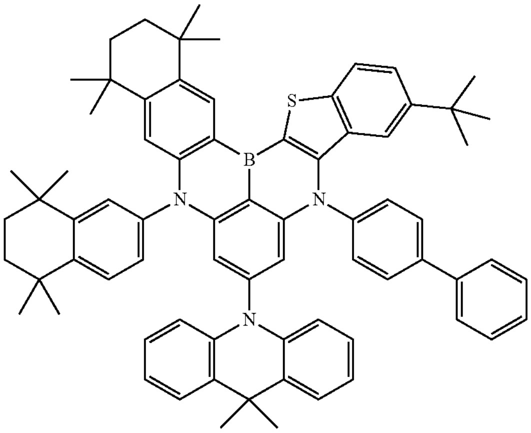
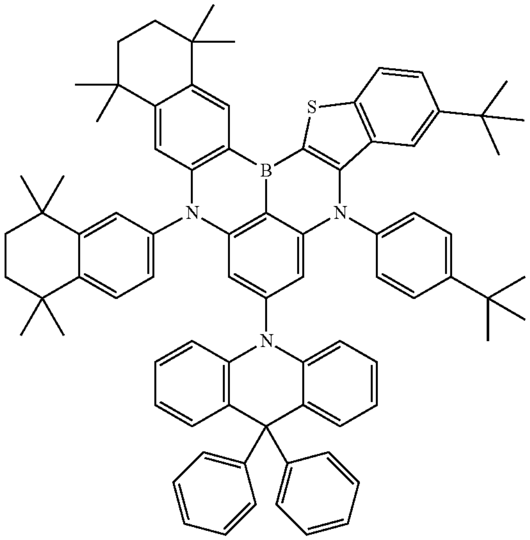
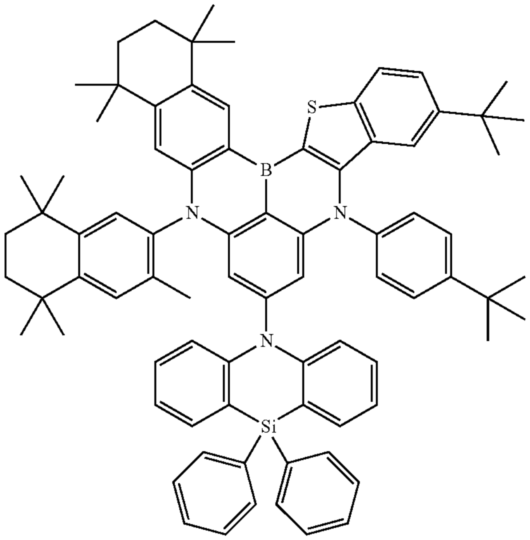

-continued
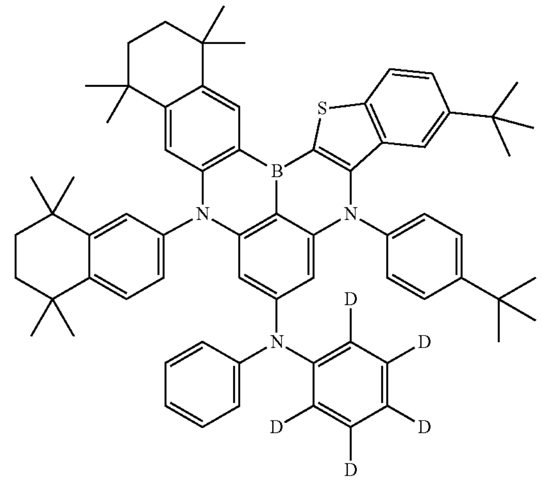
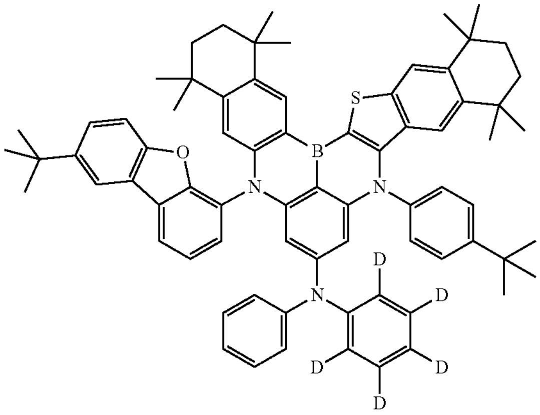
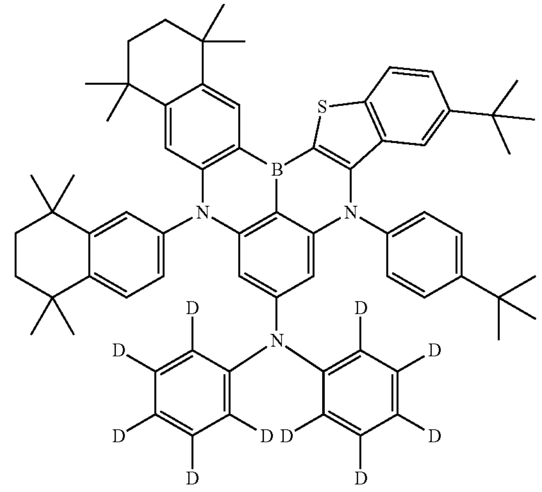
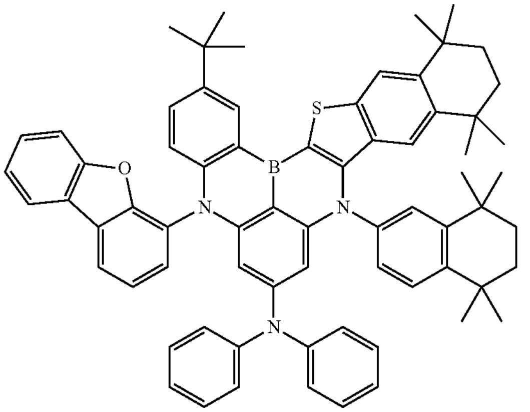
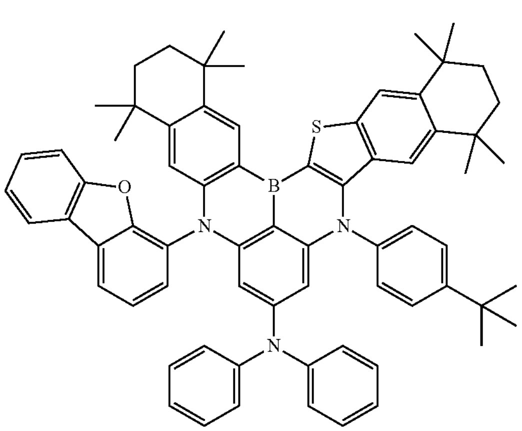
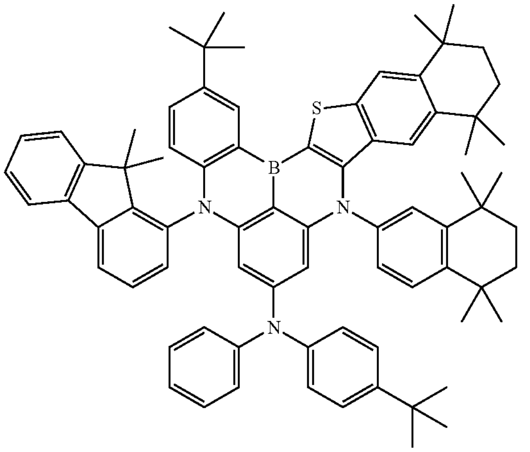
-continued -continued
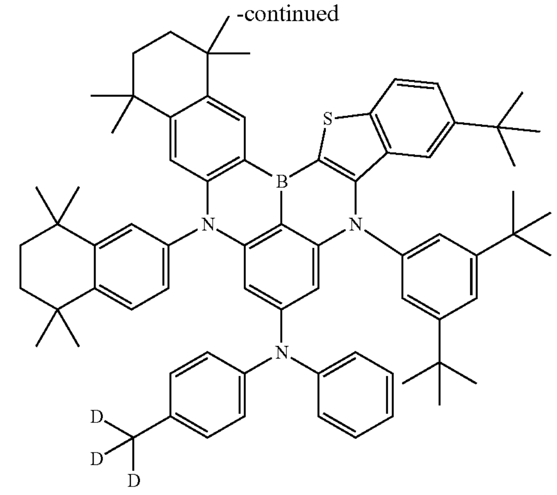
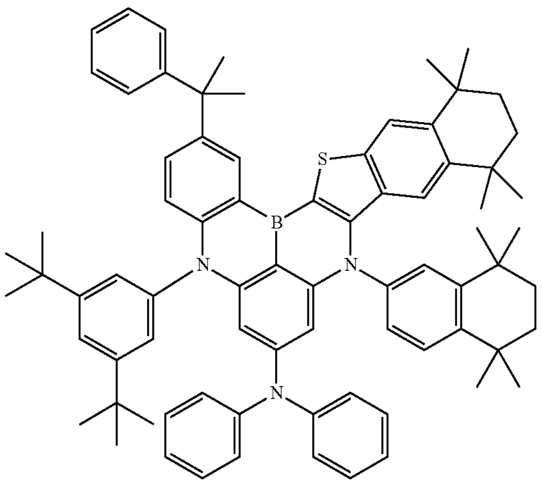
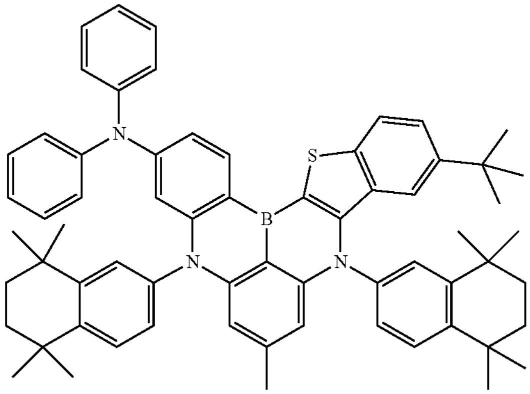
-continued
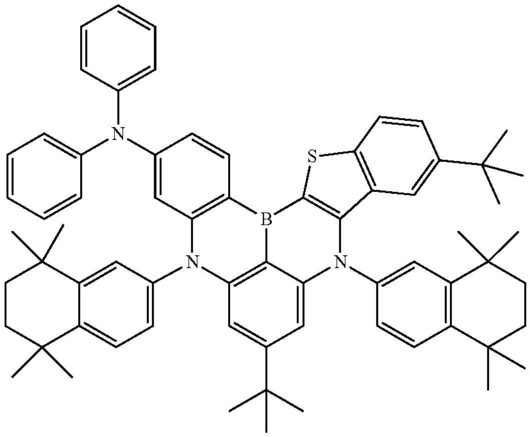
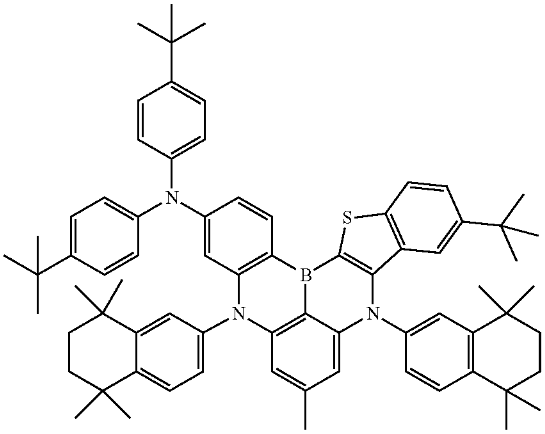
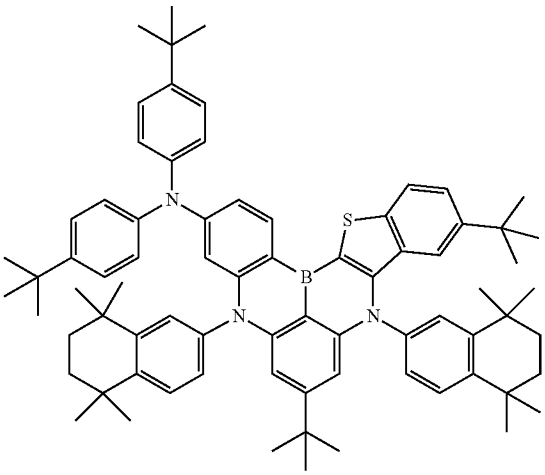

-continued
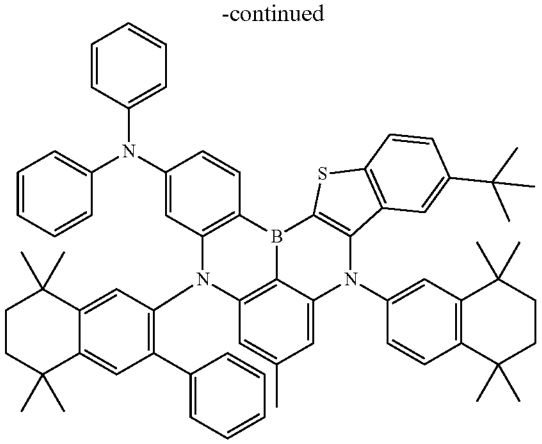
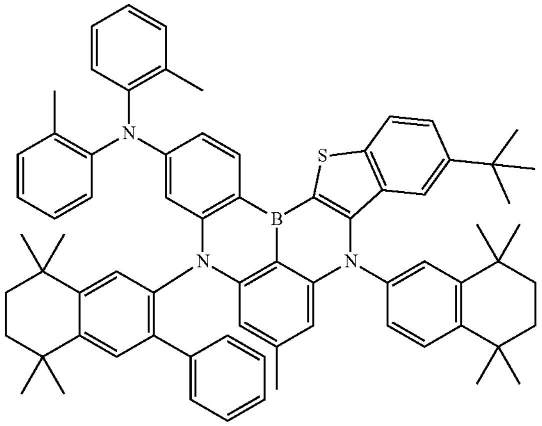
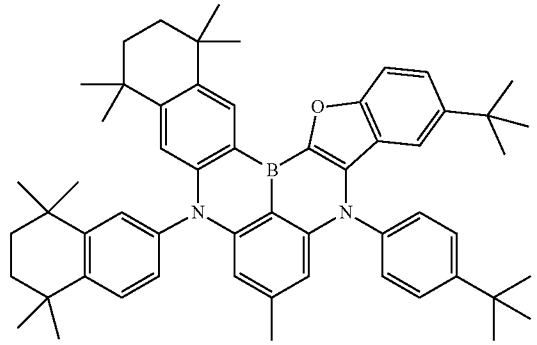
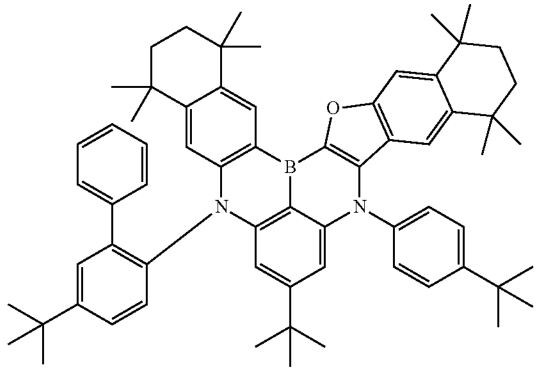
-continued
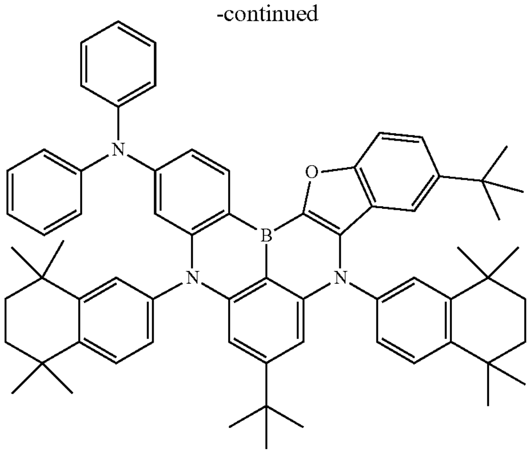
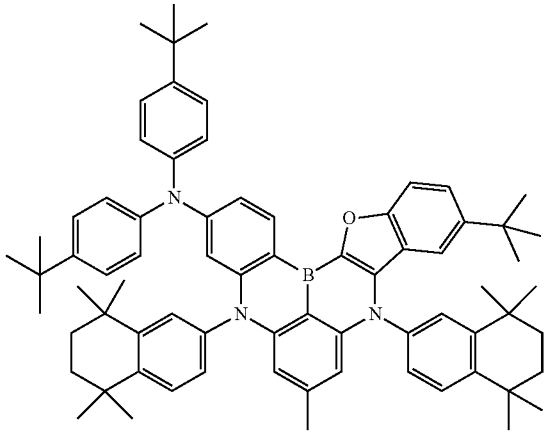
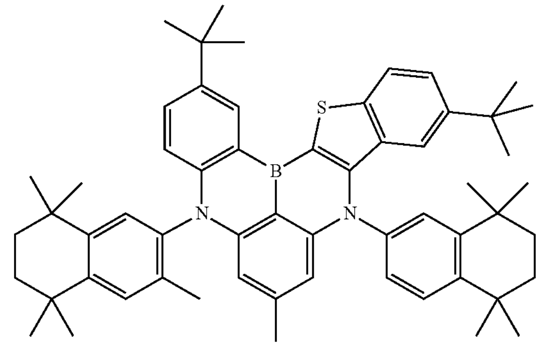
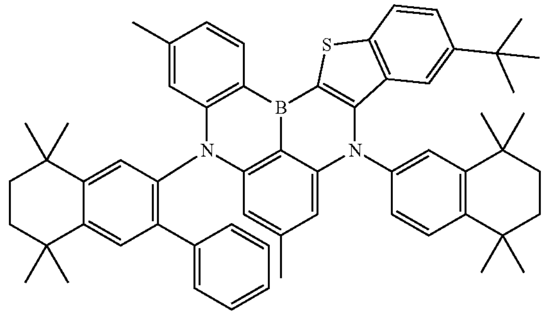

-continued
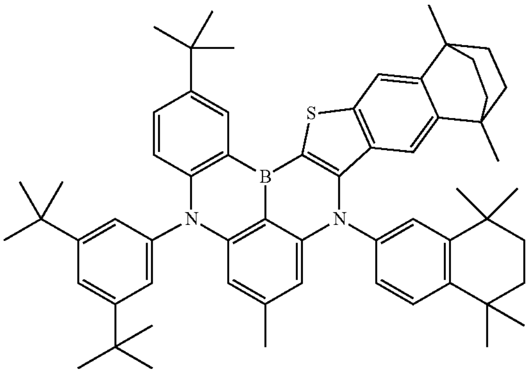
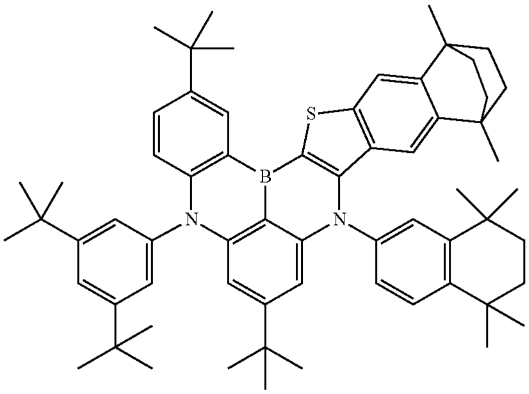
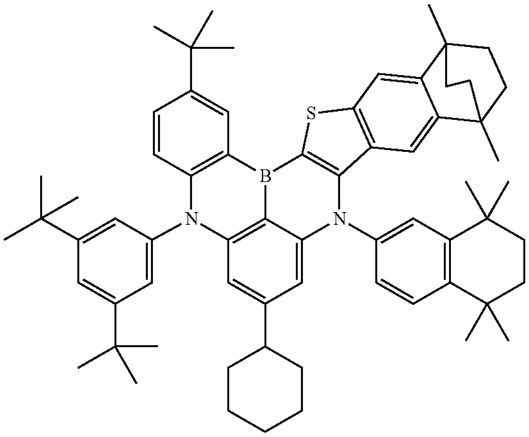
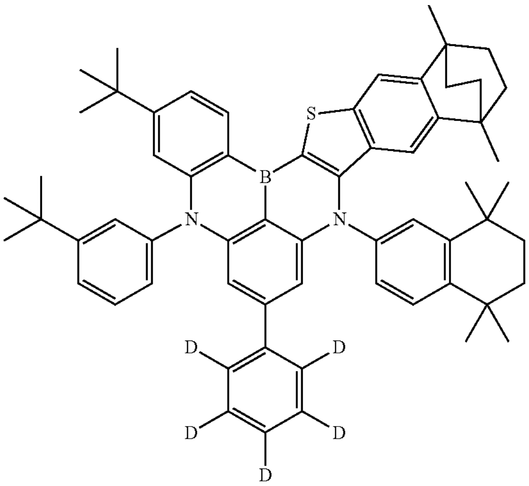
-continued
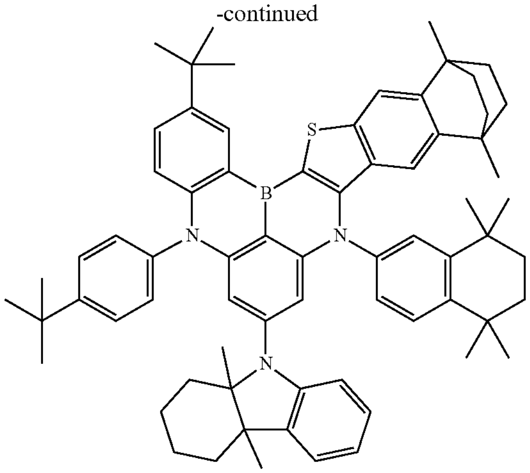
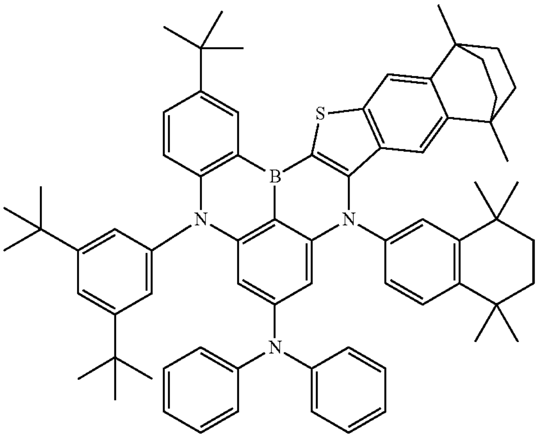
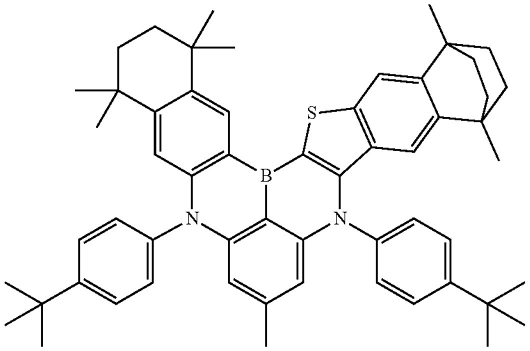
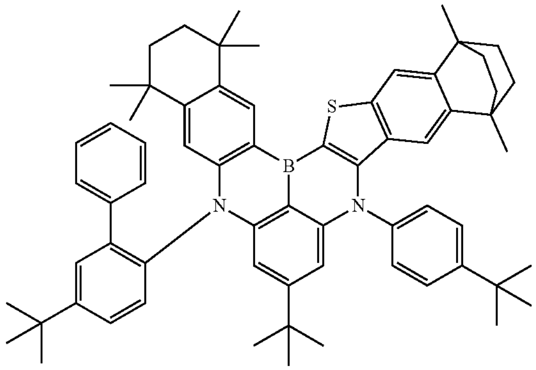

-continued
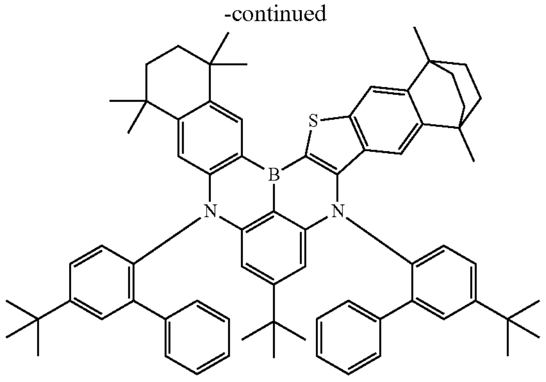
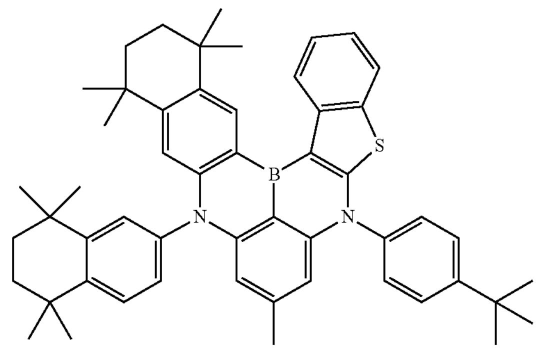
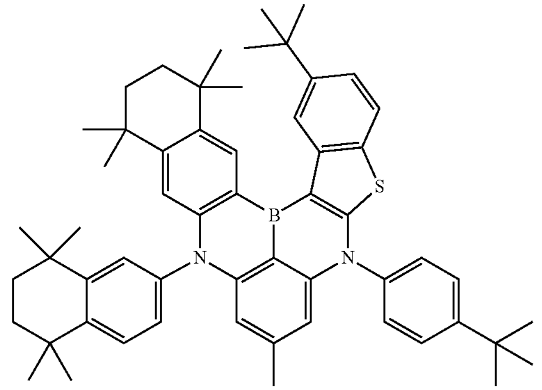
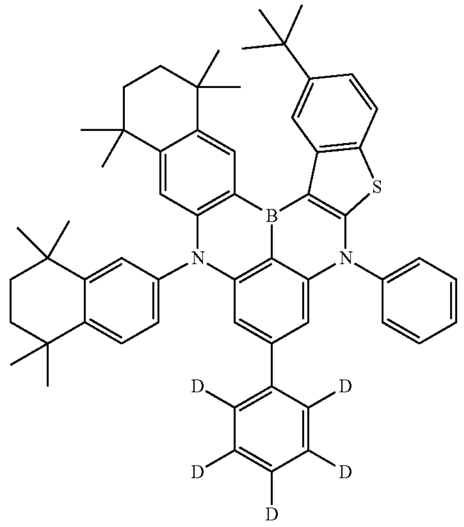
-continued
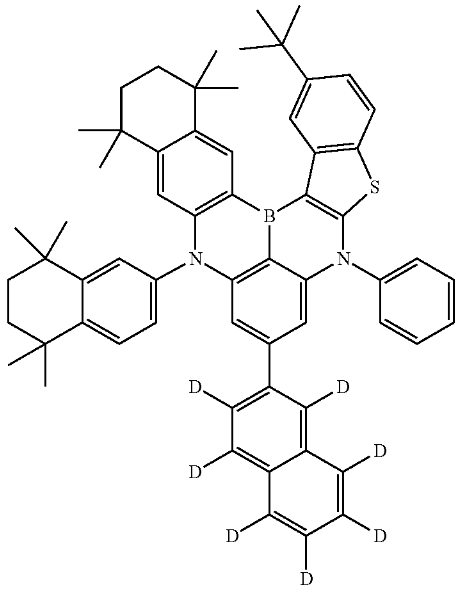
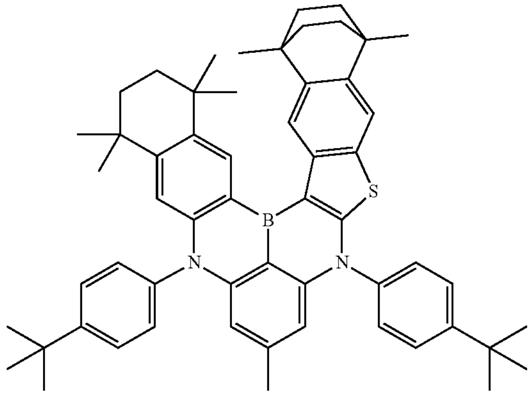
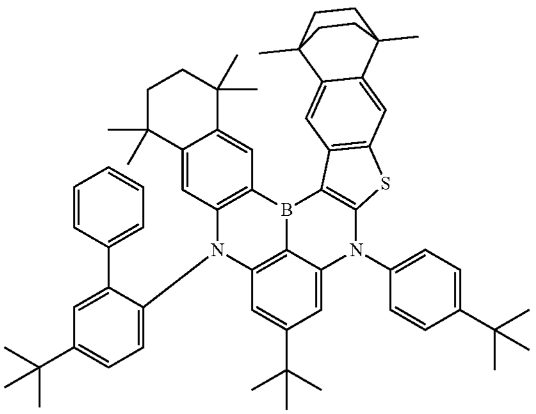

-continued
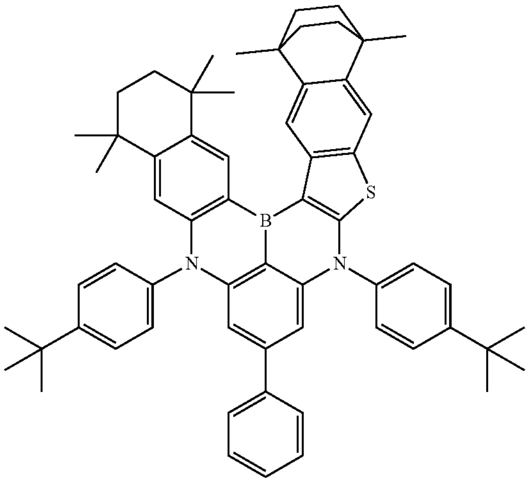
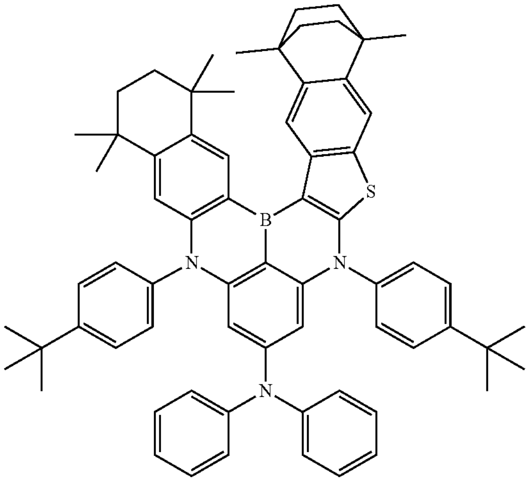
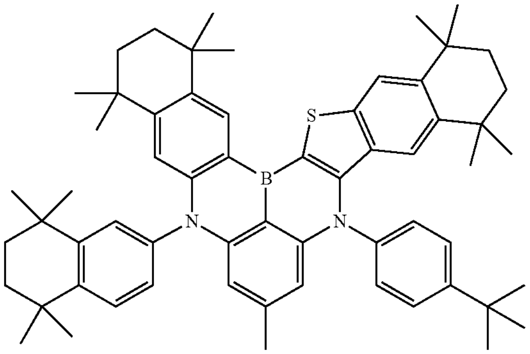
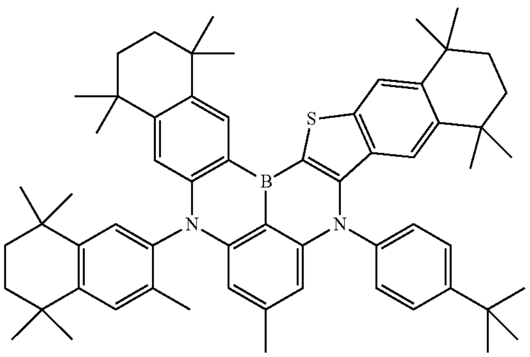
-continued
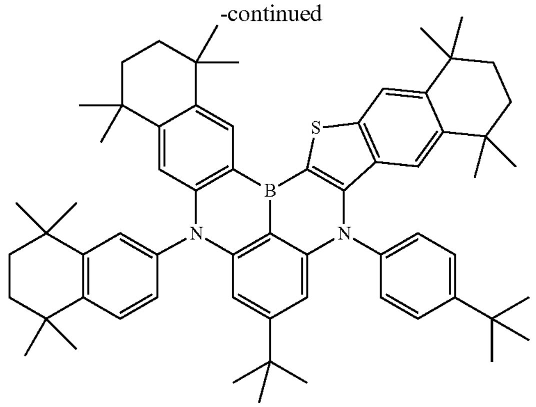
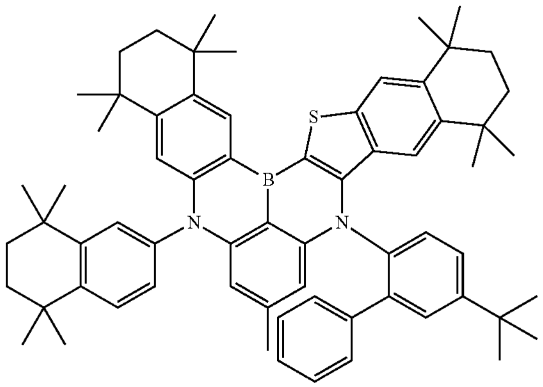
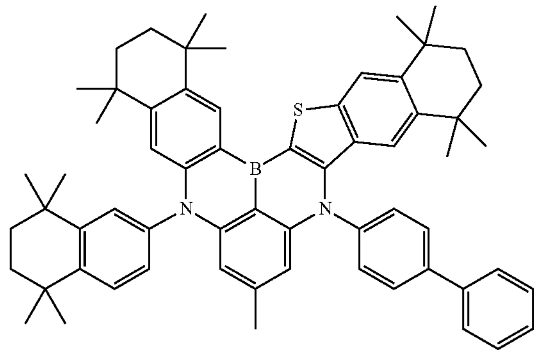
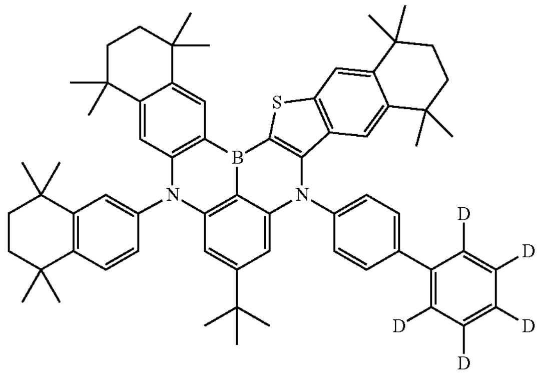

-continued
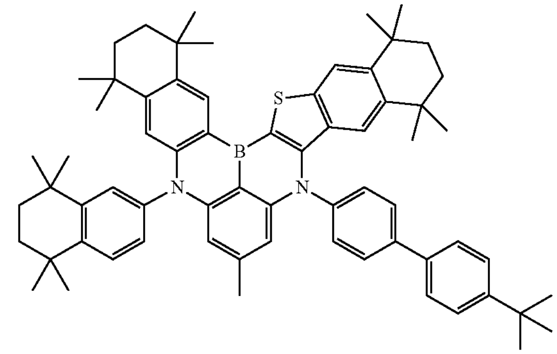
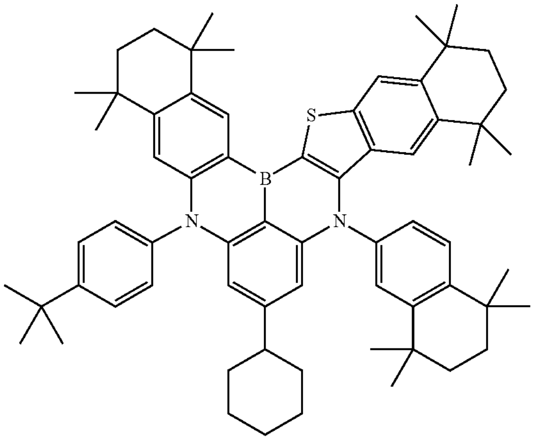
-continued
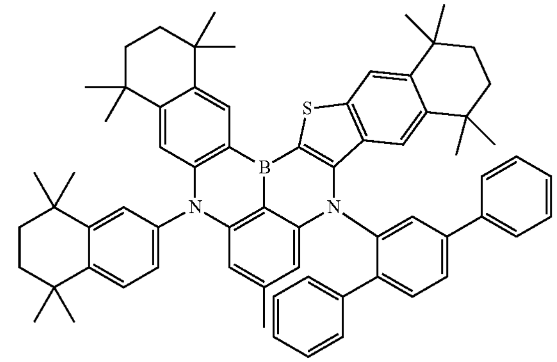
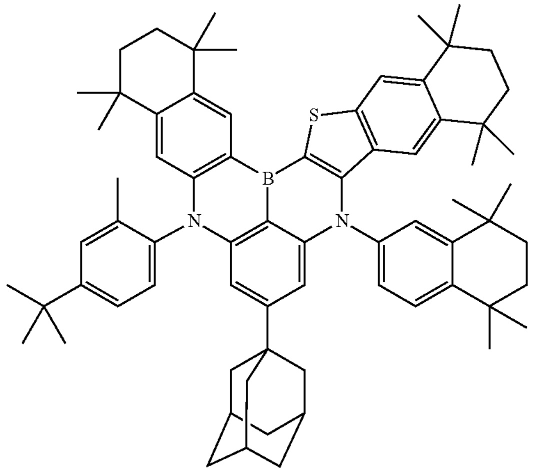
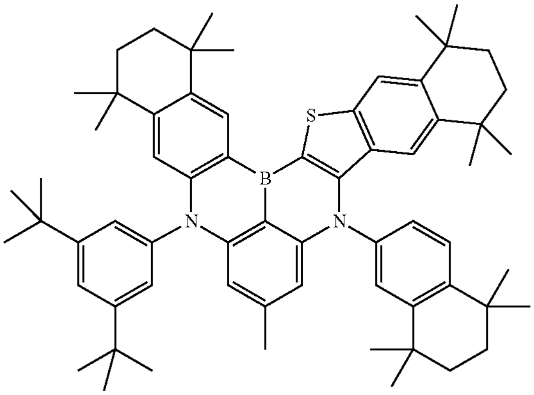
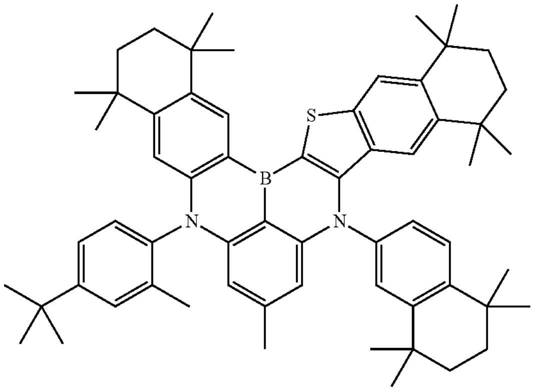
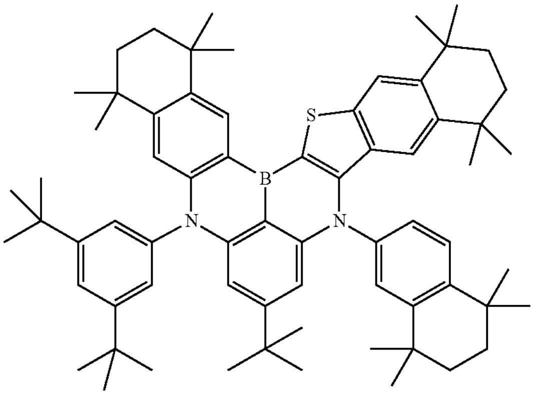
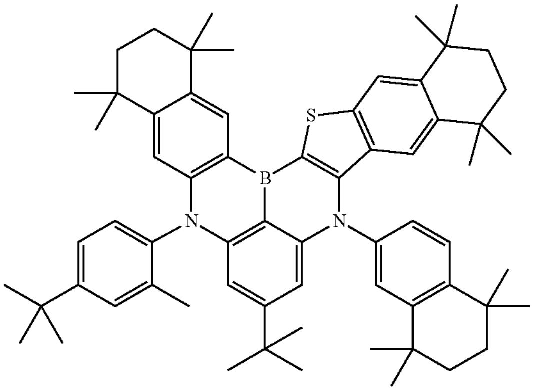

-continued
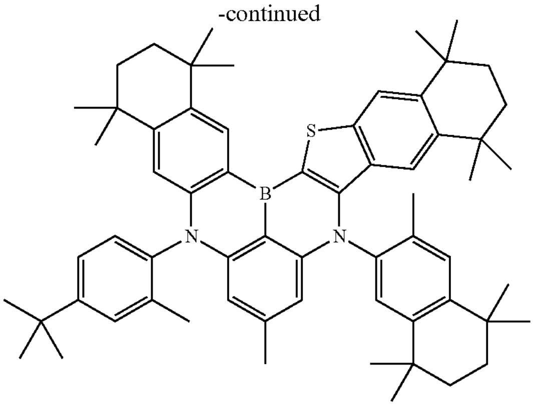
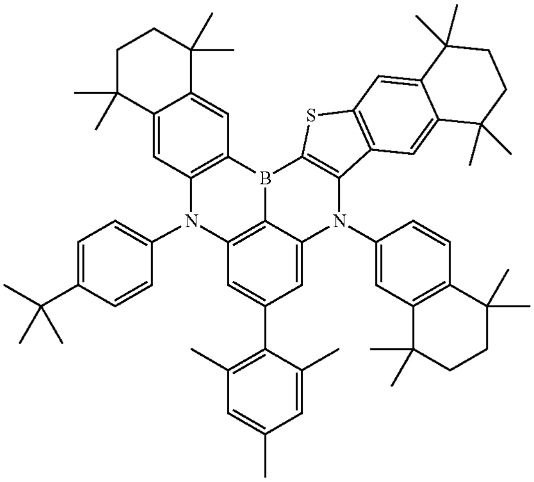
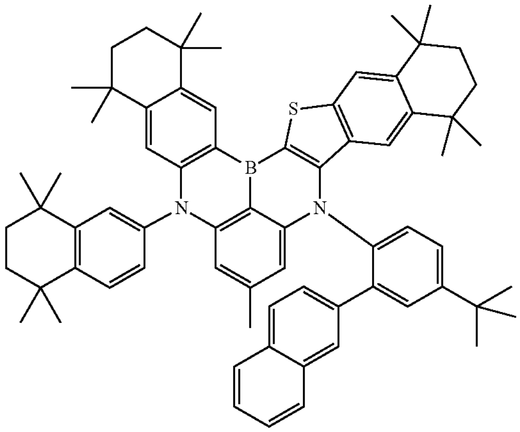
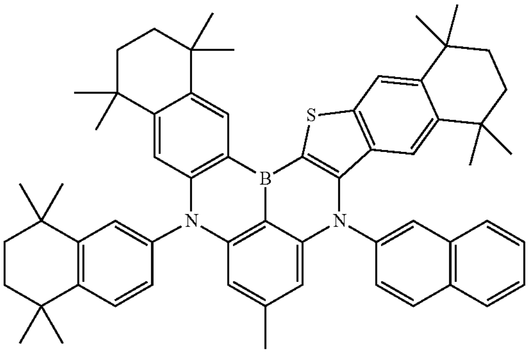
-continued
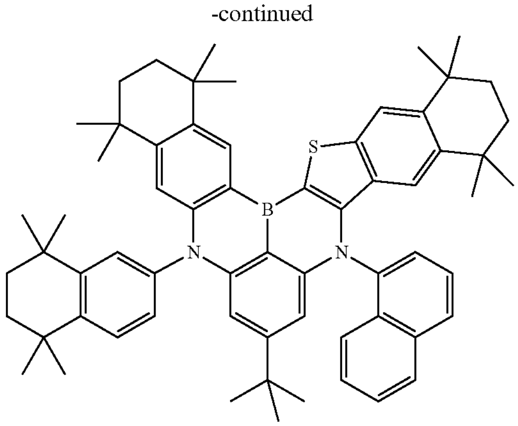
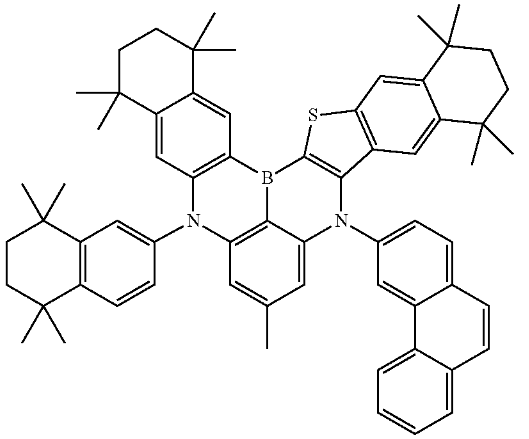
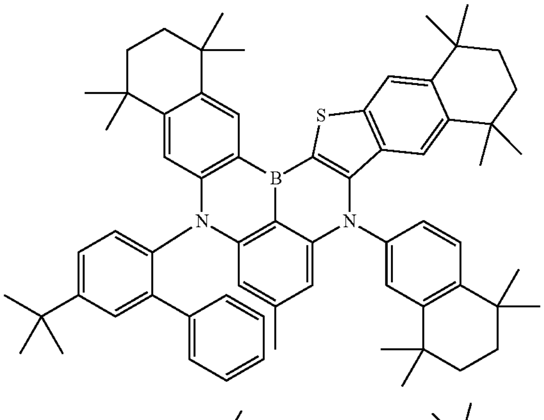
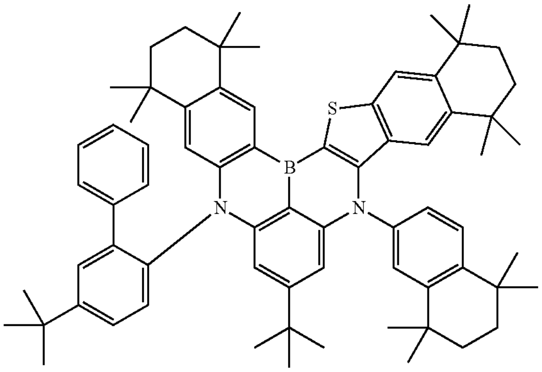

-continued
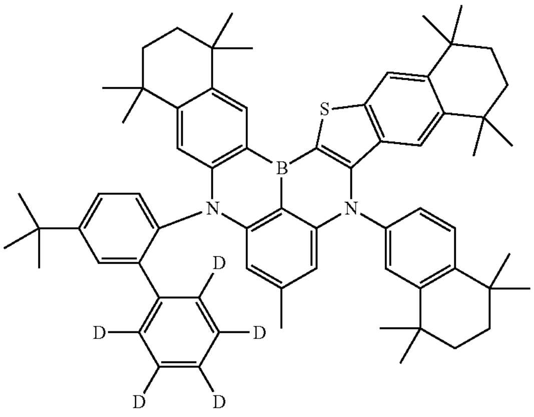
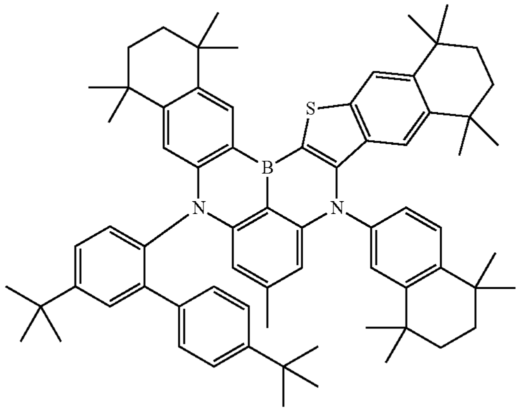
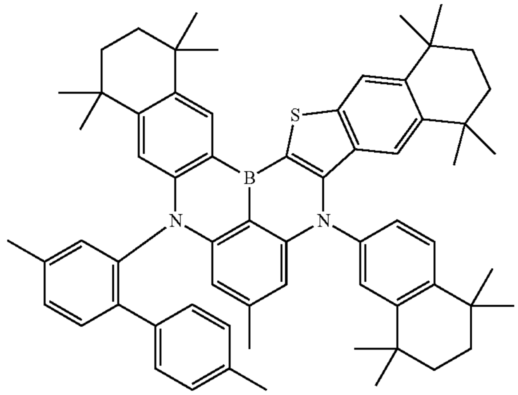
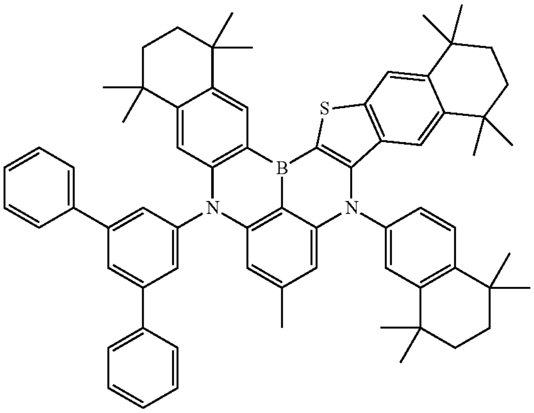
-continued
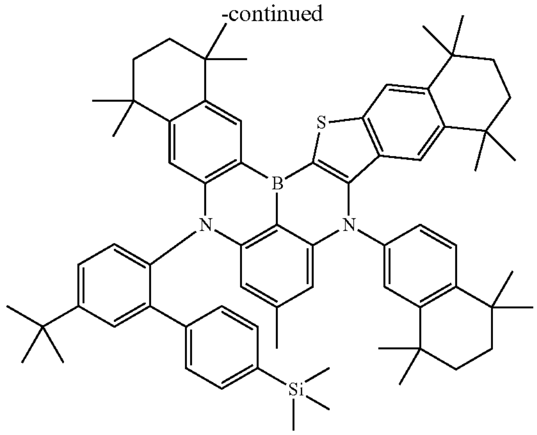
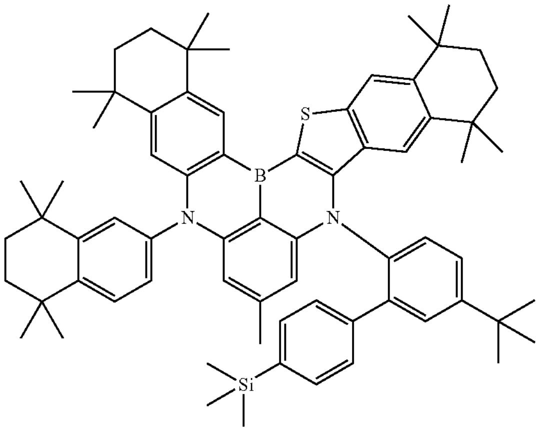
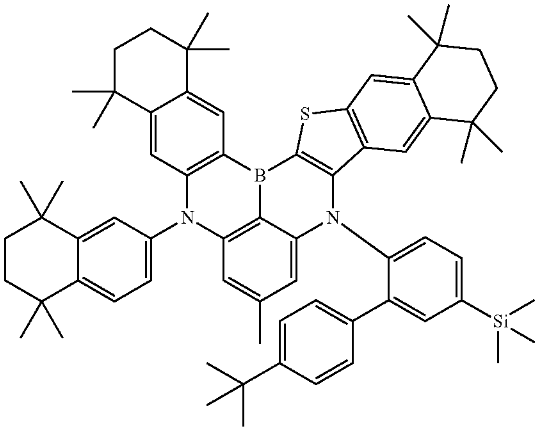
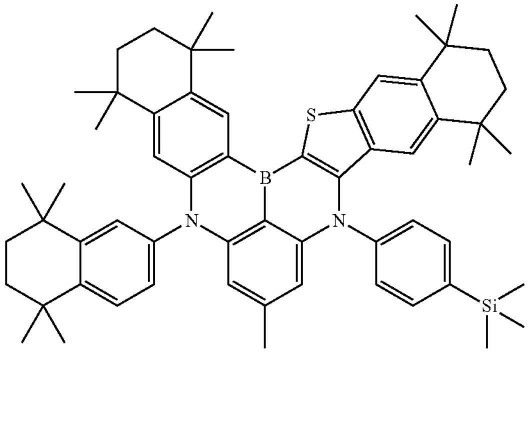

-continued
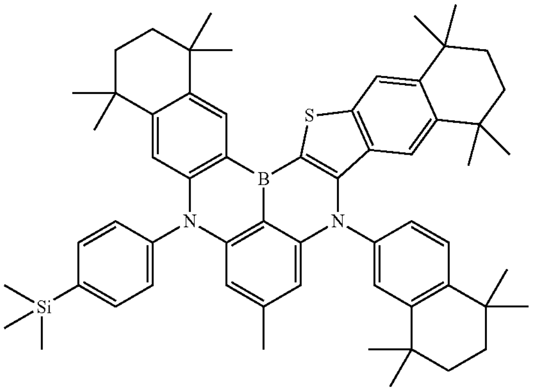
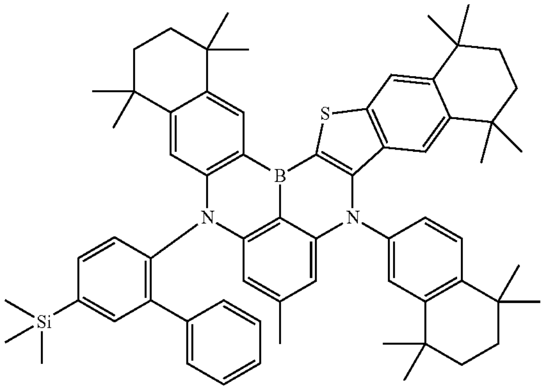
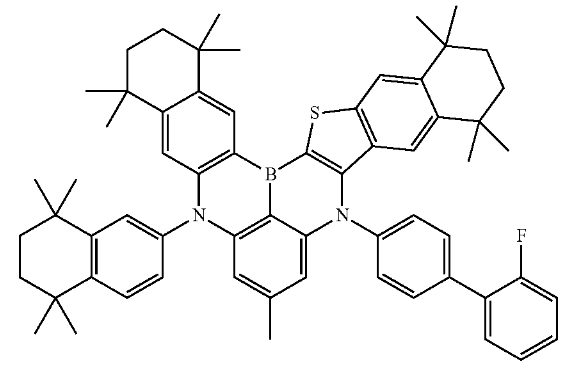
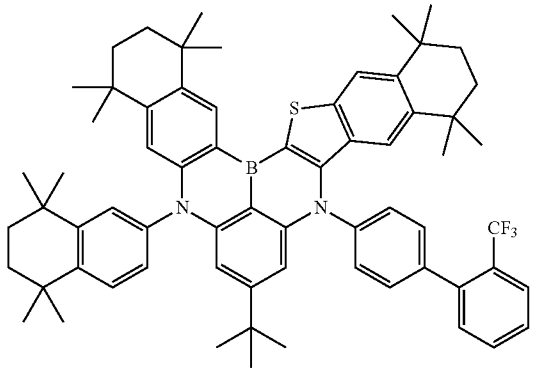
-continued
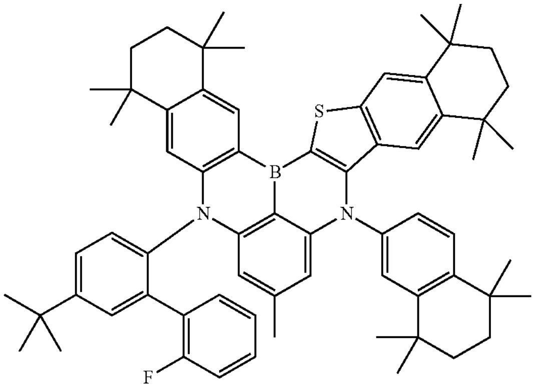
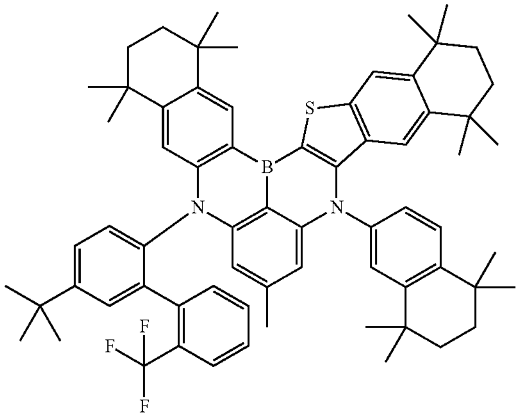
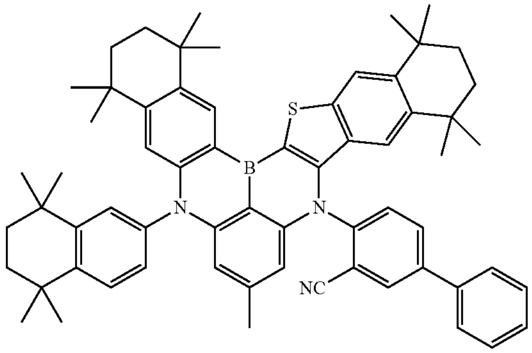
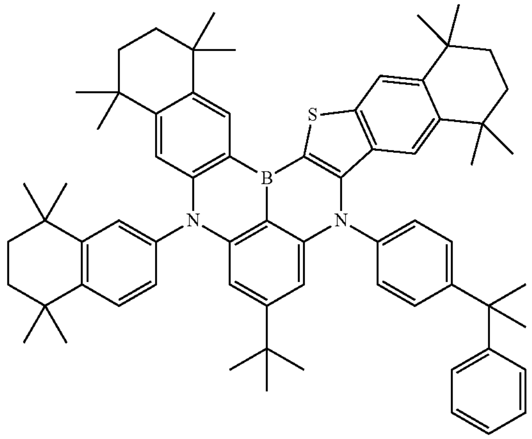

-continued
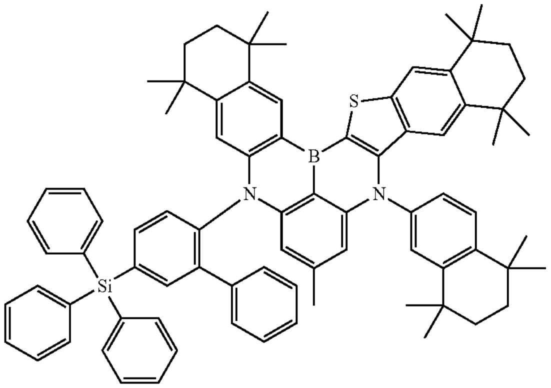
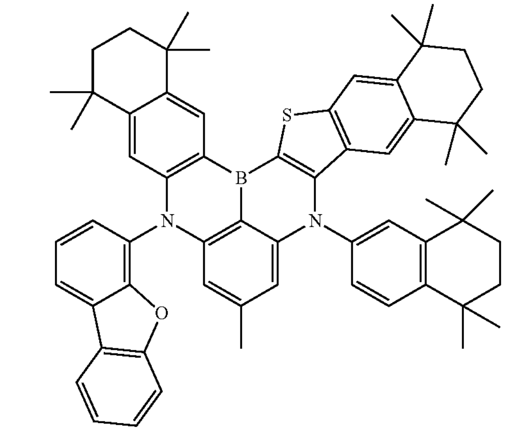
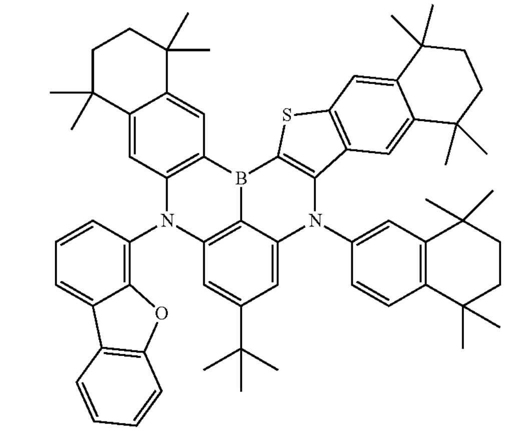
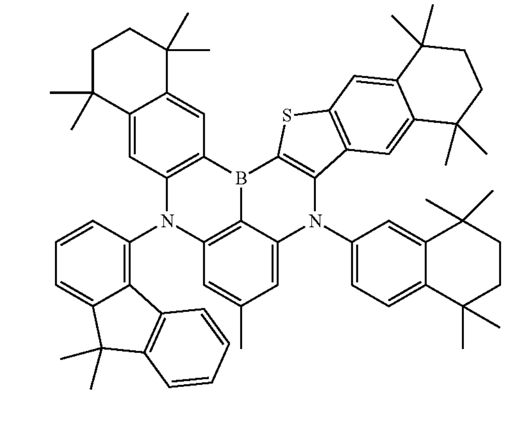
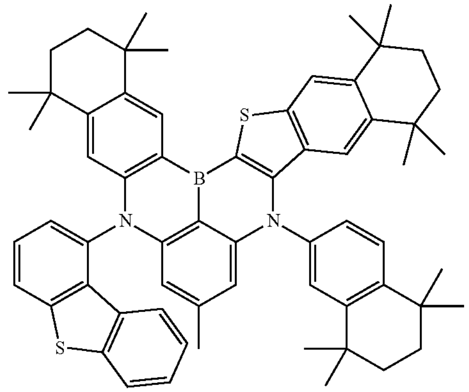
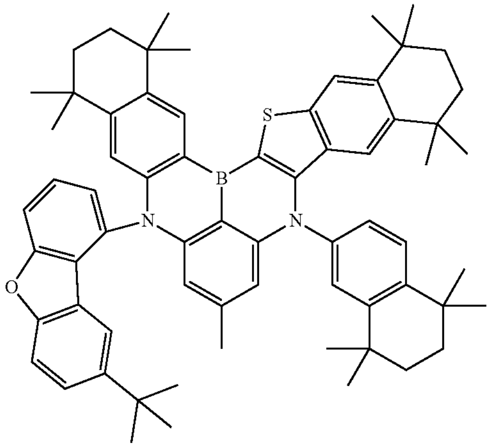
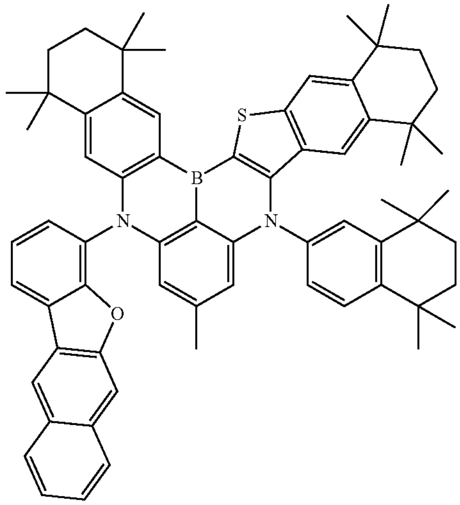
-continued -continued
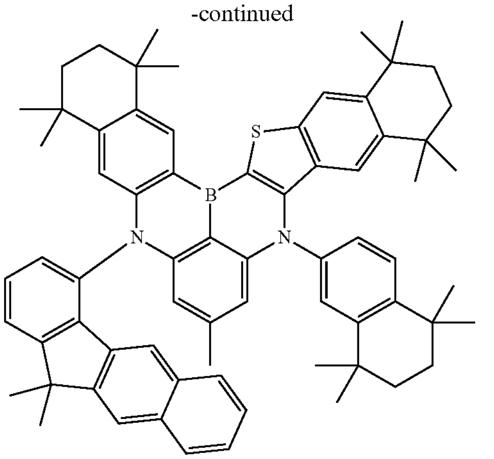
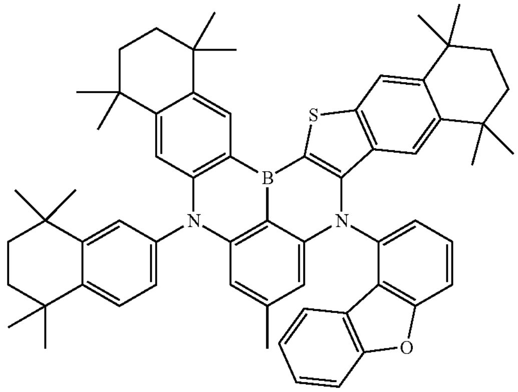
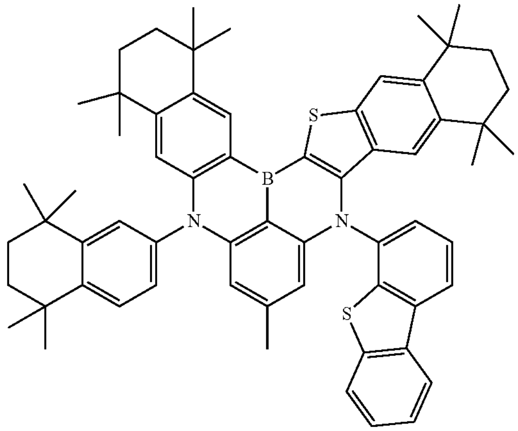
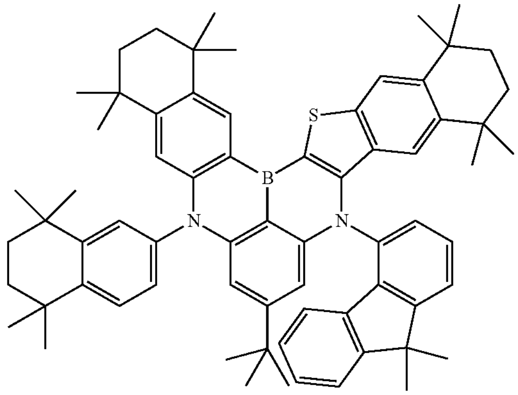
-continued
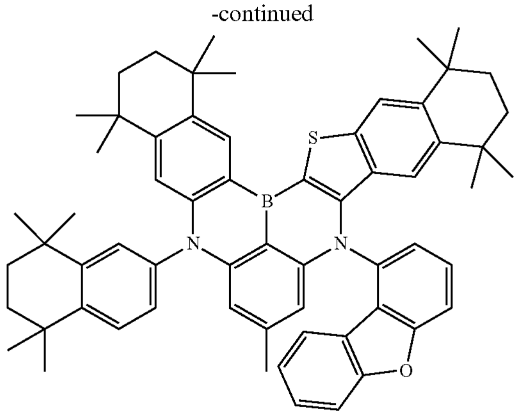
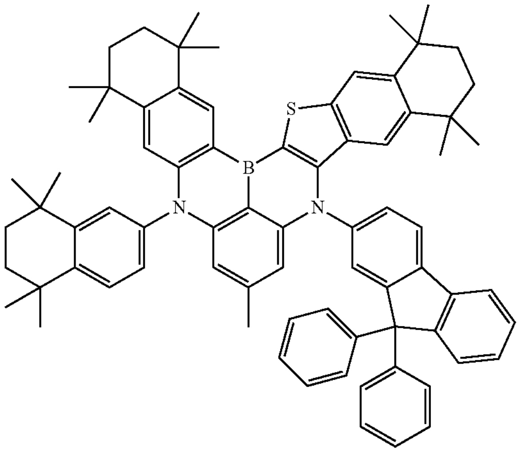
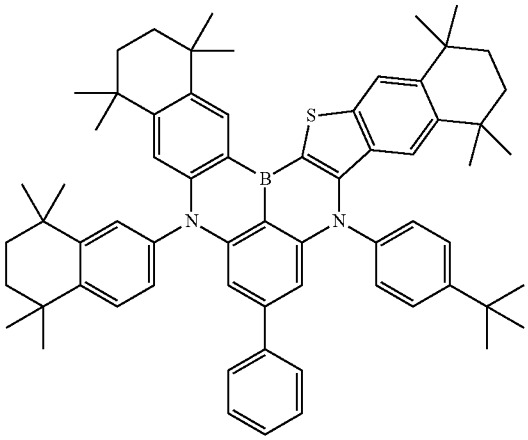

-continued
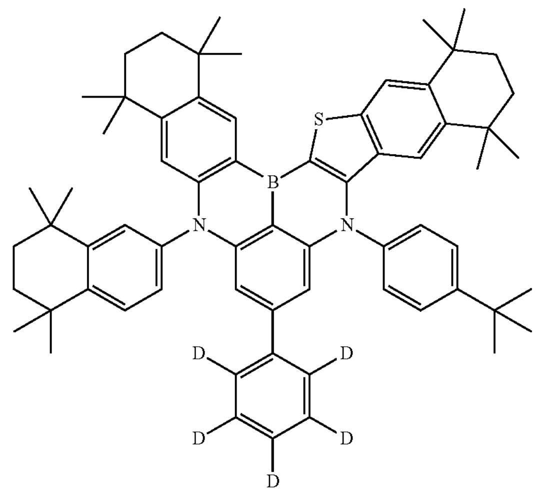
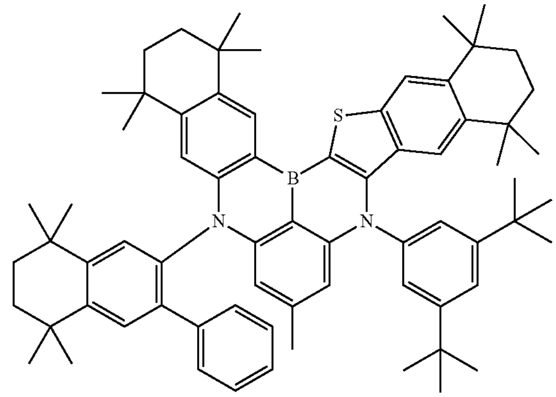
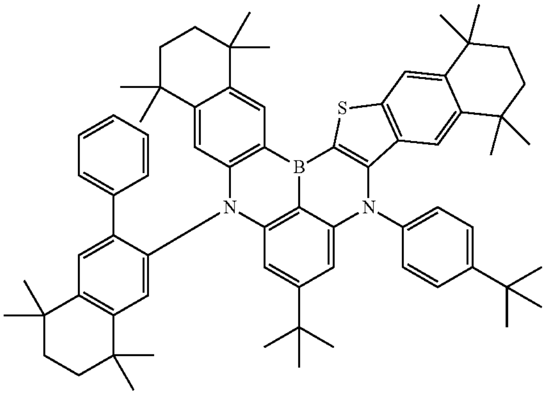
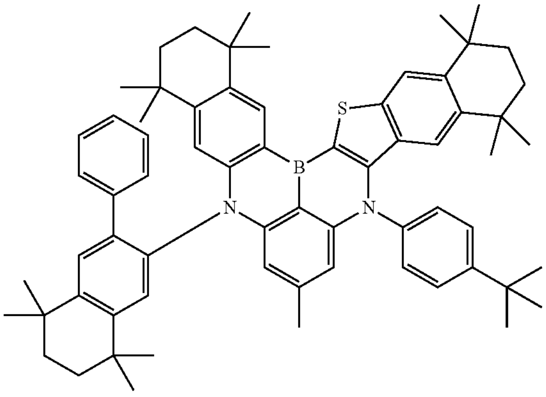
-continued
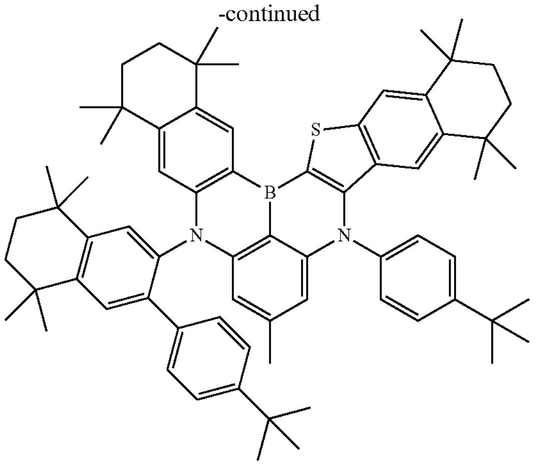
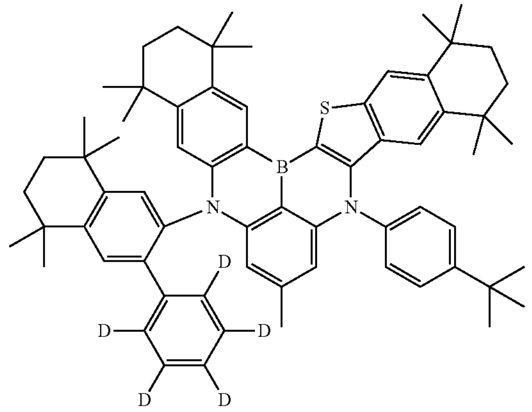
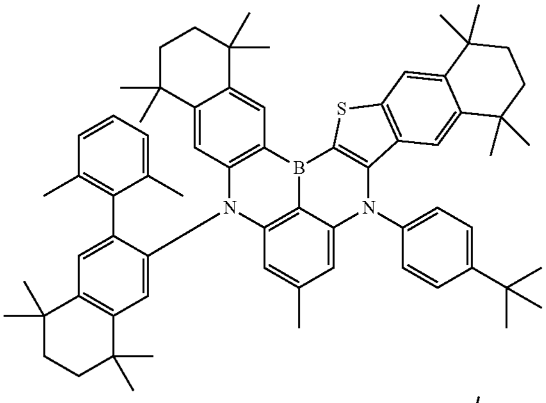
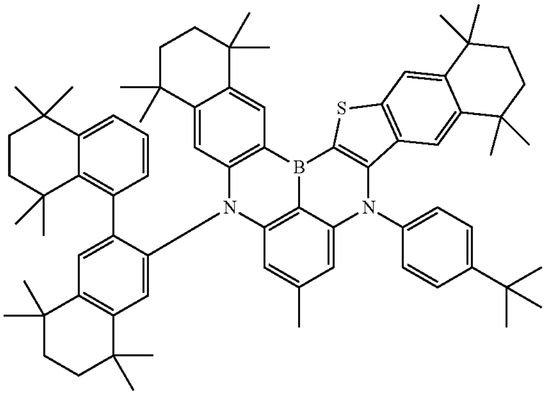

-continued
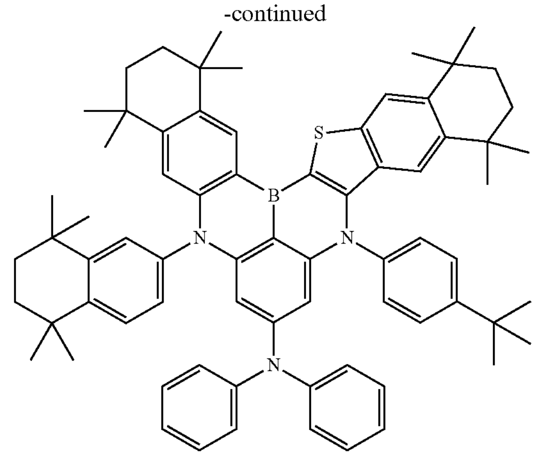
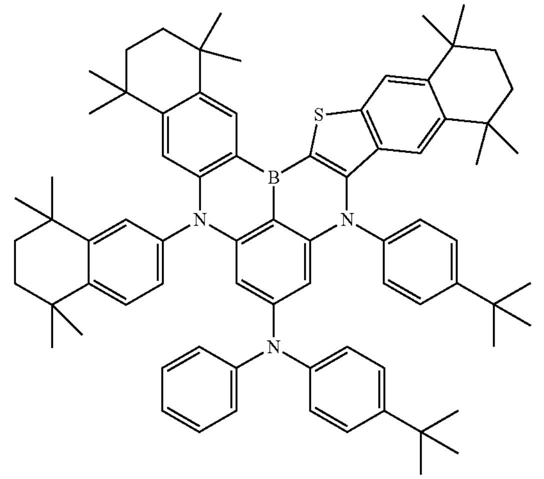
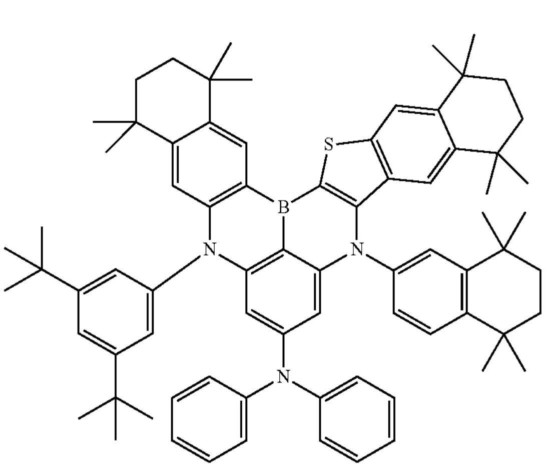
-continued
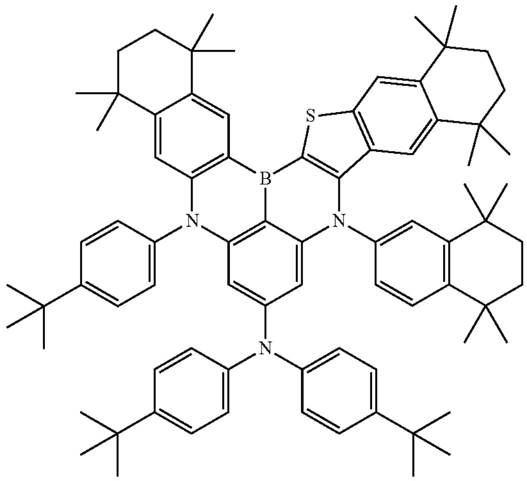
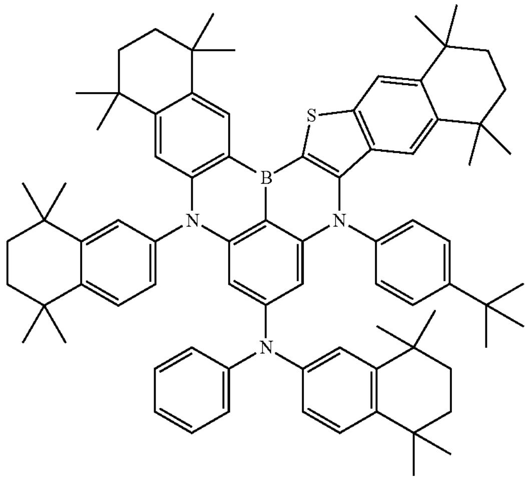
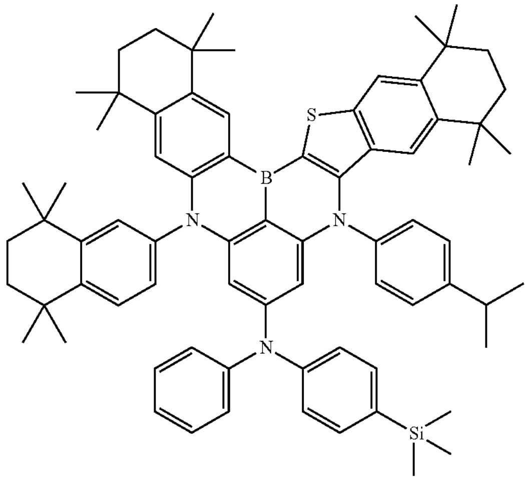

-continued
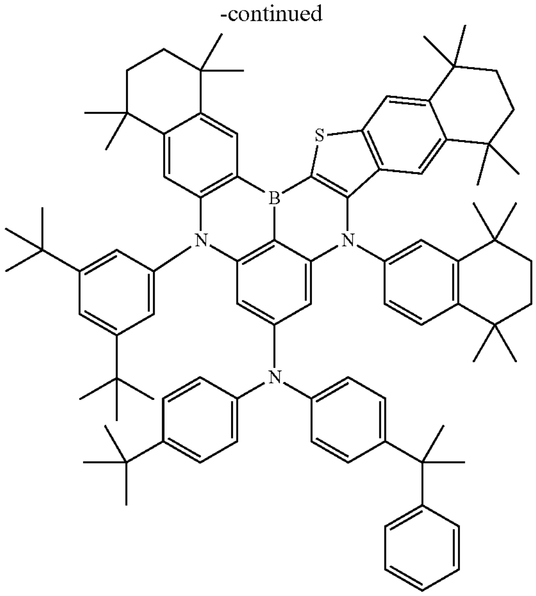
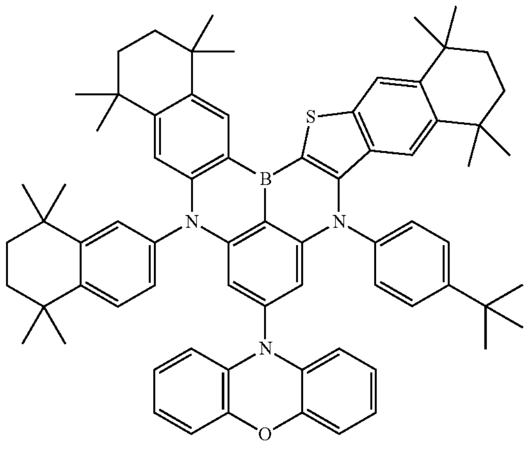
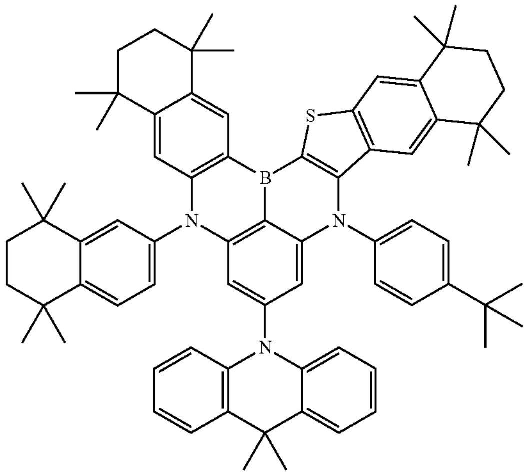
-continued
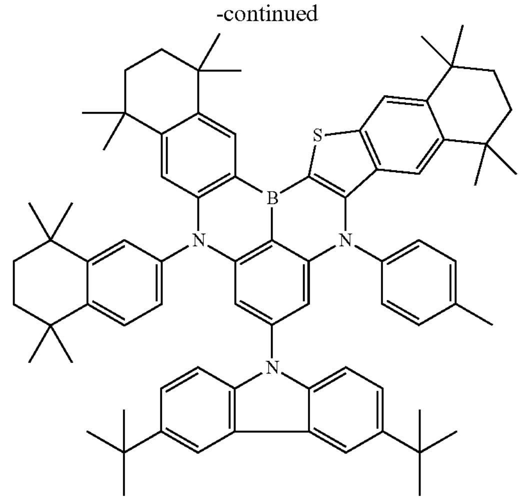
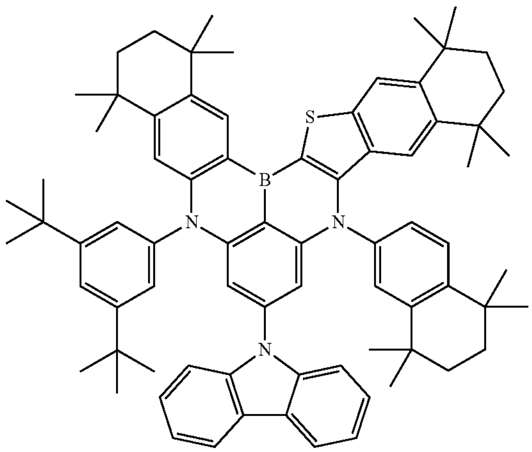
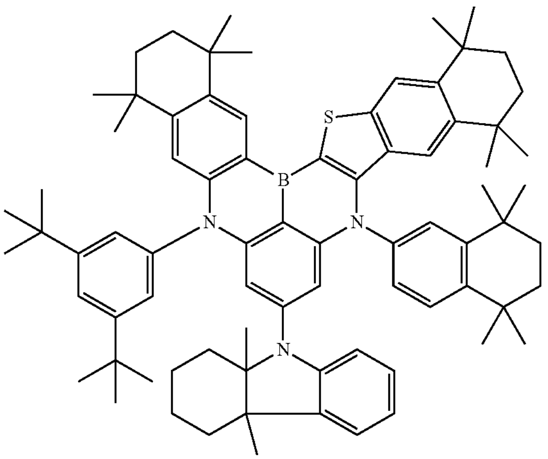

-continued
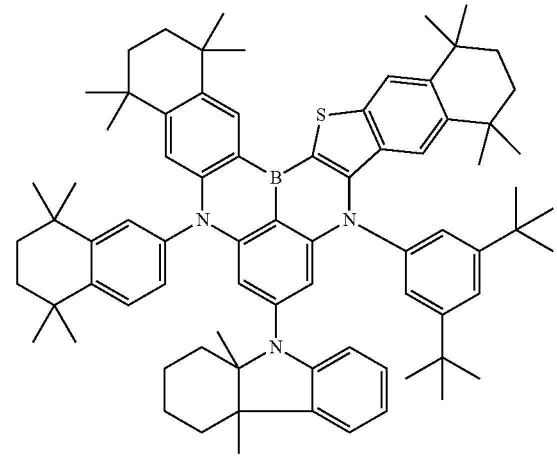
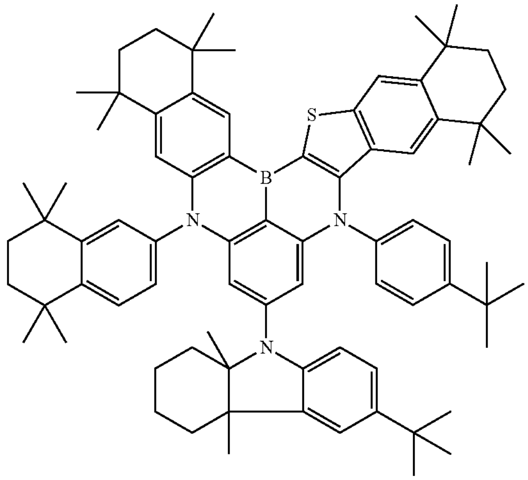
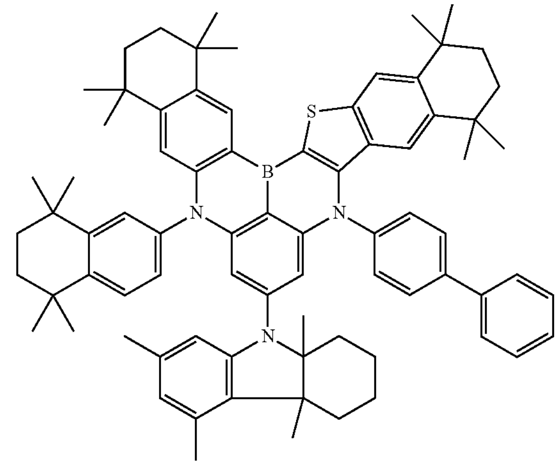
-continued
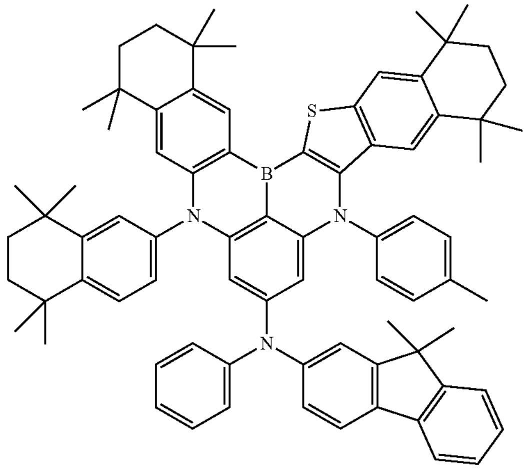
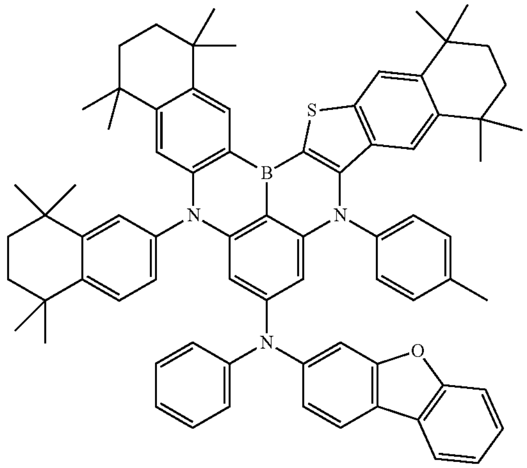
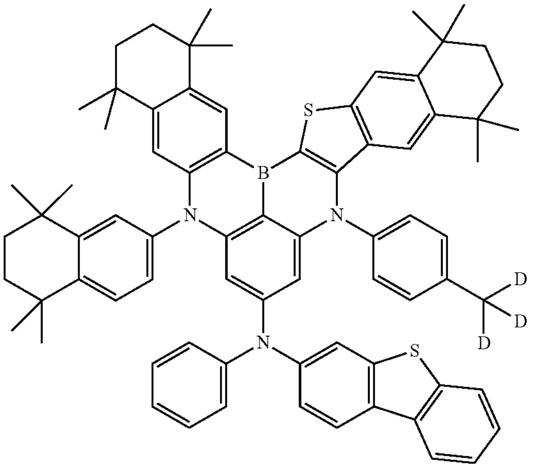

-continued
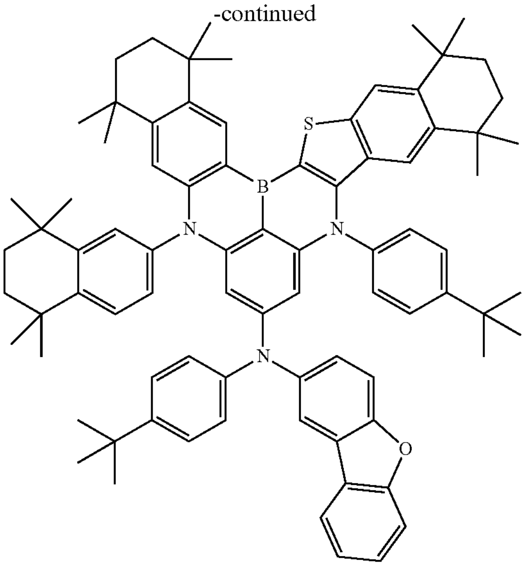
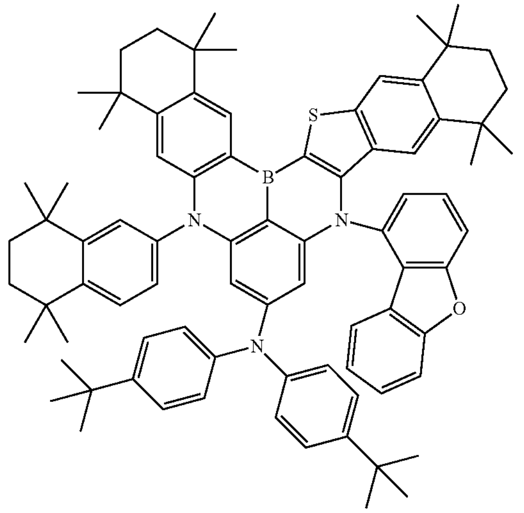
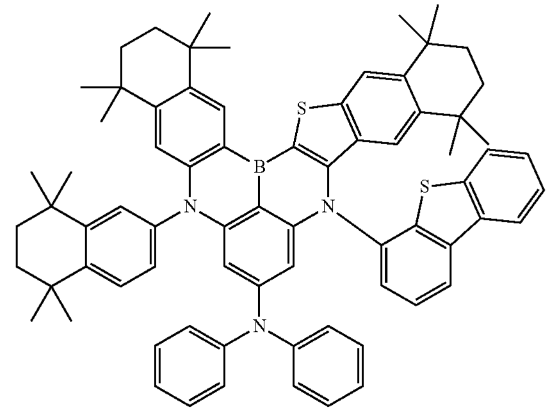
-continued
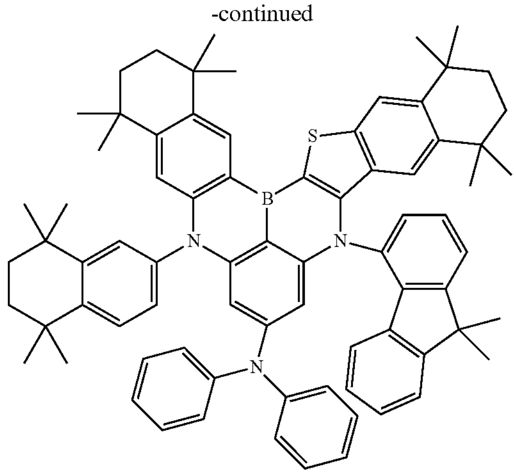
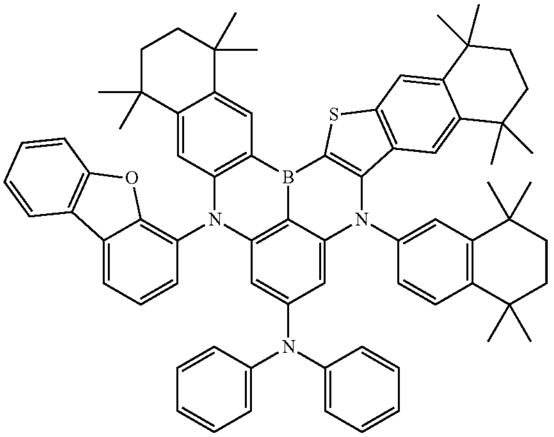
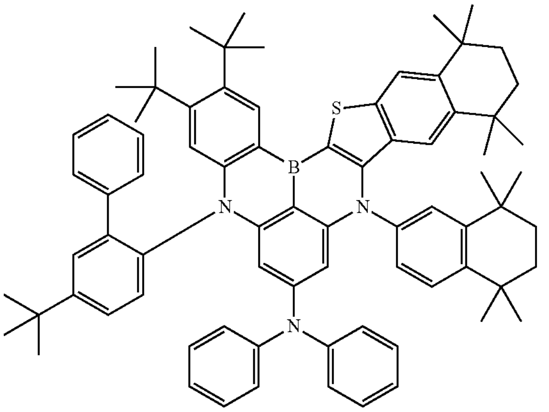
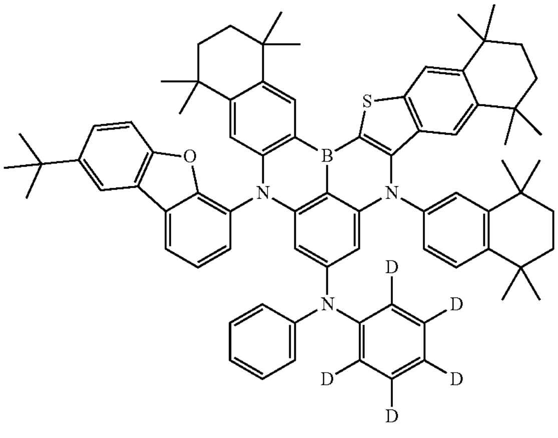

-continued
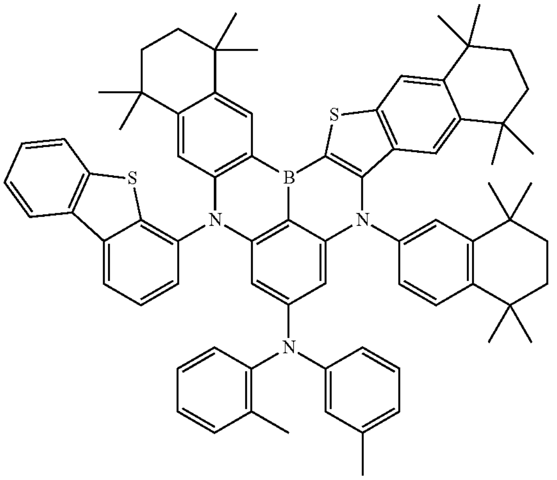
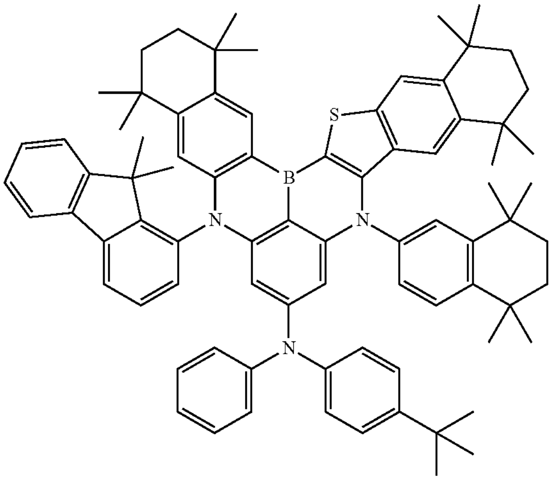
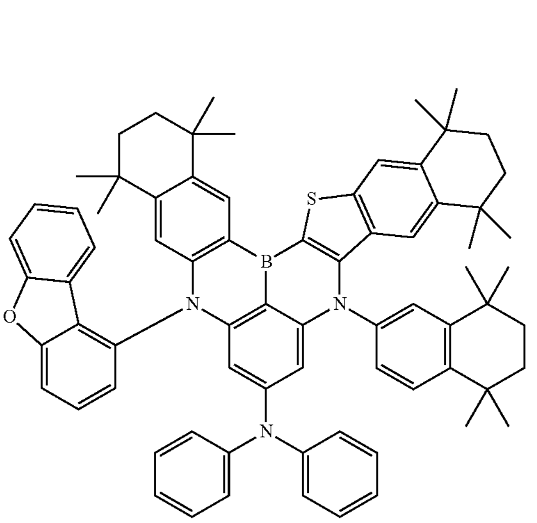
-continued
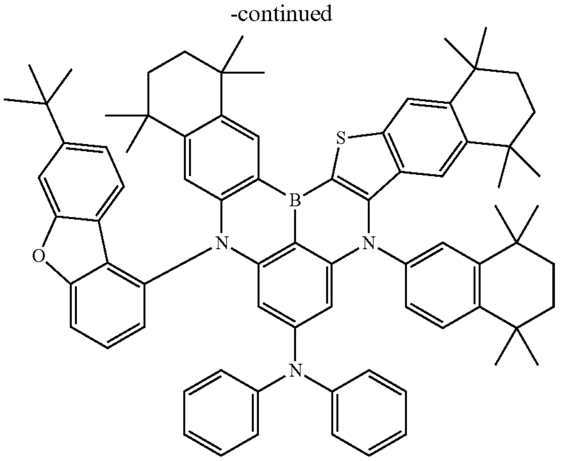
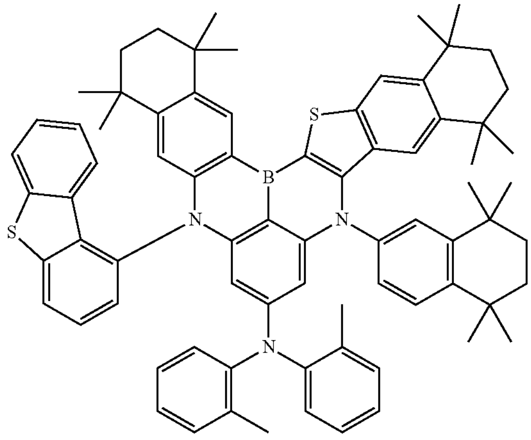
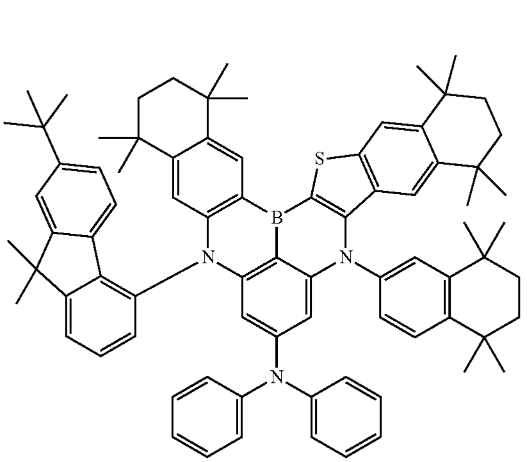

-continued
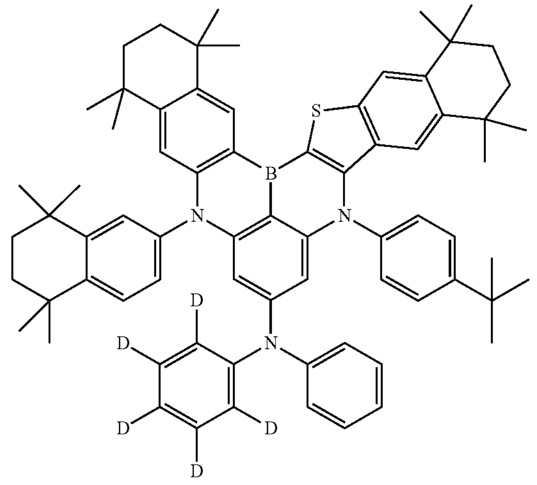
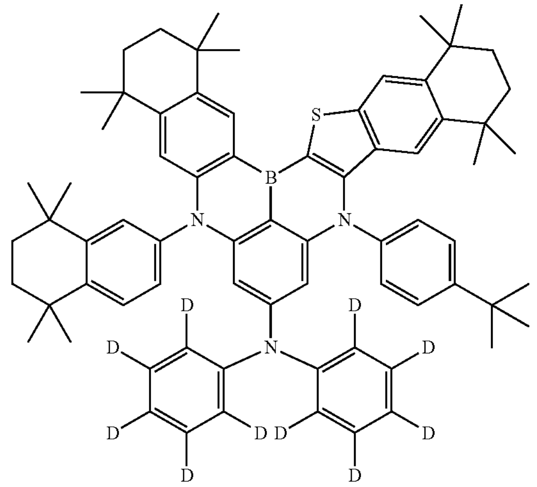
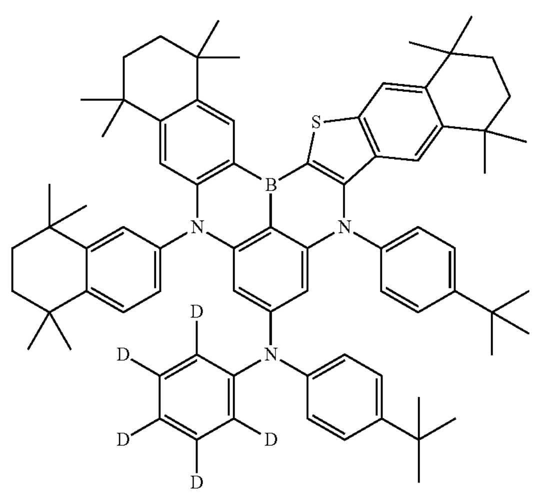
-continued
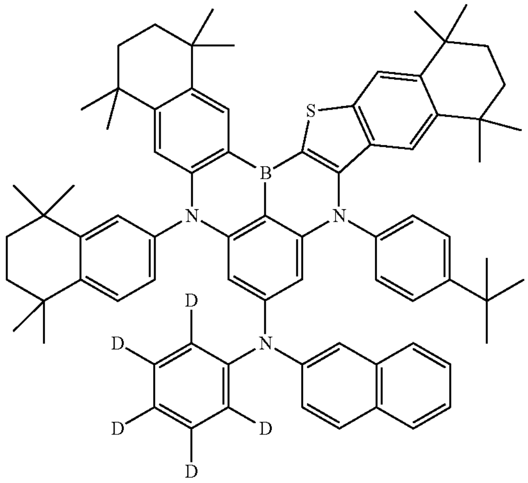
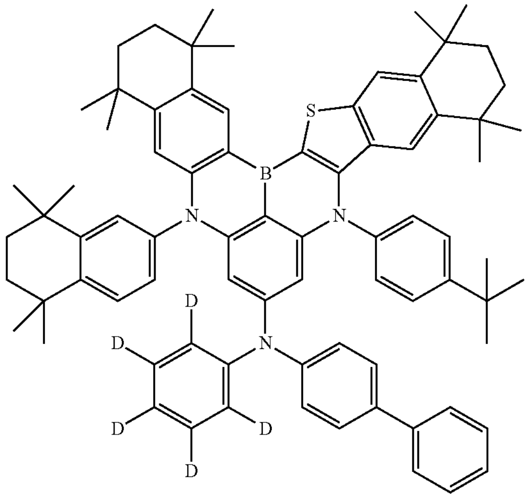
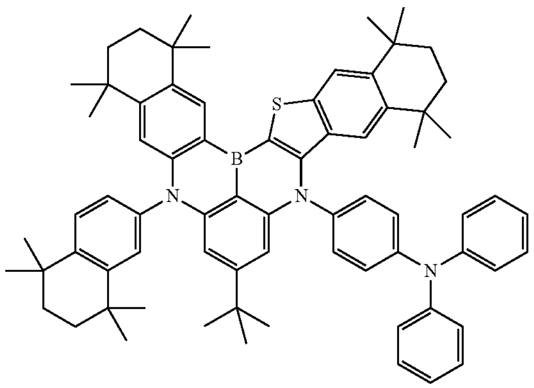

-continued
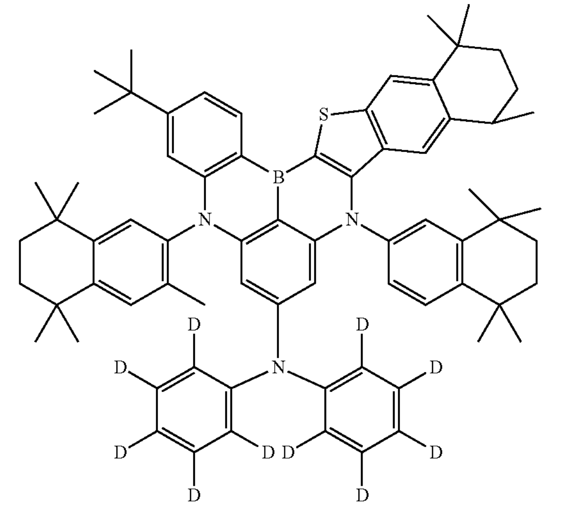
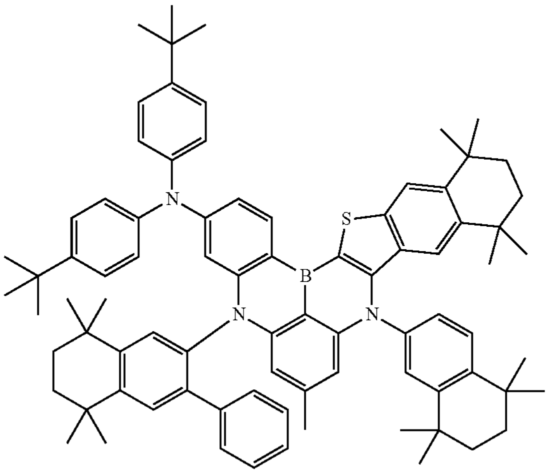
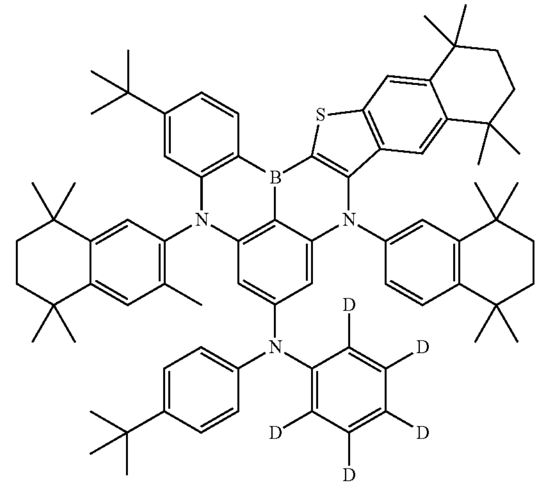
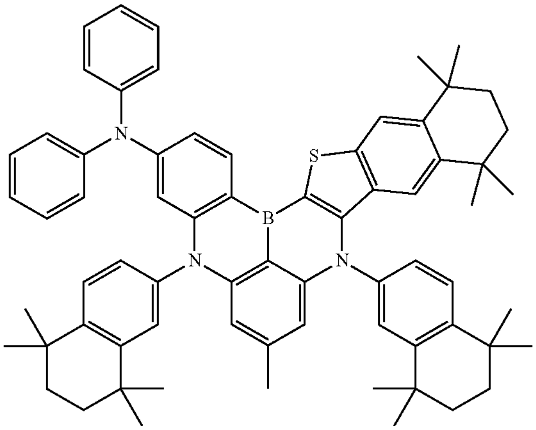
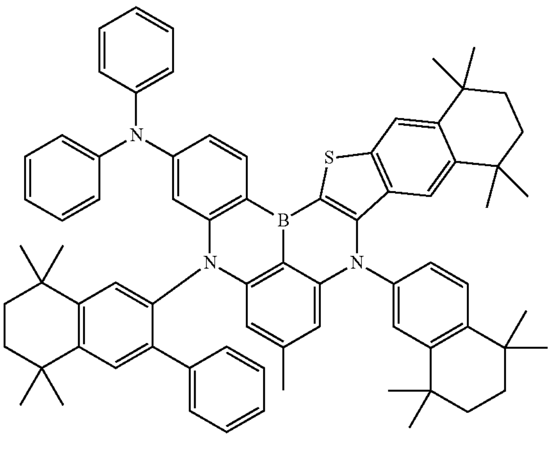
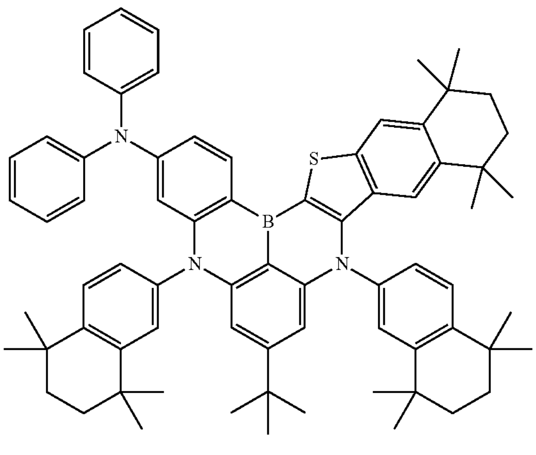
-continued -continued
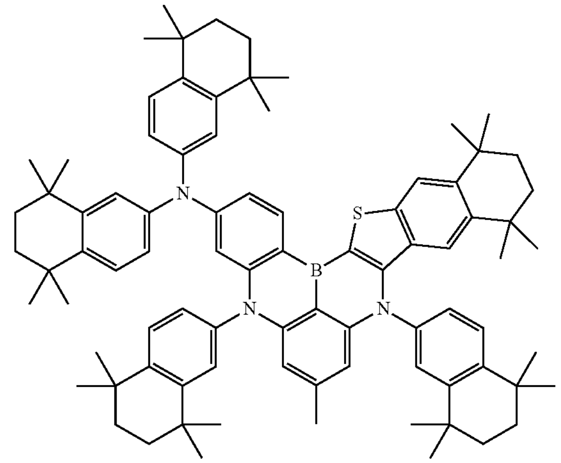
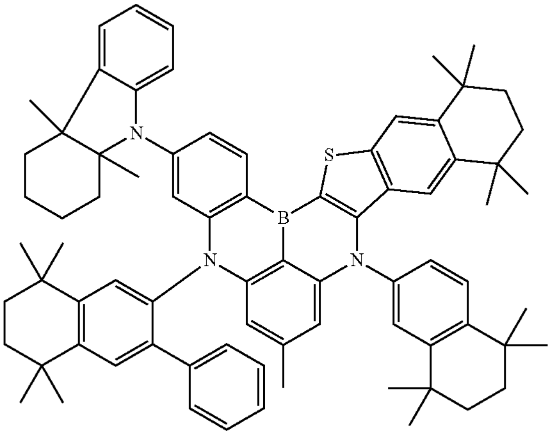
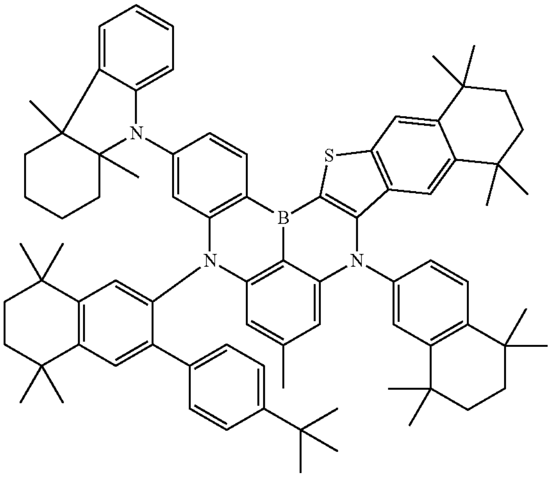
-continued
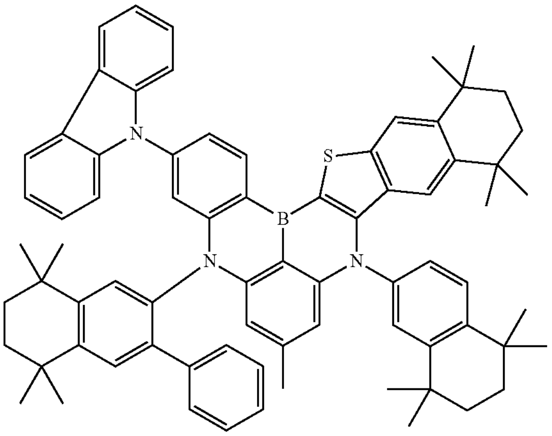
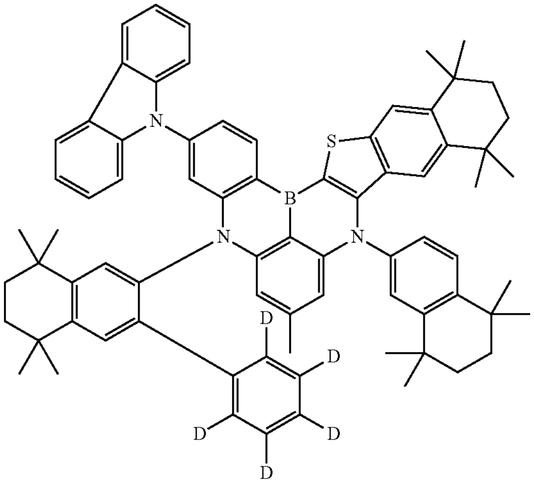
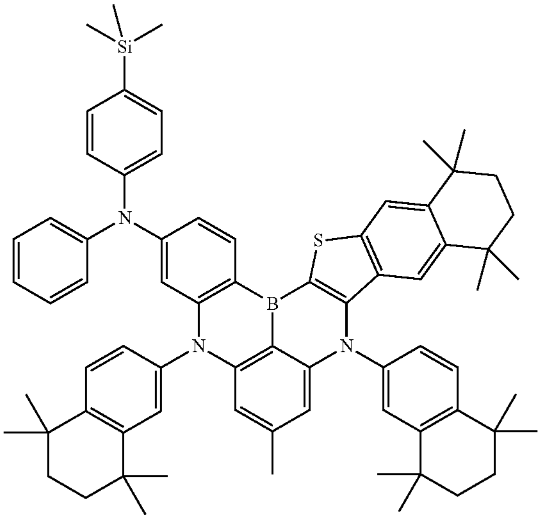

-continued
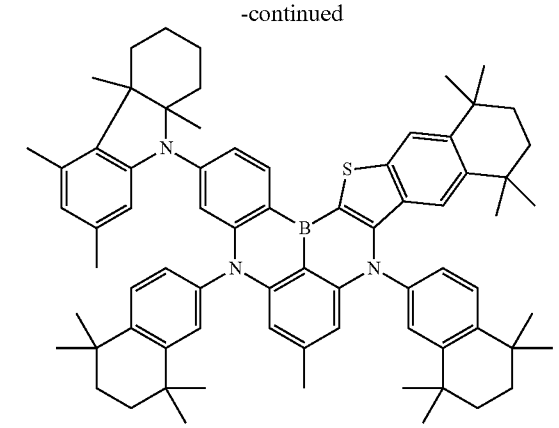
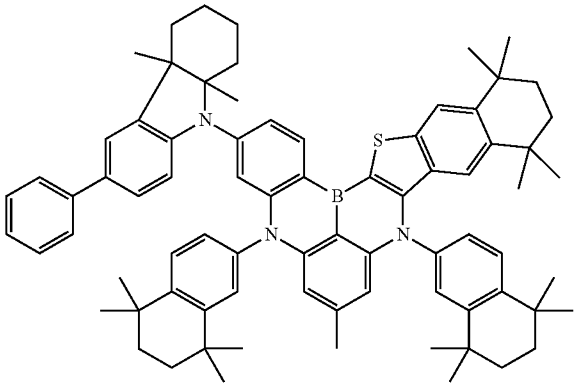
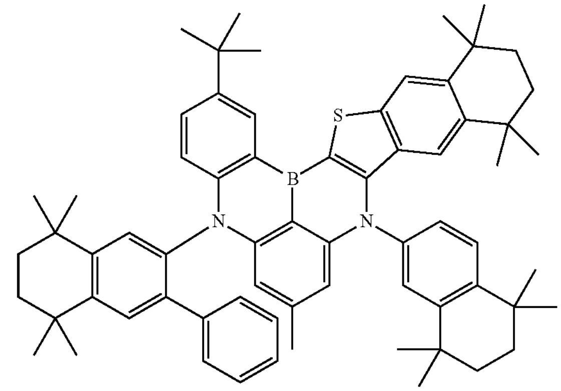
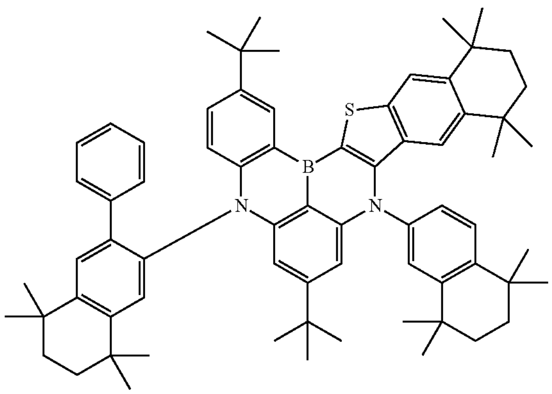
-continued
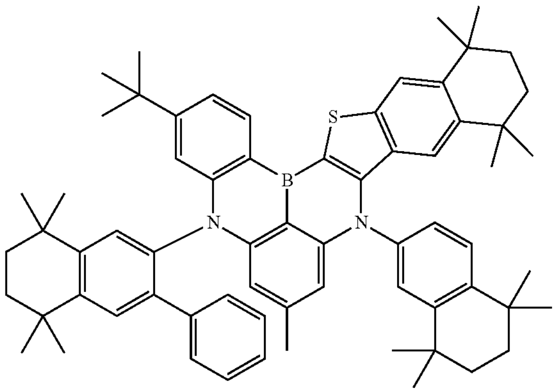
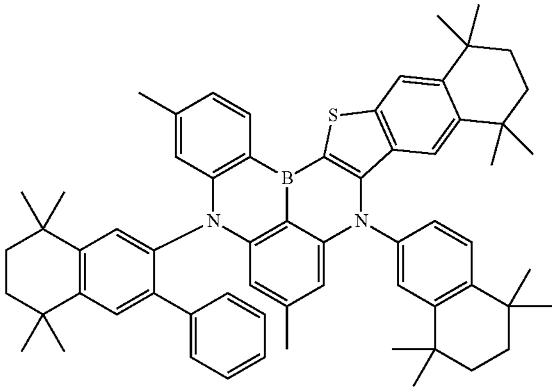
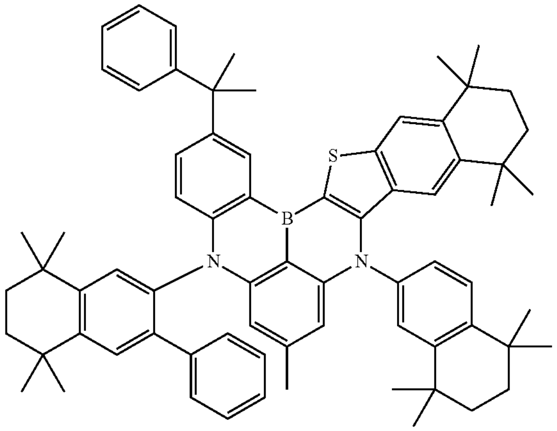
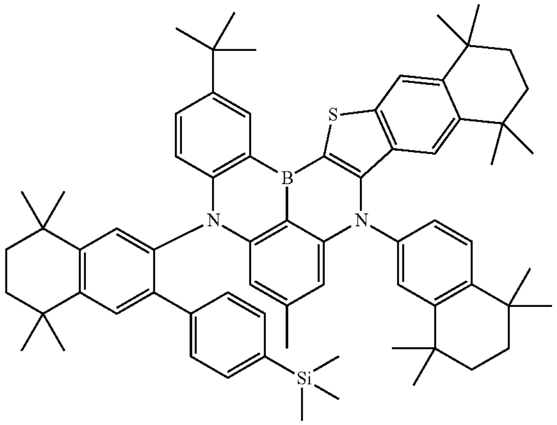

-continued
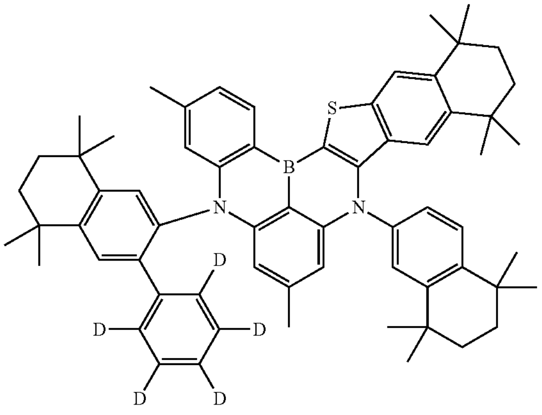
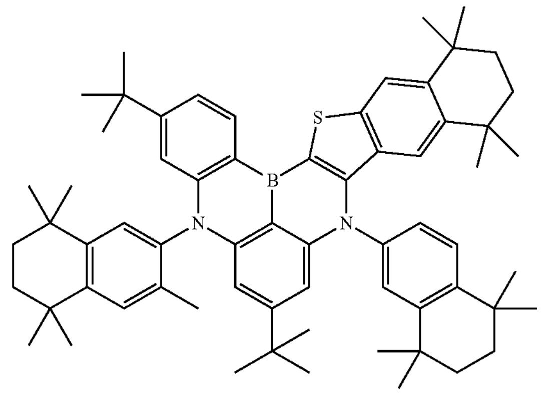
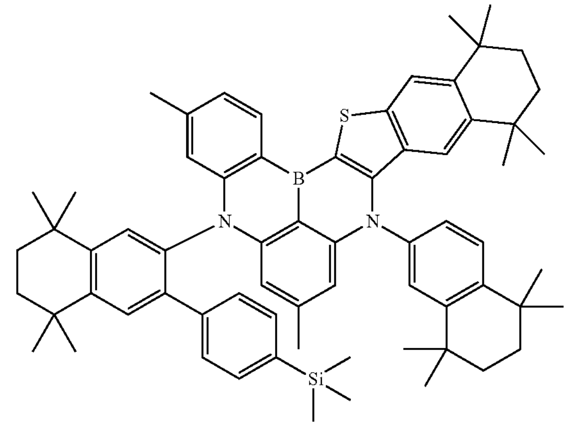
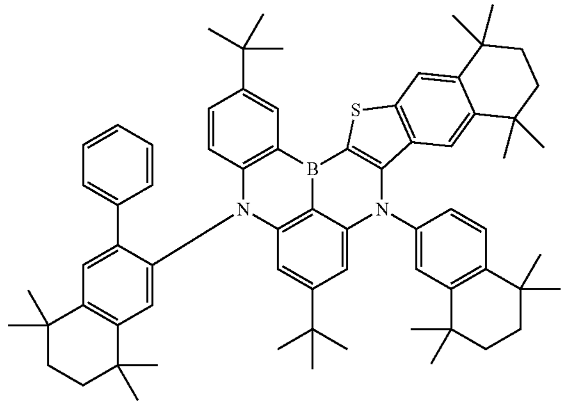
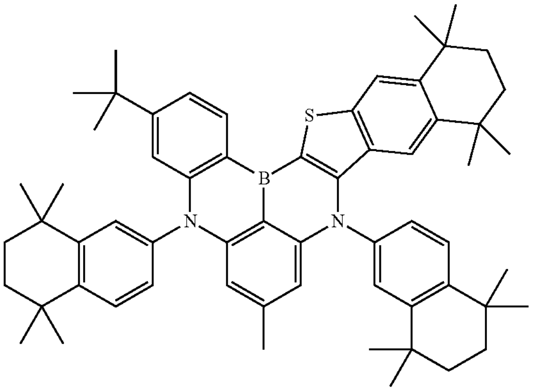
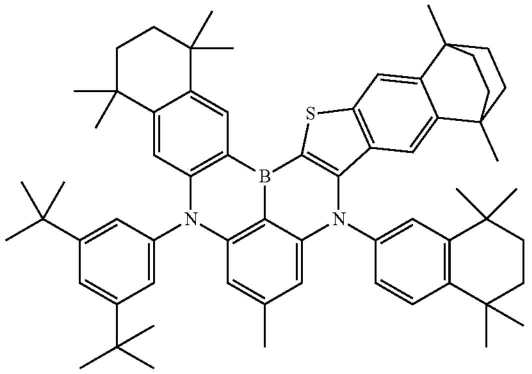
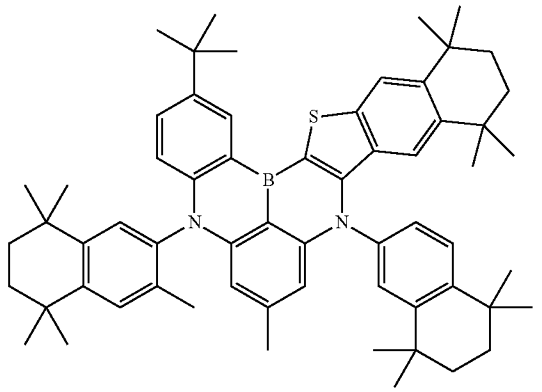
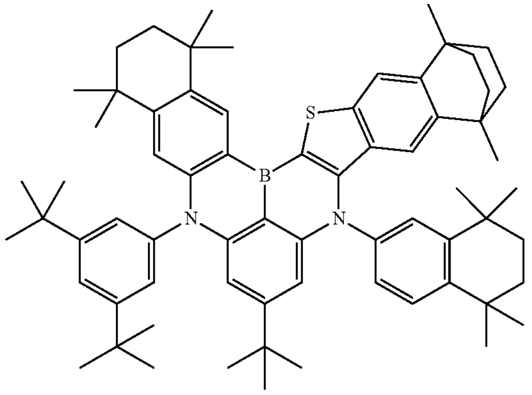
-continued -continued
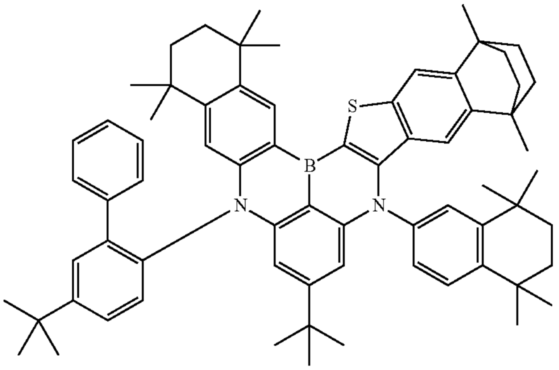
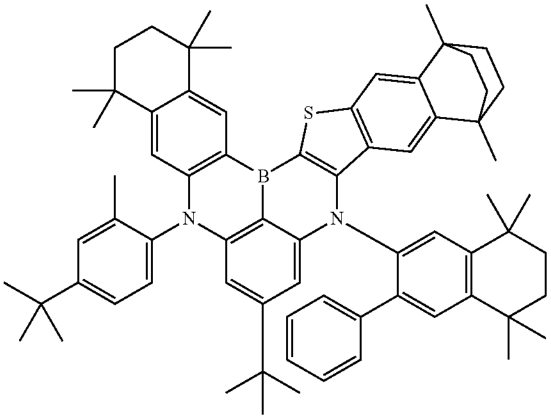
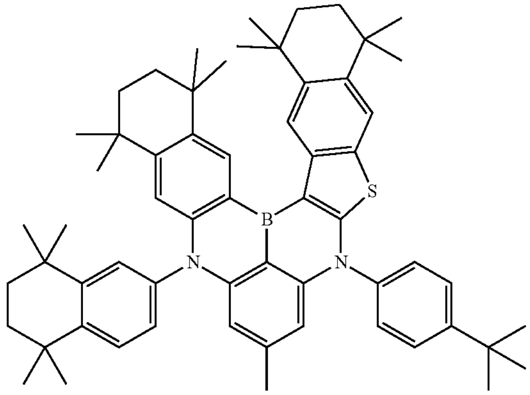
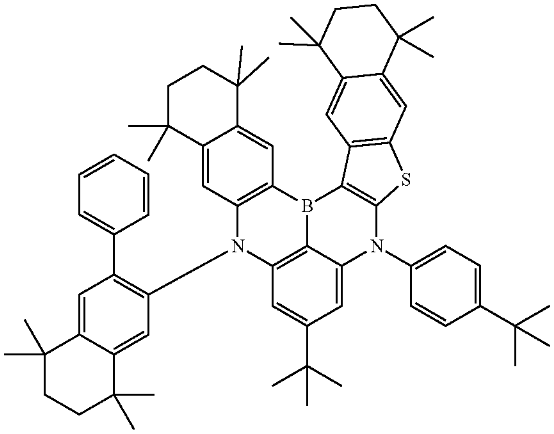
-continued
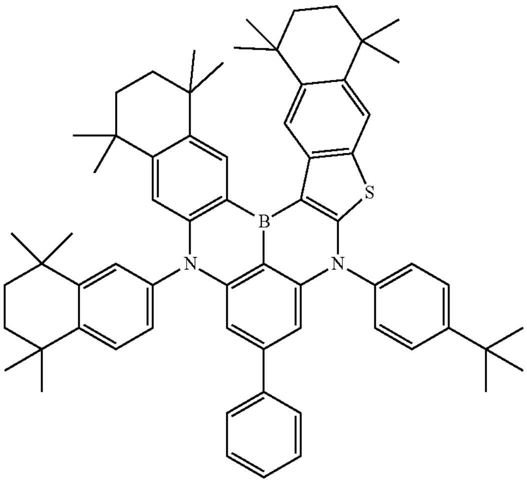
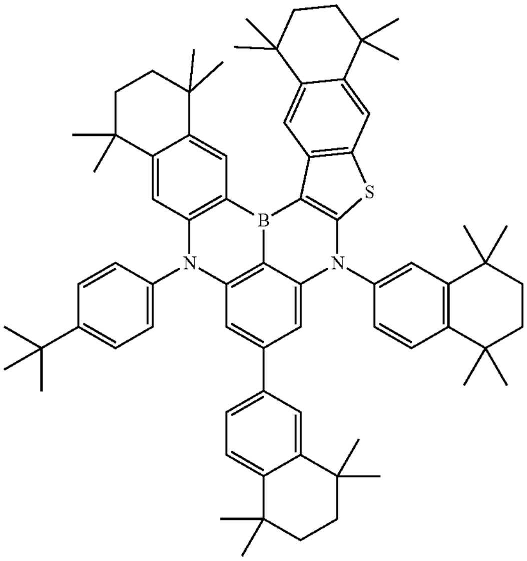
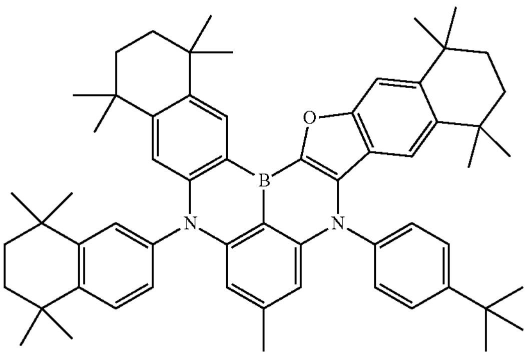

-continued
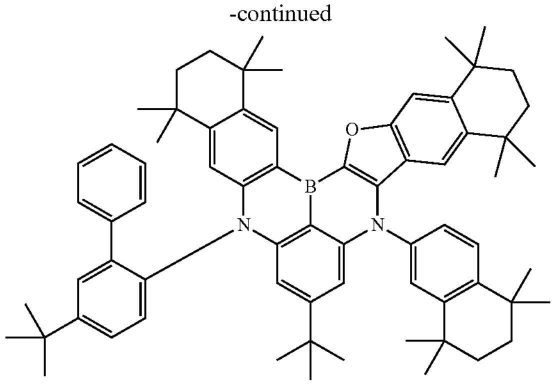
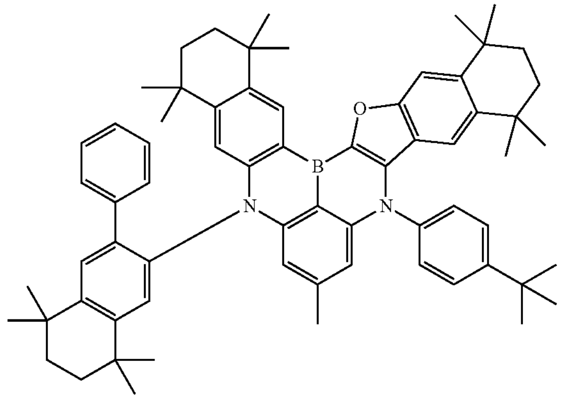
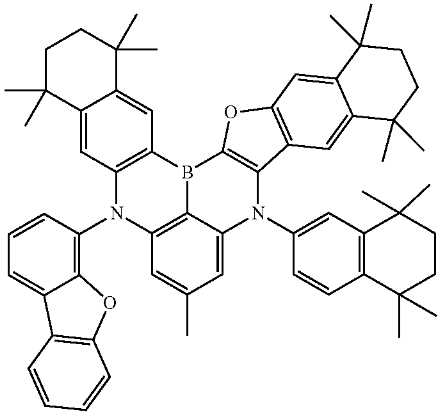
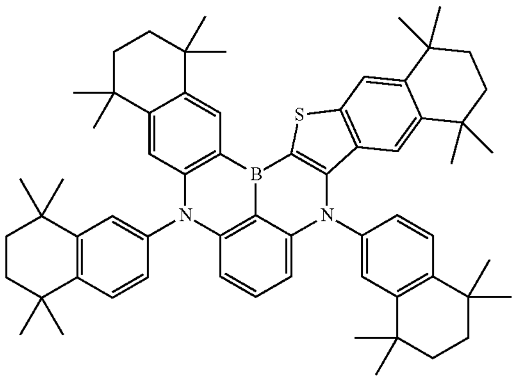
-continued
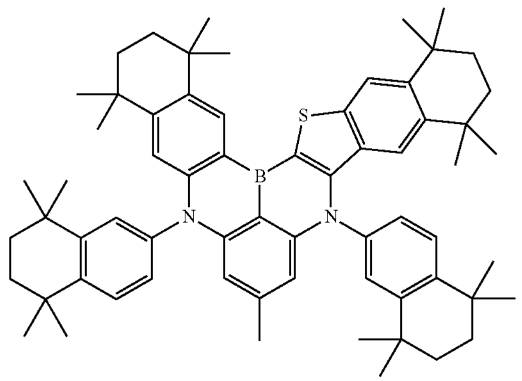
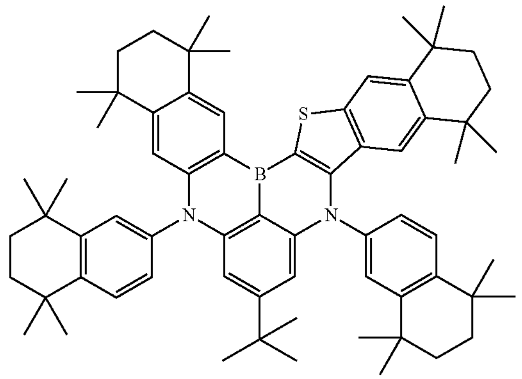
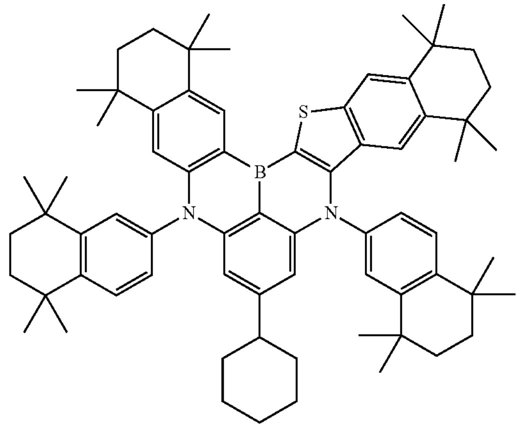
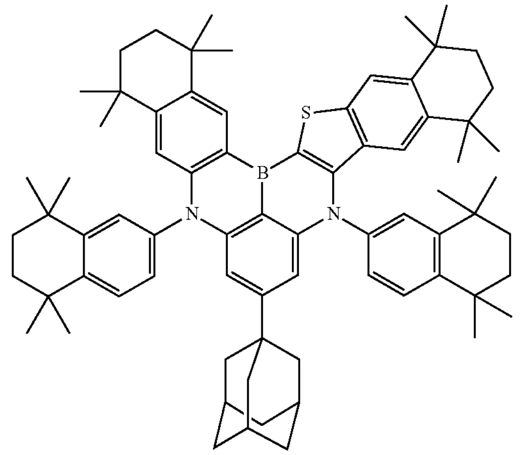

-continued
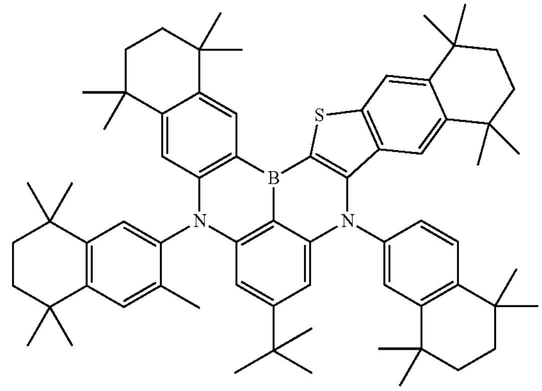
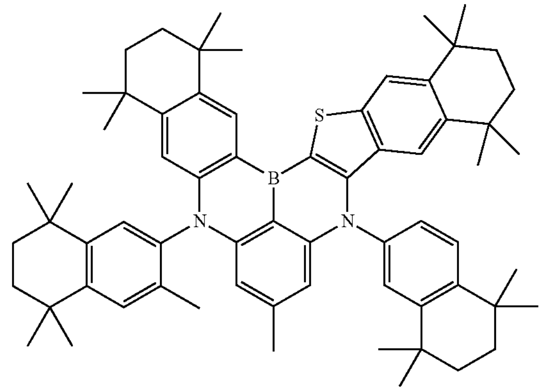
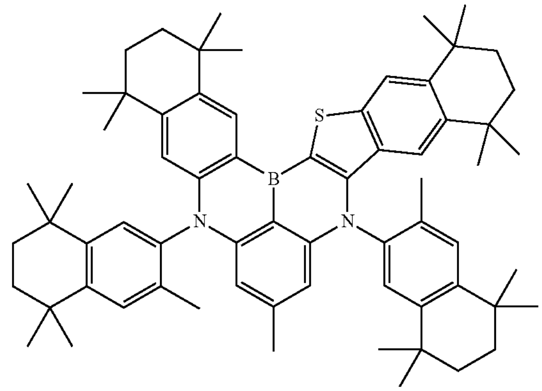
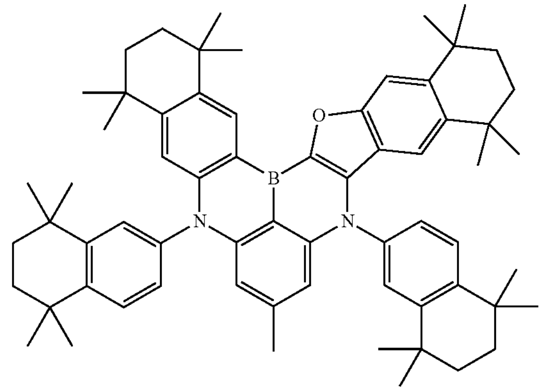
-continued
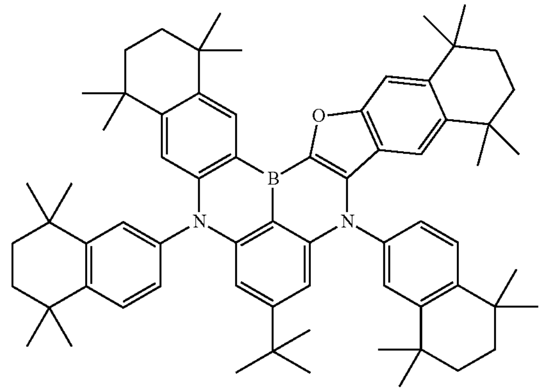
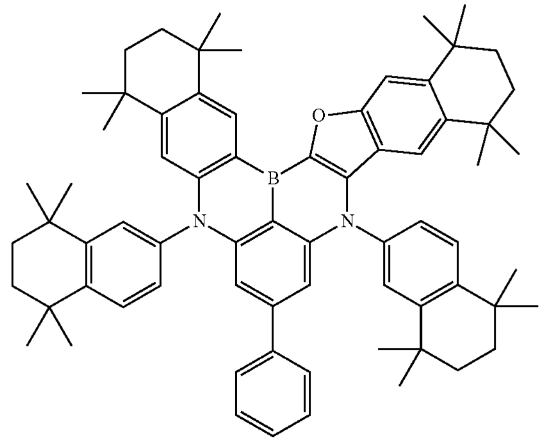
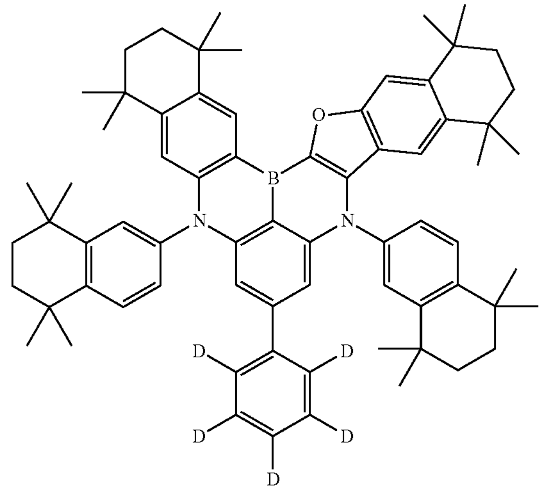

-continued
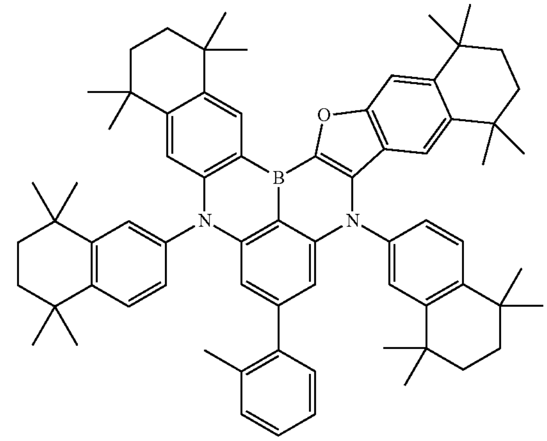
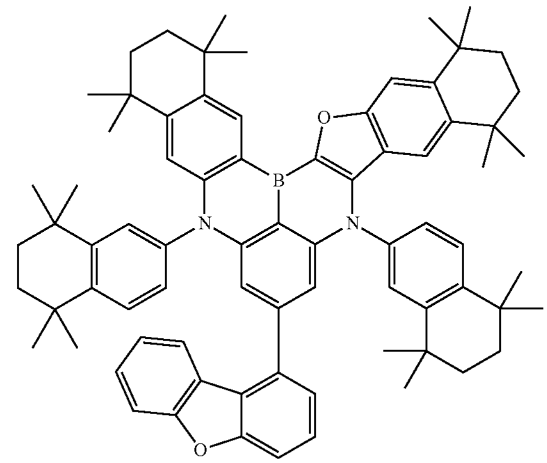
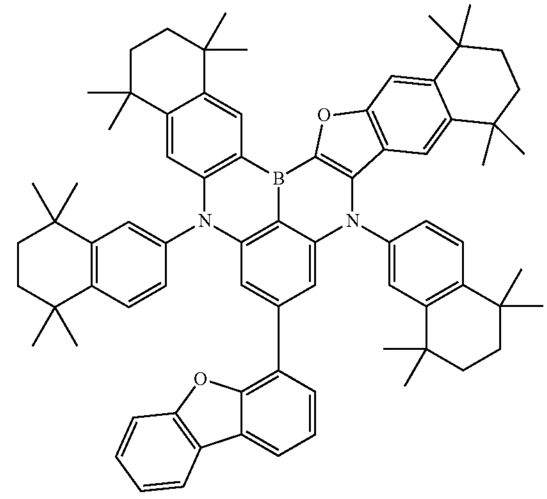
-continued
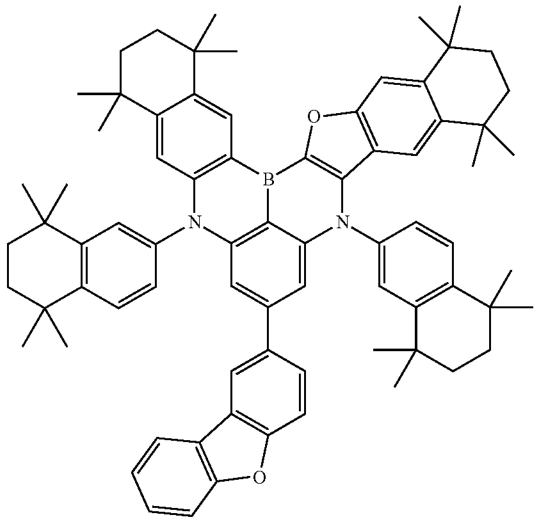
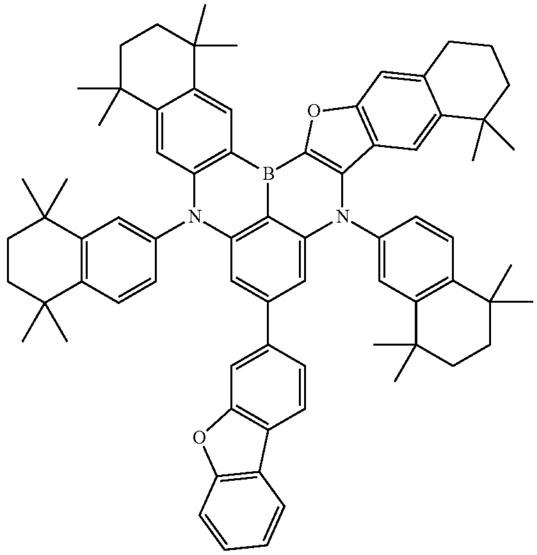
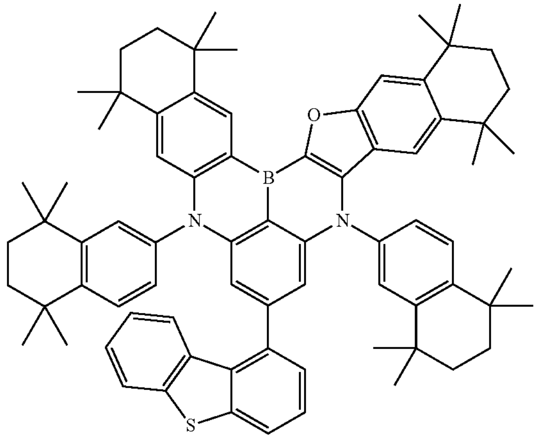

-continued
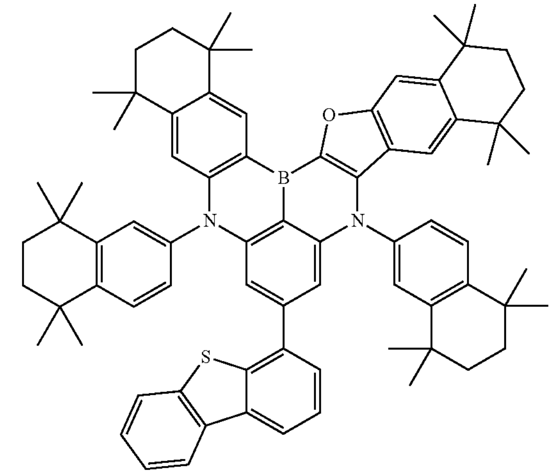
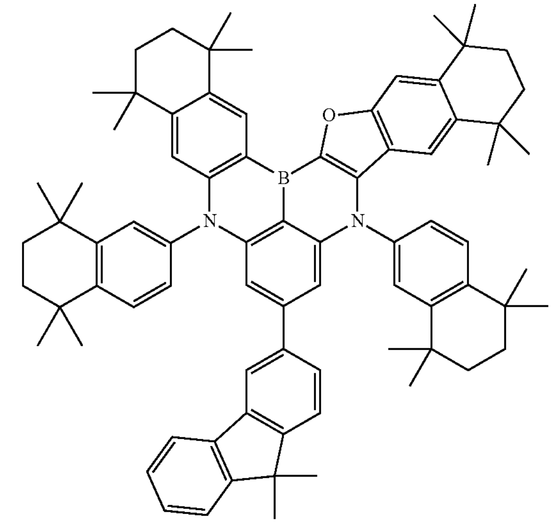
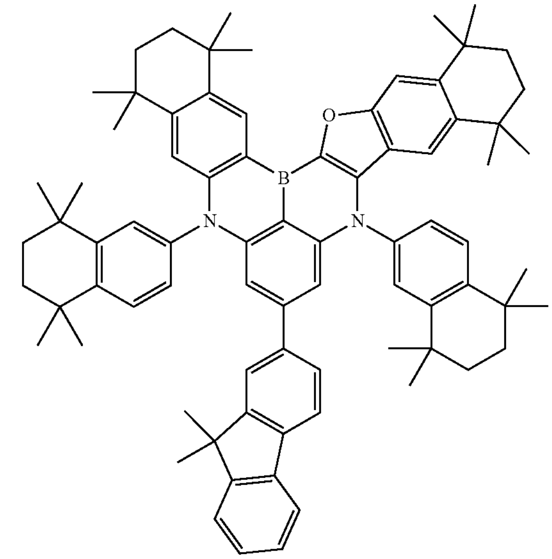
-continued
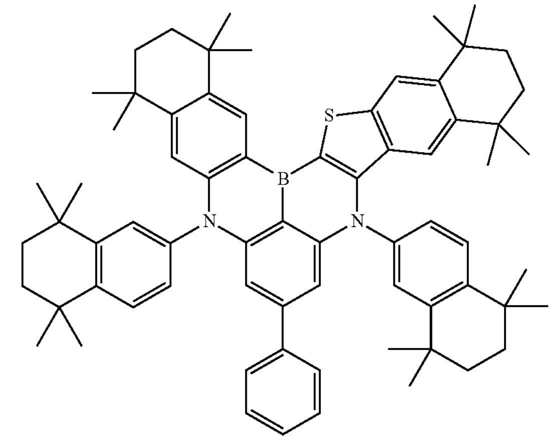
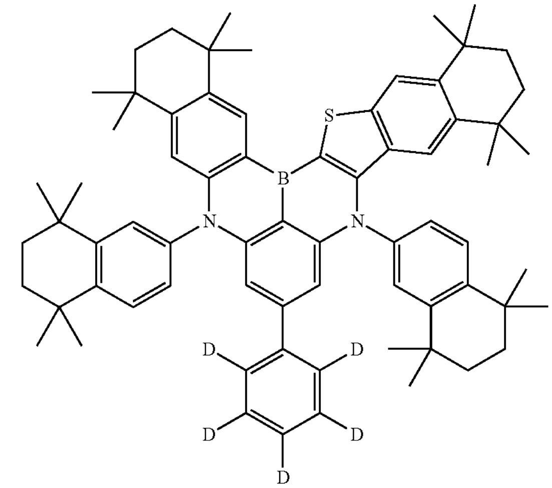
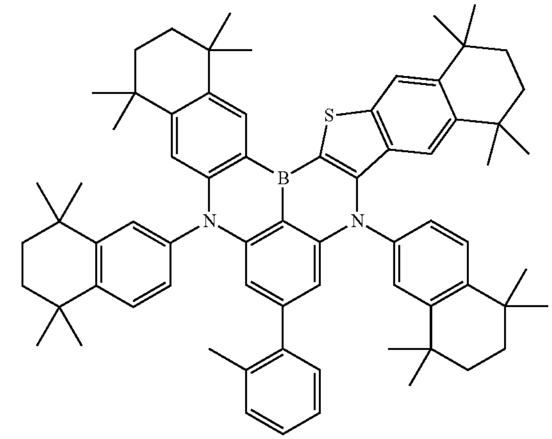

-continued
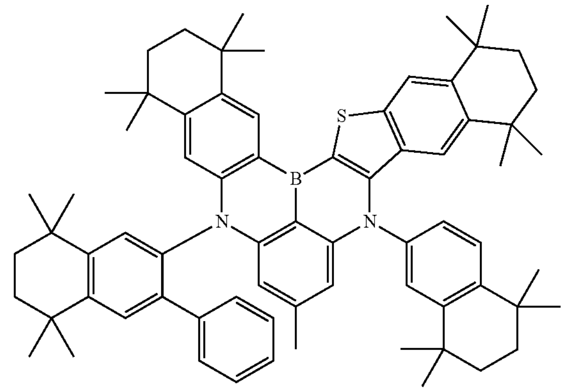
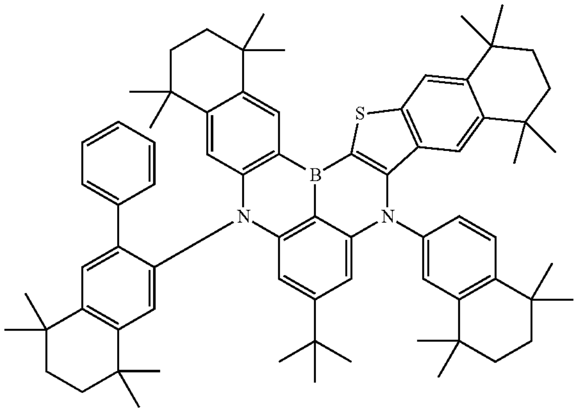
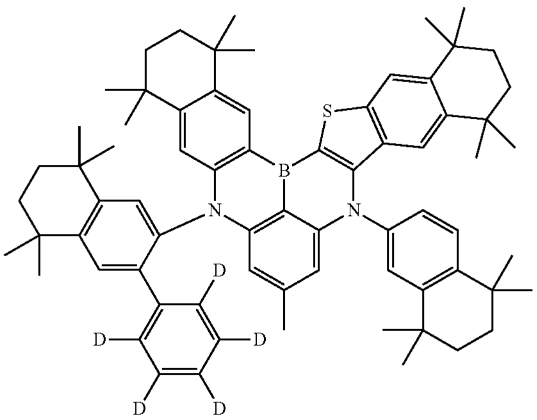
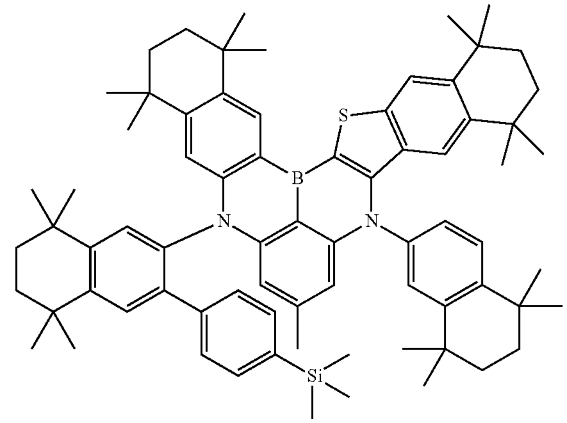
-continued
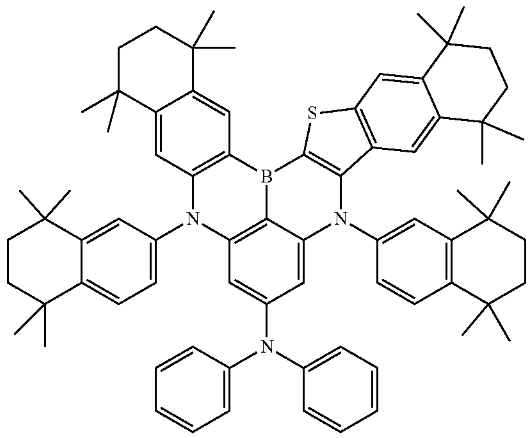
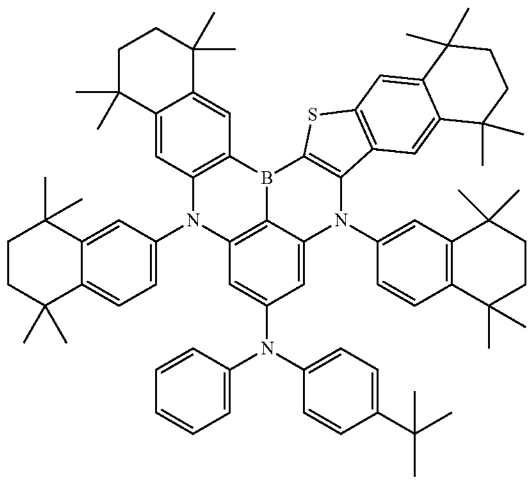
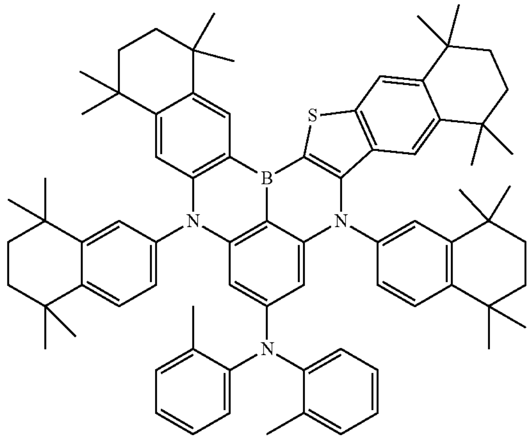

218
-continued
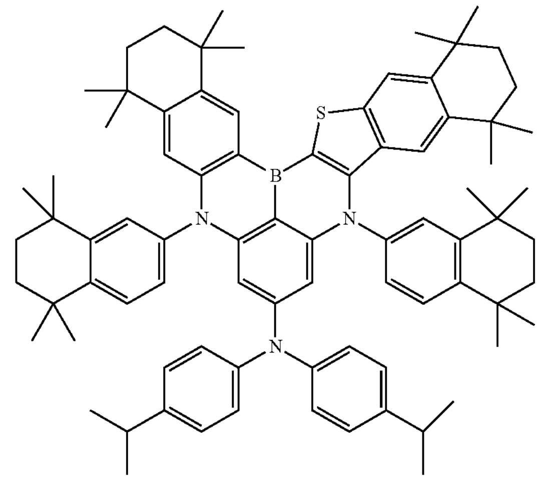
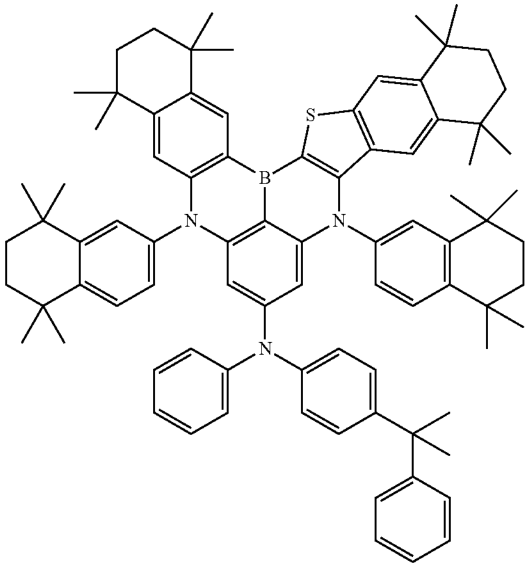
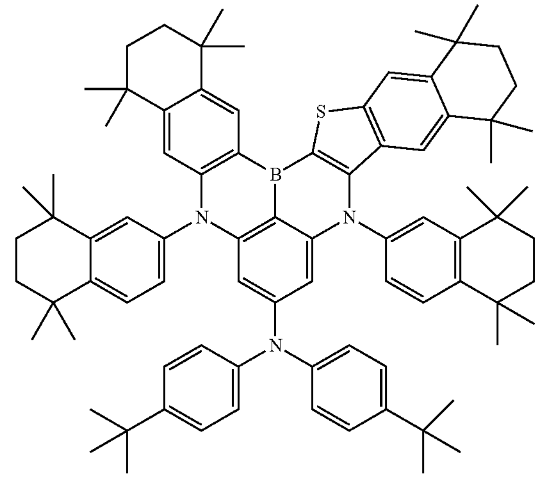
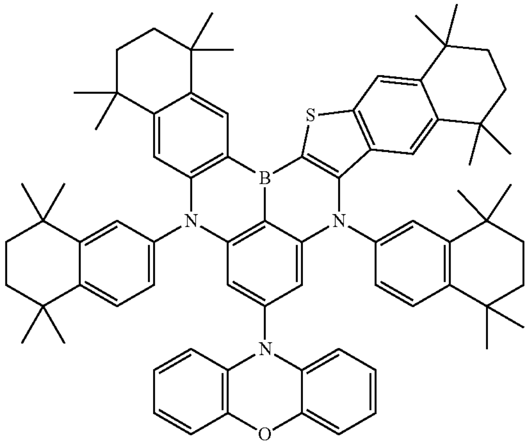
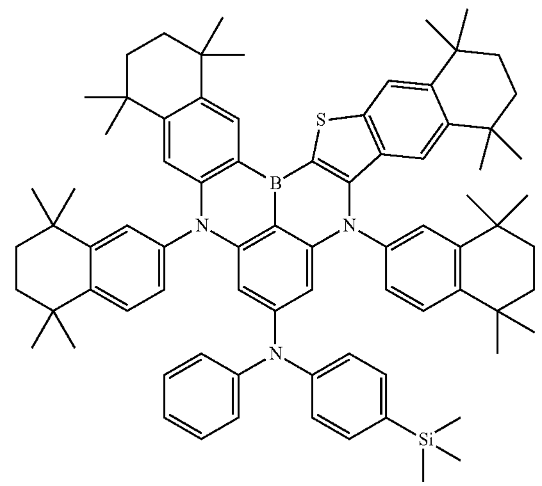
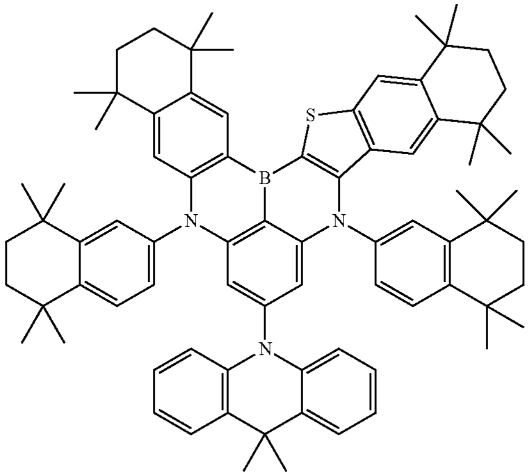

-continued
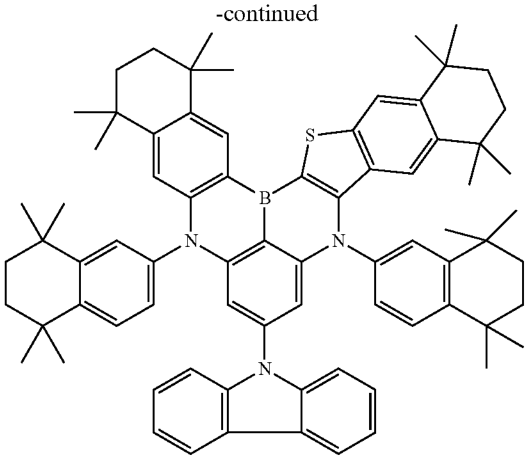
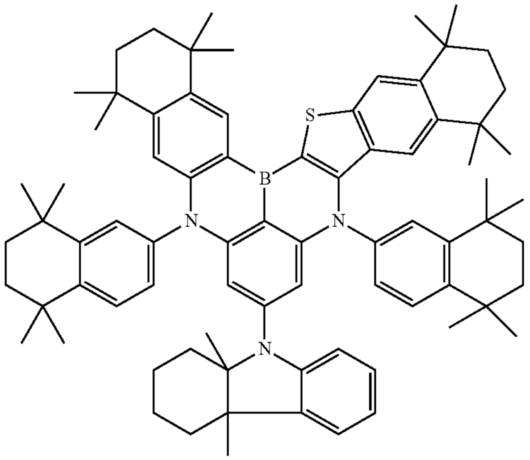
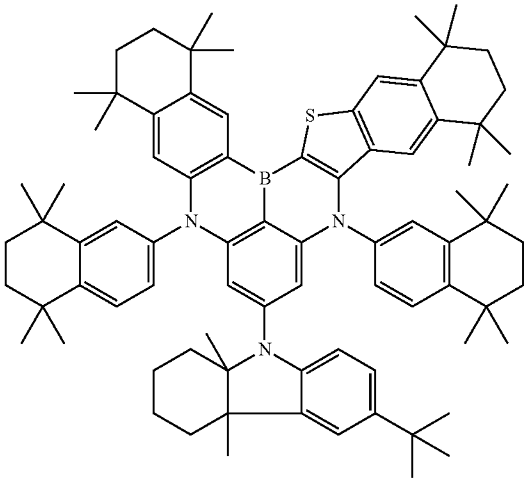
-continued
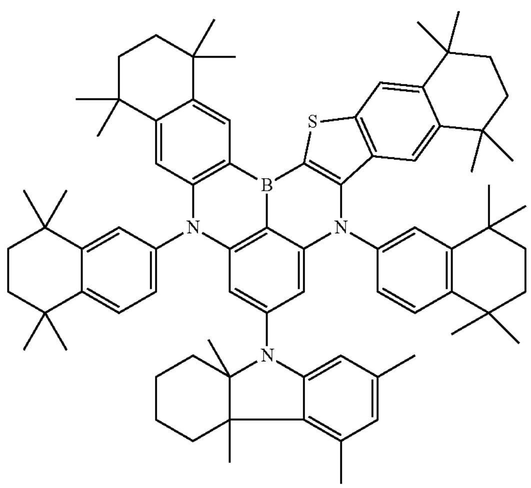
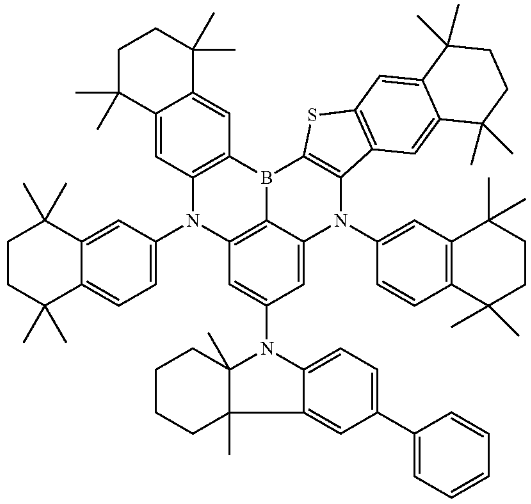
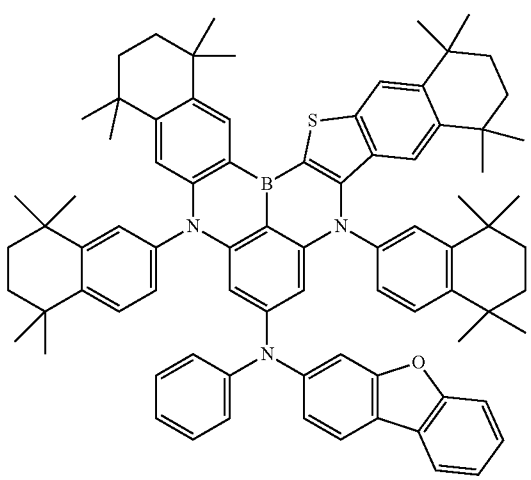

-continued
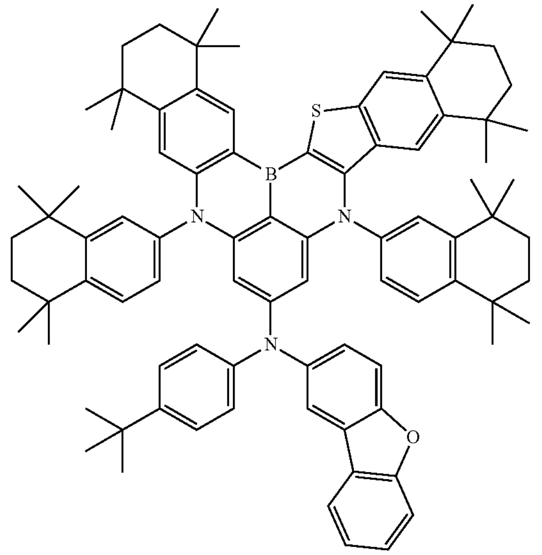
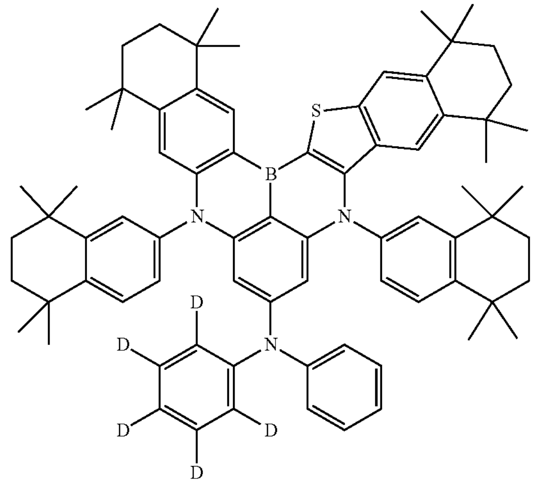
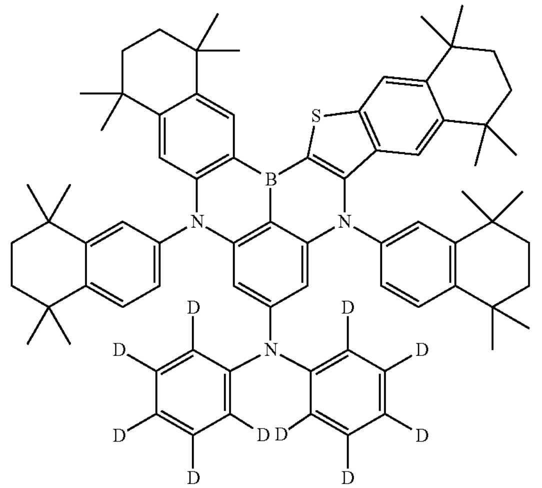
-continued
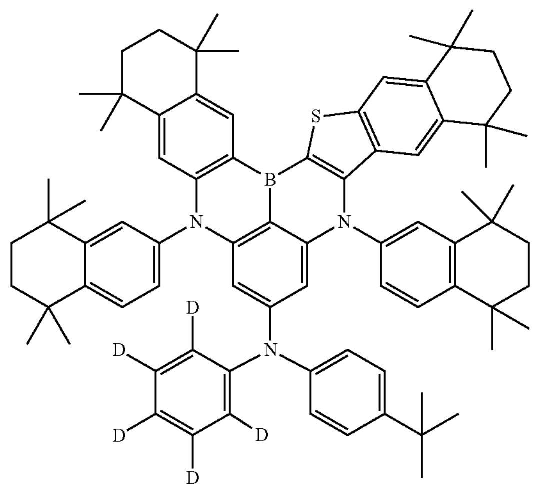
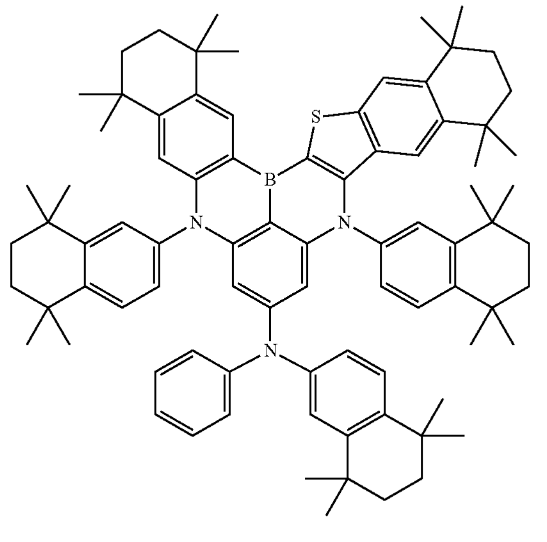
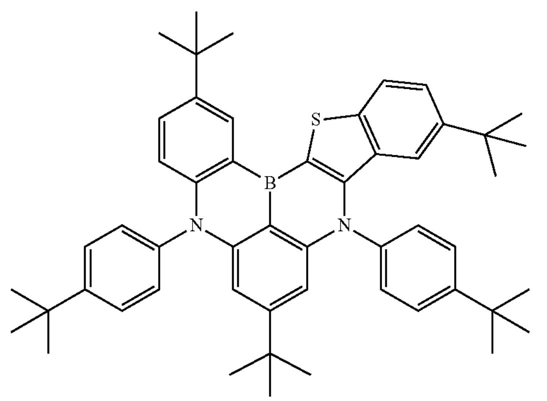

-continued
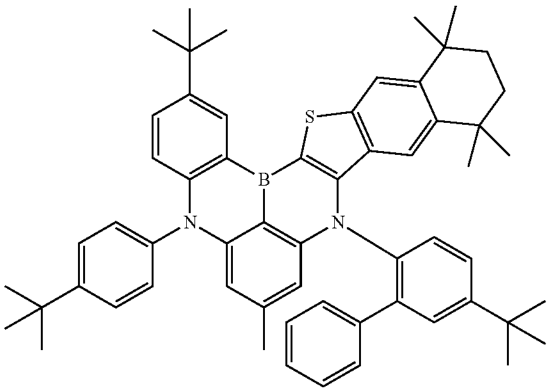
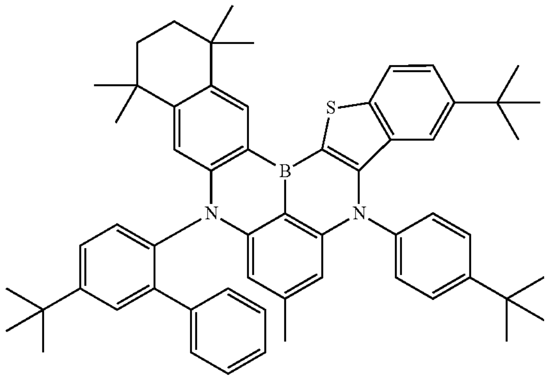
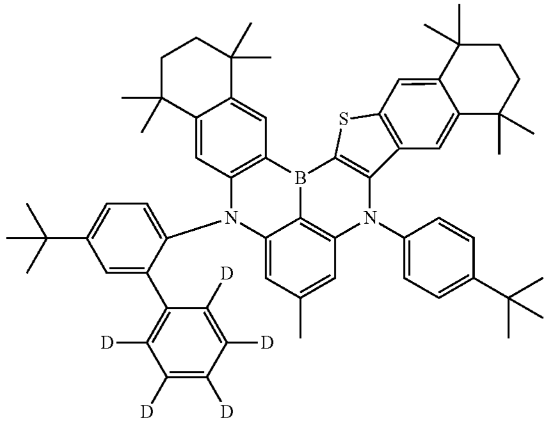
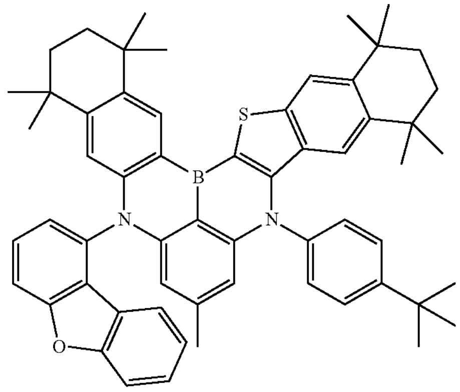
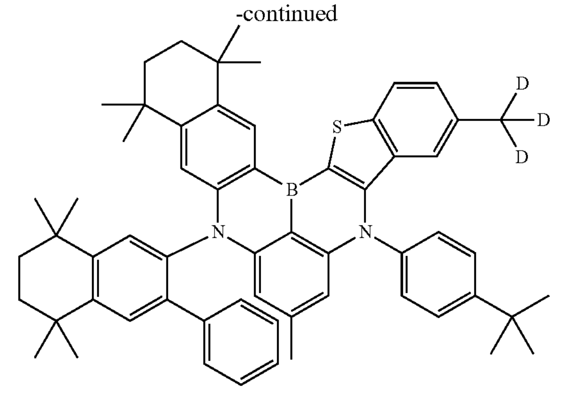
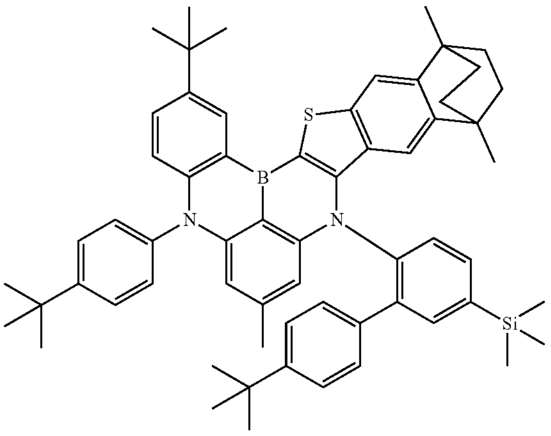
-continued
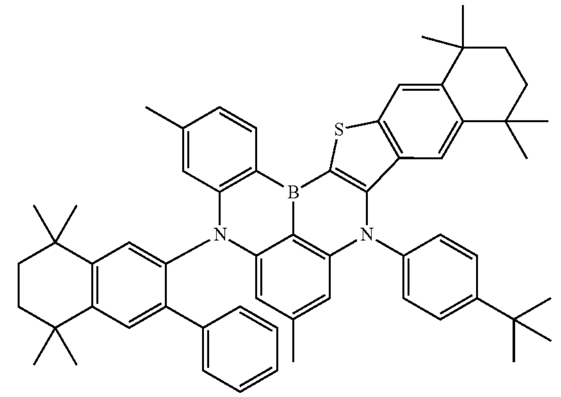
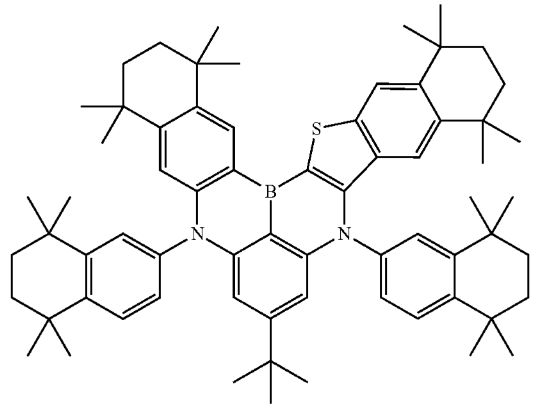

-continued
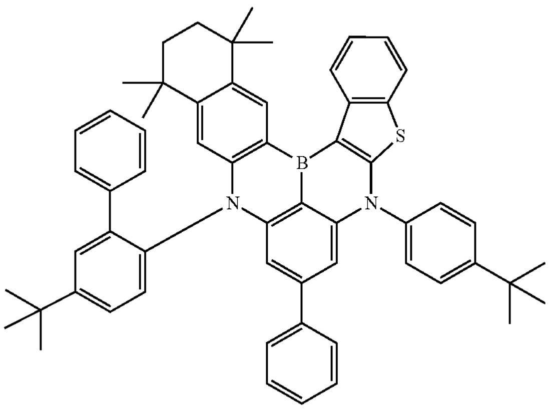
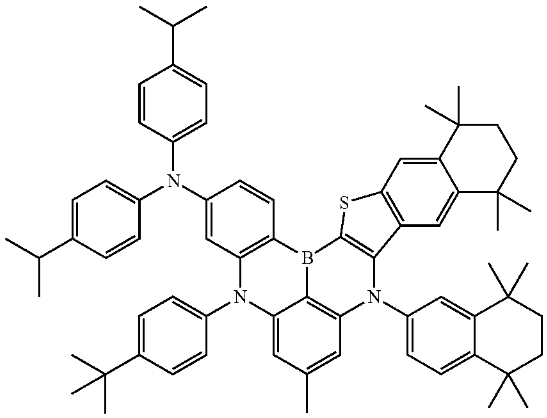
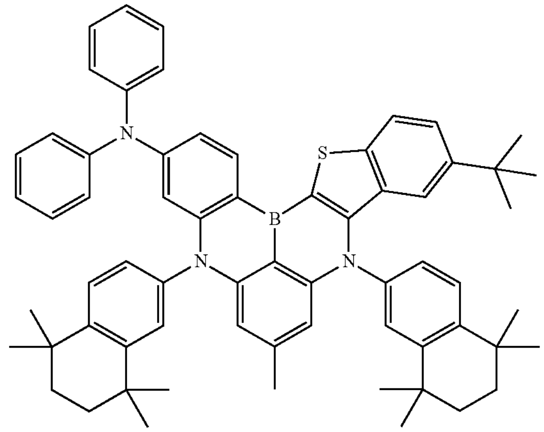
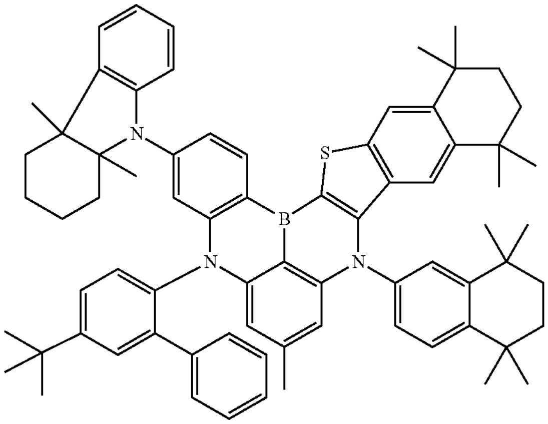
-continued
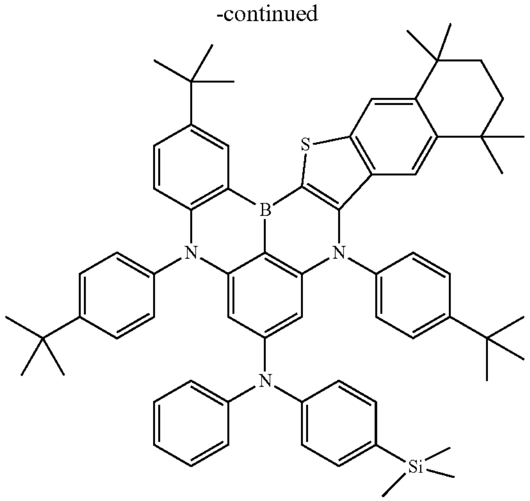
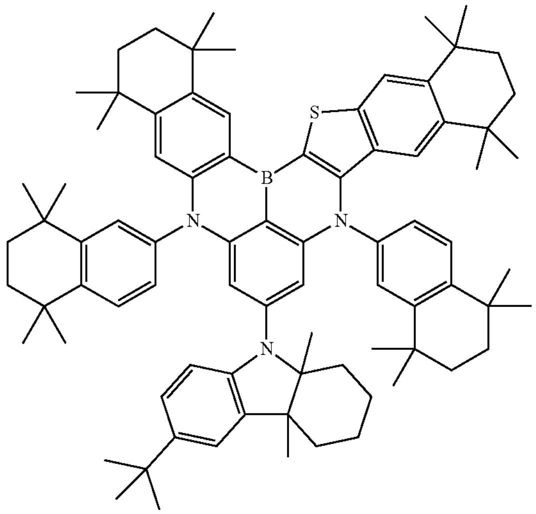
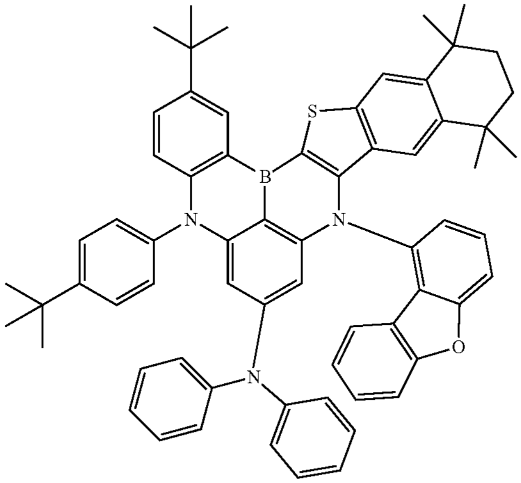

-continued
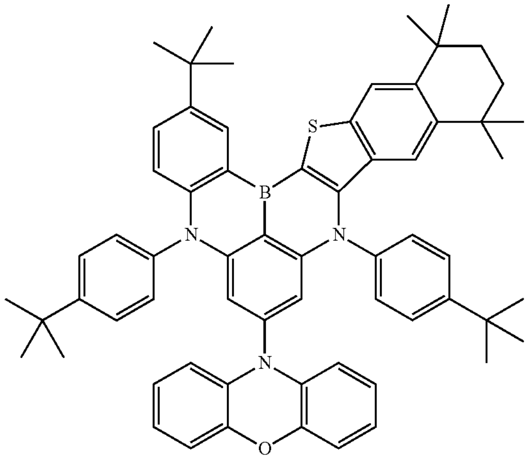
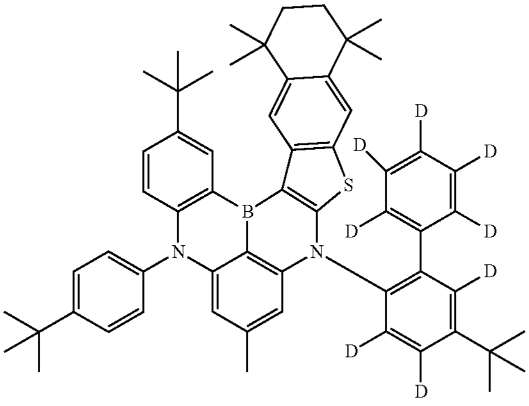
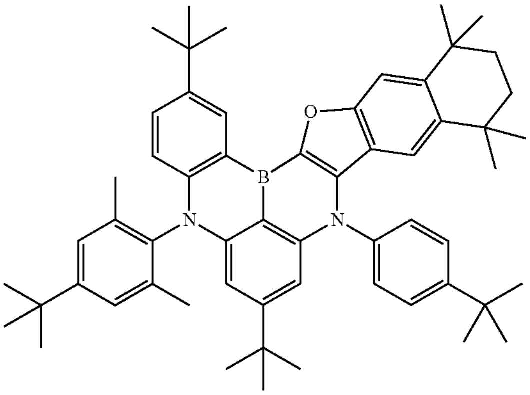
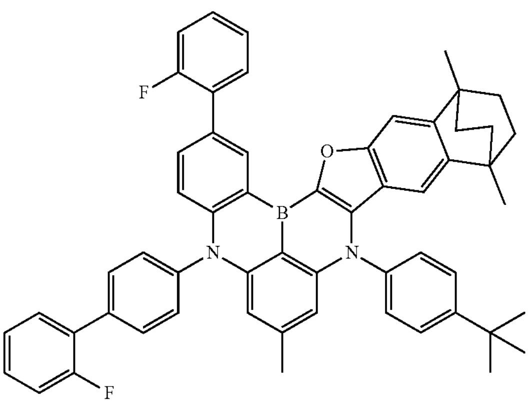
-continued
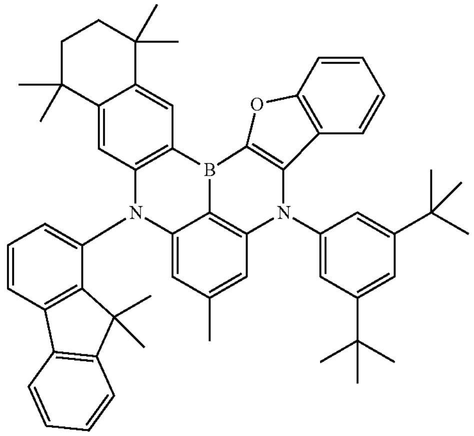
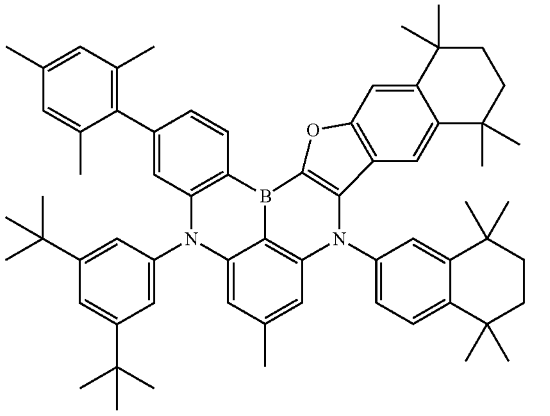
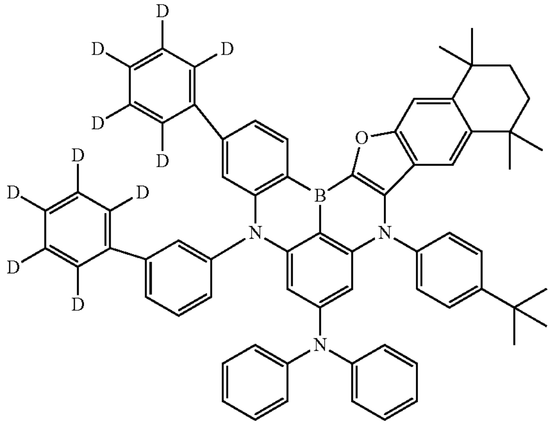

-continued

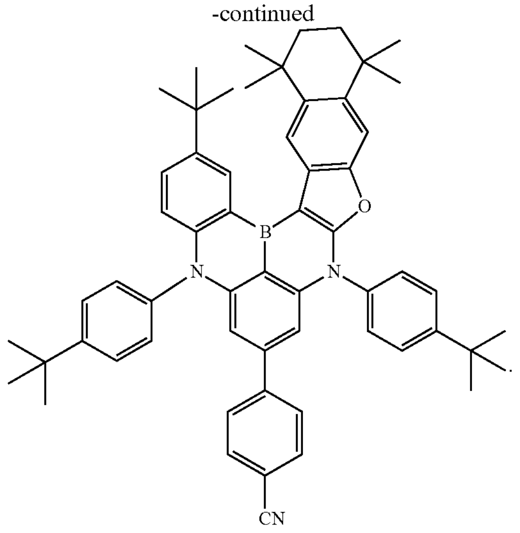

Hereinafter, Chemical Formula 2 will be described in detail.

<Chemical Formula 2>

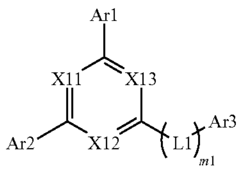

In Chemical Formula 2:

X11 to X13 are N or CR', and at least one of X11 to X13 is N;

R' is hydrogen, deuterium, a cyano group, a halogen group, a substituted or unsubstituted alkyl group, a substituted or unsubstituted alkenyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, or a substituted or unsubstituted heterocyclic group;

L1 is a direct bond, a substituted or unsubstituted arylene group, or a substituted or unsubstituted divalent heterocyclic group;

m1 is an integer of 1 to 3, and when m1 is 2 or greater, L1s are the same as or different from each other;

Ar1 and Ar2 are the same as or different from each other, and each independently a substituted or unsubstituted aryl group, or a substituted or unsubstituted heterocyclic group; and Ar3 is any one of the following Chemical Formulae 2-A to 2-C:

<Chemical Formula 2-A>

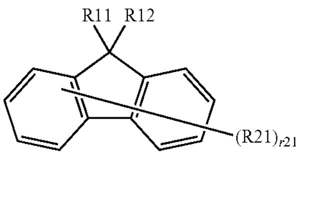

-continued

<Chemical Formula 2-B>

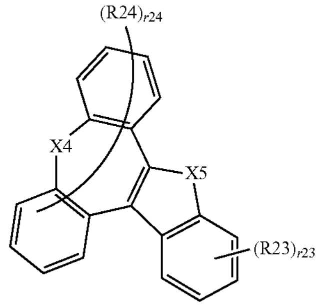

<Chemical Formula 2-C>

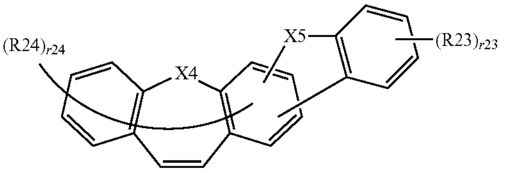

wherein in Chemical Formulae 2-A to 2-C:

R11 and R12 are a substituted or unsubstituted alkyl group or a substituted or unsubstituted aryl group, or bond to adjacent groups to form a substituted or unsubstituted ring;

X4 is O, S, or NR25;

X5 is O, S, or NR22;

any one of R21 to R25 is linked to Chemical Formula 2, and the rest are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r21 is an integer of 0 to 7, r23 is an integer of 0 to 4, and r24 is an integer of 0 to 8; and when r21, r23 and r24 are each 2 or greater, substituents in the parentheses are the same as or different from each other.

In one embodiment of the present specification, at least one of X11 to X13 is N.

In one embodiment of the present specification, at least two of X11 to X13 are N.

In one embodiment of the present specification, X11 to X13 are N.

In one embodiment of the present specification, X11 is N, and X12 and X13 are CR'.

In one embodiment of the present specification, X12 is N, and X11 and X13 are CR'.

In one embodiment of the present specification, X13 is N, and X11 and X12 are CR'.

In one embodiment of the present specification, X11 and X12 are N, and X13 is CR'.

In one embodiment of the present specification, X11 and X13 are N, and X12 is CR'.

In one embodiment of the present specification, X12 and X13 are N, and X11 is CR'.

In one embodiment of the present specification, R' is hydrogen, deuterium, a cyano group, a halogen group, a substituted or unsubstituted alkyl group, a substituted or unsubstituted alkenyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, or a substituted or unsubstituted heterocyclic group.

In one embodiment of the present specification, R' is hydrogen, deuterium, a substituted or unsubstituted alkyl group, or a substituted or unsubstituted aryl group.

In one embodiment of the present specification, R' is hydrogen or deuterium.

In one embodiment of the present specification, R' is hydrogen.

In one embodiment of the present specification, Ar1 and Ar2 are the same as or different from each other, and each independently a substituted or unsubstituted aryl group, or a substituted or unsubstituted heterocyclic group.

In one embodiment of the present specification, Ar1 and Ar2 are the same as or different from each other, and each independently a substituted or unsubstituted C6-C60 aryl group, or a substituted or unsubstituted C2-C60 heterocyclic group.

In one embodiment of the present specification, Ar1 and Ar2 are the same as or different from each other, and each independently a substituted or unsubstituted C6-C30 aryl group, or a substituted or unsubstituted C2-C30 heterocyclic group.

In one embodiment of the present specification, Ar1 and Ar2 are the same as or different from each other, and each independently a C6-C30 aryl group.

In one embodiment of the present specification, Ar1 and Ar2 are the same as or different from each other, and each independently a substituted or unsubstituted monocyclic or polycyclic C6-C20 aryl group.

In one embodiment of the present specification, Ar1 and Ar2 are the same as or different from each other, and each independently a substituted or unsubstituted phenyl group, a substituted or unsubstituted biphenyl group, a substituted or unsubstituted terphenyl group, a substituted or unsubstituted quaterphenyl group, a substituted or unsubstituted naphthyl group, a substituted or unsubstituted fluorenyl group, a substituted or unsubstituted phenanthrenyl group, or a substituted or unsubstituted a triphenylenyl group.

In one embodiment of the present specification, Ar1 and Ar2 are the same as or different from each other, and each independently a substituted or unsubstituted phenyl group, a substituted or unsubstituted biphenyl group, or a substituted or unsubstituted naphthyl group.

In one embodiment of the present specification, Ar1 and Ar2 are the same as or different from each other, and each independently a substituted or unsubstituted phenyl group.

In one embodiment of the present specification, Ar1 and Ar2 are the same as each other.

In one embodiment of the present specification, Ar1 and Ar2 are different from each other.

In one embodiment of the present specification, Ar1 and Ar2 are a phenyl group.

In one embodiment of the present specification, L1 is a direct bond, a substituted or unsubstituted C6-C60 arylene group, or a substituted or unsubstituted C2-C60 divalent heterocyclic group.

In one embodiment of the present specification, L1 is a direct bond, a substituted or unsubstituted C6-C30 arylene group, or a substituted or unsubstituted C2-C30 divalent heterocyclic group.

In one embodiment of the present specification, L1 is a direct bond, or a substituted or unsubstituted C6-C30 arylene group.

In one embodiment of the present specification, L1 is a substituted or unsubstituted C6-C30 arylene group.

In one embodiment of the present specification, L1 is a direct bond, or a substituted or unsubstituted monocyclic or polycyclic C6-C20 arylene group.

In one embodiment of the present specification, L1 is a direct bond, a substituted or unsubstituted phenylene group, a substituted or unsubstituted biphenylene group, a substituted or unsubstituted terphenylene group, or a substituted or unsubstituted naphthylene group.

In one embodiment of the present specification, L1 is a direct bond, a substituted or unsubstituted phenylene group, a substituted or unsubstituted biphenylene group, or a substituted or unsubstituted terphenylene group.

In one embodiment of the present specification, L1 is a direct bond, a phenylene group, a biphenylene group, or a terphenylene group.

In one embodiment of the present specification, L1 is a phenylene group, a biphenylene group, or a terphenylene group.

In one embodiment of the present specification, L1 is a direct bond, or a phenylene group.

In one embodiment of the present specification, L1 is a direct bond, a meta-phenylene group, or a para-phenylene group.

In one embodiment of the present specification, L1 is a direct bond, or selected from among the following structures:

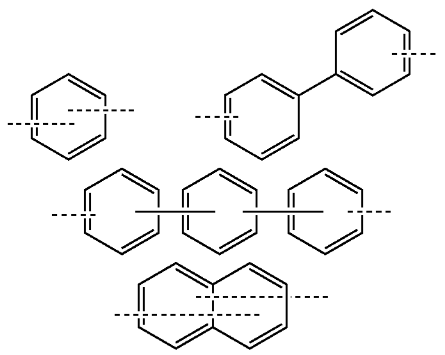

wherein in the structures, a dotted line is a position linked to Chemical Formula 2.

In one embodiment of the present specification, L1 is a direct bond, or selected from among the following structures:

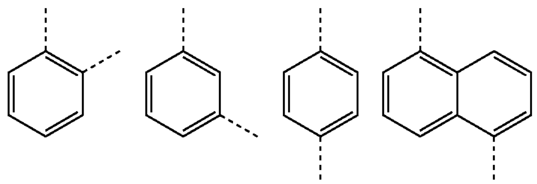

-continued
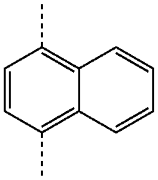
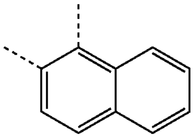
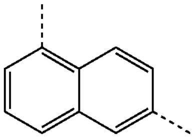
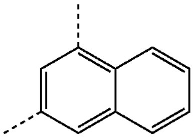
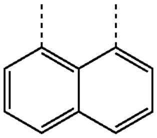
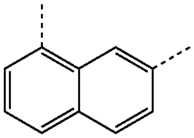
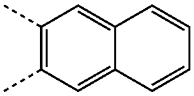
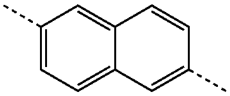
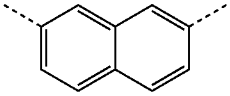
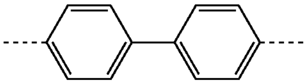
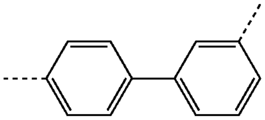
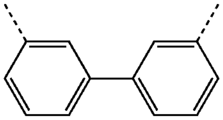
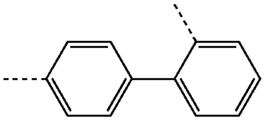
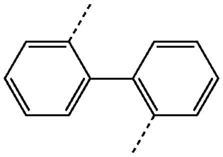
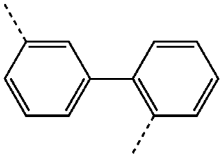
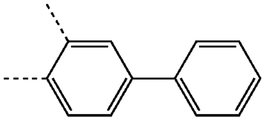
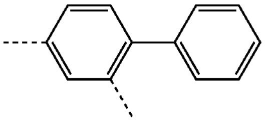
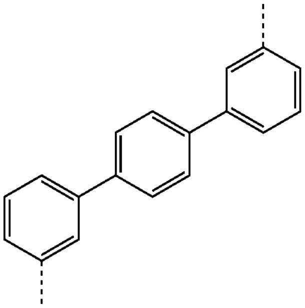
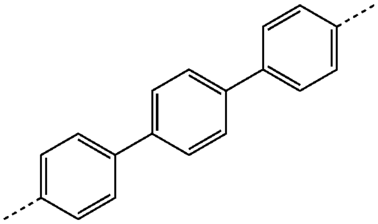
-continued
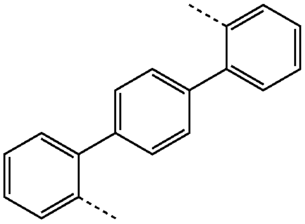
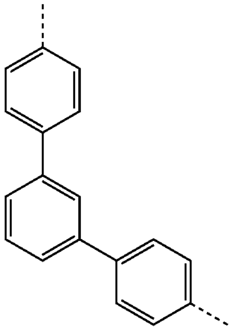
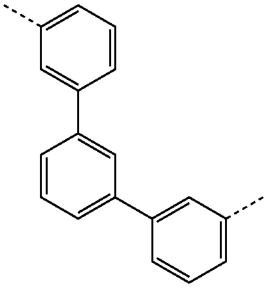
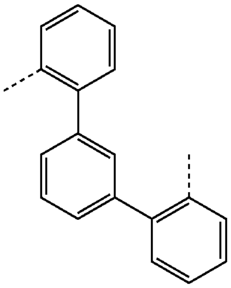
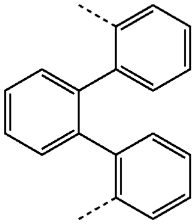
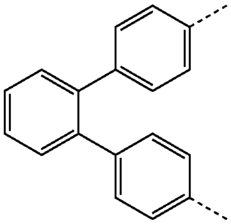
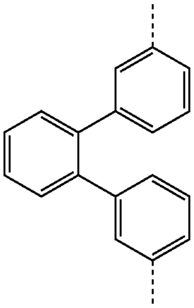
wherein in the structures, a dotted line is a position linked to Chemical Formula 2.
In one embodiment of the present specification, L1 is a direct bond, or selected from among the following structures:
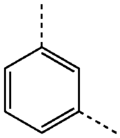
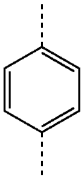
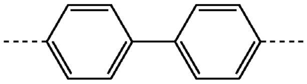

-continued

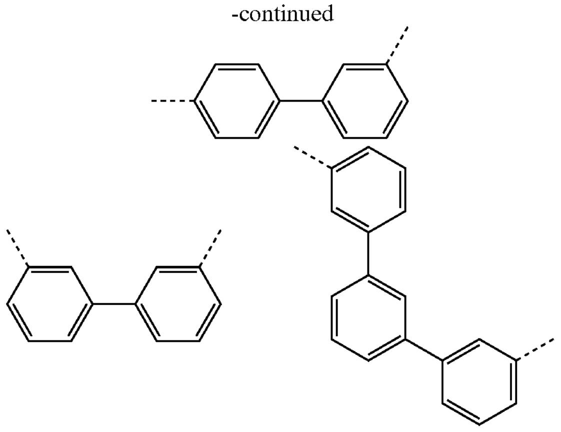

wherein in the structures, a dotted line is a position linked to Chemical Formula 2.

In one embodiment of the present specification, when m1 is 2 or greater, at least one of the two or more L1s is a meta-phenylene group.

In one embodiment of the present specification, when m1 is 2 or greater, at least one of the two or more L1s is not a direct bond.

In one embodiment of the present specification, when m1 is 2 or greater, at least one of the two or more L1s is an arylene group.

In one embodiment of the present specification, when m1 is 2 or greater, at least one of the two or more L1s is a meta-phenylene group.

In one embodiment of the present specification, m1 is 1.

In one embodiment of the present specification, m1 is 2.

In one embodiment of the present specification, m1 is 3.

In one embodiment of the present specification, Ar3 is any one of the following Chemical Formulae 2-A to 2-C:

<Chemical Formula 2-A>

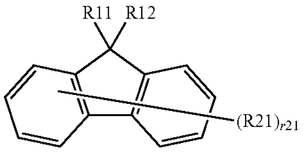

<Chemical Formula 2-B>

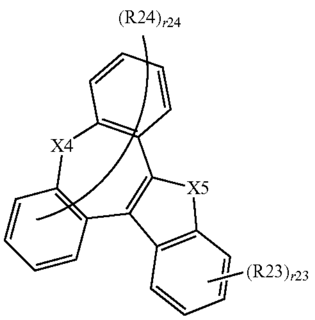

-continued

<Chemical Formula 2-C>

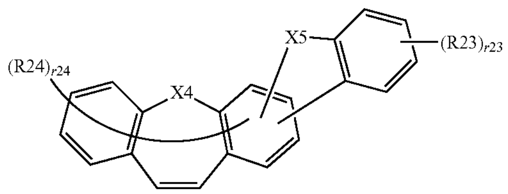

wherein in Chemical Formulae 2-A to 2-C:

R11 and R12 are a substituted or unsubstituted alkyl group or a substituted or unsubstituted aryl group, or bond to adjacent groups to form a substituted or unsubstituted ring;

X4 is O, S, or NR25;

X5 is O, S, or NR22;

any one of R21 to R25 is linked to Chemical Formula 2, and the rest are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r21 is an integer of 0 to 7, r23 is an integer of 0 to 4, and r24 is an integer of 0 to 8; and when r21, r23 and r24 are each 2 or greater, substituents in the parentheses are the same as or different from each other.

In one embodiment of the present specification, Chemical Formula 2-B is the following Chemical Formula 2-B1:

<Chemical Formula 2-B1>

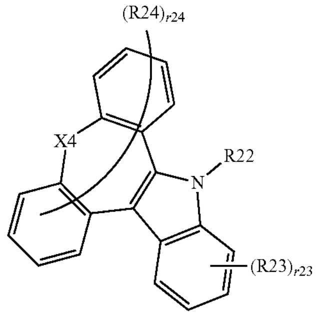

wherein in Chemical Formula 2-B1, X4, R22 to R24, r23 and r24 have the same definitions as in Chemical Formula 2-B.

In one embodiment of the present specification, any one of R21 of Chemical Formula 2-A is linked to Chemical Formula 2.

In one embodiment of the present specification, any one of R22 to R25 of Chemical Formulae 2-B and 2-C is linked to Chemical Formula 2.

In one embodiment of the present specification, any one of R22 and R25 of Chemical Formula 2-B is linked to Chemical Formula 2.

In one embodiment of the present specification, any one of R22 and R25 of Chemical Formula 2-C is linked to Chemical Formula 2.

In one embodiment of the present specification, R11 and R12 are a substituted or unsubstituted C1-C10 alkyl group or a substituted or unsubstituted C6-C30 aryl group, or bond to each other to form a substituted or unsubstituted C5-C30 ring.

In one embodiment of the present specification, R11 and R12 are a substituted or unsubstituted C1-C6 alkyl group or a substituted or unsubstituted C6-C20 aryl group, or bond to each other to form a substituted or unsubstituted C5-C20 ring.

In one embodiment of the present specification, R11 and R12 are a substituted or unsubstituted methyl group or a substituted or unsubstituted phenyl group, or bond to each other to form a substituted or unsubstituted fluorene ring.

In one embodiment of the present specification, R11 and R12 are a methyl group or a phenyl group, or bond to each other to form a fluorene ring.

In one embodiment of the present specification, Chemical Formula 2-A is selected from among the following structures:

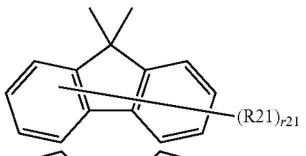

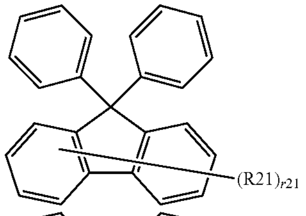

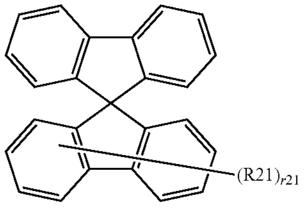

wherein in the structures, R21 and r21 have the same definitions as in Chemical Formula 2-A.

In one embodiment of the present specification, Chemical Formula 2-A is any one of the following Chemical Formulae 2-A-1 to 2-A-4.

In another embodiment, Ar3 is any one of the following Chemical Formulae 2-A-1 to 2-A-4:

<Chemical Formula 2-A-1>

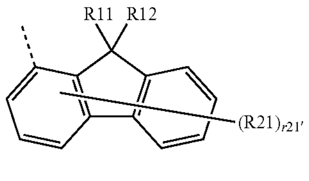

-continued

<Chemical Formula 2-A-2>

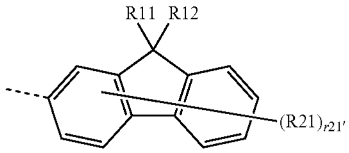

<Chemical Formula 2-A-3>

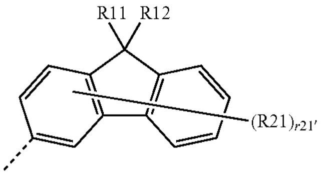

<Chemical Formula 2-A-4>

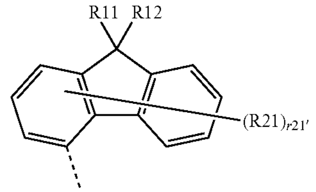

wherein in Chemical Formulae 2-A-1 to 2-A-4, R11 and R12 have the same definitions as in Chemical Formula 2;

a dotted line means a position linked to Chemical Formula 2;

R21 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bonds to adjacent substituents to form a substituted or unsubstituted ring; and r21' is an integer of 0 to 7, and when r21' is 2 or greater, R21s are the same as or different from each other.

In one embodiment of the present specification, R21 is hydrogen, deuterium, a cyano group, a halogen group, a substituted or unsubstituted C1-C10 alkyl group, a substituted or unsubstituted C1-C10 alkoxy group, a substituted or unsubstituted C1-C10 alkylthio group, a substituted or unsubstituted C3-C30 cycloalkyl group, a substituted or unsubstituted silyl group, a substituted or unsubstituted C6-C30 aryl group, a substituted or unsubstituted C6-C30 aryloxy group, a substituted or unsubstituted C6-C30 arylthio group, a substituted or unsubstituted C2-C30 heterocyclic group, or a substituted or unsubstituted amine group, or bonds to adjacent substituents to form a substituted or unsubstituted C6-C30 ring.

In one embodiment of the present specification, R21 is hydrogen or deuterium.

In one embodiment of the present specification, Chemical Formula 2-B is the following Chemical Formula 2-B-1 or 2-B-2.

In one embodiment of the present specification, Chemical Formula 2-C is any one of the following Chemical Formulae 2-C-1 to 2-C-4.

In another embodiment, Ar3 is any one of the following Chemical Formulae 2-B-1, 2-B-2 and 2-C-1 to 2-C-4:

<Chemical Formula 2-B-1>

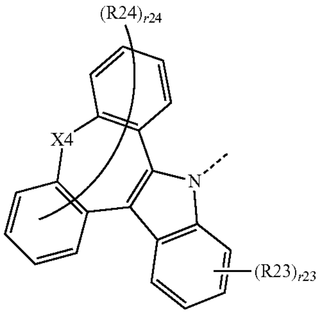

<Chemical Formula 2-B-2>

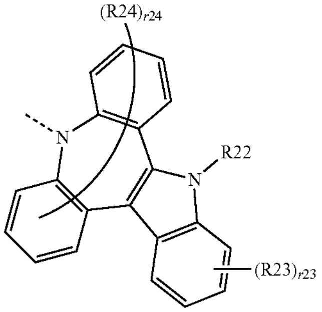

<Chemical Formula 2-C-1>

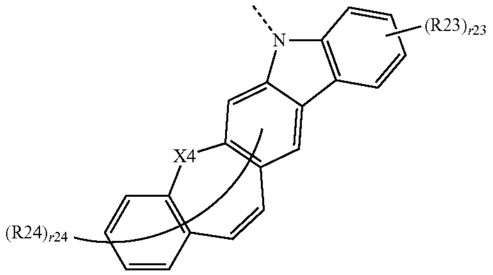

<Chemical Formula 2-C-2>

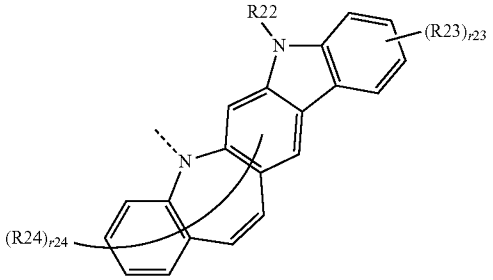

<Chemical Formula 2-C-3>

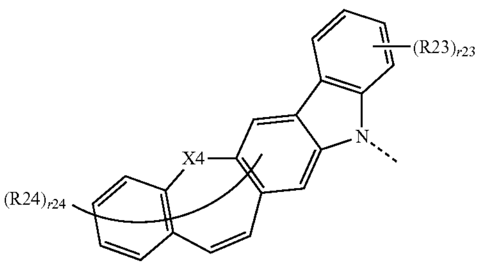

-continued

<chemical Formula 2-C-4>

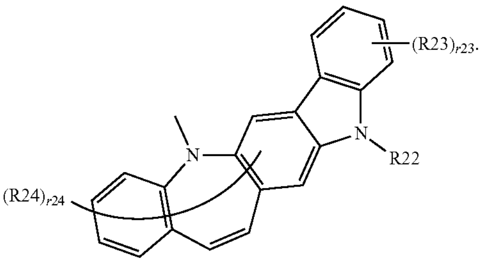

wherein in Chemical Formulae 2-B-1, 2-B-2 and 2-C-1 to 2-C-4, a dotted line, X4, R22 to R24, r23 and r24 have the same definitions as in Chemical Formula 2.

In one embodiment of the present specification, X4 of Chemical Formula 2-B is O, S, NR25.

In one embodiment of the present specification, X5 of Chemical Formula 2-B is NR22.

In one embodiment of the present specification, X4 of Chemical Formula 2-C is NR25.

In one embodiment of the present specification, X5 of Chemical Formula 2-C is NR22.

In one embodiment of the present specification, R22 to R25 not linked to Chemical Formula 2 are the same as or different from each other, and each independently is hydrogen, deuterium, a cyano group, a halogen group, a substituted or unsubstituted C1-C10 alkyl group, a substituted or unsubstituted C1-C10 alkoxy group, a substituted or unsubstituted C1-C10 alkylthio group, a substituted or unsubstituted C3-C30 cycloalkyl group, a substituted or unsubstituted silyl group, a substituted or unsubstituted C6-C30 aryl group, a substituted or unsubstituted C6-C30 aryloxy group, a substituted or unsubstituted C6-C30 arylthio group, a substituted or unsubstituted C2-C30 heterocyclic group, or a substituted or unsubstituted amine group, or bond to adjacent substituents to form a substituted or unsubstituted C6-C30 ring.

In one embodiment of the present specification, R22 to R25 not linked to Chemical Formula 2 are the same as or different from each other, and each independently is hydrogen, deuterium, a substituted or unsubstituted C6-C30 aryl group, or a substituted or unsubstituted C2-C30 heterocyclic group, or bond to adjacent substituents to form a substituted or unsubstituted C6-C30 aromatic hydrocarbon ring.

In one embodiment of the present specification, R22 is a substituted or unsubstituted C6-C20 aryl group.

In one embodiment of the present specification, R22 is a substituted or unsubstituted phenyl group.

In one embodiment of the present specification, R22 is a phenyl group.

In one embodiment of the present specification, R23 is hydrogen or deuterium.

In one embodiment of the present specification, R23 is hydrogen.

In one embodiment of the present specification, R24 is hydrogen; or deuterium, or adjacent two R24s bond to each other to form a C6-C20 aromatic hydrocarbon ring.

In one embodiment of the present specification, R24 is hydrogen; or deuterium, or adjacent two R24s bond to each other to form a benzene ring.

In one embodiment of the present specification, R24 is hydrogen, or adjacent two R24s bond to each other to form a benzene ring.

In one embodiment of the present specification, R24 of Chemical Formula 2-B is hydrogen.

In one embodiment of the present specification, R24 of Chemical Formula 2-C is hydrogen, or adjacent two R24s bond to each other to form a benzene ring.

In one embodiment of the present specification, Chemical Formula 2-B is selected from among the following structures:

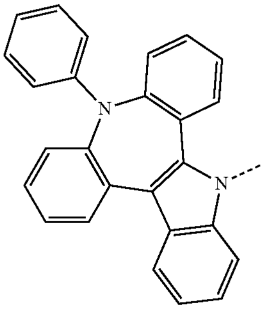

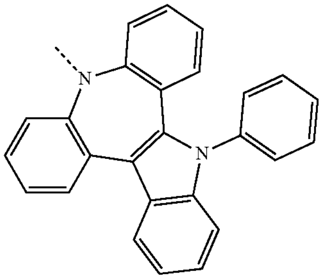

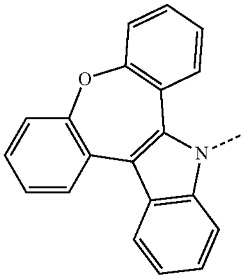

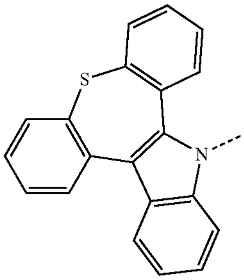

wherein in the structures, a dotted line is a position linked to Chemical Formula 2.

In one embodiment of the present specification, Chemical Formula 2-C is selected from among the following structures:

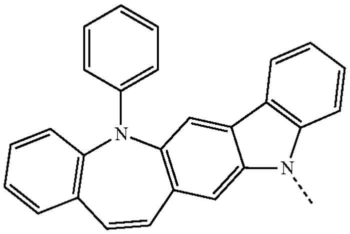

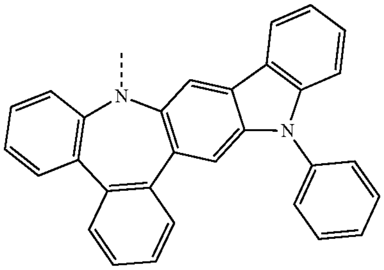

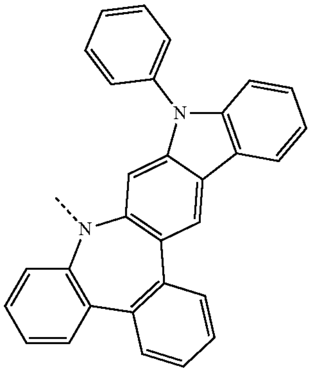

wherein in the structures, a dotted line is a position linked to Chemical Formula 2.

In one embodiment of the present specification, Chemical Formula 2 is any one of the following compounds:

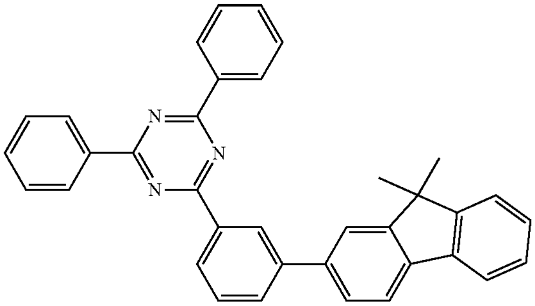

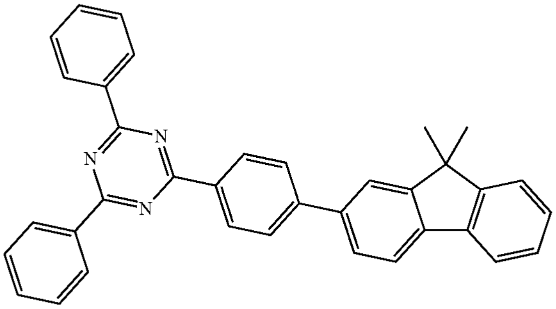

-continued
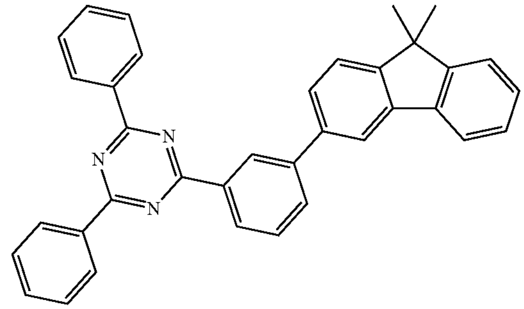
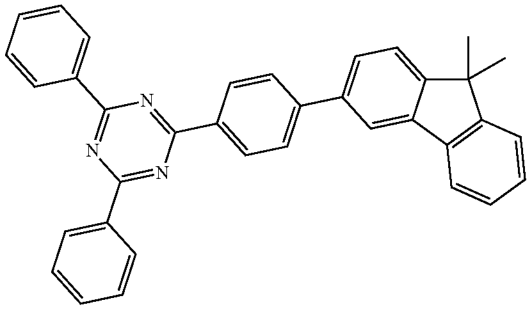
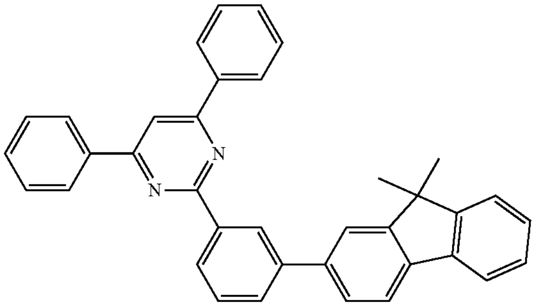
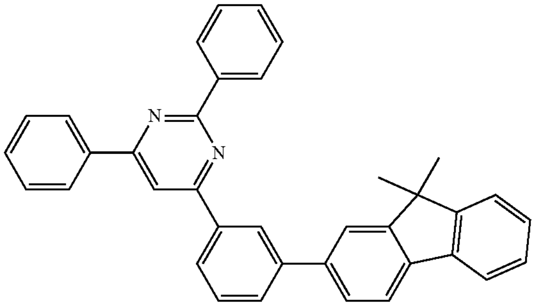
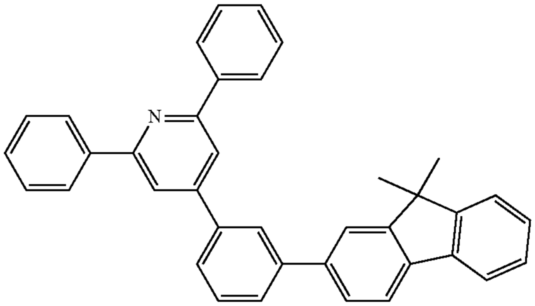
-continued
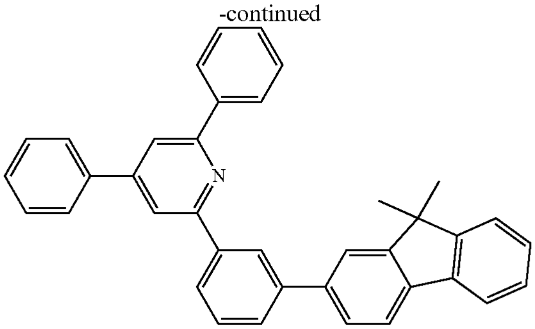
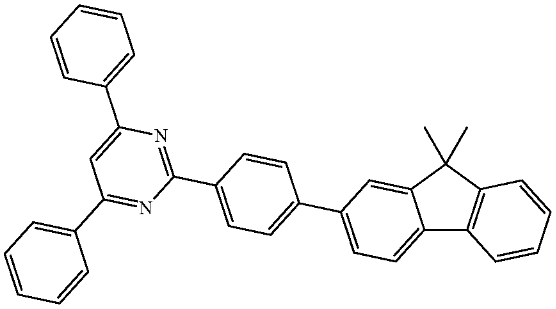
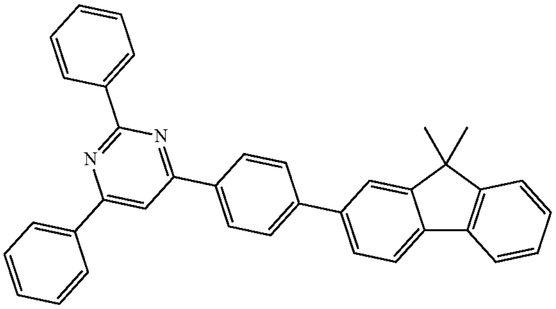
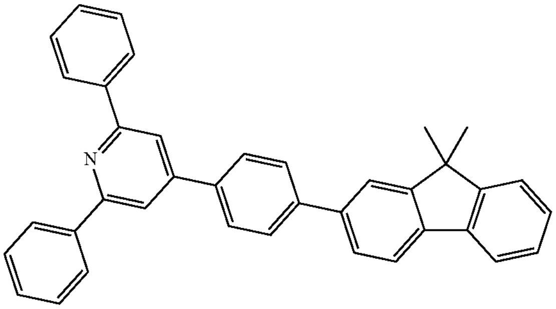
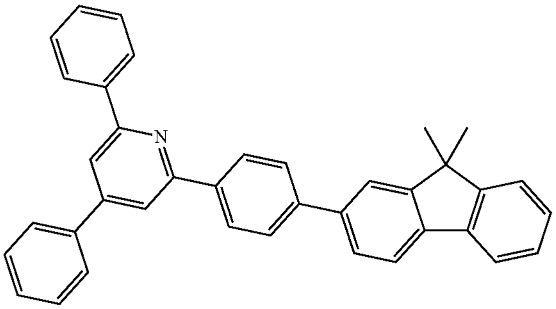

-continued
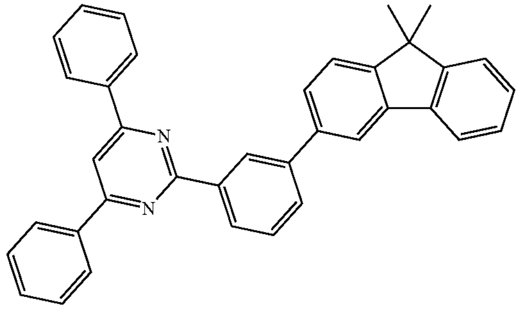
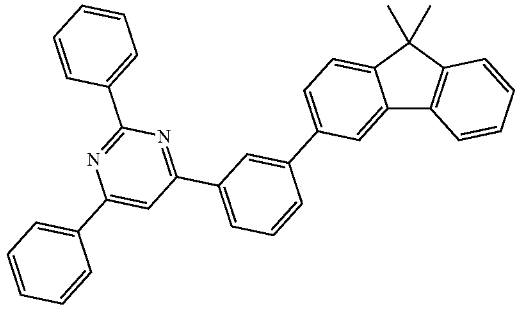
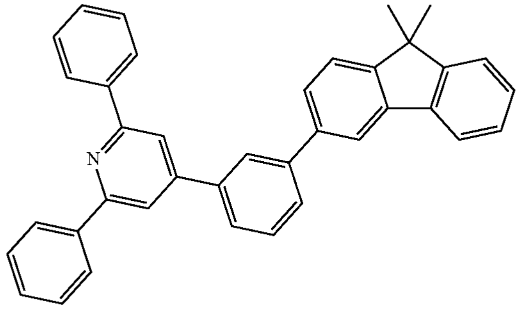
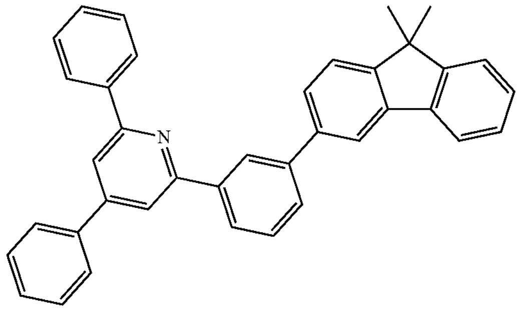
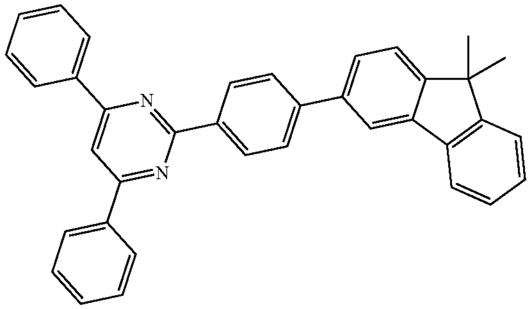
-continued
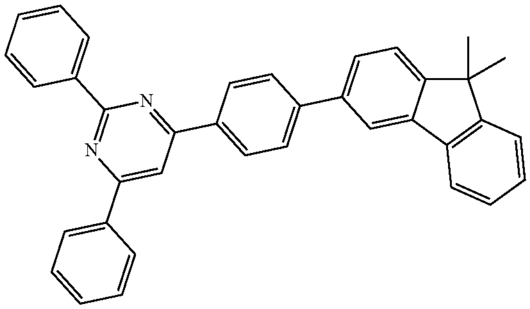
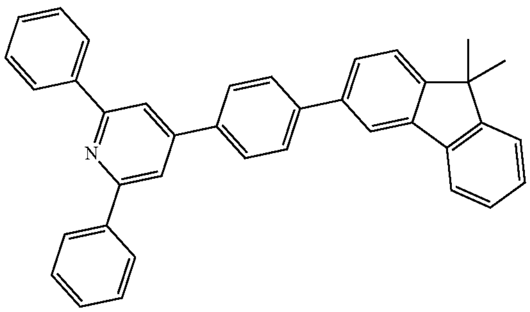
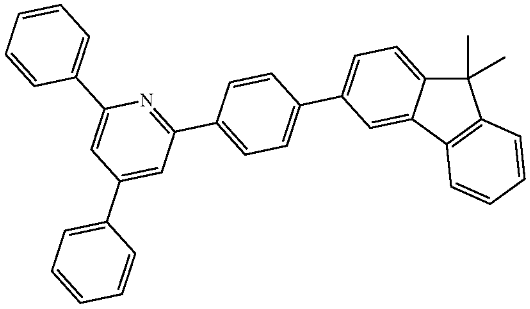
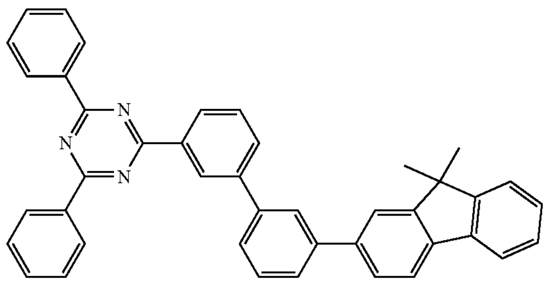
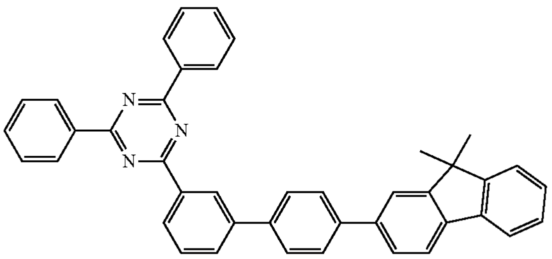

-continued
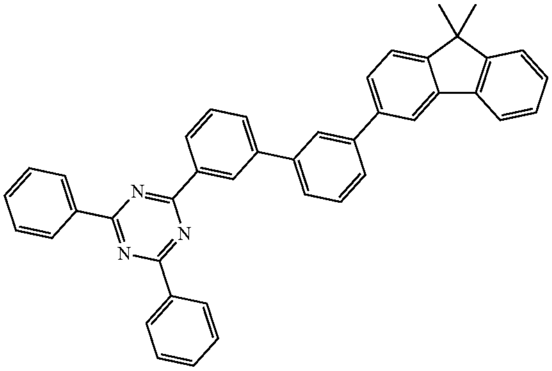
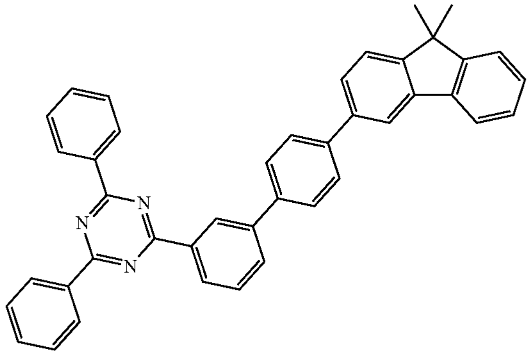
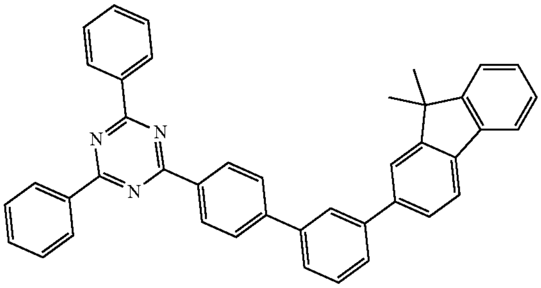
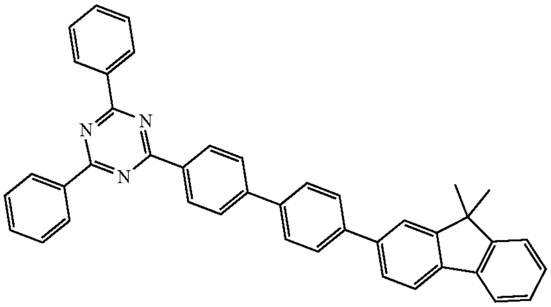
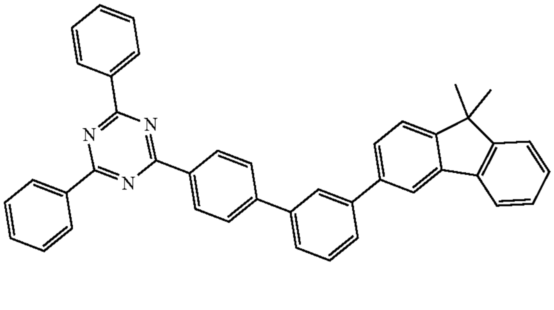
-continued
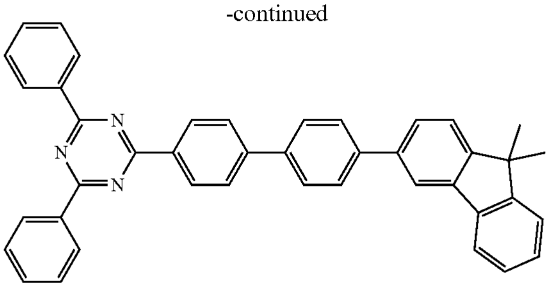
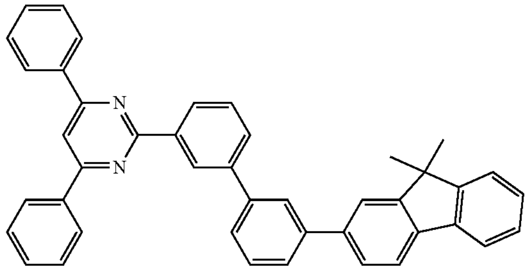
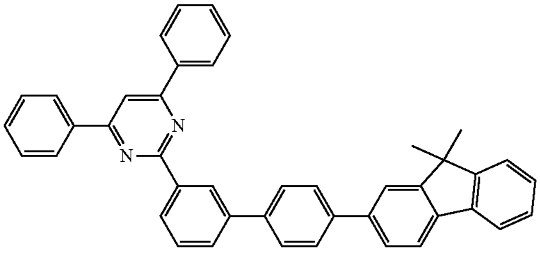
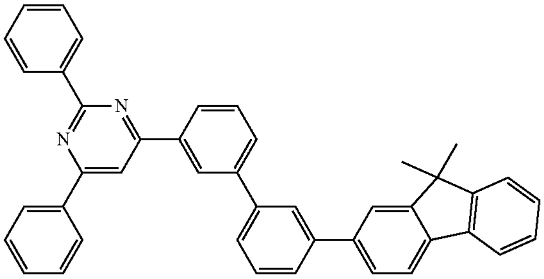
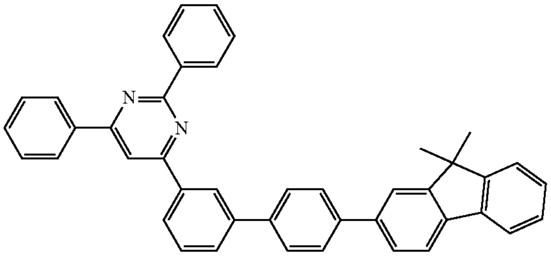
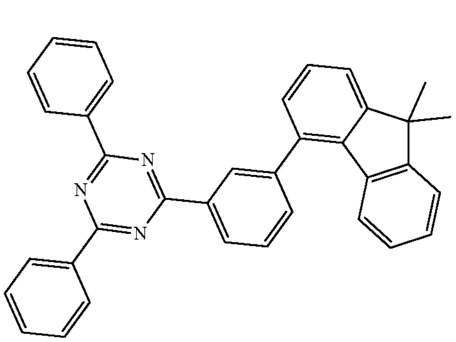

-continued
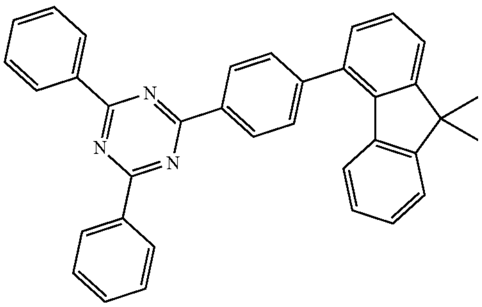
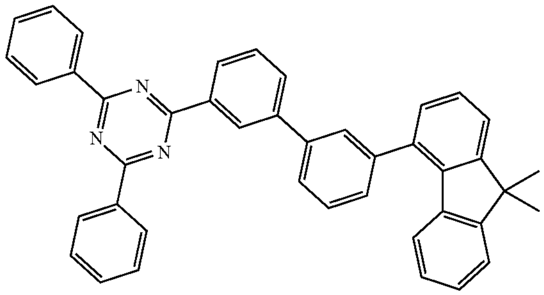
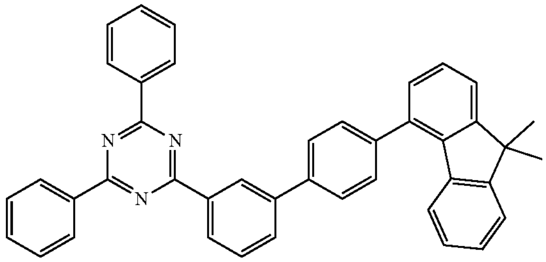
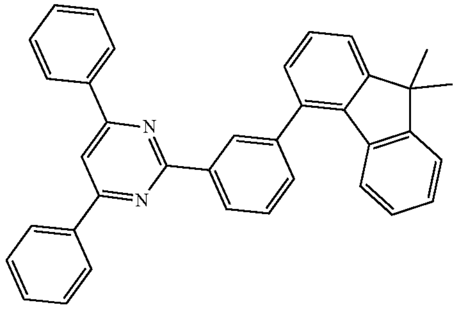
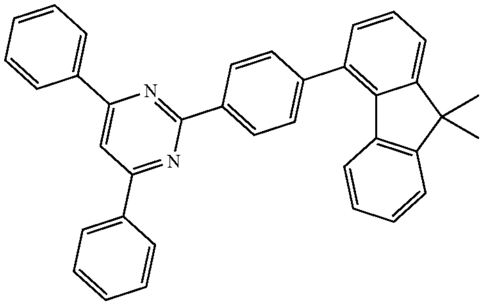
-continued
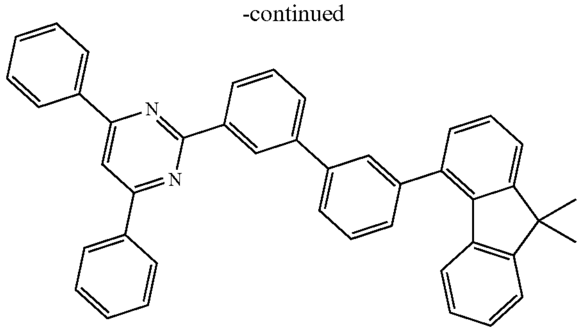
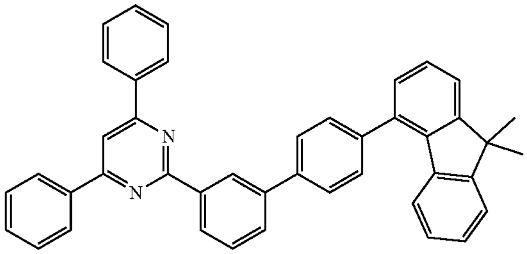
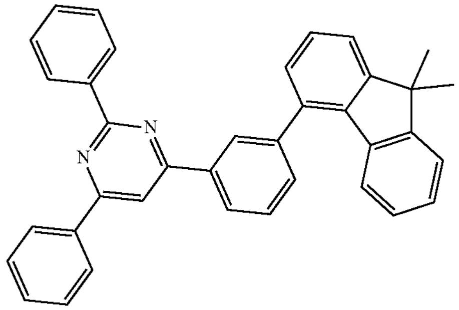
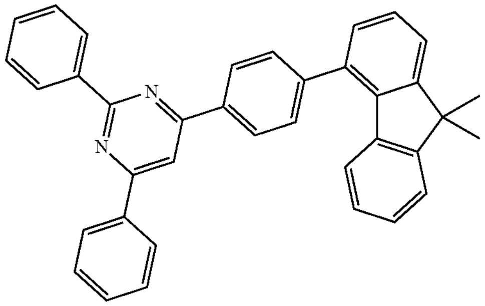
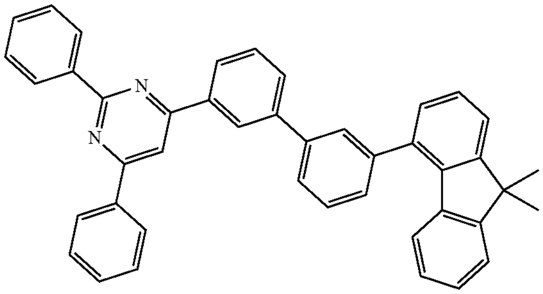
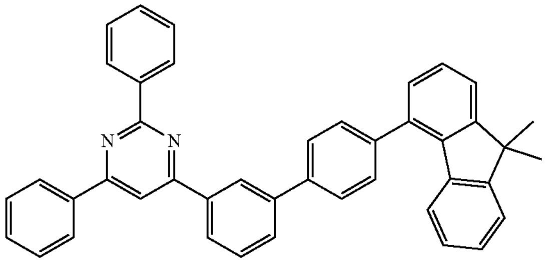

-continued
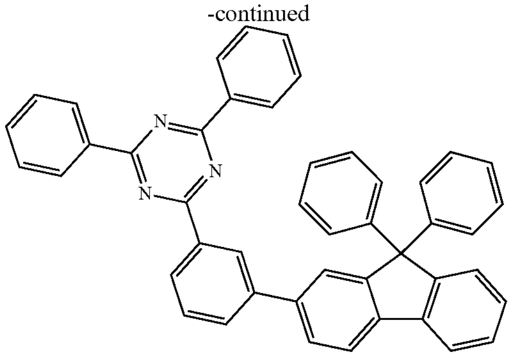
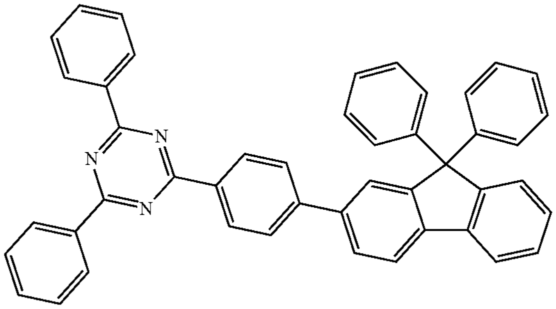
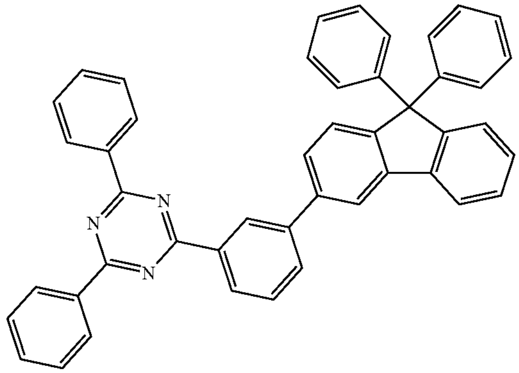
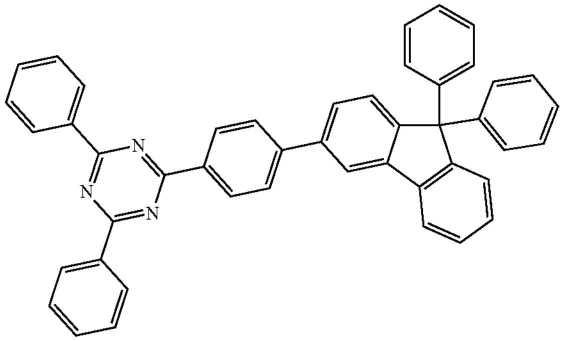
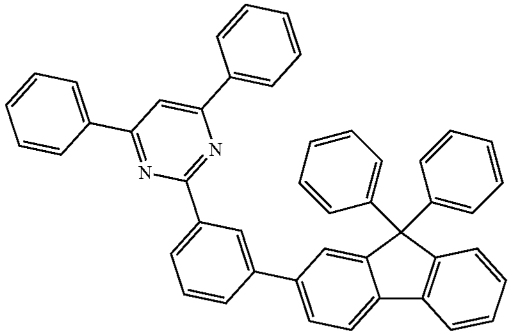
-continued
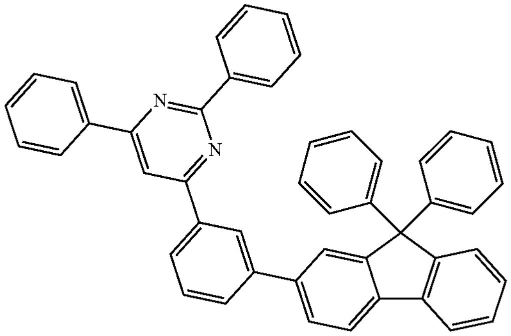
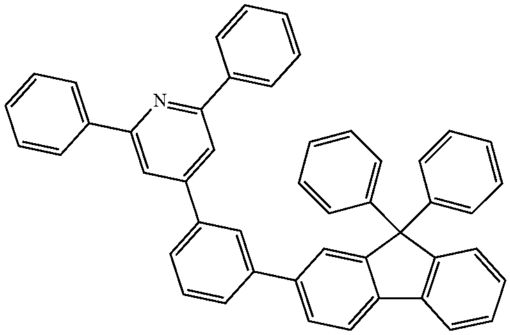
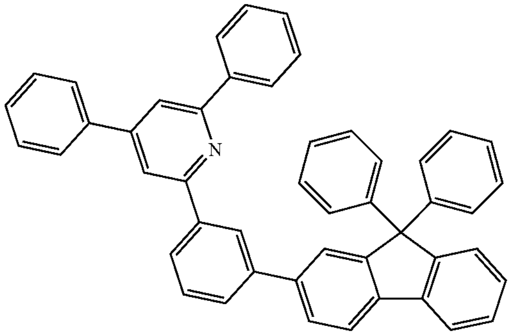
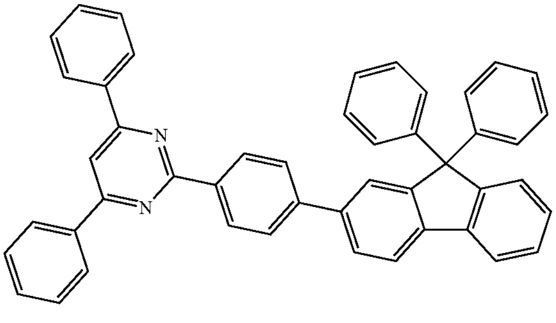
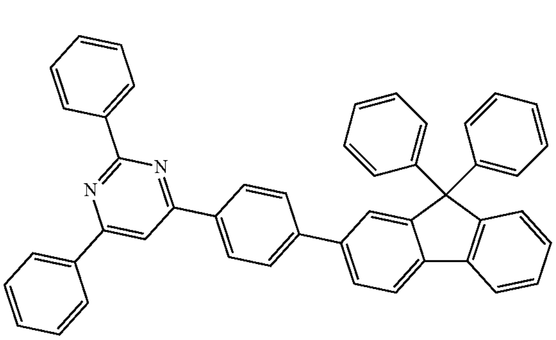

-continued
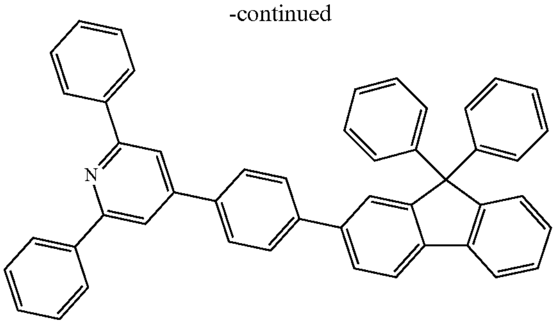
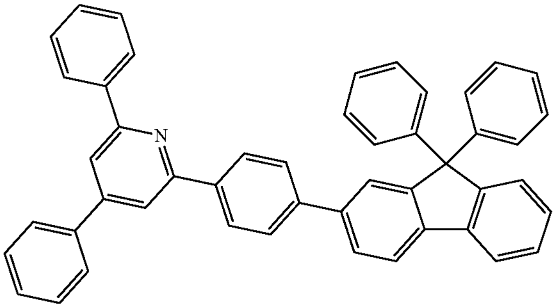
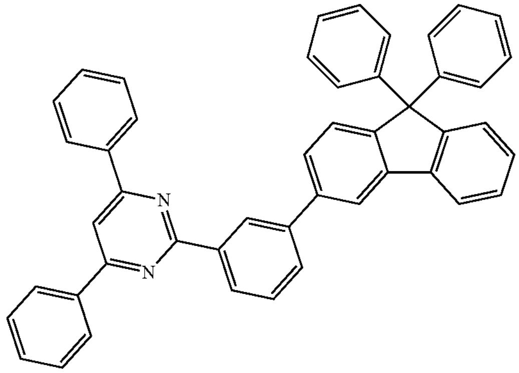
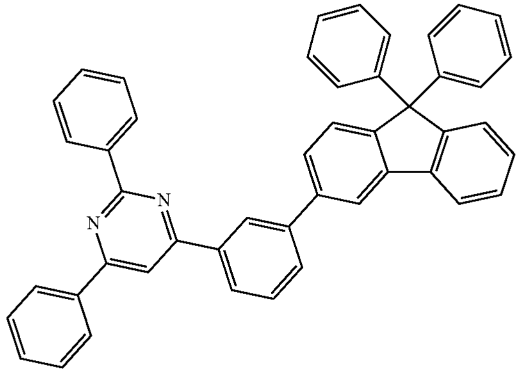
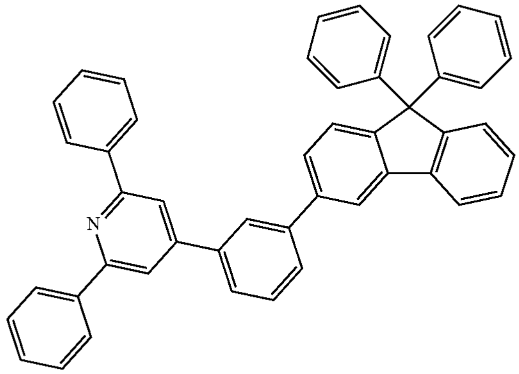
-continued
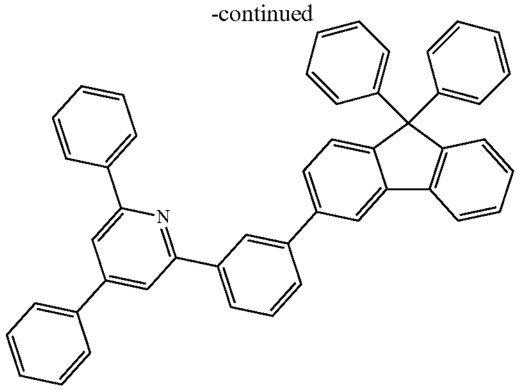
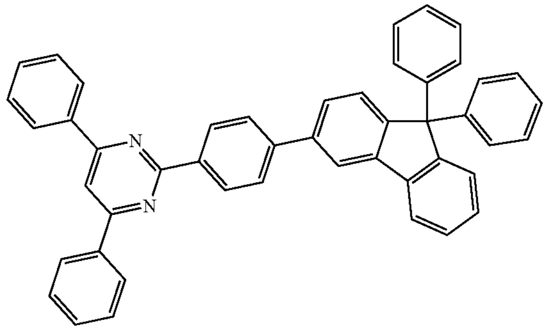
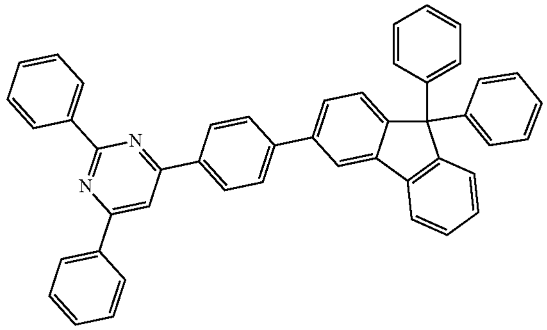
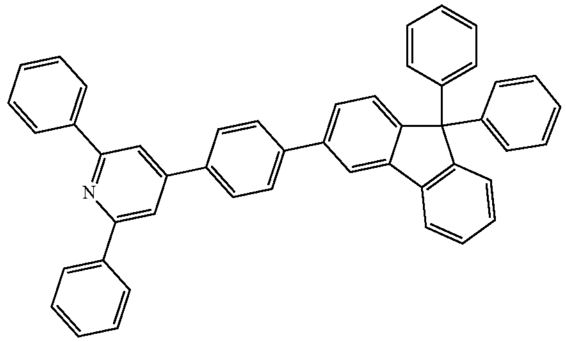
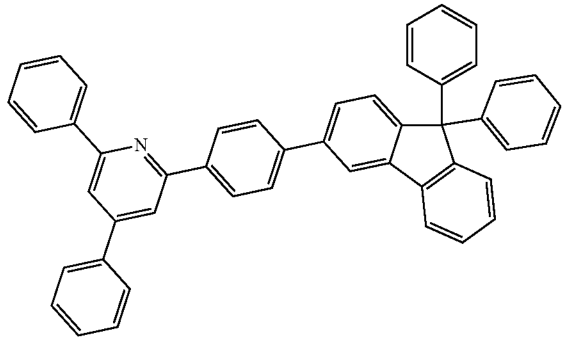

-continued
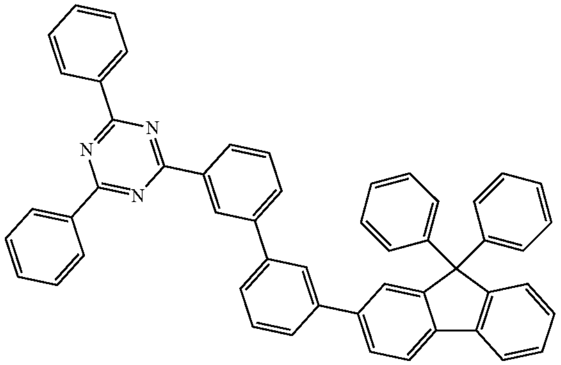
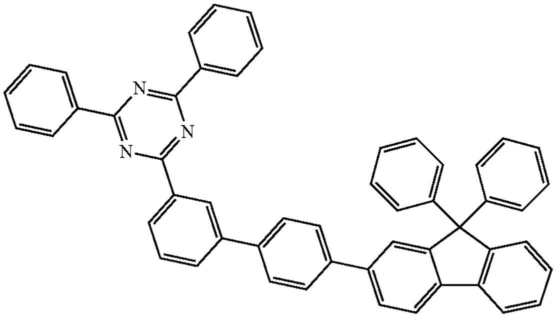
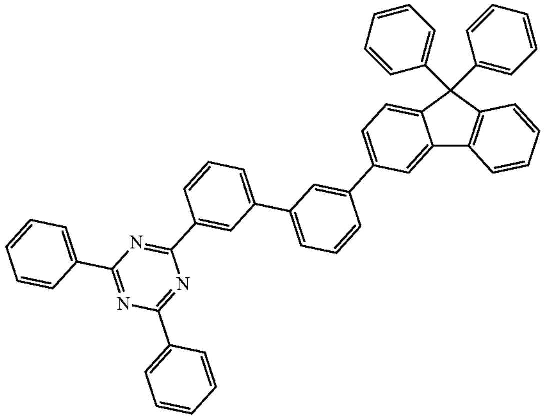
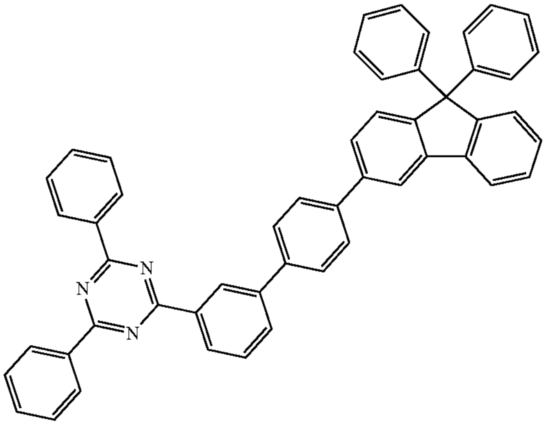
-continued
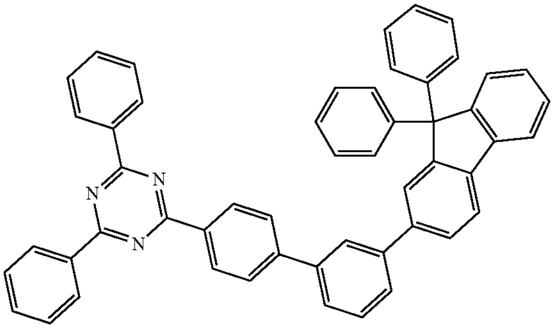
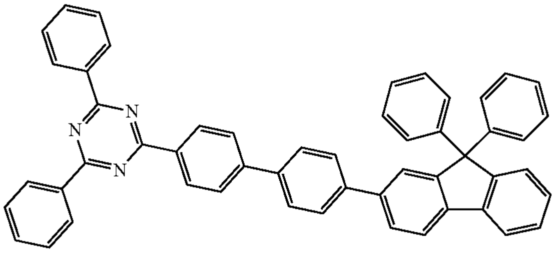
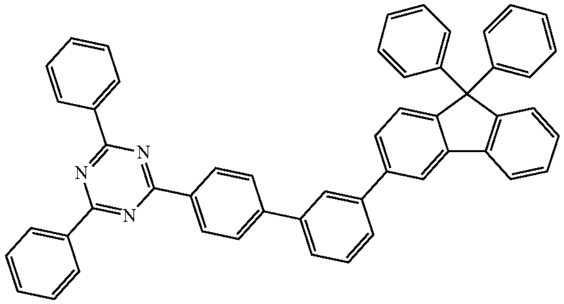
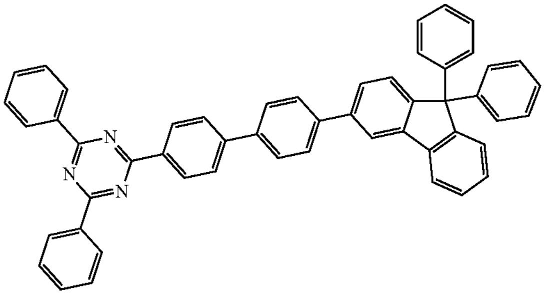
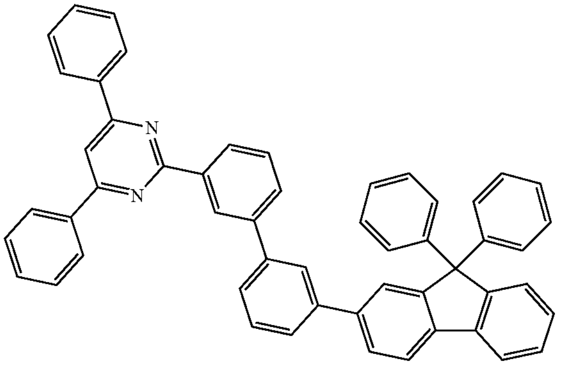

-continued
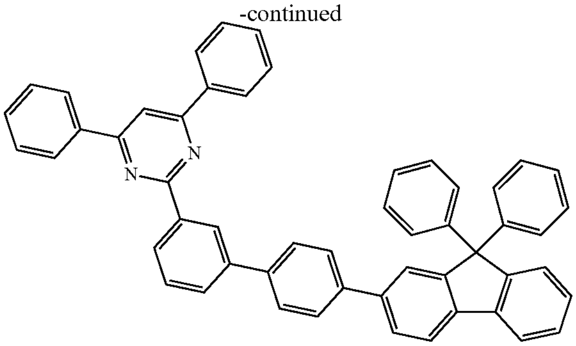
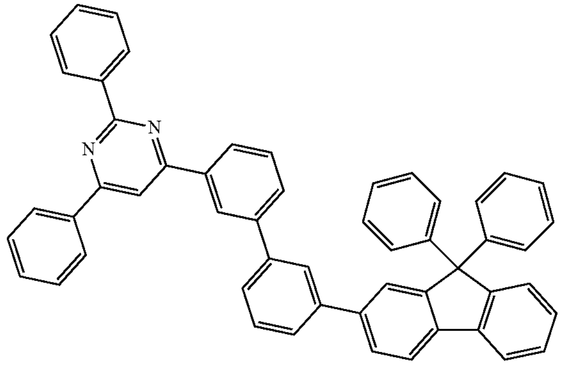
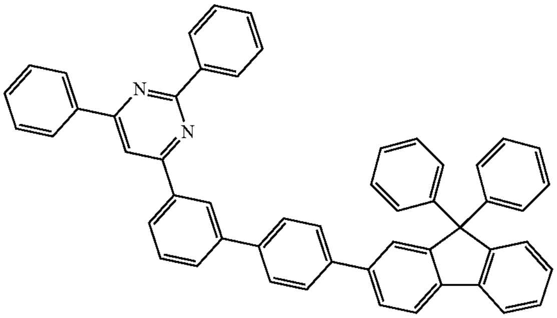
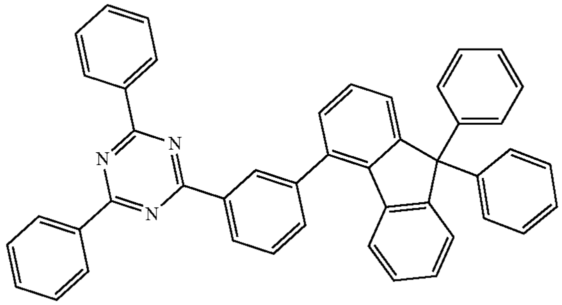
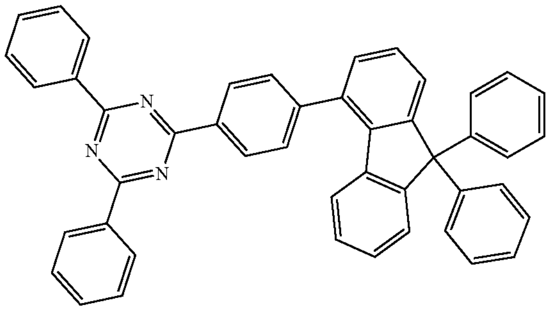
-continued
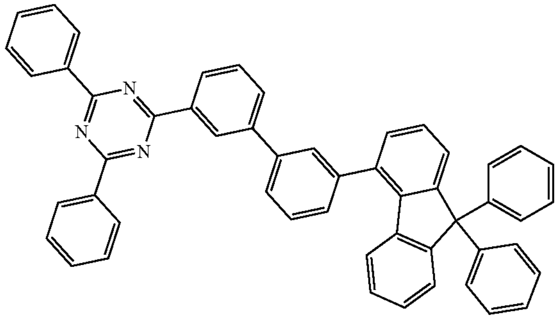
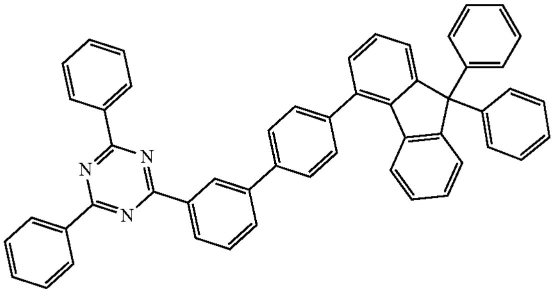
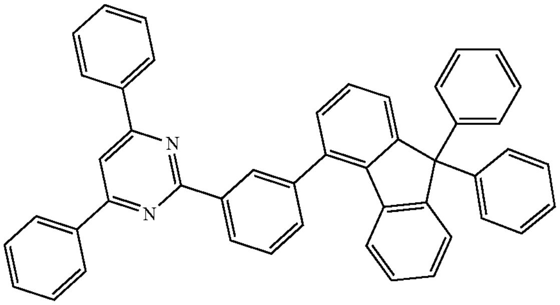
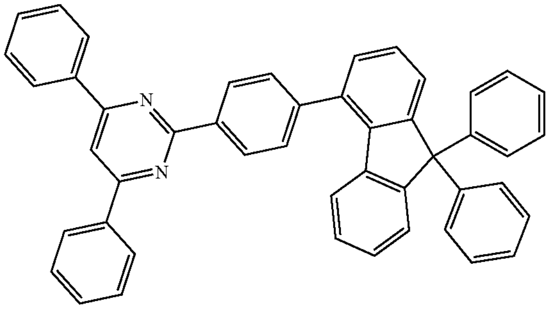
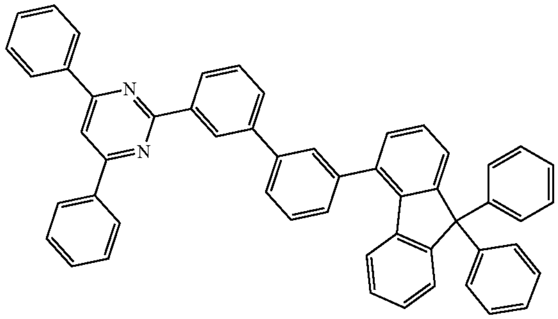

-continued
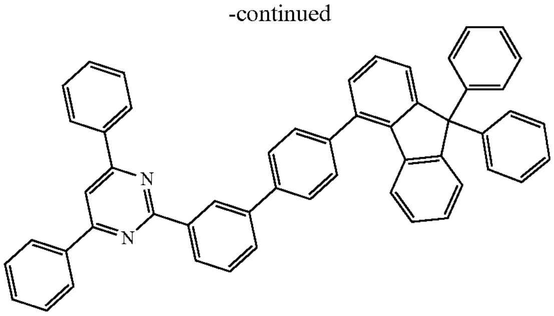
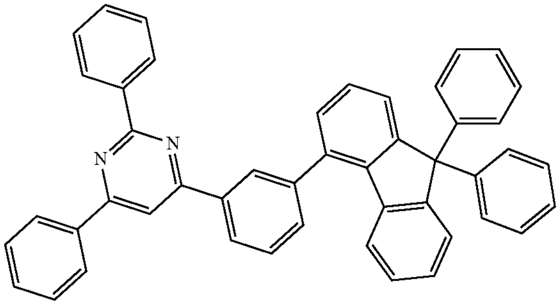
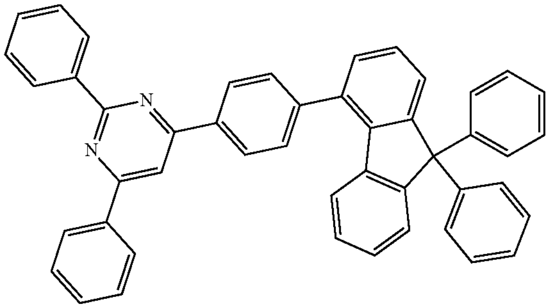
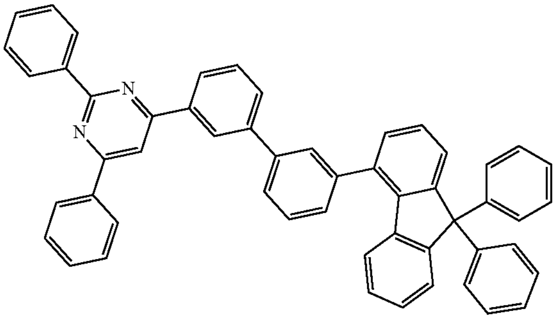
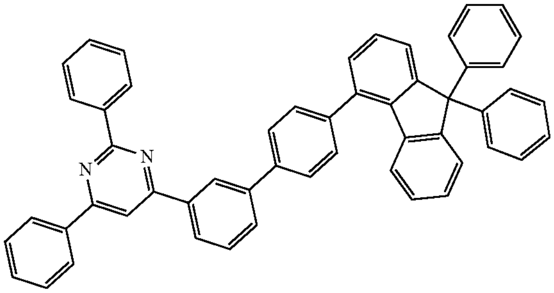
-continued
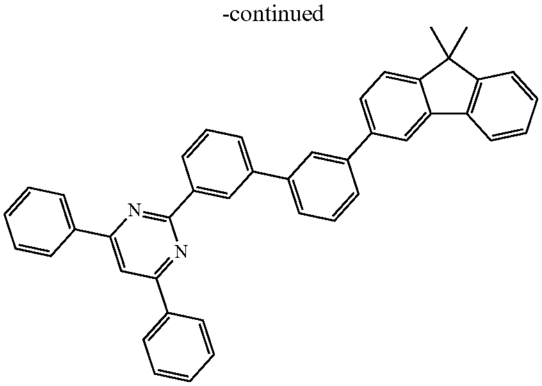
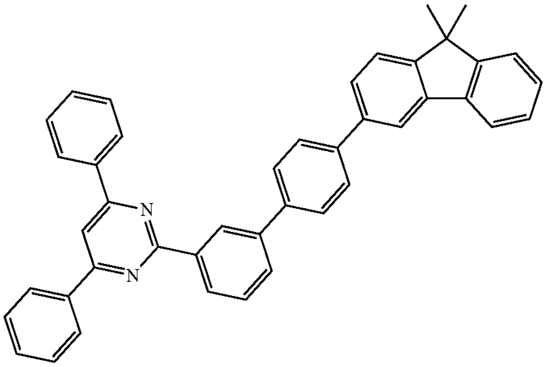
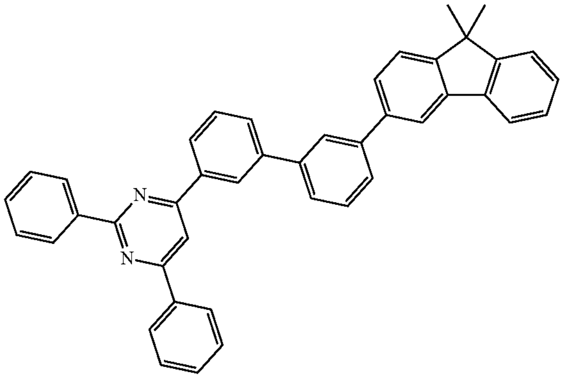
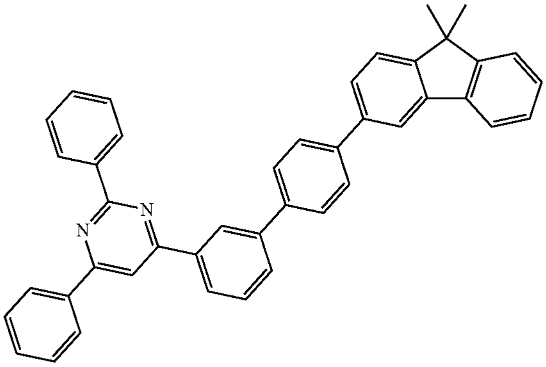

-continued
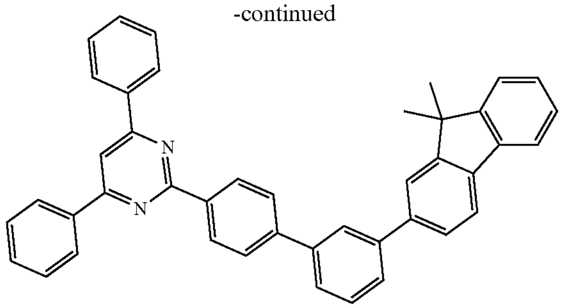
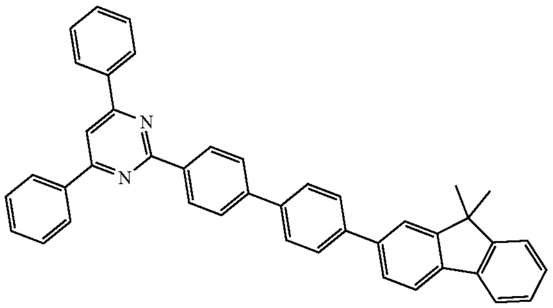
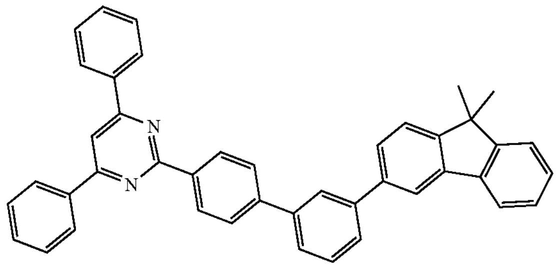
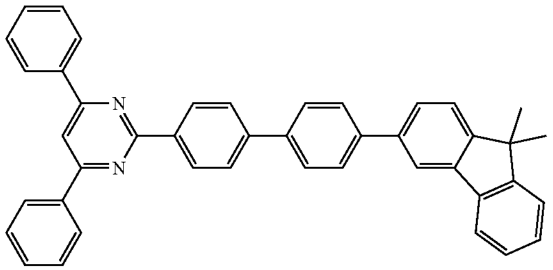
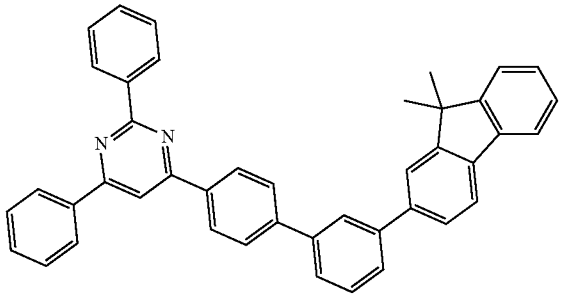
-continued
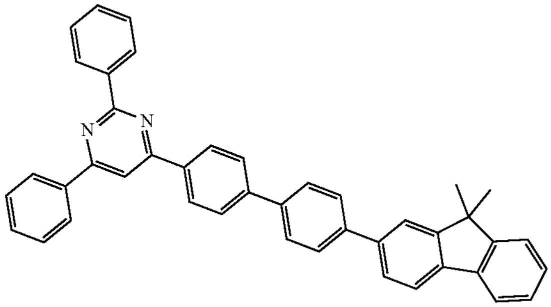
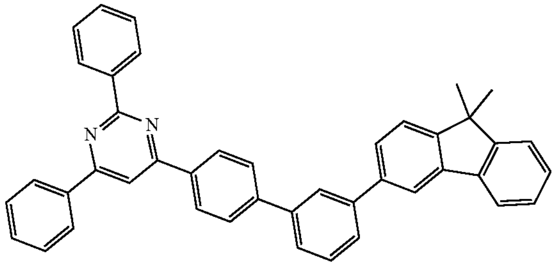
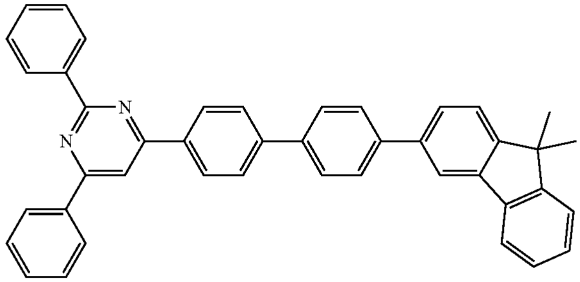
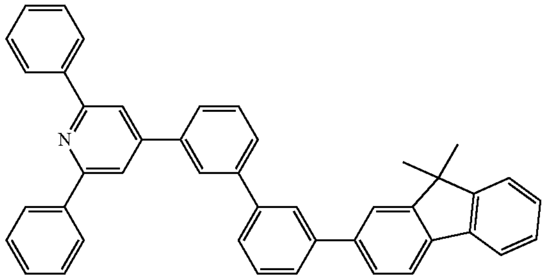
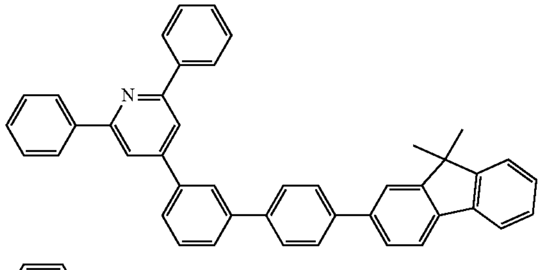
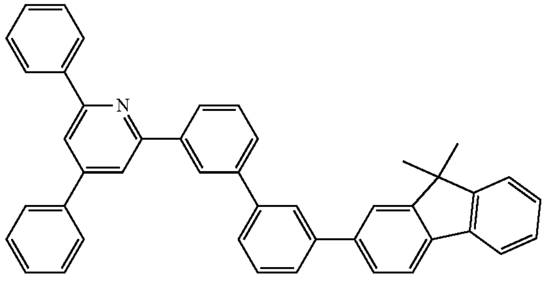

-continued
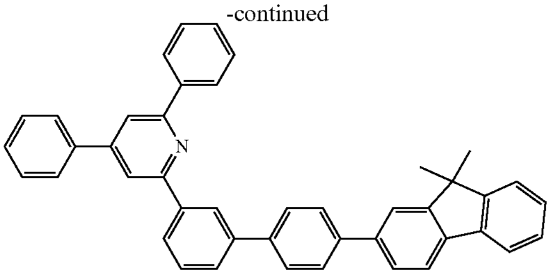
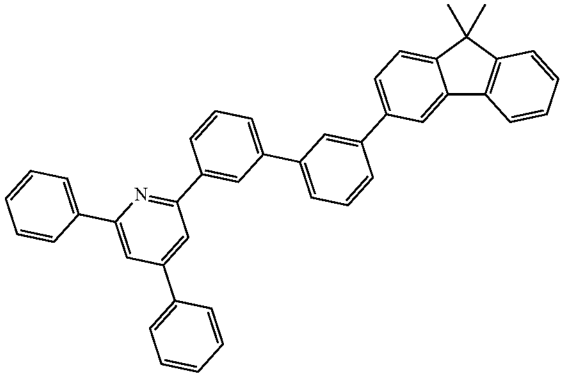
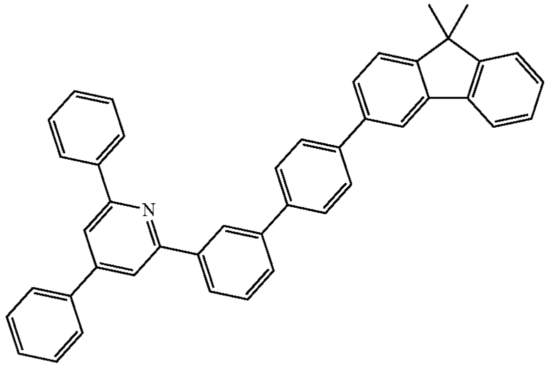
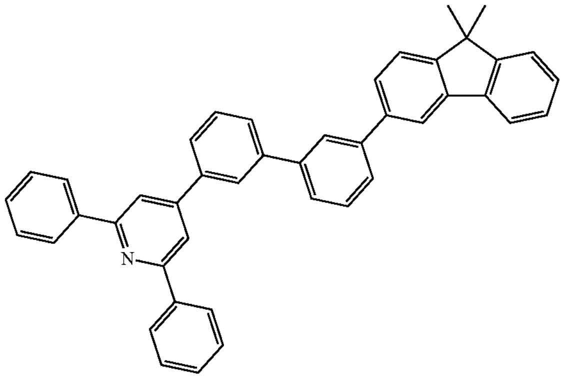
-continued
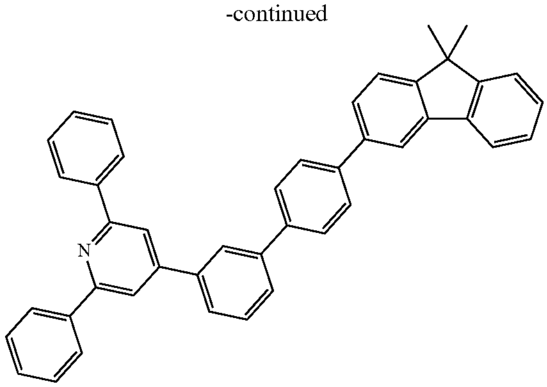
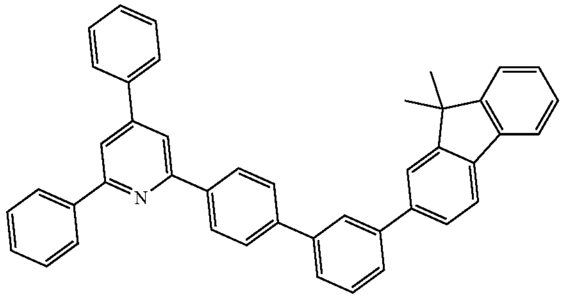
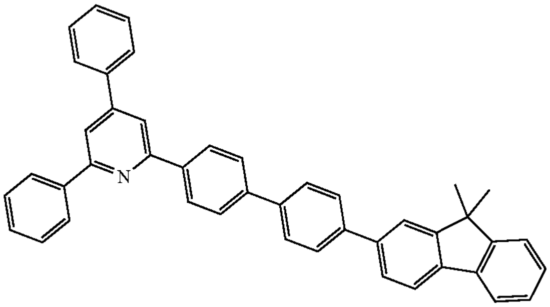
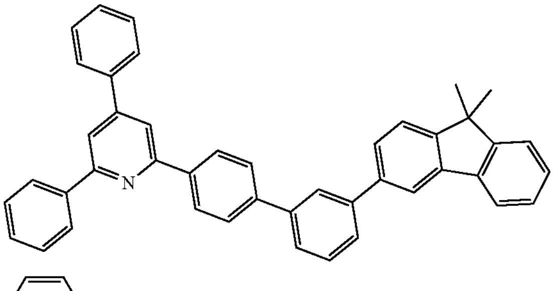
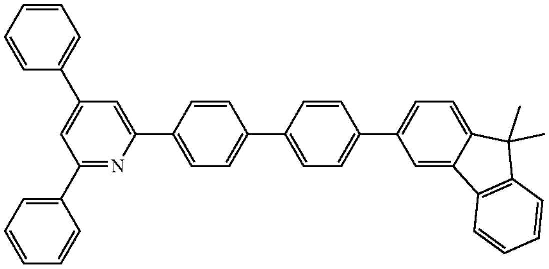

-continued
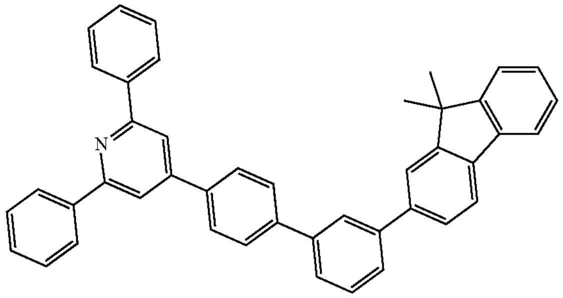
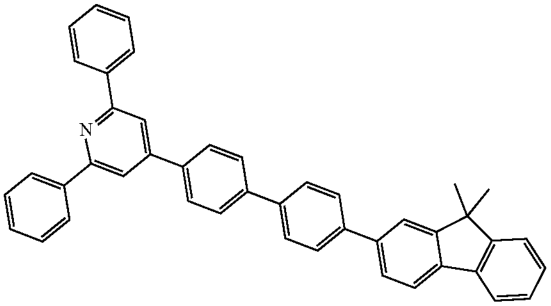
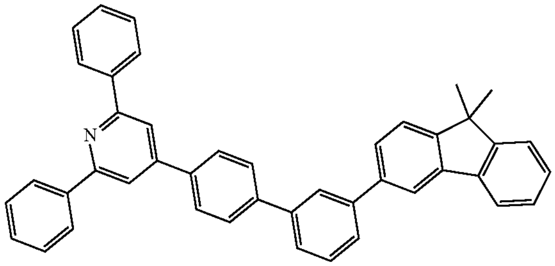
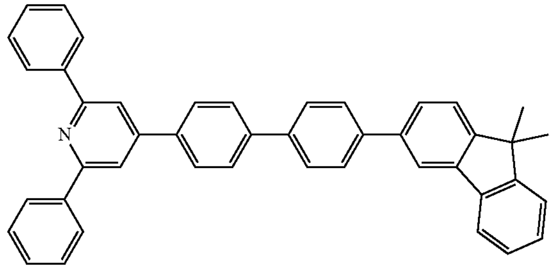
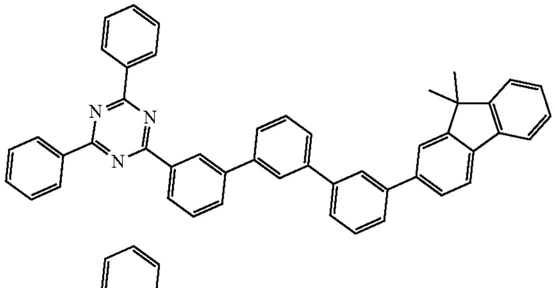
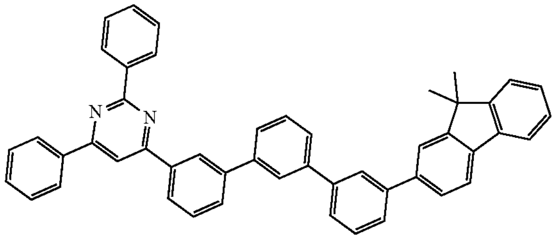
-continued
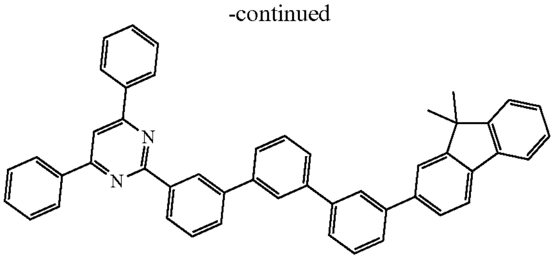
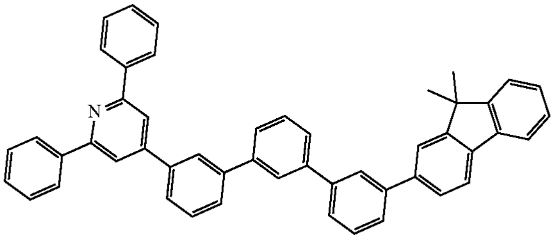
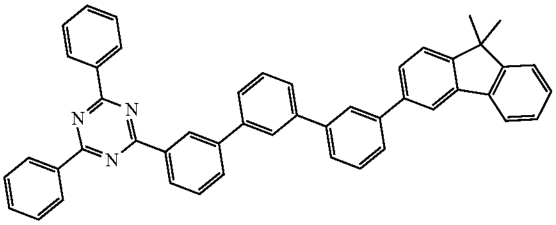
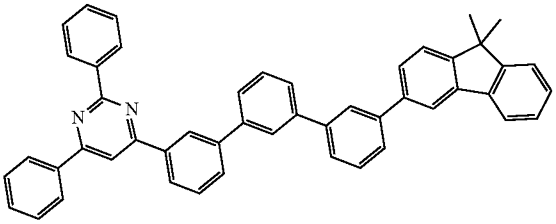
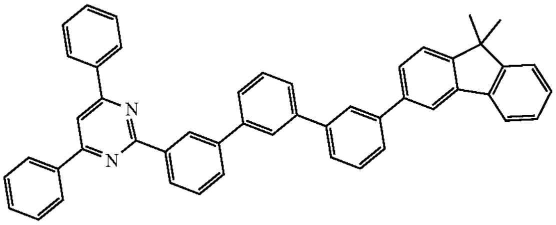
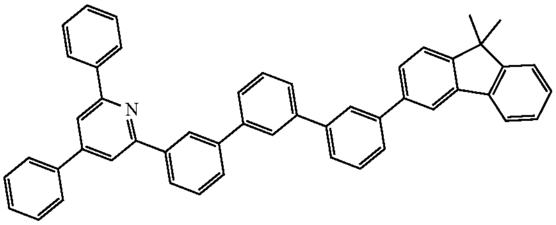
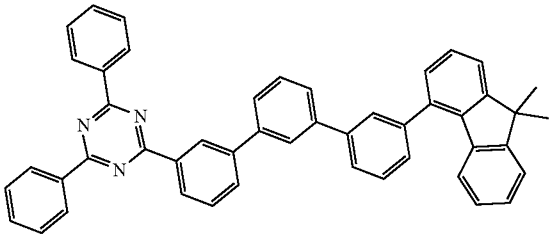

-continued
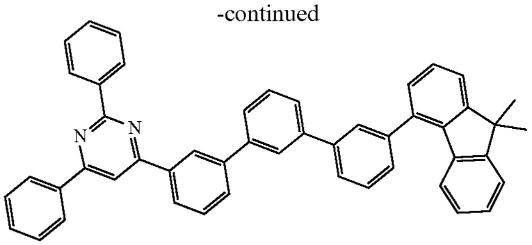
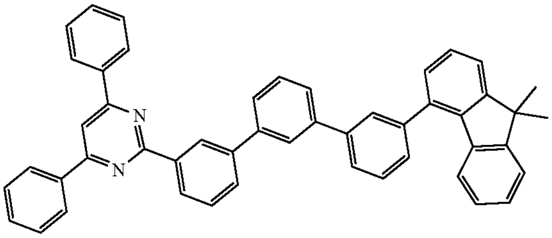
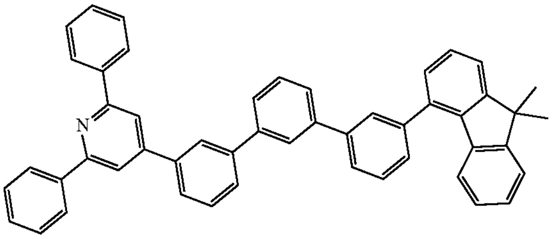
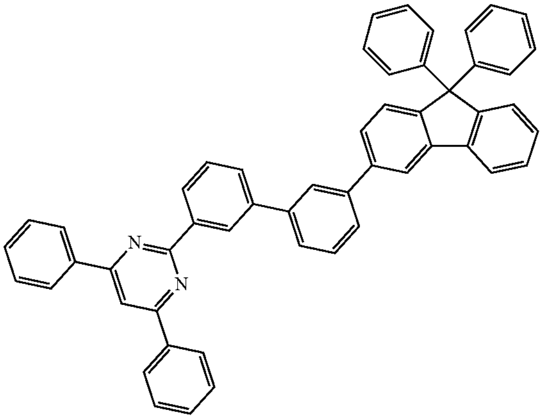
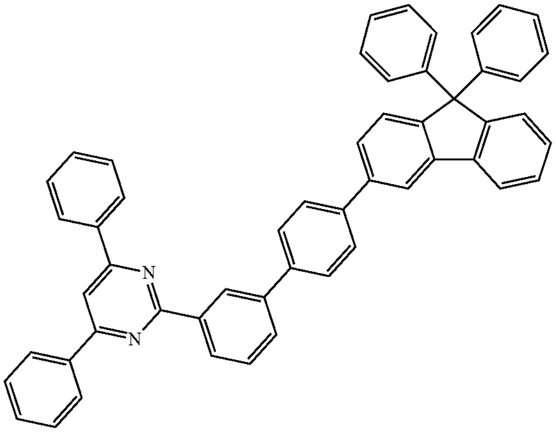
-continued
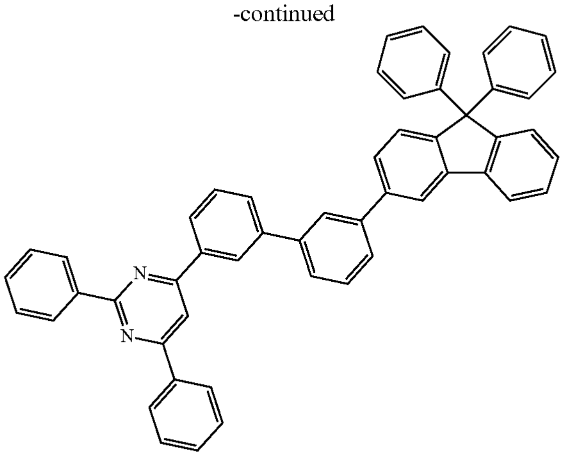
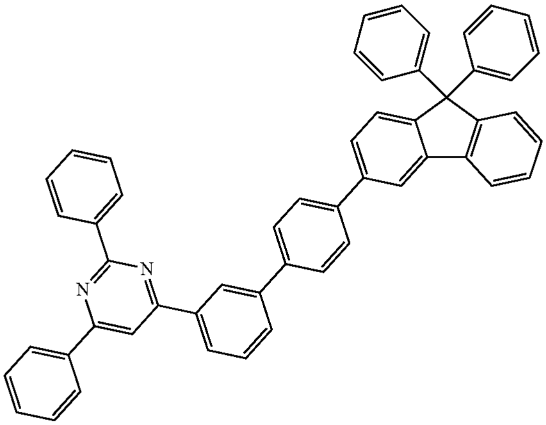
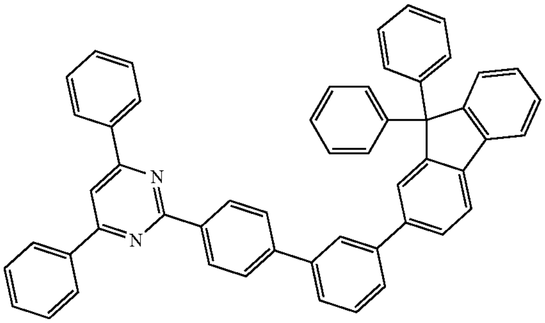
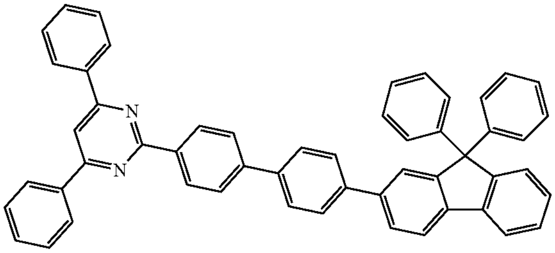
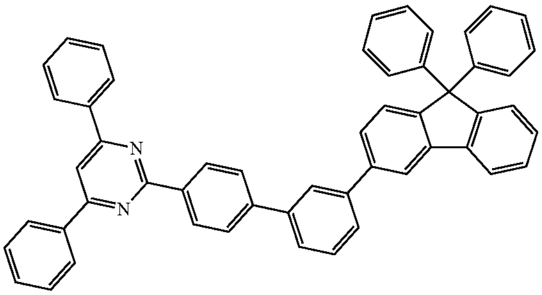

-continued
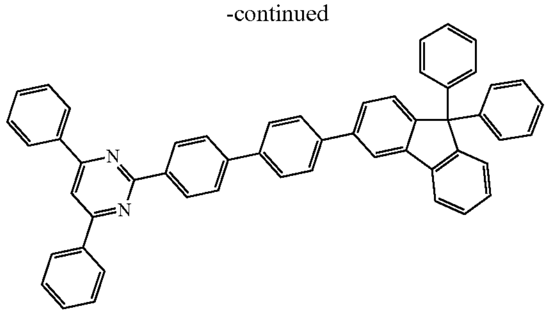
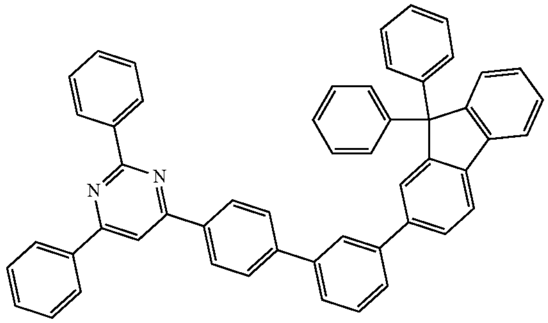
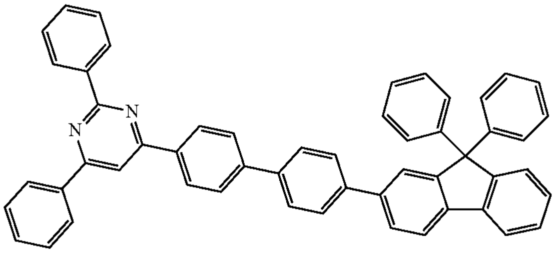
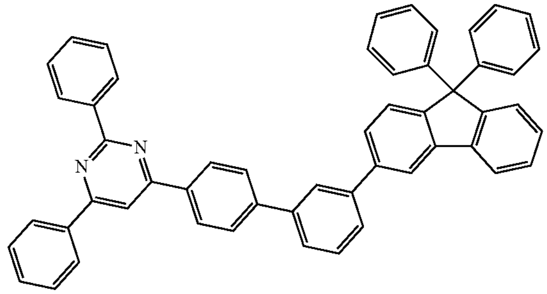
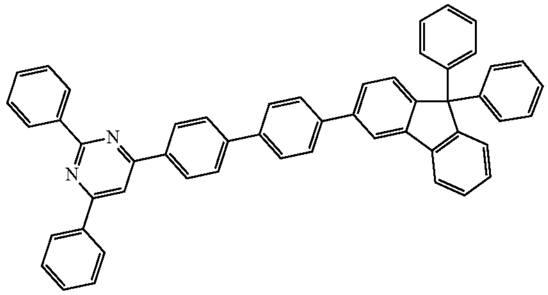
-continued
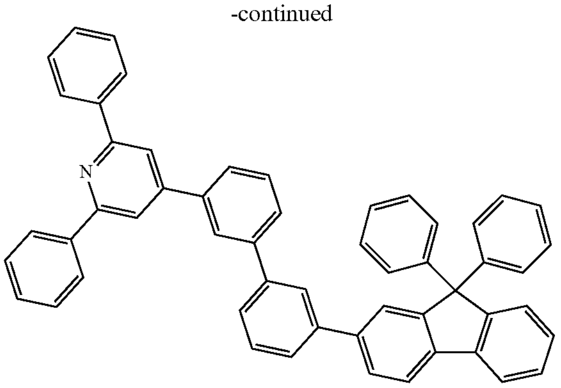
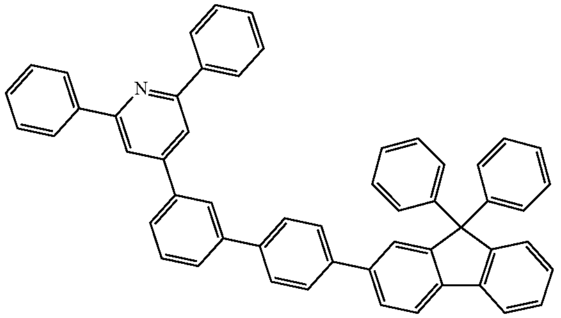
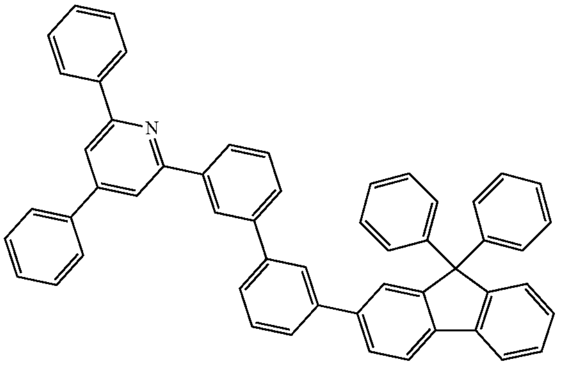
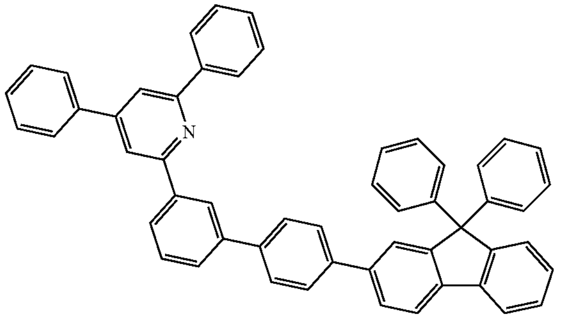

-continued
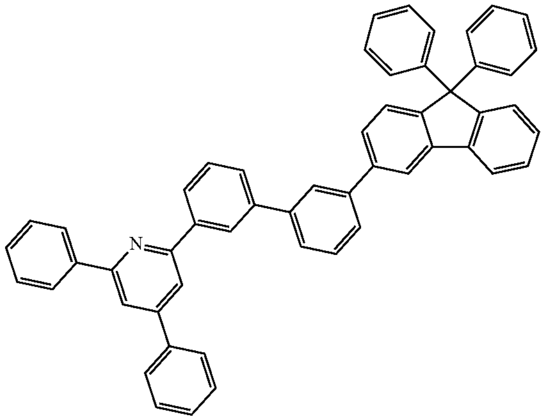
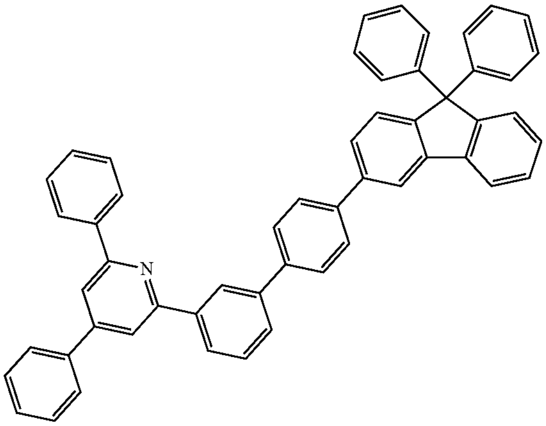
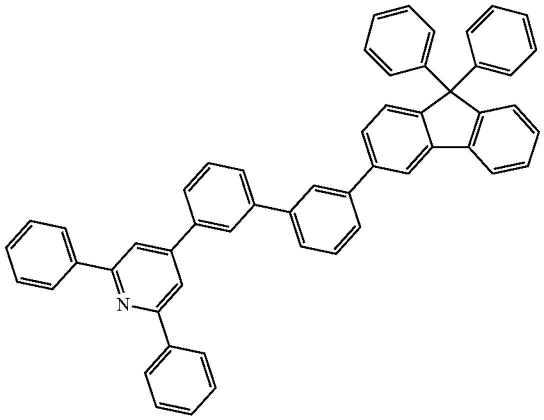
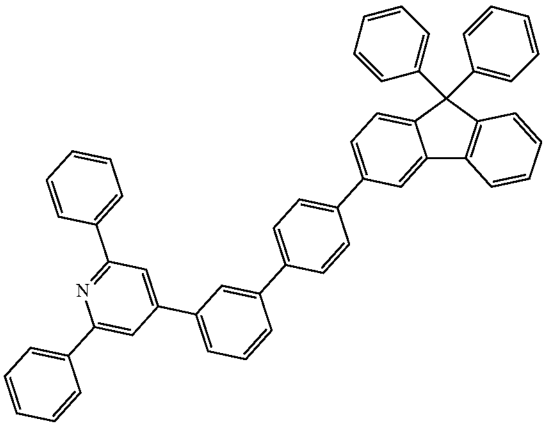
-continued
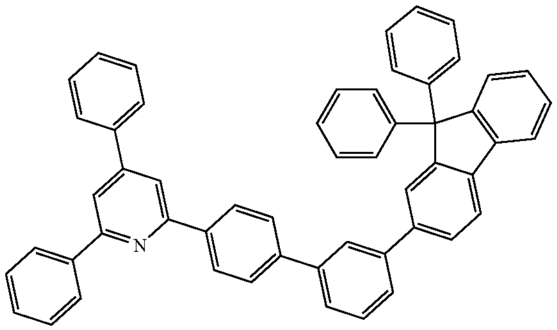
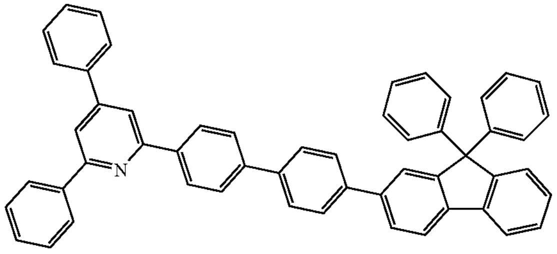
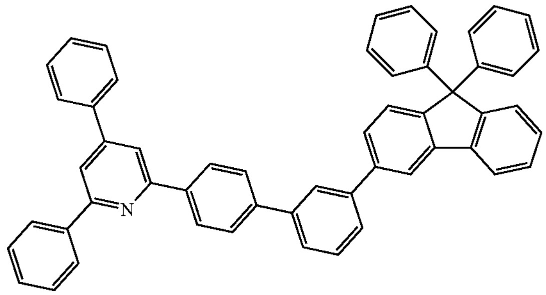
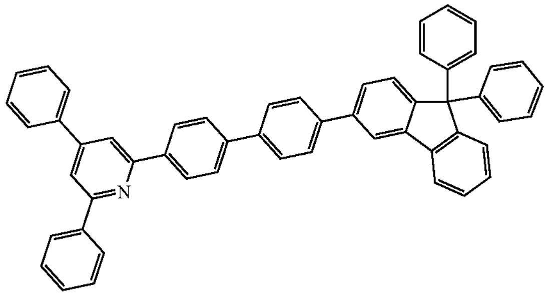
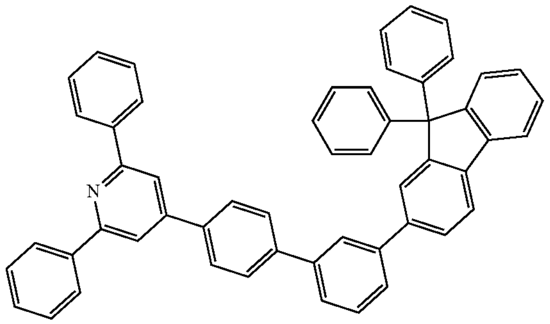

-continued
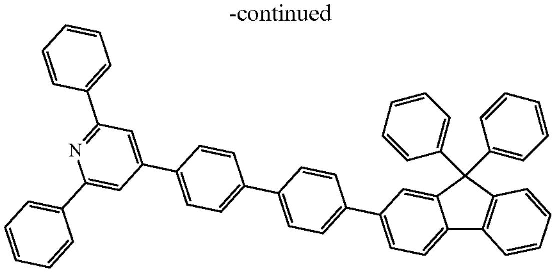
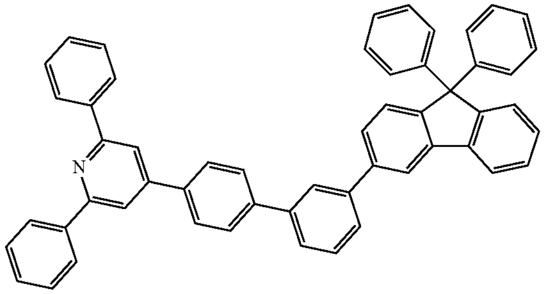
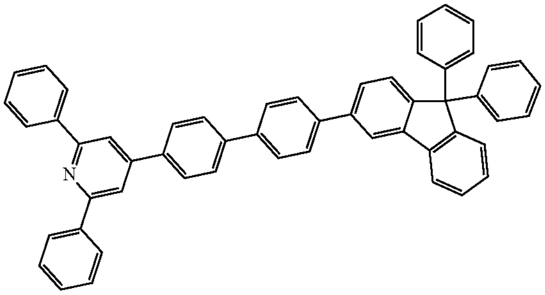
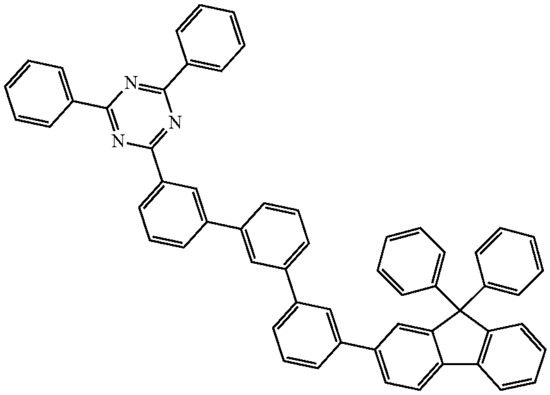
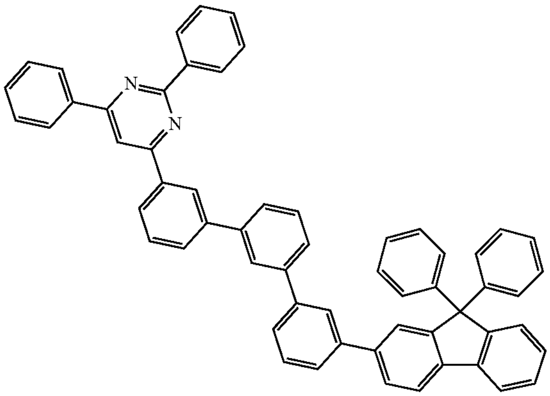
-continued
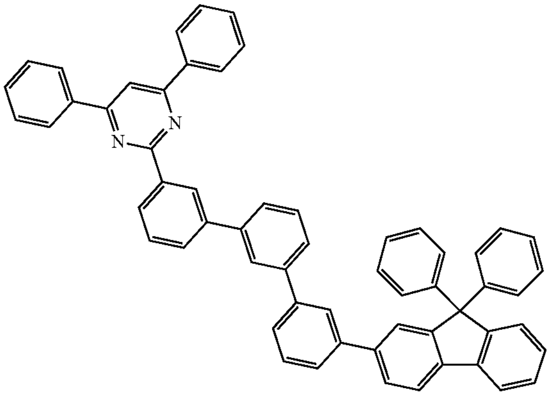
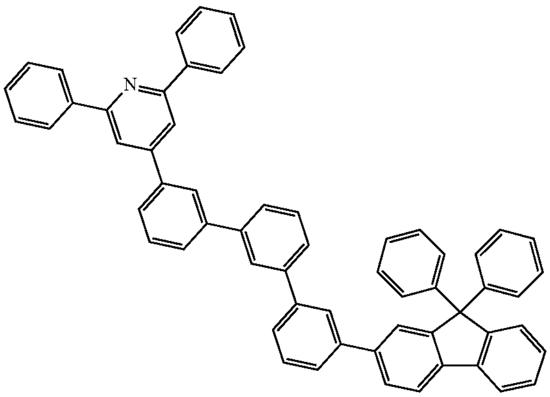
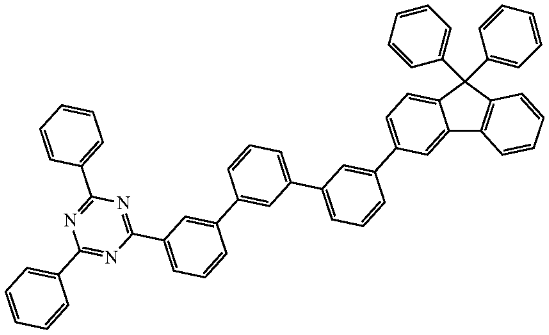
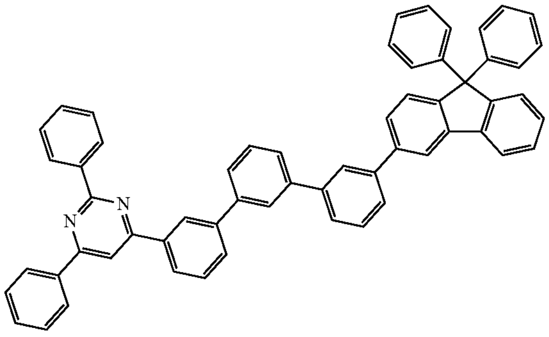

-continued
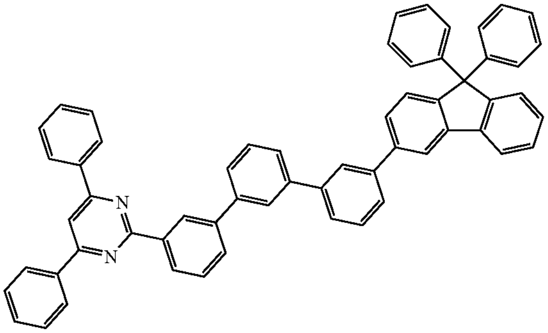
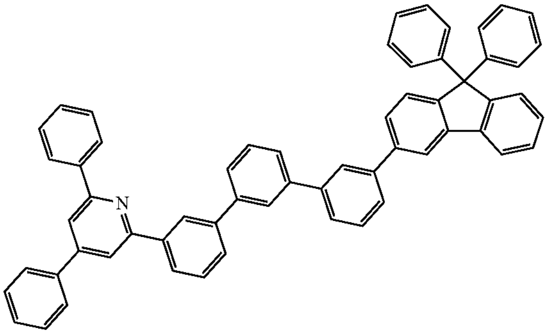
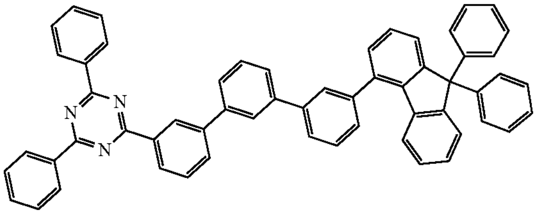
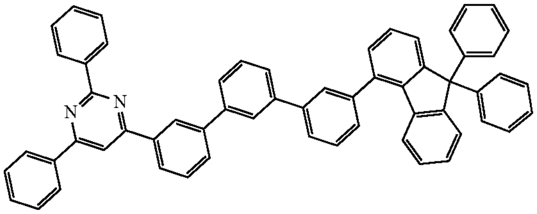
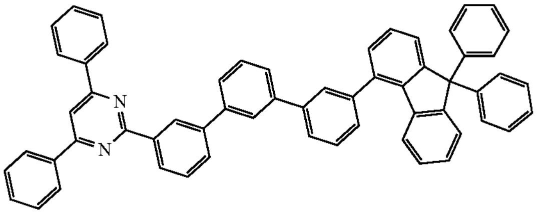
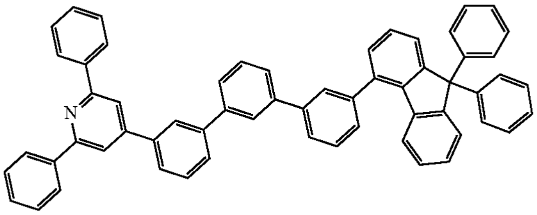
-continued
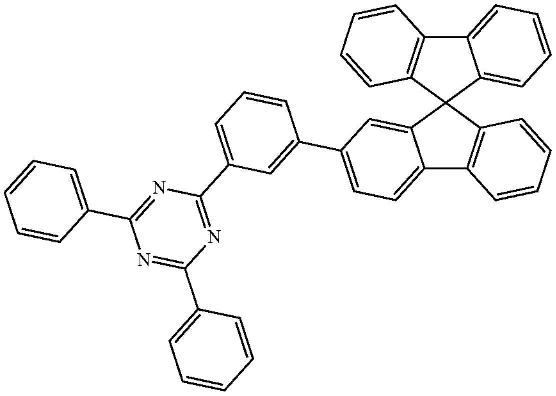
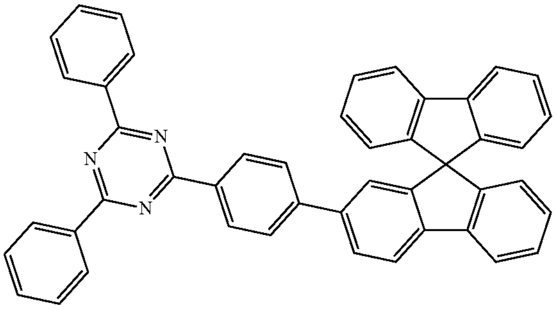
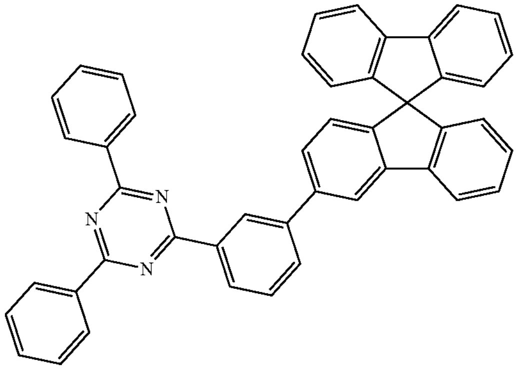
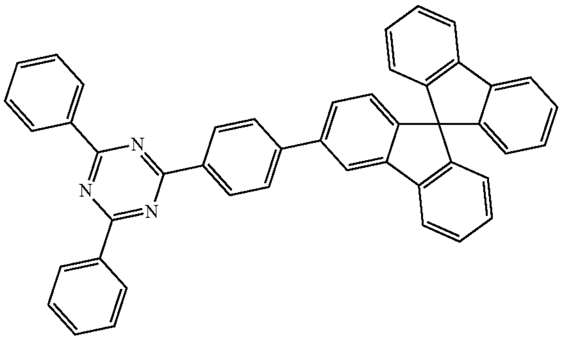

-continued
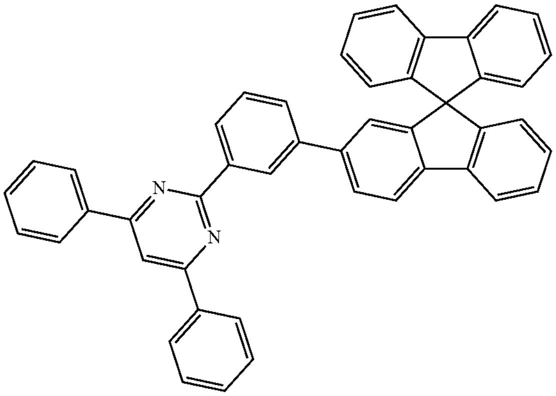
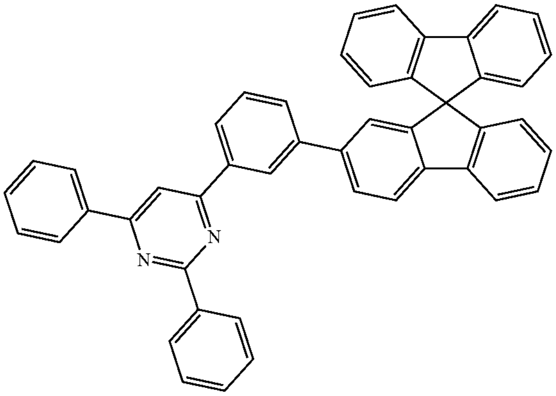
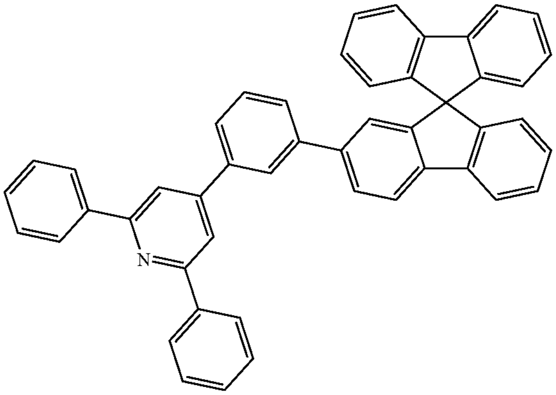
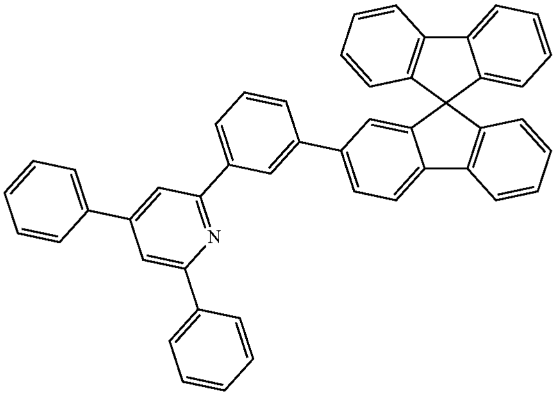
-continued
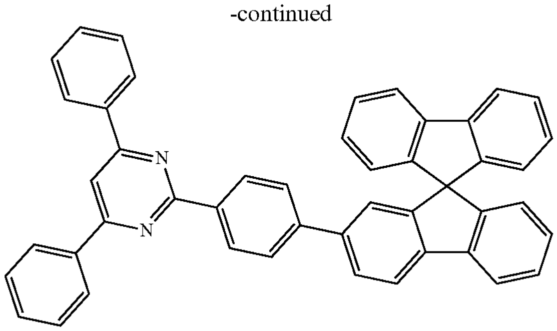
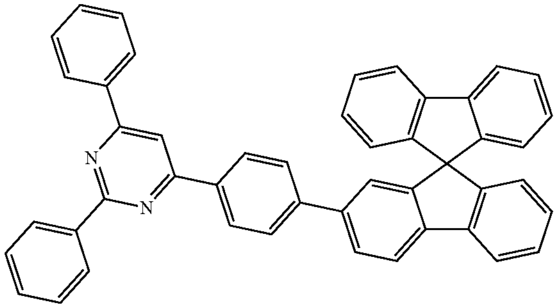
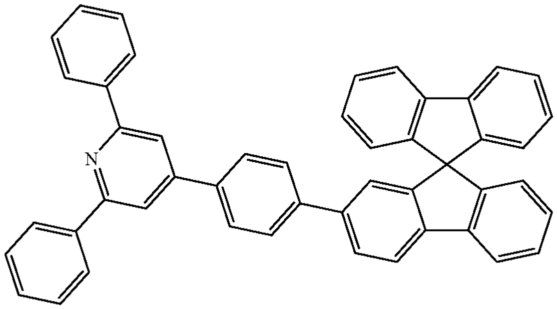
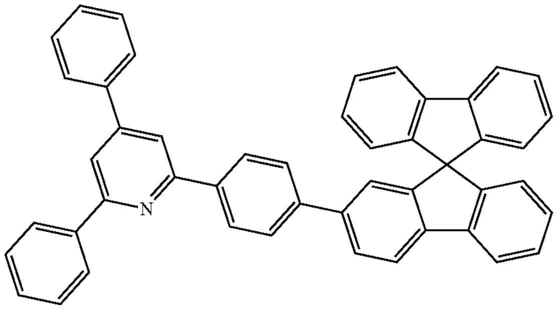
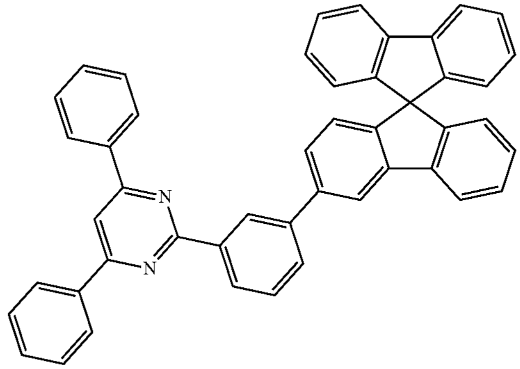

-continued
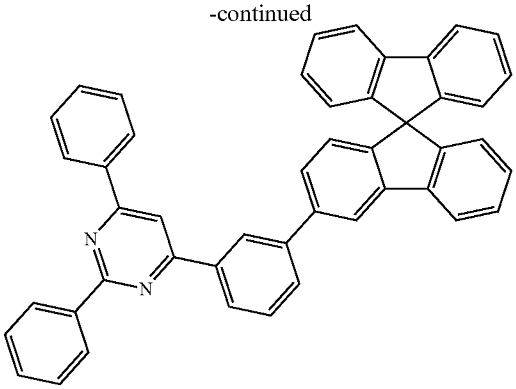
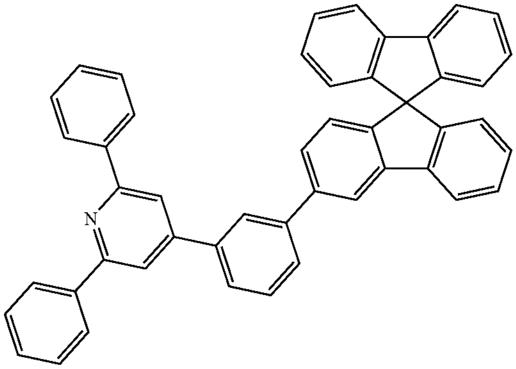
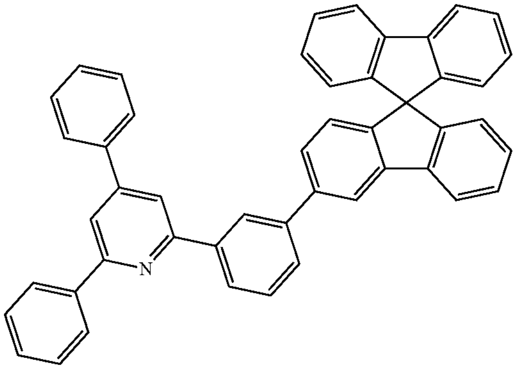
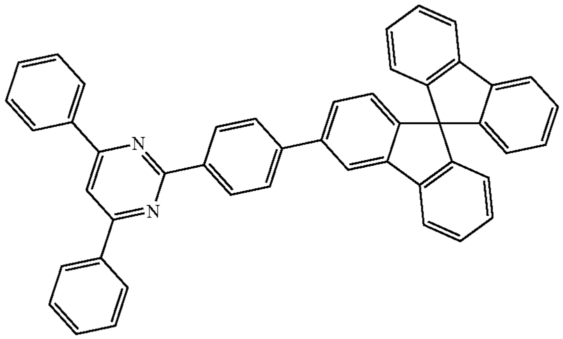
-continued
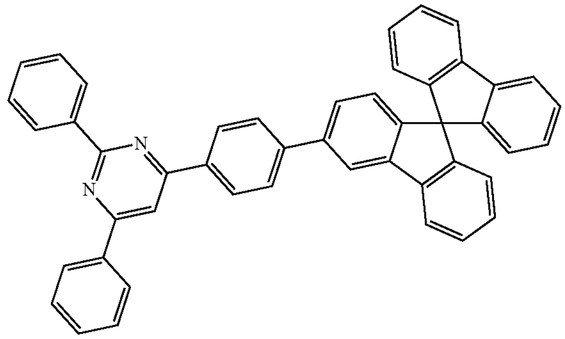
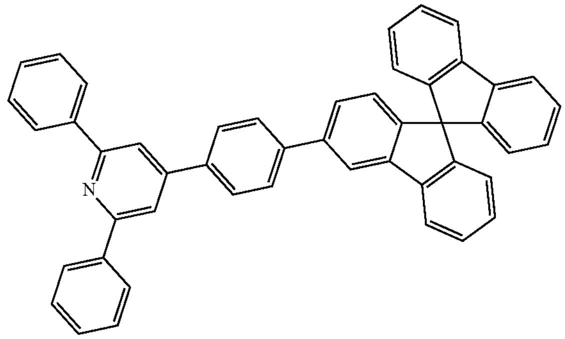
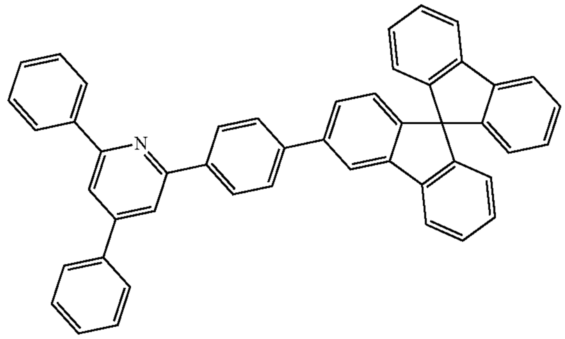
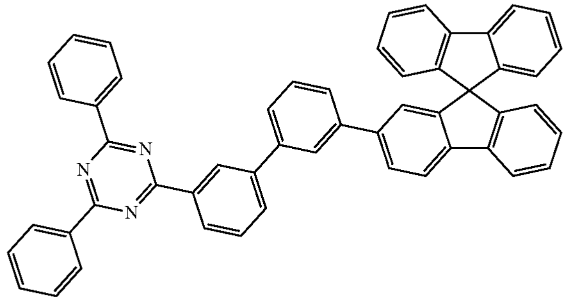
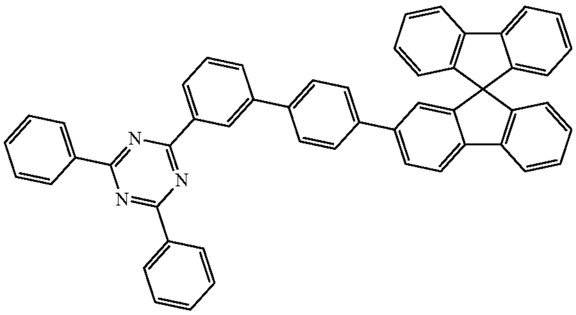

-continued
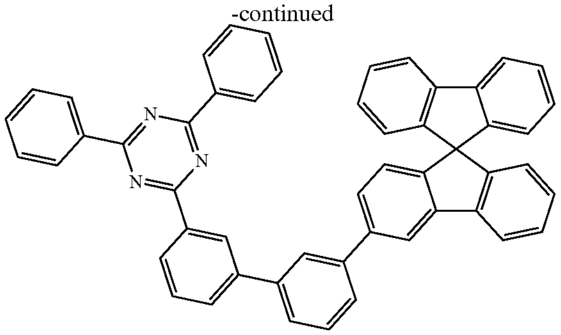
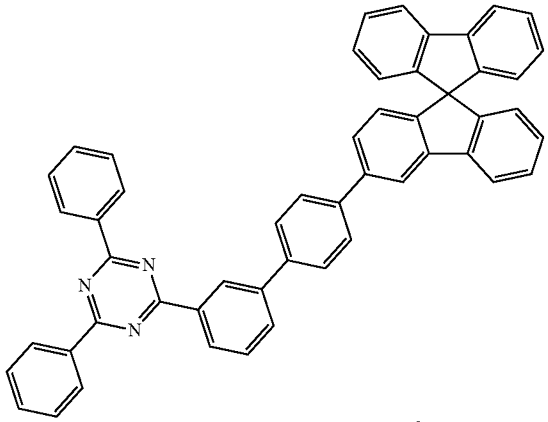
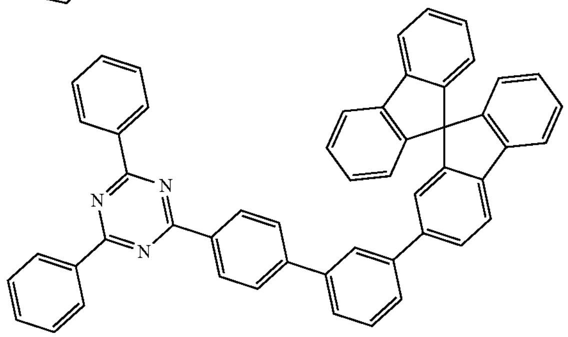
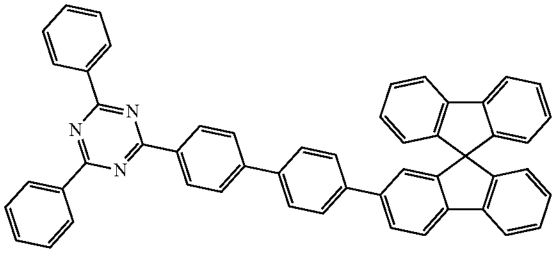
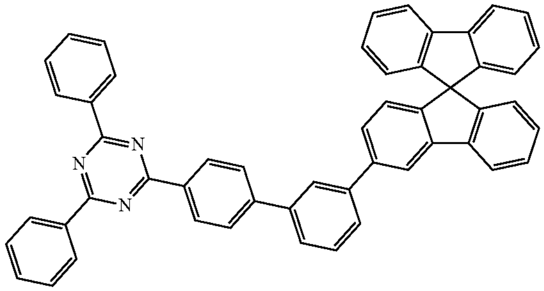
-continued
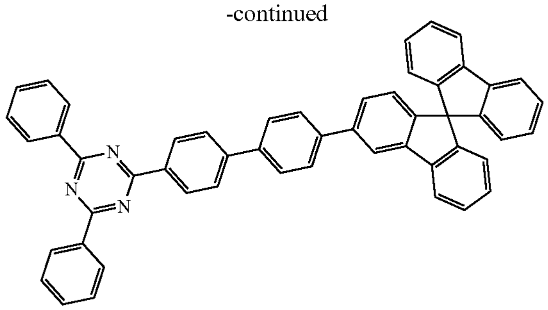
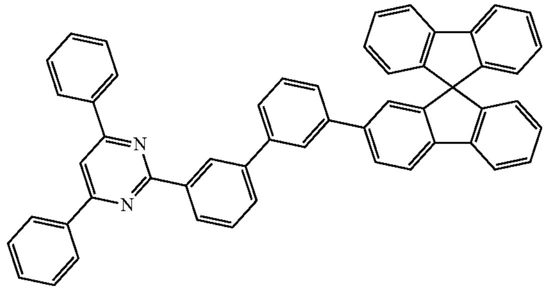
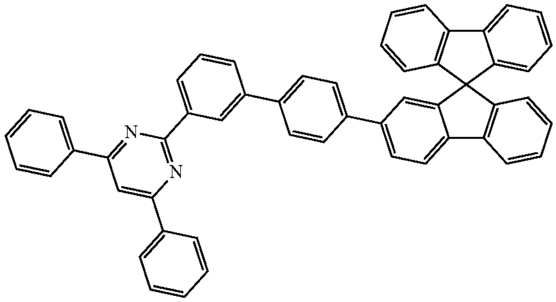
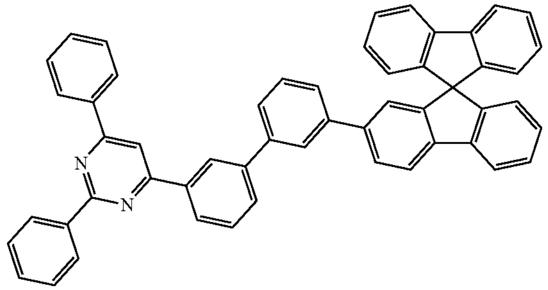
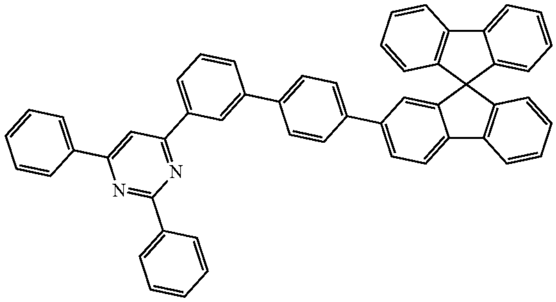

-continued
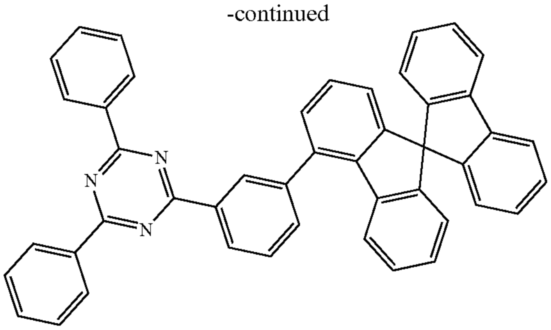
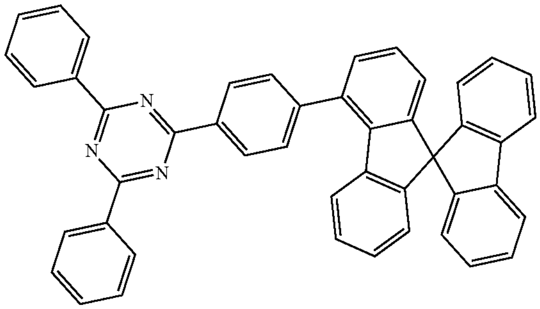
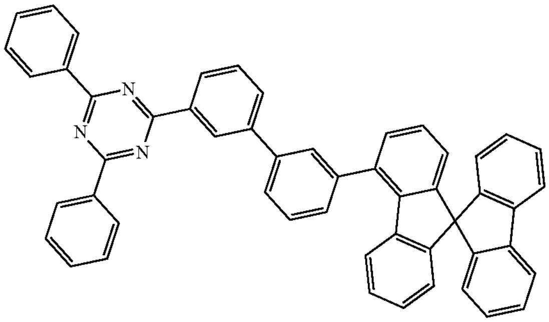
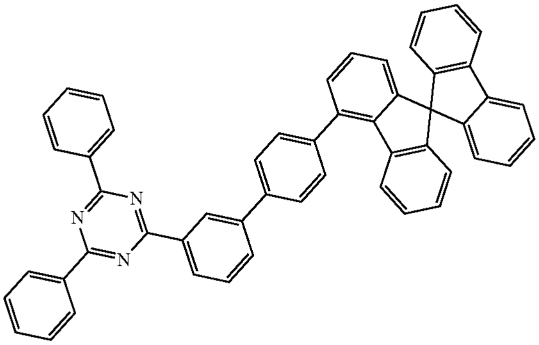
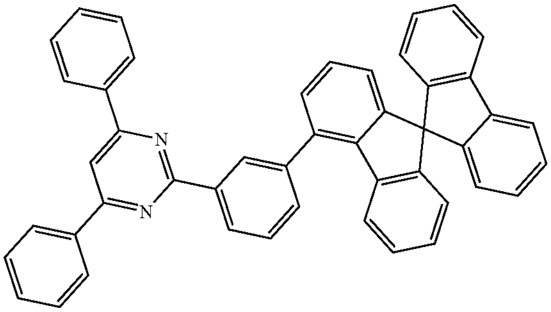
-continued
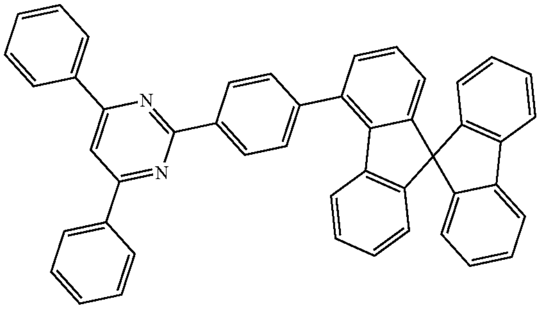
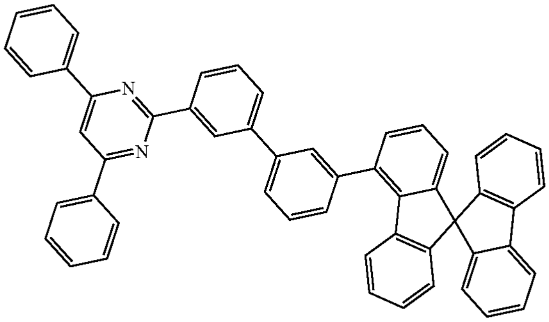
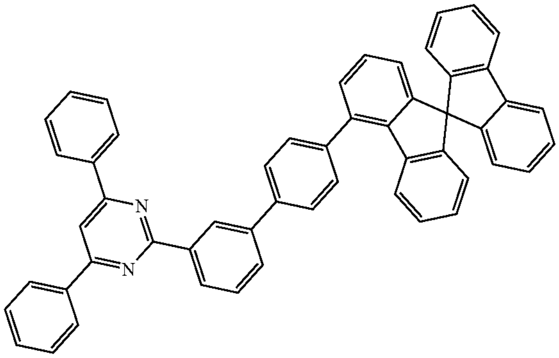
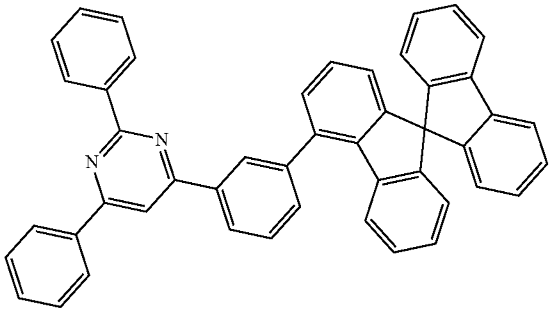
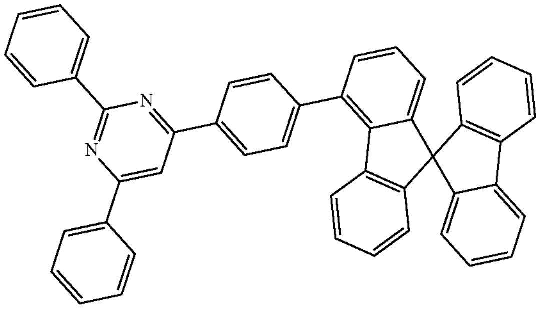

-continued
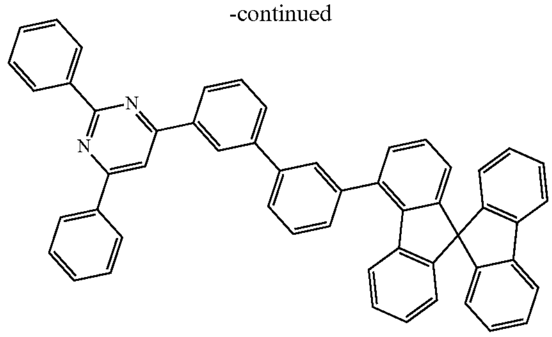
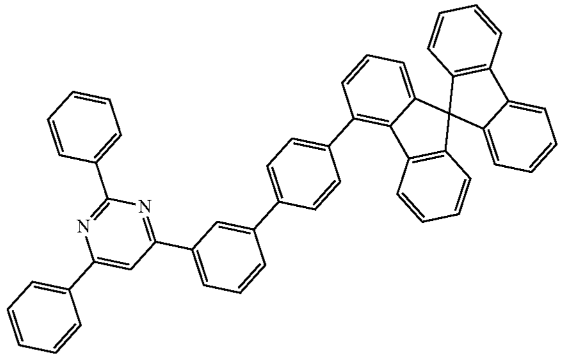
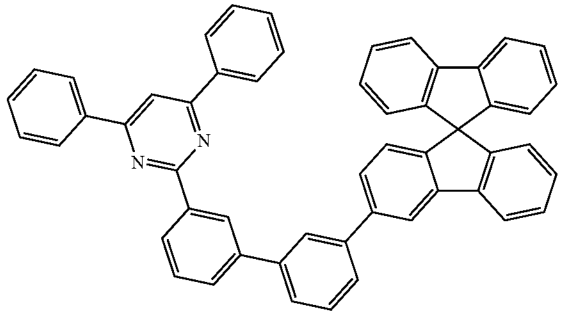
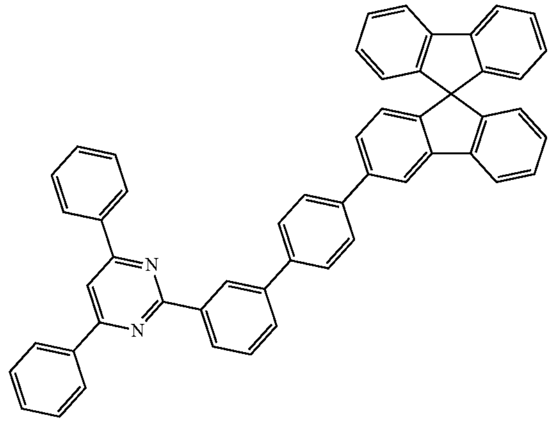
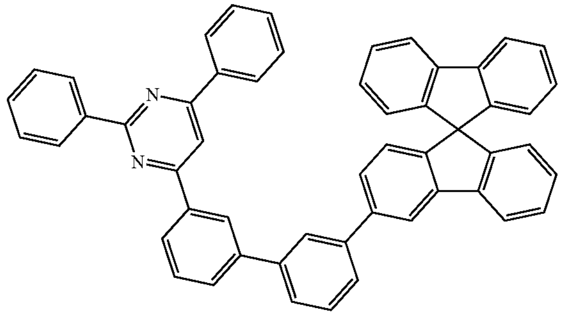
-continued
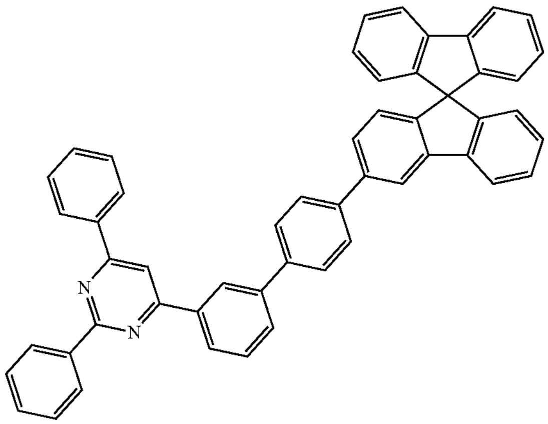
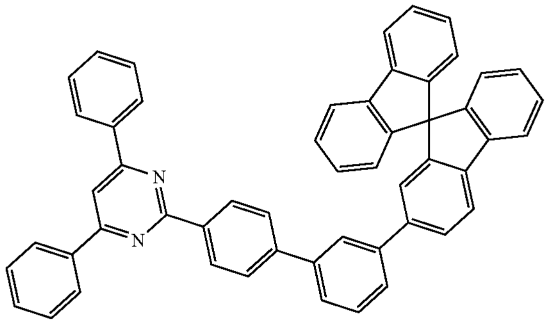
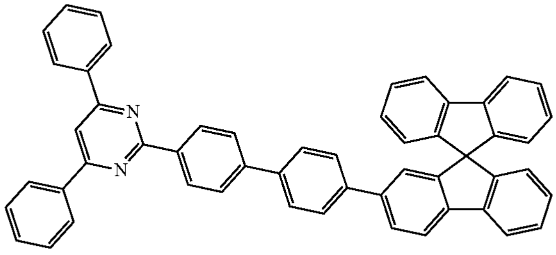
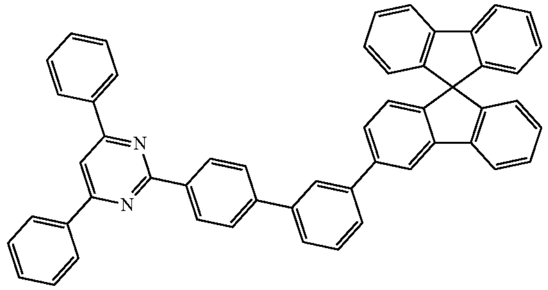
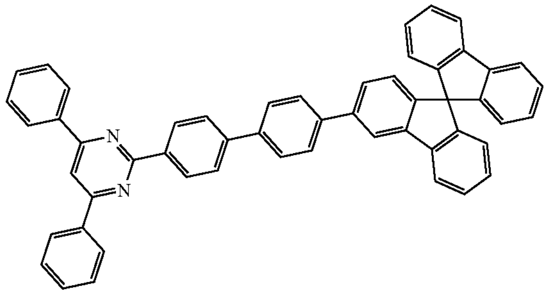

-continued
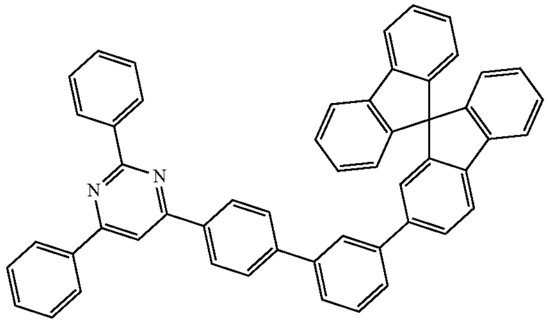
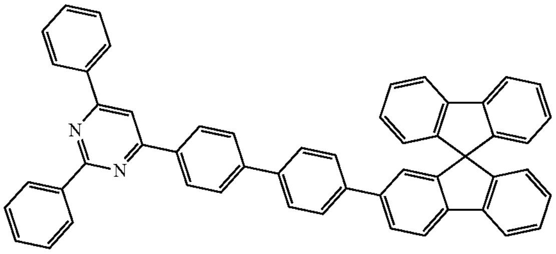
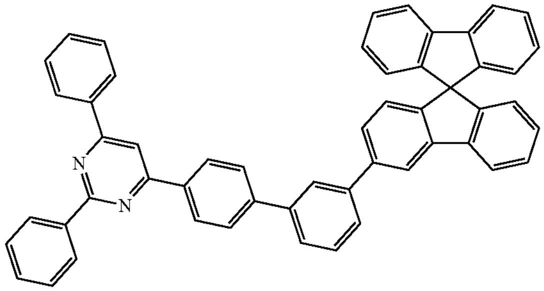
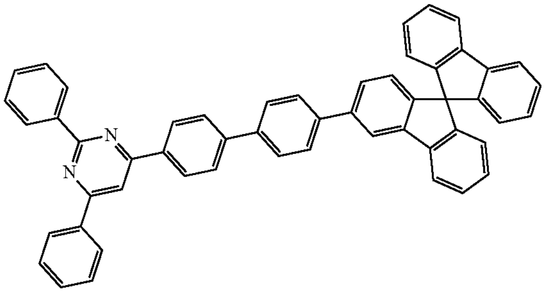
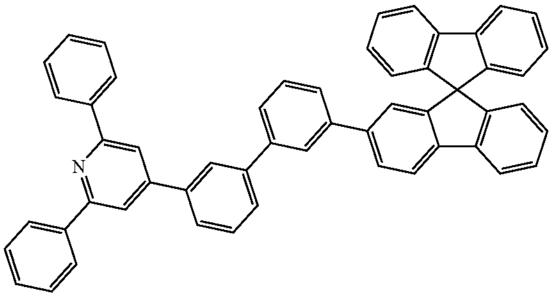
-continued
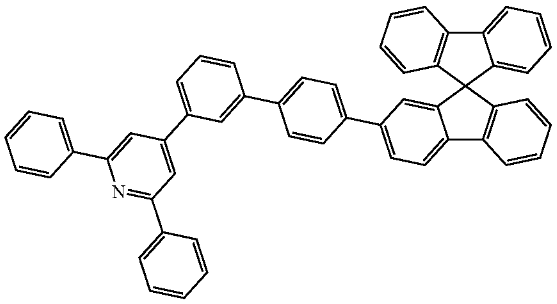
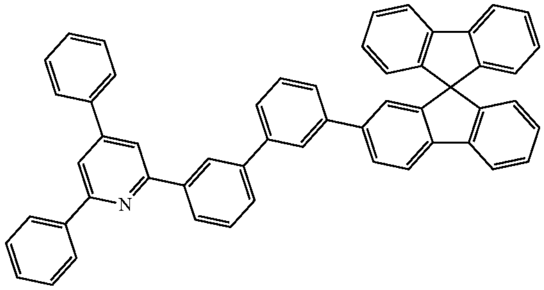
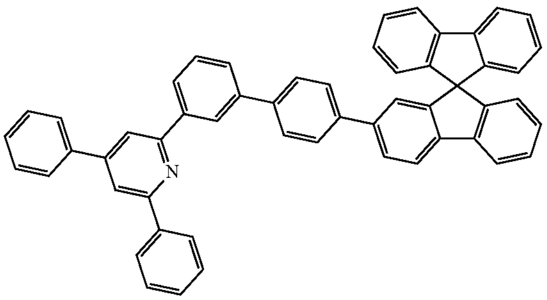
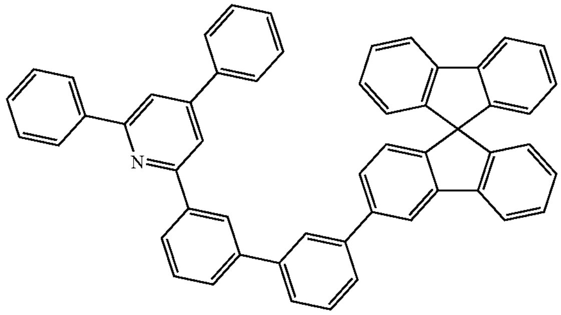
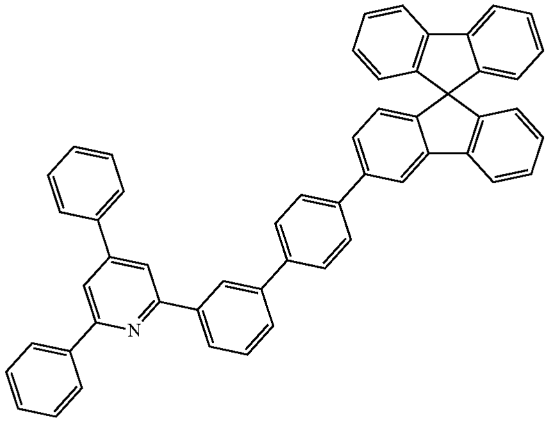

-continued
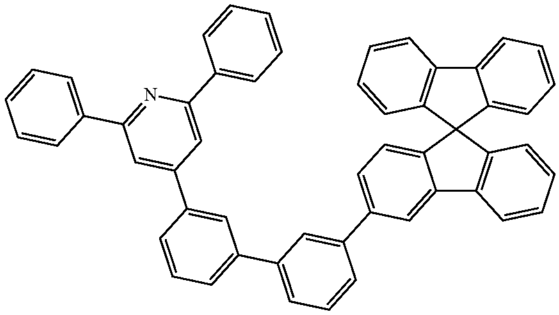
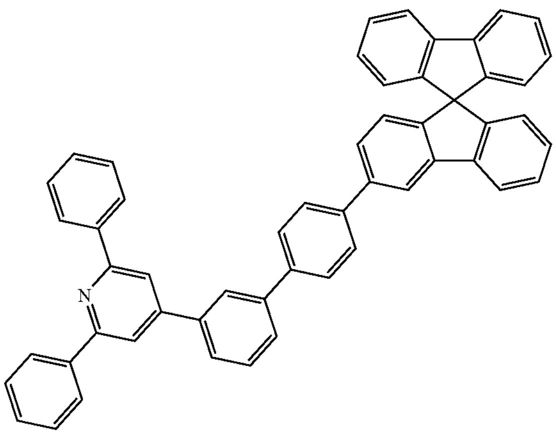
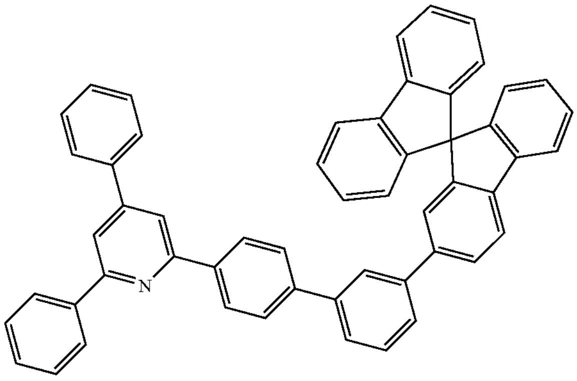
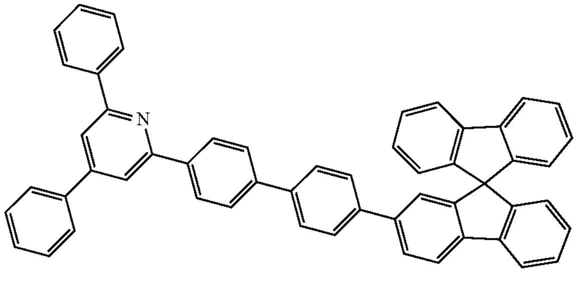
-continued
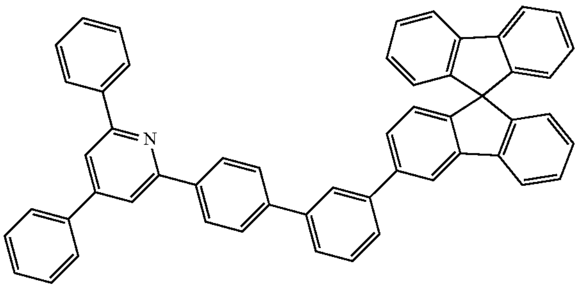
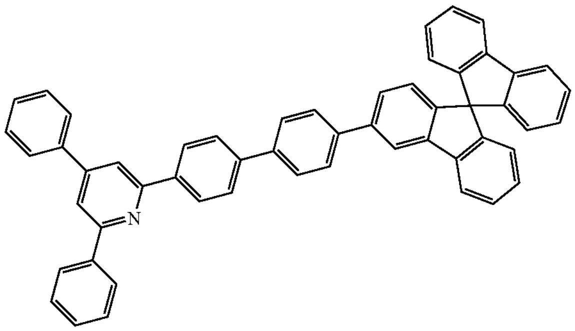
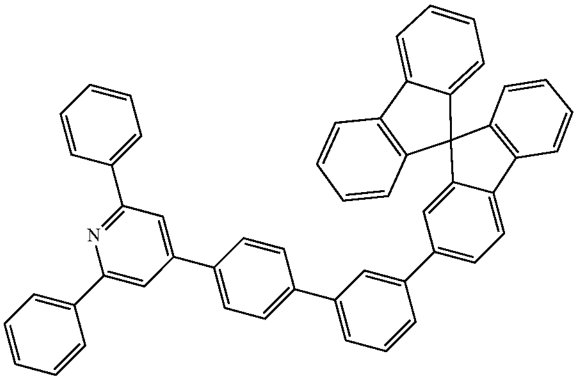
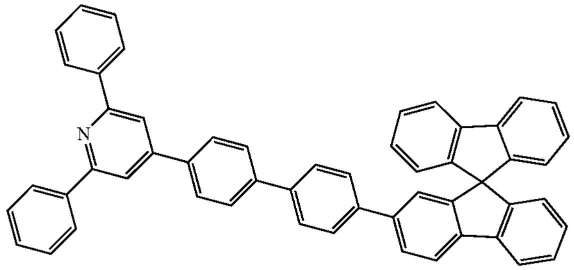
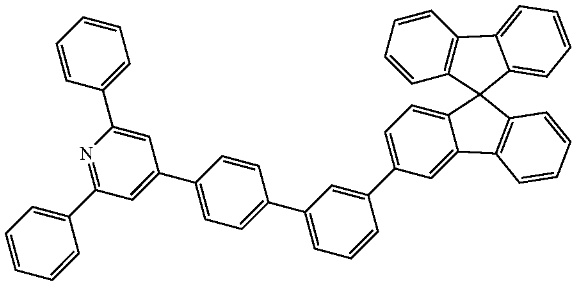

-continued
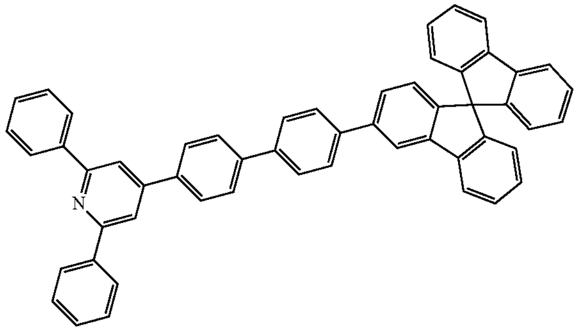
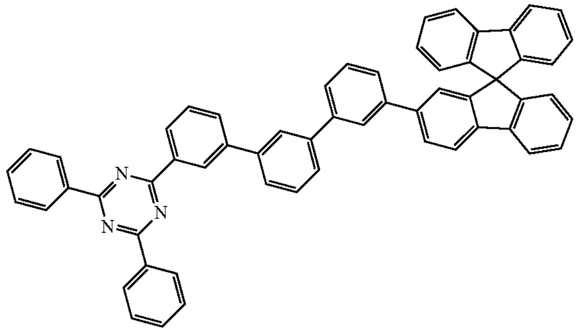
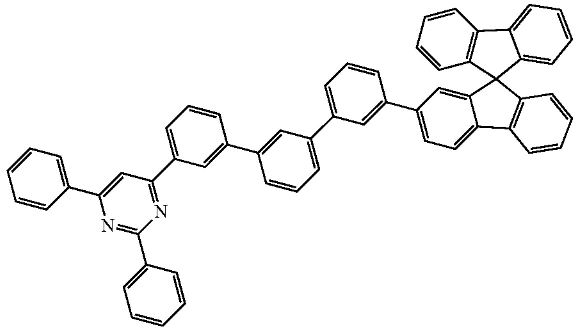
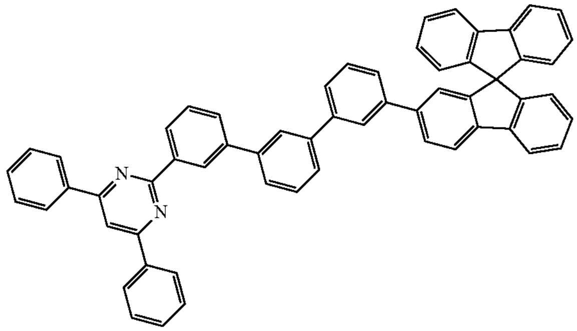
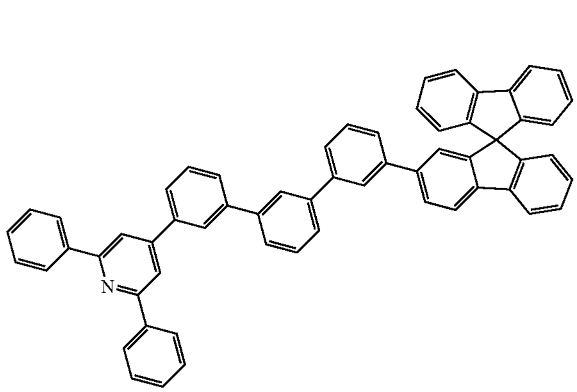
-continued
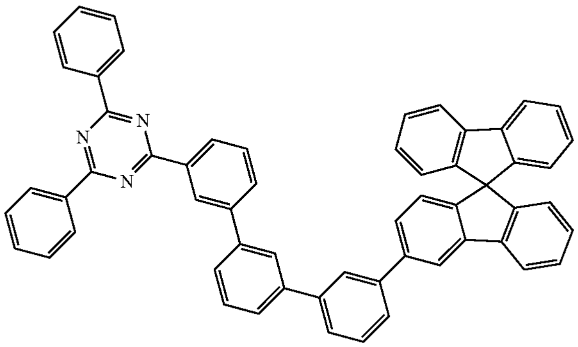
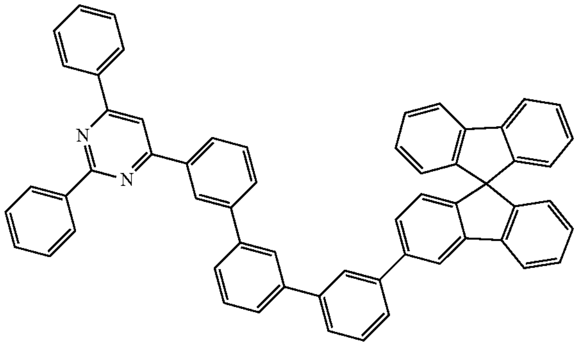
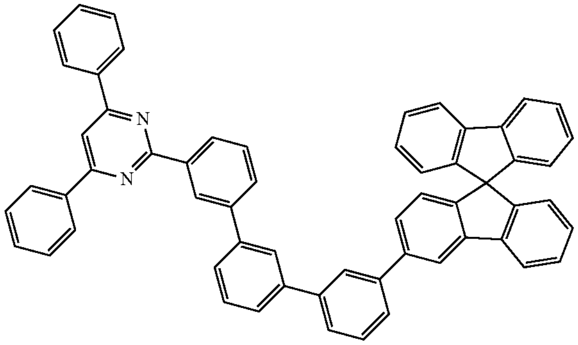
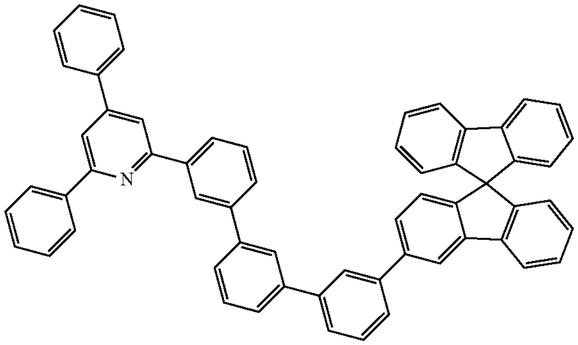
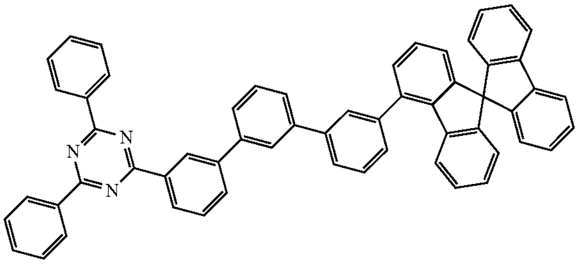

-continued
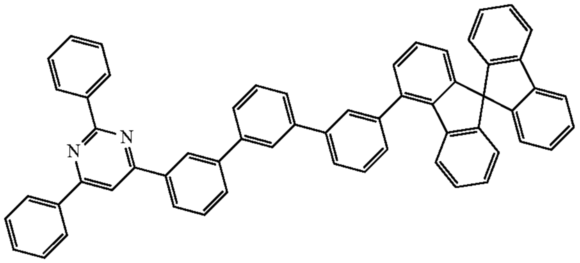
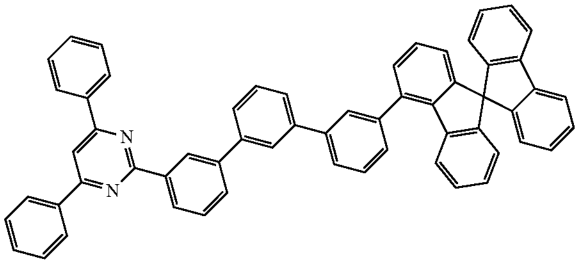
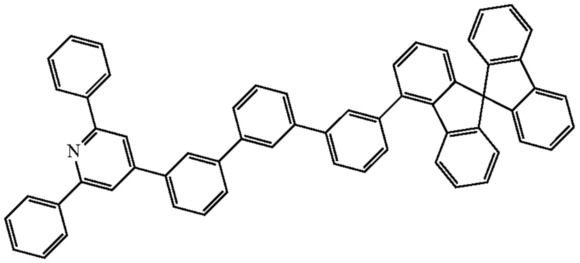
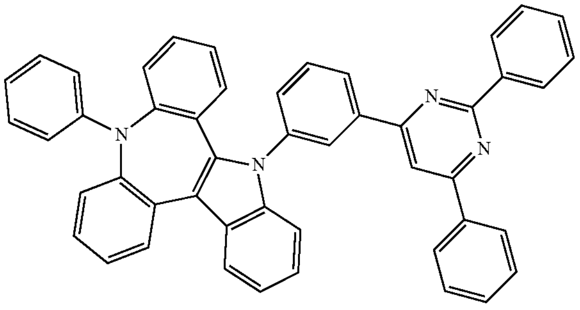
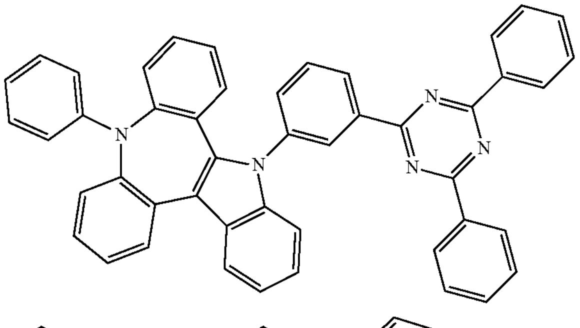
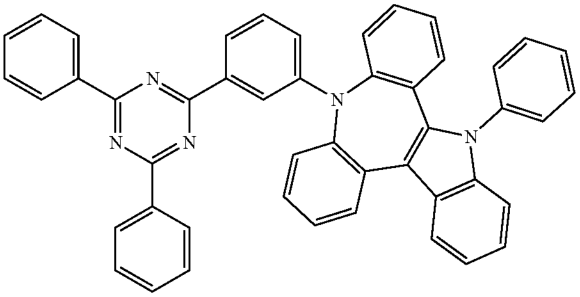
-continued
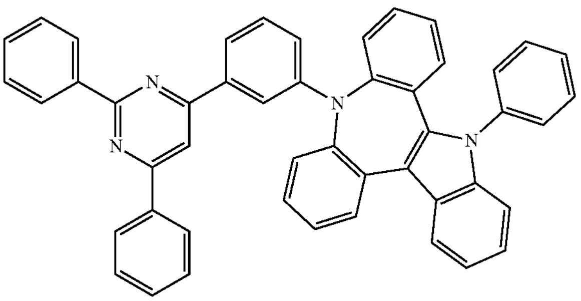
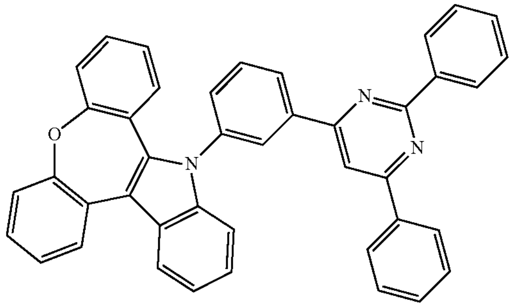
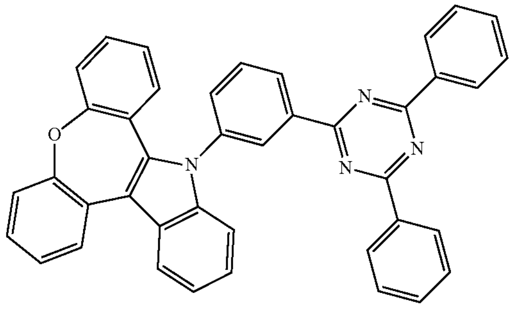
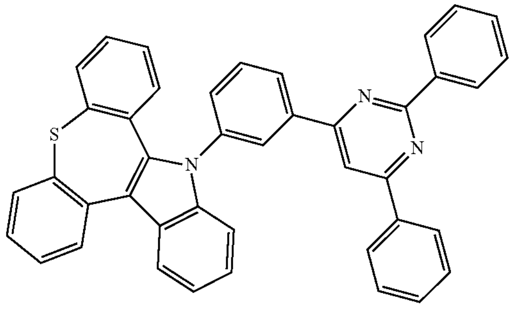
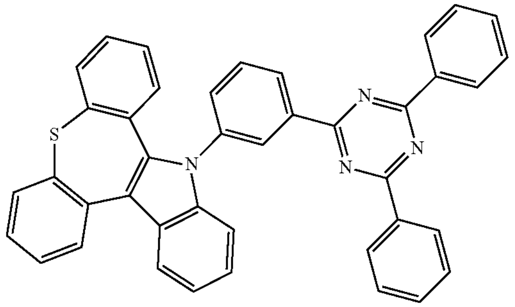

-continued
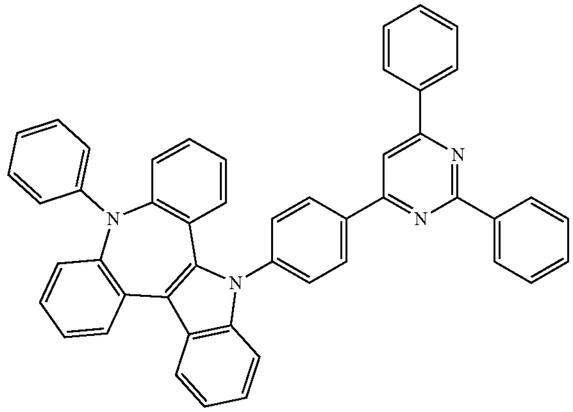
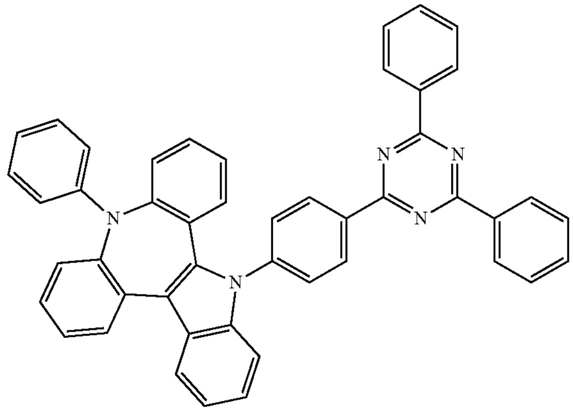
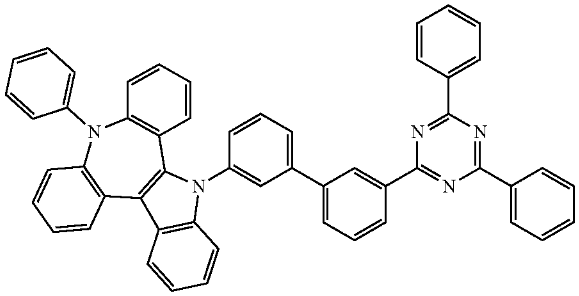
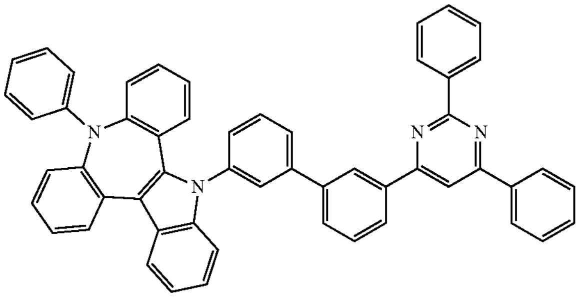
-continued
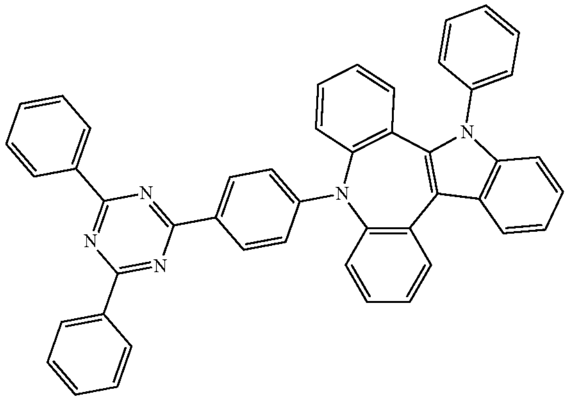
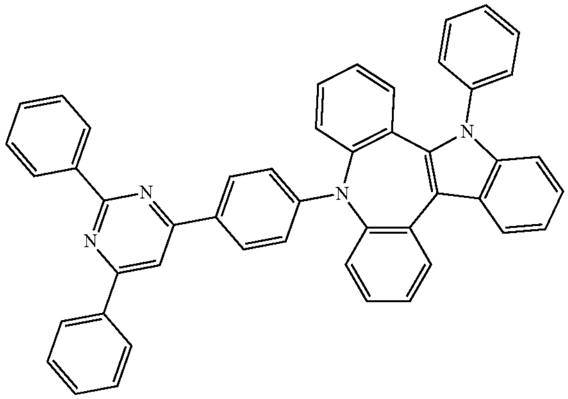
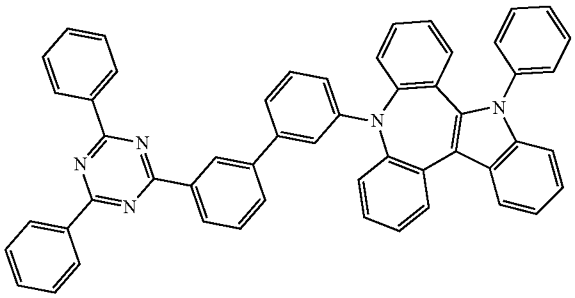
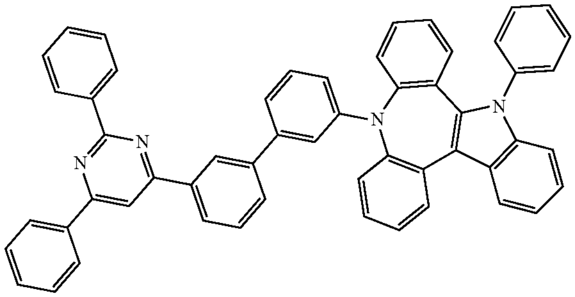

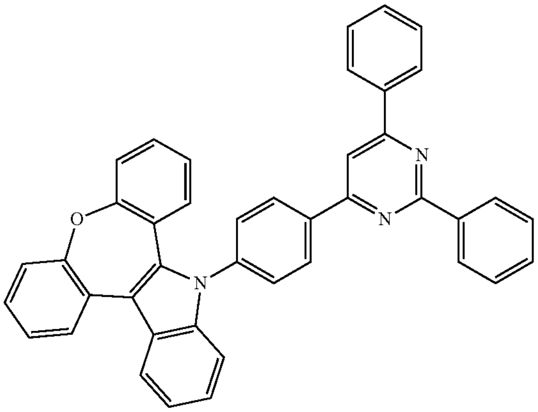
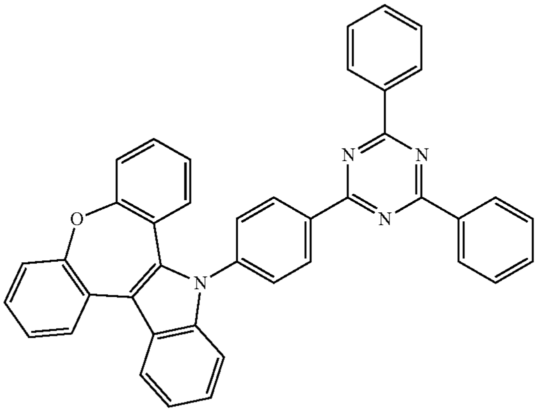
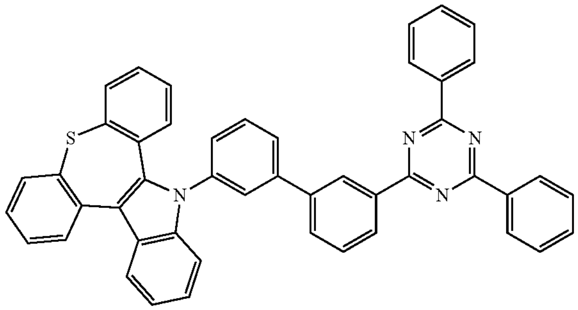
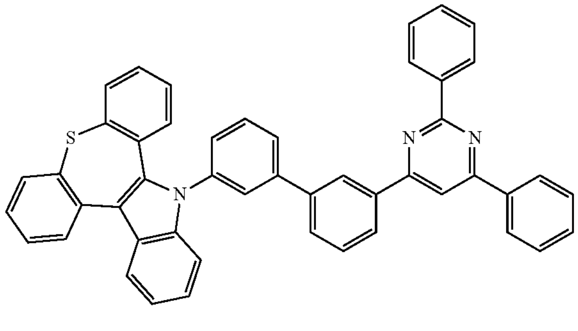
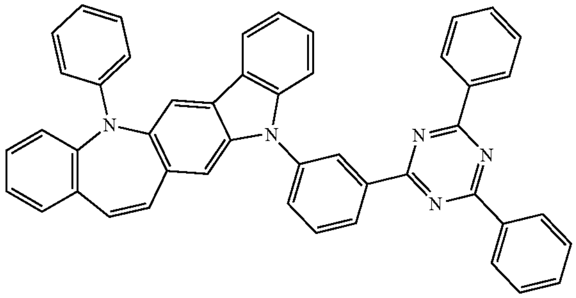
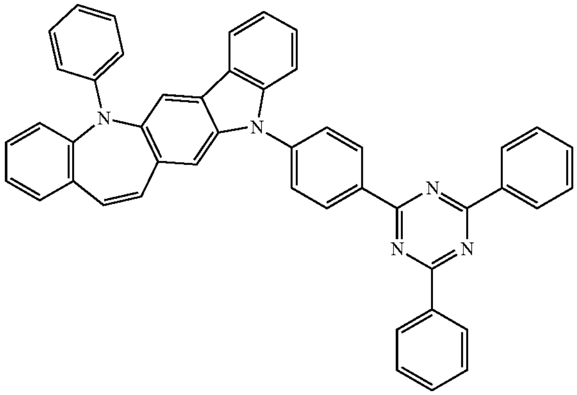
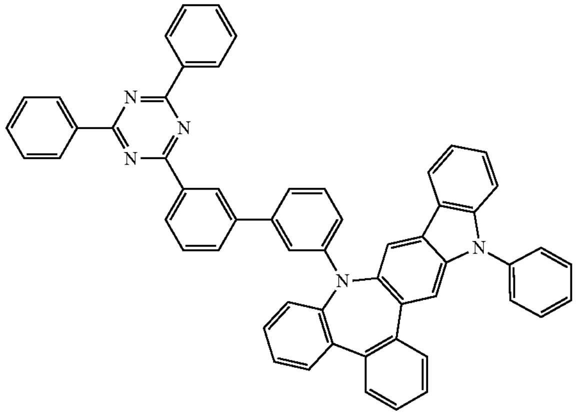
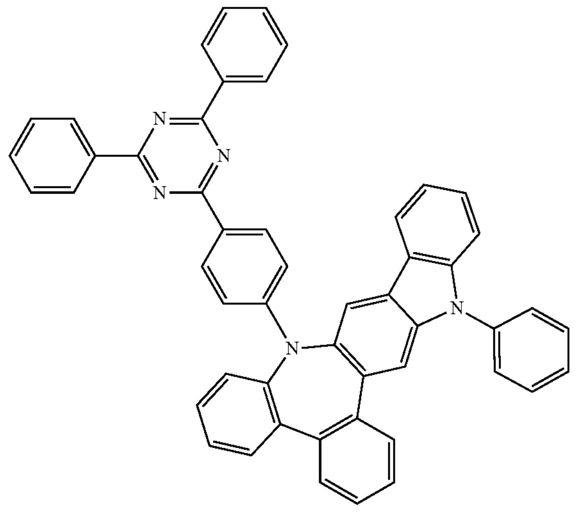

-continued

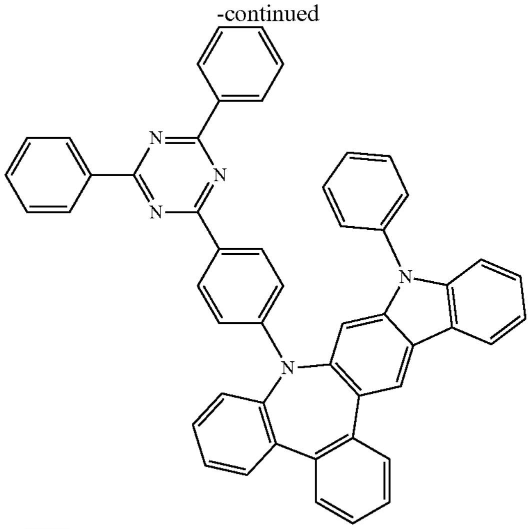

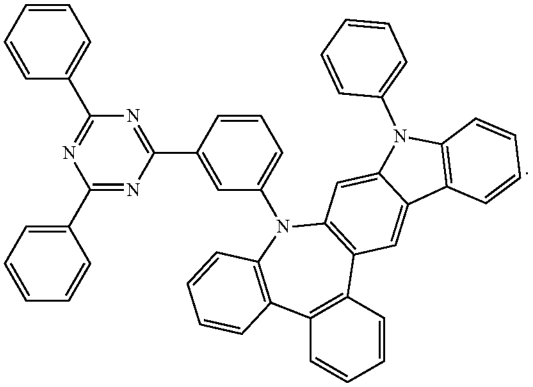

The compound of Chemical Formula 1 according to one embodiment of the present specification can have the core structure prepared as in synthesis examples to describe later. Substituents can bond using methods known in the art, and types, positions and the number of the substituents can vary depending on technologies known in the art.

The compound of Chemical Formula 2 according to one embodiment of the present specification can have the core structure prepared as in synthesis examples to describe later. Substituents can bond using methods known in the art, and types, positions and the number of the substituents can vary depending on technologies known in the art.

In the synthesis examples, processes of synthesizing compounds in which specific substituents bond to specific positions are illustrated, however, compounds corresponding to the scope of Chemical Formula 1 and the scope of Chemical Formula 2 can be synthesized using synthesis methods known in the art using starting materials, intermediate materials and the like known in the art.

In the present specification, compounds having various energy band gaps can be synthesized by introducing various substituents to the core structures of the compound of Chemical Formula 1 and the compound of Chemical Formula 2. In addition, HOMO and LUMO energy levels of the compound can also be adjusted in the present specification by introducing various substituents to the core structure having a structure as above.

In addition, one embodiment of the present specification provides an organic light emitting device including the compound of Chemical Formula 1 and the compound of Chemical Formula 2 described above.

Hereinafter, the organic light emitting device will be described.

The organic light emitting device according to the present specification includes an anode; a cathode; a light emitting layer provided between the anode and the cathode; and a first organic material layer provided between the light emitting layer and the cathode, wherein the light emitting layer includes the compound of Chemical Formula 1, and the first organic material layer includes the compound of Chemical Formula 2.

The organic light emitting device of the present specification can be manufactured using common organic light emitting device manufacturing methods and materials except that the light emitting layer is formed using the compound of Chemical Formula 1 described above, and the first organic material layer is formed using the compound of Chemical Formula 2.

The compound can be formed to an organic material layer using a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present specification can be formed in a single layer structure, but can be formed in a multilayer structure in which two or more organic material layers are laminated. For example, the organic light emitting device of the present disclosure can have a structure including one or more of a hole transfer layer, a hole injection layer, an electron blocking layer, a hole transfer and injection layer, an electron transfer layer, an electron injection layer, a hole blocking layer, and an electron transfer and injection layer as the organic material layer. However, the structure of the organic light emitting device of the present specification is not limited thereto, and can include a smaller number or a larger number of organic material layers.

In the organic light emitting device of the present specification, the first organic material layer is provided between the light emitting layer and the cathode.

In the organic light emitting device of the present specification, the first organic material layer includes an electron transfer layer or an electron injection layer, and the electron transfer layer or the electron injection layer can include the compound of Chemical Formula 2 described above.

In another organic light emitting device of the present specification, the first organic material layer includes a hole blocking layer, and the hole blocking layer can include the compound of Chemical Formula 2 described above.

According to one embodiment, the light emitting layer including the compound of Chemical Formula 1 has a thickness of 10 Å to 500 Å, and preferably 20 Å to 300 Å.

According to one embodiment, the first organic material layer including the compound of Chemical Formula 2 has a thickness of 10 Å to 500 Å, and preferably 20 Å to 100 Å.

In one embodiment of the present specification, the first organic material layer is an electron injection layer, an electron transfer layer or a hole blocking layer.

In the organic light emitting device of the present specification, the first organic material layer is a hole blocking layer.

In the organic light emitting device of the present specification, the light emitting layer can include the compound of Chemical Formula 1 as a host of the light emitting layer.

According to another embodiment, the light emitting layer can include the compound of Chemical Formula 1 as a dopant of the light emitting layer.

According to another embodiment, the light emitting layer can include two or more types of the compound of Chemical Formula 1 as a dopant of the light emitting layer.

In one embodiment of the present specification, the light emitting layer includes the compound of Chemical Formula 1 as a dopant of the light emitting layer, and can further include a host.

In one embodiment of the present specification, the light emitting layer includes the compound of Chemical Formula 1 as a dopant, and can include a fluorescent host or a phosphorescent host.

Herein, the dopant can be included in 1 parts by weight to 60 parts by weight, and is preferably included in 1 parts by weight to 10 parts by weight based on 100 parts by weight of the host. When a content of the host and a content of the dopant satisfy the above-mentioned ranges, voltage, efficiency and/or lifetime properties are improved in the organic electroluminescent device.

In one embodiment of the present specification, the light emitting layer includes an anthracene-based compound as a host.

The organic light emitting device according to one embodiment of the present specification can include an additional light emitting layer in addition to the light emitting layer including the compound of Chemical Formula 1. Herein, the additional light emitting layer includes a phosphorescent dopant or a fluorescent dopant, and includes a phosphorescent host or a fluorescent dopant. The additional light emitting layer emits red, green or blue light.

The light emitting layer can further include a host material, and the host includes fused aromatic ring derivatives, heteroring-containing compounds or the like. Specifically, anthracene derivatives, pyrene derivatives, naphthalene derivatives, pentacene derivatives, phenanthrene compounds, fluoranthene compounds or the like can be included as the fused aromatic ring derivative, and carbazole derivatives, dibenzofuran derivatives, ladder-type furan compounds, pyrimidine derivatives, triazine derivatives or the like can be included as the heteroring-containing compound, and mixtures of two or more types thereof can be included, however, the host material is not limited thereto.

According to one embodiment of the present specification, the light emitting layer includes one or more types of hosts.

According to one embodiment of the present specification, the light emitting layer includes two or more types of mixed hosts.

In one embodiment of the present specification, the light emitting layer includes the compound of Chemical Formula 1 as a dopant of the light emitting layer, and can further include a dopant.

In the organic light emitting device according to one embodiment of the present specification, the light emitting layer further includes a fluorescent dopant or a phosphorescent dopant.

Herein, as the dopant further included, phosphorescent materials such as $(4,6\text{-F2ppy})_2$Irpic, or fluorescent materials such as spiro-DPVBi, spiro-6P, distyrylbenzene (DSB), distyrylarylene (DSA), PFO-based polymers, PPV-based polymers, anthracene-based compounds, pyrene-based compounds or boron-based compounds can be used, however, the dopant further included is not limited thereto.

In another embodiment, the light emitting layer can further include other organic compounds, metals or metal compounds in addition to the compound of Chemical Formula 1.

In another embodiment, the first organic material layer can further include other organic compounds, metals or metal compounds in addition to the compound of Chemical Formula 2.

In the organic light emitting device one embodiment of the present specification, the light emitting layer has a maximum emission peak at 400 nm to 500 nm.

According to one embodiment, the first organic material layer is provided to be in contact with the light emitting layer. Herein, the meaning of being in contact is that no other organic material layers are present between the first organic material layer and the light emitting layer.

The organic light emitting device of the present specification can further include one or more organic material layers of a hole transfer layer, a hole injection layer, an electron blocking layer, an electron transfer and injection layer, an electron transfer layer, an electron injection layer, a hole blocking layer, and a hole transfer and injection layer.

The organic light emitting device the present specification can further include one or more organic material layers of a hole transfer layer, a hole injection layer, an electron blocking layer, a light emitting layer, an electron transfer and injection layer, an electron transfer layer, an electron injection layer, a hole blocking layer, and a hole transfer and injection layer.

The organic light emitting device of the present specification can further include two or more organic material layers of a hole transfer layer, a hole injection layer, an electron blocking layer, a light emitting layer, an electron transfer and injection layer, an electron transfer layer, an electron injection layer, a hole blocking layer, and a hole transfer and injection layer.

In one embodiment of the present specification, as the two or more organic material layers, two or more can be selected from the group consisting of a light emitting layer, a hole transfer layer, a hole injection layer, a hole transfer and injection layer, and an electron blocking layer.

In one embodiment of the present specification, as the two or more organic material layers, two or more can be selected from the group consisting of a light emitting layer, an electron transfer layer, an electron injection layer, an electron transfer and injection layer, an electron control layer and a hole blocking layer.

In one embodiment of the present specification, the organic material layer includes two or more light emitting layers, and at least one of the two or more light emitting layers includes the compound of Chemical Formula 1. Specifically, in one embodiment of the present specification, the compound of Chemical Formula 1 can be included in one of the two or more light emitting layers, or can be included in each of the two or more light emitting layers.

In addition, in one embodiment of the present specification, when the compound of Chemical Formula 1 is included in each of the two or more light emitting layers, materials other than the compound of Chemical Formula 1 can be the same as or different from each other.

In one embodiment of the present specification, the organic material layer includes two or more electron transfer layers, and at least one of the two or more electron transfer layers includes the compound of Chemical Formula 2. Specifically, in one embodiment of the present specification, the compound of Chemical Formula 2 can be included in one of the two or more electron transfer layers, or can be included in each of the two or more electron transfer layers.

In addition, in one embodiment of the present specification, when the compound of Chemical Formula 2 is included in each of the two or more electron transfer layers, materials other than the compound of Chemical Formula 2 can be the same as or different from each other.

The first organic material layer including the compound of Chemical Formula 2 can further include an n-type dopant. As the n-type dopant, those known in the art can be used, and for example, metals or metal complexes can be used. For example, the first organic material layer including the compound of Chemical Formula 2 can further include lithium quinolate (LiQ). According to one embodiment, the compound of Chemical Formula 2 and the n-type dopant can be included in a weight ratio of 2:8 to 8:2, and for example, 4:6 to 6:4. According to one embodiment, the compound of Chemical Formula 2 and the n-type dopant can be included in a weight ratio of 1:1.

In one embodiment of the present specification, the organic light emitting device can be an organic light emitting device having a structure in which an anode, one or more organic material layers and a cathode are consecutively laminated on a substrate (normal type).

In one embodiment of the present specification, the organic light emitting device can be an organic light emitting device having a structure in a reverse direction in which a cathode, one or more organic material layers and an anode are consecutively laminated on a substrate (inverted type).

In the organic light emitting device of the present disclosure, the organic material layer can include an electron blocking layer, and as the electron blocking layer, materials known in the art can be used.

The organic light emitting device can have, for example, lamination structures as below, however, the structure is not limited thereto.

(1) an anode/a hole transfer layer/a light emitting layer/a cathode
(2) an anode/a hole injection layer/a hole transfer layer/a light emitting layer/a cathode
(3) an anode/a hole injection layer/a hole buffer layer/a hole transfer layer/a light emitting layer/a cathode
(4) an anode/a hole transfer layer/a light emitting layer/an electron transfer layer/a cathode
(5) an anode/a hole transfer layer/a light emitting layer/an electron transfer layer/an electron injection layer/a cathode
(6) an anode/a hole injection layer/a hole transfer layer/a light emitting layer/an electron transfer layer/a cathode
(7) an anode/a hole injection layer/a hole transfer layer/a light emitting layer/an electron transfer layer/an electron injection layer/a cathode
(8) an anode/a hole injection layer/a hole buffer layer/a hole transfer layer/a light emitting layer/an electron transfer layer/a cathode
(9) an anode/a hole injection layer/a hole buffer layer/a hole transfer layer/a light emitting layer/an electron transfer layer/an electron injection layer/a cathode
(10) an anode/a hole transfer layer/an electron blocking layer/a light emitting layer/an electron transfer layer/a cathode
(11) an anode/a hole transfer layer/an electron blocking layer/a light emitting layer/an electron transfer layer/an electron injection layer/a cathode
(12) an anode/a hole injection layer/a hole transfer layer/an electron blocking layer/a light emitting layer/an electron transfer layer/a cathode
(13) an anode/a hole injection layer/a hole transfer layer/an electron blocking layer/a light emitting layer/an electron transfer layer/an electron injection layer/a cathode
(14) an anode/a hole transfer layer/a light emitting layer/a hole blocking layer/an electron transfer layer/a cathode
(15) an anode/a hole transfer layer/a light emitting layer/a hole blocking layer/an electron transfer layer/an electron injection layer/a cathode
(16) an anode/a hole injection layer/a hole transfer layer/a light emitting layer/a hole blocking layer/an electron transfer layer/a cathode
(17) an anode/a hole injection layer/a hole transfer layer/a light emitting layer/a hole blocking layer/an electron transfer layer/an electron injection layer/a cathode The organic light emitting device of the present specification can have structures as illustrated in FIG. 1 and FIG. 2, however, the structure is not limited thereto.

FIG. 1 illustrates a structure of the organic light emitting device in which a substrate (1), an anode (2), a light emitting layer (6), an electron blocking layer (7) and a cathode (9) are consecutively laminated. In such a structure, the compound of Chemical Formula 1 can be included in the light emitting layer (6), and the compound of Chemical Formula 2 can be included in the electron blocking layer (7).

FIG. 2 illustrates a structure of the organic light emitting device in which a substrate (1), an anode (2), a hole injection layer (3), a first hole transfer layer (4), a second hole transfer layer (5), a light emitting layer (6), a hole blocking layer (7), an electron transfer and injection layer (8) and a cathode (9) are consecutively laminated. In such a structure, the compound of Chemical Formula 1 can be included in the light emitting layer (6), and the compound of Chemical Formula 2 can be included in the hole blocking layer (7) or the electron transfer and injection layer (8).

In one embodiment of the present specification, the first organic material layer and the light emitting layer can be provided adjacently. For example, the first organic material layer and the light emitting layer can be provided to be physically in contact with each other.

When the organic light emitting device includes a plurality of organic material layers, the organic material layers can be formed with materials the same as or different from each other.

The organic material layer can further include one or more layers of a hole transfer layer, a hole injection layer, an electron blocking layer, an electron transfer and injection layer, an electron transfer layer, an electron injection layer, a hole blocking layer, and a hole transfer and injection layer.

The organic material layer can have a multilayer structure including a hole injection layer, a hole transfer layer, a hole injection and transfer layer, an electron blocking layer, a light emitting layer, an electron transfer layer, an electron injection layer, an electron transfer and injection layer and the like, but is not limited thereto, and can have a single layer structure. In addition, using various polymer materials, the organic material layer can be prepared to a smaller number of layers using a solvent process instead of a deposition method, for example, spin coating, dip coating, doctor blading, screen printing, inkjet printing, a thermal transfer method or the like.

The anode is an electrode that injects holes, and as the anode material, materials having large work function are normally preferred so that hole injection to an organic material layer is smooth. Specific examples of the anode material usable in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, but are not limited thereto.

The cathode is an electrode that injects electrons, and as the cathode material, materials having small work function are normally preferred so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

The hole injection layer is a layer performing a role of smoothly injecting holes from an anode to a light emitting layer. The hole injection material is a material capable of favorably receiving holes from an anode at a low voltage, and the highest occupied molecular orbital (HOMO) of the hole injection material is preferably in between the work function of the anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto. The hole injection layer can have a thickness of 1 nm to 150 nm. The hole injection layer having a thickness of 1 nm or greater has an advantage of preventing hole injection properties from declining, and the thickness being 150 nm or less has an advantage of preventing a driving voltage from increasing to enhance hole migration caused by the hole injection layer being too thick.

The hole transfer layer can perform a role of smoothly transferring holes. As the hole transfer material, materials capable of receiving holes from an anode or a hole injection layer, moving the holes to a light emitting layer, and having high mobility for the holes are suited. Specific examples thereof include arylamine-based organic materials, conductive polymers, block copolymers having conjugated parts and non-conjugated parts together, and the like, but are not limited thereto.

A hole buffer layer can be further provided between the hole injection layer and the hole transfer layer, and can include hole injection or transfer materials known in the art.

An electron blocking layer can be provided between the hole transfer layer and the light emitting layer. As the electron blocking layer, the compounds described above, or materials known in the art can be used.

The light emitting layer can emit red, green or blue light, and can be formed with a phosphorescent material or a fluorescent material. The light emitting material is a material capable of emitting light in a visible region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq3); carbazole-based compounds; dimerized styryl compounds; BAlq; 10-hydroxybenzoquinoline-metal compounds; benzoxazole-, benzothiazole- and benzimidazole-based compounds; poly(p-phenylenevinylene) (PPV)-based polymers; spiro compounds; polyfluorene, rubrene, and the like, but are not limited thereto.

As the host material of the light emitting layer, fused aromatic ring derivatives, heteroring-containing compounds or the like can be included. Specifically, anthracene derivatives, pyrene derivatives, naphthalene derivatives, pentacene derivatives, phenanthrene compounds, fluoranthene compounds or the like can be included as the fused aromatic ring derivative, and carbazole derivatives, dibenzofuran derivatives, ladder-type furan compounds, pyrimidine derivatives or the like can be included as the heteroring-containing compound, however, the host material is not limited thereto.

When the light emitting layer emits red light, phosphorescent materials such as bis(1-phenylisoquinoline)acetylacetonate iridium (PIQIr(acac)), bis(1-phenylquinoline)acetylacetonate iridium (PQIr(acac)), tris(1-phenylquinoline) iridium (PQIr) or octaethylporphyrin platinum (PtOEP), or fluorescent materials such as tris(8-hydroxyquinolino)aluminum (Alq3) can be used as the light emitting dopant, however, the light emitting dopant is not limited thereto. When the light emitting layer emits green light, phosphorescent materials such as fac-tris(2-phenylpyridine)iridium ($Ir(ppy)_3$), or fluorescent materials such as tris(8-hydroxyquinolino)aluminum (Alq3), anthracene-based compounds, pyrene-based compounds or boron-based compounds can be used as the light emitting dopant, however, the light emitting dopant is not limited thereto. When the light emitting layer emits blue light, phosphorescent materials such as $(4,6\text{-}F2ppy)_2Irpic$, or fluorescent materials such as spiro-DPVBi, spiro-6P, distyrylbenzene (DSB), distyrylarylene (DSA), PFO-based polymers, PPV-based polymers, anthracene-based compounds, pyrene-based compounds or boron-based compounds can be used as the light emitting dopant, however, the light emitting dopant is not limited thereto.

A hole blocking layer can be provided between the electron transfer layer and the light emitting layer, and materials known in the art can be used.

The electron transfer layer can perform a role of smoothly transferring electrons. As the electron transfer material, materials capable of favorably receiving electrons from a cathode, moving the electrons to a light emitting layer, and having high mobility for the electrons are suited. Specific examples thereof include the compounds described above, Al complexes of 8-hydroxyquinoline; complexes including $Alq_3$; organic radical compounds; hydroxyflavon-metal complexes, and the like, but are not limited thereto. The electron transfer layer can have a thickness of 1 nm to 50 nm. The electron transfer layer having a thickness of 1 nm or greater has an advantage of preventing electron transfer properties from declining, and the thickness being 50 nm or less has an advantage of preventing a driving voltage from increasing to enhance electron migration caused by the electron transfer layer being too thick.

The electron injection layer can perform a role of smoothly injecting electrons. As the electron injection material, compounds having an electron transferring ability, having an electron injection effect from a cathode, having an excellent electron injection effect for a light emitting layer or light emitting material, and preventing excitons generated in the light emitting layer from moving to a hole injection layer, and in addition thereto, having an excellent thin film forming ability are preferred. Specific examples thereof can include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxy-quinolinato)copper, bis(8-hydroxyquinolinato)manganese, tris(8-hydroxyquinolinato)aluminum, tris(2-methyl-8-hydroxy-quinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)-chlorogallium, bis(2-methyl-8-quinolinato) (o-cresolato)-gallium, bis(2-methyl-8-quinolinato) (1-naphtholato)aluminum, bis(2-methyl-8-quinolinato) (2-naphtholato)gallium and the like, but is not limited thereto.

The hole blocking layer is a layer blocking holes from reaching a cathode, and can be generally formed under the same condition as the hole injection layer. Specific examples thereof can include oxadiazole derivatives, triazole derivatives, phenanthroline derivatives, BCP, aluminum complexes and the like, but are not limited thereto.

The organic light emitting device according to the present disclosure can be a top-emission type, a bottom-emission type or a dual-emission type depending on the materials used.

EXAMPLES

Hereinafter, the present specification will be described in detail with reference to examples. However, the examples according to the present specification can be modified to various other forms, and the scope of the present application is not to be construed as being limited to the examples described below. The examples of the present application are provided in order to more fully describe the present specification to those having average knowledge in the art.

SYNTHESIS EXAMPLE

Synthesis Example 1. Synthesis of Compound A-2-1

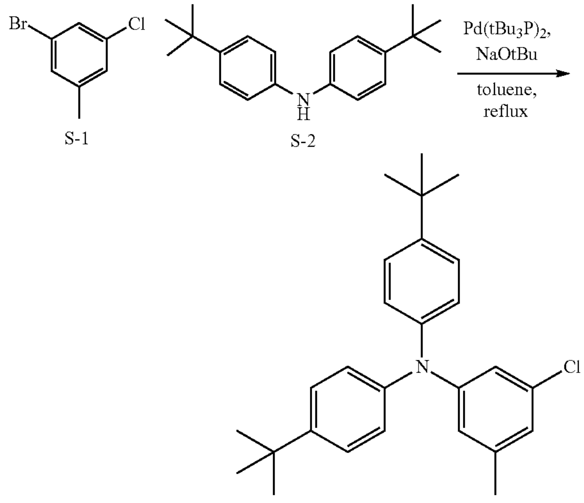

S-1 S-2

A-2-1

After dissolving 1-bromo-3-chloro-5-methylbenzene (146 mmol, 30 g, 1 eq.) and bis(4-(tert-butyl)phenyl)amine (146 mmol, 41.1 g, 1 eq.) in toluene (0.2 M, 730 ml) in a 3-neck flask, sodium tert-butoxide (219 mmol, 21 g, 1.5 eq.) and bis(tri-tert-butylphosphine) palladium (0) (1.46 mmol, 0.75 g, 0.01 eq.) were introduced thereto, and the result was stirred for 1 hour under reflux under an argon atmosphere. When the reaction was finished, the result was cooled to room temperature, then distilled water was introduced thereto, and the reaction solution was transferred to a separatory funnel and extracted. The extract was dried with $MgSO_4$ and concentrated, and the sample was purified using silica gel column chromatography to obtain Compound A-2-1 (49 g, yield 83%, MS [M+H]+=405).

Synthesis Example 2. Synthesis of Compound A-2-2

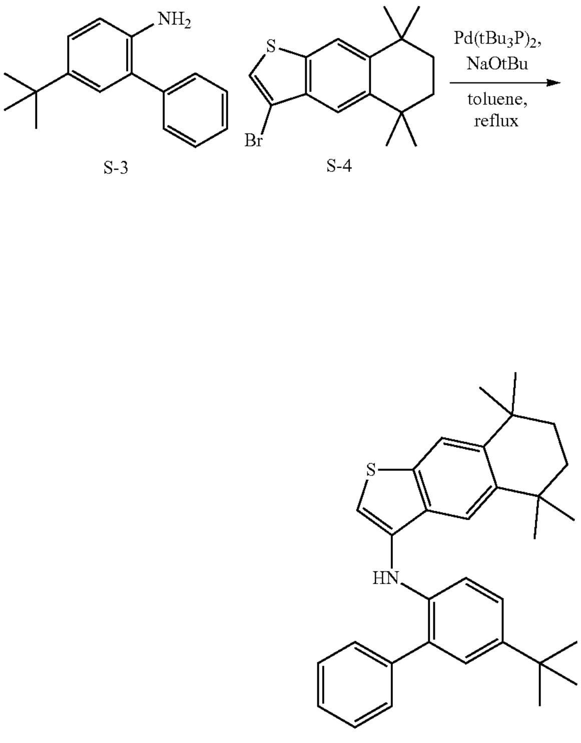

S-3 S-4

A-2-2

After dissolving 5-tert-butyl-[1,1'-biphenyl]-2-amine (66.6 mmol, 15 g, 1 eq.) and 3-bromo-5,5,8,8-tetramethyl-5,6,7,8-tetrahydronaphtho[2,3-b]thiophene (66.6 mmol, 21.5 g, 1 eq.) in toluene (0.2 M, 335 ml) in a 3-neck flask, sodium tert-butoxide (99.9 mmol, 9.60 g, 1.5 eq.) and bis(tri-tert-butylphosphine)palladium(0) (0.666 mmol, 0.340 g, 0.01 eq.) were introduced thereto, and the result was stirred for 12 hours under reflux under an argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound A-2-2 (24.2 g, yield 78%, MS[M+H]+=468).

Synthesis Example 3. Synthesis of Compound A-2-3

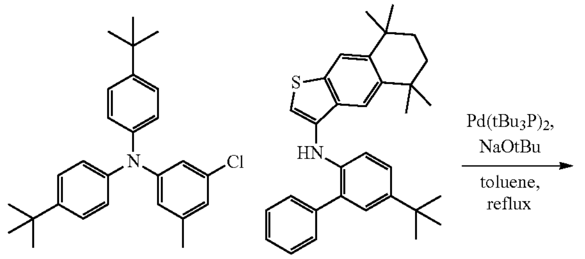

A-2-1

A-2-2

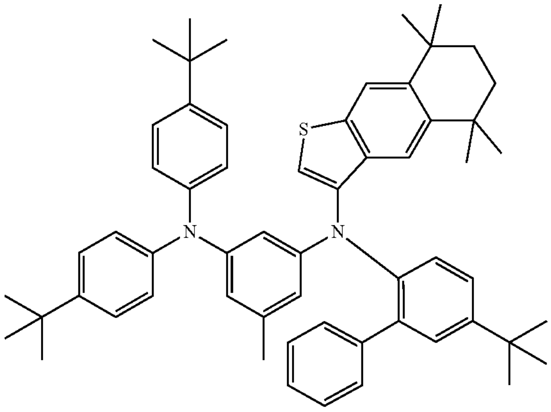

A-2-3

After dissolving Compound A-2-1 (49.3 mmol, 20 g, 1 eq.) and Compound A-2-2 (49.3 mmol, 23.0 g, 1 eq.) in toluene (0.2 M, 250 ml) in a 3-neck flask, sodium tert-butoxide (73.9 mmol, 7.10 g, 1.5 eq.) and bis(tri-tert-butylphosphine)palladium(0) (0.493 mmol, 0.252 g, 0.01 eq.) were introduced thereto, and the result was stirred for 12 hours under reflux under an argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound A-2-3 (36.1 g, yield 88%, MS[M+H]+=837).

Synthesis Example 4. Synthesis of Compound A-2

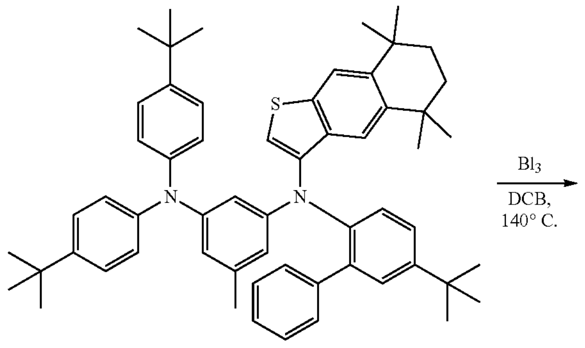

A-2-3

-continued

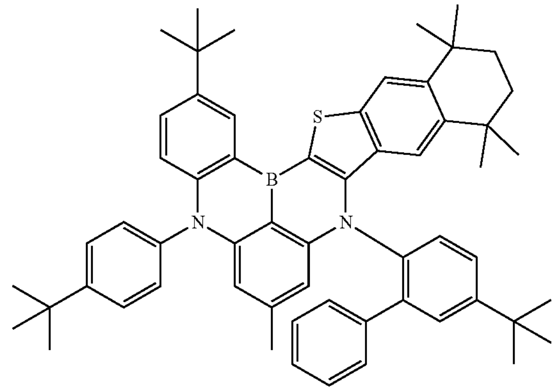

A-2

After dissolving Compound A-2-3 (43.1 mmol, 36.1 g, 1 eq.) in 1,2-dichlorobenzene (0.1 M, 430 ml) in a 3-neck flask, boron triiodide (69.0 mmol, 27.0 g, 1.6 eq.) was introduced thereto, and the result was stirred for 3 hours at 140° C. under an argon atmosphere. The reaction material was cooled to 0° C., and after adding N,N-diisopropylethylamine (388 mmol, 50.2 g, 9 eq.) thereto, the result was stirred for 1 hour. The result was extracted in a separatory funnel using toluene and $H_2O$. The extract was dried with $MgSO_4$ and concentrated, and the sample was purified using silica gel column chromatography and then went through sublimation purification to obtain Compound A-2 (7.1 g, yield 19%, MS[M+H]+=603).

Synthesis Example 5. Synthesis of Compound A-18-1

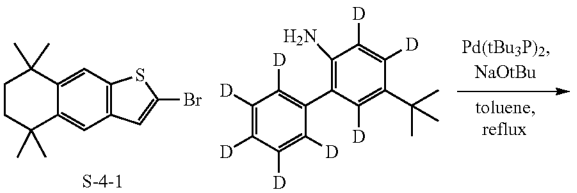

S-4-1

S-5

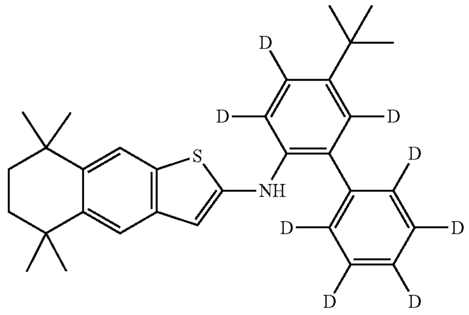

A-18-1

Compound A-18-1 (18.2 g, yield 95%, MS[M+H]+=476) was obtained in the same manner as in Synthesis Example 2 except that Compounds 5-4-1 (13 g, 1 eq.) and S-5 were used instead of Compounds S-3 and S-4.

Synthesis Example 6. Synthesis of Compound A-18-2

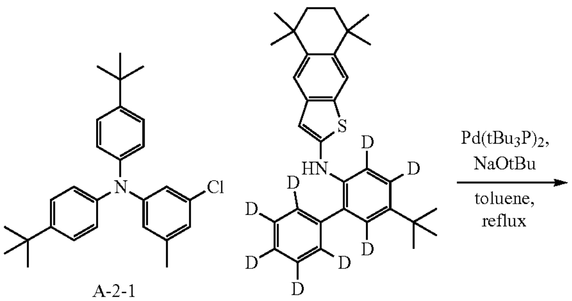

A-2-1

A-18-1

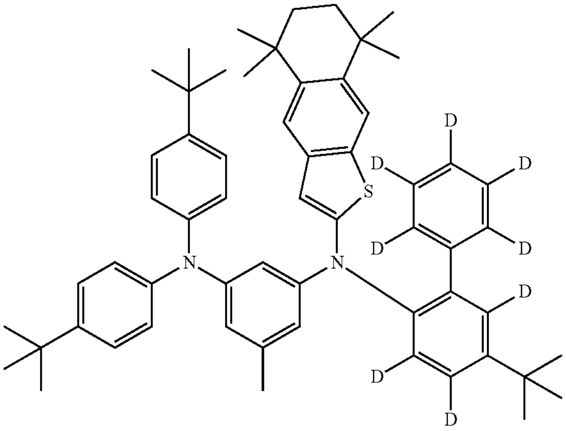

A-18-2

Compound A-18-2 (18.4 g, yield 59%, MS[M+H]+=845) was obtained in the same manner as in Synthesis Example 3 except that Compounds A-2-1 (15 g. 1 eq.) and A-18-1 were used instead of Compounds A-2-1 and A-2-2.

Synthesis Example 7. Synthesis of Compound A-18

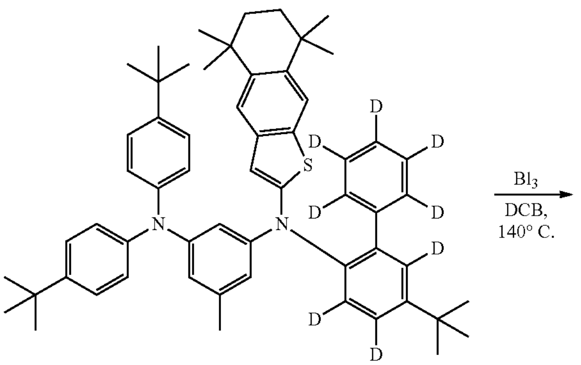

A-18-2

-continued

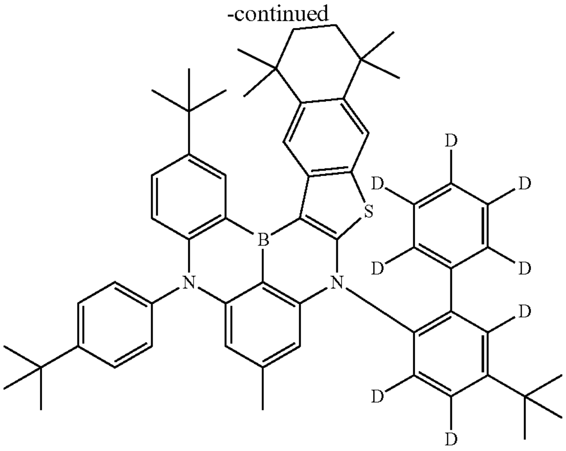

A-18

Compound A-18 (3.2 g, yield 59%, MS[M+H]+=853) was obtained in the same manner as in Synthesis Example 4 except that Compound A-18-2 (18.4 g. 1 eq.) was used instead of Compound A-2-3.

Synthesis Example 8. Synthesis of Compound A-7-1

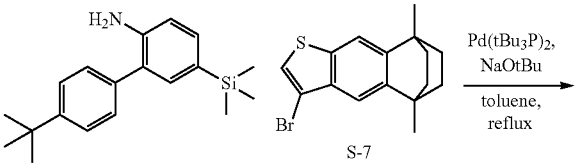

S-6

S-7

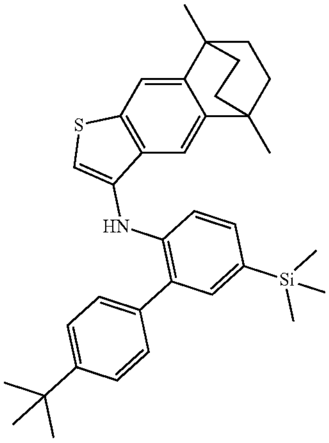

A-7-1

Compound A-7-1 (14.6 g, yield 62%, MS[M+H]+=538) was obtained in the same manner as in Synthesis Example 2 except that Compounds S-6 (13 g, 1 eq.) and S-7 were used instead of Compounds S-3 and S-4.

Synthesis Example 9. Synthesis of Compound A-7-2

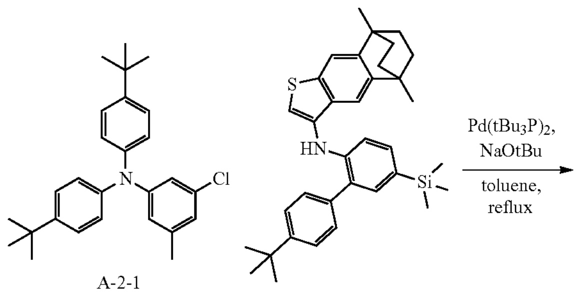

A-2-1

A-7-1

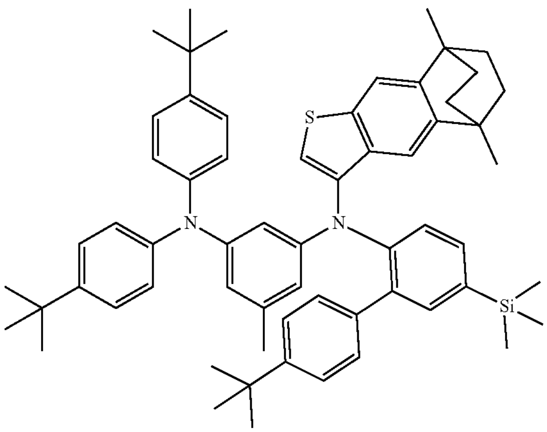

A-7-2

Compound A-7-2 (16.5 g, yield 74%, MS[M+H]+=907) was obtained in the same manner as in Synthesis Example 3 except that Compounds A-2-1 (10 g. 1 eq.) and A-7-1 were used instead of Compounds A-2-1 and A-2-2.

Synthesis Example 10. Synthesis of Compound A-7

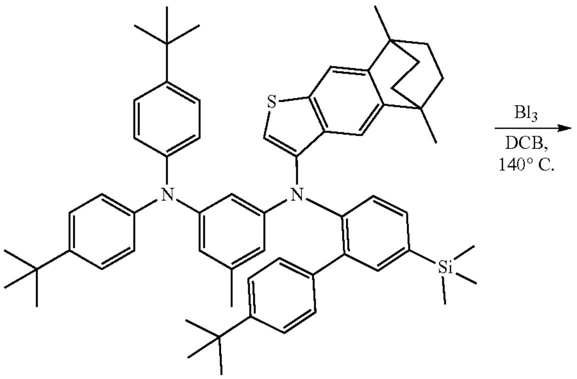

A-7-2

-continued

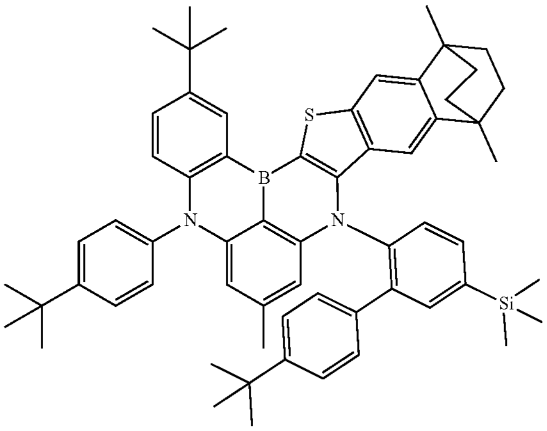

A-7

Compound A-7 (2.8 g, yield 17%, MS[M+H]+=915) was obtained in the same manner as in Synthesis Example 4 except that Compound A-7-2 (16.5 g. 1 eq.) was used instead of Compound A-2-3.

Synthesis Example 10-2. Synthesis of Compound A-1-1

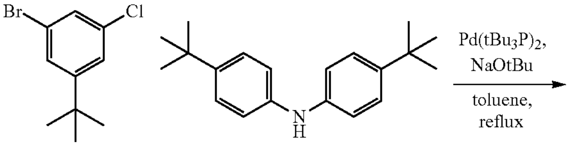

S-8

S-2

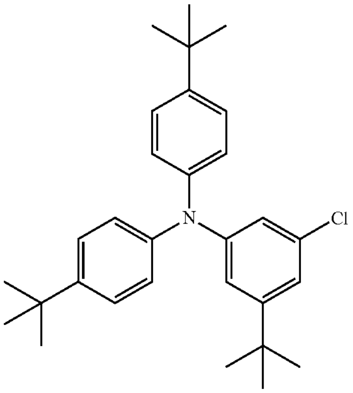

A-1-1

Compound A-1-1 (50.4 g, yield 74%, MS[M+H]+=448) was obtained in the same manner as in Synthesis Example 1 except that Compound S-8 (1 eq.) was used instead of Compound S-1.

Synthesis Example 11. Synthesis of Compound A-1-2

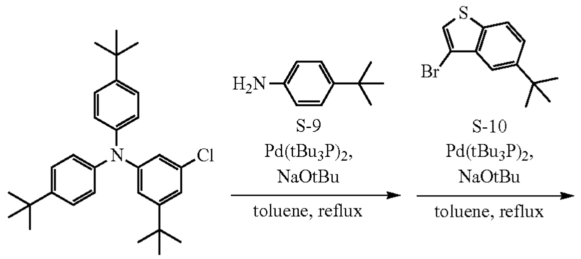

A-1-1

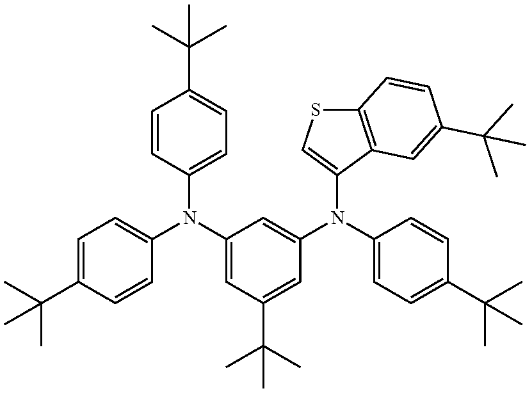

A-1-2

After dissolving Compound A-1-1 (29.4 g, 49.6 mmol, 1 eq.), 4-(tert-butyl)aniline (7.78 g, 52.1 mmol, 1.05 eq.), $Pd(Pt-Bus)_2$ (0.25 g, 0.01 eq.) and NaOt-Bu (7.2 g, 1.5 eq.) in toluene (250 ml), the result was stirred under reflux. When the reaction was finished, the result was cooled to room temperature, and then the reaction material was transferred to a separatory funnel and extracted. The result was dried with $MgSO_4$, filtered and concentrated, and the next reaction proceeded without further purification.

After dissolving Compound S-10 (11.1 g, 51.1 mmol, 1.5 eq.), $Pd(Pt-Bus)_2$ (0.25 g, 0.1 eq.) and NaOt-Bu (7.2 g, 1.5 eq.) in toluene (204 ml), the result was stirred under reflux. When the reaction was finished, the result was cooled to room temperature, and then the reaction material was transferred to a separatory funnel and extracted. The result was dried with $MgSO_4$, filtered and concentrated, and purified using column chromatography to obtain Compound A-1-2 (22.9 g, 55%).

MS: $[M+H]^+$=749

Synthesis Example 12. Synthesis of Compound A-1

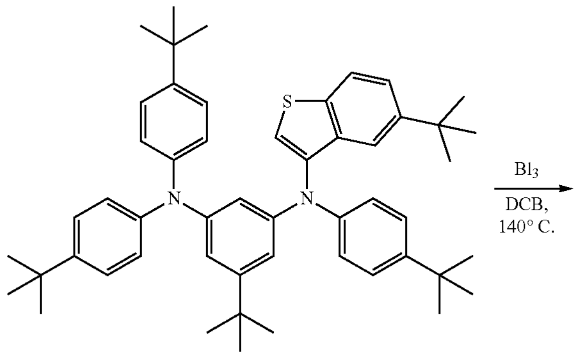

A-1-2

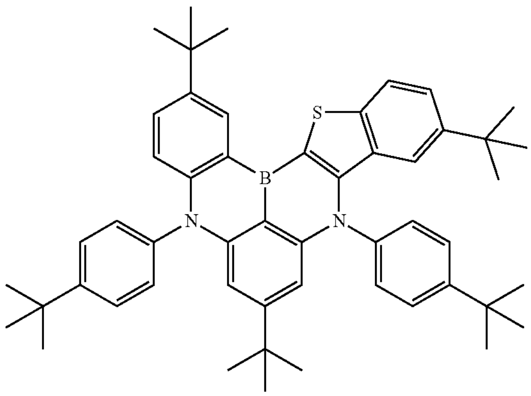

A-1

Compound A-1 (2.8 g, yield 17%, MS[M+H]+=757) was obtained in the same manner as in Synthesis Example 4 except that Compound A-1-2 (16.5 g. 1 eq.) was used instead of Compound A-2-3.

Synthesis Example 13. Synthesis of Compound A-3-1

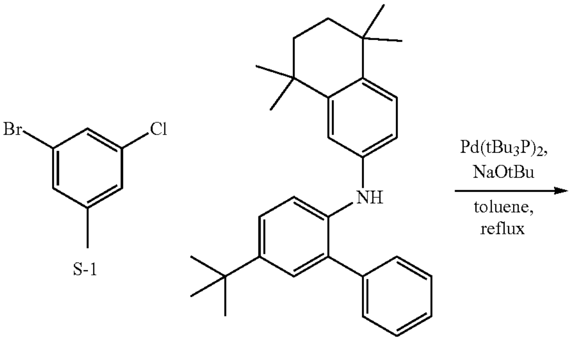

S-1

S-11

-continued

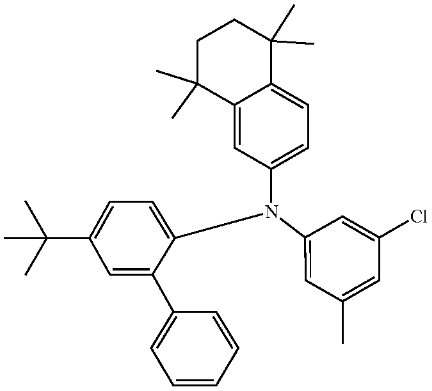

A-3-1

Compound A-3-1 (17.9 g, yield 68%, MS[M+H]+=536) was obtained in the same manner as in Synthesis Example 1 except that Compound S-11 (20.3 g. 1 eq.) was used instead of Compound S-2.

Synthesis Example 14. Synthesis of Compound A-3-2

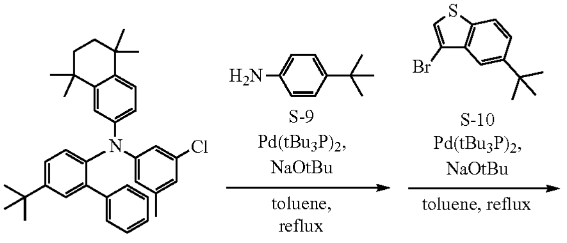

A-3-1

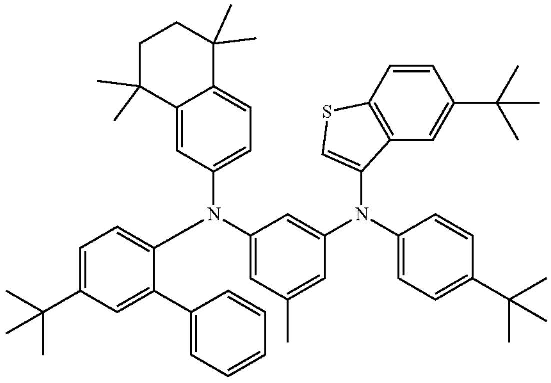

A-3-2

Compound A-3-2 (9.6 g, yield 57%, MS[M+H]+=838) was obtained in the same manner as in Synthesis Example 11 except that Compound A-3-1 (1 eq.) was used instead of Compound A-1-1.

Synthesis Example 15. Synthesis of Compound A-3

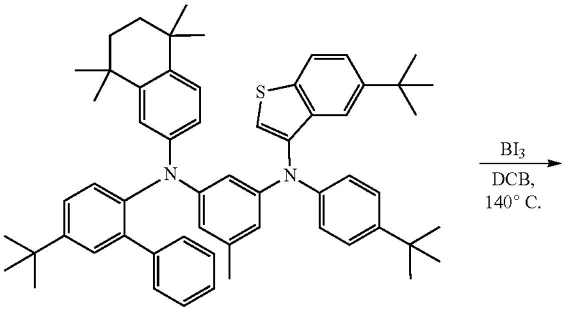

A-3-2

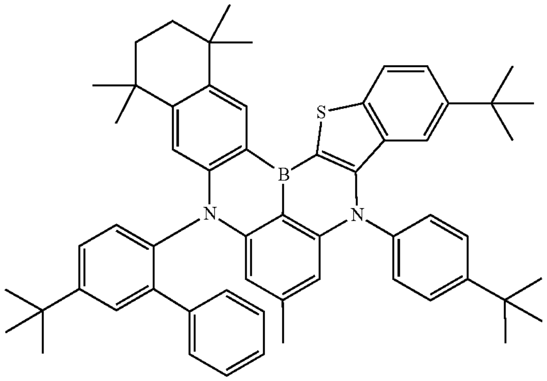

A-3

Compound A-3 (3.1 g, yield 22%, MS[M+H]+=846) was obtained in the same manner as in Synthesis Example 4 except that Compound A-3-2 (1 eq.) was used instead of Compound A-2-3.

Synthesis Example 15. Synthesis of Compound A-4-1

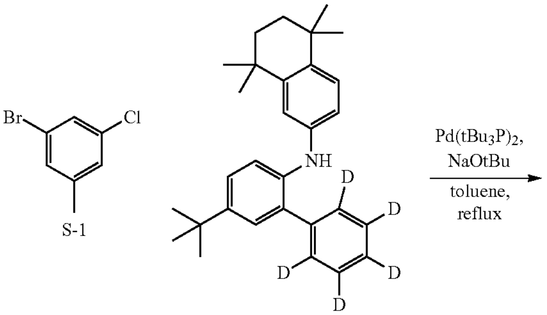

S-1

S-12

-continued

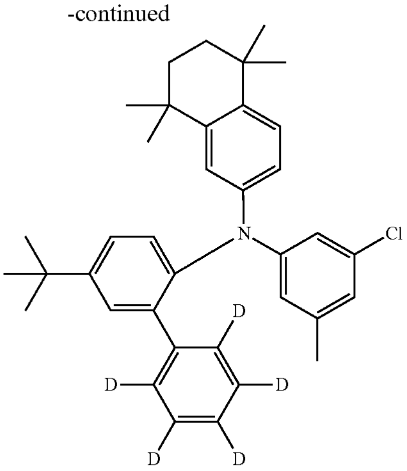

A-4-1

Compound A-4-1 (17.9 g, yield 68%, MS[M+H]+=541) was obtained in the same manner as in Synthesis Example 1 except that Compound 5-12 (20.3 g. 1 eq.) was used instead of Compound S-2.

Synthesis Example 16. Synthesis of Compound A-4-2

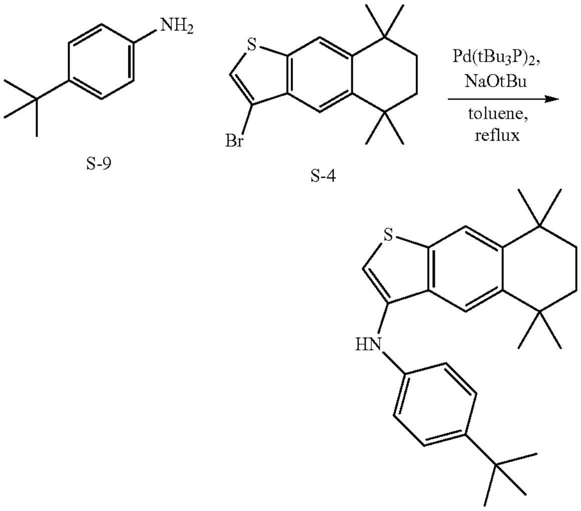

S-9

S-4

A-4-2

Compound A-4-2 (15.5 g, yield 59%, MS[M+H]+=392) was obtained in the same manner as in Synthesis Example 2 except that Compound S-9 (10 g, 1 eq.) was used instead of Compound S-3.

Synthesis Example 17. Synthesis of Compound A-4-3

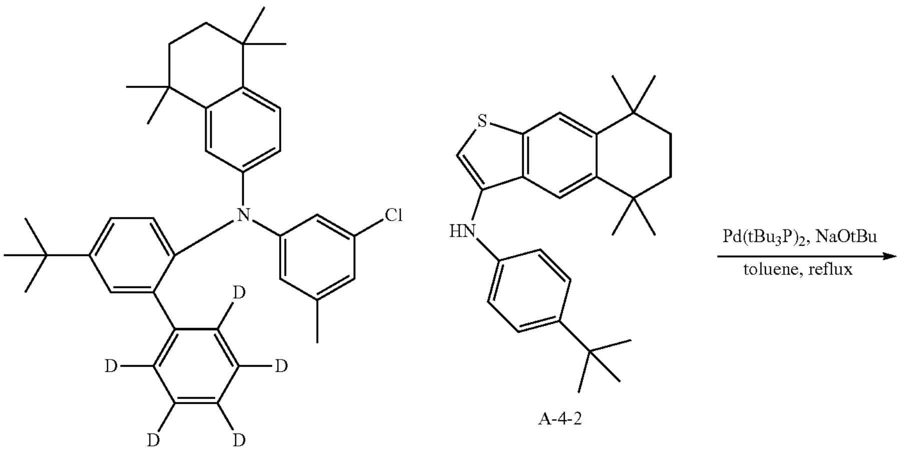

A-4-1

A-4-2

-continued
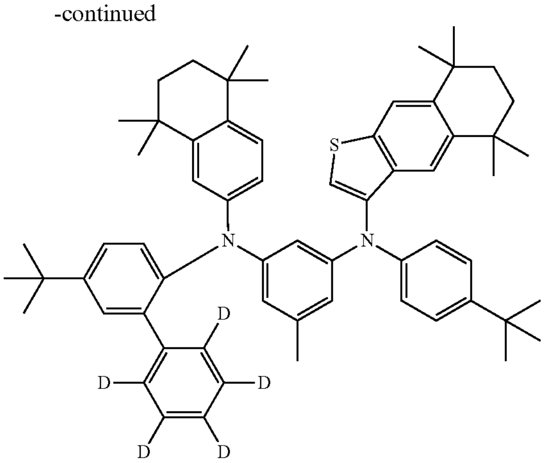
A-4-3
Compound A-4-3 (18.8 g, yield 71%, MS[M+H]+=857) was obtained in the same manner as in Synthesis Example 3 except that Compounds A-4-1 (16 g. 1 eq.) and A-4-2 (11.6 g. 1 eq.) were used instead of Compounds A-2-1 and A-2-2.
Synthesis Example 18. Synthesis of Compound A-4
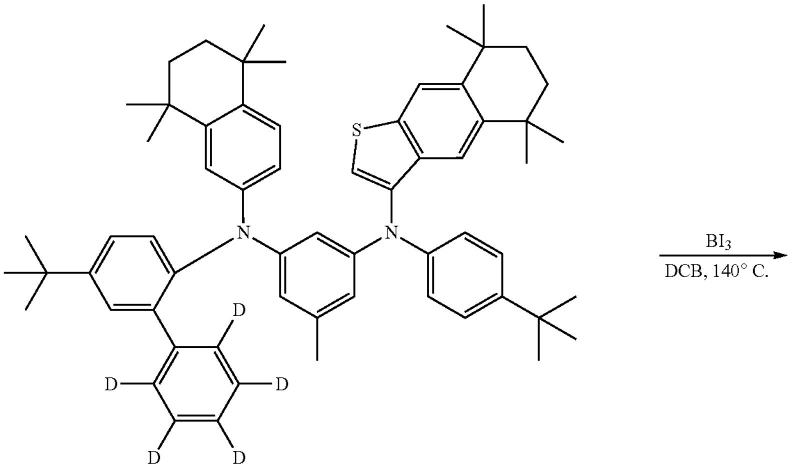
A-4-3
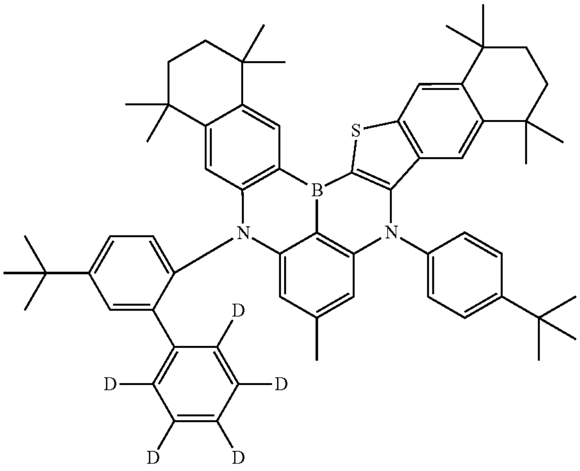
A-4

Compound A-4 (4.2 g, yield 23%, MS[M+H]+=905) was obtained in the same manner as in Synthesis Example 4 except that Compound A-4-3 (18 g. 1 eq.) was used instead of Compound A-2-3.

Synthesis Example 19. Synthesis of Compound A-5-1

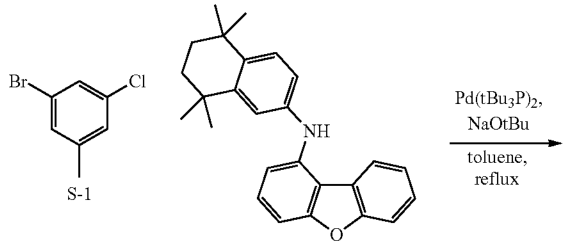

S-1

S-13

-continued

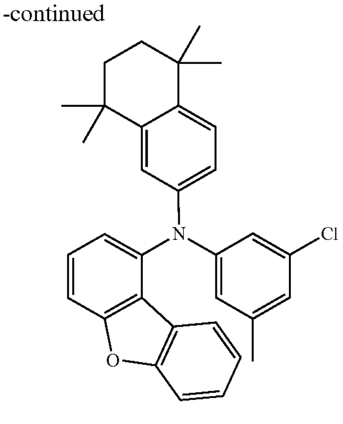

A-5-1

Compound A-5-1 (18.5 g, yield 77%, MS[M+H]+=494) was obtained in the same manner as in Synthesis Example 1 except that Compound S-13 (18 g. 1 eq.) was used instead of Compound S-2, and xylene was used instead of toluene.

Synthesis Example 20. Synthesis of Compound A-5-2

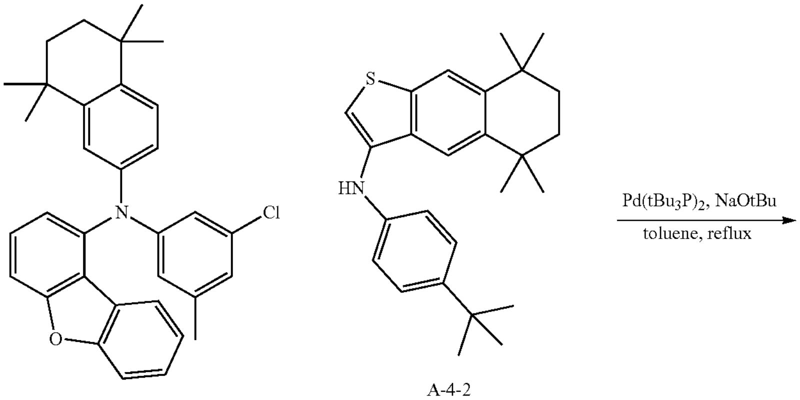

A-5-1

A-4-2

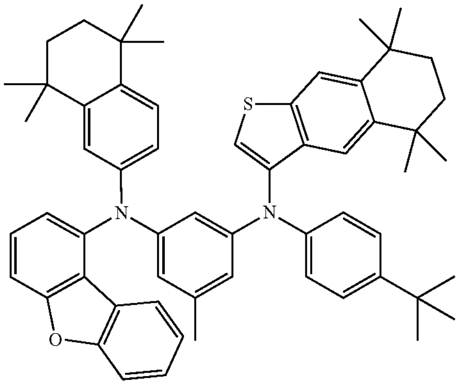

A-5-2

Compound A-5-2 (9.9 g, yield 64%, MS[M+H]+=849) was obtained in the same manner as in Synthesis Example 3 except that Compounds A-5-1 (9 g. 1 eq.) and A-4-2 (7.1 g. 1 eq.) were used instead of Compounds A-2-1 and A-2-2.

Synthesis Example 21. Synthesis of Compound A-5

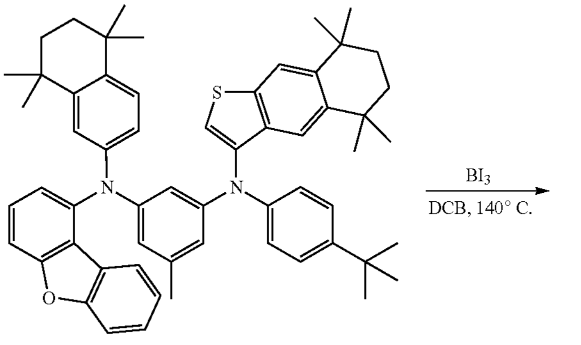

A-5-2

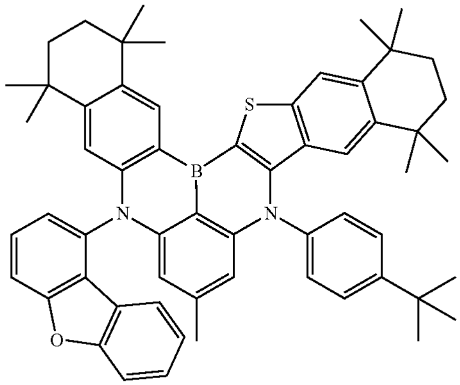

A-5

Compound A-5 (3.5 g, yield 35%, MS[M+H]+=857) was obtained in the same manner as in Synthesis Example 4 except that Compound A-5-2 (9.9 g. 1 eq.) was used instead of Compound A-2-3.

Synthesis Example 22. Synthesis of Compound A-6-1

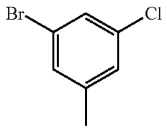

S-1

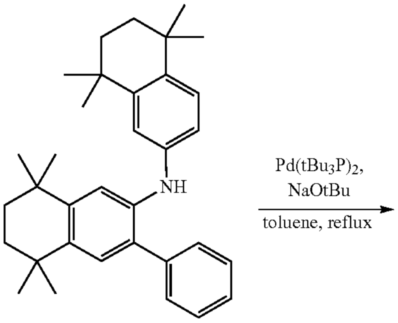

S-14

-continued

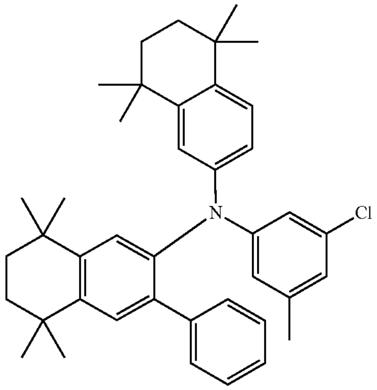

A-6-1

Compound A-6-1 (124.1 g, yield 84%, MS[M+H]+=590) was obtained in the same manner as in Synthesis Example 1 except that Compound S-14 (22.7 g. 1 eq.) was used instead of Compound S-2.

Synthesis Example 23. Synthesis of Compound A-6-2

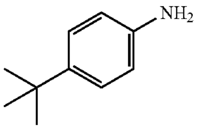

S-9

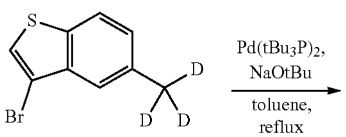

S-15

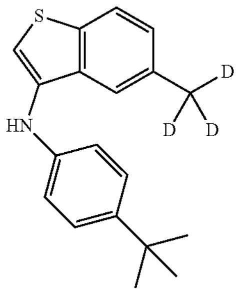

A-6-2

Compound A-6-2 (8.8 g, yield 55%, MS[M+H]+=299) was obtained in the same manner as in Synthesis Example 2 except that Compounds S-9 (8 g, 1 eq.) and S-15 (12.3 g) were used instead of Compounds S-3 and S-4.

Synthesis Example 24. Synthesis of Compound A-6-3

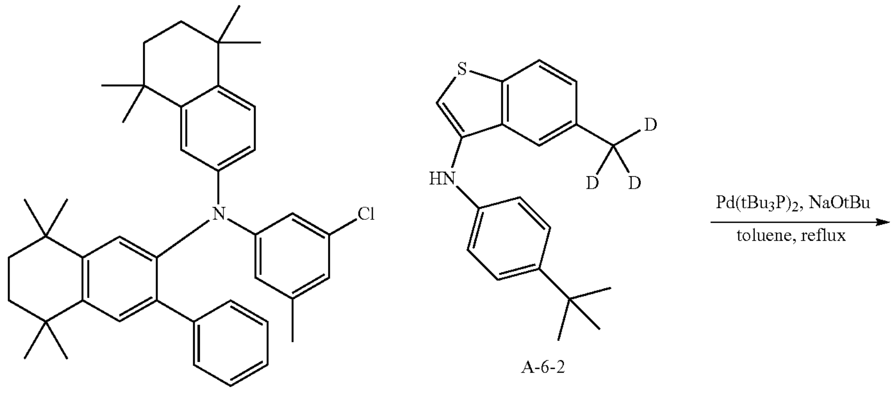

A-6-1

A-6-2

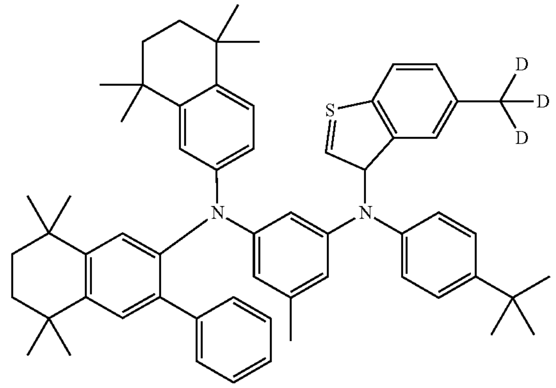

A-6-3

Compound A-6-3 (10.6 g, yield 61%, MS[M+H]+=523) was obtained in the same manner as in Synthesis Example 3 except that Compounds A-6-1 (12 g. 1 eq.) and A-6-2 (6.1 g) were used instead of Compounds A-2-1 and A-2-2.

Synthesis Example 25. Synthesis of Compound A-6

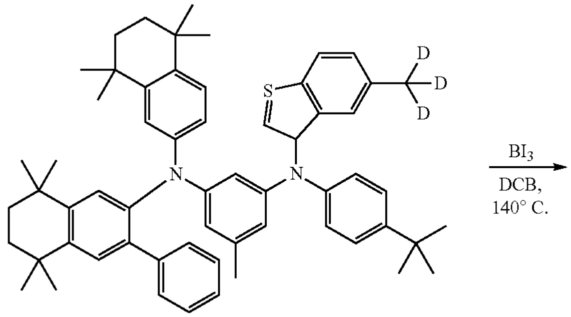

A-6-3

-continued

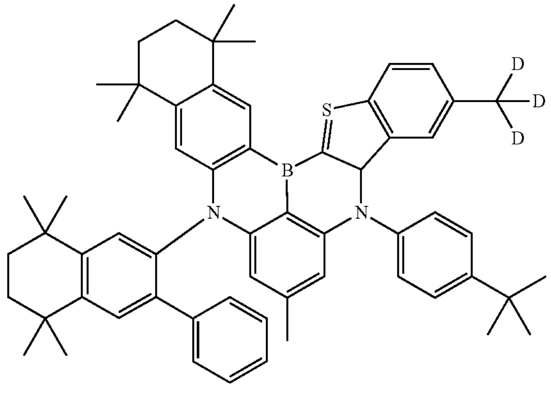

A-6

Compound A-6 (2.5 g, yield 26%, MS[M+H]+=861) was obtained in the same manner as in Synthesis Example 4 except that Compound A-6-3 (9.5 g. 1 eq.) was used instead of Compound A-2-3.

Synthesis Example 26. Synthesis of Compound A-11-1

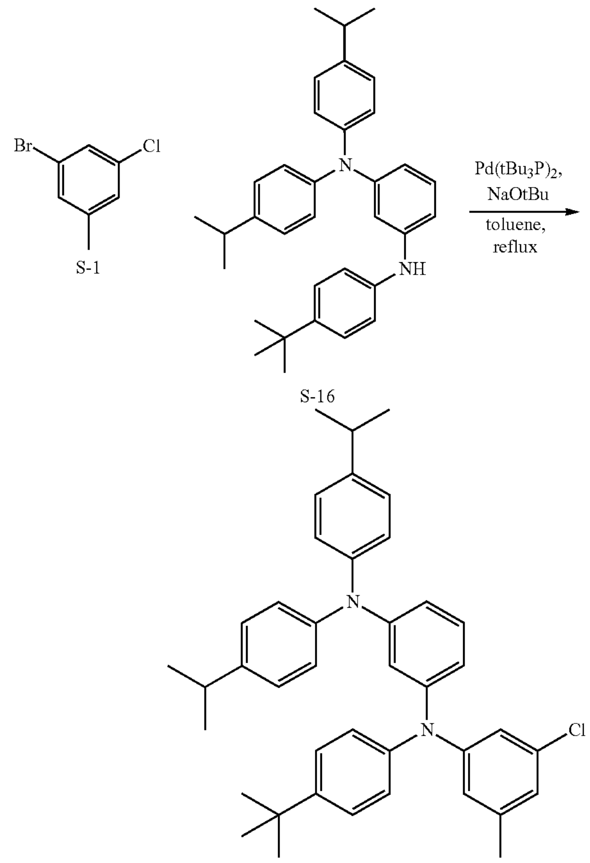

A-11-1

Compound A-11-1 (18.0 g, yield 77%, MS[M+H]+=601) was obtained in the same manner as in Synthesis Example 1 except that Compound S-16 (18.6 g. 1 eq.) was used instead of Compound S-2.

Synthesis Example 27. Synthesis of Compound A-11-2

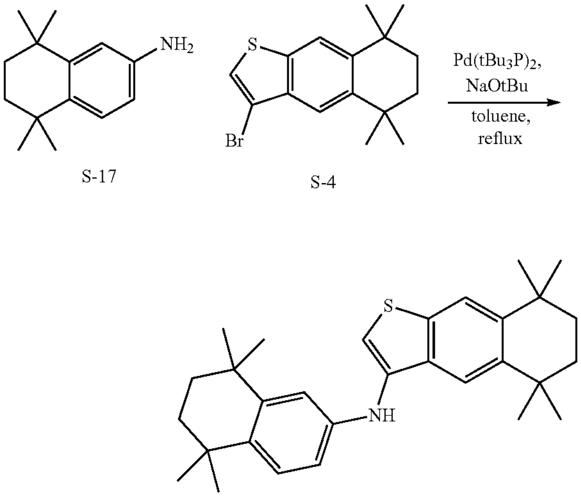

A-11-2

Compound A-11-2 (12.5 g, yield 71%, MS [M+H]+=446) was obtained in the same manner as in Synthesis Example 2 except that Compounds 5-17 (8 g, 1 eq.) and S-4 (12.7 g) were used instead of Compounds S-3 and S-4.

Synthesis Example 28. Synthesis of Compound A-11

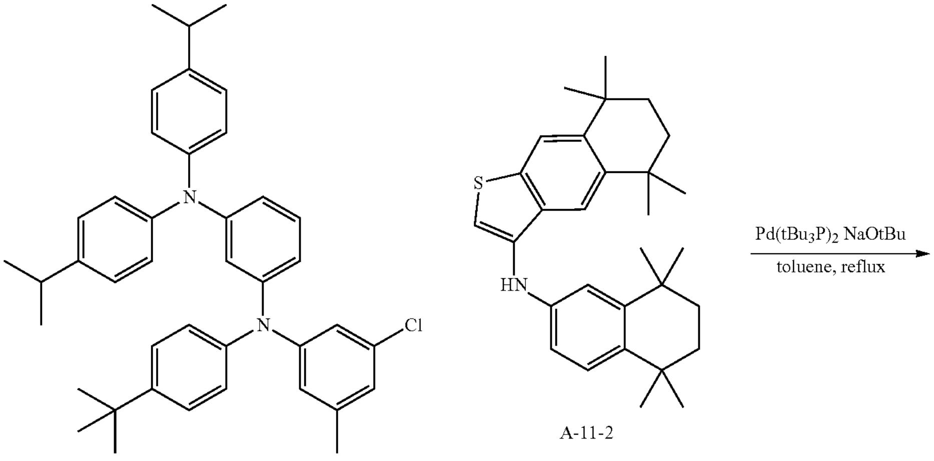

A-11-1

-continued

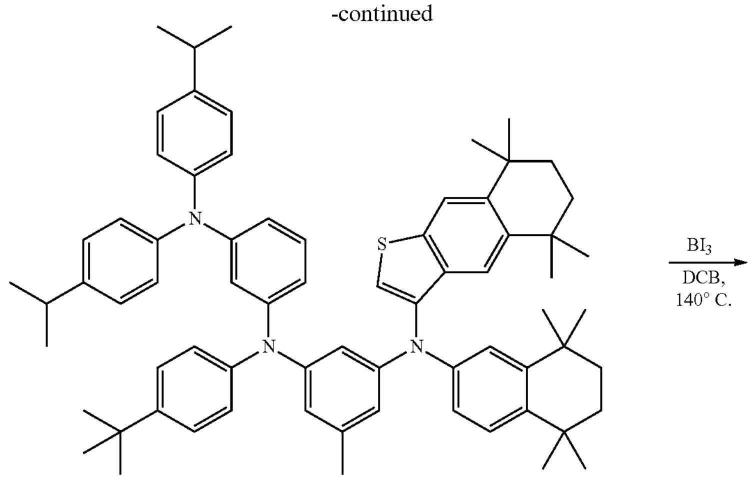

A-11-3

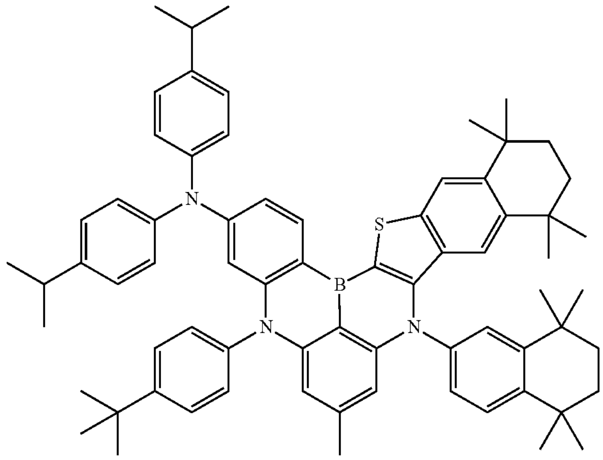

A-11

Compound A-11-3 (18.5 g, yield 71%, MS[M+H]+=1010) was obtained in the same manner as in Synthesis Example 3 except that Compounds A-11-1 (15.5 g. 1 eq.) and A-11-2 (11.5 g) were used instead of Compounds A-2-1 and A-2-2.

Compound A-11 (3.2 g, yield 22%, MS[M+H]+=1017) was obtained in the same manner as in Synthesis Example 4 except that Compound A-11-3 (14.5 g. 1 eq.) was used instead of Compound A-2-3.

Synthesis Example 29. Synthesis of Compound A-8-1

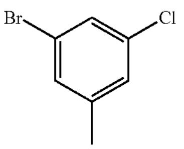

S-1

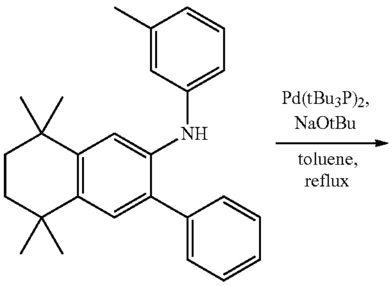

S-18

-continued

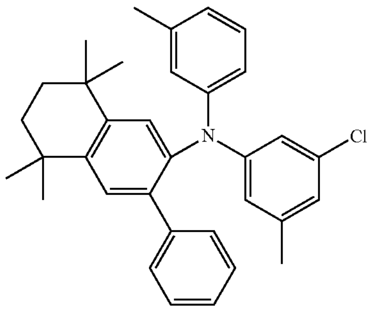

A-8-1

Compound A-8-1 (16.5 g, yield 66%, MS[M+H]+=494) was obtained in the same manner as in Synthesis Example 1 except that Compound 5-18 (1 eq.) was used instead of Compound S-2.

Synthesis Example 30. Synthesis of Compound A-8

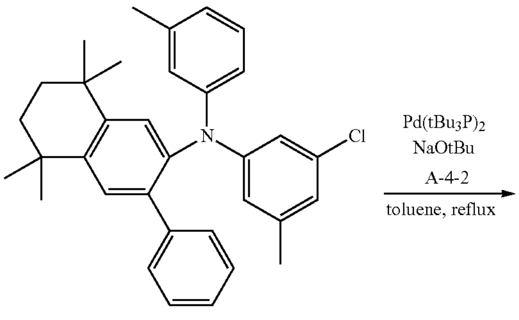

A-8-1

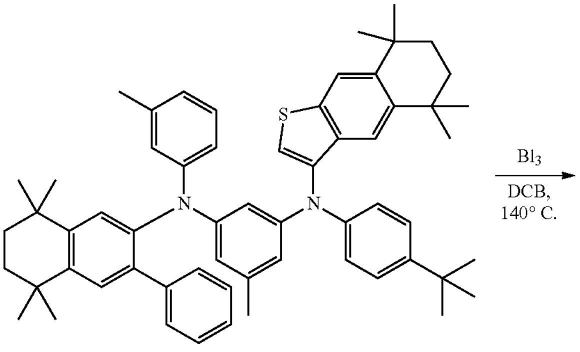

A-8-2

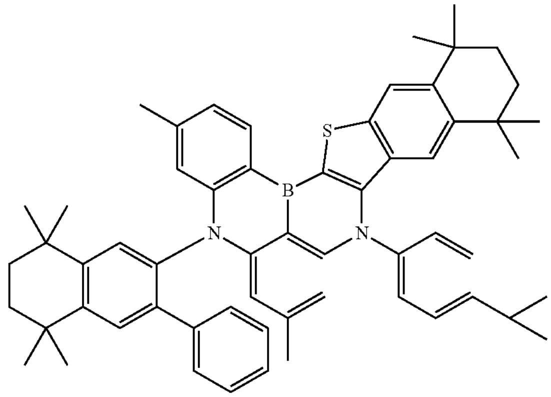

A-8

Compound A-8-2 (9.1 g, yield 62%, MS[M+H]+=850) was obtained in the same manner as in Synthesis Example 3 except that Compounds A-8-1 (1 eq.) and A-4-2 were used instead of Compounds A-2-1 and A-2-2.

Compound A-8 (3.4 g, yield 27%, MS[M+H]+=858) was obtained in the same manner as in Synthesis Example 4 except that Compound A-8-2 (1 eq.) was used instead of Compound A-2-3.

Synthesis Example 31. Synthesis of Compound A-9-1

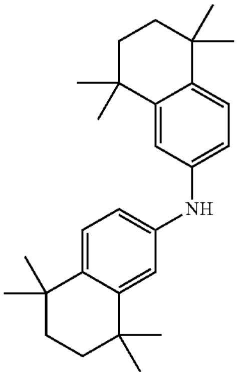

S-19

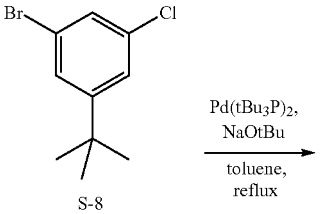

S-8

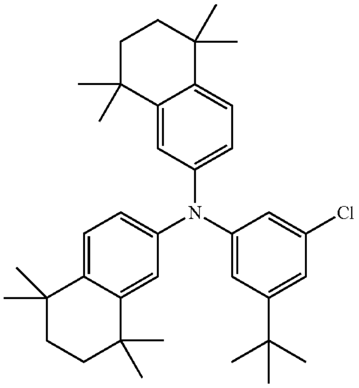

A-9-1

Compound A-9-1 (35.5 g, yield 79%, MS[M+H]+=556) was obtained in the same manner as in Synthesis Example 1 except that Compounds S-8 (20 g. 1 eq.) and S-19 (31.5 g) were used instead of Compounds S-1 and S-2.

Synthesis Example 32. Synthesis of Compound A-9

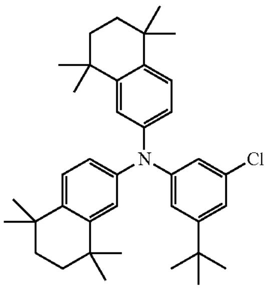

A-9-1

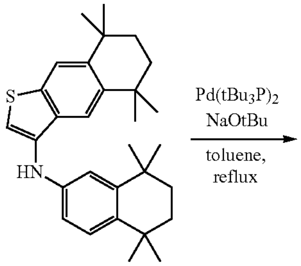

A-11-2

-continued

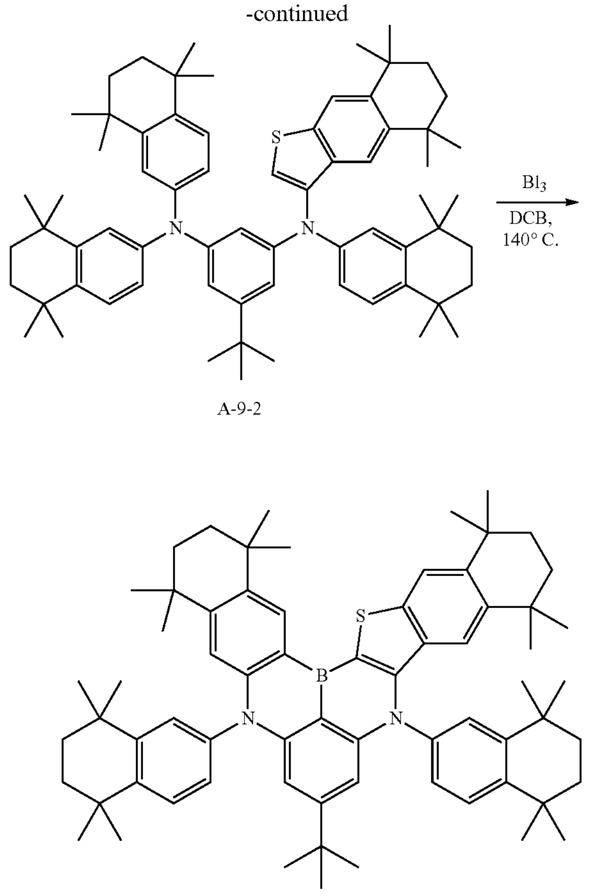

A-9-2

A-9

Compound A-9-2 (11.8 g, yield 68%, MS[M+H]+=966) was obtained in the same manner as in Synthesis Example 3 except that Compounds A-9-1 (10 g. 1 eq.) and A-11-2 (8 g) were used instead of Compounds A-2-1 and A-2-2.

Compound A-9 (3.9 g, yield 39%, MS[M+H]+=973) was obtained in the same manner as in Synthesis Example 4 except that Compound A-9-2 (10 g. 1 eq.) was used instead of Compound A-2-3.

Synthesis Example 33. Synthesis of Compound A-10-1

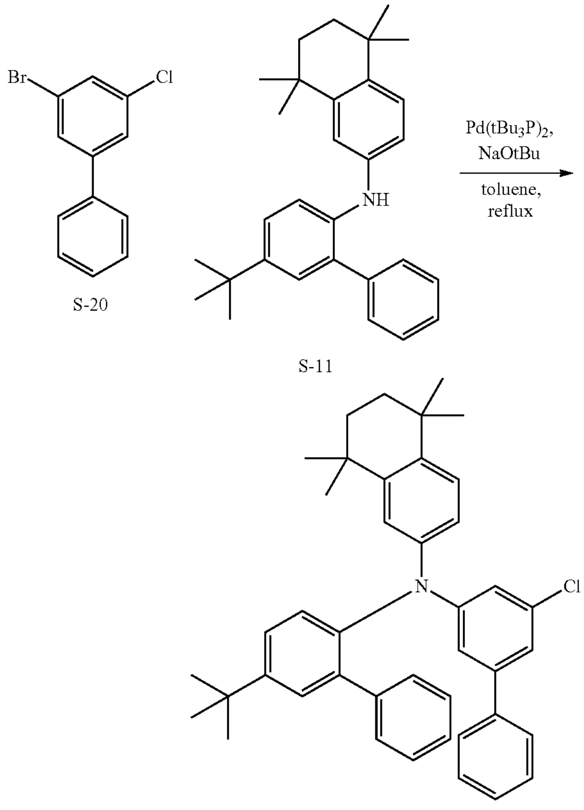

S-20

S-11

A-10-1

Compound A-10-1 (19.9 g, yield 68%, MS[M+H]+=598) was obtained in the same manner as in Synthesis Example 1 except that Compounds S-20 and S-11 (20.3 g. 1 eq.) were used instead of Compounds S-1 and S-2.

Synthesis Example 34. Synthesis of Compound A-10-2

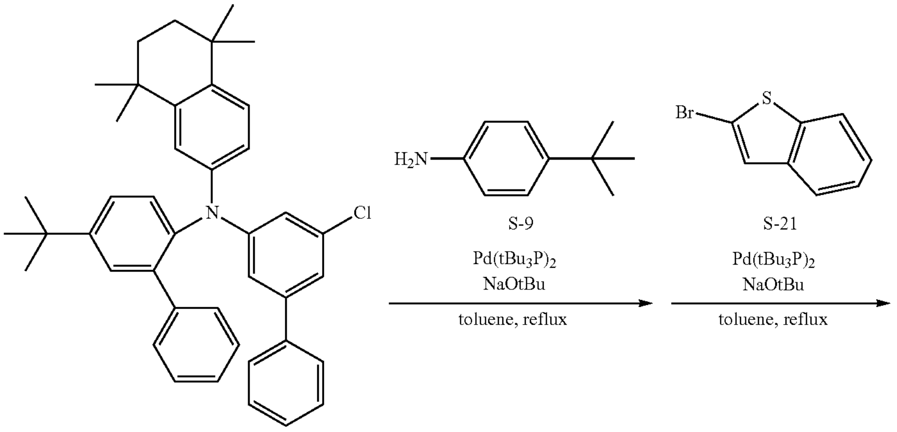

A-10-1

S-9

S-21

-continued

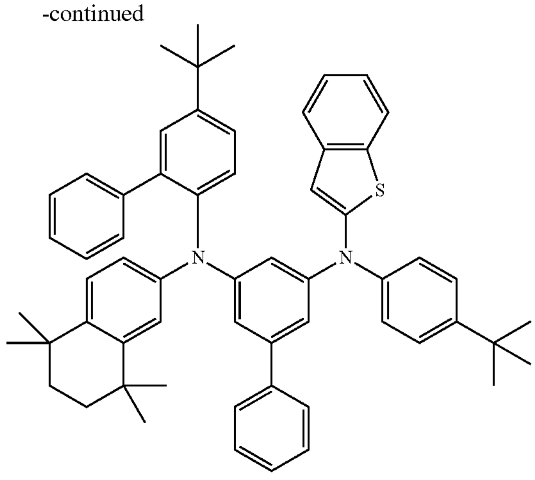

A-10-2

Compound A-10-2 (9.1 g, yield 57%, MS[M+H]+=843) was obtained in the same manner as in Synthesis Example 11 except that Compounds A-10-1 (1 eq.) and S-21 were used instead of Compounds A-1-1 and S-10.

Synthesis Example 35. Synthesis of Compound A-10

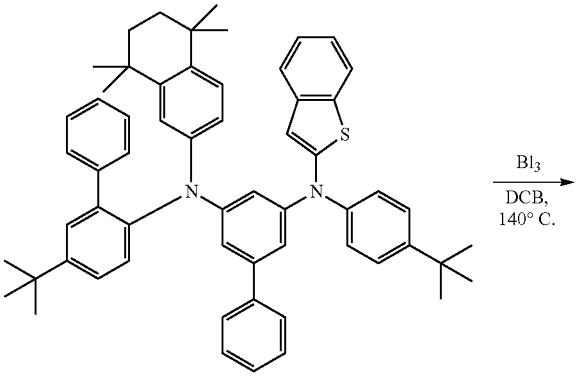

A-10-2

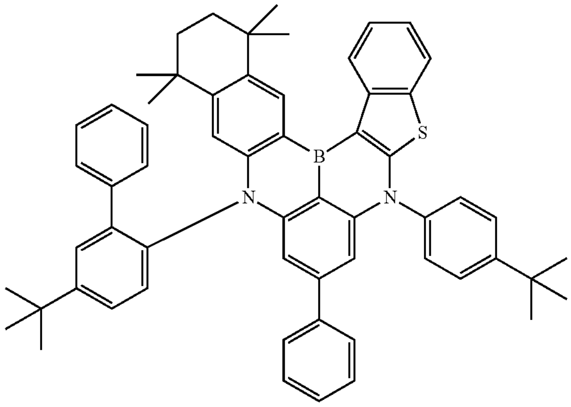

A-10

Compound A-10 (1.9 g, yield 12%, MS[M+H]+=851) was obtained in the same manner as in Synthesis Example 4 except that Compound A-10-2 (1 eq.) was used instead of Compound A-2-3.

Synthesis Example 36. Synthesis of Compound A-12-1

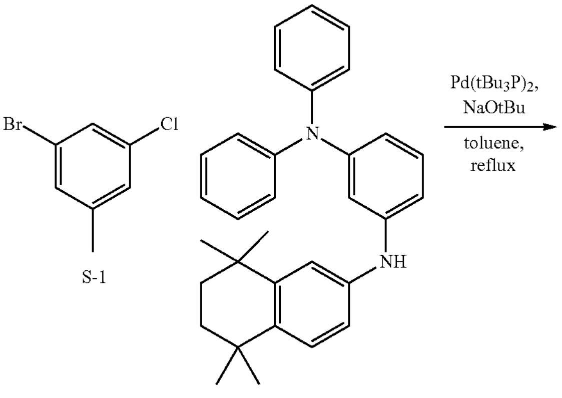

S-1

S-22

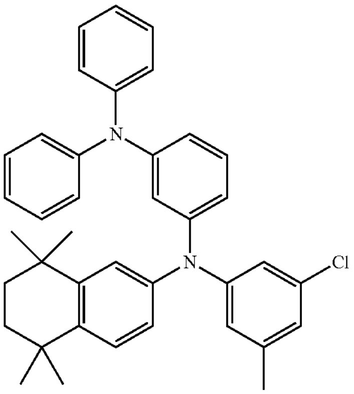

A-12-1

Compound A-12-1 (21.1 g, yield 67%, MS[M+H]+=571) was obtained in the same manner as in Synthesis Example 1 except that Compound S-22 (1 eq.) was used instead of Compound S-2.

Synthesis Example 37. Synthesis of Compound A-12-2

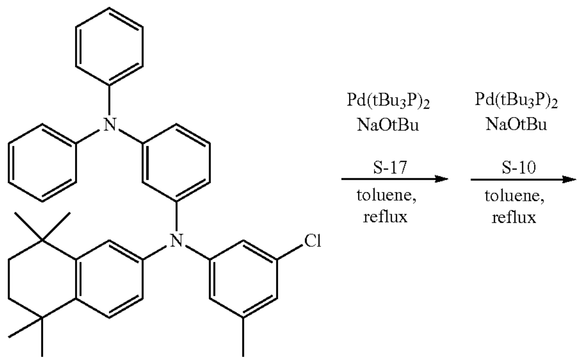

A-12-1

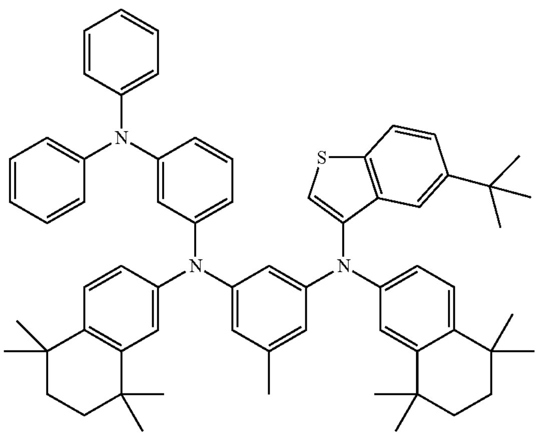

A-12-2

Compound A-12-2 (10.2 g, yield 53%, MS[M+H]+=927) was obtained in the same manner as in Synthesis Example 11 except that Compounds A-12-1 (1 eq.) and S-17 were used instead of Compounds A-1-1 and S-9.

Synthesis Example 38. Synthesis of Compound A-12

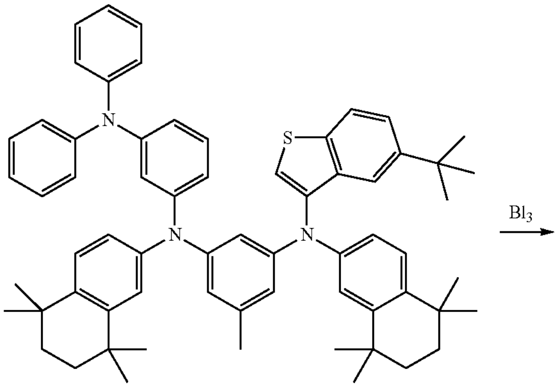

A-12-2

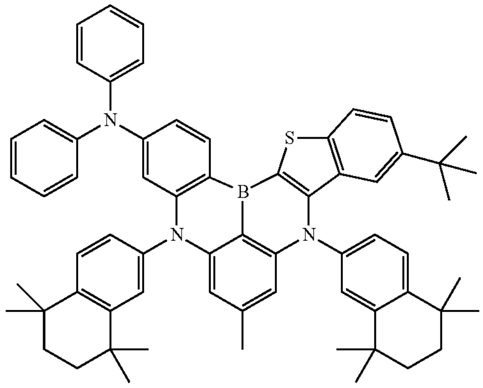

A-12

Compound A-12 (1.7 g, yield 15%, MS[M+H]+=935) was obtained in the same manner as in Synthesis Example 4 except that Compound A-12-2 (1 eq.) was used instead of Compound A-2-3.

Synthesis Example 39. Synthesis of Compound A-13-2

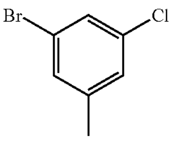

S-1

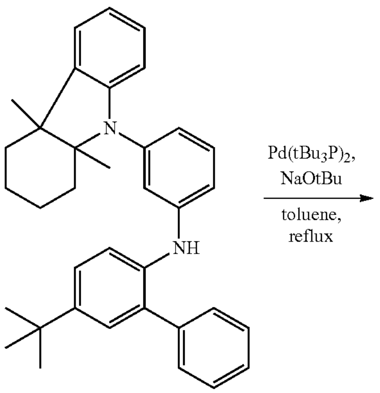

S-23

-continued

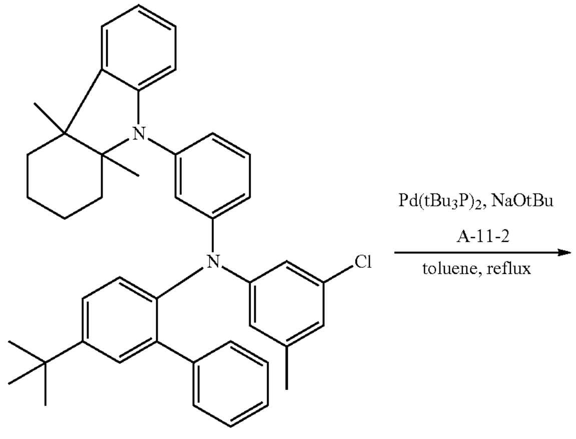

A-13-1

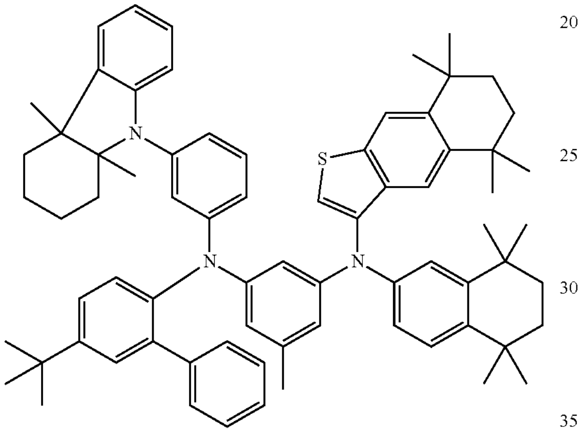

A-13-2

Compound A-13-1 (24 g, yield 68%, MS[M+H]+=625) was obtained in the same manner as in Synthesis Example 1 except that Compound 5-23 (1 eq.) was used instead of Compound S-2.

Compound A-13-2 (18.1 g, yield 69%, MS[M+H]+=1035) was obtained in the same manner as in Synthesis Example 3 except that Compounds A-13-1 (1 eq.) and A-11-2 were used instead of Compounds A-2-1 and A-2-2.

Synthesis Example 40. Synthesis of Compound A-13

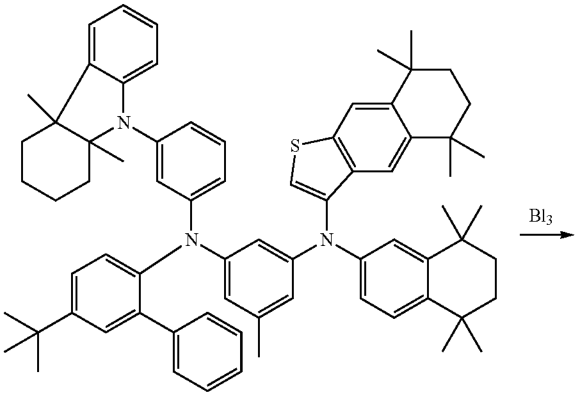

A-13-2

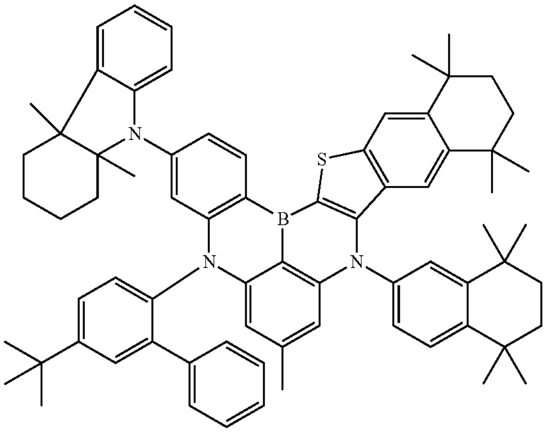

A-13

Compound A-13 (3.3 g, yield 24%, MS[M+H]+=1043) was obtained in the same manner as in Synthesis Example 4 except that Compound A-13-2 (1 eq.) was used instead of Compound A-2-3.

Synthesis Example 41. Synthesis of Compound A-14-1

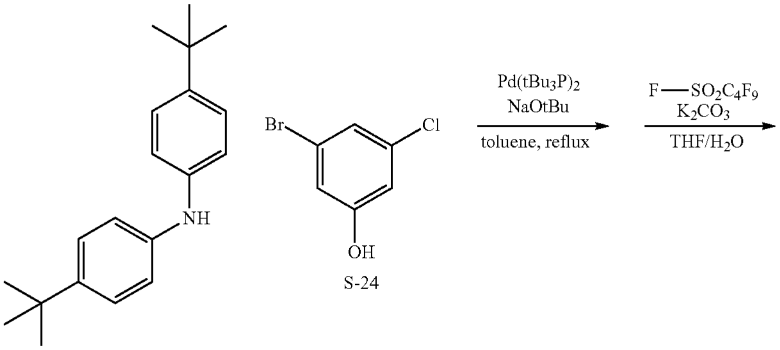

S-2

S-24

-continued

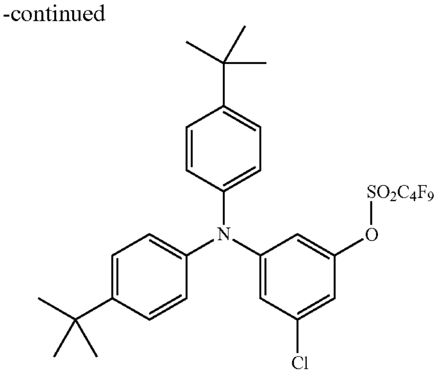

A-14-1

Preparation was conducted in the same manner as in Synthesis Example 1 except that Compounds 5-24 (20 g. 1 eq.) and S-2 (27.1 g) were used instead of Compounds S-1 and S-2, and the next reaction proceeded without further purification.

After dissolving the reaction product that did not go through purification in tetrahydrofuran (THF) (240 mL), potassium carbonate (17.3 g, 1.3 eq.) dissolved in water (80 mL) was slowly added thereto. Perfluorobutanesulfonyl fluoride (43.7 g, 1.5 eq.) was added thereto, and the result was stirred for 2 hours at room temperature. When the reaction was completed, the reaction solution was separated by water and ethyl acetate thereto, and then filtered after treating with $MgSO_4$ (anhydrous). The filtered solution was removed by distillation under vacuum, and purified using a column chromatography method to obtain Compound A-14-1 (44.7 g, yield 67%).

Synthesis Example 42. Synthesis of Compound A-14-2

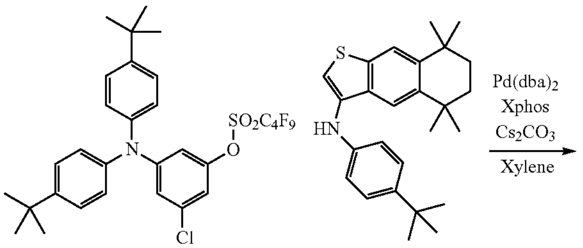

A-14-1 A-4-2

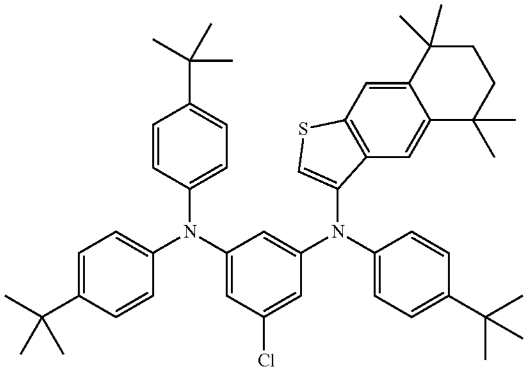

A-14-2

A flask holding Compound A-14-1 (12 g, 17.4 mmol, 1 eq.), Compound A-4-2 (7.2 g, 1.05 eq.), palladium(0) bis (dibenzylideneacetone) ($Pd(dba)_2$) (0.1 g, 0.01 eq.), 2-dicyclohexylphosphino-2',4',6'-triisopropylbiphenyl (Xphos) (0.17 g, 0.02 eq.), $Cs_2CO_3$ (17 g, 3 eq.) and xylene (90 ml) was heated to 140° C., and the mixture was stirred for 12 hours. The reaction solution was cooled to room temperature, separated by adding sat. aq. $NH_4Cl$ and toluene thereto, and the solution was removed by distillation under vacuum. The result was purified using silica gel column chromatography (ethyl acetate/hexane) to obtain Compound A-14-2 (9.8 g, yield 72%, MS[M+H]+=781).

Synthesis Example 43. Synthesis of Compound A-14-3

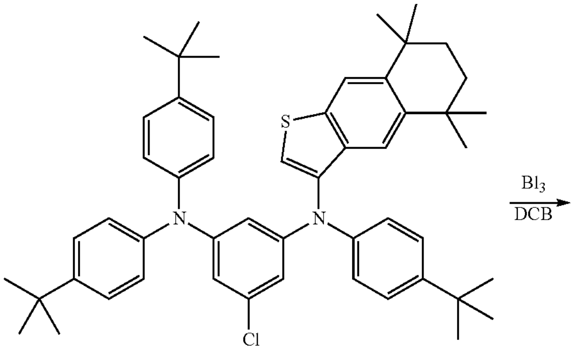

A-14-2

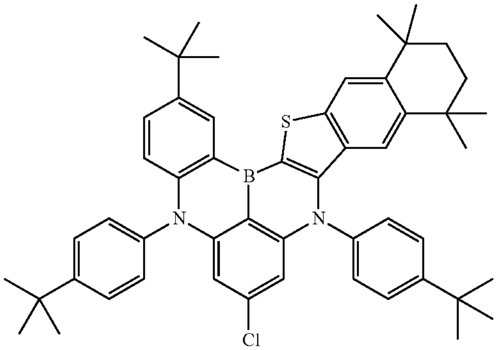

A-14-3

Compound A-14-3 (4.0 g, yield 42%, MS[M+H]+=775) was obtained in the same manner as in Synthesis Example 4 except that Compound A-14-2 (9.7 g. 1 eq.) was used instead of Compound A-2-3.

Synthesis Example 44. Synthesis of Compound A-14

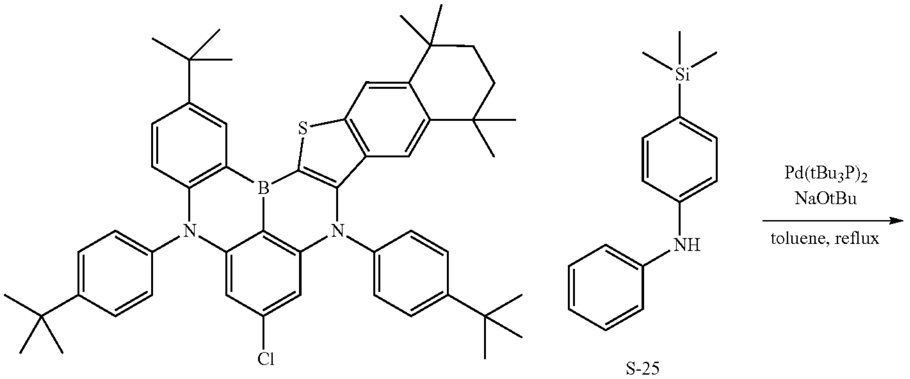

A-14-3

S-25

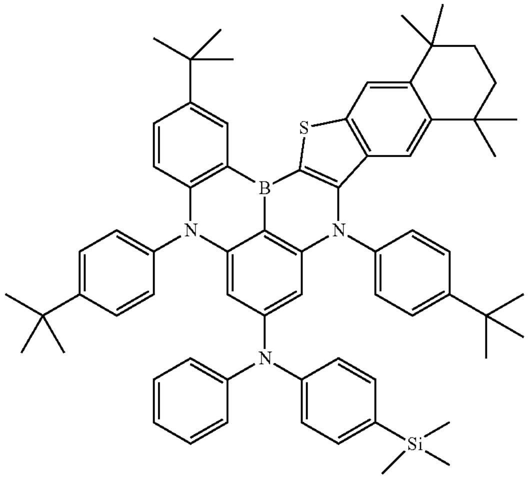

A-14

Compound A-14 (3.8 g, yield 74%, MS[M+H]+=995) was obtained in the same manner as in Synthesis Example 3 except that Compounds A-14-3 (4 g. 1 eq.) and S-25 (1.5 g, 1.2 eq.) were used instead of Compounds A-2-1 and A-2-2.

Synthesis Example 45. Synthesis of Compound A-15-1

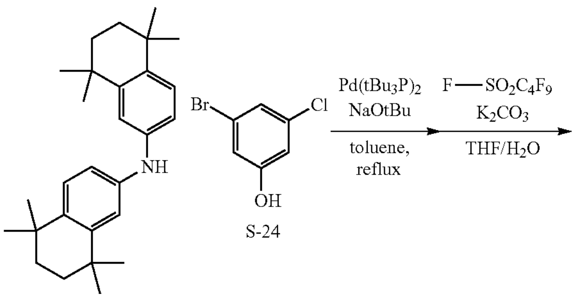

S-24

S-19

-continued

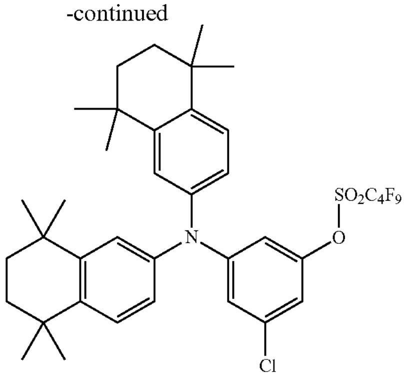

A-15-1

Compound A-15-1 (38.2 g, yield 65%) was obtained in the same manner as in Synthesis Example 41 except that Compound S-19 (1 eq.) was used instead of Compound S-2.

Synthesis Example 46. Synthesis of Compound A-15-2

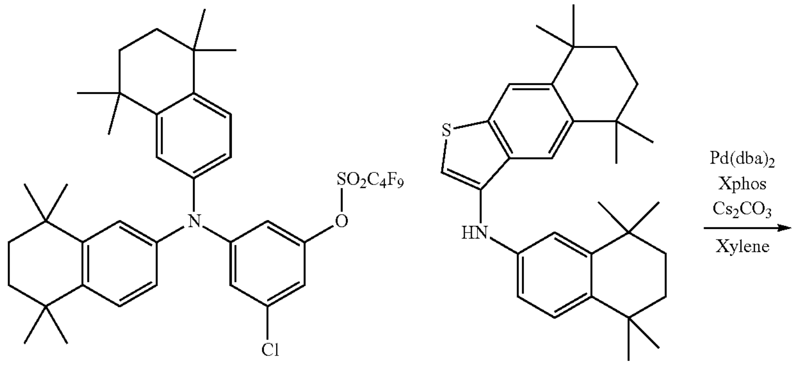

A-15-1

A-11-2

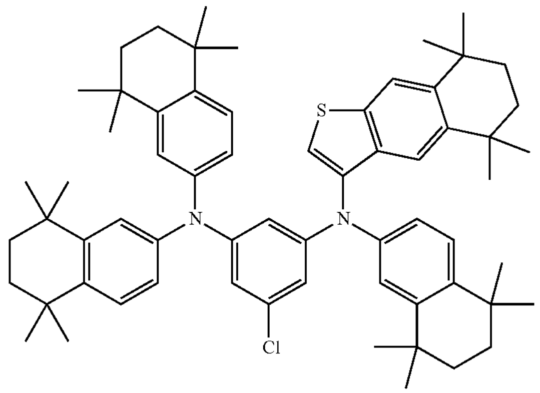

A-15-2

Compound A-15-2 (17.6 g, yield 55%, MS[M+H]+=944) was obtained in the same manner as in Synthesis Example 42 except that Compounds A-15-1 (1 eq.) and A-11-2 were used instead of Compounds A-14-1 and A-4-2.

Synthesis Example 47. Synthesis of Compound A-15-3

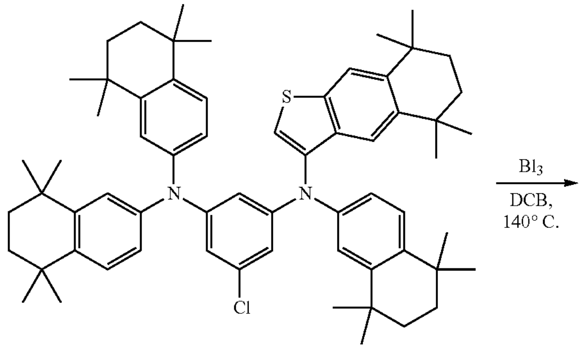

A-15-2

-continued

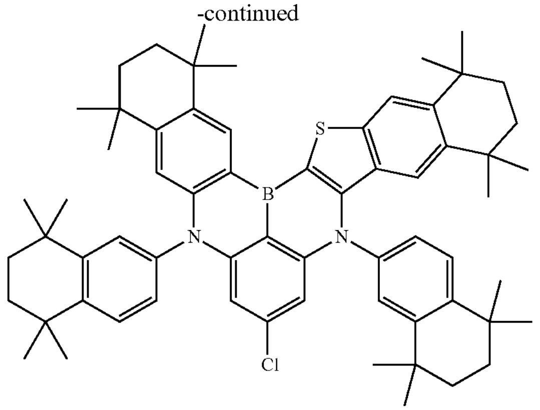

A-15-3

Compound A-15-3 (7.6 g, yield 58%, MS[M+H]+=952) was obtained in the same manner as in Synthesis Example 4 except that Compound A-15-2 (9.7 g. 1 eq.) was used instead of Compound A-2-3.

Synthesis Example 48. Synthesis of Compound A-15

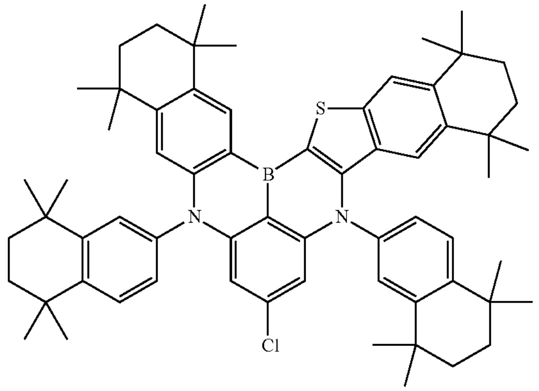

A-15-3

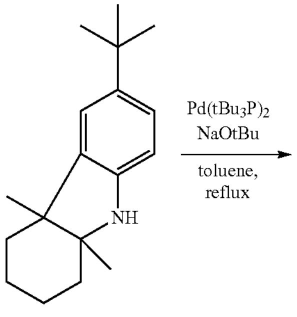

S-26

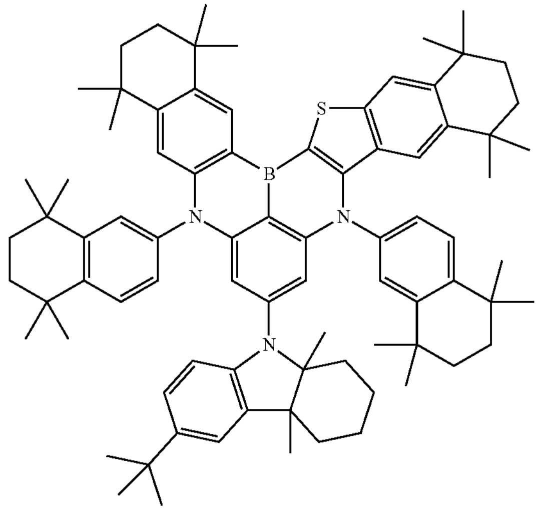

A-15

Compound A-15 (4.1 g, yield 71%, MS[M+H]+=1173) was obtained in the same manner as in Synthesis Example 3 except that Compounds A-15-3 (1 eq.) and 5-26 (1.2 eq.) were used instead of Compounds A-2-1 and A-2-2.

Synthesis Example 49. Synthesis of Compound A-16-1

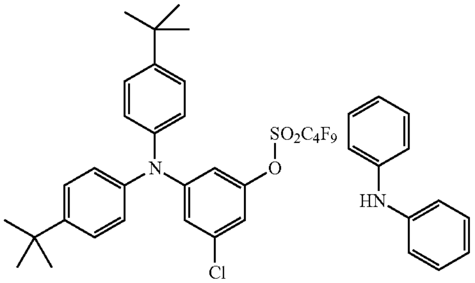

A-14-1

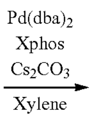

-continued

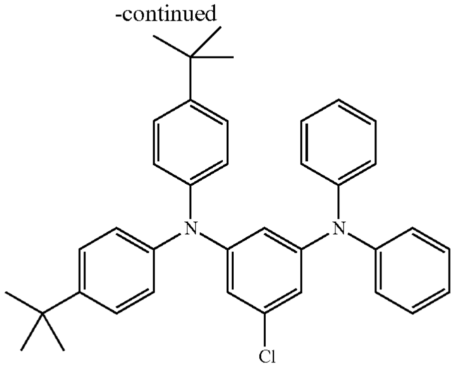

A-16-1

Compound A-16-1 (18.7 g, yield 73%, MS[M+H]+=559) was obtained in the same manner as in Synthesis Example 42 except that diphenylamine was used instead of Compound A-4-2.

Synthesis Example 50. Synthesis of Compound A-16-3

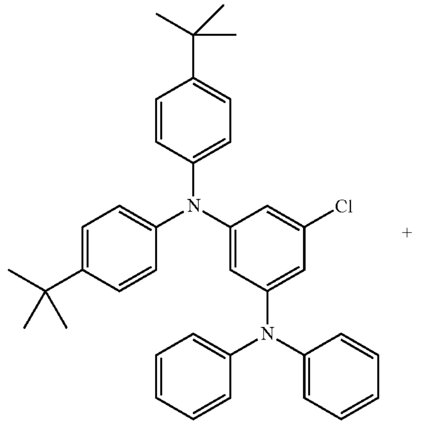

A-16-1

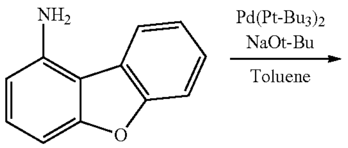

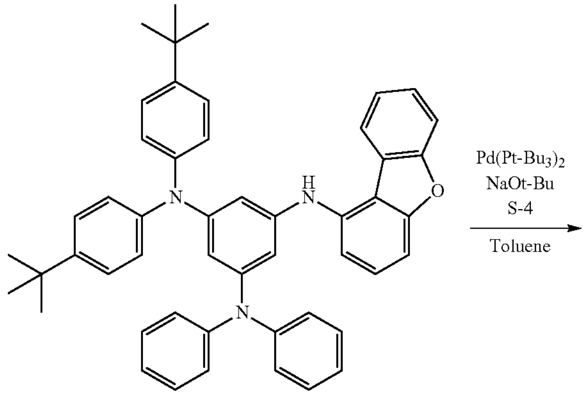

A-16-2

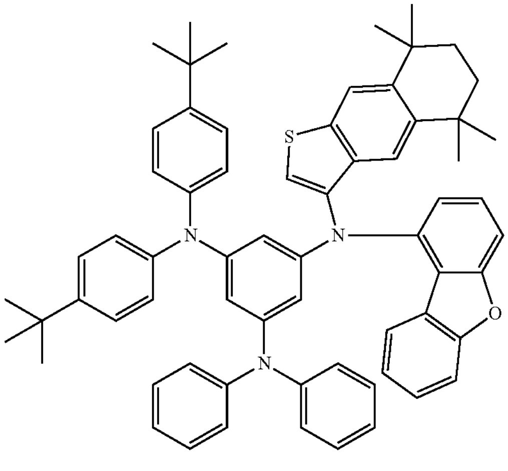

A-16-3

Compound A-16-3 (15.7 g, yield 58%, MS[M+H]+=949) was obtained in the same manner as in Synthesis Example 11 except that Compound A-16-1 (16 g, 1 eq.), dibenzo[b, d]furan-1-amine and Compound S-4 were used instead of Compounds A-1-1, S-9 and S-10.

Synthesis Example 51. Synthesis of Compound A-16

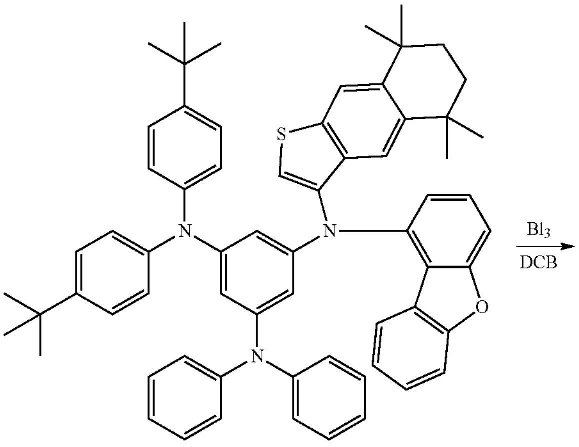

A-16-3

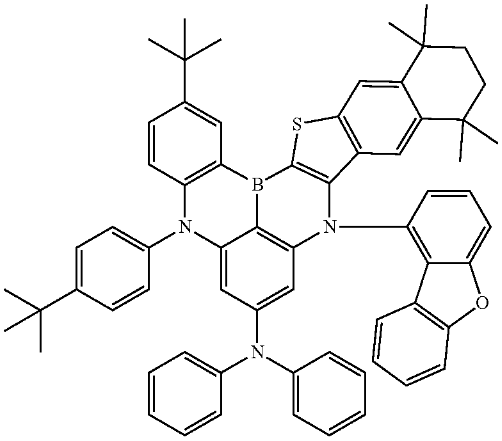

A-16

Compound A-16 (2.1 g, yield 21%, MS[M+H]+=957) was obtained in the same manner as in Synthesis Example 4 except that Compound A-16-3 (10 g. 1 eq.) was used instead of Compound A-2-3.

Synthesis Example 52. Synthesis of Compound B-1-1

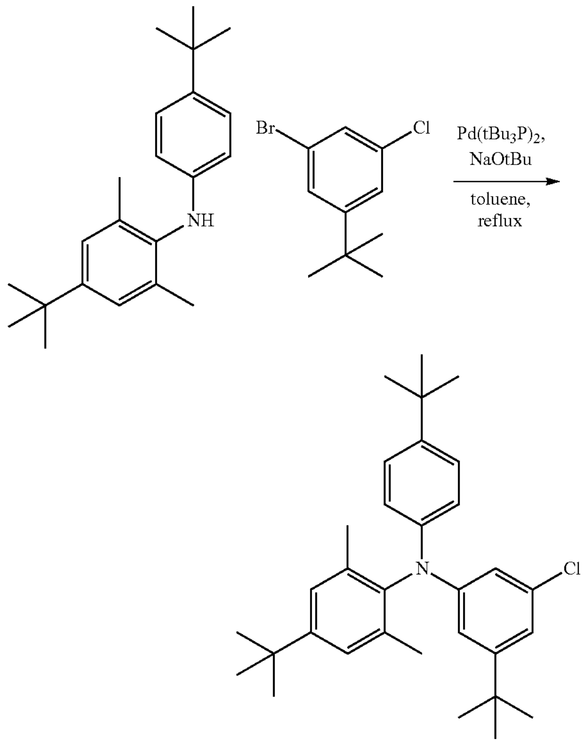

B-1-1

After dissolving 1-bromo-3-chloro-5-tert-butylbenzene (121 mmol, 30 g) and 4-tert-butyl-N-(4-tert-butylphenyl)-2,6-dimethylaniline (121 mmol, 37.5 g) in toluene (0.2 M, 605 ml) in a 3-neck flask, sodium tert-butoxide (182 mmol, 17.5 g) and bis(tri-tert-butylphosphine)palladium(0) (1.2 mmol, 0.62 g) were introduced thereto, and the result was stirred for 4 hours under reflux under an argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound B-1-1 (51.2 g, yield 89%, MS[M+H]+=476).

Synthesis Example 53. Synthesis of Compound B-1-2

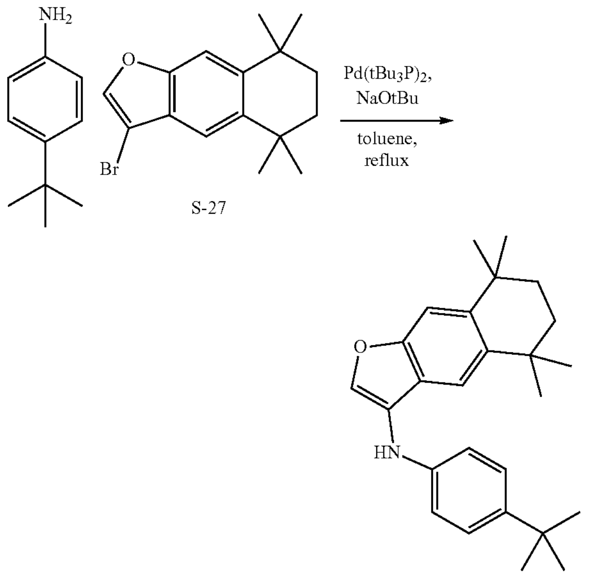

S-27

B-1-2

After dissolving Compound S-27 (97.6 mmol, 30 g) and 4-tert-butylaniline (97.6 mmol, 14.6 g) in toluene (0.2 M, 488 ml) in a 3-neck flask, sodium tert-butoxide (146.5 mmol, 14.1 g) and bis(tri-tert-butylphosphine) palladium (0) (0.98 mmol, 0.5 g) were introduced thereto, and the result was stirred for 6 hours under reflux under an argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound B-1-2 (35.4 g, yield 97%, MS[M+H]+=376).

Synthesis Example 54. Synthesis of Compound B-1-3

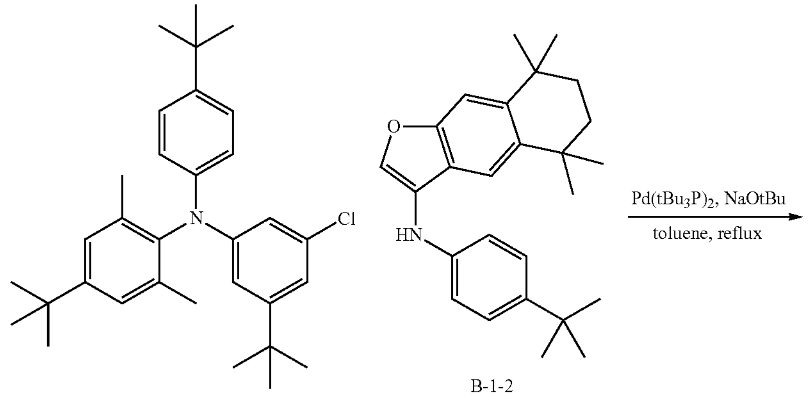

B-1-2

B-1-1

-continued

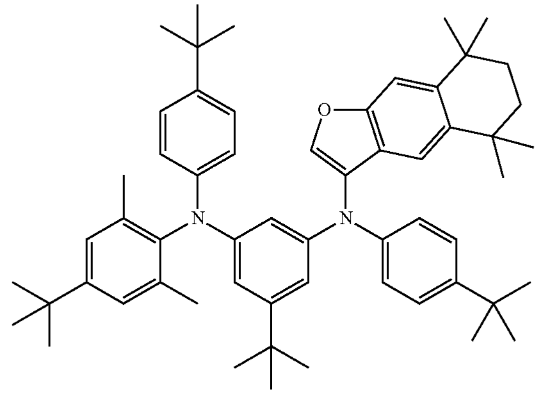

B-1-3

After dissolving Compound B-1-1 (44.1 mmol, 21 g) and Compound B-1-2 (44.1 mmol, 16.6 g) in toluene (0.2 M, 220 ml) in a 3-neck flask, sodium tert-butoxide (66.2 mmol, 6.4 g) and bis(a tri-tert-butylphosphine)palladium(0) (0.44 mmol, 0.23 g) were introduced thereto, and the result was stirred for 6 hours under reflux under an argon atmosphere. When the reaction was finished, the result was cooled to room temperature, then $H_2O$ was introduced thereto, and the reaction solution was transferred to a separatory funnel and extracted. The extract was dried with $MgSO_4$ and concentrated, and the sample was purified using silica gel column chromatography to obtain Compound B-1-3 (21.8 g, yield 61%, MS[M+H]+=815).

Synthesis Example 55. Synthesis of Compound B-1

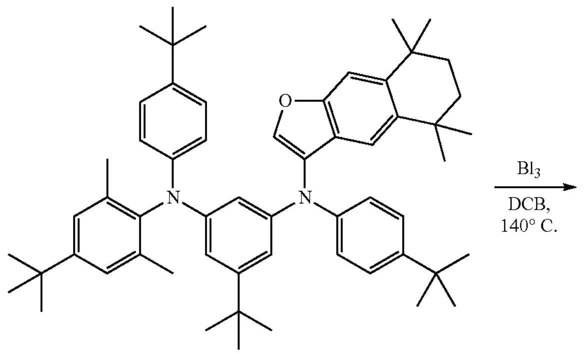

B-1-3

-continued

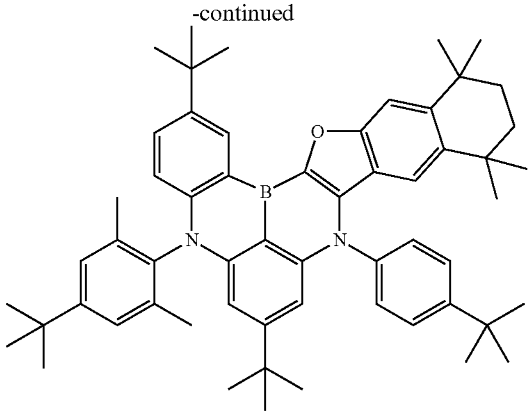

B-1

Compound B-1 (5.3 g, yield 21%, MS[M+H]+=957) was obtained in the same manner as in Synthesis Example 4 except that Compound B-1-3 (21.8 g. 1 eq.) was used instead of Compound A-2-3, and the stirring was conducted at 140° C.

Synthesis Example 56. Synthesis of Compound B-2-1

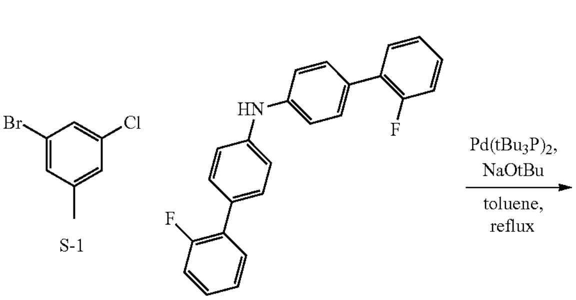

S-1

S-28

-continued
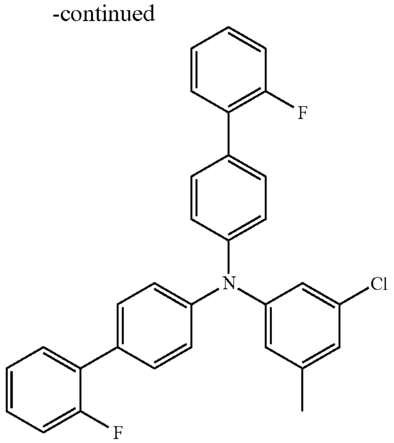
B-2-1
Compound B-2-1 (15.2 g, yield 88%, MS[M+H]+=482) was obtained in the same manner as in Synthesis Example 1 except that Compound S-28 was used instead of Compound S-2.
Synthesis Example 57. Synthesis of Compound B-2
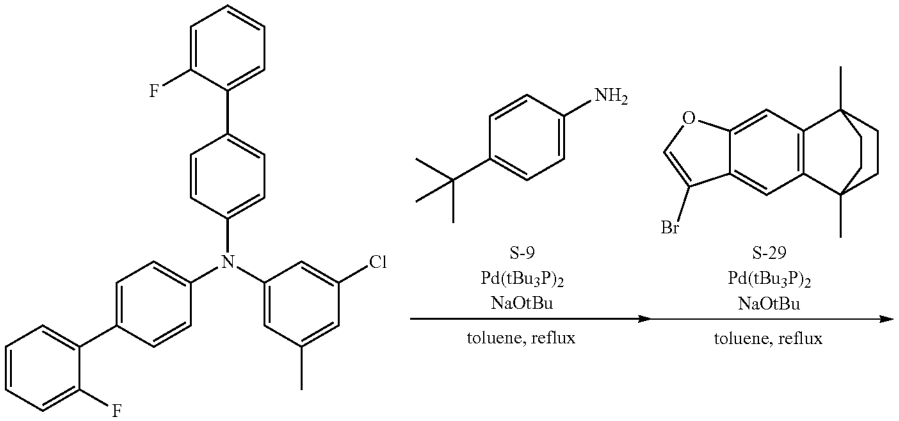
B-2-1
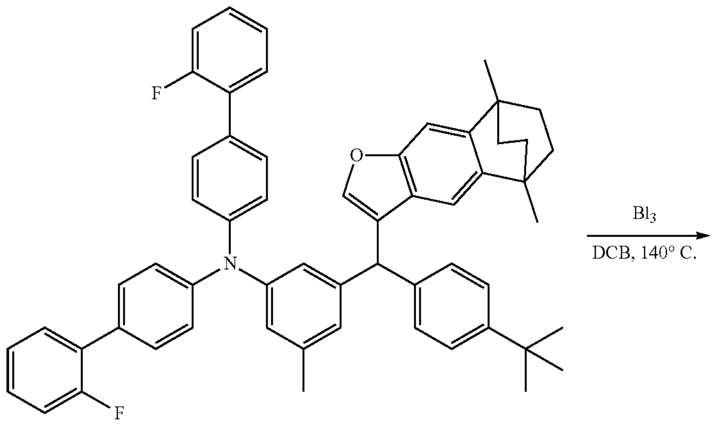
B-2-2

-continued

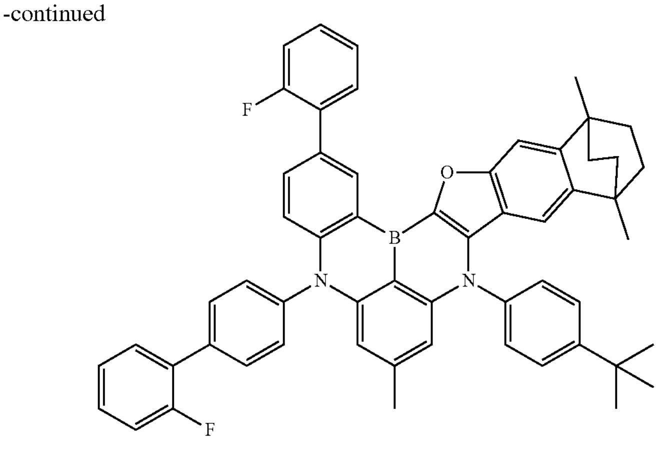

B-2

Compound B-2-2 (12.6 g, yield 47%, MS[M+H]+=819) was obtained in the same manner as in Synthesis Example 11 except that Compounds B-2-1 (15 g, 1 eq.) and 5-29 were used instead of Compounds A-1-1 and 5-10.

Compound B-2 (3.5 g, yield 38%, MS[M+H]+=827) was obtained in the same manner as in Synthesis Example 55 except that Compound B-2-2 (9 g. 1 eq.) was used instead of Compound B-1-3.

Synthesis Example 58. Synthesis of Compound B-3-1

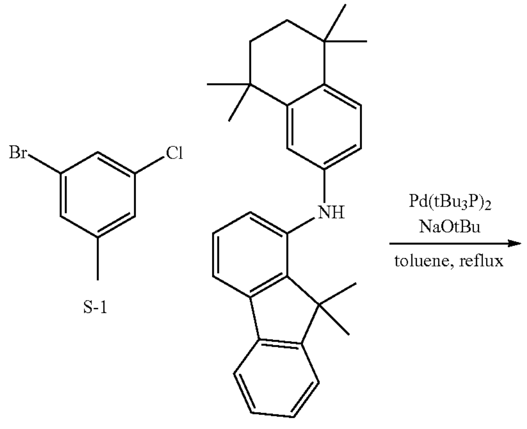

S-1

S-30

-continued

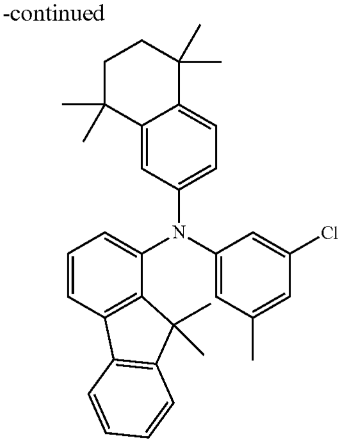

B-3-1

Compound B-3-1 (11.1 g, yield 78%, MS[M+H]+=520) was obtained in the same manner as in Synthesis Example 1 except that Compound S-30 was used instead of Compound S-2.

Synthesis Example 59. Synthesis of Compound B-3

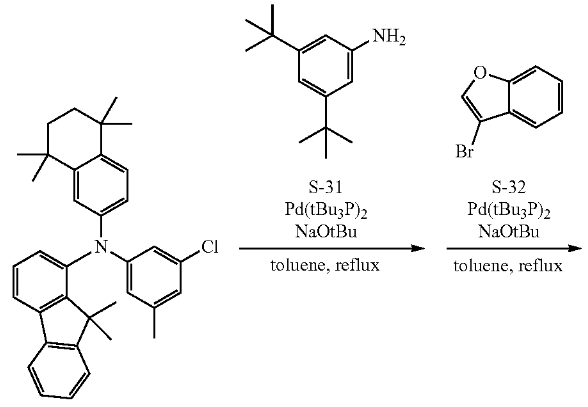

B-3-1

-continued

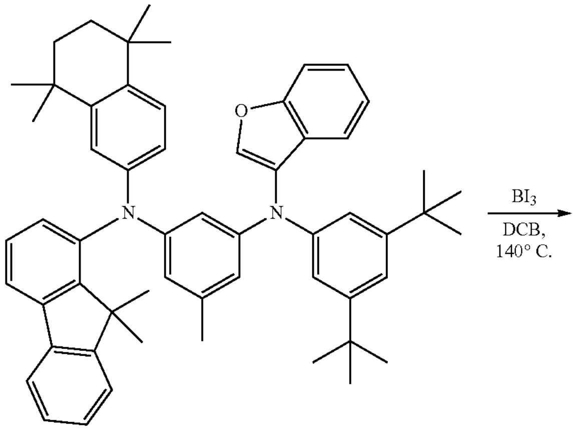

B-3-2

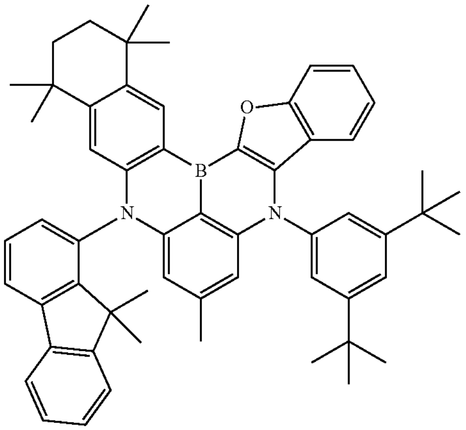

B-3

Compound B-3-2 (8.7 g, yield 56%, MS[M+H]+=806) was obtained in the same manner as in Synthesis Example 11 except that Compounds B-3-1 (10 g, 1 eq.), S-31 and S-32 were used instead of Compounds A-1-1, S-9 and S-10.

Compound B-3 (2.3 g, yield 26%, MS[M+H]+=813) was obtained in the same manner as in Synthesis Example 55 except that Compound B-3-2 (8.7 g. 1 eq.) was used instead of Compound B-1-3.

Synthesis Example 60. Synthesis of Compound B-4-1

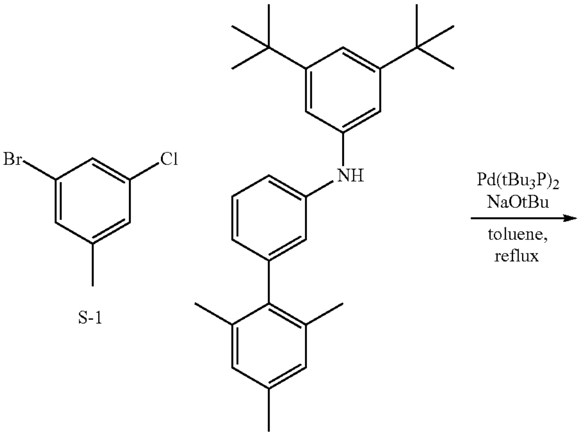

S-1

S-33

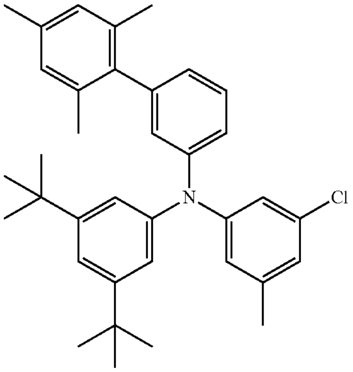

B-4-1

Compound B-4-1 (16.3 g, yield 73%, MS[M+H]+=524) was obtained in the same manner as in Synthesis Example 1 except that Compound 5-33 was used instead of Compound S-2.

Synthesis Example 61. Synthesis of Compound B-4

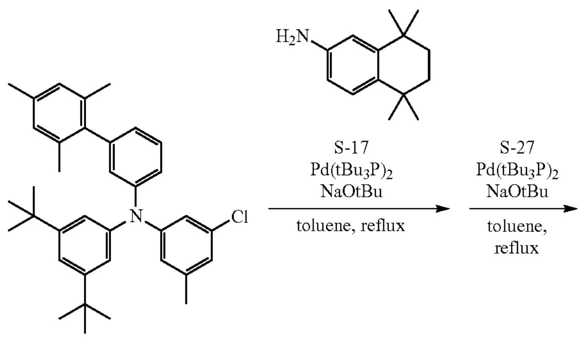

B-4-1

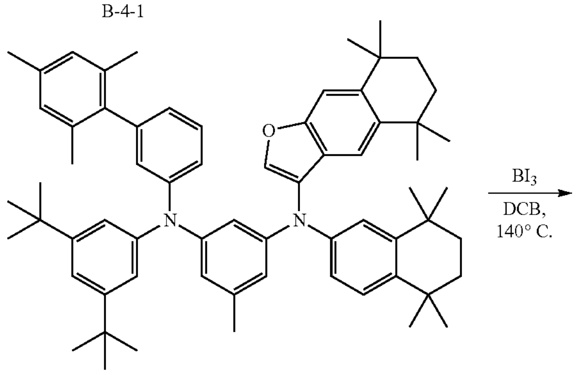

B-4-2

-continued

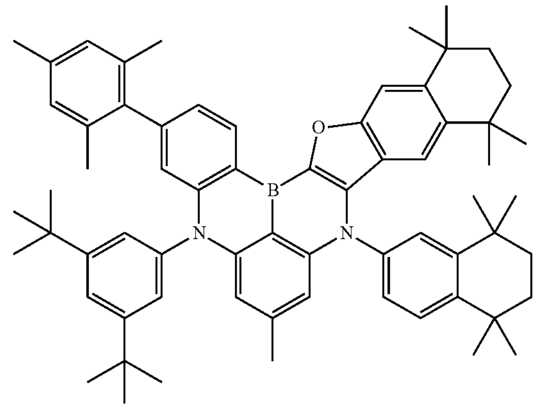

B-4

Compound B-4-2 (12.8 g, yield 52%, MS[M+H]+=918) was obtained in the same manner as in Synthesis Example 11 except that Compounds B-4-1 (14 g, 1 eq.), S-17 and 5-27 were used instead of Compounds A-1-1, S-9 and S-10.

Compound B-4 (2.8 g, yield 25%, MS[M+H]+=926) was obtained in the same manner as in Synthesis Example 55 except that Compound B-4-2 (11 g. 1 eq.) was used instead of Compound B-1-3.

Synthesis Example 62. Synthesis of Compound B-5-1

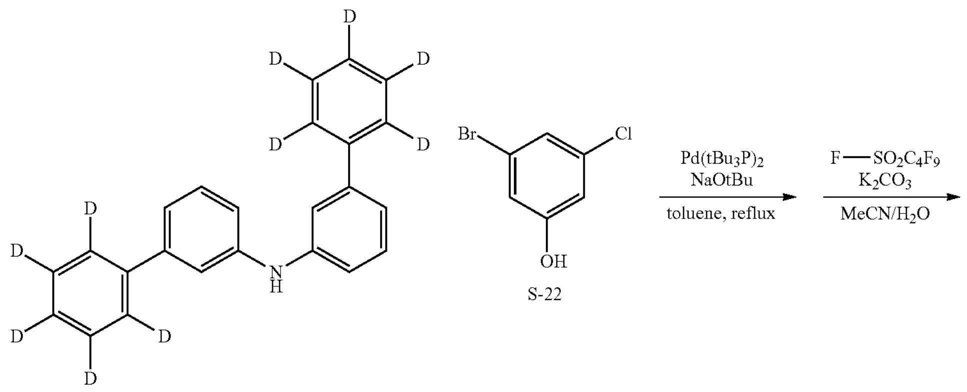

S-22

S-34

-continued

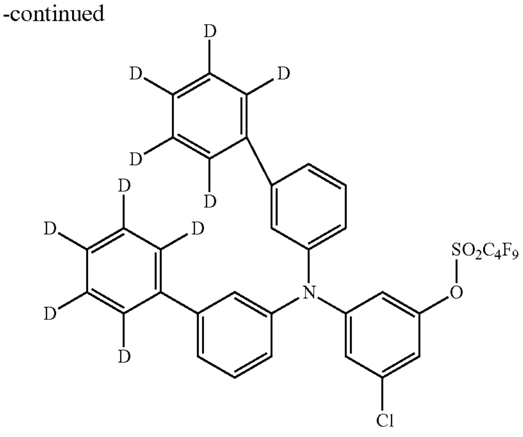

B-5-1

Compound B-5-1 (19.1 g, yield 79%) was obtained in the same manner as in Synthesis Example 41 except that Compound S-34 was used instead of Compound S-2.

Synthesis Example 63. Synthesis of Compound B-5-2

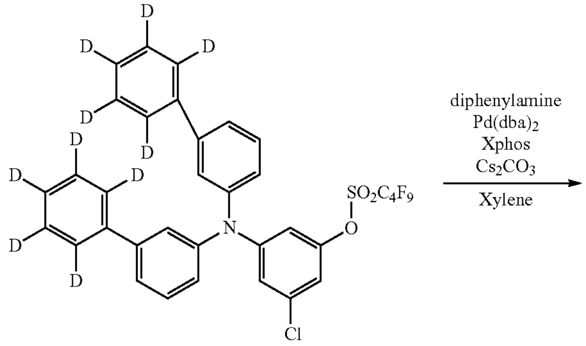

B-5-1

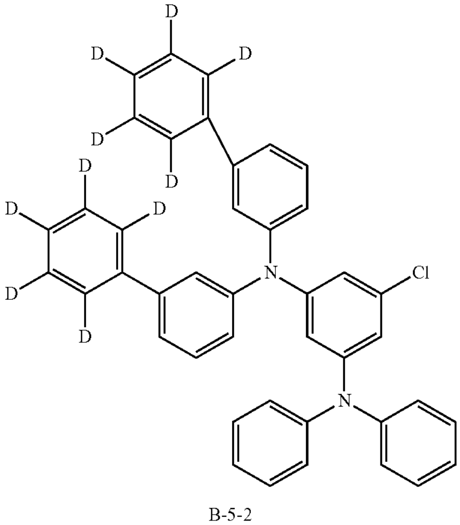

B-5-2

Compound B-5-2 (10.7 g, yield 72%, MS[M+H]+=609) was obtained in the same manner as in Synthesis Example 42 except that Compound B-5-1 (18 g, 1 eq.) and diphenylamine were used instead of Compounds A-14-1 and A-4-2.

Synthesis Example 64. Synthesis of Compound B-5

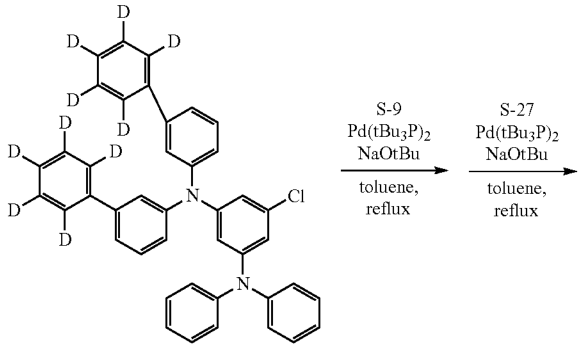

B-5-2

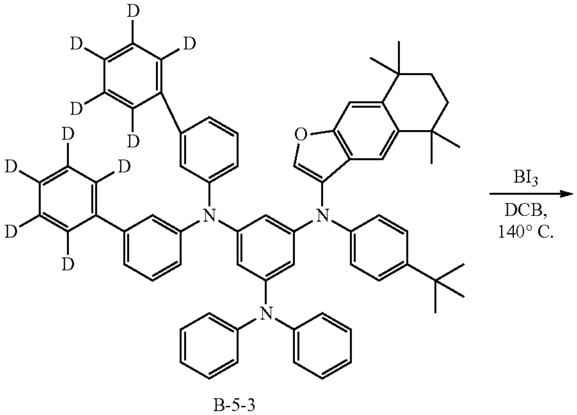

B-5-3

-continued

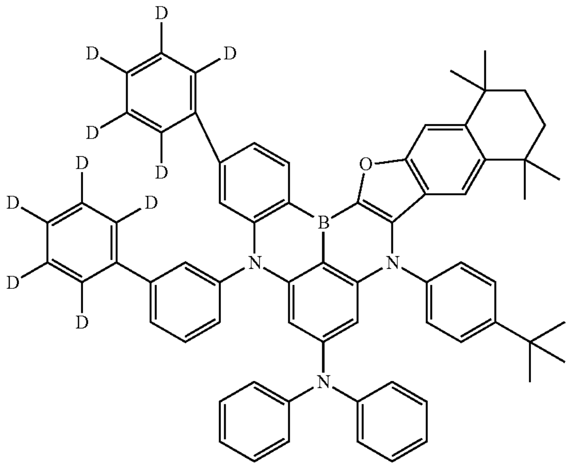

B-5

Compound B-5-3 (7.8 g, yield 47%, MS[M+H]+=949) was obtained in the same manner as in Synthesis Example 11 except that Compounds B-5-2 (10.7 g, 1 eq.) and S-27 were used instead of Compounds A-1-1 and S-10.

Compound B-5 (1.7 g, yield 21%, MS[M+H]+=957) was obtained in the same manner as in Synthesis Example 55 except that Compound B-5-3 (7.8 g. 1 eq.) was used instead of Compound B-1-3.

Synthesis Example 65. Synthesis of Compound B-6-1

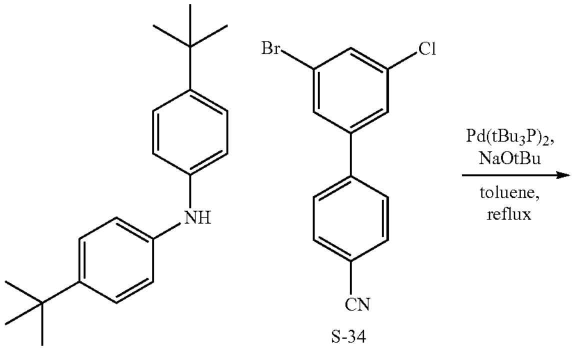

S-34

-continued

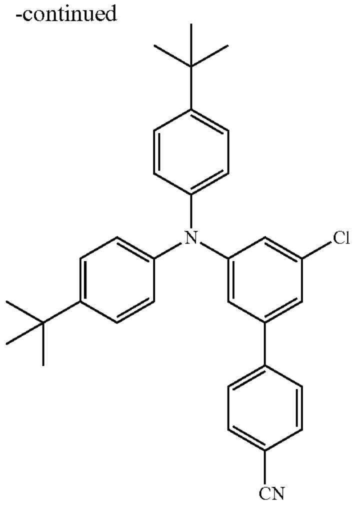

B-6-1

Compound B-6-1 (20.1 g, yield 80%, MS[M+H]+=493) was obtained in the same manner as in Synthesis Example 1 except that Compound S-34 was used instead of Compound S-1.

Synthesis Example 66. Synthesis of Compound B-6-2

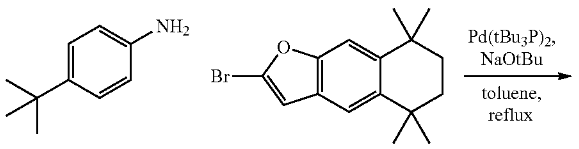

S-35

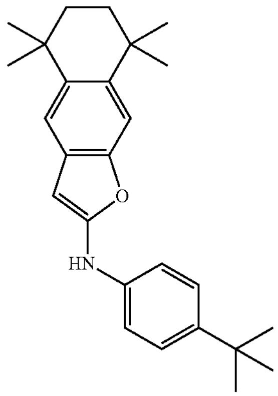

B-6-2

Compound B-6-2 (20.6 g, yield 70%, MS[M+H]+=376) was obtained in the same manner as in Synthesis Example 53 except that Compound S-35 was used instead of Compound S-27.

Synthesis Example 67. Synthesis of Compound B-6

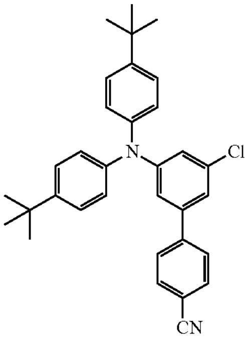

B-6-1

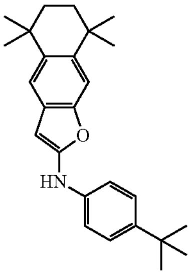

B-6-2

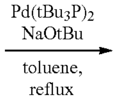

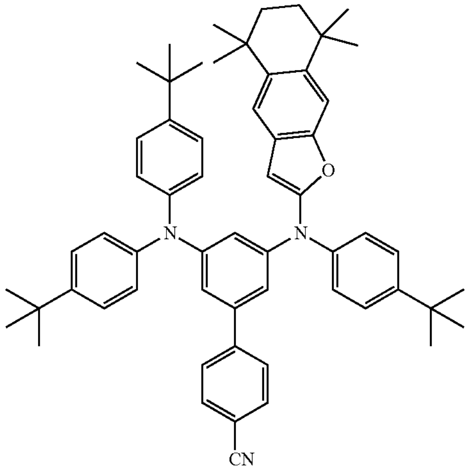

B-6-3

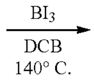

-continued

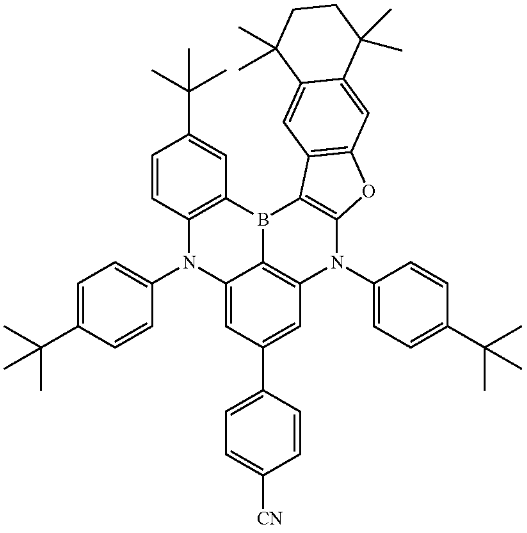

B-6

Compound B-6-3 (21.2 g, yield 69%, MS[M+H]+=833) was obtained in the same manner as in Synthesis Example 3 except that Compounds B-6-1 (19.4 g. 1 eq.) and B-6-2 were used instead of Compounds A-2-1 and A-2-2.

Compound B-6 (1.3 g, yield 12%, MS[M+H]+=841) was obtained in the same manner as in Synthesis Example 55 except that Compound B-6-3 (11 g. 1 eq.) was used instead of Compound B-1-3.

Synthesis Example 68. Synthesis of Compound A-17

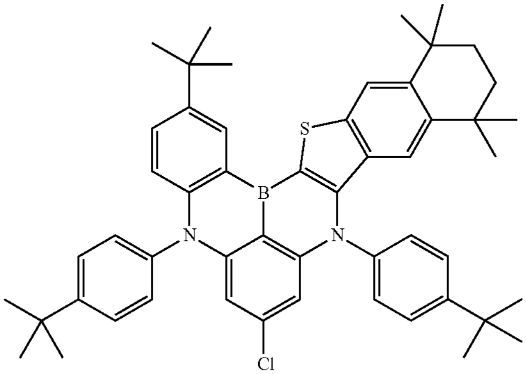

A-14-3

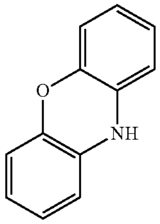

S-35

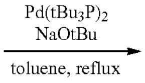

-continued

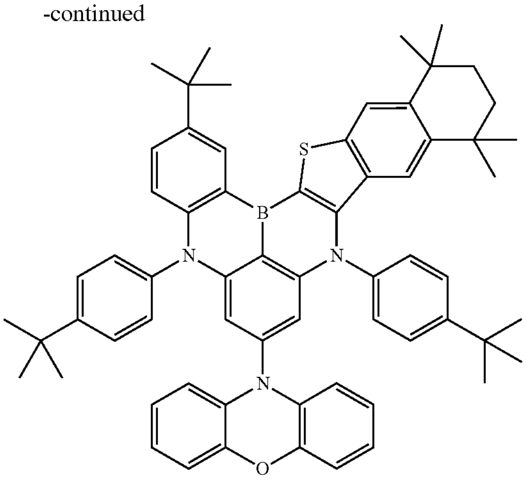

A-17

Compound A-17 (1.9 g, yield 78%, MS[M+H]+=937) was obtained in the same manner as in Synthesis Example 3 except that Compounds A-14-3 (2 g. 1 eq.) and S-35 (0.6 g, 1.2 eq.) were used instead of Compounds A-2-1 and A-2-2.

Synthesis Example 69. Synthesis of Compound E-1

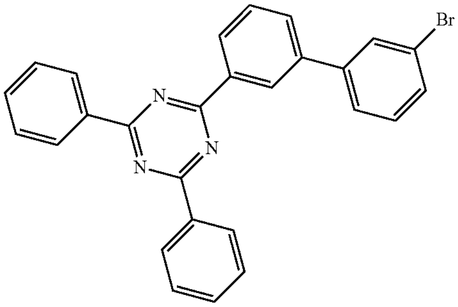

E-1-1

+

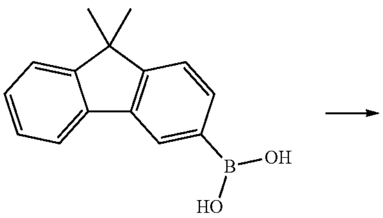

E-1-2

-continued

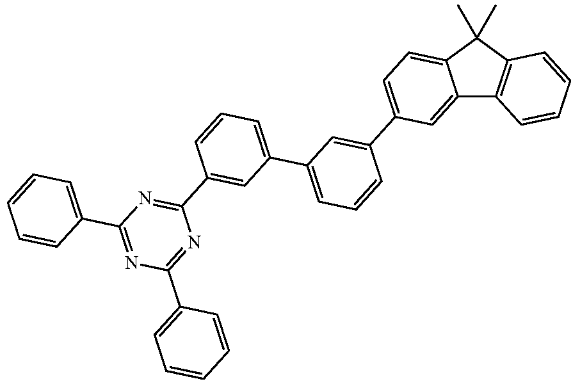

E-1

E-1-1 (20 g, 43.1 mmol) and E-1-2 (10.3 g, 43.1 mmol) were introduced to tetrahydrofuran (400 ml), and stirred and refluxed under the nitrogen atmosphere. After that, potassium carbonate (17.9 g, 129.2 mmol) dissolved in water (18 ml) was introduced thereto, and after sufficiently stirring the result, tetrakistriphenyl-phosphinopalladium (1.5 g, 1.3 mmol) was introduced thereto. The result was reacted for 1 hour, then cooled to room temperature, and, after separating the organic layer and the water layer, the organic layer was distilled. This was introduced and dissolved again in chloroform (20 times, 498 mL), and washed twice with water. The organic layer was separated, stirred after introducing anhydrous magnesium sulfate thereto, then filtered, and the filtrate was vacuum distilled. The concentrated compound was recrystallized with chloroform and ethyl acetate to prepare white sold Compound E-1 (15.7 g, 63%, MS: [M+H]+=578).

Synthesis Example 70: Preparation of Compound E-2

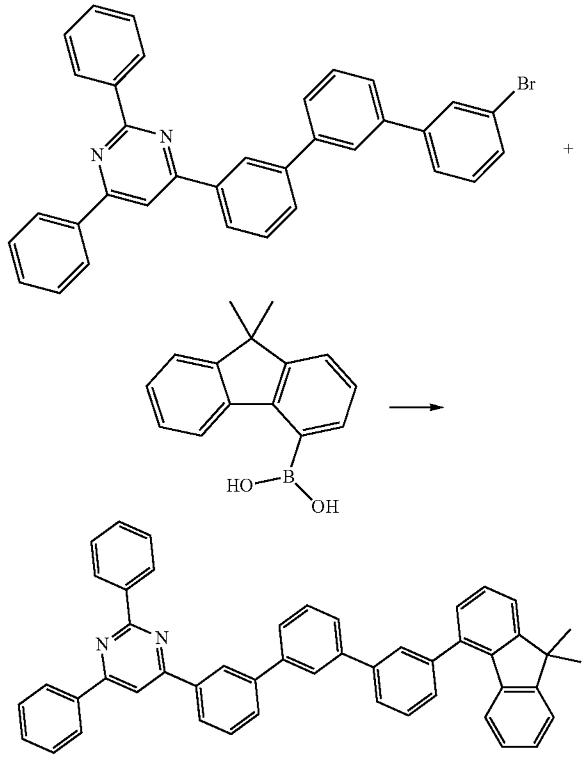

E-2

Compound E-2 was prepared in the same manner as in Synthesis Example 69 except for employing each staring material as in the reaction formula.

MS: $[M+H]^+=653$

Synthesis Example 71: Preparation of Compound E-3

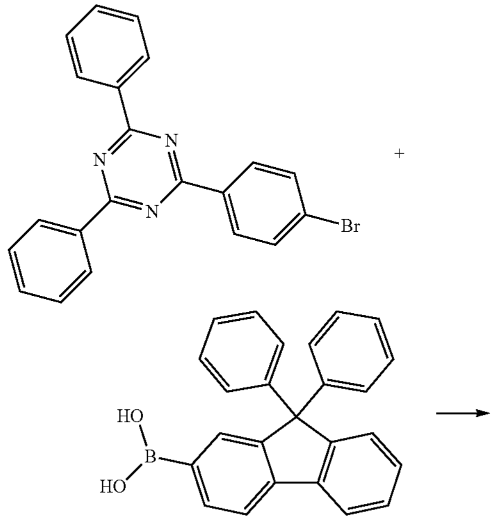

-continued

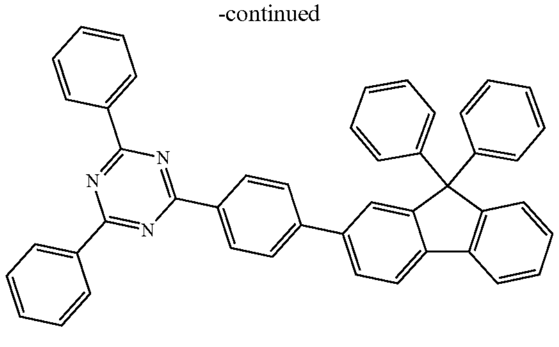

E-3

Compound E-3 was prepared in the same manner as in Synthesis Example 69 except for employing each staring material as in the reaction formula.

MS: $[M+H]^+=626$

Synthesis Example 72: Preparation of Compound E-4

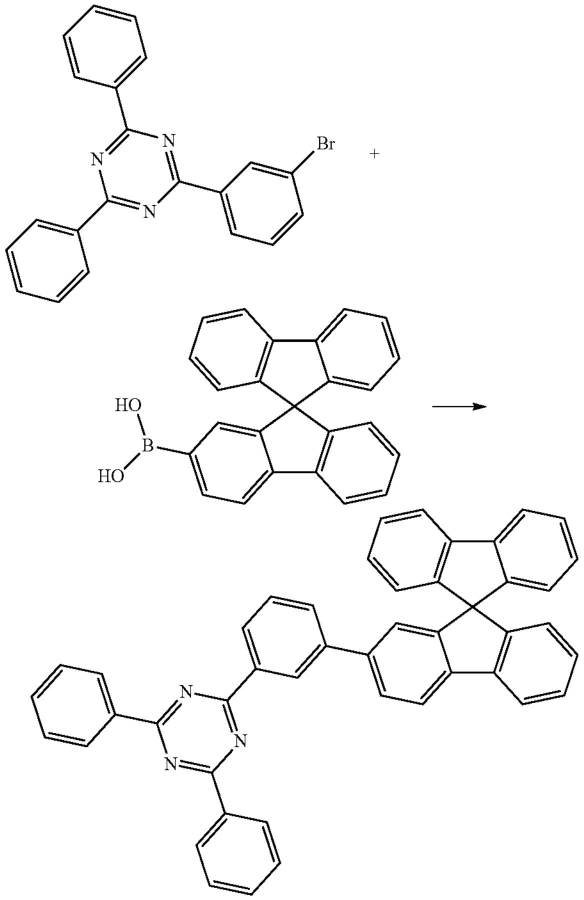

E-4

Compound E-4 was prepared in the same manner as in Synthesis Example 69 except for employing each staring material as in the reaction formula.

MS: $[M+H]^+=624$

Synthesis Example 73: Preparation of Compound E-5

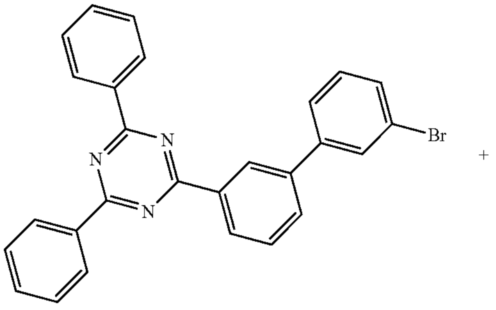

E-5-1

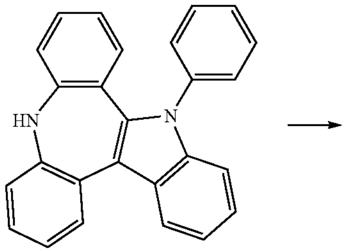

E-5-2

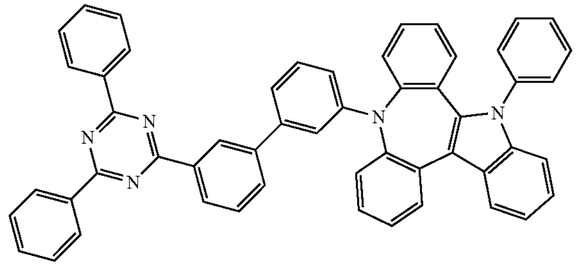

E-5

E-5-1 (20 g, 43.1 mmol) and E-5-2 (15.4 g, 43.1 mmol) were introduced to xylene (400 ml), and stirred and refluxed under the nitrogen atmosphere. After that, sodium tertiary-butoxide (12.4 g, 129.2 mmol) was introduced thereto, and after sufficiently stirring the result, bis(tri-tertiary-butylphosphine)palladium (0.7 g, 1.3 mmol) was introduced thereto. The result was reacted for 3 hours, then cooled to room temperature, and the organic layer was filtered to remove the salts, and the filtered organic layer was distilled. This was introduced and dissolved again in chloroform (10 times, 320 mL), and washed twice with water. The organic layer was separated, stirred after introducing anhydrous magnesium sulfate thereto, then filtered, and the filtrate was vacuum distilled. The concentrated compound was purified through a silica column using chloroform and ethyl acetate to prepare white sold Compound E-5 (20.4 g, 64%, MS: [M+H]+=742).

EXAMPLE

Example 1-1

A glass substrate on which indium tin oxide (ITO) was coated as a thin film to a thickness of 1,000 Å was placed in distilled water containing dissolved detergent and ultrasonically cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonically cleaned with solvents of isopropyl alcohol, acetone and methanol, then dried, and then transferred to a plasma cleaner. The substrate was cleaned for 5 minutes using oxygen plasma, and then transferred to a vacuum deposition apparatus.

On the transparent ITO electrode prepared as above, the following HI-A compound was thermal vacuum deposited to a thickness of 600 Å to form a hole injection layer. A first hole transfer layer and a second hole transfer layer were formed on the hole injection layer by consecutively vacuum depositing the following HAT compound to 50 Å and the following HT-A compound to 60 Å.

Subsequently, a light emitting layer was formed on the second hole transfer layer by vacuum depositing the following BH compound and Compound A-1 prepared in Synthesis Example 12 in a weight ratio of 25:2 to a film thickness of 200 Å.

On the light emitting layer, a hole blocking layer was formed by vacuum depositing Compound E-1 prepared in Synthesis Example 69 to a thickness of 50 Å, and an electron transfer and injection layer was formed to a thickness of 300 Å by vacuum depositing the following ET-A compound and the following LiQ compound in a weight ratio of 1:1. On the electron transfer and injection layer, a cathode was formed by consecutively depositing lithium fluoride (LiF) to a thickness of 10 Å and aluminum to a thickness of 1000 Å.

In the above-described process, the deposition rates of the organic materials were maintained at 0.4 Å/sec to 0.9 Å/sec, the deposition rates of the lithium fluoride and the aluminum of the cathode were maintained at 0.3 Å/sec and 2 Å/sec, respectively, and the degree of vacuum during the deposition was maintained at $1\times10^{-7}$ torr to $5\times10^{-5}$ torr, and as a result, an organic light emitting device was manufactured.

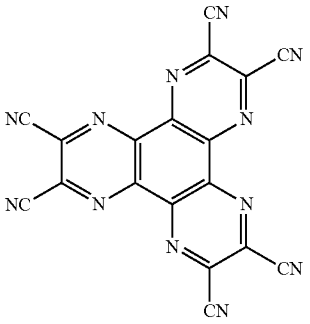

HAT

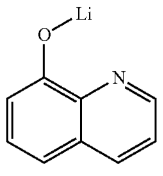

LiQ

-continued
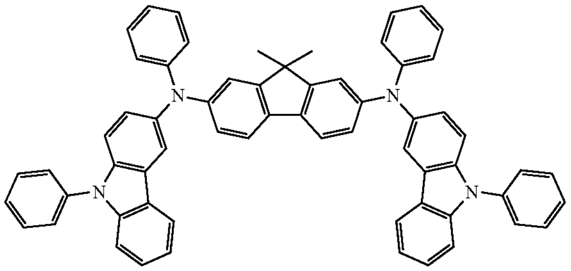
HI-A
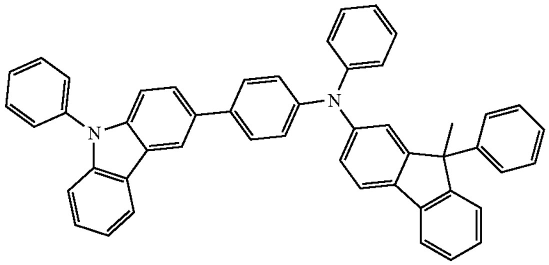
HT-A
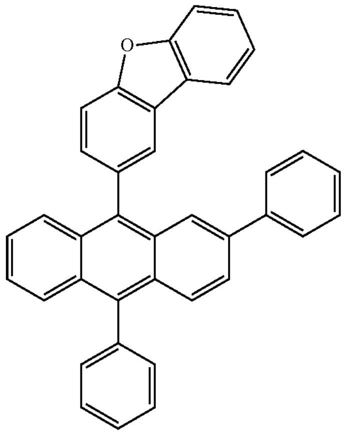
BH
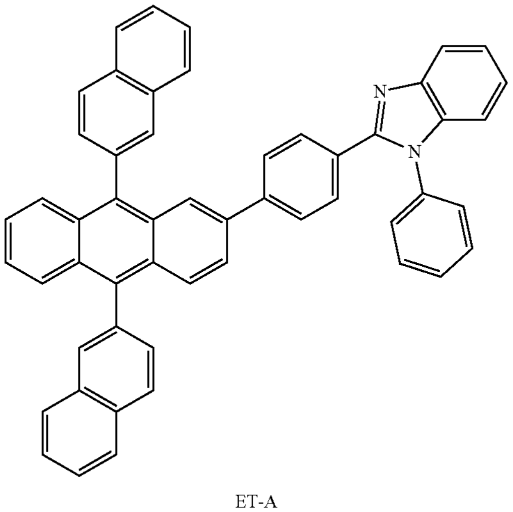 [SMILES: c1ccc(-n2c(-c3ccc(-c4ccc5c(-c6ccc7ccccc7c6)c6ccccc6c(-c6ccc7ccccc7c6)c5c4)cc3)nc3ccccc32)cc1 ; "ET-A"]
ET-A
Examples 1-2 to 1-120
Organic light emitting devices were manufactured in the same manner as in Example 1-1 except that compounds described in the following Table 1 were each used instead of Compounds A-1 and E-1.
A-1
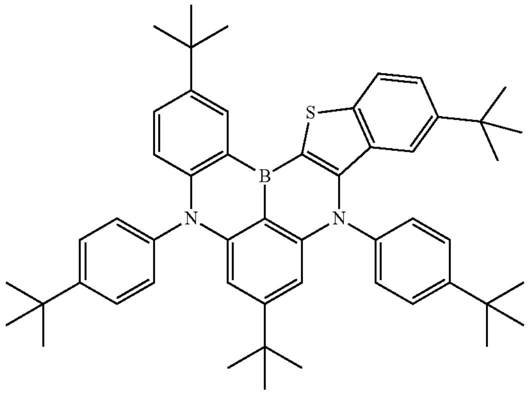
A-2
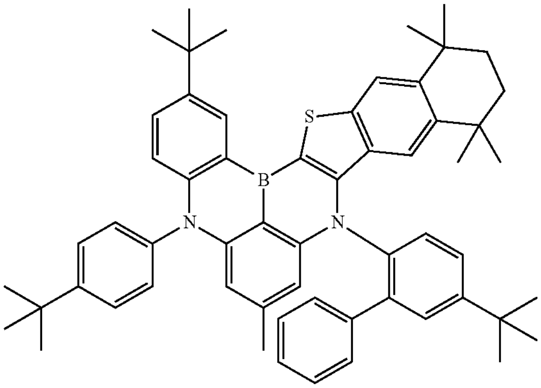
A-3
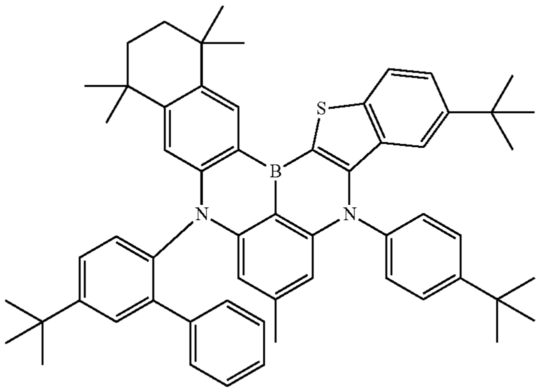

-continued
A-4
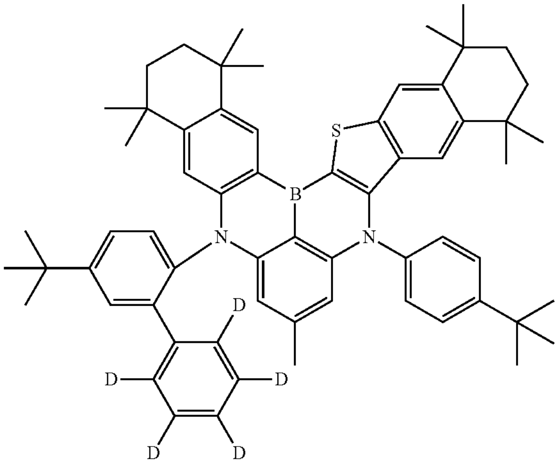
A-5
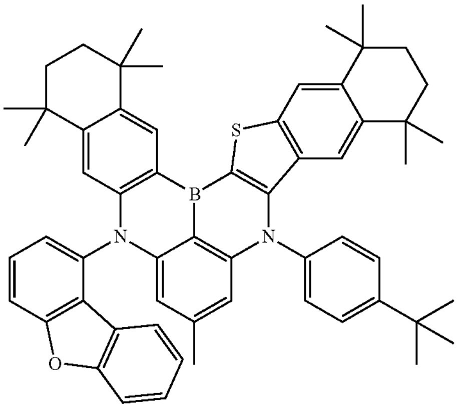
A-6
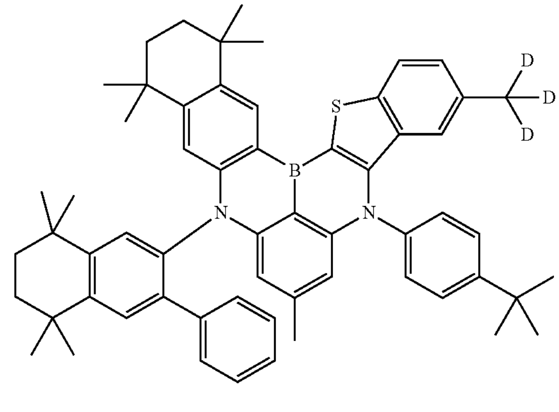
-continued
A-7
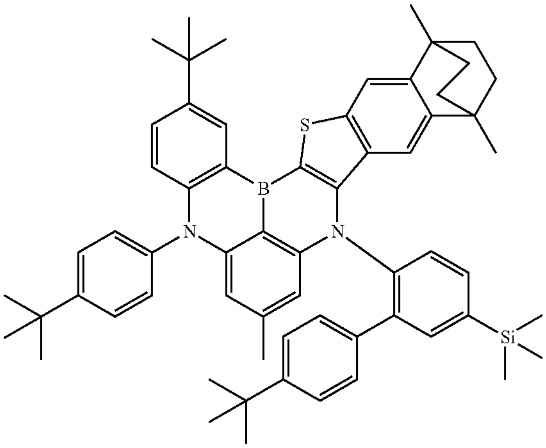
A-8
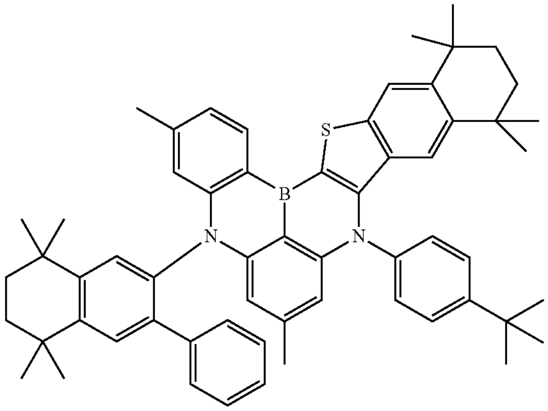
A-9
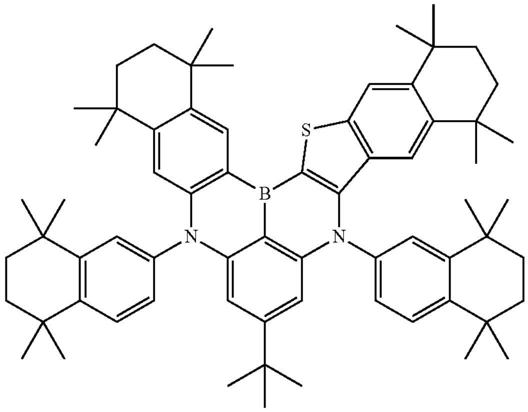

A-10
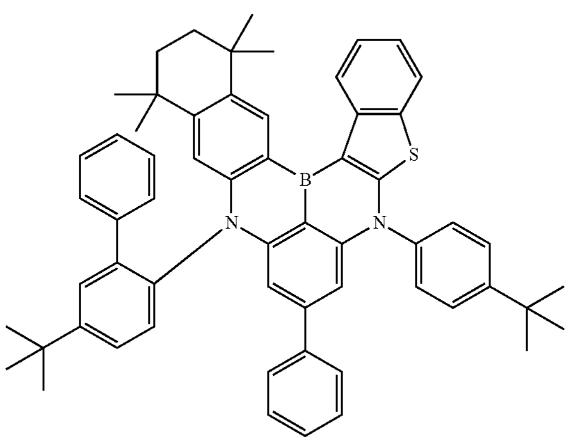
A-11
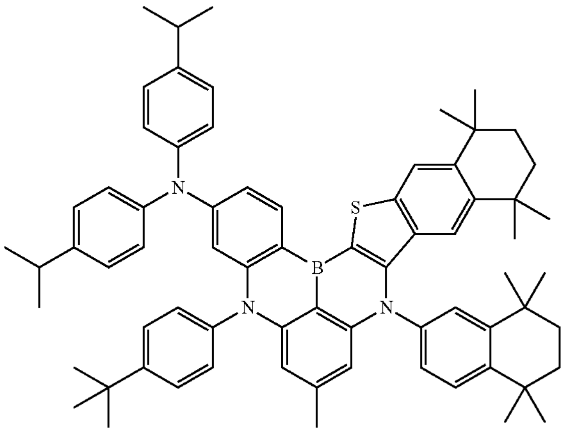
A-12
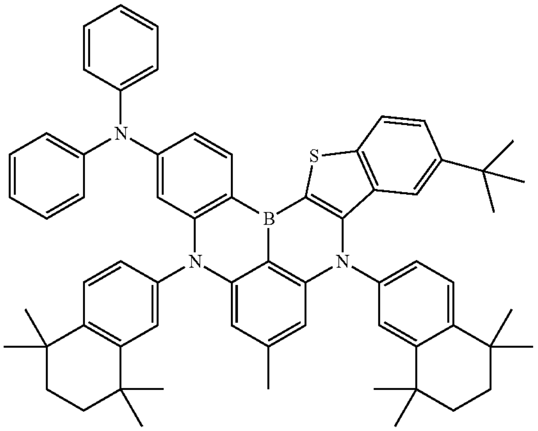
A-13
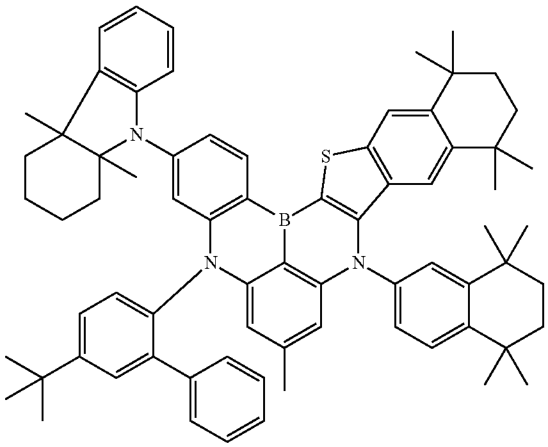
A-14
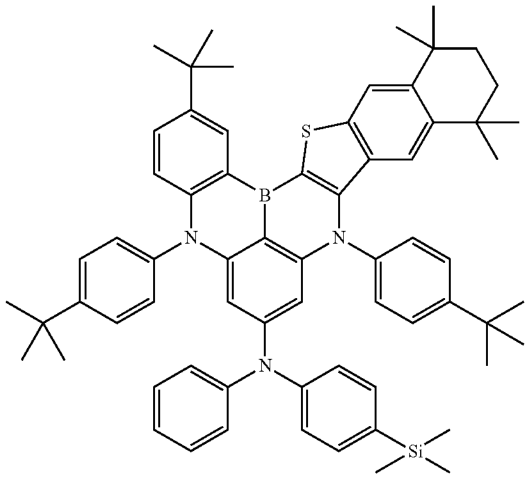
A-15
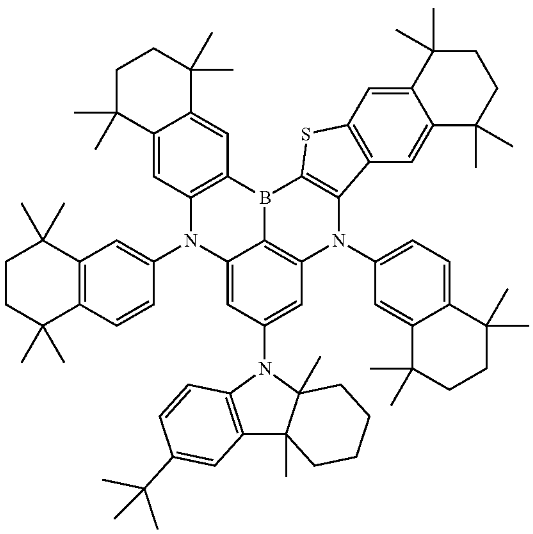

A-16
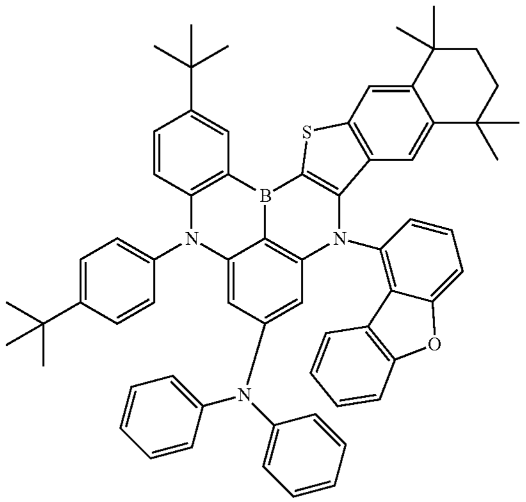
A-17
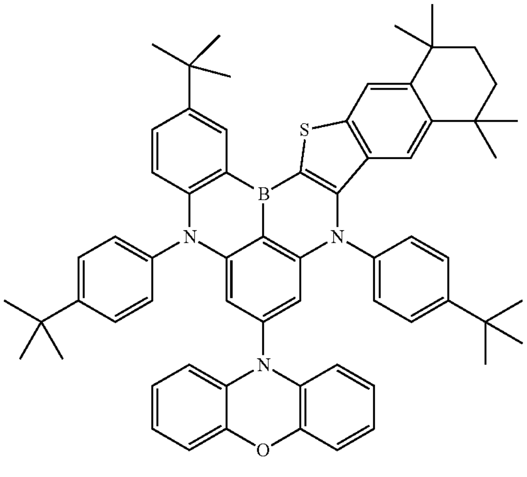
A-18
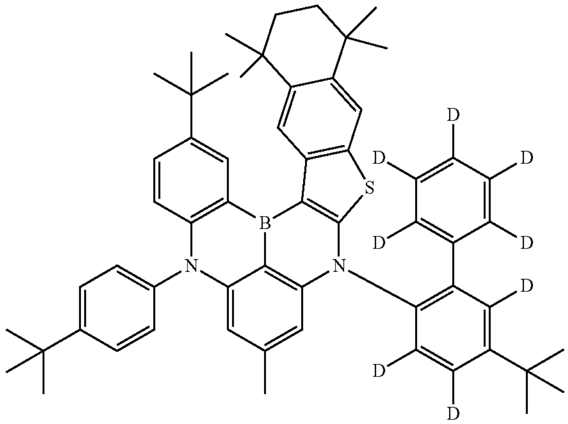
B-1
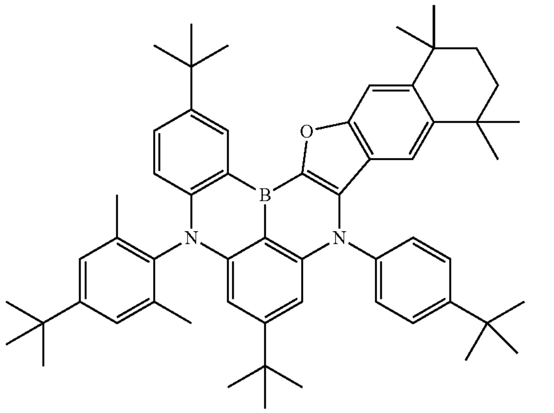
B-2
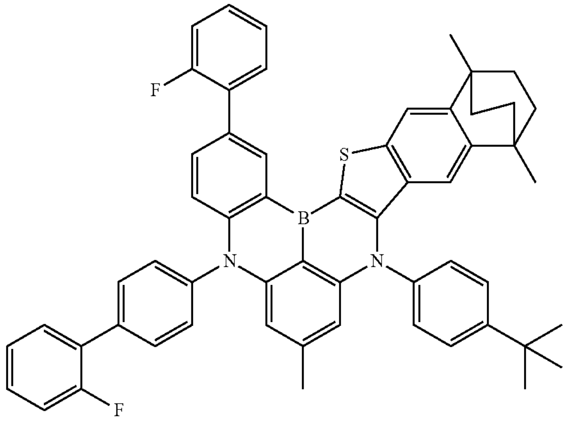
B-3
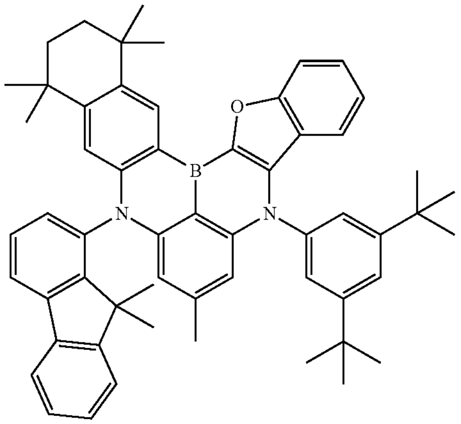

-continued
B-4
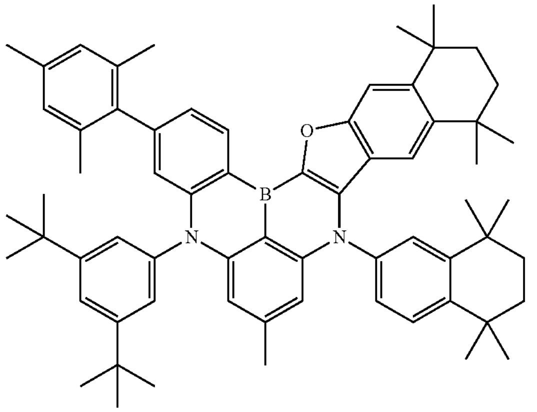
B-5
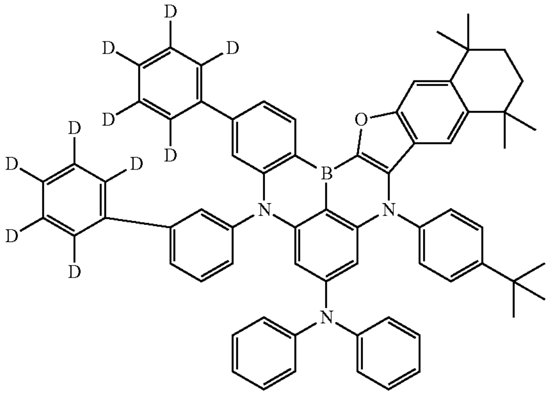
B-6
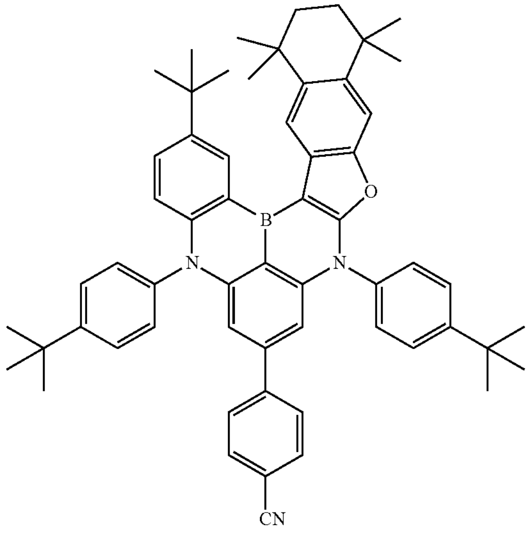
-continued
E-1
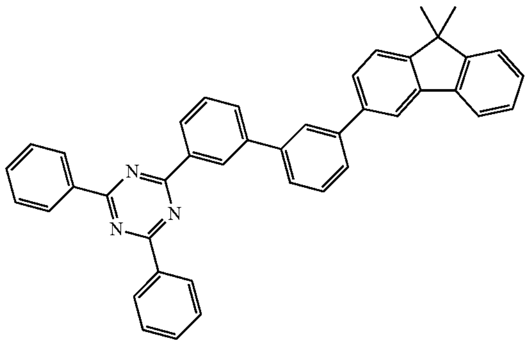
E-2
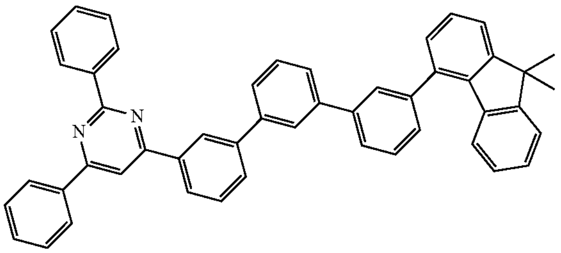
E-3
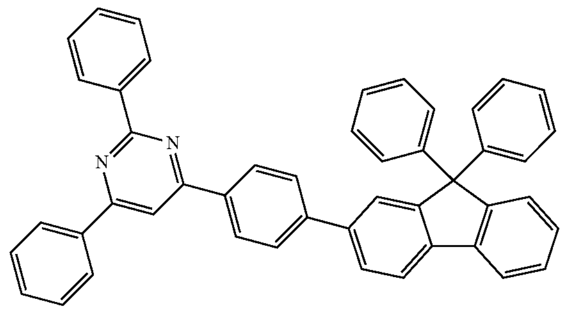
E-4
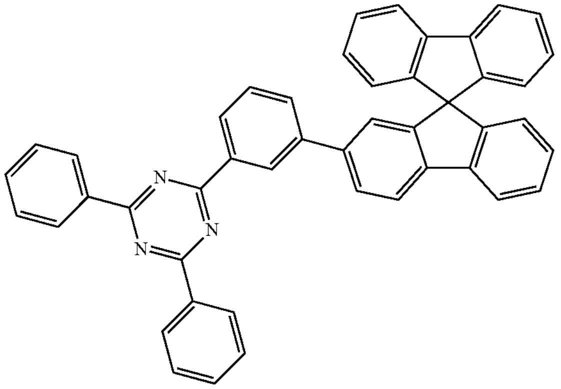

-continued
E-5
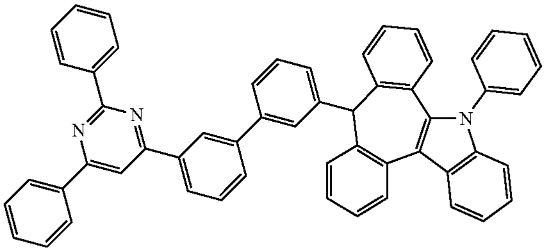
Comparative Examples 1-1 to 1-126
Organic light emitting devices were manufactured in the same manner as in Example 1-1 except that compounds described in the following Table 1 were each used instead of Compounds A-1 and E-1.
BD-A
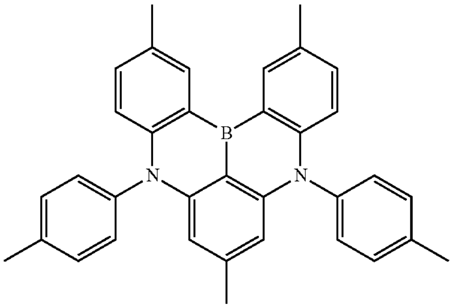
BD-B
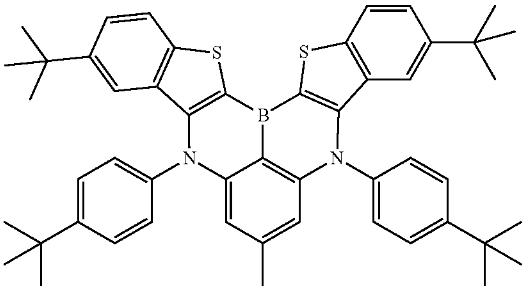
BD-C
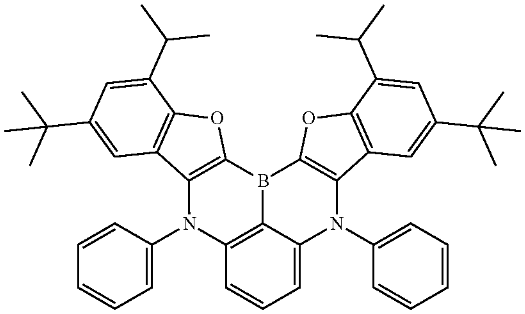
-continued
BD-D
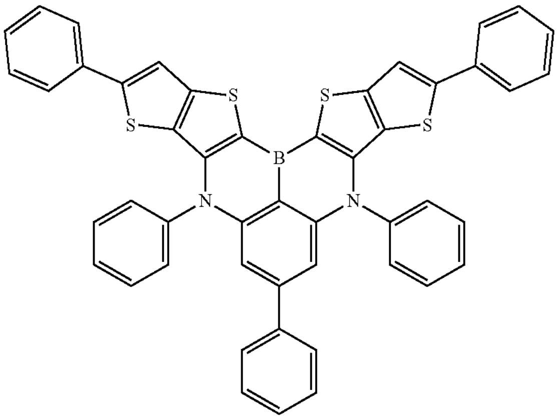
BD-E
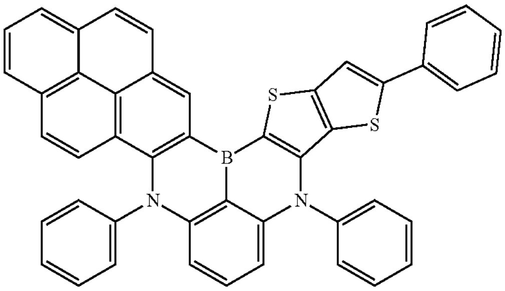
ET-B
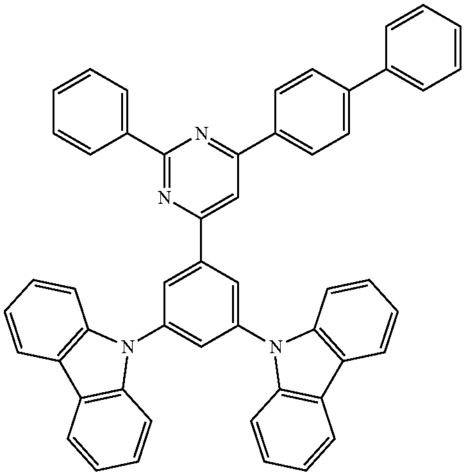
ET-C
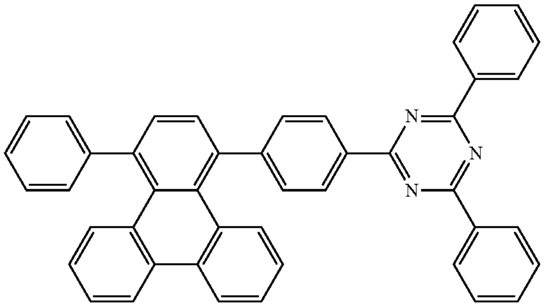

-continued

ET-D

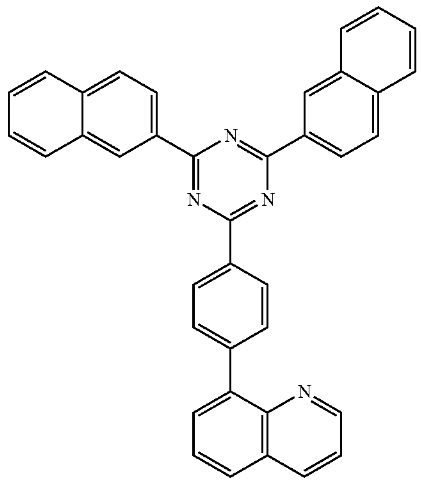

For each of the organic light emitting devices manufactured in Examples 1-1 to 1-120 and Comparative Examples 1-1 to 1-126, driving voltage and light emission efficiency were measured at current density of 10 mA/$cm^2$, and time (T90) taken to become 90% with respect to initial luminance was measured at current density of 20 mA/$cm^2$. The results are shown in the following Table 1.

TABLE 1

| Entry | Dopant | Hole Blocking Layer | Voltage (V@10 mA/$cm^2$) | Efficiency (cd/A@10 mA/$cm^2$) | Color Coordinate (x, y) | Lifetime (h) T90@20 mA/$cm^2$) |
|---|---|---|---|---|---|---|
| Example 1-1 | A-1 | E-1 | 3.75 | 6.09 | (0.135, 0.088) | 224 |
| Example 1-2 | A-2 | E-1 | 3.71 | 6.36 | (0.135, 0.089) | 289 |
| Example 1-3 | A-3 | E-1 | 3.71 | 6.27 | (0.135, 0.087) | 234 |
| Example 1-4 | A-4 | E-1 | 3.75 | 6.46 | (0.135, 0.088) | 302 |
| Example 1-5 | A-5 | E-1 | 3.75 | 6.42 | (0.135, 0.089) | 255 |
| Example 1-6 | A-6 | E-1 | 3.71 | 6.41 | (0.135, 0.087) | 244 |
| Example 1-7 | A-7 | E-1 | 3.71 | 6.22 | (0.135, 0.088) | 232 |
| Example 1-8 | A-8 | E-1 | 3.75 | 6.20 | (0.135, 0.088) | 252 |
| Example 1-9 | A-9 | E-1 | 3.71 | 6.76 | (0.135, 0.089) | 298 |
| Example 1-10 | A-10 | E-1 | 3.71 | 6.11 | (0.135, 0.087) | 240 |
| Example 1-11 | A-11 | E-1 | 3.75 | 6.26 | (0.135, 0.088) | 271 |
| Example 1-12 | A-12 | E-1 | 3.75 | 6.14 | (0.135, 0.089) | 254 |
| Example 1-13 | A-13 | E-1 | 3.71 | 6.64 | (0.135, 0.087) | 261 |
| Example 1-14 | A-14 | E-1 | 3.71 | 6.24 | (0.135, 0.088) | 236 |
| Example 1-15 | A-15 | E-1 | 3.75 | 6.61 | (0.135, 0.088) | 281 |
| Example 1-16 | A-16 | E-1 | 3.71 | 6.33 | (0.135, 0.089) | 265 |
| Example 1-17 | A-17 | E-1 | 3.71 | 6.31 | (0.135, 0.087) | 227 |
| Example 1-18 | A-18 | E-1 | 3.75 | 6.18 | (0.135, 0.088) | 218 |
| Example 1-19 | B-1 | E-1 | 3.75 | 6.34 | (0.135, 0.089) | 254 |
| Example 1-20 | B-2 | E-1 | 3.71 | 6.19 | (0.135, 0.087) | 259 |
| Example 1-21 | B-3 | E-1 | 3.71 | 6.11 | (0.135, 0.088) | 205 |
| Example 1-22 | B-4 | E-1 | 3.75 | 6.20 | (0.135, 0.088) | 234 |
| Example 1-23 | B-5 | E-1 | 3.71 | 6.27 | (0.135, 0.089) | 232 |
| Example 1-24 | B-6 | E-1 | 3.71 | 6.12 | (0.135, 0.087) | 252 |
| Example 1-25 | A-1 | E-2 | 3.76 | 6.19 | (0.135, 0.088) | 216 |
| Example 1-26 | A-2 | E-2 | 3.73 | 6.47 | (0.135, 0.089) | 278 |
| Example 1-27 | A-3 | E-2 | 3.73 | 6.38 | (0.135, 0.087) | 225 |
| Example 1-28 | A-4 | E-2 | 3.76 | 6.57 | (0.135, 0.088) | 291 |
| Example 1-29 | A-5 | E-2 | 3.76 | 6.53 | (0.135, 0.088) | 246 |
| Example 1-30 | A-6 | E-2 | 3.73 | 6.51 | (0.135, 0.089) | 234 |
| Example 1-31 | A-7 | E-2 | 3.73 | 6.33 | (0.135, 0.087) | 223 |
| Example 1-32 | A-8 | E-2 | 3.76 | 6.30 | (0.135, 0.088) | 242 |
| Example 1-33 | A-9 | E-2 | 3.73 | 6.87 | (0.135, 0.089) | 287 |
| Example 1-34 | A-10 | E-2 | 3.73 | 6.21 | (0.135, 0.087) | 231 |
| Example 1-35 | A-11 | E-2 | 3.76 | 6.37 | (0.135, 0.088) | 261 |
| Example 1-36 | A-12 | E-2 | 3.76 | 6.24 | (0.135, 0.088) | 244 |
| Example 1-37 | A-13 | E-2 | 3.73 | 6.75 | (0.135, 0.089) | 251 |
| Example 1-38 | A-14 | E-2 | 3.73 | 6.34 | (0.135, 0.087) | 227 |
| Example 1-39 | A-15 | E-2 | 3.76 | 6.72 | (0.135, 0.088) | 270 |
| Example 1-40 | A-16 | E-2 | 3.73 | 6.43 | (0.135, 0.089) | 255 |

TABLE 1-continued

| Entry | Dopant | Hole Blocking Layer | Voltage (V@10 mA/cm$^2$) | Efficiency (cd/A@10 mA/cm$^2$) | Color Coordinate (x, y) | Lifetime (h) T90@20 mA/cm$^2$) |
|---|---|---|---|---|---|---|
| Example 1-41 | A-17 | E-2 | 3.73 | 6.42 | (0.135, 0.087) | 218 |
| Example 1-42 | A-18 | E-2 | 3.76 | 6.28 | (0.135, 0.088) | 210 |
| Example 1-43 | B-1 | E-2 | 3.76 | 6.45 | (0.135, 0.088) | 244 |
| Example 1-44 | B-2 | E-2 | 3.73 | 6.30 | (0.135, 0.089) | 249 |
| Example 1-45 | B-3 | E-2 | 3.73 | 6.22 | (0.135, 0.087) | 197 |
| Example 1-46 | B-4 | E-2 | 3.76 | 6.30 | (0.135, 0.088) | 225 |
| Example 1-47 | B-5 | E-2 | 3.73 | 6.37 | (0.135, 0.089) | 223 |
| Example 1-48 | B-6 | E-2 | 3.73 | 6.22 | (0.135, 0.087) | 242 |
| Example 1-49 | A-1 | E-3 | 3.78 | 5.99 | (0.135, 0.088) | 242 |
| Example 1-50 | A-2 | E-3 | 3.75 | 6.26 | (0.135, 0.088) | 311 |
| Example 1-51 | A-3 | E-3 | 3.75 | 6.17 | (0.135, 0.089) | 252 |
| Example 1-52 | A-4 | E-3 | 3.78 | 6.35 | (0.135, 0.087) | 326 |
| Example 1-53 | A-5 | E-3 | 3.78 | 6.32 | (0.135, 0.088) | 275 |
| Example 1-54 | A-6 | E-3 | 3.75 | 6.30 | (0.135, 0.089) | 263 |
| Example 1-55 | A-7 | E-3 | 3.75 | 6.12 | (0.135, 0.087) | 250 |
| Example 1-56 | A-8 | E-3 | 3.78 | 6.09 | (0.135, 0.088) | 271 |
| Example 1-57 | A-9 | E-3 | 3.75 | 6.65 | (0.135, 0.088) | 321 |
| Example 1-58 | A-10 | E-3 | 3.75 | 6.01 | (0.135, 0.089) | 258 |
| Example 1-59 | A-11 | E-3 | 3.78 | 6.16 | (0.135, 0.087) | 292 |
| Example 1-60 | A-12 | E-3 | 3.78 | 6.04 | (0.135, 0.088) | 273 |
| Example 1-61 | A-13 | E-3 | 3.75 | 6.53 | (0.135, 0.089) | 281 |
| Example 1-62 | A-14 | E-3 | 3.75 | 6.14 | (0.135, 0.087) | 254 |
| Example 1-63 | A-15 | E-3 | 3.78 | 6.50 | (0.135, 0.088) | 303 |
| Example 1-64 | A-16 | E-3 | 3.75 | 6.22 | (0.135, 0.088) | 286 |
| Example 1-65 | A-17 | E-3 | 3.75 | 6.21 | (0.135, 0.089) | 245 |
| Example 1-66 | A-18 | E-3 | 3.78 | 6.08 | (0.135, 0.087) | 235 |
| Example 1-67 | B-1 | E-3 | 3.78 | 6.24 | (0.135, 0.088) | 273 |
| Example 1-68 | B-2 | E-3 | 3.75 | 6.09 | (0.135, 0.089) | 279 |
| Example 1-69 | B-3 | E-3 | 3.75 | 6.01 | (0.135, 0.087) | 221 |
| Example 1-70 | B-4 | E-3 | 3.78 | 6.09 | (0.135, 0.088) | 252 |
| Example 1-71 | B-5 | E-3 | 3.75 | 6.17 | (0.135, 0.088) | 250 |
| Example 1-72 | B-6 | E-3 | 3.75 | 6.02 | (0.135, 0.089) | 271 |
| Example 1-73 | A-1 | E-4 | 3.75 | 6.14 | (0.135, 0.087) | 221 |
| Example 1-74 | A-2 | E-4 | 3.71 | 6.42 | (0.135, 0.088) | 284 |
| Example 1-75 | A-3 | E-4 | 3.71 | 6.32 | (0.135, 0.089) | 230 |
| Example 1-76 | A-4 | E-4 | 3.75 | 6.52 | (0.135, 0.087) | 298 |
| Example 1-77 | A-5 | E-4 | 3.75 | 6.48 | (0.135, 0.088) | 252 |
| Example 1-78 | A-6 | E-4 | 3.71 | 6.46 | (0.135, 0.088) | 240 |
| Example 1-79 | A-7 | E-4 | 3.71 | 6.27 | (0.135, 0.089) | 228 |
| Example 1-80 | A-8 | E-4 | 3.75 | 6.25 | (0.135, 0.087) | 248 |
| Example 1-81 | A-9 | E-4 | 3.71 | 6.82 | (0.135, 0.088) | 294 |
| Example 1-82 | A-10 | E-4 | 3.71 | 6.16 | (0.135, 0.089) | 236 |
| Example 1-83 | A-11 | E-4 | 3.75 | 6.31 | (0.135, 0.087) | 267 |
| Example 1-84 | A-12 | E-4 | 3.75 | 6.19 | (0.135, 0.088) | 250 |
| Example 1-85 | A-13 | E-4 | 3.71 | 6.69 | (0.135, 0.088) | 257 |
| Example 1-86 | A-14 | E-4 | 3.71 | 6.29 | (0.135, 0.089) | 232 |
| Example 1-87 | A-15 | E-4 | 3.75 | 6.66 | (0.135, 0.087) | 277 |
| Example 1-88 | A-16 | E-4 | 3.71 | 6.38 | (0.135, 0.088) | 261 |
| Example 1-89 | A-17 | E-4 | 3.71 | 6.36 | (0.135, 0.089) | 224 |
| Example 1-90 | A-18 | E-4 | 3.75 | 6.23 | (0.135, 0.087) | 215 |
| Example 1-91 | B-1 | E-4 | 3.75 | 6.39 | (0.135, 0.088) | 250 |
| Example 1-92 | B-2 | E-4 | 3.71 | 6.24 | (0.135, 0.088) | 255 |
| Example 1-93 | B-3 | E-4 | 3.71 | 6.16 | (0.135, 0.089) | 202 |
| Example 1-94 | B-4 | E-4 | 3.75 | 6.25 | (0.135, 0.087) | 230 |
| Example 1-95 | B-5 | E-4 | 3.71 | 6.32 | (0.135, 0.088) | 228 |
| Example 1-96 | B-6 | E-4 | 3.71 | 6.17 | (0.135, 0.089) | 248 |
| Example 1-97 | A-1 | E-5 | 3.79 | 5.84 | (0.135, 0.087) | 235 |
| Example 1-98 | A-2 | E-5 | 3.75 | 6.10 | (0.135, 0.088) | 302 |
| Example 1-99 | A-3 | E-5 | 3.75 | 6.01 | (0.135, 0.088) | 245 |
| Example 1-100 | A-4 | E-5 | 3.79 | 6.19 | (0.135, 0.089) | 316 |
| Example 1-101 | A-5 | E-5 | 3.79 | 6.16 | (0.135, 0.087) | 267 |
| Example 1-102 | A-6 | E-5 | 3.75 | 6.14 | (0.135, 0.088) | 255 |
| Example 1-103 | A-7 | E-5 | 3.75 | 5.96 | (0.135, 0.089) | 243 |
| Example 1-104 | A-8 | E-5 | 3.79 | 5.94 | (0.135, 0.087) | 263 |
| Example 1-105 | A-9 | E-5 | 3.75 | 6.48 | (0.135, 0.088) | 312 |
| Example 1-106 | A-10 | E-5 | 3.75 | 5.85 | (0.135, 0.088) | 251 |
| Example 1-107 | A-11 | E-5 | 3.79 | 6.00 | (0.135, 0.089) | 284 |
| Example 1-108 | A-12 | E-5 | 3.79 | 5.88 | (0.135, 0.087) | 266 |
| Example 1-109 | A-13 | E-5 | 3.75 | 6.36 | (0.135, 0.088) | 273 |
| Example 1-110 | A-14 | E-5 | 3.75 | 5.98 | (0.135, 0.089) | 247 |
| Example 1-111 | A-15 | E-5 | 3.79 | 6.33 | (0.135, 0.087) | 294 |
| Example 1-112 | A-16 | E-5 | 3.75 | 6.06 | (0.135, 0.088) | 277 |
| Example 1-113 | A-17 | E-5 | 3.75 | 6.05 | (0.135, 0.088) | 238 |
| Example 1-114 | A-18 | E-5 | 3.79 | 5.92 | (0.135, 0.089) | 228 |
| Example 1-115 | B-1 | E-5 | 3.79 | 6.08 | (0.135, 0.087) | 265 |
| Example 1-116 | B-2 | E-5 | 3.75 | 5.93 | (0.135, 0.088) | 271 |

TABLE 1-continued

| Entry | Dopant | Hole Blocking Layer | Voltage (V@10 mA/cm²) | Efficiency (cd/A@10 mA/cm²) | Color Coordinate (x, y) | Lifetime (h) T90@20 mA/cm²) |
|---|---|---|---|---|---|---|
| Example 1-117 | B-3 | E-5 | 3.75 | 5.86 | (0.135, 0.089) | 214 |
| Example 1-118 | B-4 | E-5 | 3.79 | 5.94 | (0.135, 0.087) | 245 |
| Example 1-119 | B-5 | E-5 | 3.75 | 6.01 | (0.135, 0.088) | 243 |
| Example 1-120 | B-6 | E-5 | 3.75 | 5.87 | (0.135, 0.088) | 263 |
| Comparative Example 1-1 | BD-A | — | 3.90 | 5.00 | (0.135, 0.089) | 150 |
| Comparative Example 1-2 | BD-B | — | 4.10 | 3.50 | (0.135, 0.087) | 180 |
| Comparative Example 1-3 | BD-C | — | 4.08 | 3.60 | (0.135, 0.088) | 122 |
| Comparative Example 1-4 | BD-D | — | 4.02 | 4.45 | (0.135, 0.089) | 116 |
| Comparative Example 1-5 | BD-E | — | 4.17 | 3.65 | (0.135, 0.087) | 98 |
| Comparative Example 1-6 | A-1 | — | 3.86 | 5.08 | (0.135, 0.088) | 173 |
| Comparative Example 1-7 | A-2 | — | 3.82 | 5.30 | (0.135, 0.088) | 222 |
| Comparative Example 1-8 | A-3 | — | 3.82 | 5.23 | (0.135, 0.089) | 180 |
| Comparative Example 1-9 | A-4 | — | 3.86 | 5.38 | (0.135, 0.087) | 233 |
| Comparative Example 1-10 | A-5 | — | 3.86 | 5.35 | (0.135, 0.088) | 197 |
| Comparative Example 1-11 | A-6 | — | 3.82 | 5.34 | (0.135, 0.089) | 188 |
| Comparative Example 1-12 | A-7 | — | 3.82 | 5.19 | (0.135, 0.087) | 179 |
| Comparative Example 1-13 | A-8 | — | 3.86 | 5.17 | (0.135, 0.088) | 194 |
| Comparative Example 1-14 | A-9 | — | 3.82 | 5.63 | (0.135, 0.088) | 230 |
| Comparative Example 1-15 | A-10 | — | 3.82 | 5.09 | (0.135, 0.089) | 185 |
| Comparative Example 1-16 | A-11 | — | 3.86 | 5.22 | (0.135, 0.087) | 209 |
| Comparative Example 1-17 | A-12 | — | 3.86 | 5.12 | (0.135, 0.088) | 195 |
| Comparative Example 1-18 | A-13 | — | 3.82 | 5.53 | (0.135, 0.089) | 201 |
| Comparative Example 1-19 | A-14 | — | 3.82 | 5.20 | (0.135, 0.087) | 182 |
| Comparative Example 1-20 | A-15 | — | 3.86 | 5.51 | (0.135, 0.088) | 216 |
| Comparative Example 1-21 | A-16 | — | 3.82 | 5.27 | (0.135, 0.088) | 204 |
| Comparative Example 1-22 | A-17 | — | 3.82 | 5.26 | (0.135, 0.089) | 175 |
| Comparative Example 1-23 | A-18 | — | 3.86 | 5.15 | (0.135, 0.087) | 168 |
| Comparative Example 1-24 | B-1 | — | 3.86 | 5.29 | (0.135, 0.088) | 195 |
| Comparative Example 1-25 | B-2 | — | 3.82 | 5.16 | (0.135, 0.089) | 200 |
| Comparative Example 1-26 | B-3 | — | 3.82 | 5.10 | (0.135, 0.087) | 158 |
| Comparative Example 1-27 | B-4 | — | 3.86 | 5.17 | (0.135, 0.088) | 180 |
| Comparative Example 1-28 | B-5 | — | 3.82 | 5.23 | (0.135, 0.088) | 179 |
| Comparative Example 1-29 | B-6 | — | 3.82 | 5.10 | (0.135, 0.089) | 194 |
| Comparative Example 1-30 | A-1 | ET-B | 3.82 | 5.28 | (0.135, 0.087) | 138 |
| Comparative Example 1-31 | A-2 | ET-B | 3.78 | 5.52 | (0.135, 0.088) | 178 |
| Comparative Example 1-32 | A-3 | ET-B | 3.78 | 5.44 | (0.135, 0.089) | 144 |
| Comparative Example 1-33 | A-4 | ET-B | 3.82 | 5.60 | (0.135, 0.087) | 186 |
| Comparative Example 1-34 | A-5 | ET-B | 3.82 | 5.57 | (0.135, 0.088) | 157 |
| Comparative Example 1-35 | A-6 | ET-B | 3.78 | 5.55 | (0.135, 0.088) | 150 |
| Comparative Example 1-36 | A-7 | ET-B | 3.78 | 5.39 | (0.135, 0.089) | 143 |

TABLE 1-continued

| Entry | Dopant | Hole Blocking Layer | Voltage (V@10 mA/cm$^2$) | Efficiency (cd/A@10 mA/cm$^2$) | Color Coordinate (x, y) | Lifetime (h) T90@20 mA/cm$^2$) |
|---|---|---|---|---|---|---|
| Comparative Example 1-37 | A-8 | ET-B | 3.82 | 5.37 | (0.135, 0.087) | 155 |
| Comparative Example 1-38 | A-9 | ET-B | 3.78 | 5.86 | (0.135, 0.088) | 184 |
| Comparative Example 1-39 | A-10 | ET-B | 3.78 | 5.29 | (0.135, 0.088) | 148 |
| Comparative Example 1-40 | A-11 | ET-B | 3.82 | 5.43 | (0.135, 0.089) | 167 |
| Comparative Example 1-41 | A-12 | ET-B | 3.82 | 5.32 | (0.135, 0.087) | 156 |
| Comparative Example 1-42 | A-13 | ET-B | 3.78 | 5.75 | (0.135, 0.088) | 161 |
| Comparative Example 1-43 | A-14 | ET-B | 3.78 | 5.41 | (0.135, 0.089) | 145 |
| Comparative Example 1-44 | A-15 | ET-B | 3.82 | 5.73 | (0.135, 0.087) | 173 |
| Comparative Example 1-45 | A-16 | ET-B | 3.78 | 5.48 | (0.135, 0.088) | 163 |
| Comparative Example 1-46 | A-17 | ET-B | 3.78 | 5.47 | (0.135, 0.088) | 140 |
| Comparative Example 1-47 | A-18 | ET-B | 3.82 | 5.36 | (0.135, 0.089) | 134 |
| Comparative Example 1-48 | B-1 | ET-B | 3.82 | 5.50 | (0.135, 0.087) | 156 |
| Comparative Example 1-49 | B-2 | ET-B | 3.78 | 5.37 | (0.135, 0.088) | 160 |
| Comparative Example 1-50 | B-3 | ET-B | 3.78 | 5.30 | (0.135, 0.088) | 126 |
| Comparative Example 1-51 | B-4 | ET-B | 3.82 | 5.37 | (0.135, 0.089) | 144 |
| Comparative Example 1-52 | B-5 | ET-B | 3.78 | 5.43 | (0.135, 0.087) | 143 |
| Comparative Example 1-53 | B-6 | ET-B | 3.78 | 5.30 | (0.135, 0.088) | 155 |
| Comparative Example 1-54 | A-1 | ET-C | 3.90 | 5.18 | (0.135, 0.089) | 136 |
| Comparative Example 1-55 | A-2 | ET-C | 3.86 | 5.41 | (0.135, 0.087) | 175 |
| Comparative Example 1-56 | A-3 | ET-C | 3.86 | 5.33 | (0.135, 0.088) | 142 |
| Comparative Example 1-57 | A-4 | ET-C | 3.90 | 5.49 | (0.135, 0.088) | 184 |
| Comparative Example 1-58 | A-5 | ET-C | 3.90 | 5.46 | (0.135, 0.089) | 155 |
| Comparative Example 1-59 | A-6 | ET-C | 3.86 | 5.45 | (0.135, 0.087) | 148 |
| Comparative Example 1-60 | A-7 | ET-C | 3.86 | 5.29 | (0.135, 0.088) | 141 |
| Comparative Example 1-61 | A-8 | ET-C | 3.90 | 5.27 | (0.135, 0.088) | 153 |
| Comparative Example 1-62 | A-9 | ET-C | 3.86 | 5.75 | (0.135, 0.089) | 181 |
| Comparative Example 1-63 | A-10 | ET-C | 3.86 | 5.19 | (0.135, 0.087) | 146 |
| Comparative Example 1-64 | A-11 | ET-C | 3.90 | 5.32 | (0.135, 0.088) | 165 |
| Comparative Example 1-65 | A-12 | ET-C | 3.90 | 5.22 | (0.135, 0.089) | 154 |
| Comparative Example 1-66 | A-13 | ET-C | 3.86 | 5.64 | (0.135, 0.087) | 159 |
| Comparative Example 1-67 | A-14 | ET-C | 3.86 | 5.30 | (0.135, 0.088) | 143 |
| Comparative Example 1-68 | A-15 | ET-C | 3.90 | 5.62 | (0.135, 0.088) | 171 |
| Comparative Example 1-69 | A-16 | ET-C | 3.86 | 5.38 | (0.135, 0.089) | 161 |
| Comparative Example 1-70 | A-17 | ET-C | 3.86 | 5.37 | (0.135, 0.087) | 138 |
| Comparative Example 1-71 | A-18 | ET-C | 3.90 | 5.25 | (0.135, 0.088) | 133 |
| Comparative Example 1-72 | B-1 | ET-C | 3.90 | 5.39 | (0.135, 0.088) | 154 |
| Comparative Example 1-73 | B-2 | ET-C | 3.86 | 5.26 | (0.135, 0.089) | 158 |
| Comparative Example 1-74 | B-3 | ET-C | 3.86 | 5.20 | (0.135, 0.087) | 124 |

TABLE 1-continued

| Entry | Dopant | Hole Blocking Layer | Voltage (V@10 mA/cm$^2$) | Efficiency (cd/A@10 mA/cm$^2$) | Color Coordinate (x, y) | Lifetime (h) T90@20 mA/cm$^2$) |
|---|---|---|---|---|---|---|
| Comparative Example 1-75 | B-4 | ET-C | 3.90 | 5.27 | (0.135, 0.088) | 142 |
| Comparative Example 1-76 | B-5 | ET-C | 3.86 | 5.33 | (0.135, 0.089) | 141 |
| Comparative Example 1-77 | B-6 | ET-C | 3.86 | 5.20 | (0.135, 0.087) | 153 |
| Comparative Example 1-78 | A-1 | ET-D | 3.94 | 5.23 | (0.135, 0.088) | 121 |
| Comparative Example 1-79 | A-2 | ET-D | 3.90 | 5.46 | (0.135, 0.088) | 155 |
| Comparative Example 1-80 | A-3 | ET-D | 3.90 | 5.38 | (0.135, 0.089) | 126 |
| Comparative Example 1-81 | A-4 | ET-D | 3.94 | 5.55 | (0.135, 0.087) | 163 |
| Comparative Example 1-82 | A-5 | ET-D | 3.94 | 5.51 | (0.135, 0.088) | 138 |
| Comparative Example 1-83 | A-6 | ET-D | 3.90 | 5.50 | (0.135, 0.088) | 131 |
| Comparative Example 1-84 | A-7 | ET-D | 3.90 | 5.34 | (0.135, 0.089) | 125 |
| Comparative Example 1-85 | A-8 | ET-D | 3.94 | 5.32 | (0.135, 0.087) | 135 |
| Comparative Example 1-86 | A-9 | ET-D | 3.90 | 5.80 | (0.135, 0.088) | 161 |
| Comparative Example 1-87 | A-10 | ET-D | 3.90 | 5.24 | (0.135, 0.089) | 129 |
| Comparative Example 1-88 | A-11 | ET-D | 3.94 | 5.37 | (0.135, 0.087) | 146 |
| Comparative Example 1-89 | A-12 | ET-D | 3.94 | 5.27 | (0.135, 0.088) | 137 |
| Comparative Example 1-90 | A-13 | ET-D | 3.90 | 5.70 | (0.135, 0.088) | 141 |
| Comparative Example 1-91 | A-14 | ET-D | 3.90 | 5.36 | (0.135, 0.089) | 127 |
| Comparative Example 1-92 | A-15 | ET-D | 3.94 | 5.67 | (0.135, 0.087) | 151 |
| Comparative Example 1-93 | A-16 | ET-D | 3.90 | 5.43 | (0.135, 0.088) | 143 |
| Comparative Example 1-94 | A-17 | ET-D | 3.90 | 5.42 | (0.135, 0.088) | 122 |
| Comparative Example 1-95 | A-18 | ET-D | 3.94 | 5.30 | (0.135, 0.089) | 118 |
| Comparative Example 1-96 | B-1 | ET-D | 3.94 | 5.44 | (0.135, 0.087) | 137 |
| Comparative Example 1-97 | B-2 | ET-D | 3.90 | 5.31 | (0.135, 0.088) | 140 |
| Comparative Example 1-98 | B-3 | ET-D | 3.90 | 5.25 | (0.135, 0.089) | 110 |
| Comparative Example 1-99 | B-4 | ET-D | 3.94 | 5.32 | (0.135, 0.087) | 126 |
| Comparative Example 1-100 | B-5 | ET-D | 3.90 | 5.38 | (0.135, 0.088) | 125 |
| Comparative Example 1-101 | B-6 | ET-D | 3.90 | 5.25 | (0.135, 0.088) | 135 |
| Comparative Example 1-102 | BD-A | E-1 | 3.82 | 5.60 | (0.135, 0.089) | 168 |
| Comparative Example 1-103 | BD-B | E-1 | 4.01 | 3.92 | (0.135, 0.087) | 202 |
| Comparative Example 1-104 | BD-C | E-1 | 3.99 | 4.03 | (0.135, 0.088) | 136 |
| Comparative Example 1-105 | BD-D | E-1 | 3.94 | 4.98 | (0.135, 0.088) | 129 |
| Comparative Example 1-106 | BD-E | E-1 | 4.09 | 4.09 | (0.135, 0.089) | 109 |
| Comparative Example 1-107 | BD-A | E-2 | 3.80 | 5.70 | (0.135, 0.087) | 162 |
| Comparative Example 1-108 | BD-B | E-2 | 3.99 | 3.99 | (0.135, 0.088) | 194 |
| Comparative Example 1-109 | BD-C | E-2 | 3.97 | 4.10 | (0.135, 0.089) | 131 |
| Comparative Example 1-110 | BD-D | E-2 | 3.92 | 5.07 | (0.135, 0.087) | 125 |
| Comparative Example 1-111 | BD-E | E-2 | 4.07 | 4.16 | (0.135, 0.088) | 105 |
| Comparative Example 1-112 | BD-A | E-3 | 3.82 | 5.40 | (0.135, 0.088) | 179 |

TABLE 1-continued

| Entry | Dopant | Hole Blocking Layer | Voltage (V@10 mA/cm$^2$) | Efficiency (cd/A@10 mA/cm$^2$) | Color Coordinate (x, y) | Lifetime (h) T90@20 mA/cm$^2$) |
|---|---|---|---|---|---|---|
| Comparative Example 1-113 | BD-B | E-3 | 4.01 | 3.78 | (0.135, 0.089) | 214 |
| Comparative Example 1-114 | BD-C | E-3 | 3.99 | 3.89 | (0.135, 0.087) | 145 |
| Comparative Example 1-115 | BD-D | E-3 | 3.94 | 4.81 | (0.135, 0.088) | 137 |
| Comparative Example 1-116 | BD-E | E-3 | 4.09 | 3.94 | (0.135, 0.088) | 116 |
| Comparative Example 1-117 | BD-A | E-4 | 3.82 | 5.65 | (0.135, 0.089) | 165 |
| Comparative Example 1-118 | BD-B | E-4 | 4.01 | 3.96 | (0.135, 0.087) | 198 |
| Comparative Example 1-119 | BD-C | E-4 | 3.99 | 4.07 | (0.135, 0.088) | 134 |
| Comparative Example 1-120 | BD-D | E-4 | 3.94 | 5.03 | (0.135, 0.089) | 127 |
| Comparative Example 1-121 | BD-E | E-4 | 4.09 | 4.12 | (0.135, 0.087) | 107 |
| Comparative Example 1-122 | BD-A | E-5 | 3.85 | 5.55 | (0.135, 0.088) | 174 |
| Comparative Example 1-123 | BD-B | E-5 | 4.05 | 3.89 | (0.135, 0.088) | 209 |
| Comparative Example 1-124 | BD-C | E-5 | 4.03 | 4.00 | (0.135, 0.089) | 141 |
| Comparative Example 1-125 | BD-D | E-5 | 3.97 | 4.94 | (0.135, 0.087) | 134 |
| Comparative Example 1-126 | BD-E | E-5 | 4.12 | 4.05 | (0.135, 0.088) | 113 |

As shown in Table 1, it was identified that the organic light emitting device using the compound of Chemical Formula 1 of the present disclosure in a light emitting layer, and the compound of Chemical Formula 2 in an electron transfer region exhibited significant effects in terms of driving voltage, efficiency and lifetime.

Specifically, Chemical Formula 1 according to the present disclosure includes a 5-membered heteroring including an oxygen atom or a sulfur atom, which lowers first triplet excitation energy of the compound and thereby increases a difference between first singlet excitation energy and the first triplet excitation energy, and as a result, results of particularly improving lifetime properties of the organic light emitting device including the same are obtained. In addition, Chemical Formula 2 according to the present disclosure enhances electron migration properties by including a monocyclic ring including N, and, by including a fluorene group or a fused cyclic ring group containing N, O or S, enhances effects of hole blocking and electron transfer by forming a wide band gap of the molecule, and as a result, effects of particularly enhancing efficiency of the organic light emitting device including the same are obtained.

Herein, it was identified that, when low voltage and high efficiency properties were strengthened in the organic light emitting device by using the compound of Chemical Formula 2 in a hole blocking layer and thereby reducing an energy barrier between the interfaces, and lifetime of the organic light emitting device was enhanced by using the compound of Chemical Formula 1 in a light emitting layer, low voltage, high efficiency and long lifetime properties of the organic light emitting device were further strengthened in general through combining Chemical Formula 1 and Chemical Formula 2.

Accordingly, it was identified that the organic light emitting device using both the compound of Chemical Formula 1 and the compound of Chemical Formula 2 according to the present disclosure in a light emitting layer and a hole blocking layer accomplished superior results in voltage, efficiency and lifetime properties.

The invention claimed is:

1. An organic light emitting device, comprising:

an anode;

a cathode;

a light emitting layer provided between the anode and the cathode; and a first organic material layer provided between the light emitting layer and the cathode, wherein the first organic material layer is a hole blocking layer having a thickness of 10 Å to 50 Å, wherein the light emitting layer includes a compound selected from among the following Chemical Formulae 103 to 106, and the first organic material layer includes a compound of the following Chemical Formula 2:

<Chemical Formula 103>

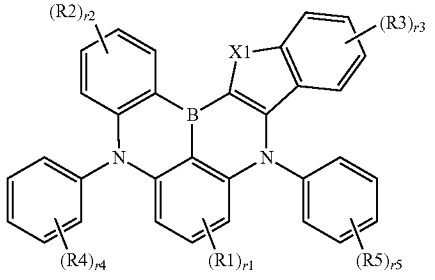

-continued

<Chemical Formula 104>

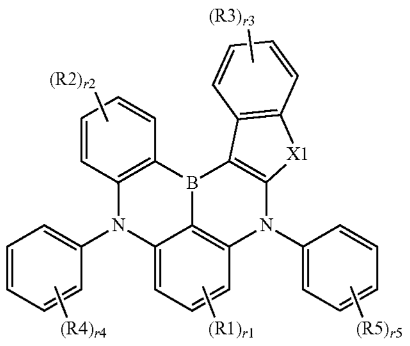

<Chemical Formula 105>

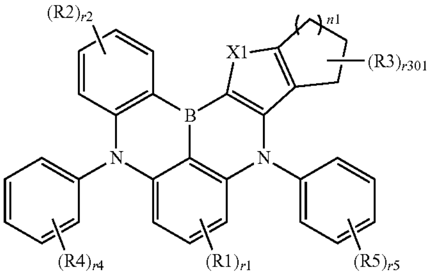

<Chemical Formula 106>

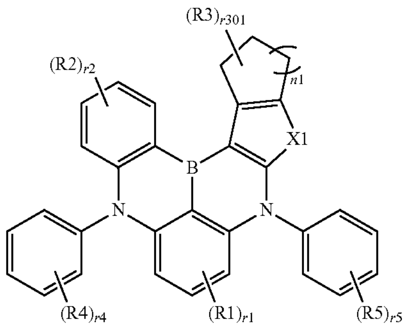

wherein in Chemical Formulae 103 to 106:

X1 is O or S;

R1 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r1 is an integer of 0 to 3, and when r1 is 2 or 3, the R1s are the same as or different from each other;

n1 is 1 or 2:

(a) r2 is 2 and the two R2 substituents bond together to form a substituted cyclohexyl ring of the following formula:

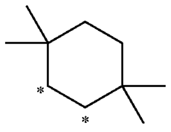

where * means a fused position and r3 and r301 each is an integer of 0 to 4, and R3 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, and when r3 or r301 is 2 to 4, the R3s are the same as or different from each other, or adjacent R3 substituents bond together to form a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring; or (b) r2 is an integer of 0 to 4 and R2 is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, and when r2 is 2 to 4, the R2s are the same as or different from each other, or adjacent R2 substituents bond together to form a substituted or unsubstituted aromatic hydrocarbon ring, a substituted or unsubstituted aliphatic hydrocarbon ring, or a substituted or unsubstituted fused ring of aromatic hydrocarbon ring and aliphatic hydrocarbon ring; and r3 and r301 each is 2 and the R3 substituents bond together to form a cyclohexyl ring that is unsubstituted or substituted with deuterium, a methyl group or $CD_3$ or form an adamantyl ring that is unsubstituted or substituted with deuterium, a methyl group or $CD_3$;

R4 and R5 are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or adjacent R4 substituents or adjacent R5 substituents bond to each other to form a substituted or unsubstituted ring; and r4 and r5 are each an integer of 0 to 5, and when r4 and r5 are 2 to 5, the substituents in the parentheses are the same as or different from each other;

<Chemical Formula 2>

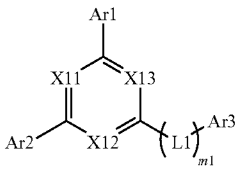

wherein in Chemical Formula 2:

X11 to X13 are N or CR', and at least one of X11 to X13 is N;

R' is hydrogen, deuterium, a cyano group, a halogen group, a substituted or unsubstituted alkyl group, a substituted or unsubstituted alkenyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, or a substituted or unsubstituted heterocyclic group;

L1 is a direct bond; a substituted or unsubstituted arylene group or a substituted or unsubstituted divalent heterocyclic group;

m1 is an integer of 1 to 3, and when m1 is 2 or greater, the L1s are the same as or different from each other;

Ar1 and Ar2 are the same as or different from each other, and each independently is a substituted or unsubstituted aryl group or a substituted or unsubstituted heterocyclic group; and Ar3 is Chemical Formula 2-C:

<Chemical Formula 2-C>

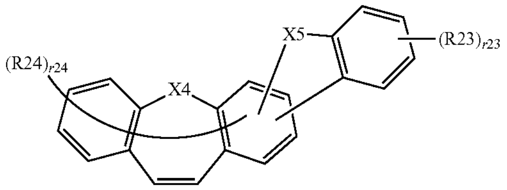

wherein in Chemical Formula 2-C:

X4 is O, S, or NR25;

X5 is O, S, or NR22;

any one of R23 to R25 is linked to Chemical Formula 2, and the rest are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

r23 is an integer of 0 to 4, and r24 is an integer of 0 to 8; and when r23 and r24 are 2 or greater, substituents in the parentheses are the same as or different from each other.

2. The organic light emitting device of claim 1, wherein R1 is any one of the following Chemical Formulae 1-B-1 to 1-B-4:

<Chemical Formula 1-B-1>

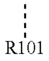

<Chemical Formula 1-B-2>

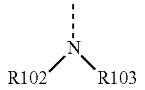

<Chemical Formula 1-B-3>

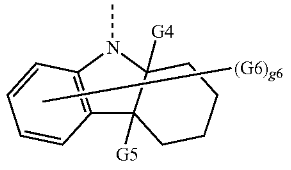

<Chemical Formula 1-B-4>

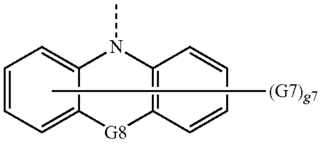

wherein in Chemical Formulae 1-B-1 to 1-B-4:

G8 is a direct bond, —O—, —S—, —CG9G10-, or —SiG9G10-;

R101 to R103 and G4 to G7 are the same as or different from each other, and each independently is hydrogen, deuterium, a cyano group, a halogen group, a substituted or unsubstituted alkyl group, a substituted or unsubstituted alkoxy group, a substituted or unsubstituted alkylthio group, a substituted or unsubstituted cycloalkyl group, a substituted or unsubstituted silyl group, a substituted or unsubstituted aryl group, a substituted or unsubstituted aryloxy group, a substituted or unsubstituted arylthio group, a substituted or unsubstituted heterocyclic group, or a substituted or unsubstituted amine group, or bond to adjacent substituents to form a substituted or unsubstituted ring;

G9 and G10 are the same as or different from each other, and each independently is hydrogen, deuterium, a substituted or unsubstituted alkyl group, or a substituted or unsubstituted aryl group, or bond to adjacent substituents to form a substituted or unsubstituted ring;

g6 is an integer of 0 to 12, and g7 is an integer of 0 to 8;

when g6 and g7 are each 2 or greater, substituents in the parentheses are the same as or different from each other; and a dotted line means a position bonding to Chemical Formula 1.

3. The organic light emitting device of claim 1, wherein Ar3 is any one of the following Chemical Formulae 2-C-1 to 2-C-4:

<Chemical Formula 2-C-1>

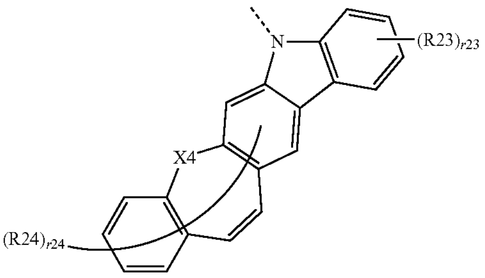

<Chemical Formula 2-C-2>

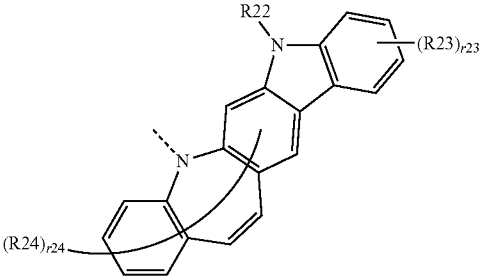

<Chemical Formula 2-C-3>

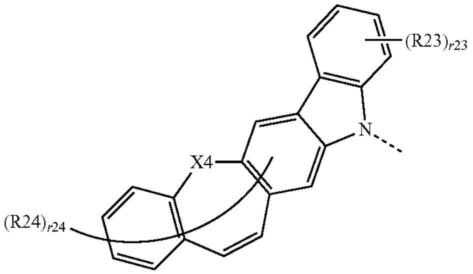

<Chemical Formula 2-C-4>

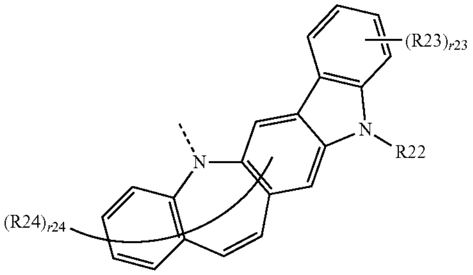

wherein in Chemical Formulae 2-C-1 to 2-C-4:

a dotted line, X4, R23, R24, r23 and r24 have the same definitions as in Chemical Formula 2.

4. The organic light emitting device of claim 1, wherein L1 is a direct bond or a C6-C30 arylene group; and Ar1 and Ar2 are the same as or different from each other, and each independently is a C6-C30 aryl group.

5. The organic light emitting device of claim 1, wherein the compound of Chemical Formula 1 is any one of the following compounds:

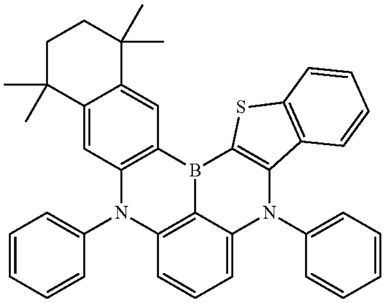

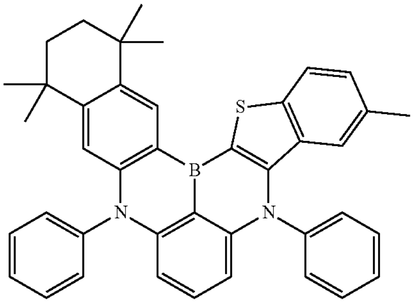

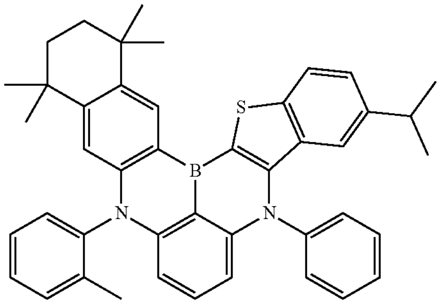

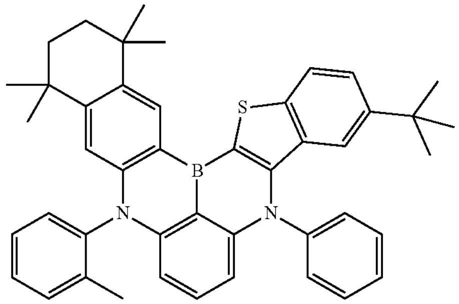

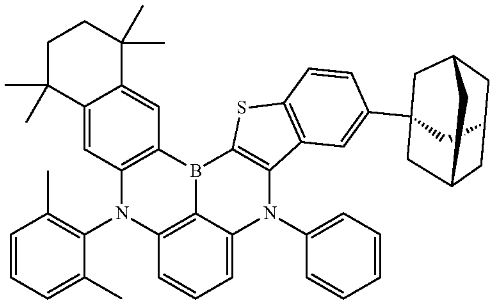

-continued
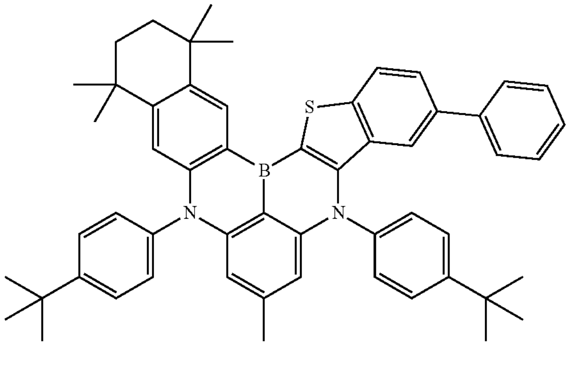
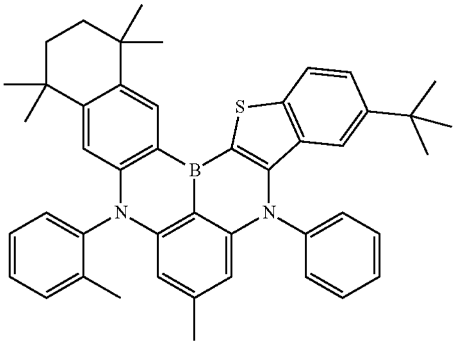
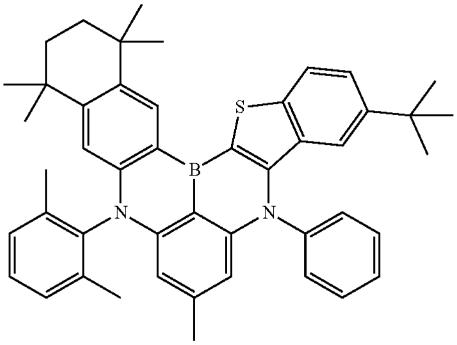
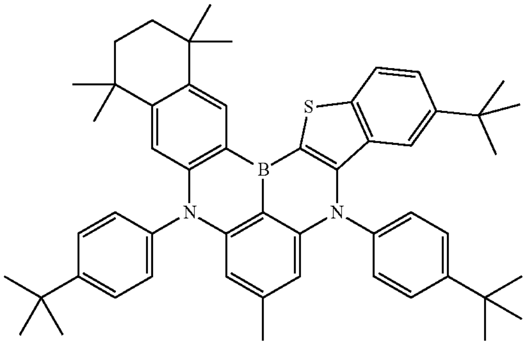
-continued
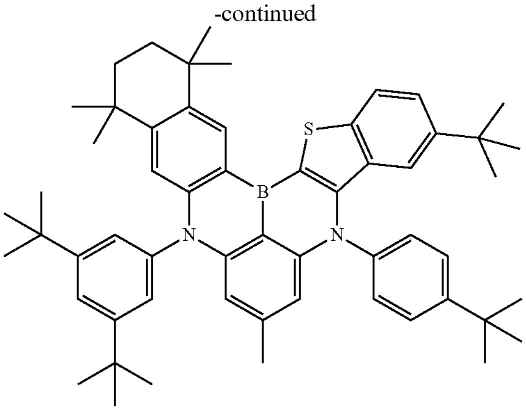
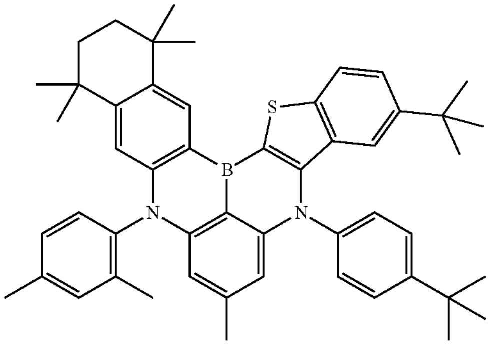
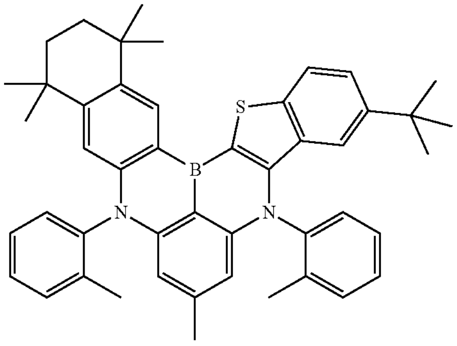
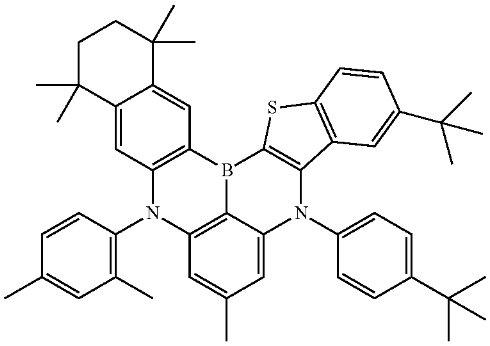

-continued
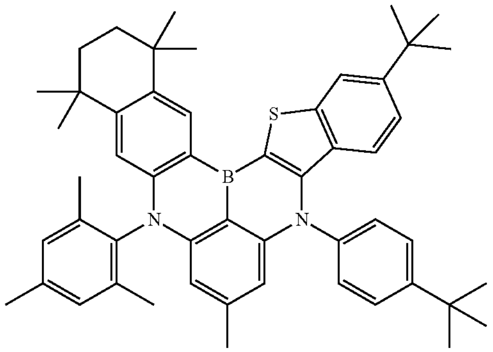
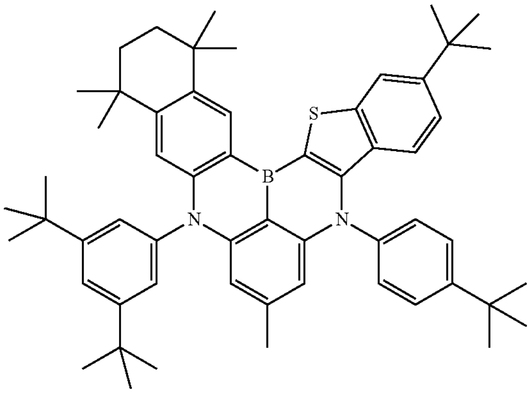
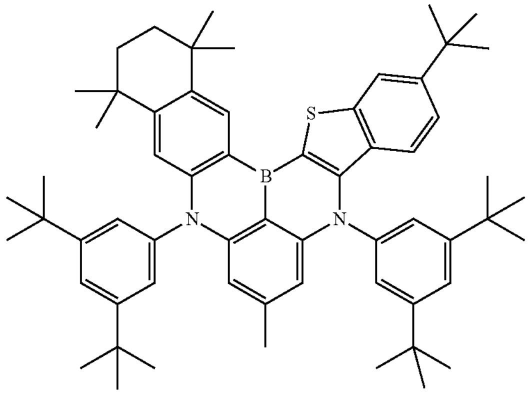
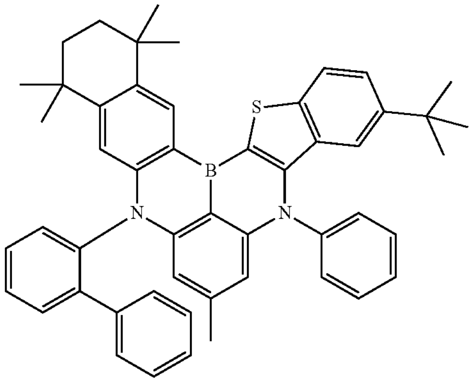
-continued
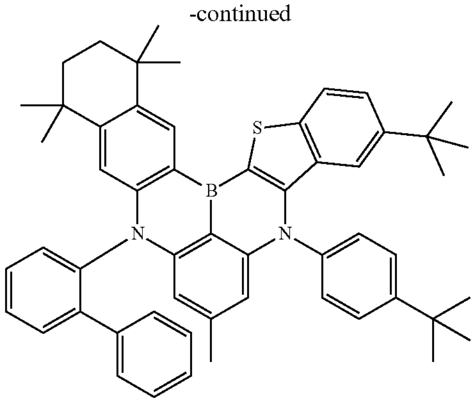
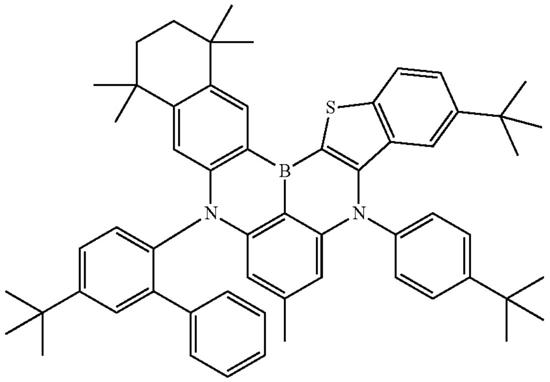
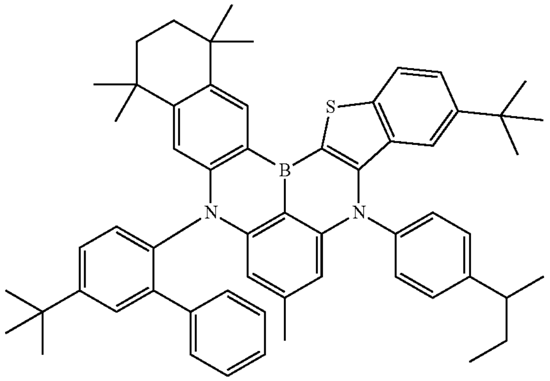
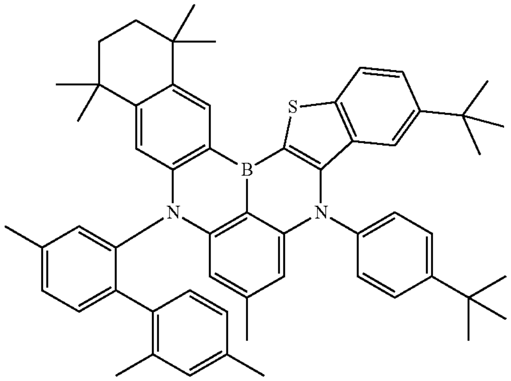

-continued
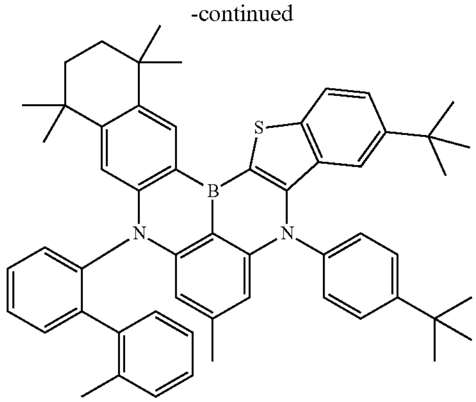
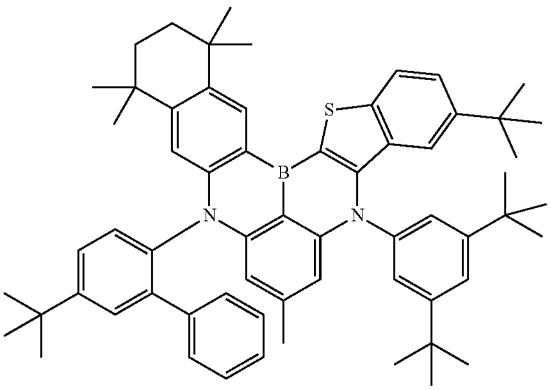
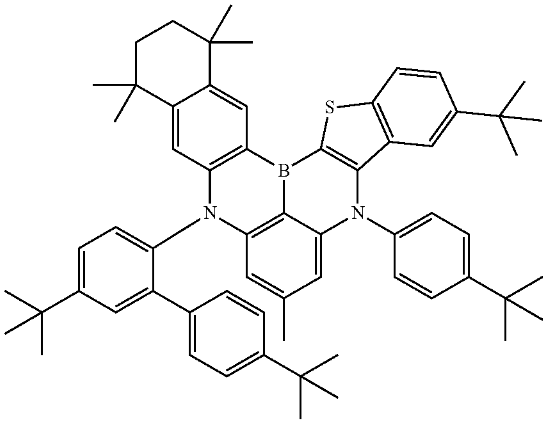
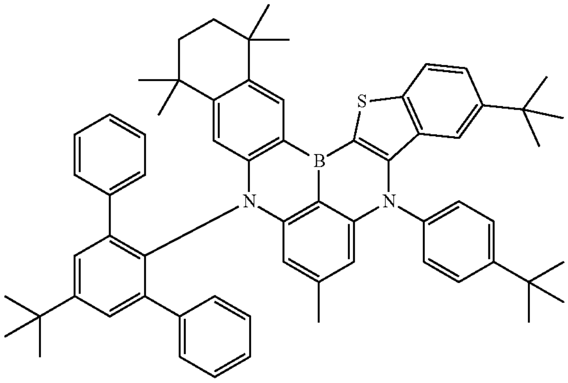
-continued
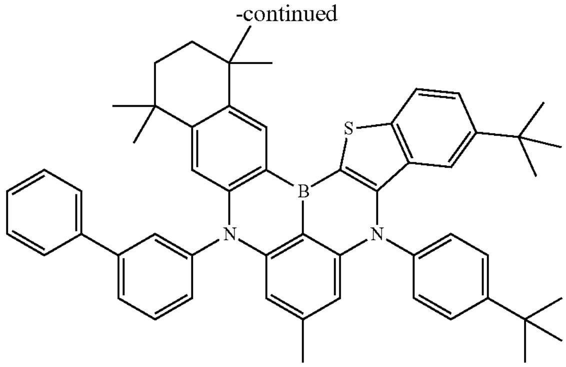
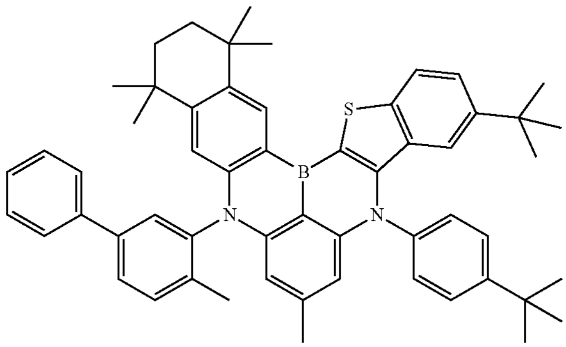
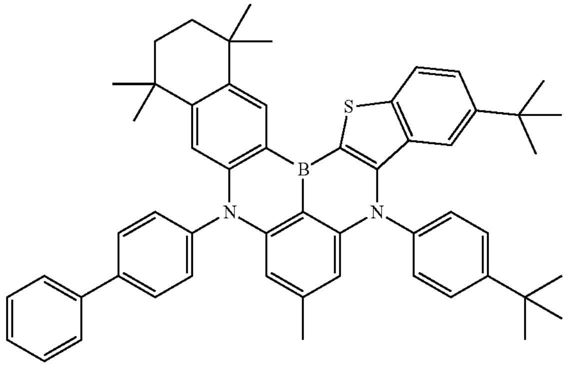
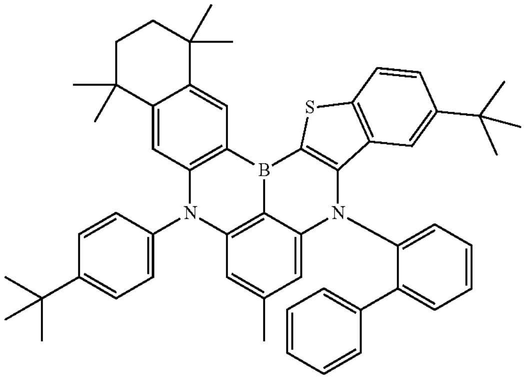

-continued
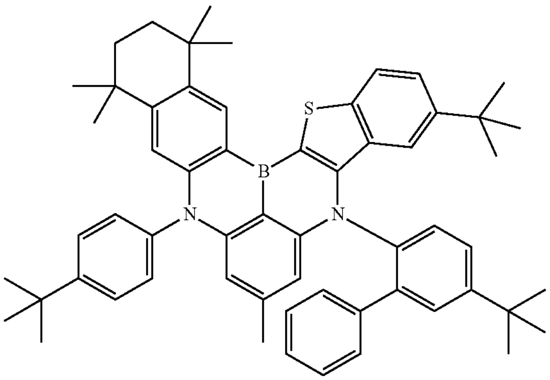
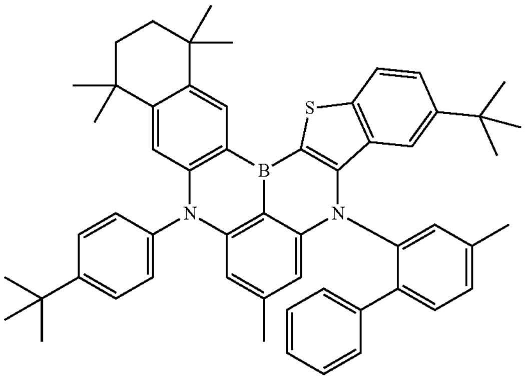
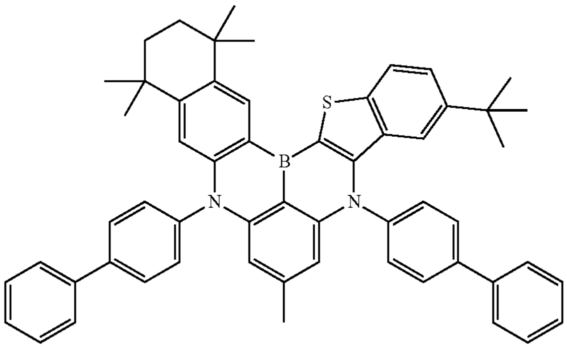
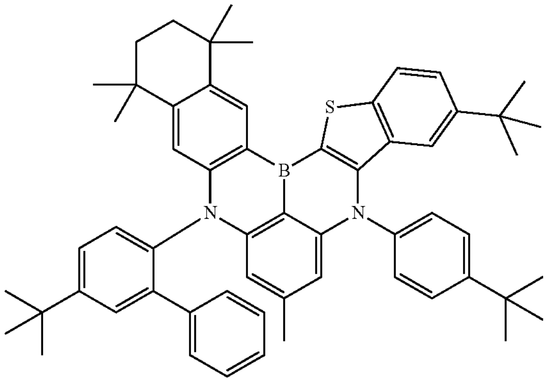
-continued
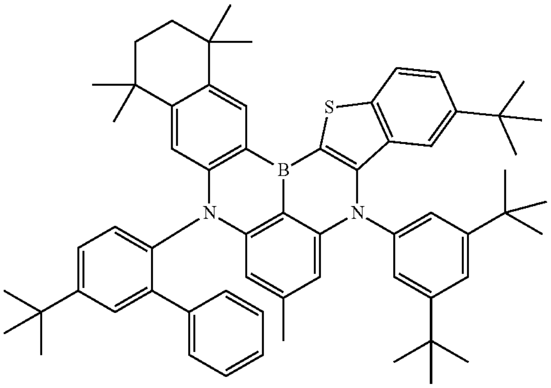
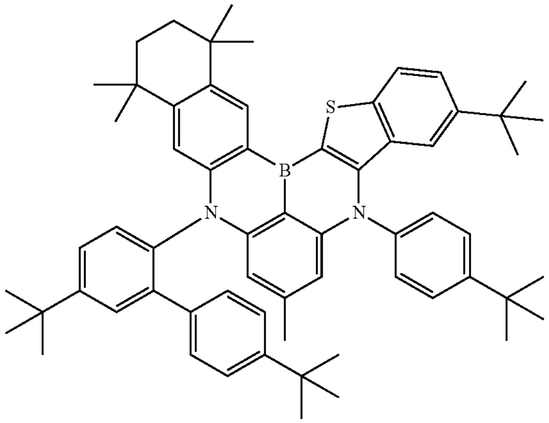
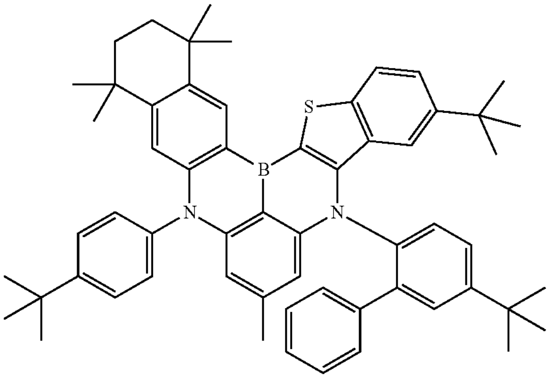
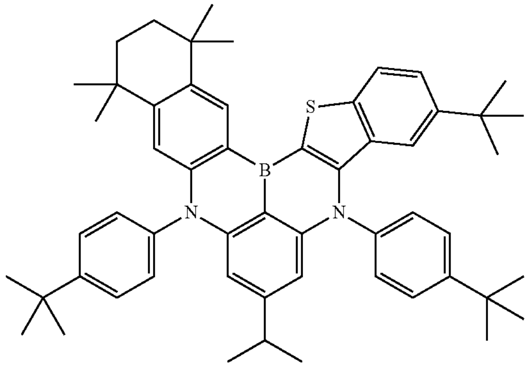

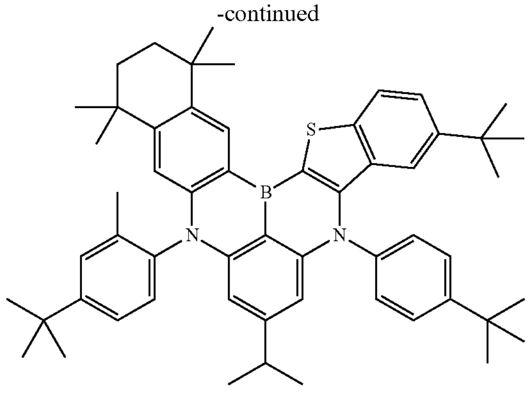
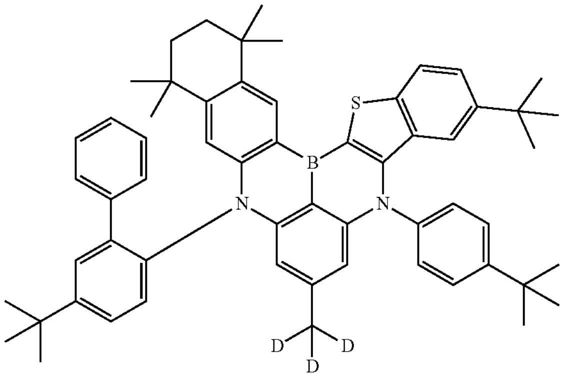
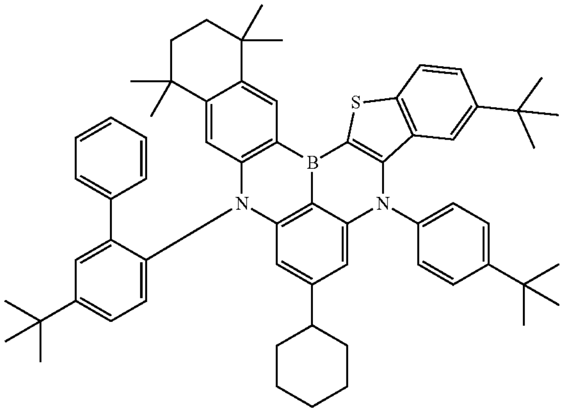
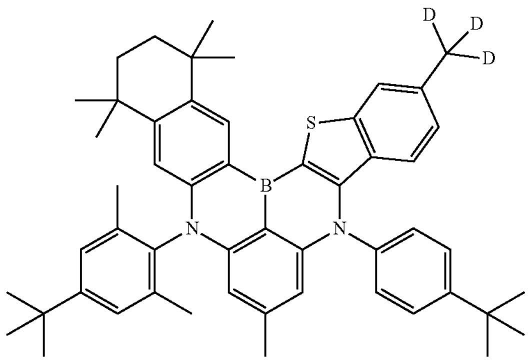
-continued
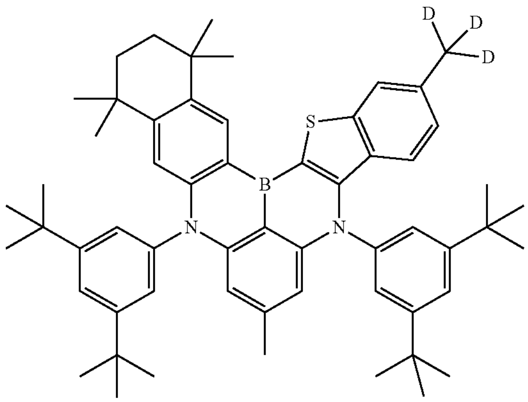
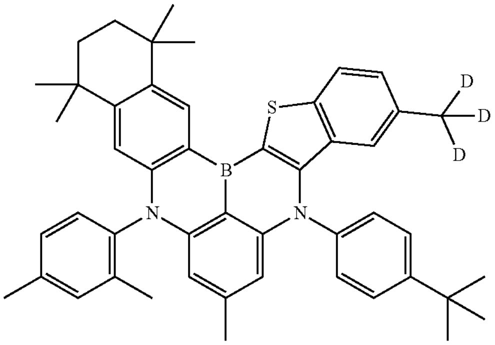
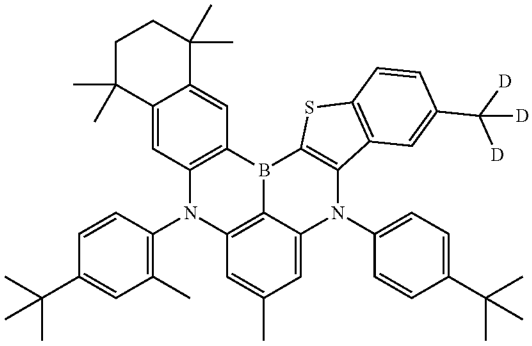
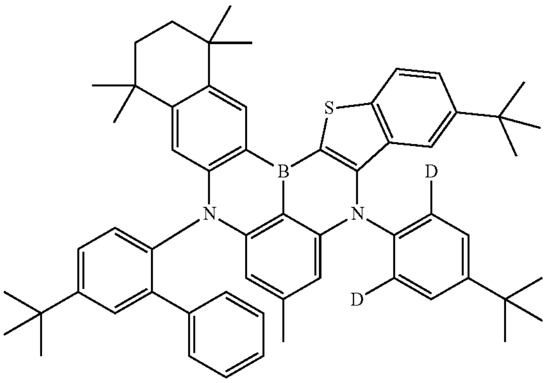

-continued
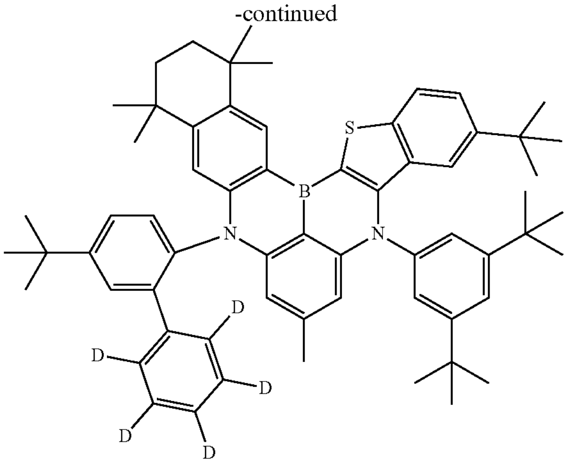
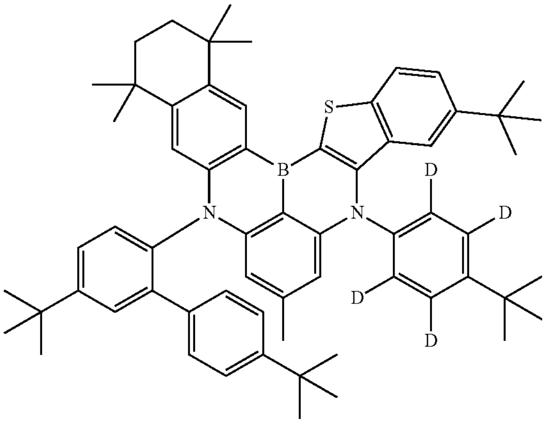
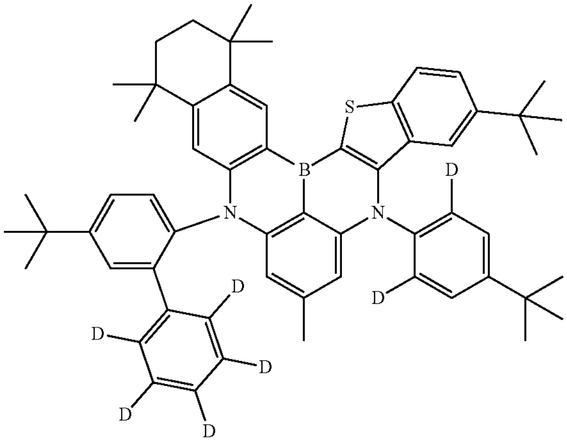
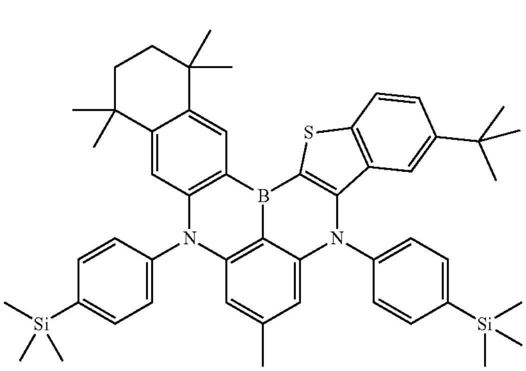
-continued
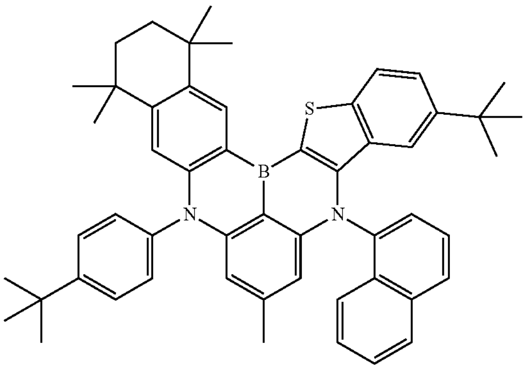
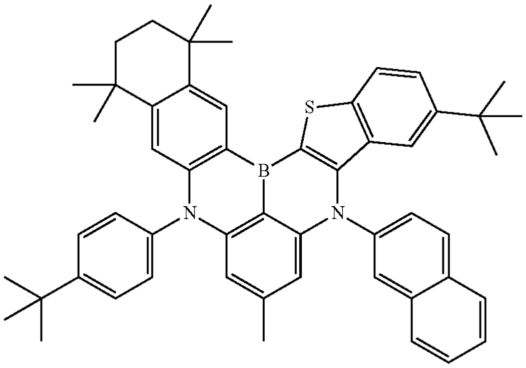
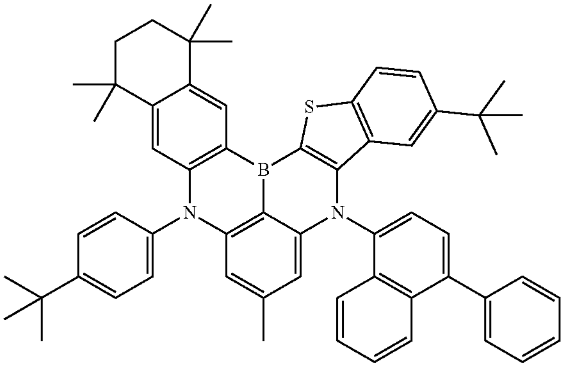
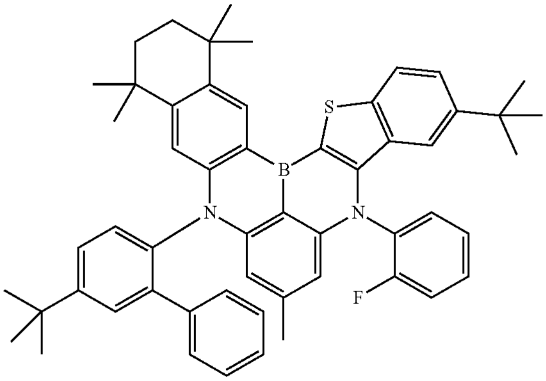

-continued
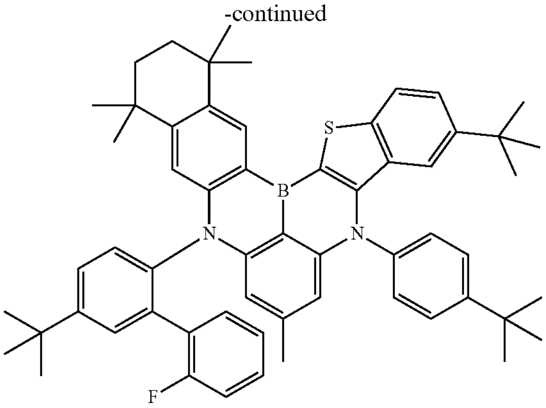
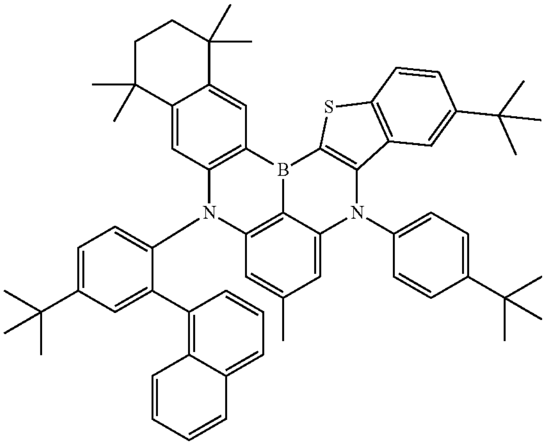
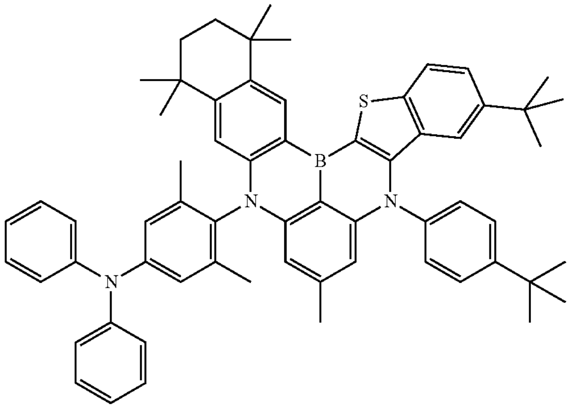
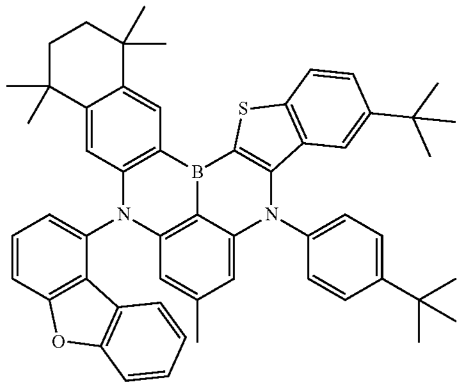
-continued
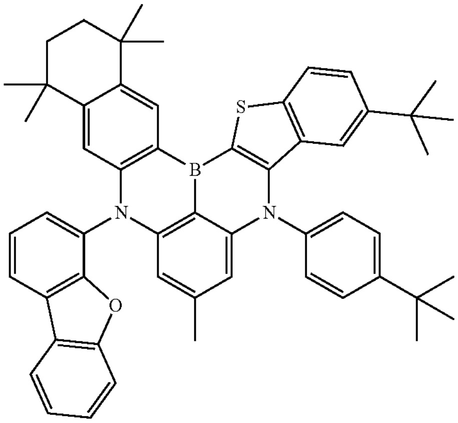
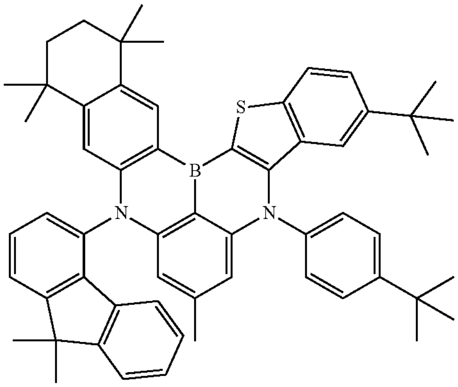
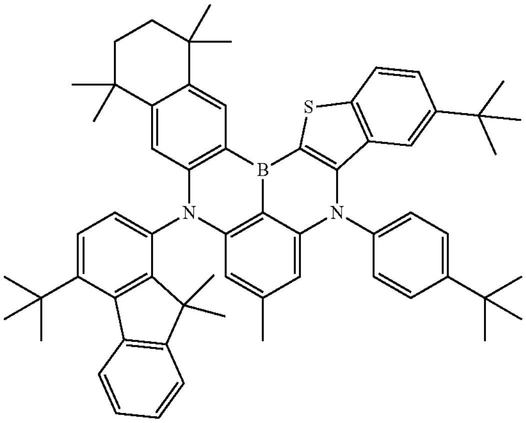
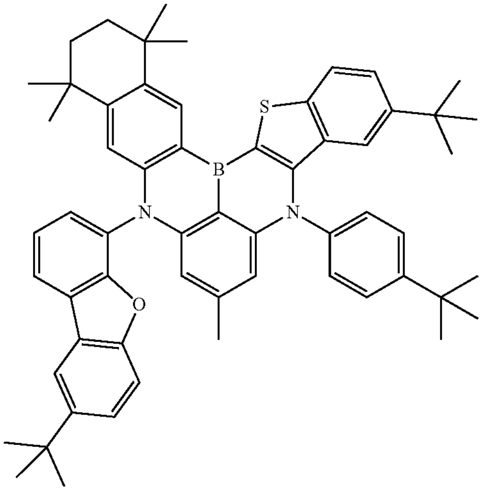

-continued
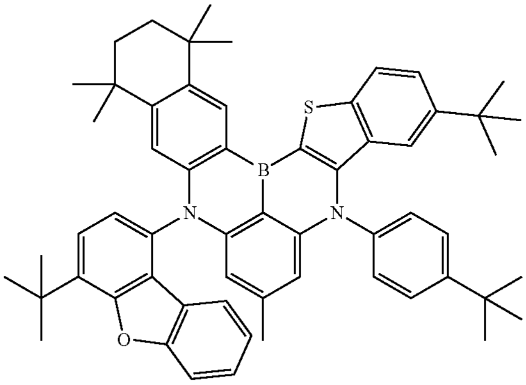
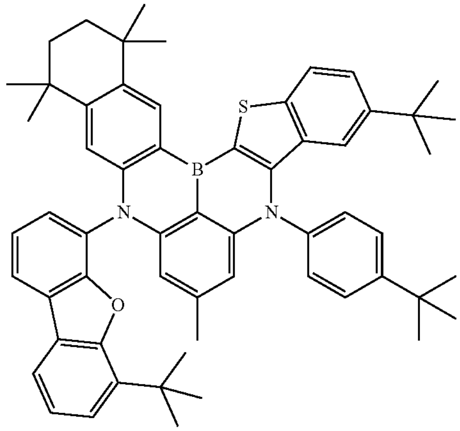
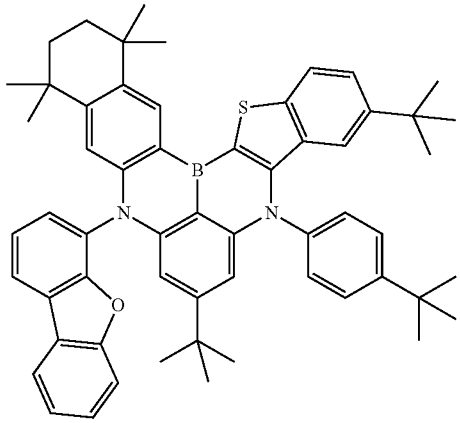
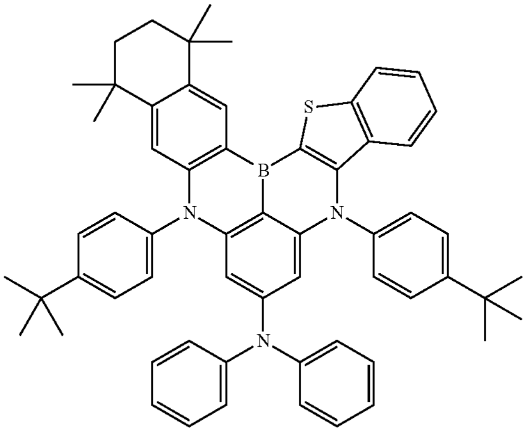
-continued
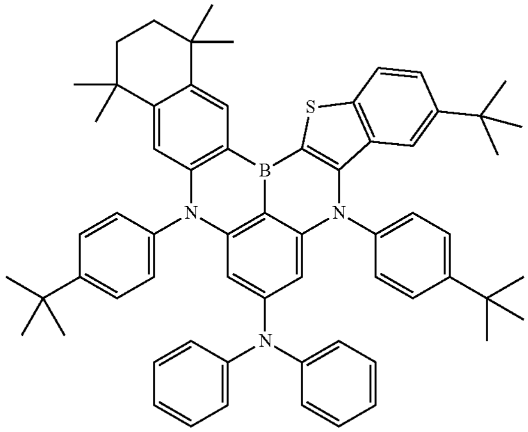
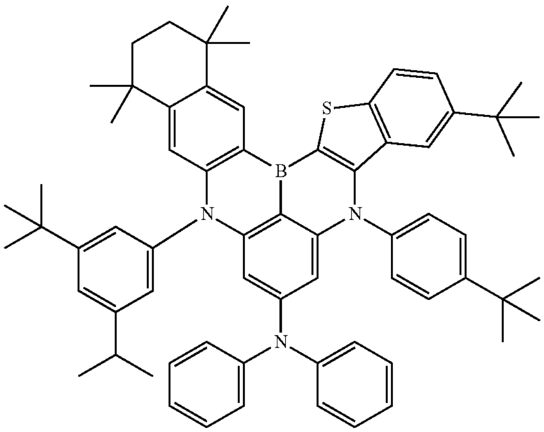
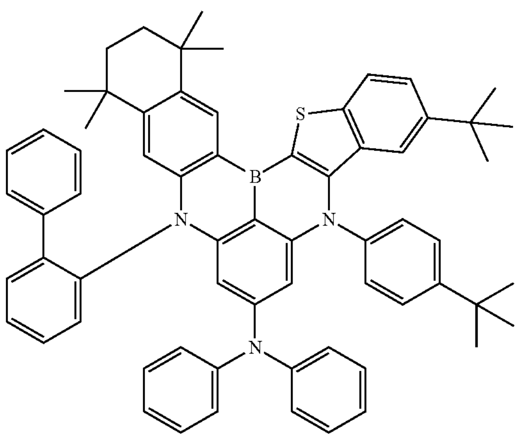

-continued
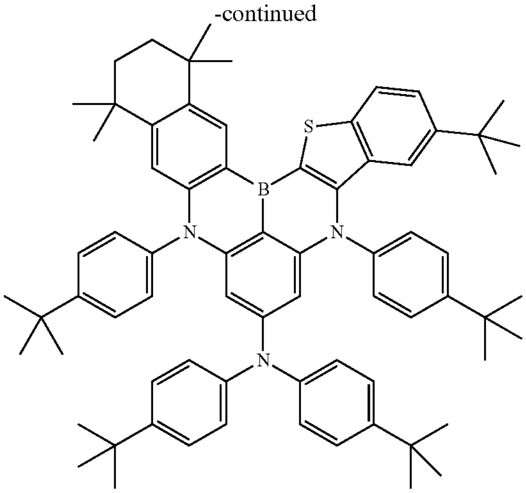
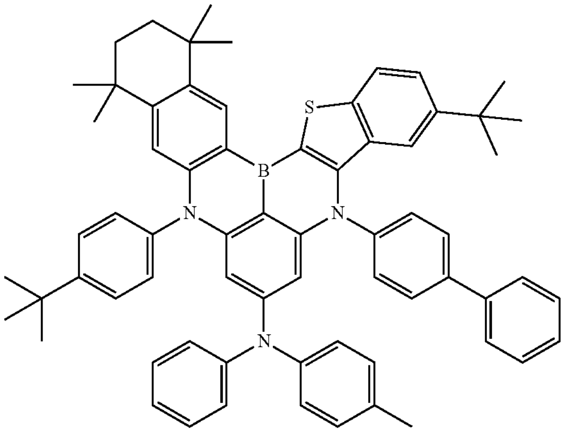
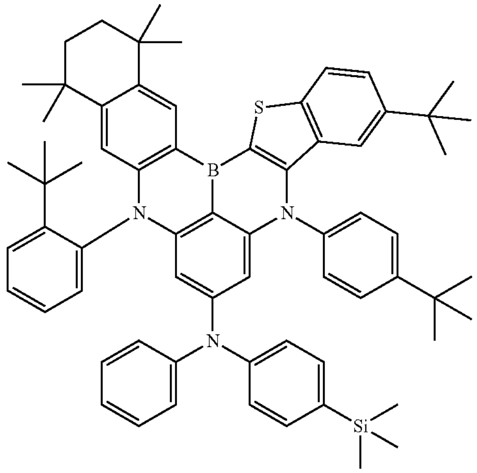
-continued
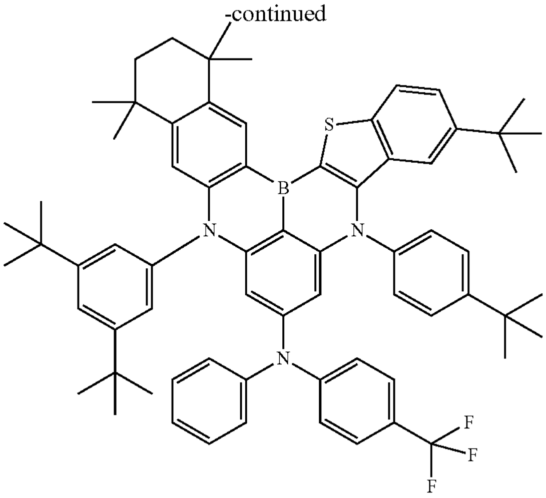
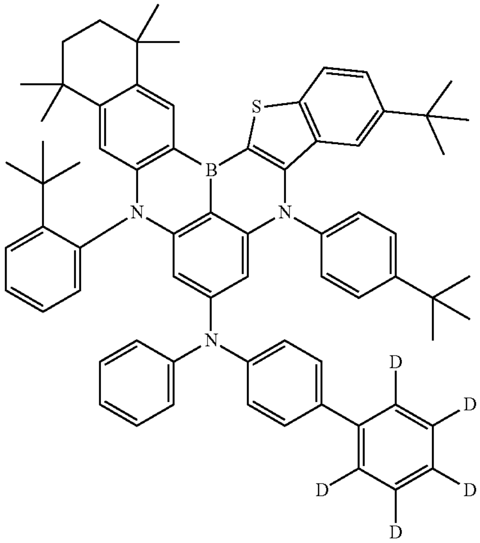
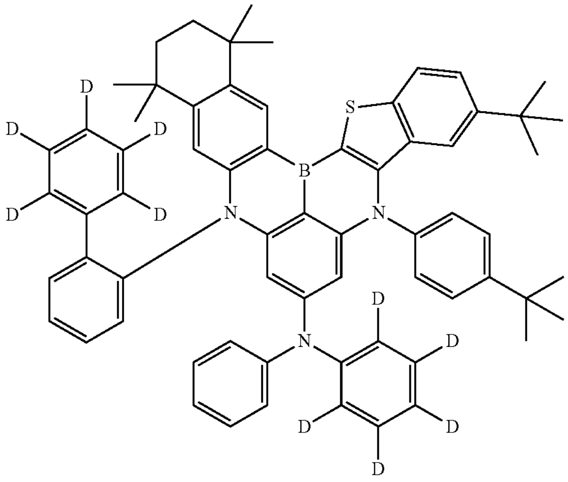

-continued
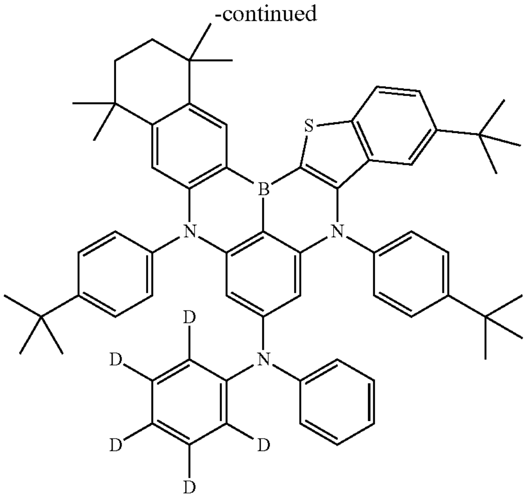
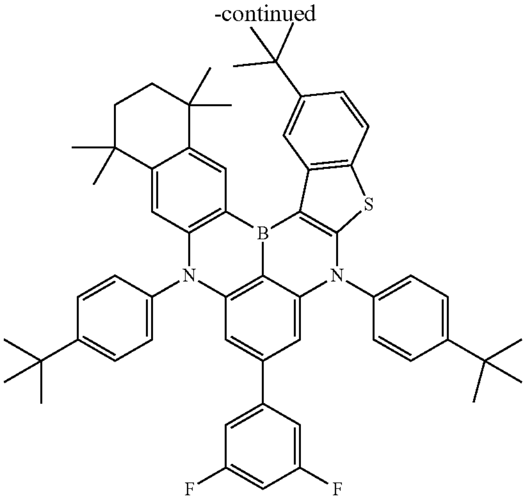
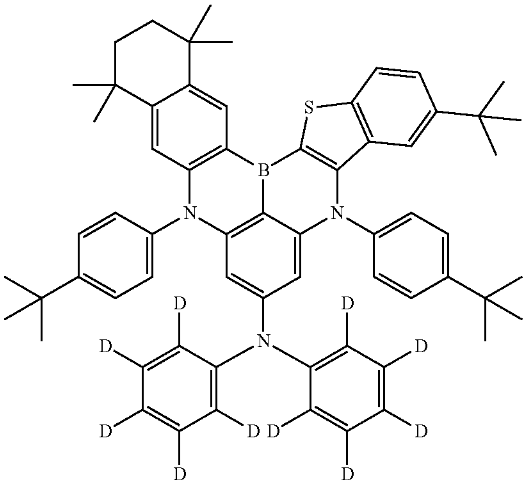
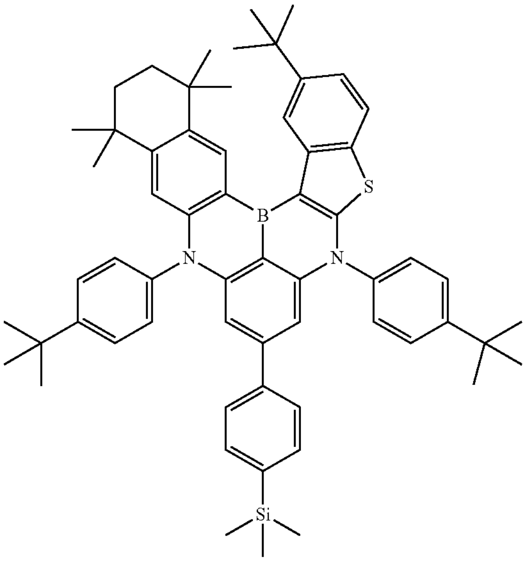
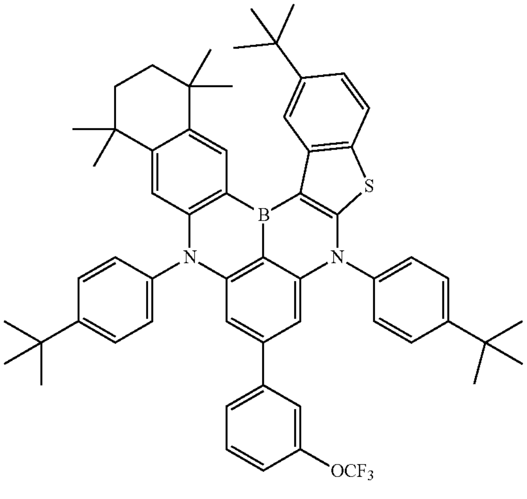
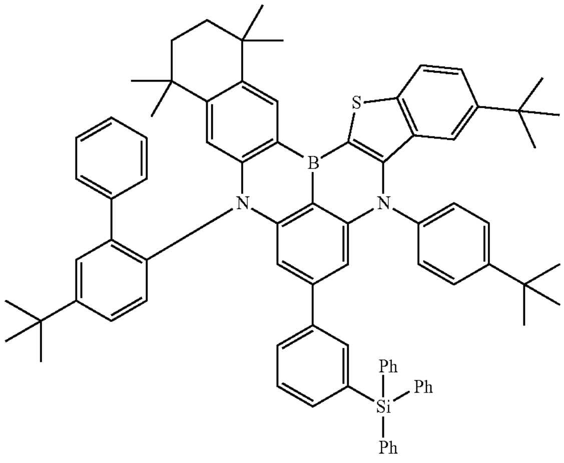
-continued -continued
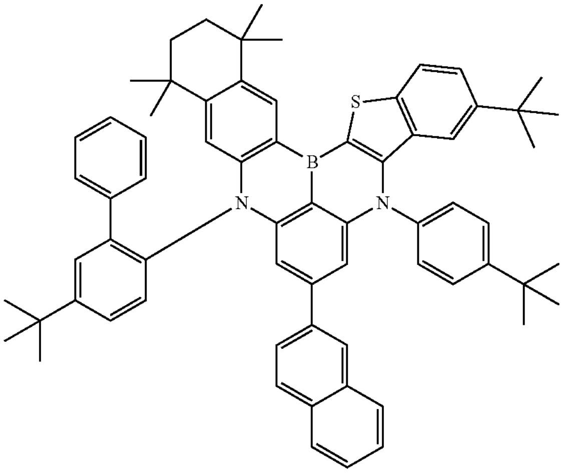
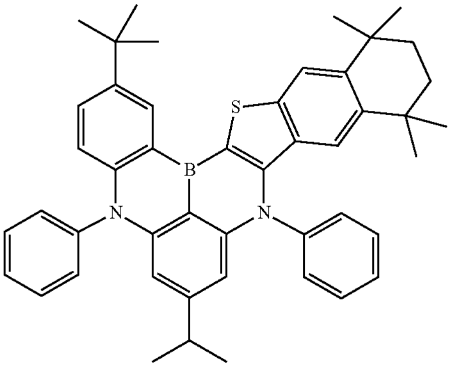
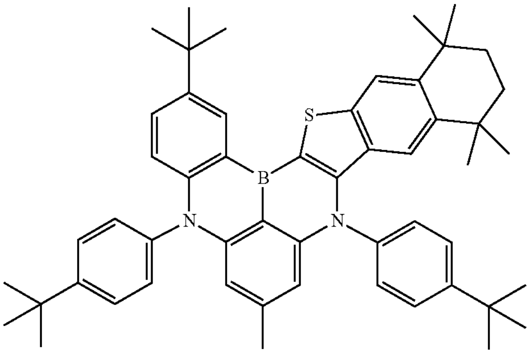
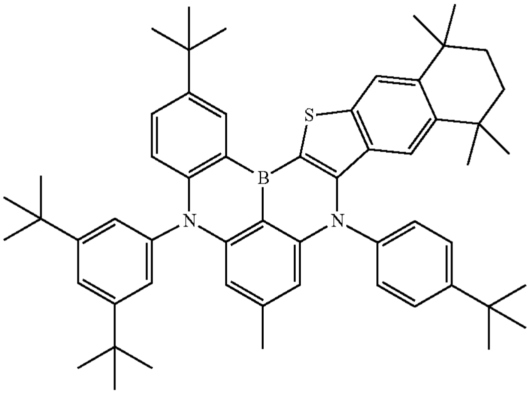
-continued
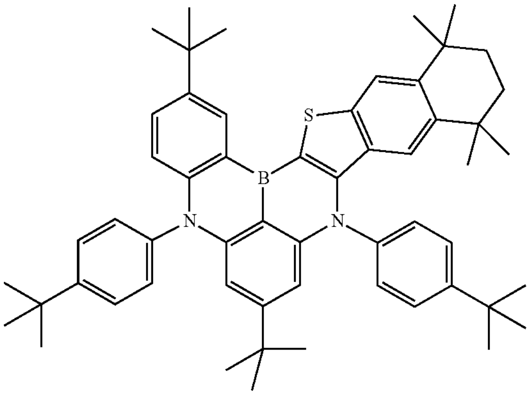
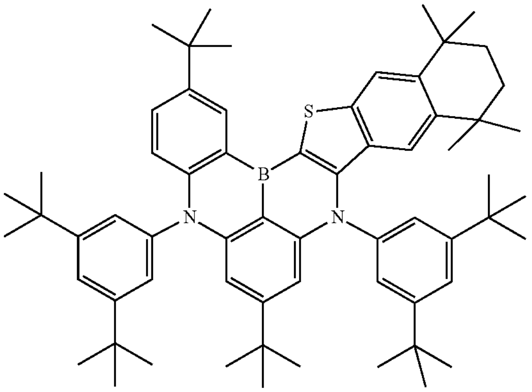
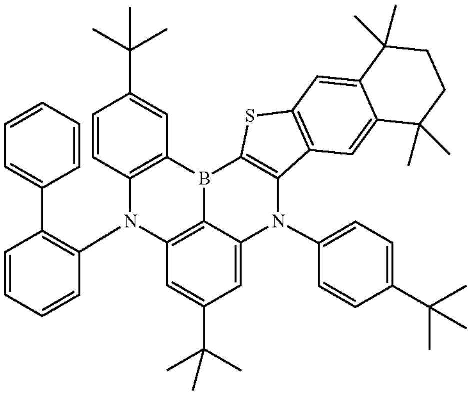
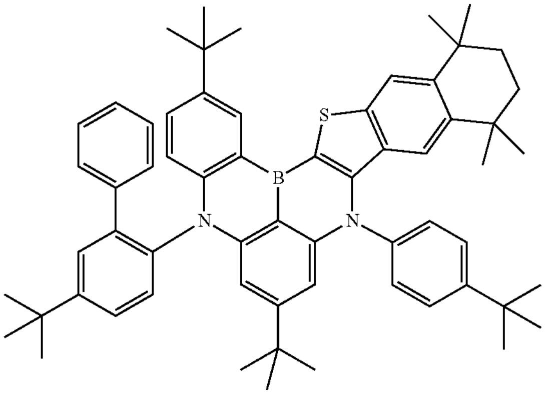

-continued
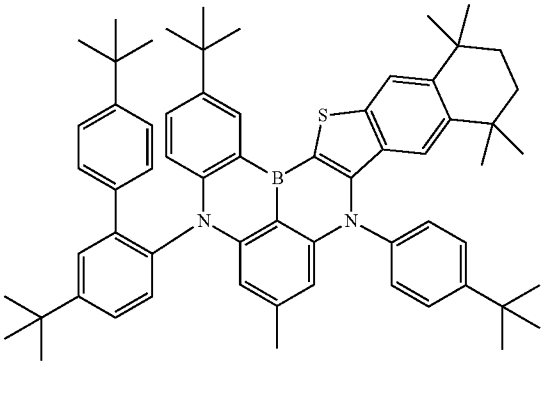
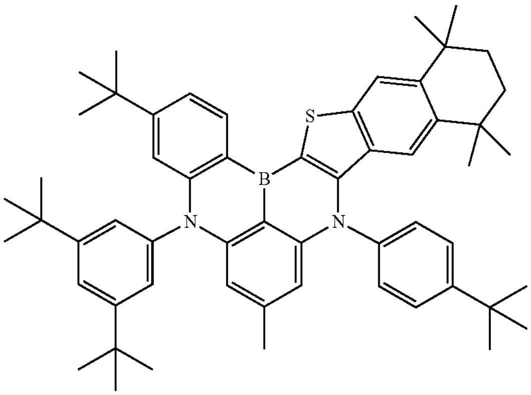
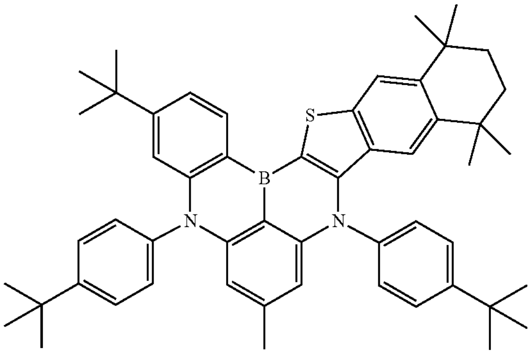
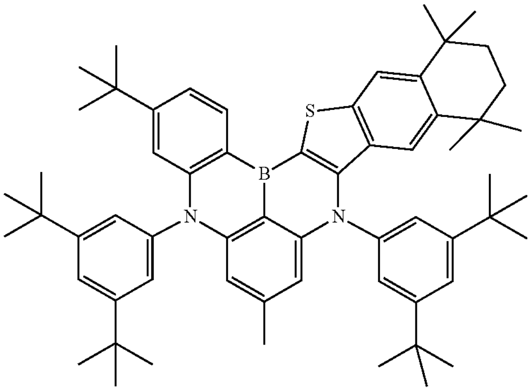
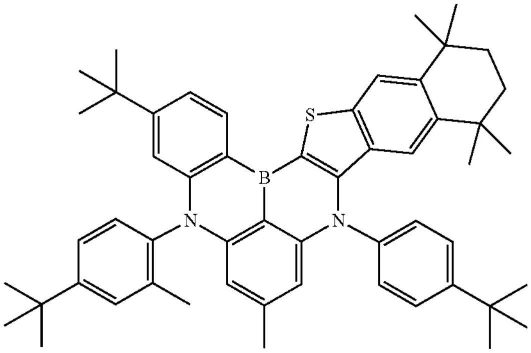
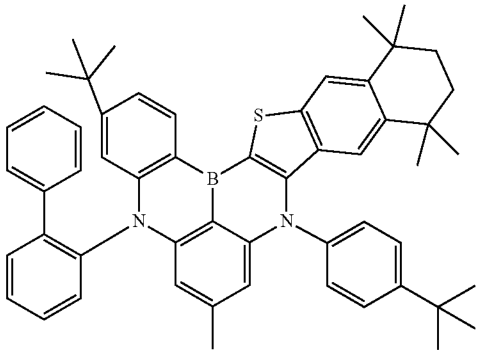
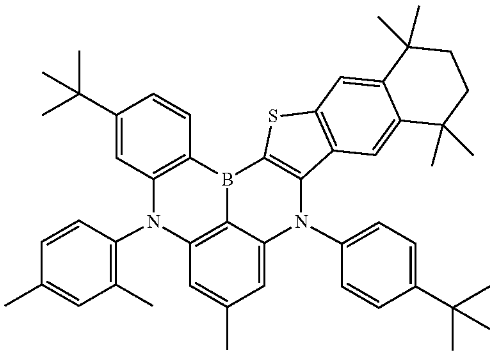
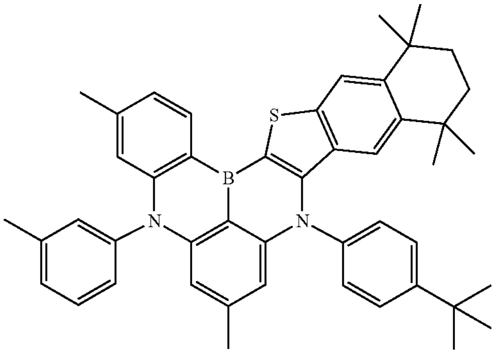
-continued -continued
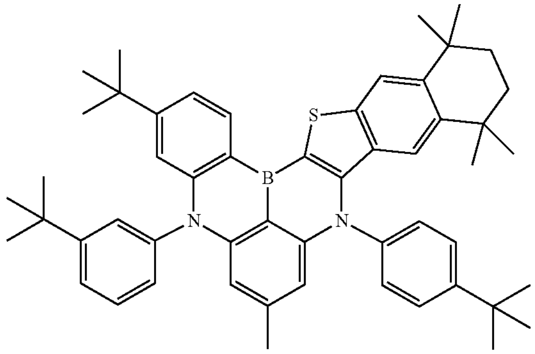
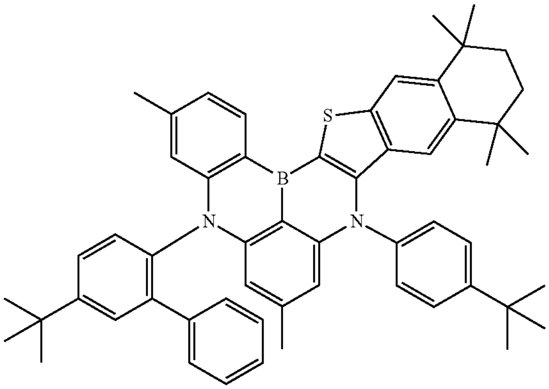
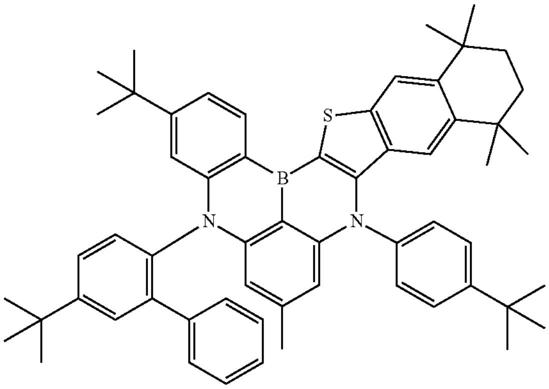
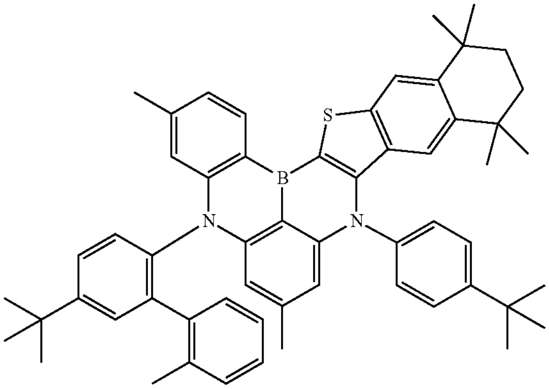
-continued
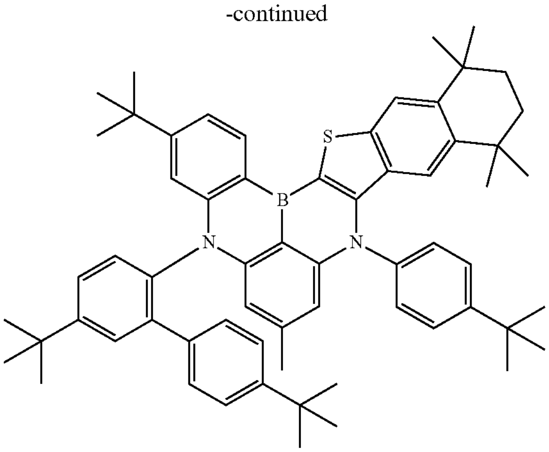
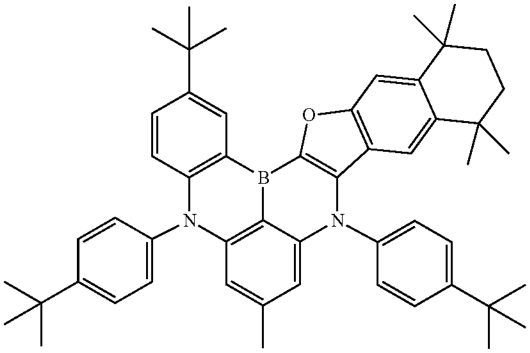
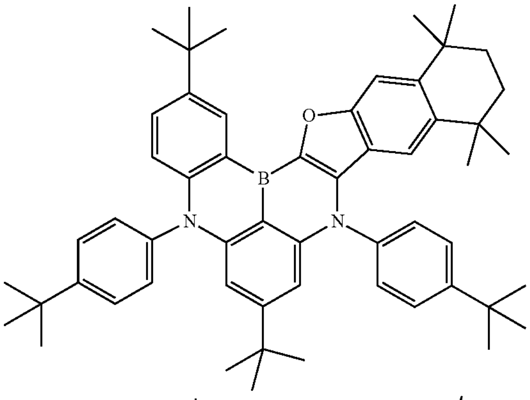
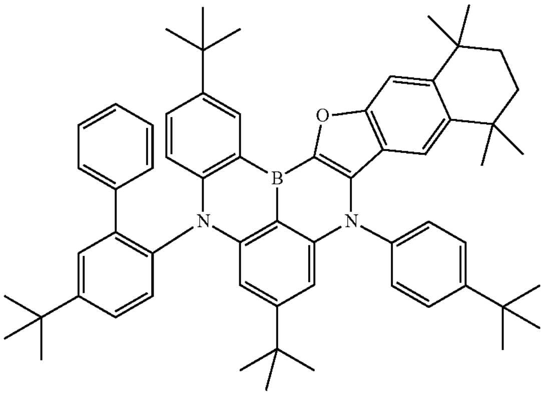

-continued
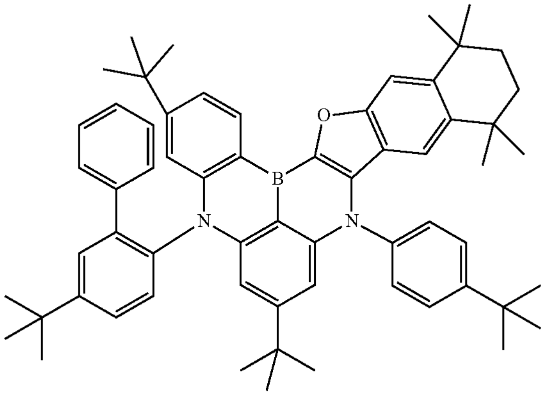
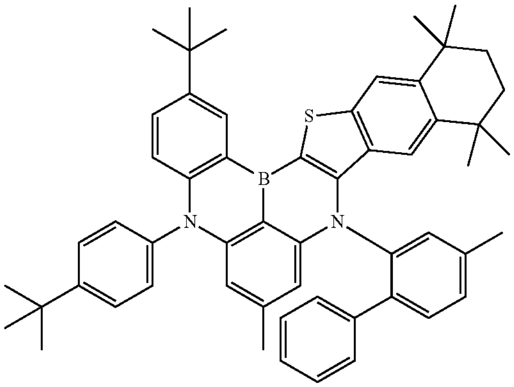
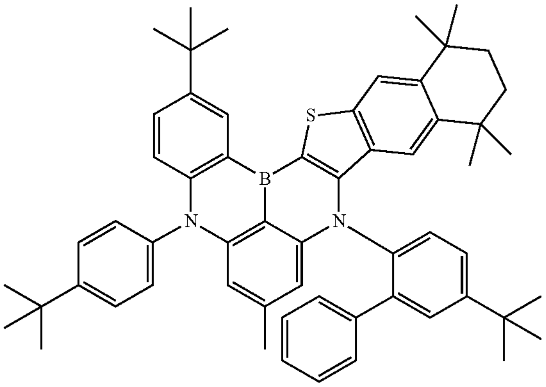
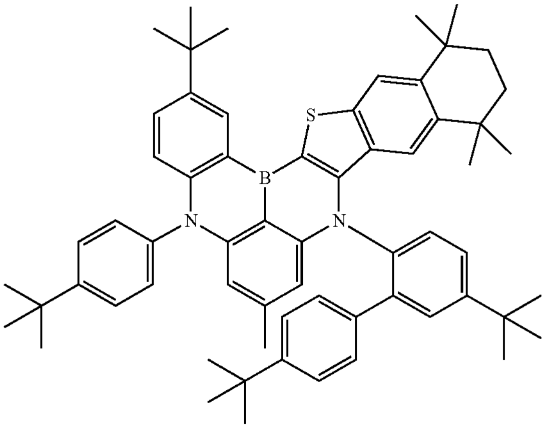
-continued
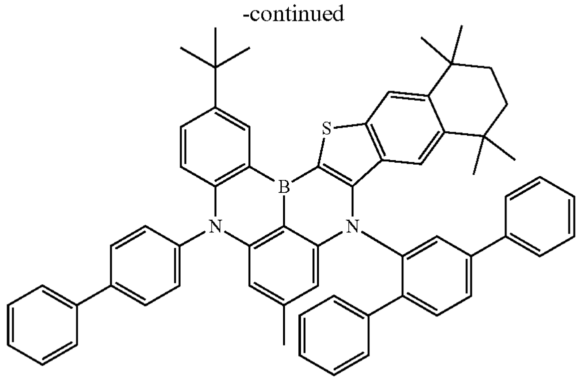
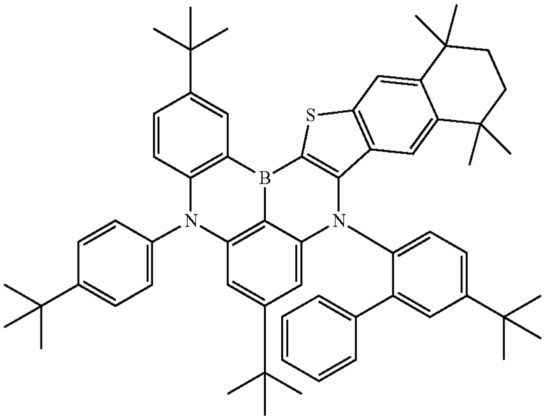
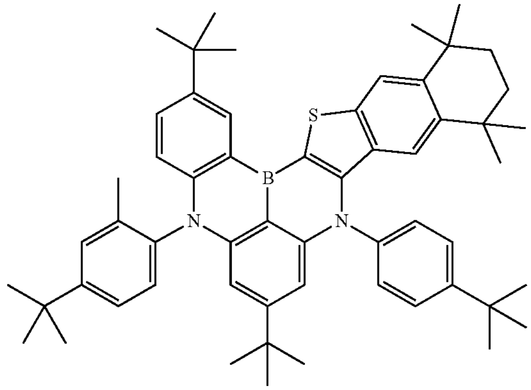
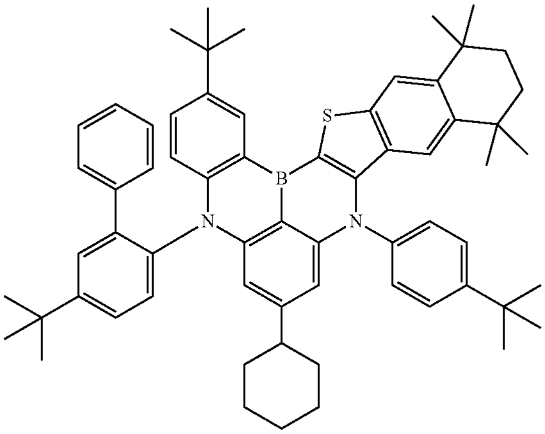

-continued
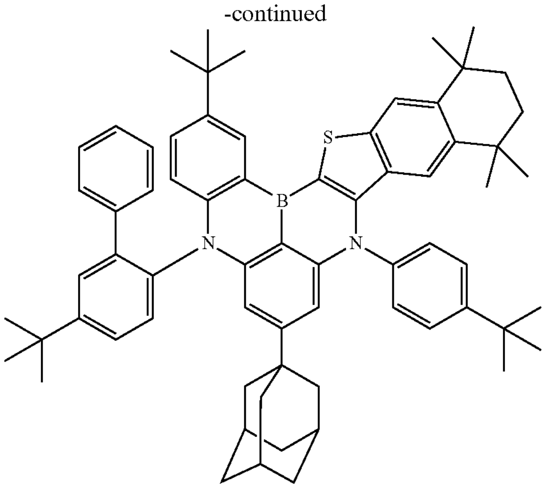
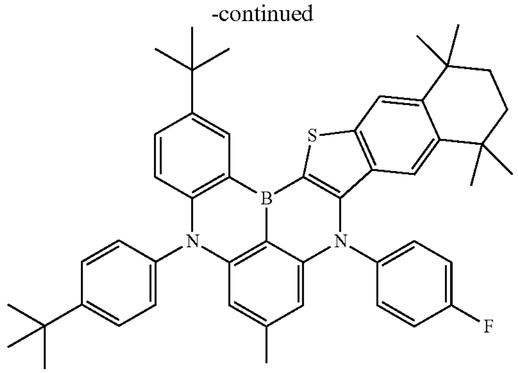
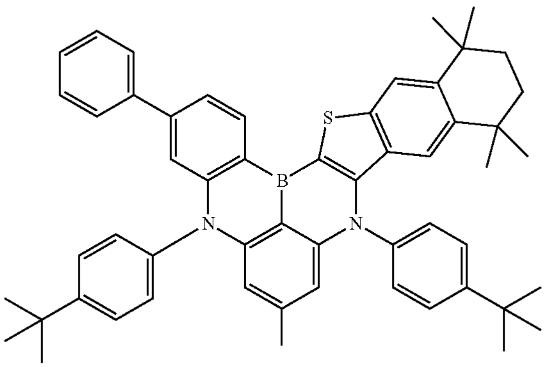
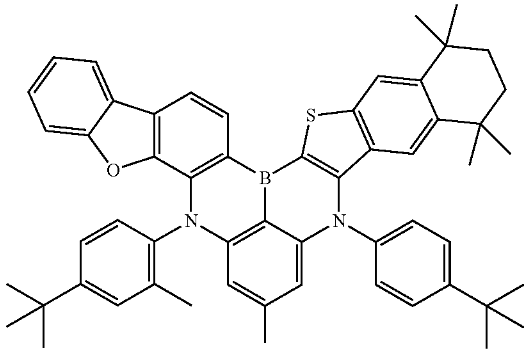
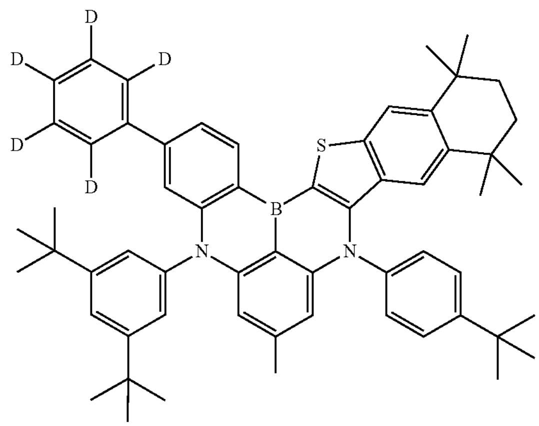
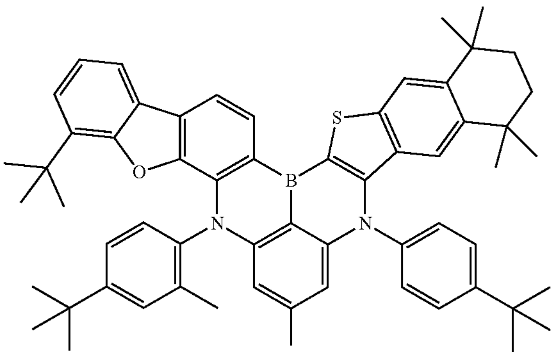
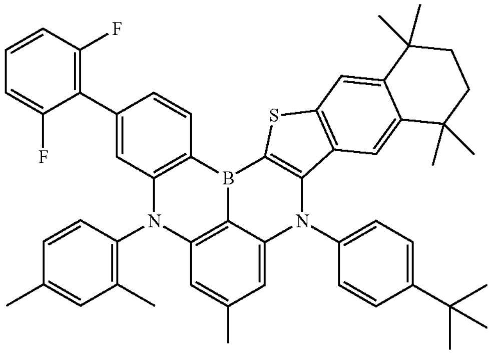
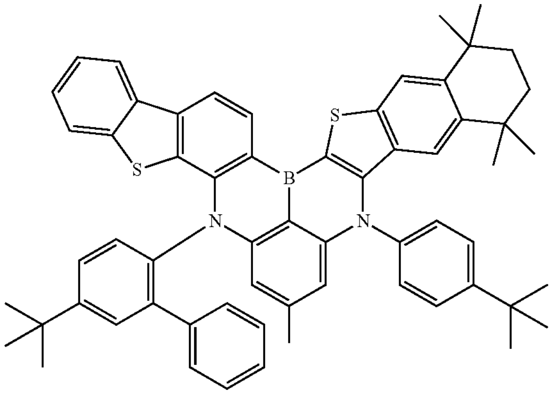
-continued -continued
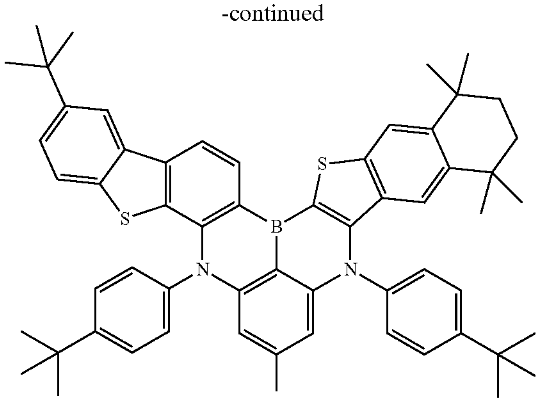
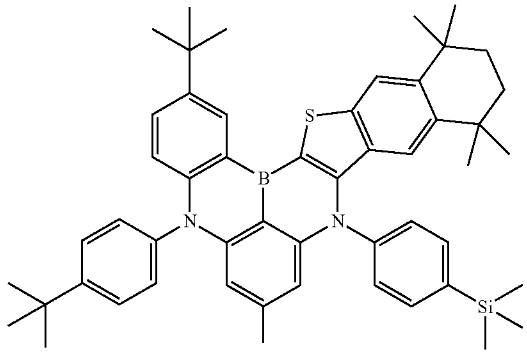
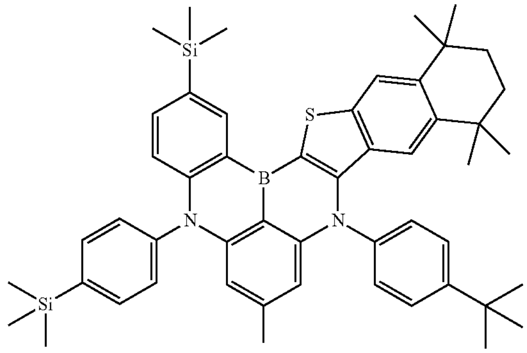
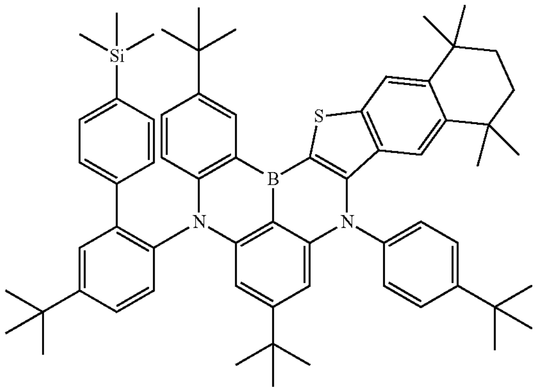
-continued
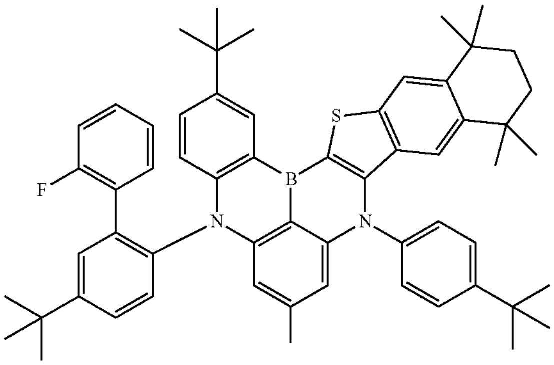
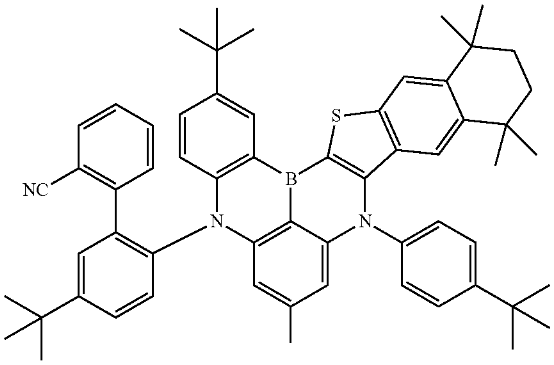
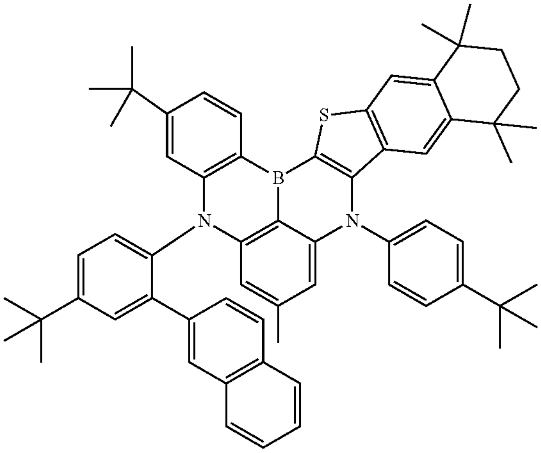
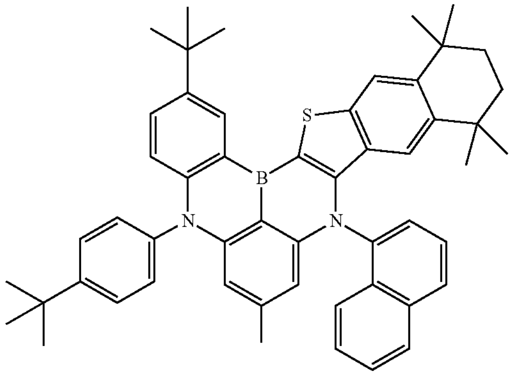

-continued
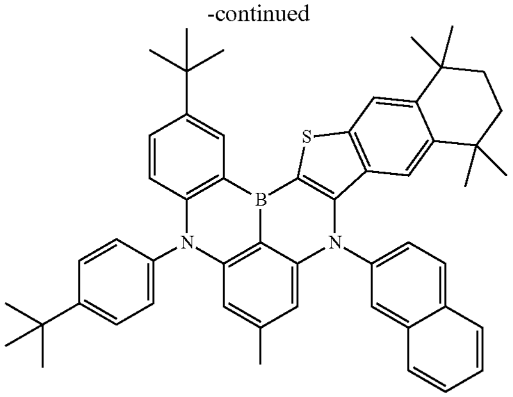
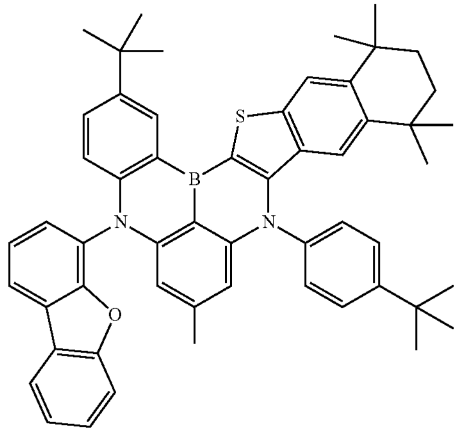
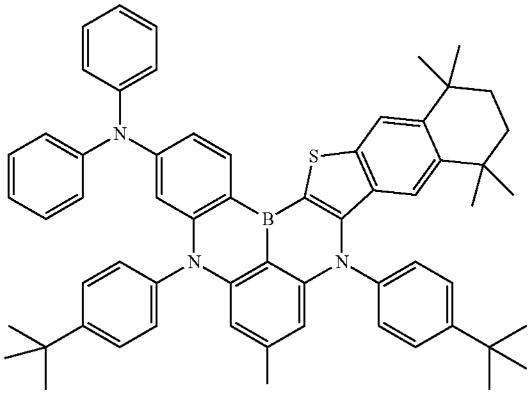
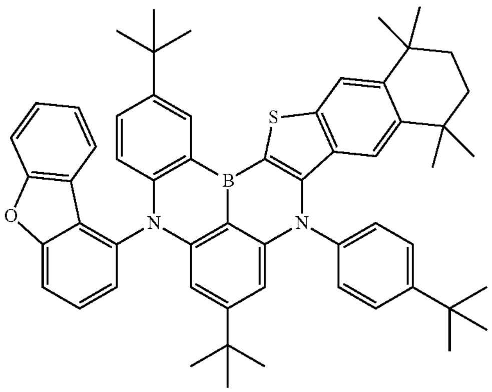
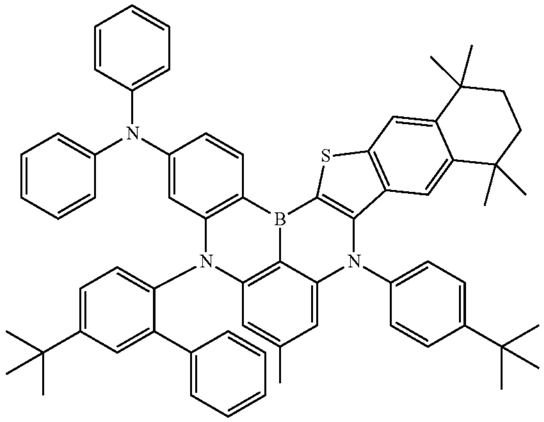
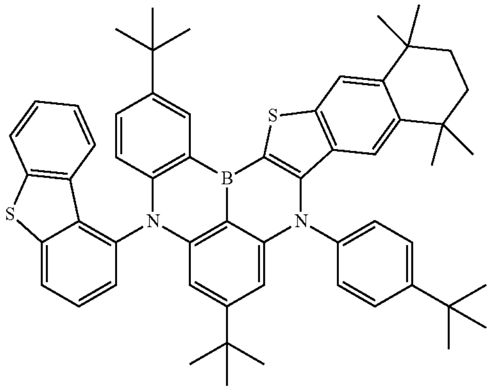
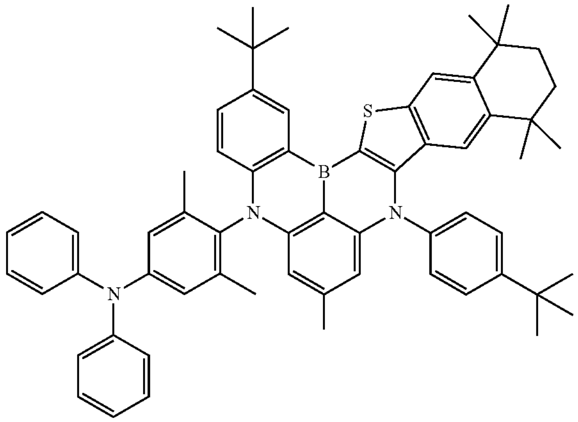
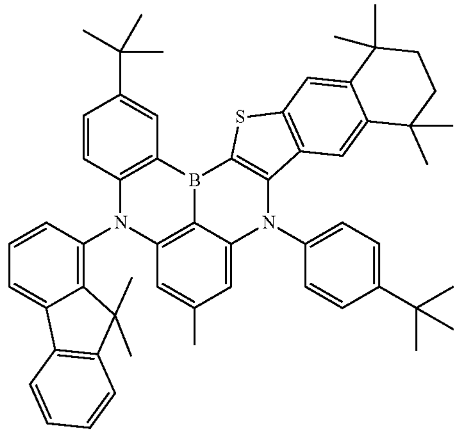

-continued
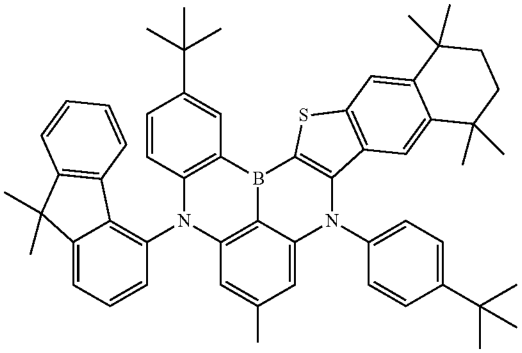
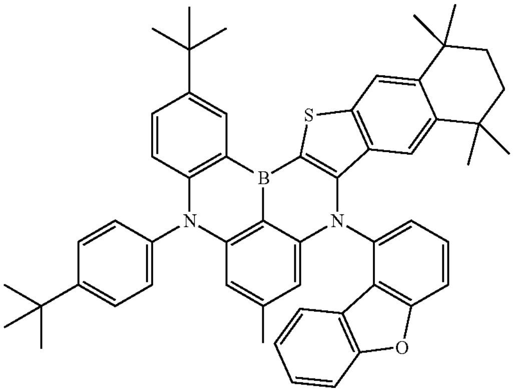
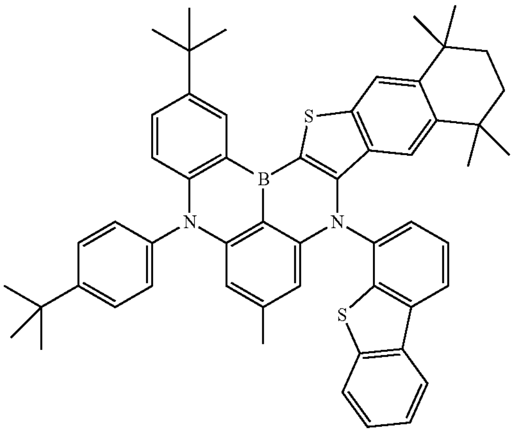
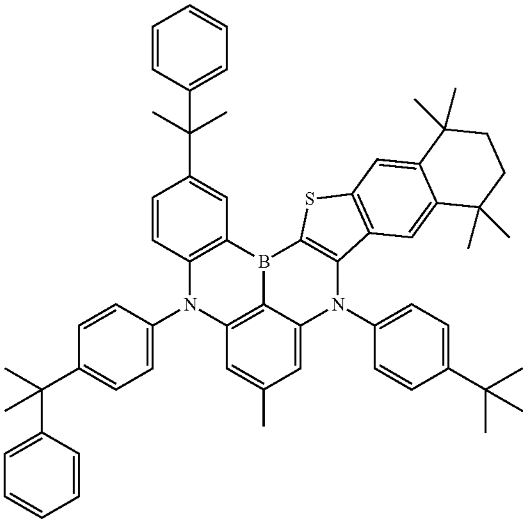
-continued
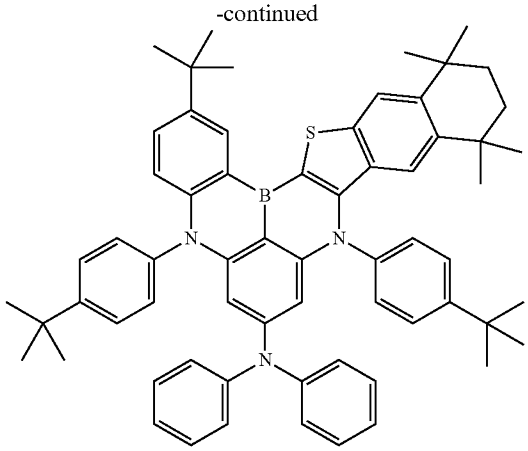
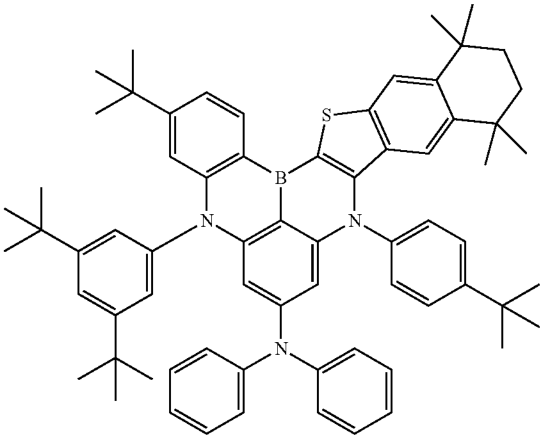
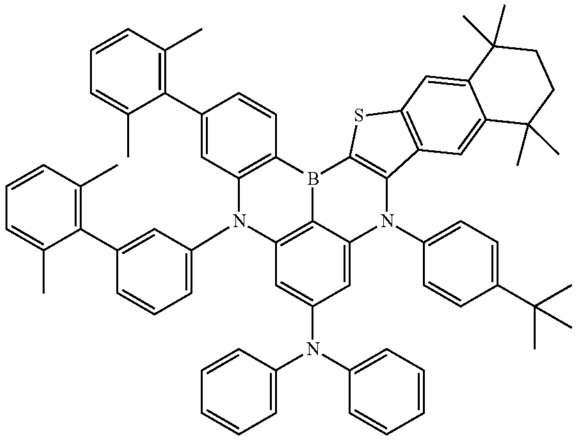

-continued
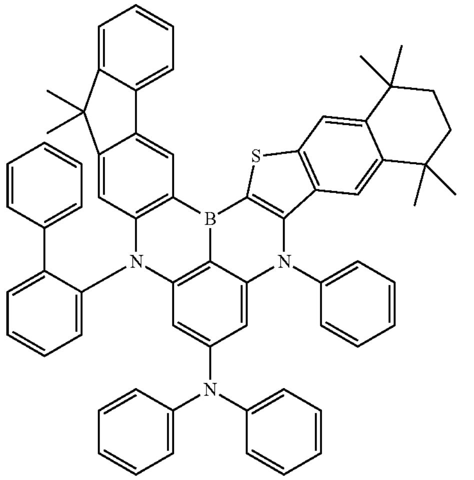
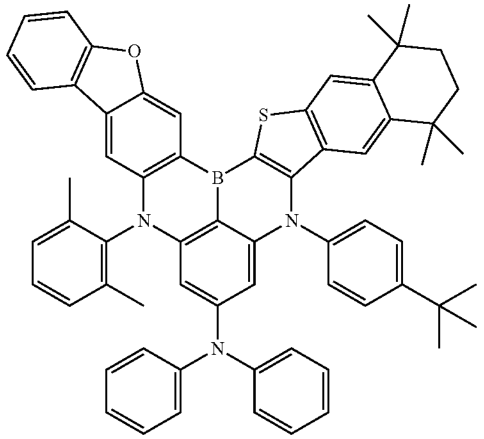
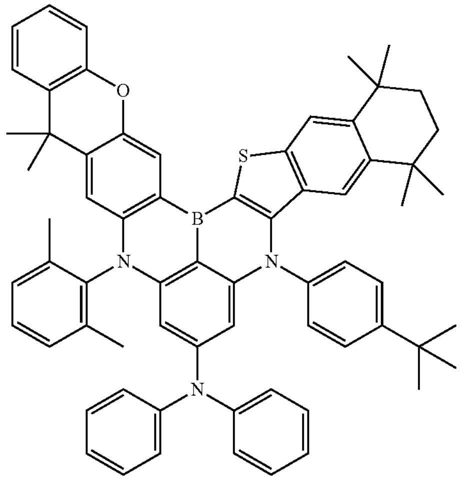
-continued
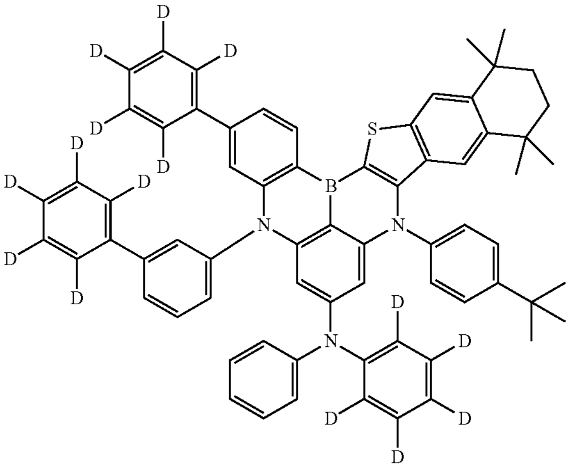
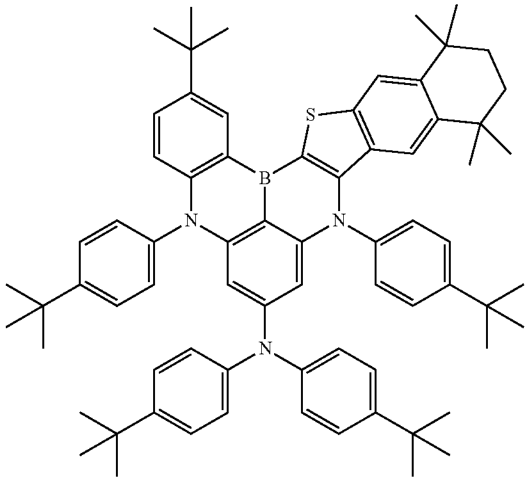
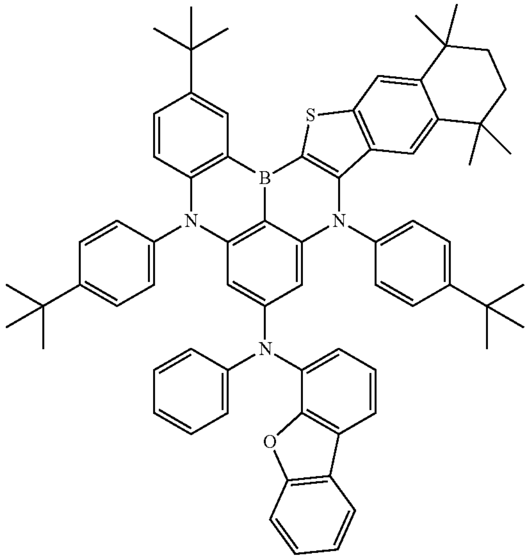 [SMILES: CC(C)(C)c1ccc(N2c3ccc(C(C)(C)C)cc3B3c4sc5cc6c(cc5c4N(c4ccc(C(C)(C)C)cc4)c4cc(N(c5ccccc5)c5cccc7c5oc5ccccc57)cc2c43)C(C)(C)CCC6(C)C)cc1]

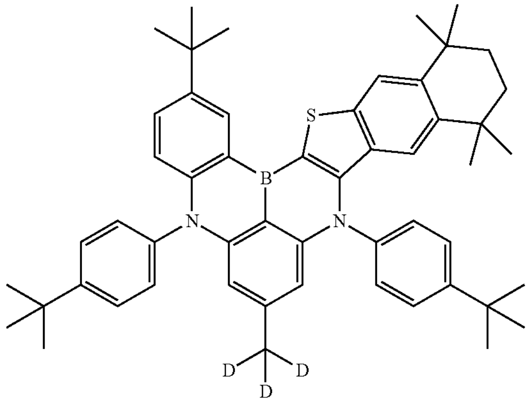
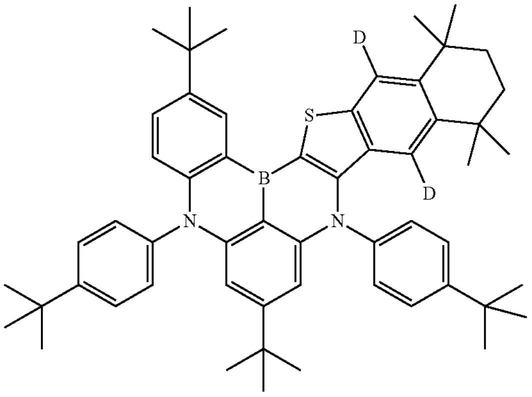
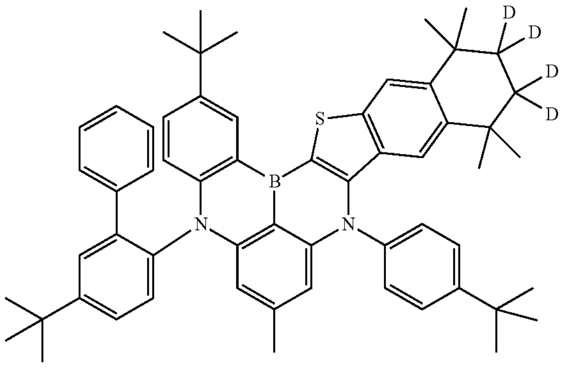
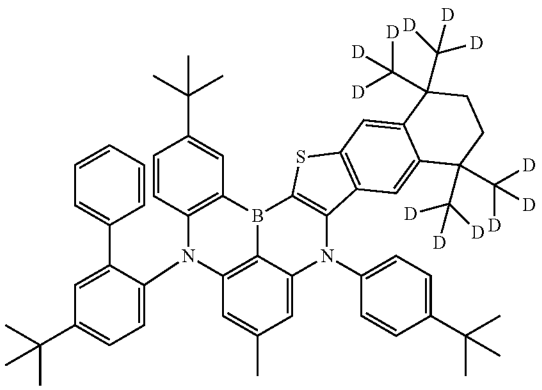
-continued
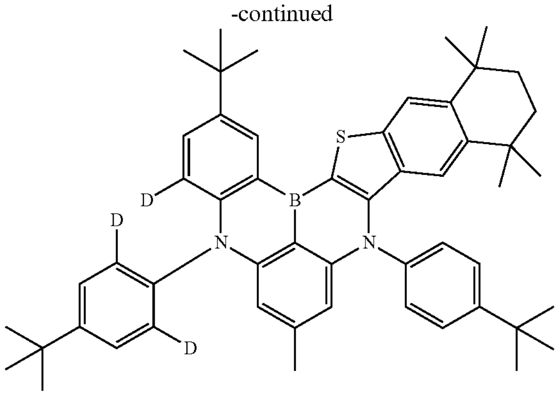
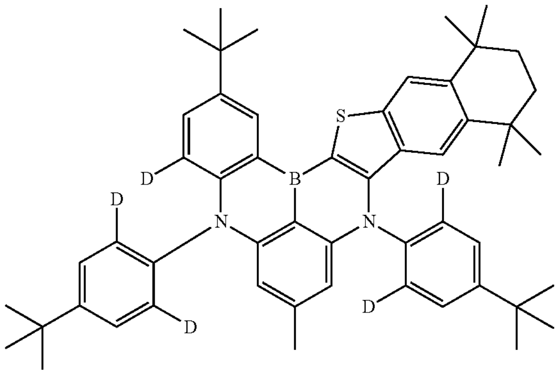
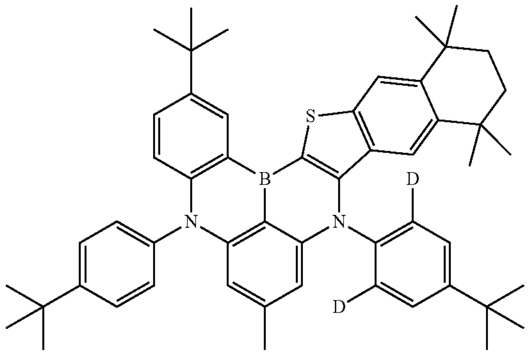
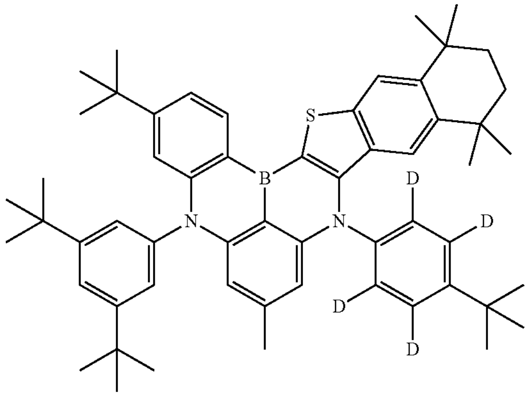

-continued
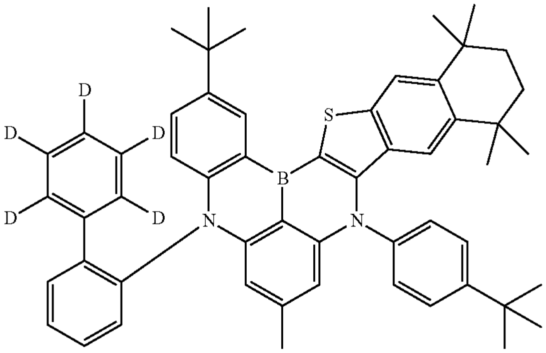
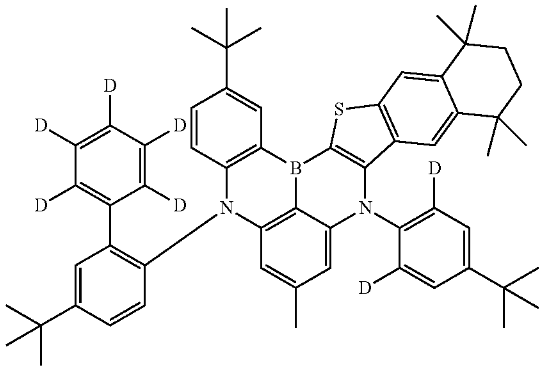
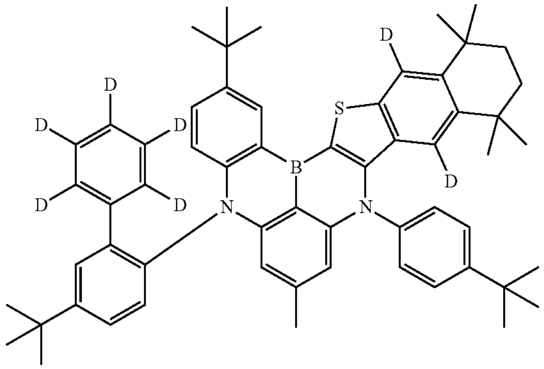
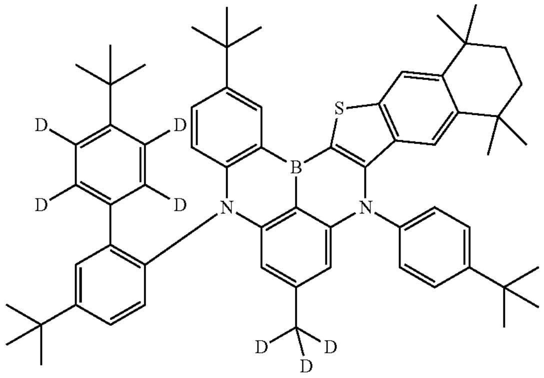
-continued
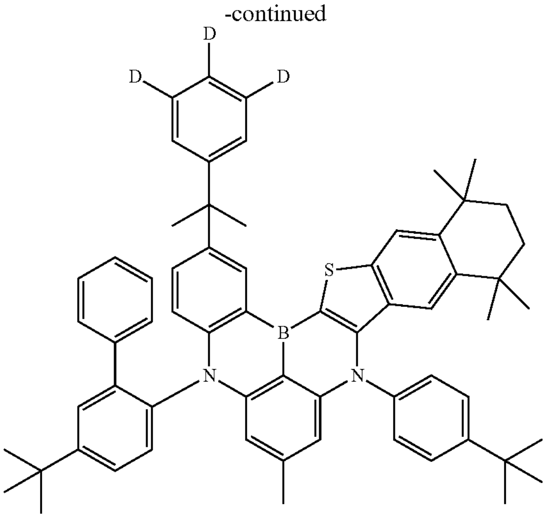
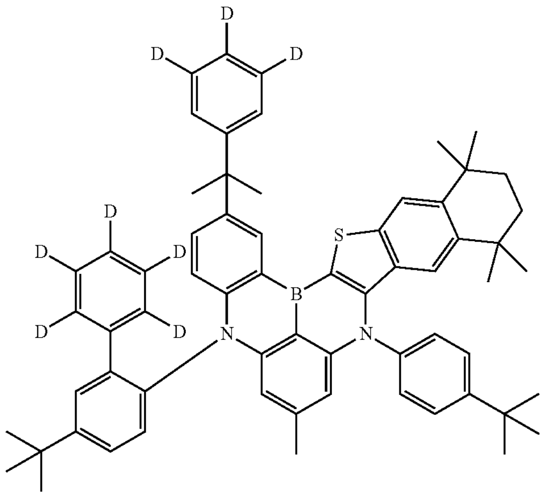
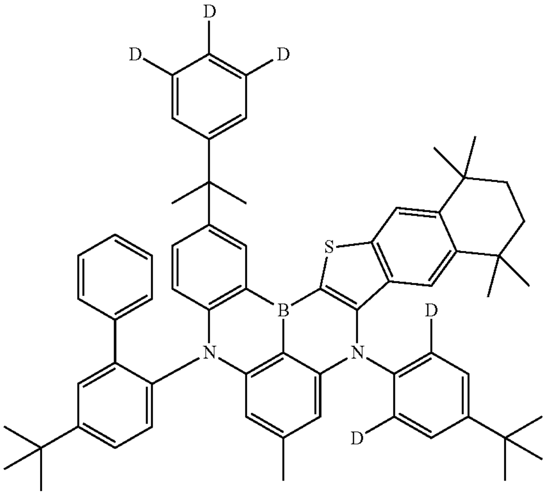

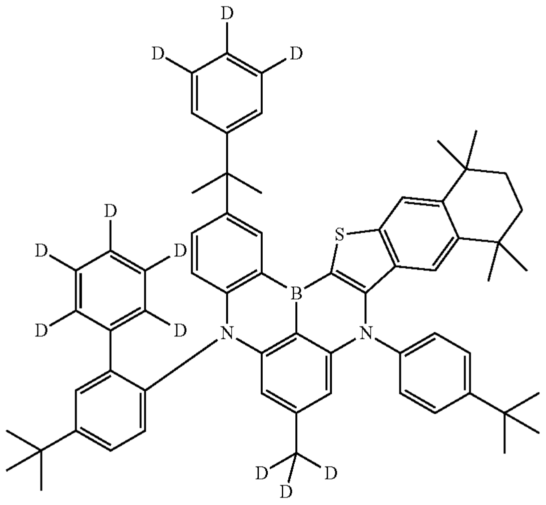
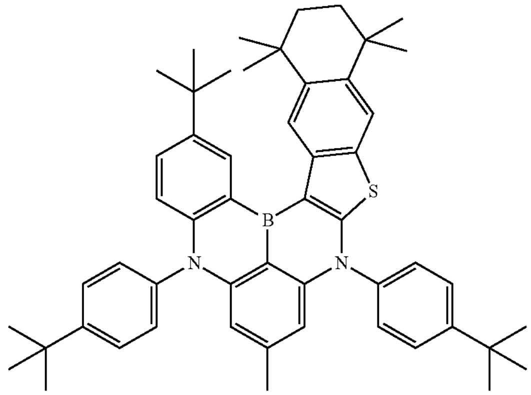
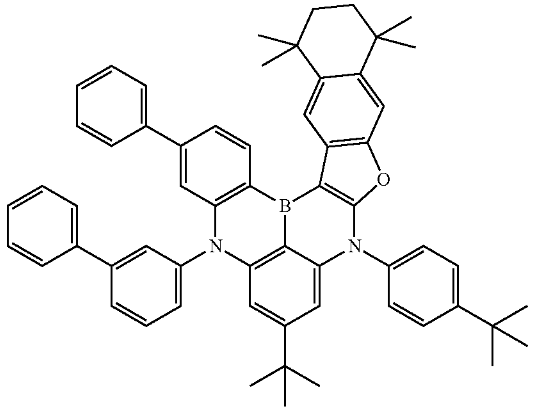
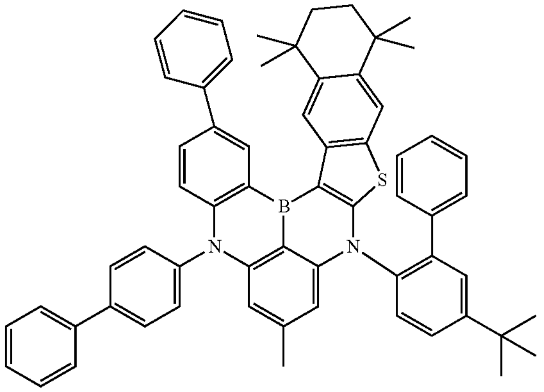
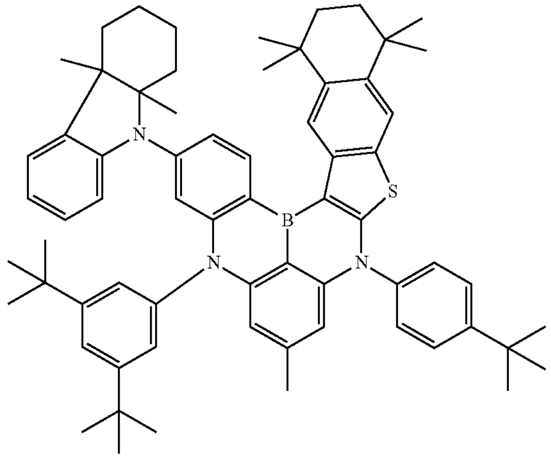
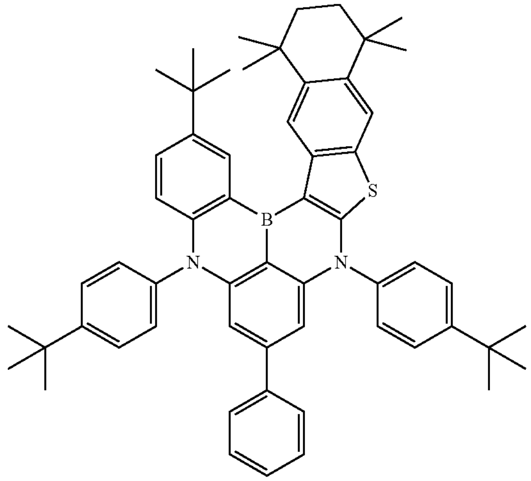
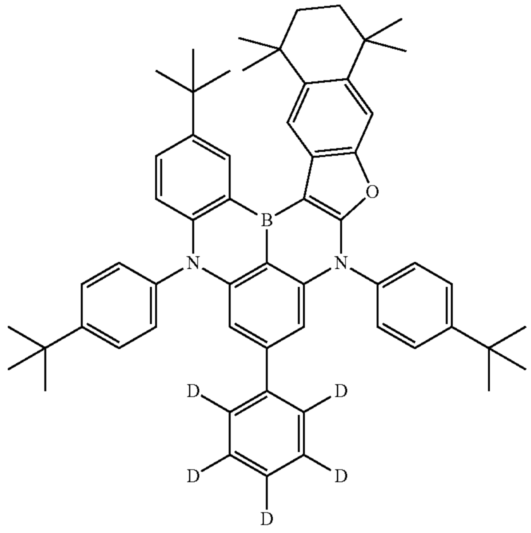

-continued
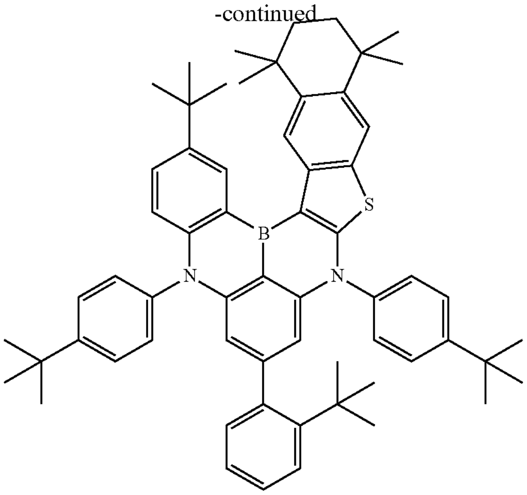
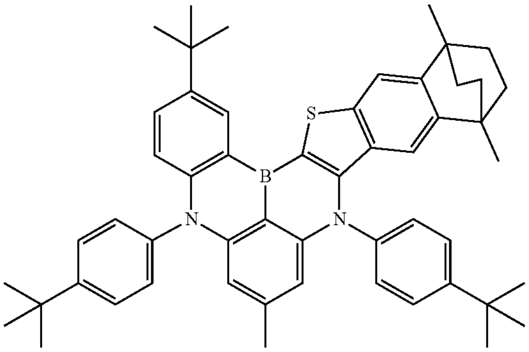
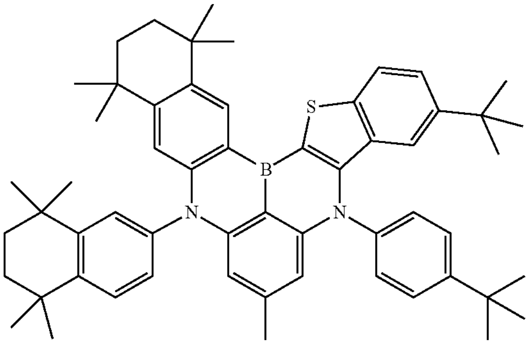
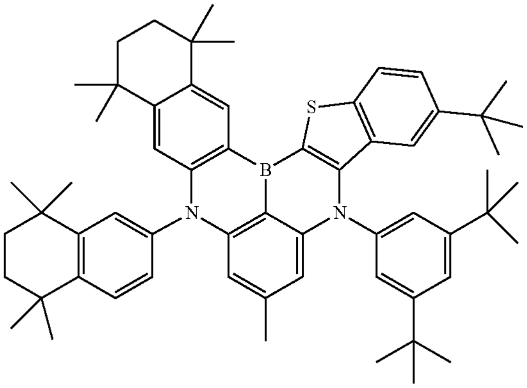
-continued
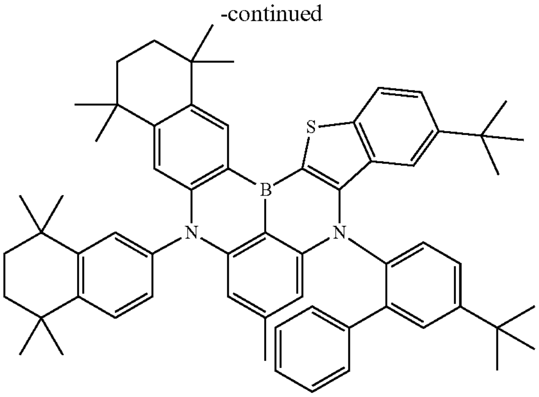
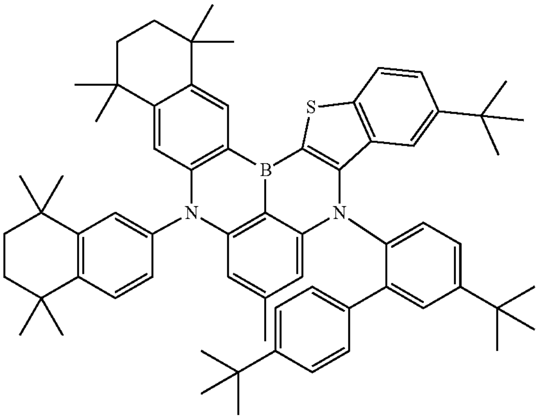
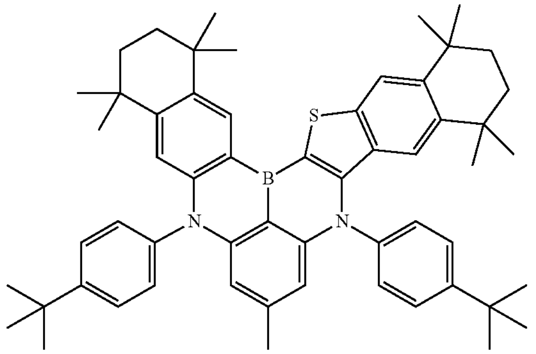
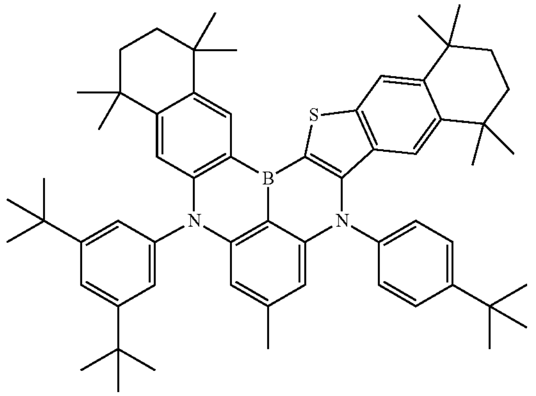

-continued
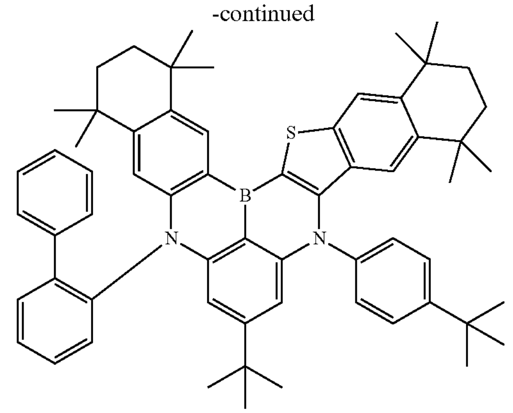
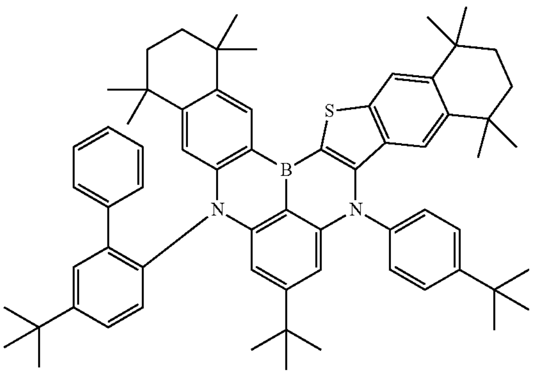
-continued
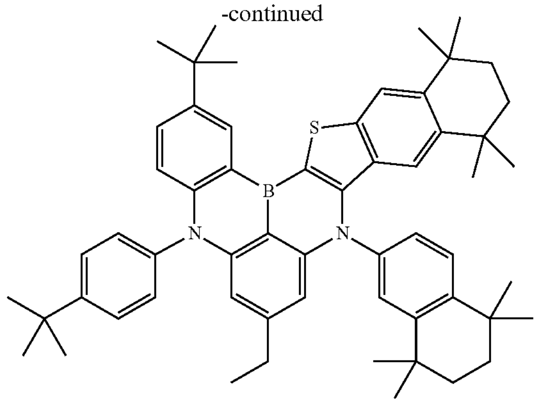
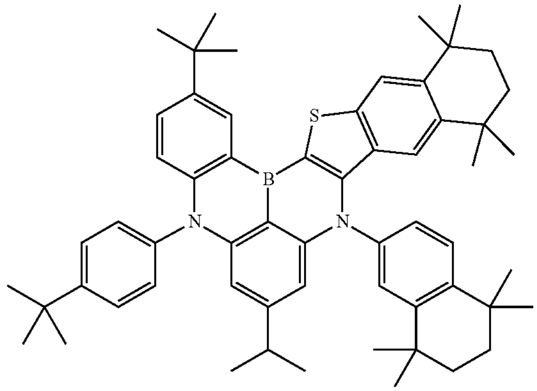
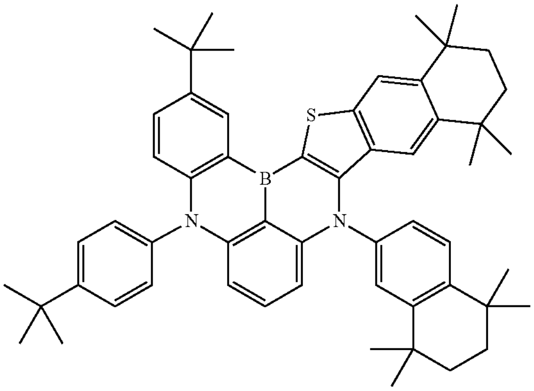
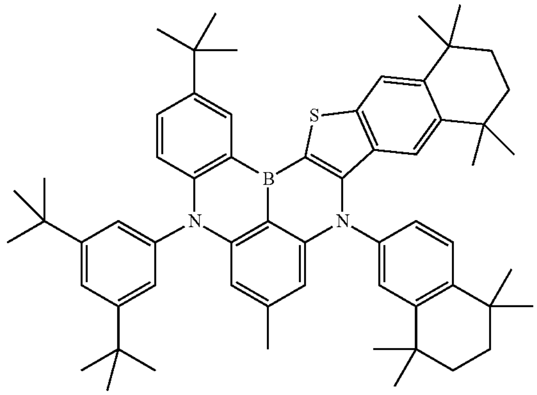
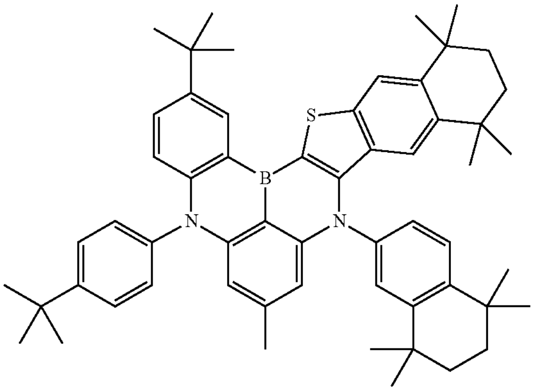
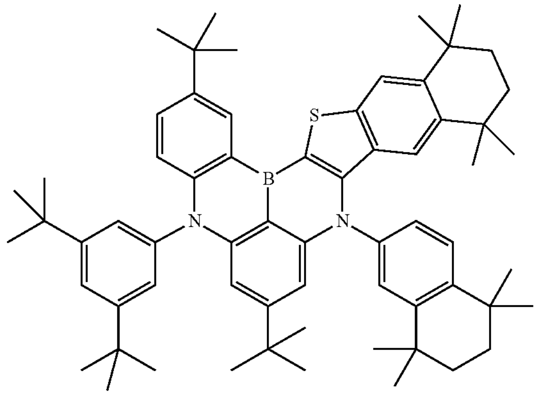

-continued
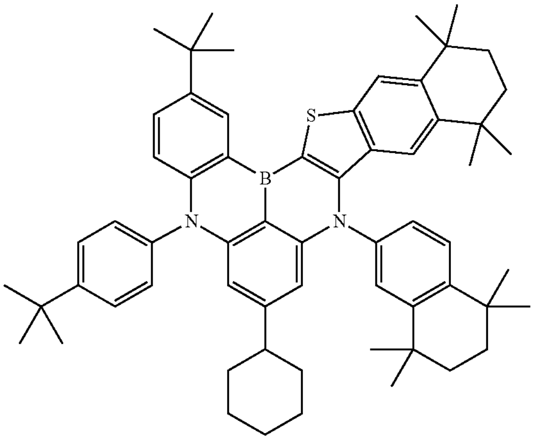
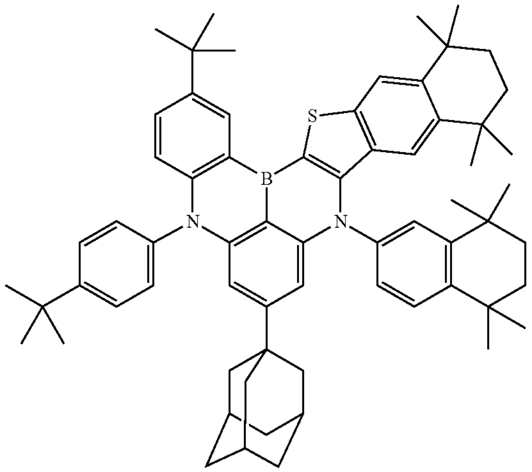
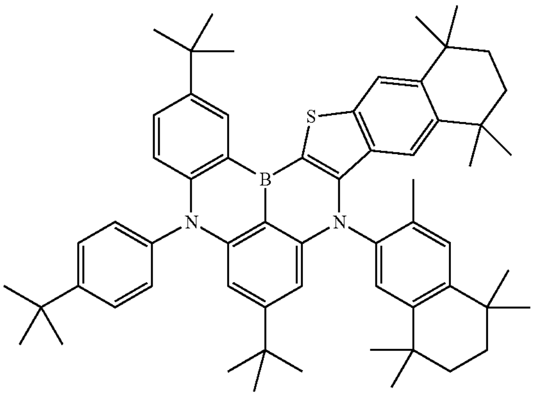
-continued
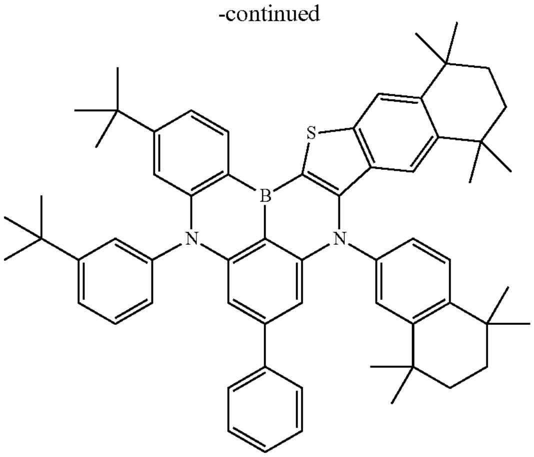
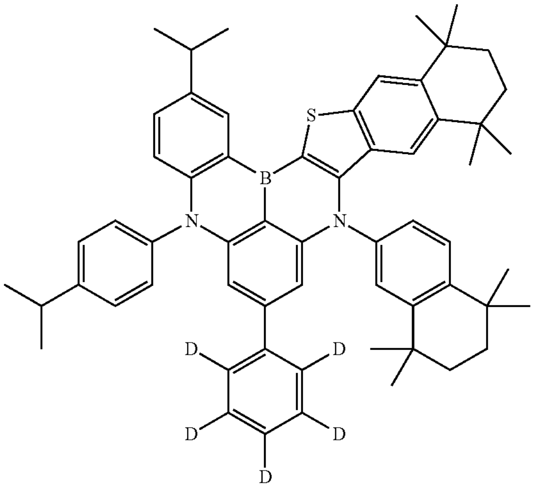
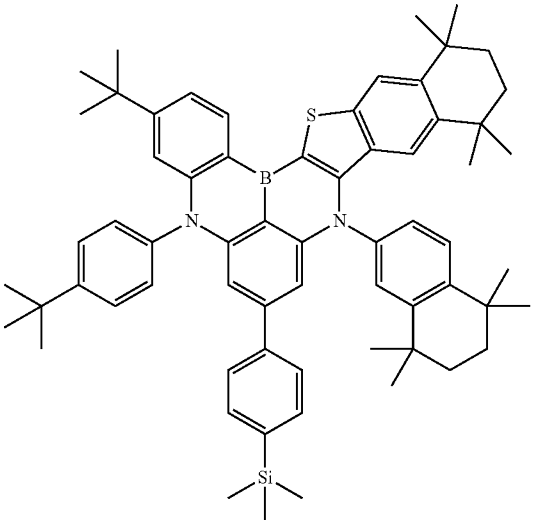

-continued
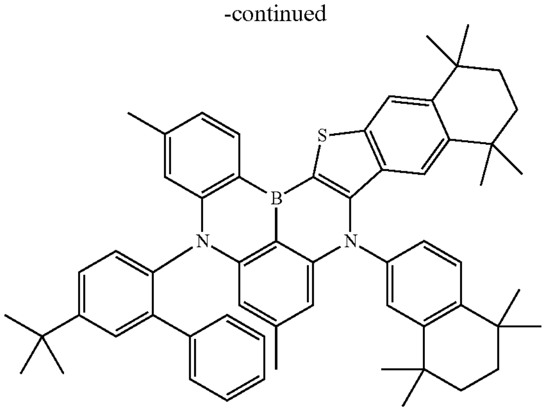
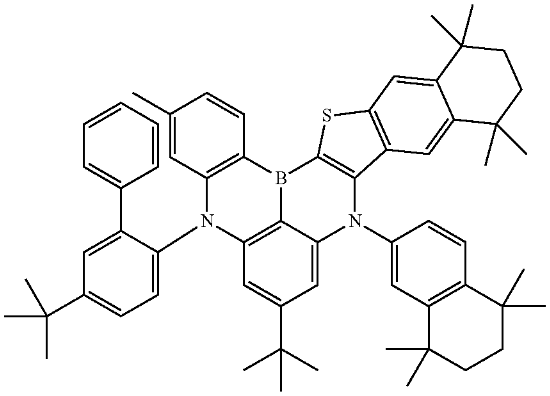
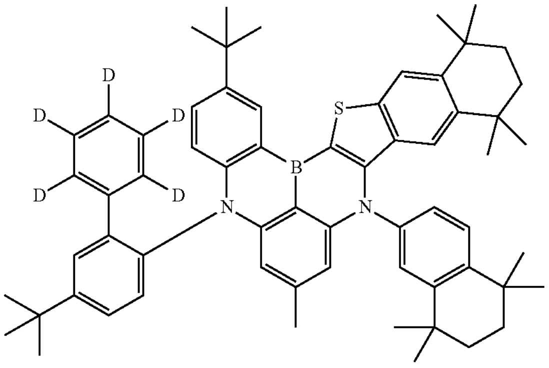
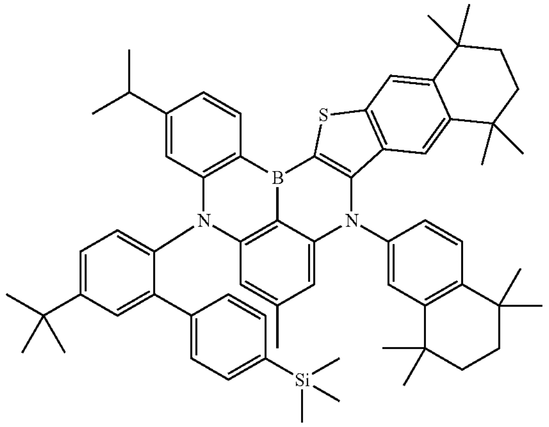
-continued
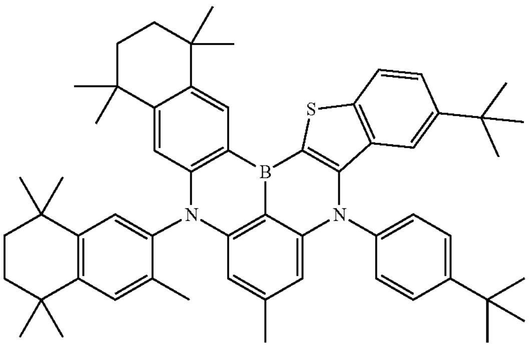
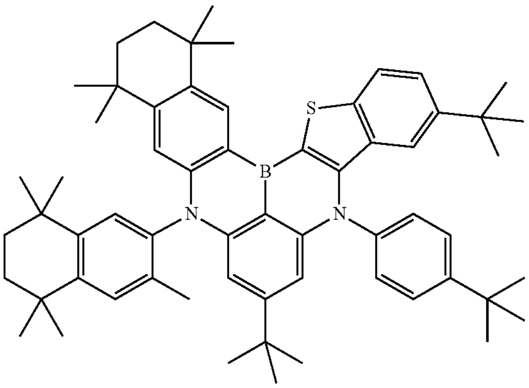
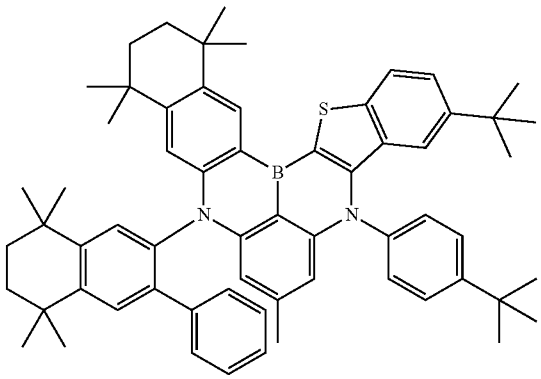
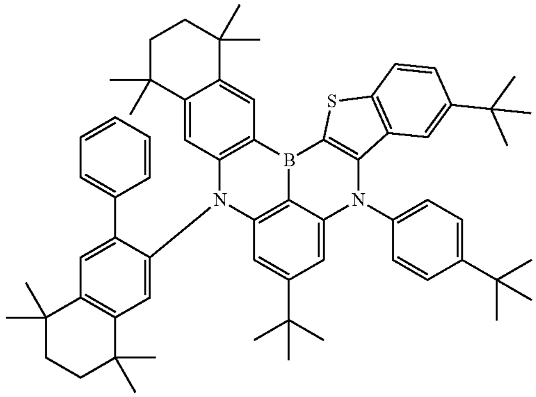

-continued
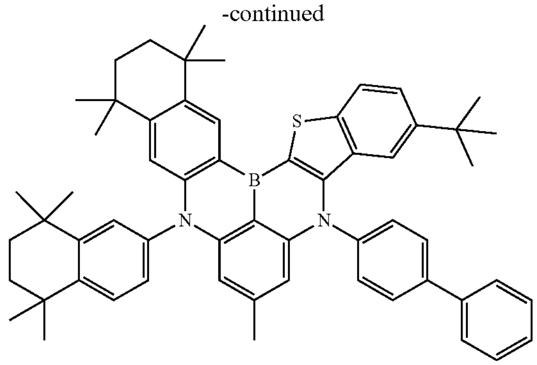
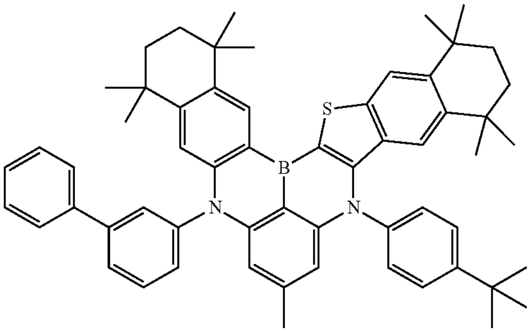
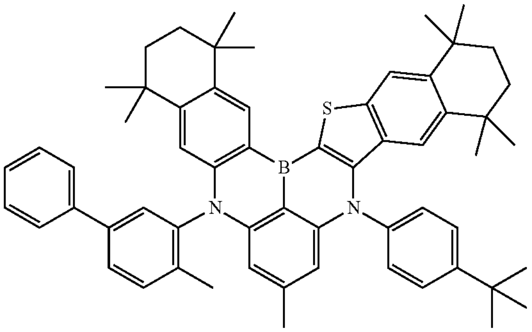
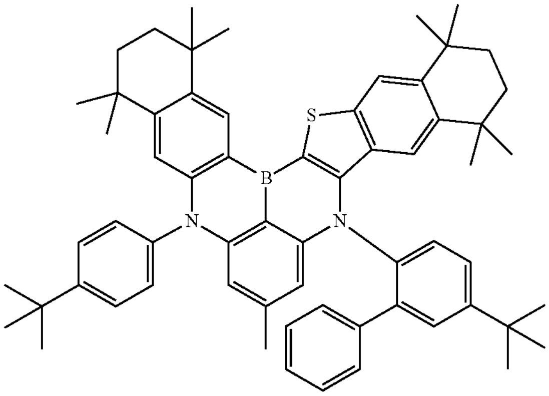
-continued
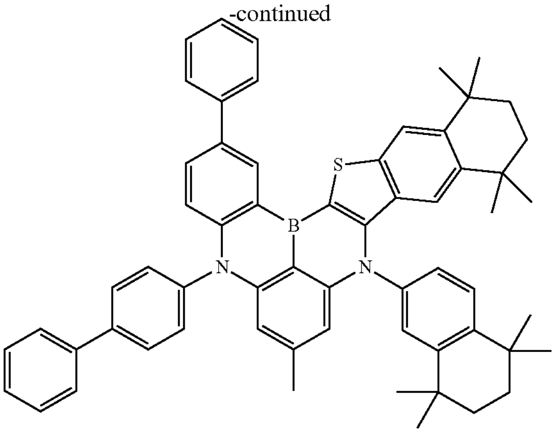
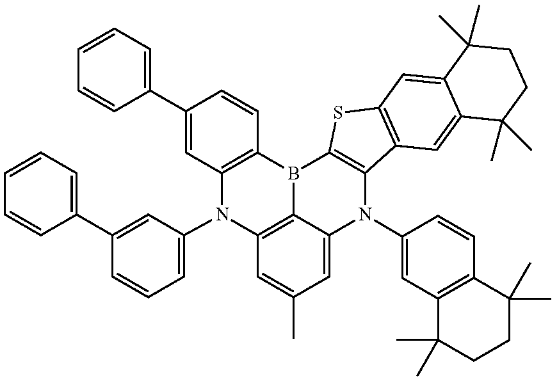
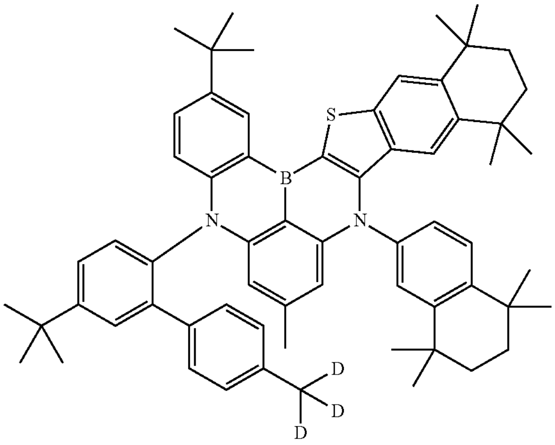
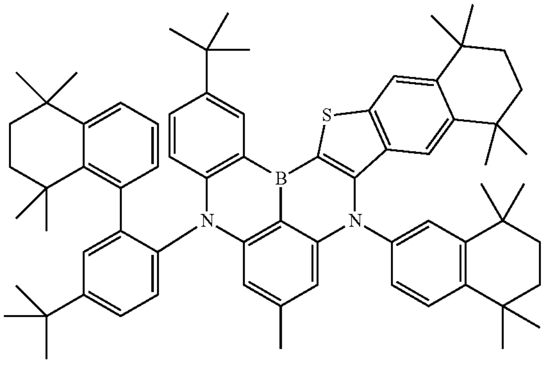

-continued
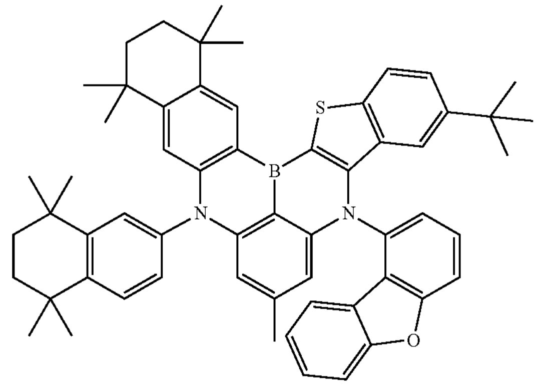
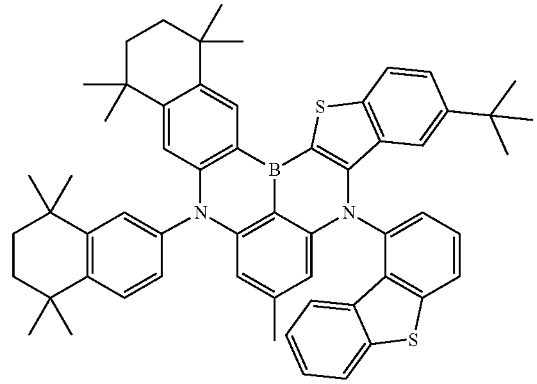
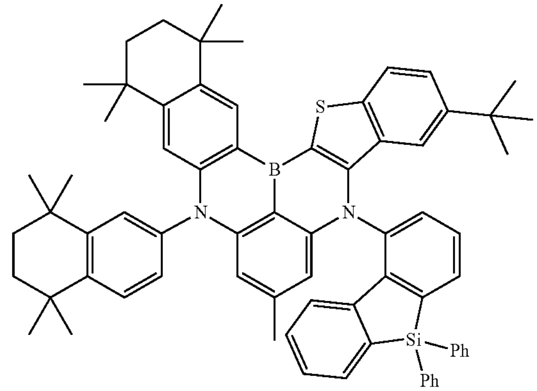
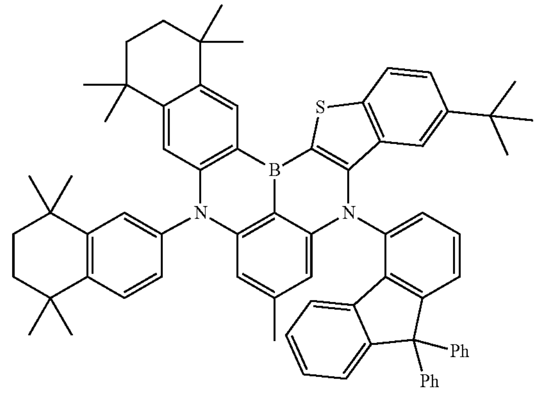
-continued
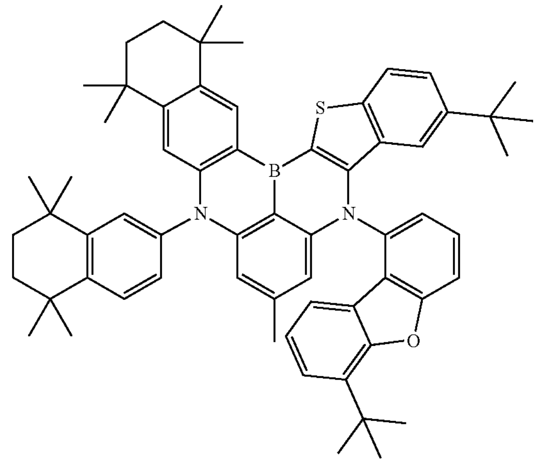
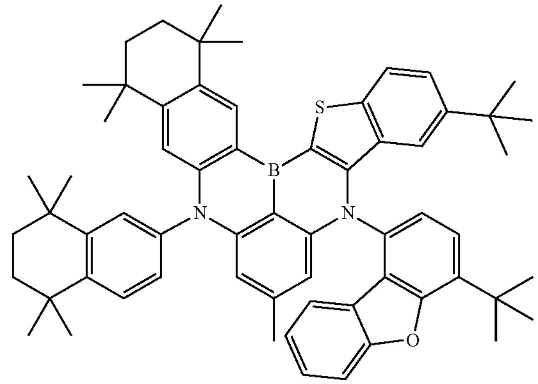
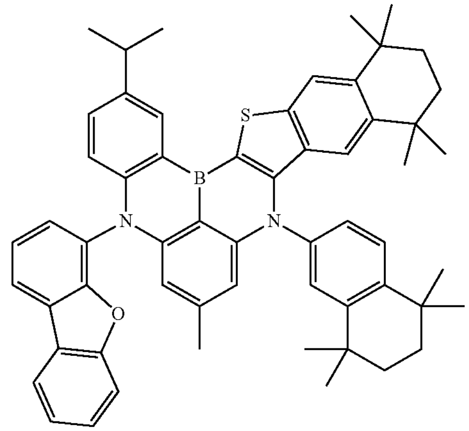
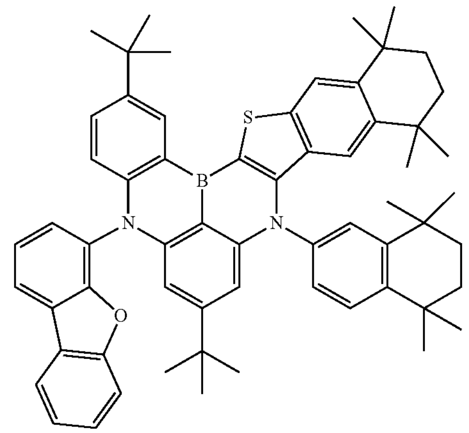

-continued
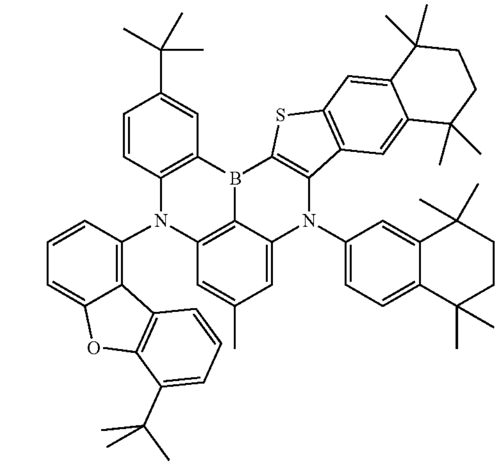
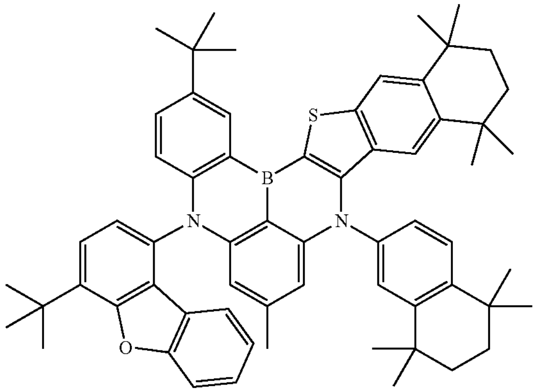
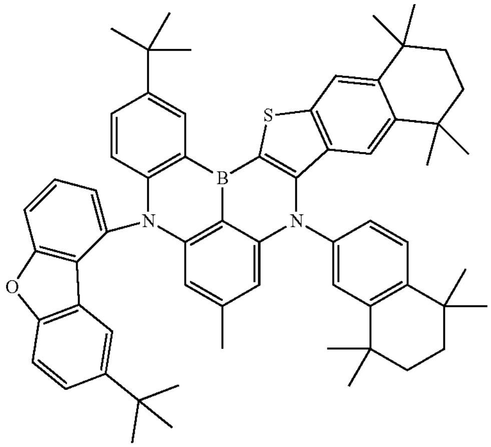
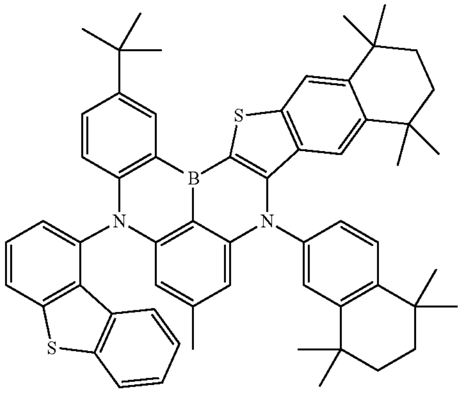
-continued
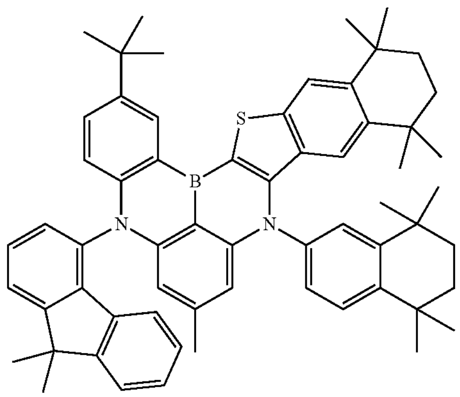
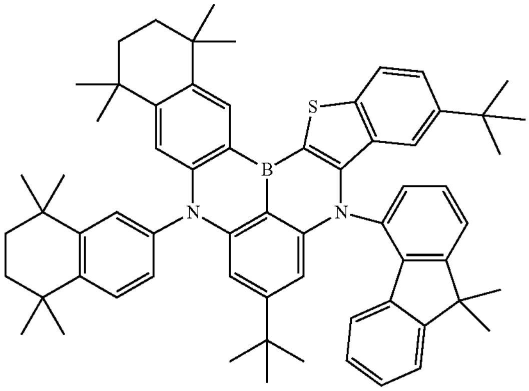
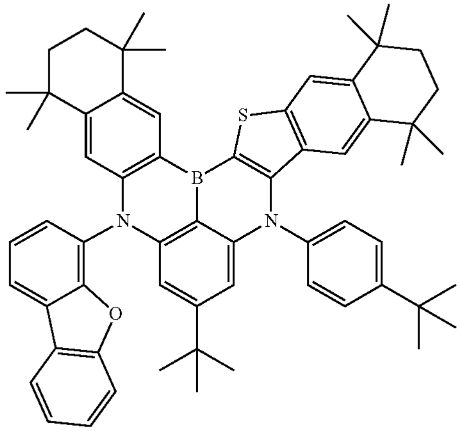
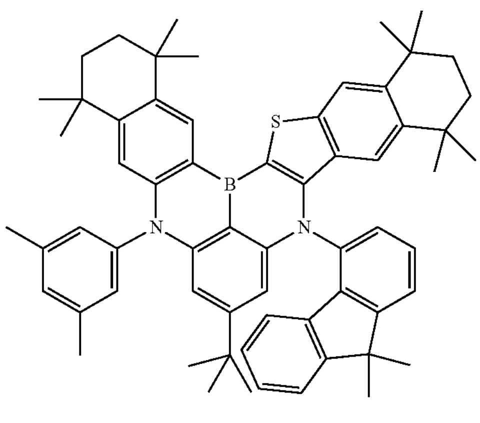

-continued
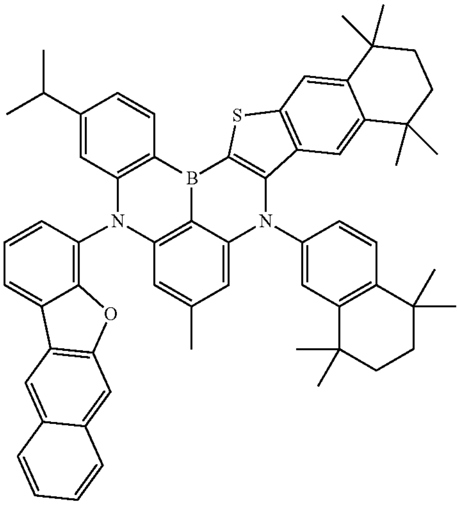
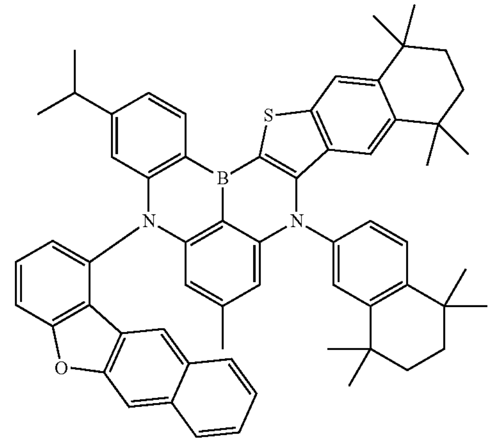
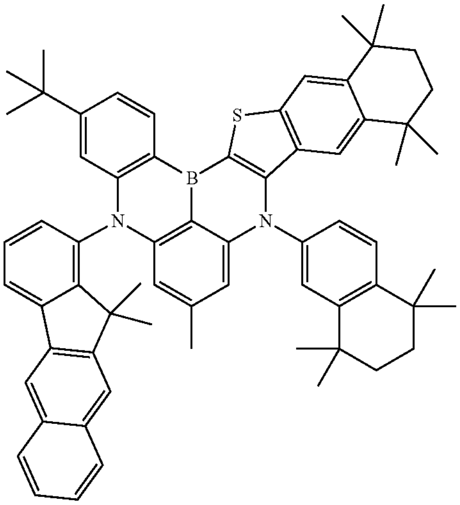
-continued
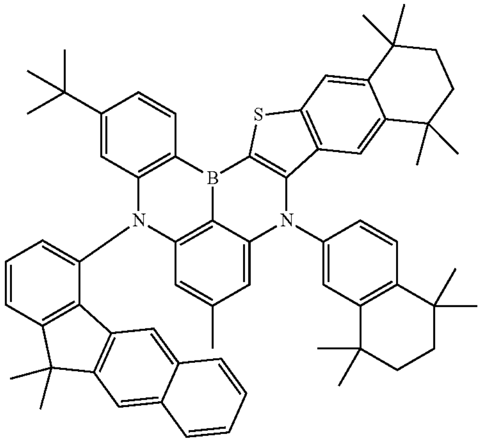
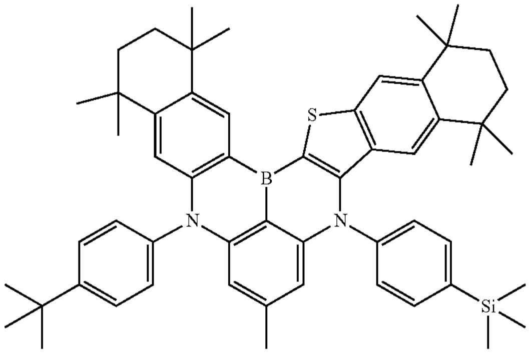
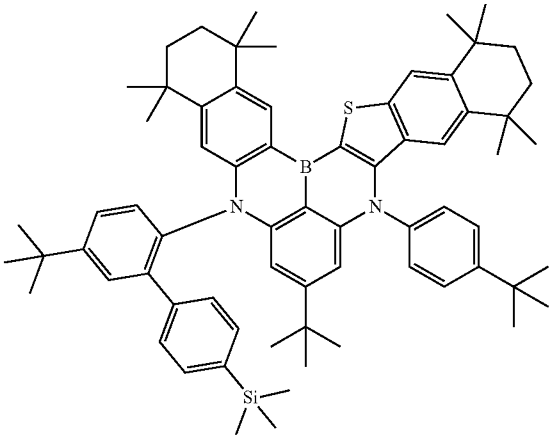
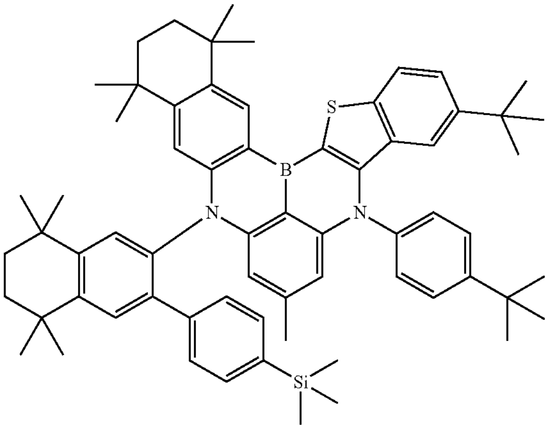

-continued
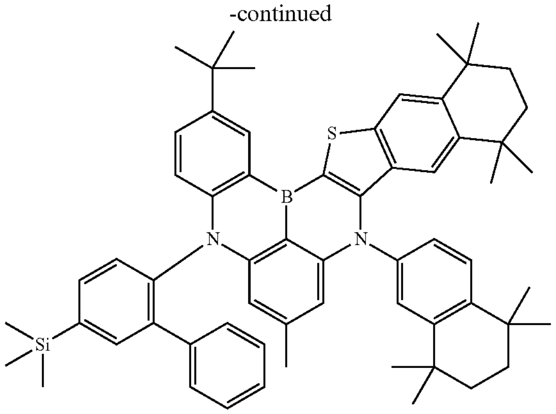
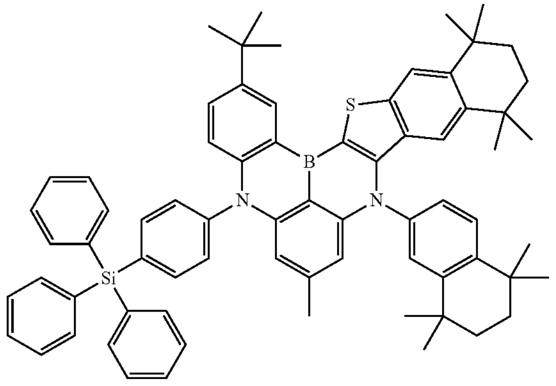
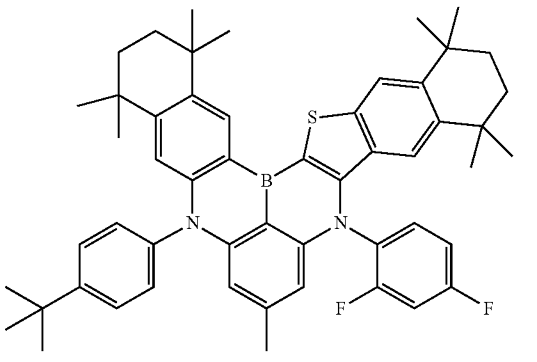
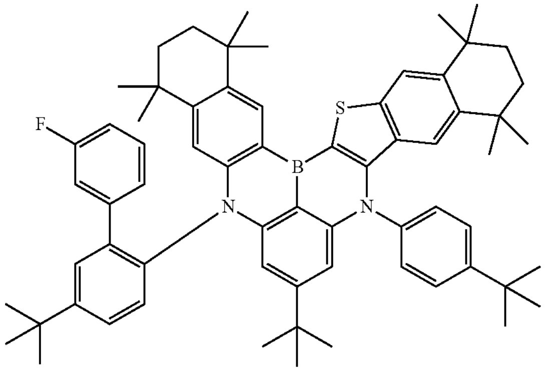
-continued
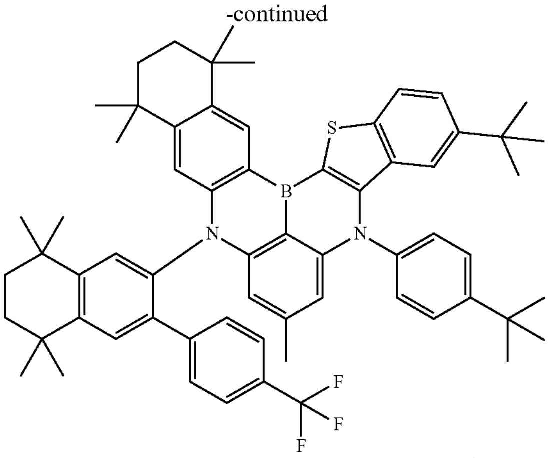
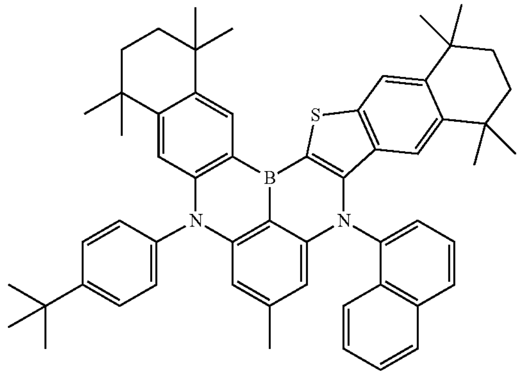
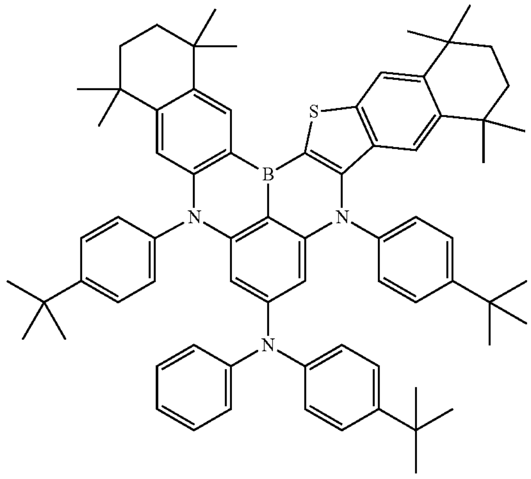
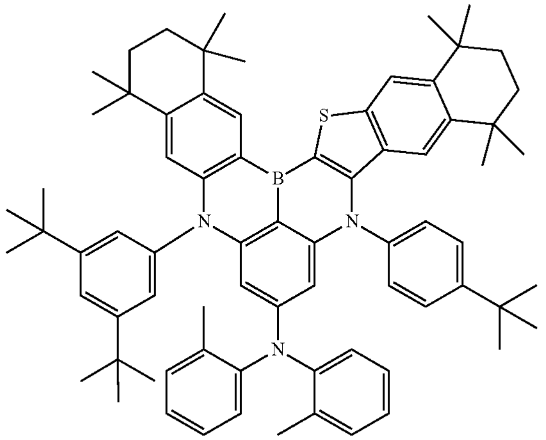

-continued
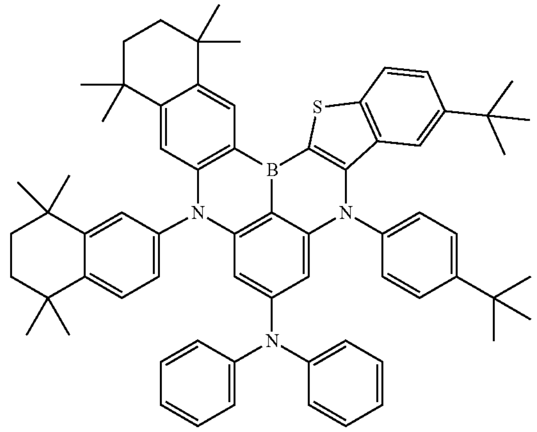
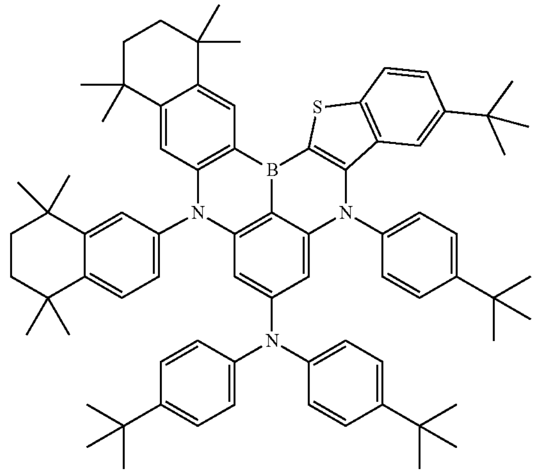
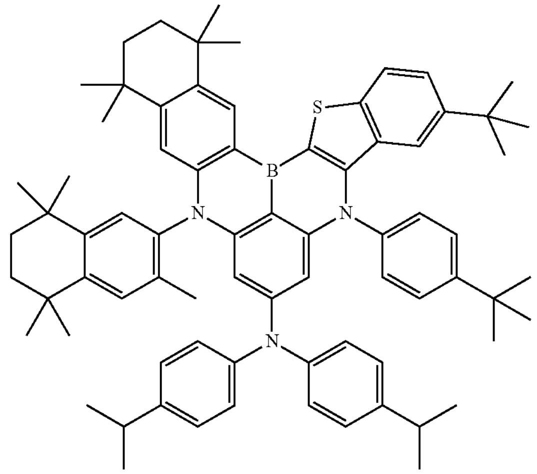
-continued
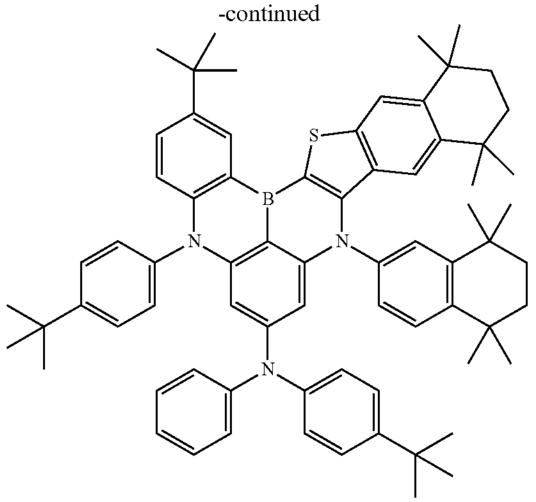
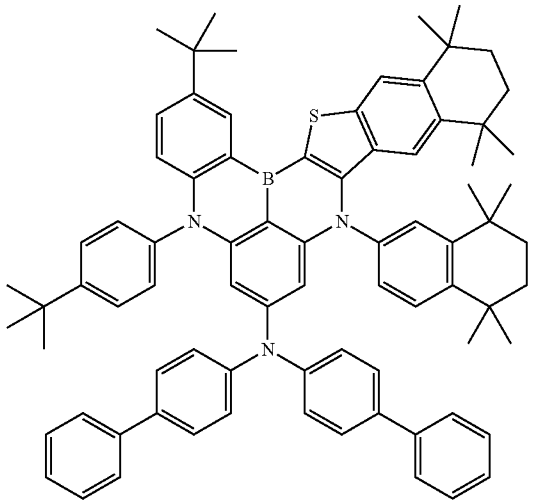
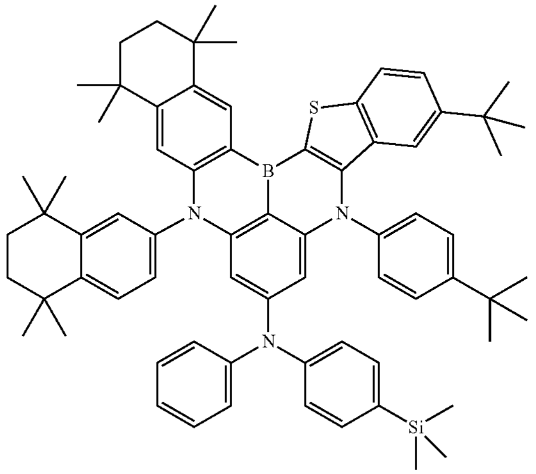

-continued
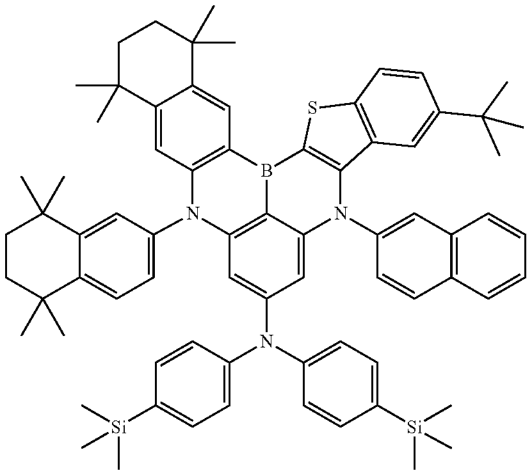
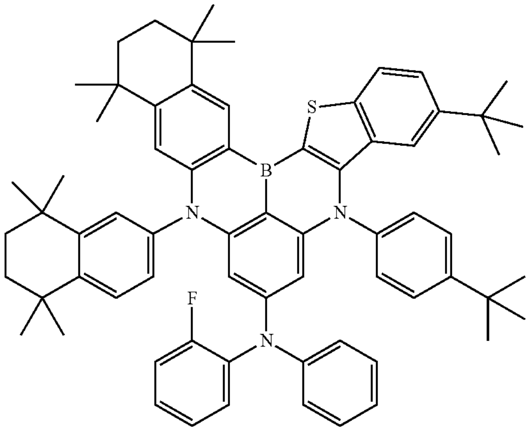
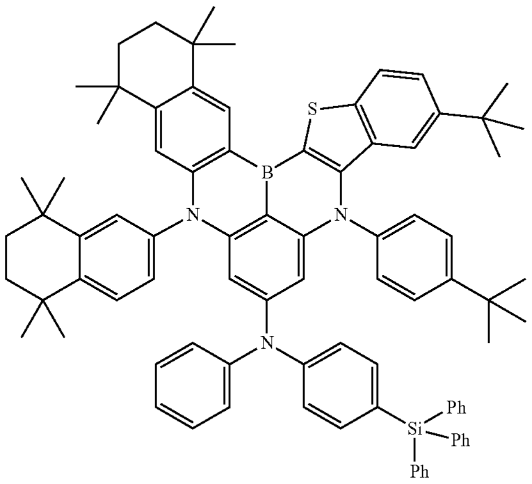
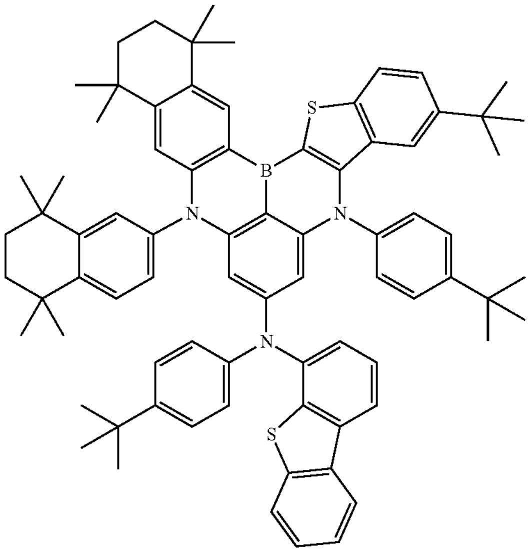
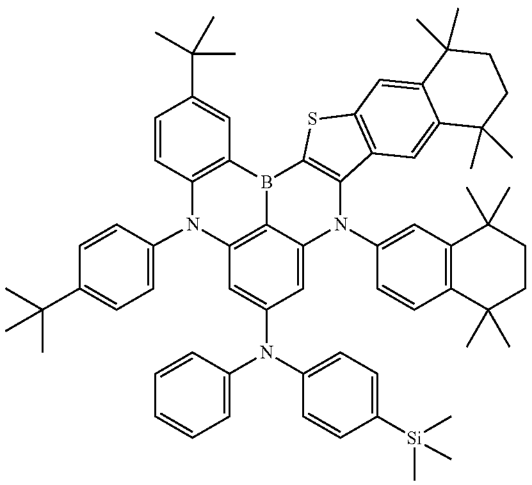
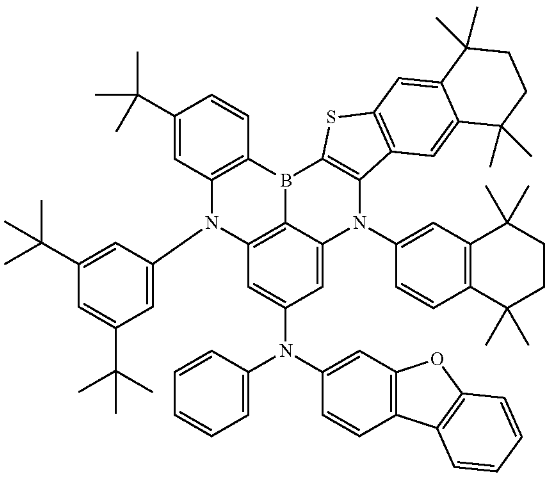
-continued -continued
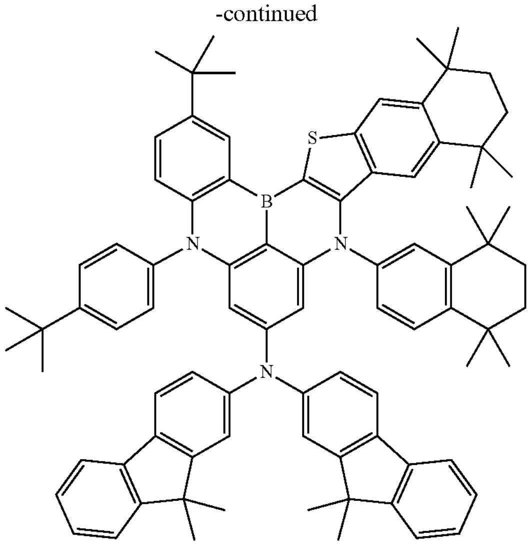
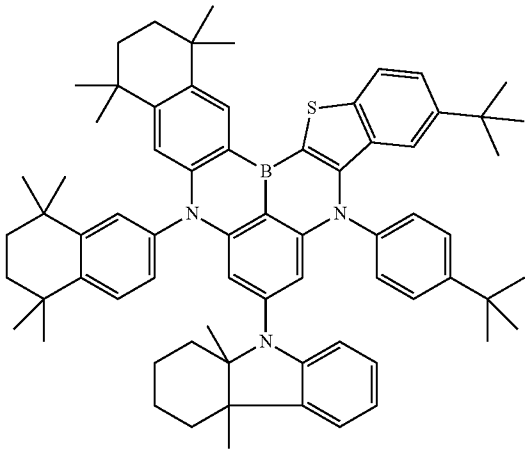
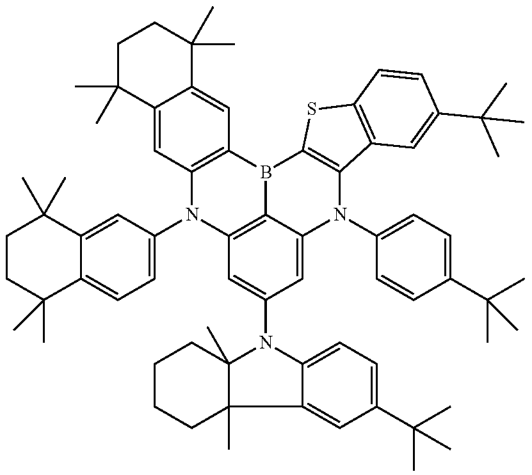
-continued
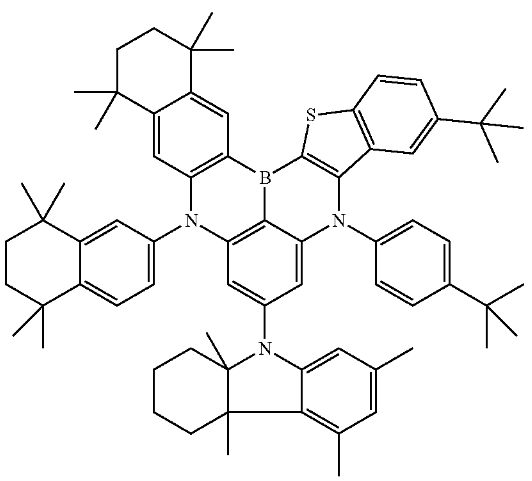
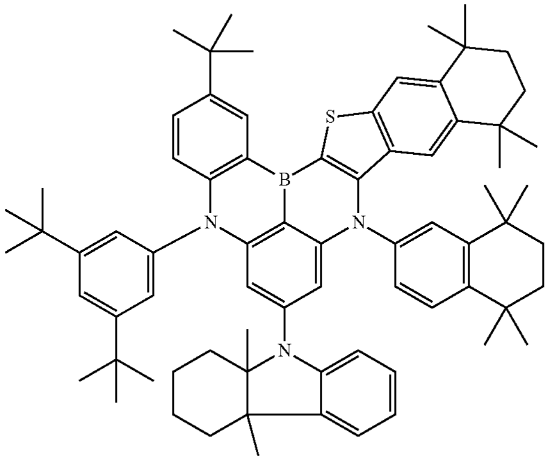
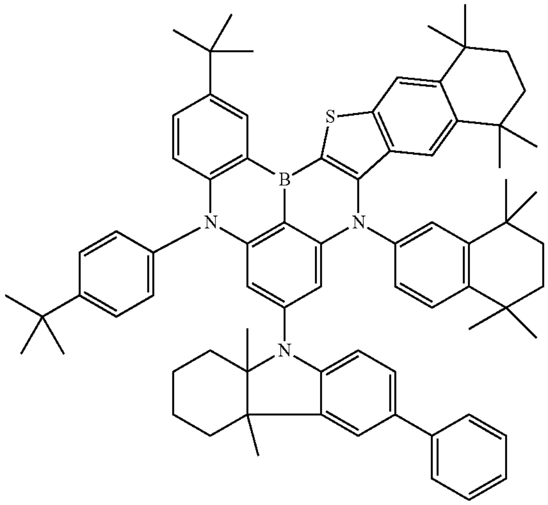

-continued
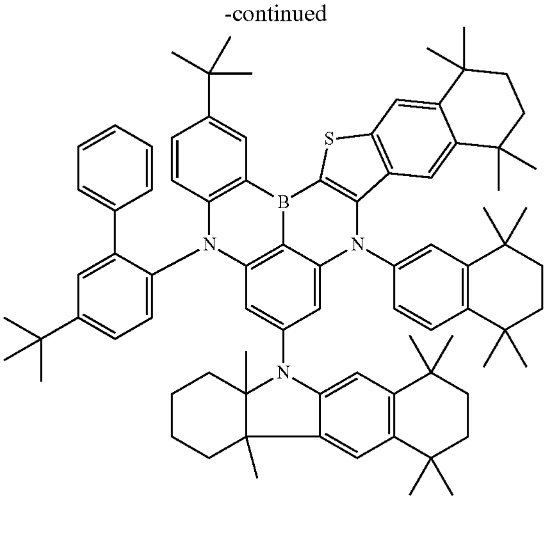
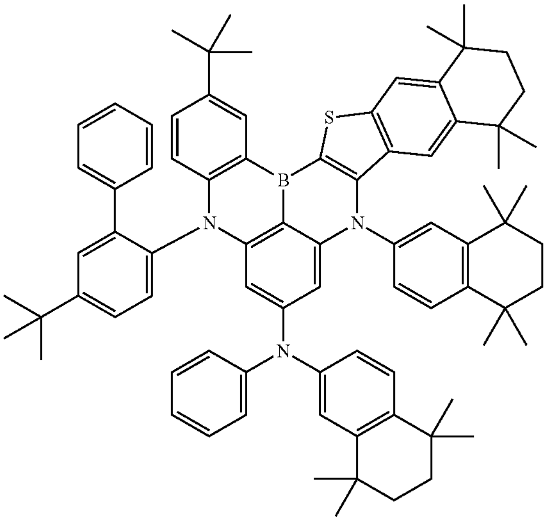
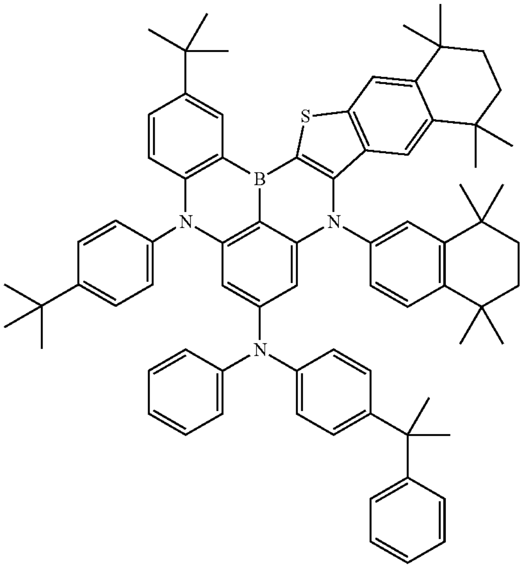
-continued
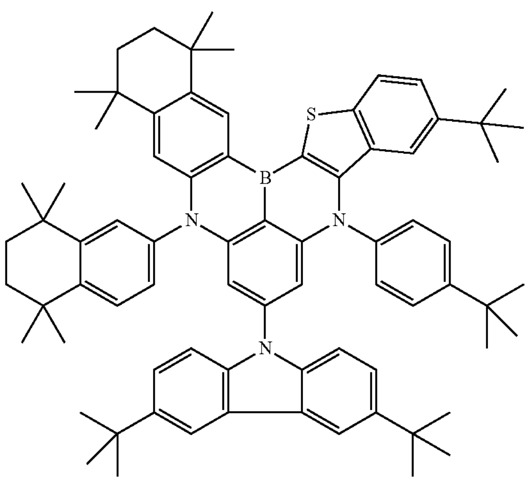
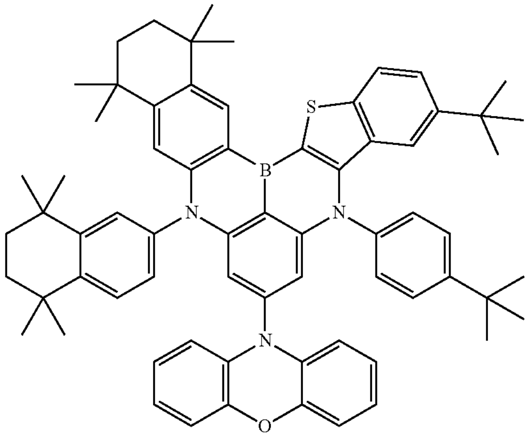
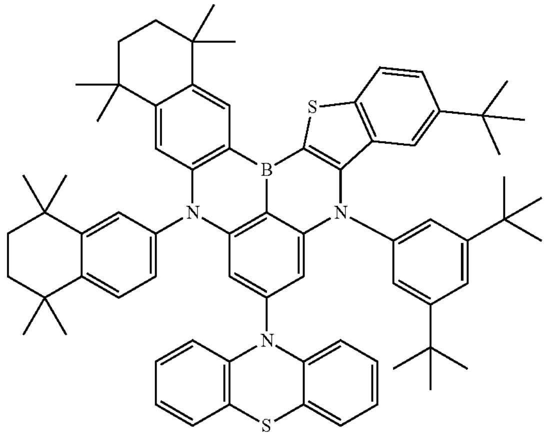

-continued
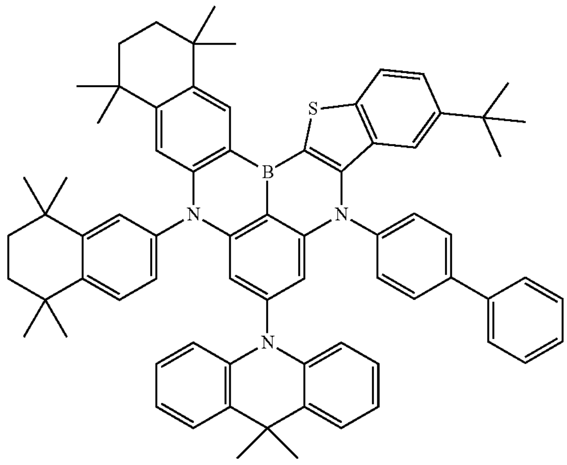
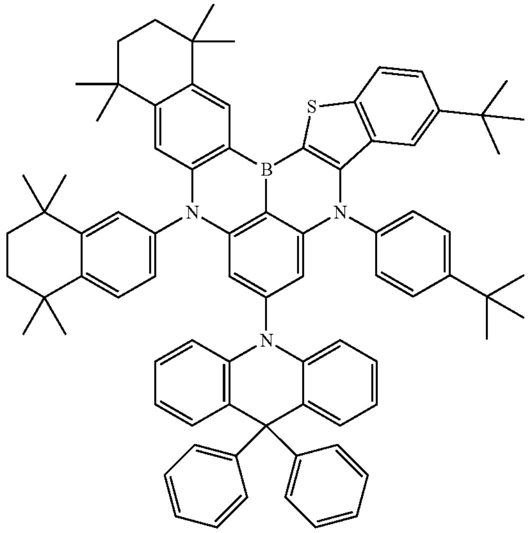
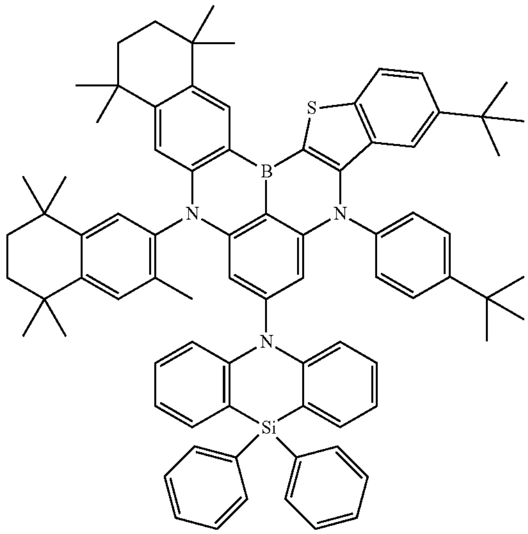
-continued
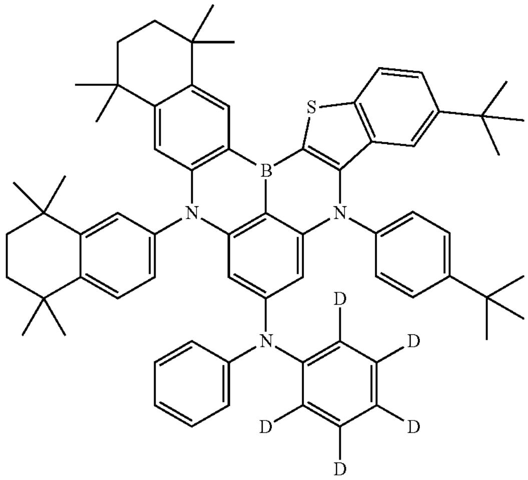
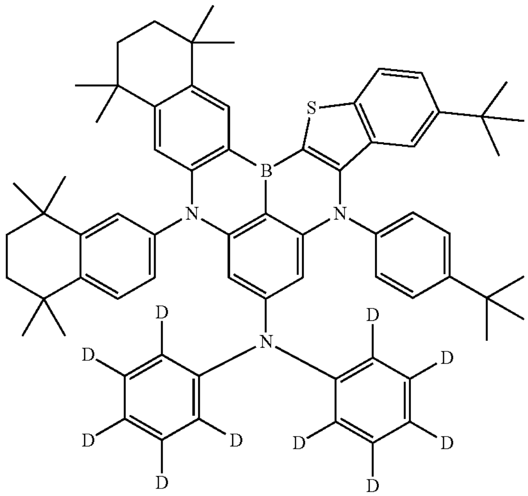
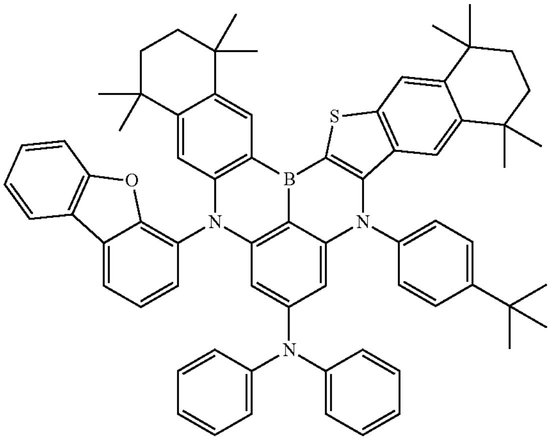

-continued
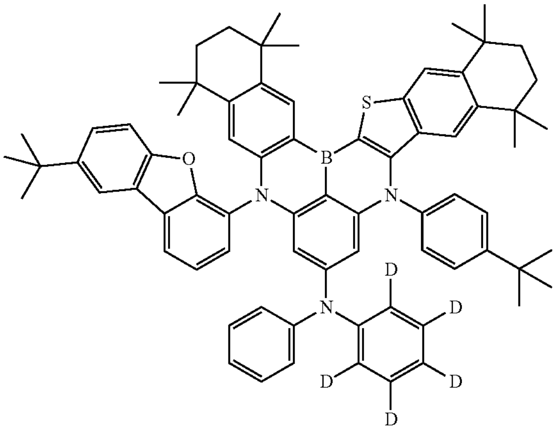
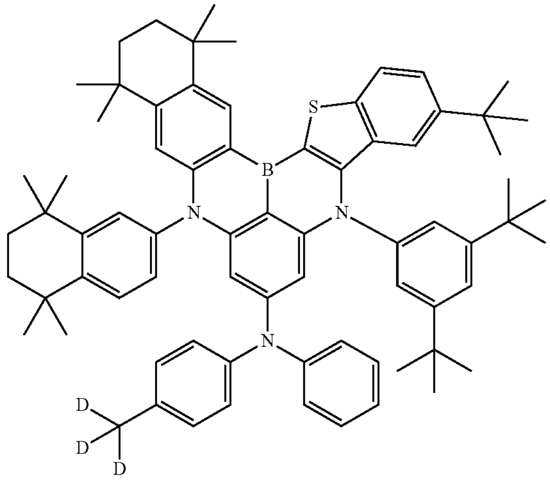
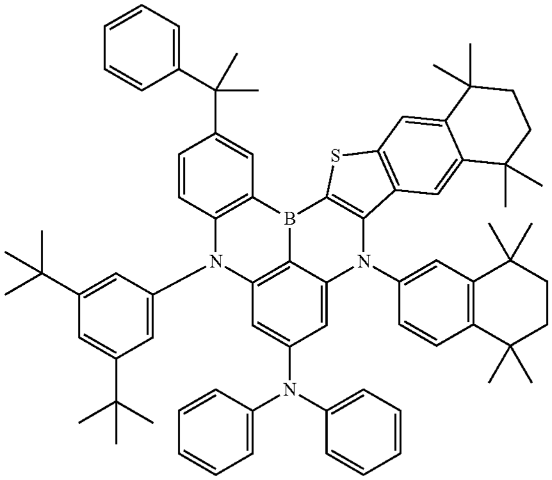
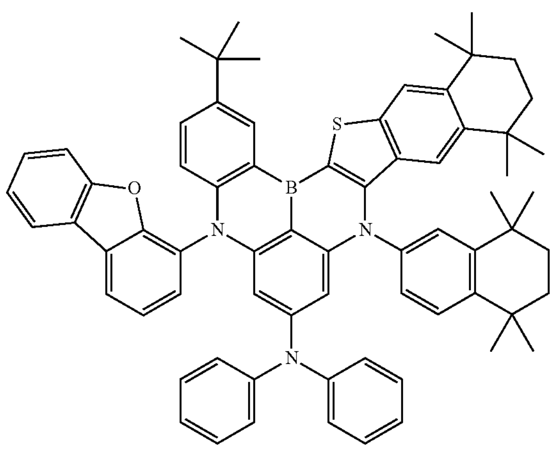
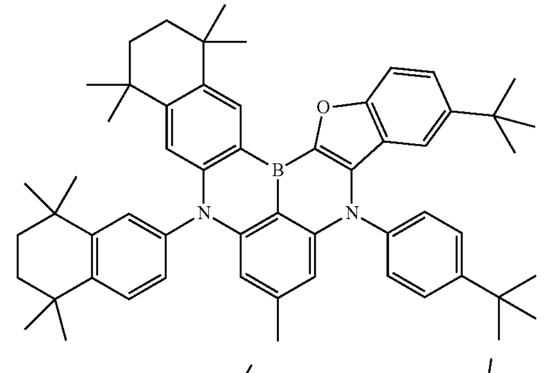
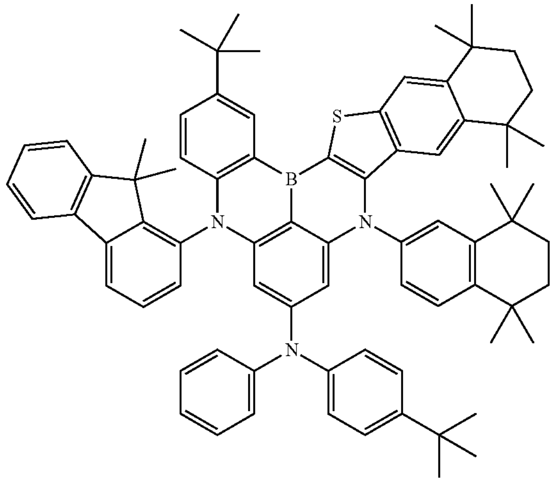
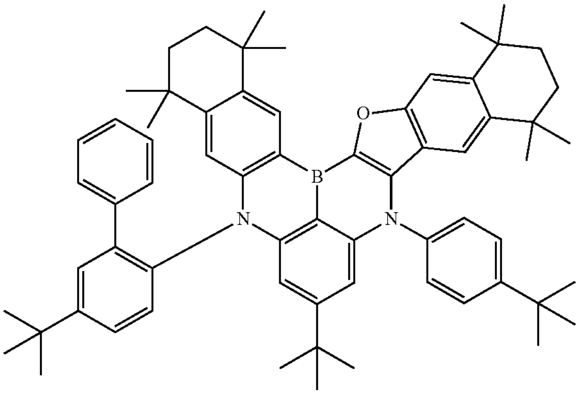
-continued -continued
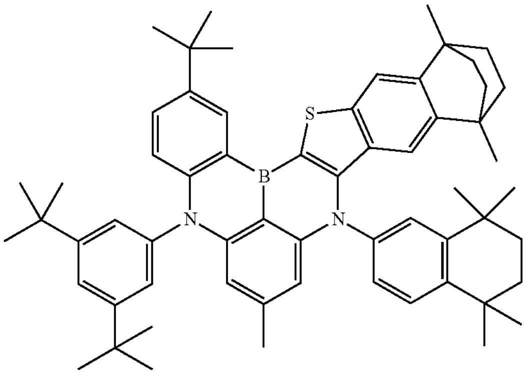
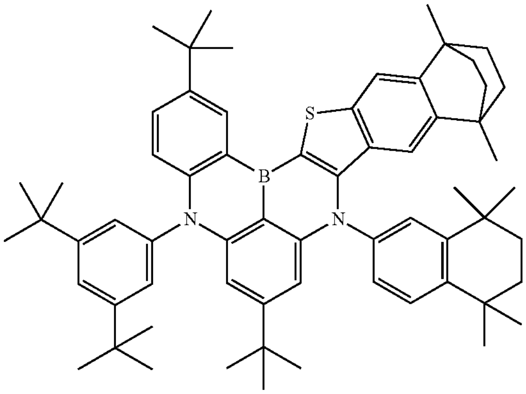
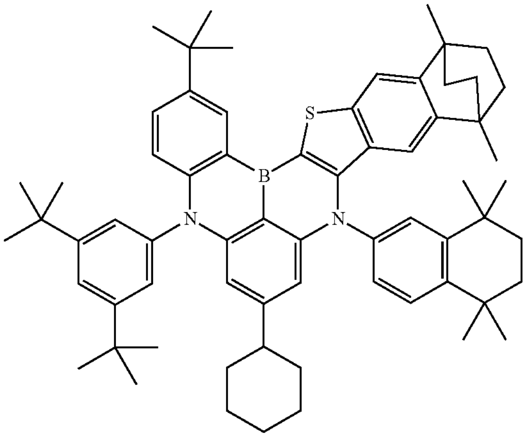
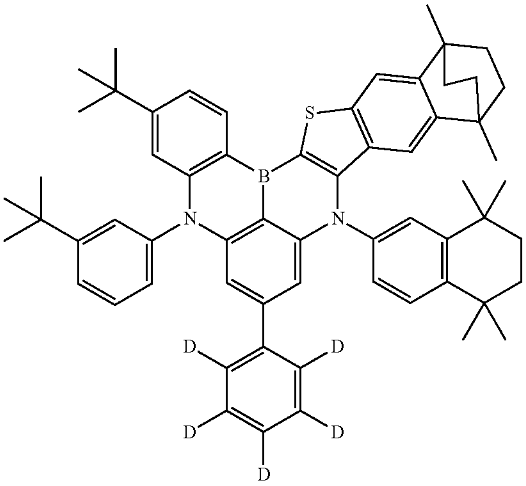
-continued
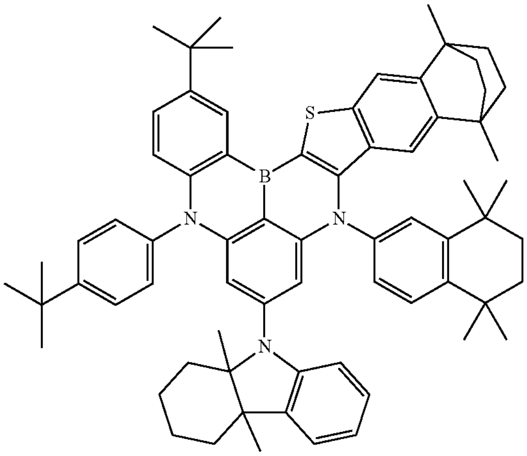
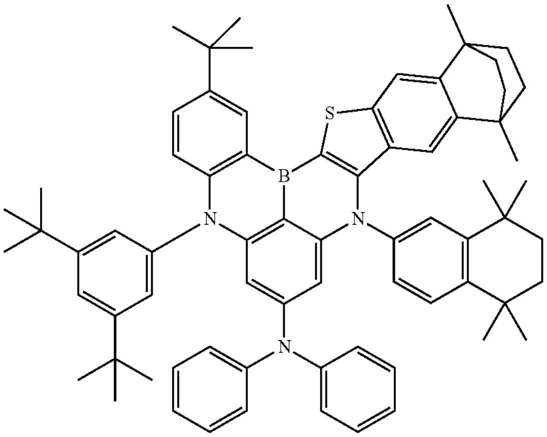
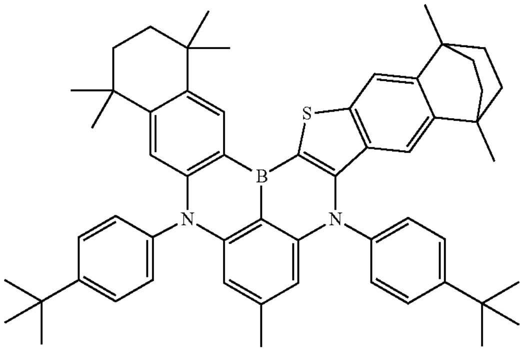
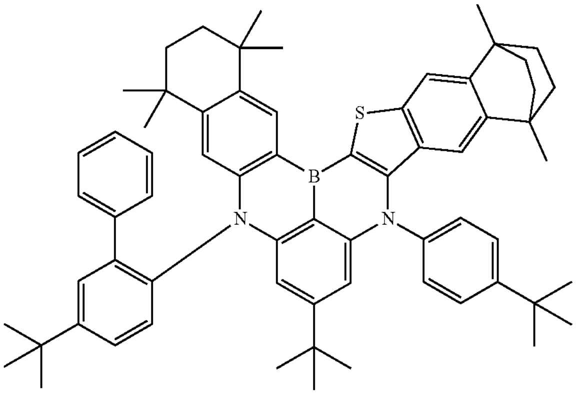

-continued
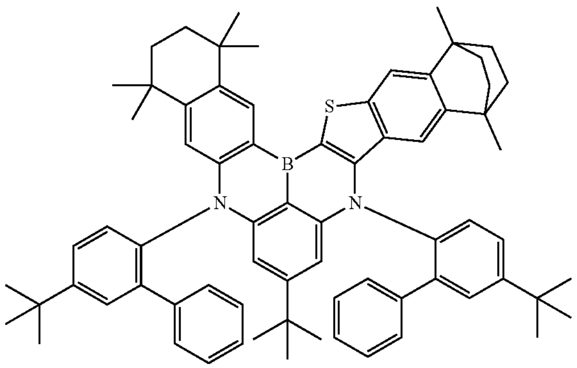
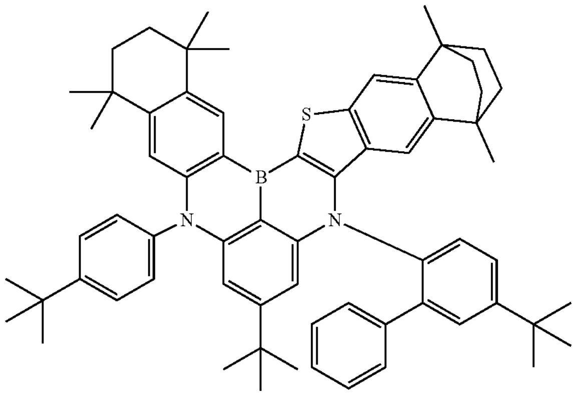
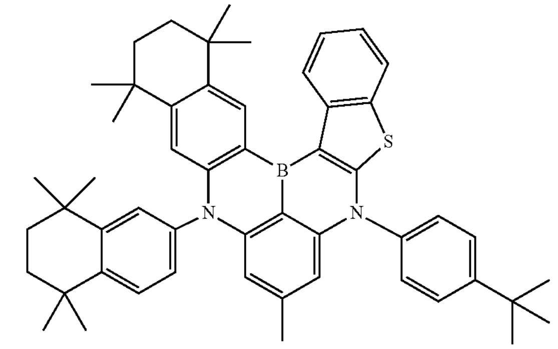
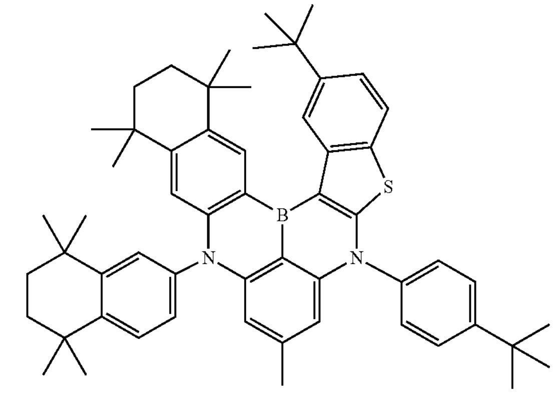
-continued
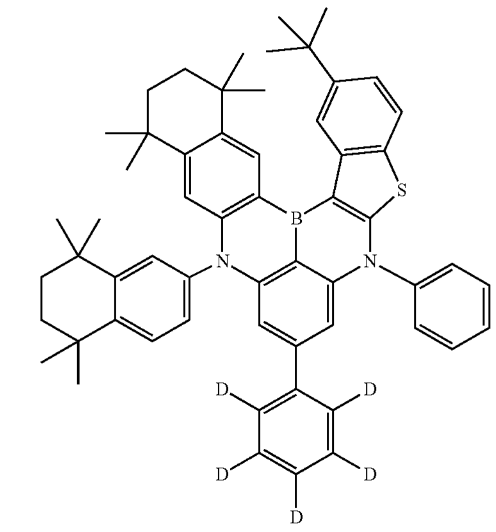
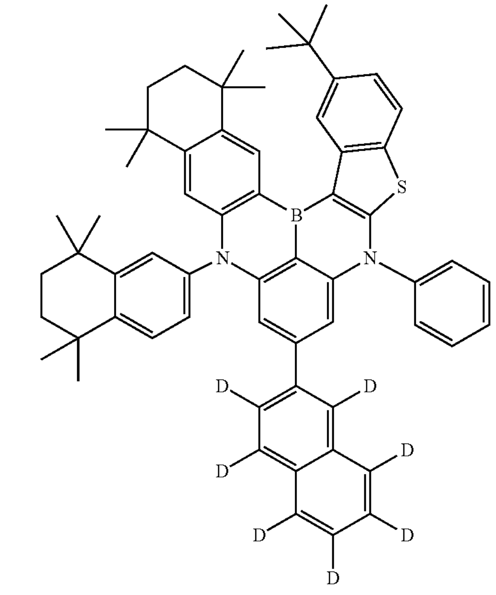
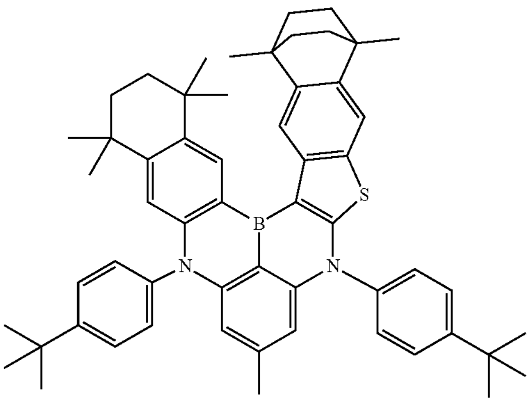

-continued
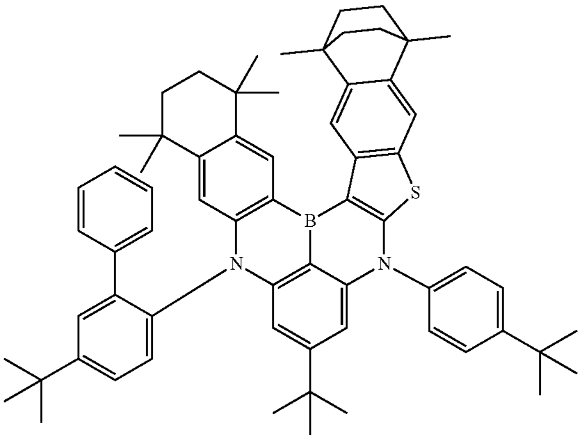
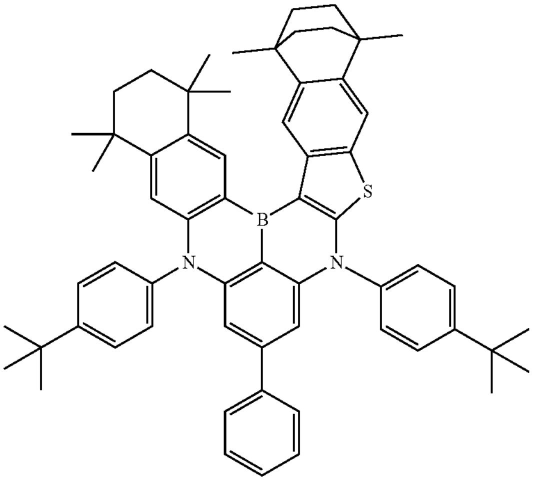
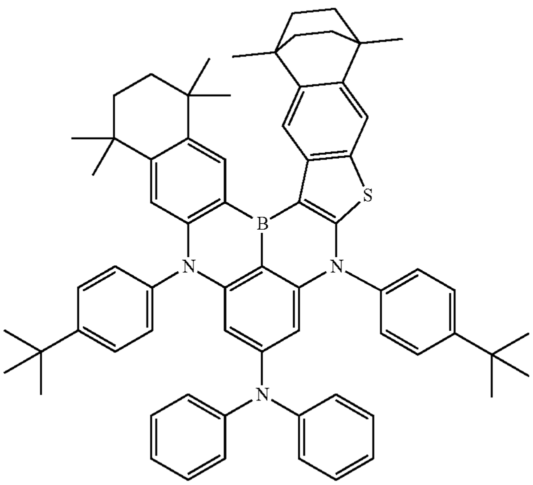
-continued
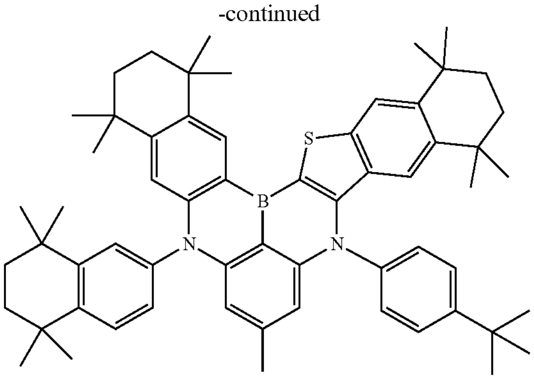
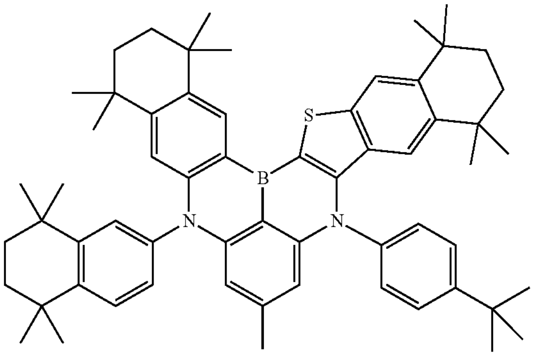
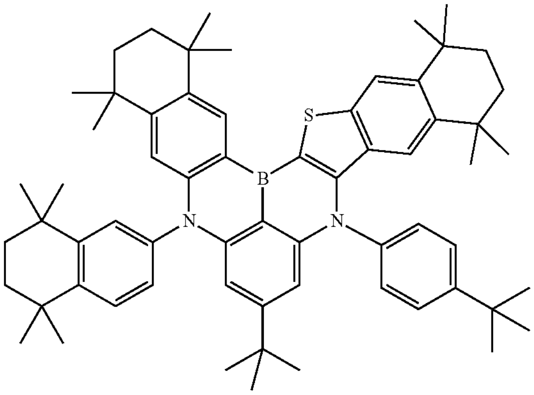
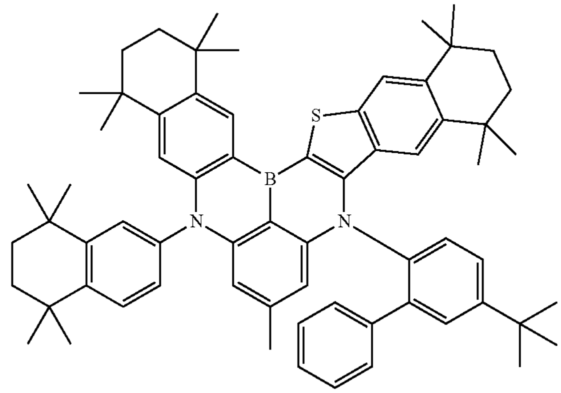

-continued
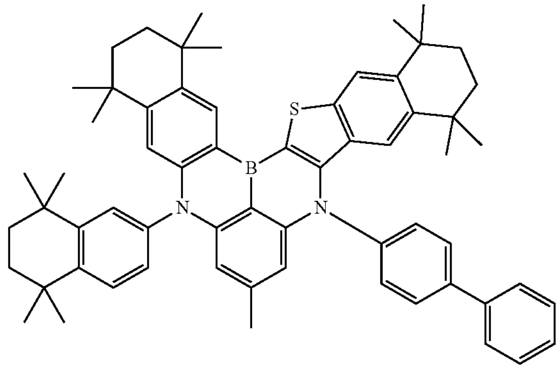
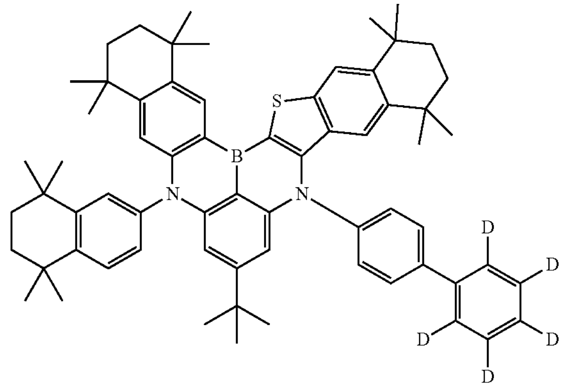
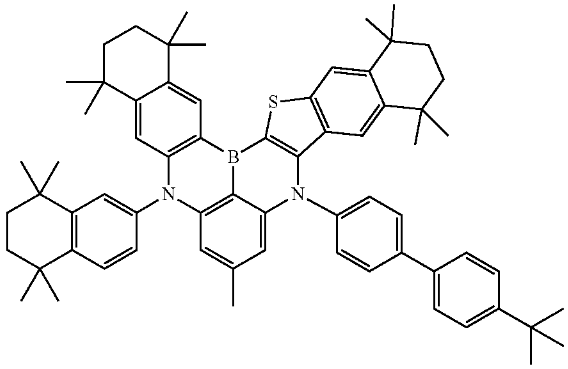
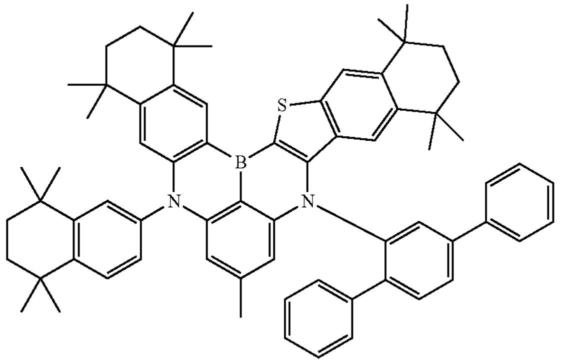
-continued
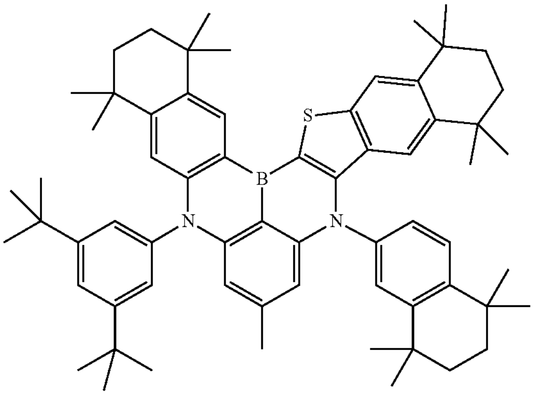
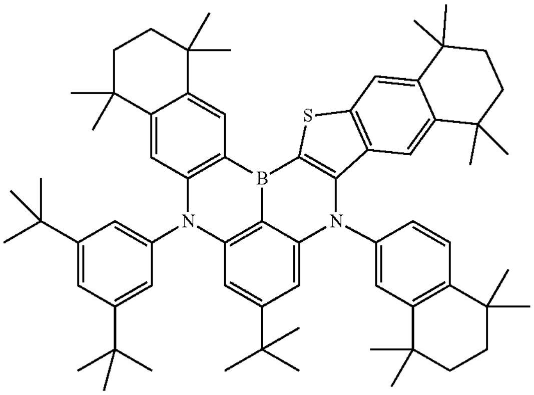
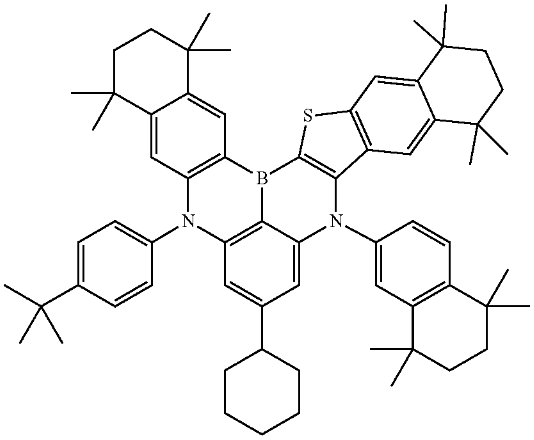
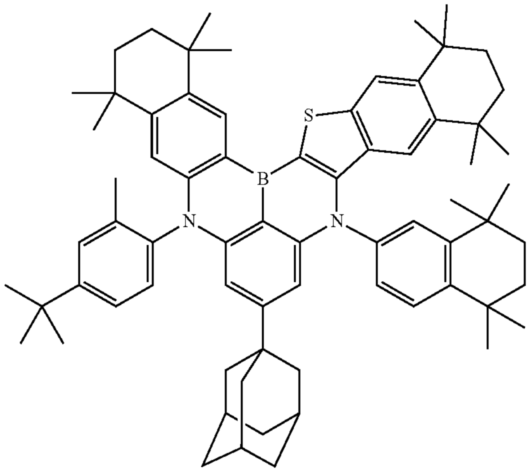

-continued
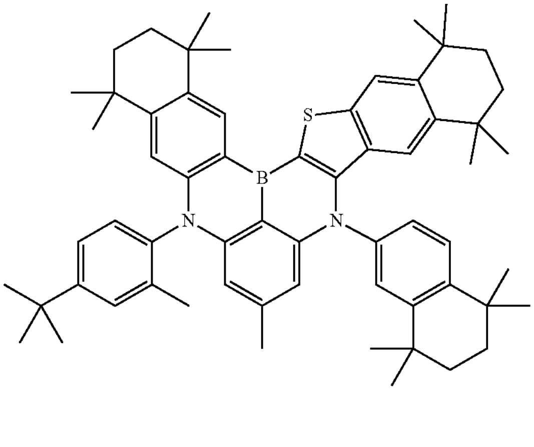
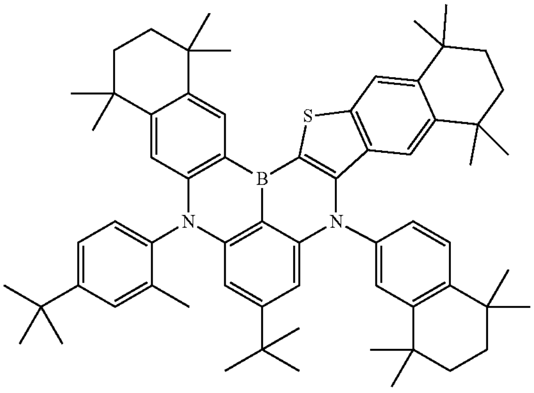
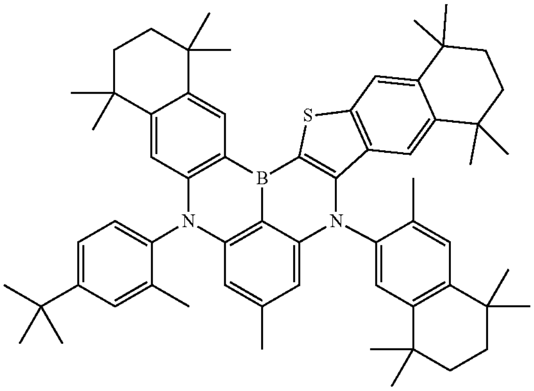
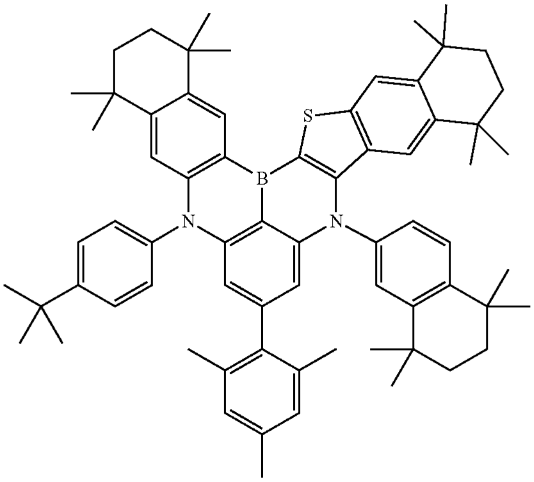
-continued
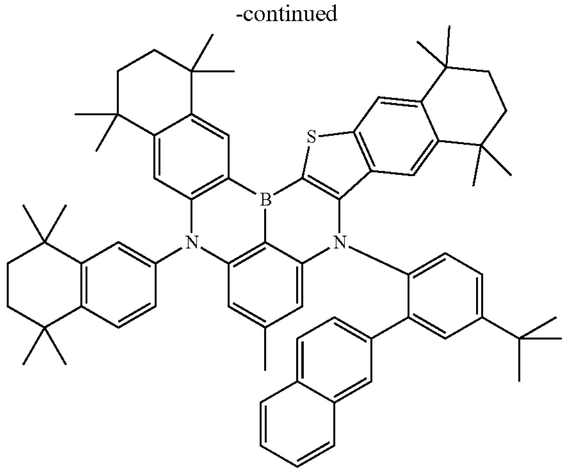
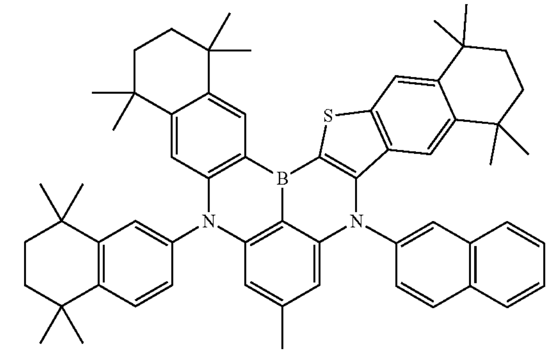
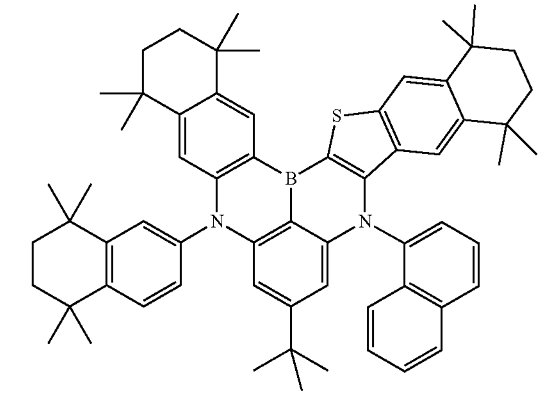
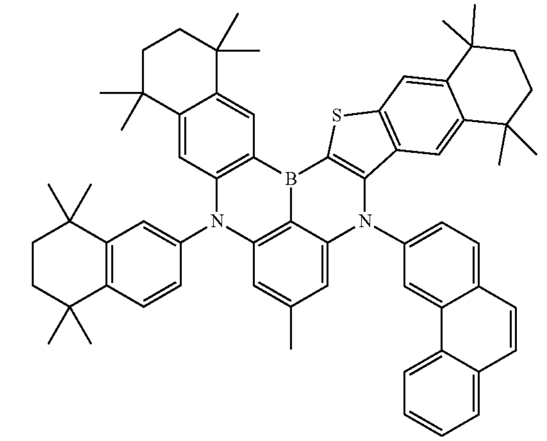

-continued
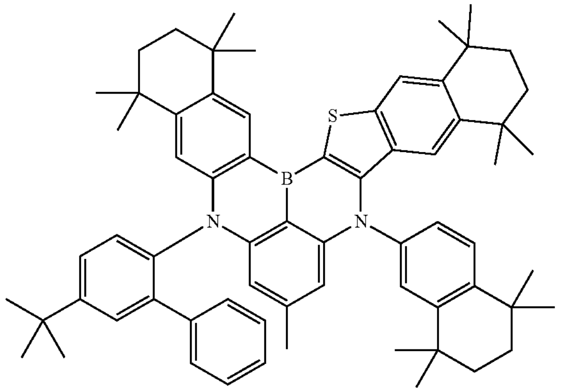
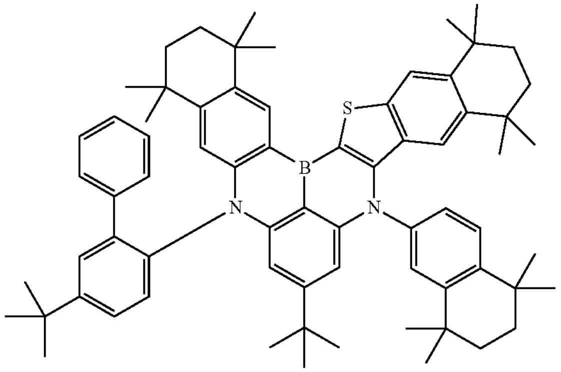
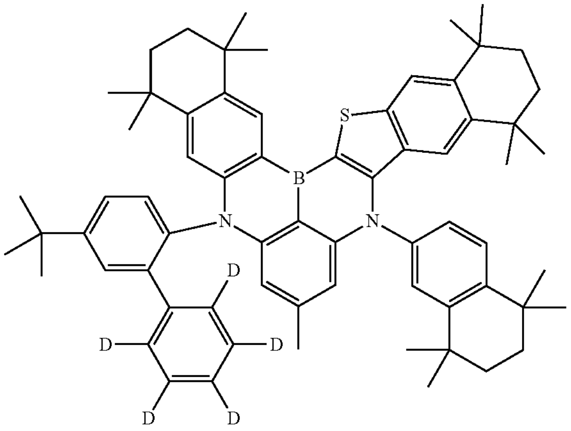
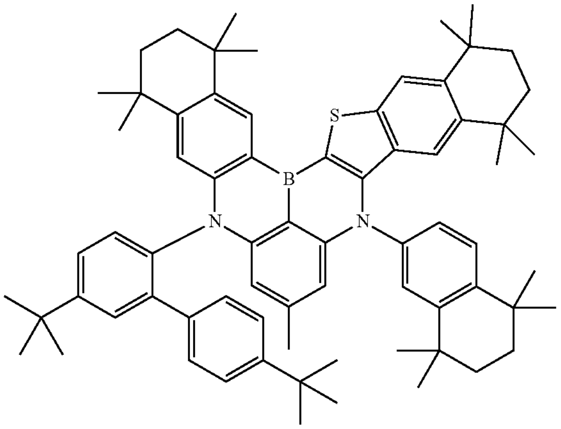
-continued
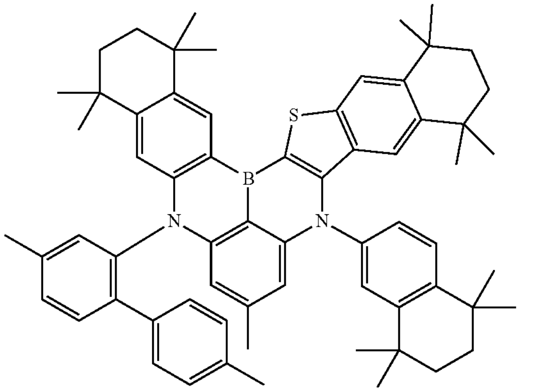
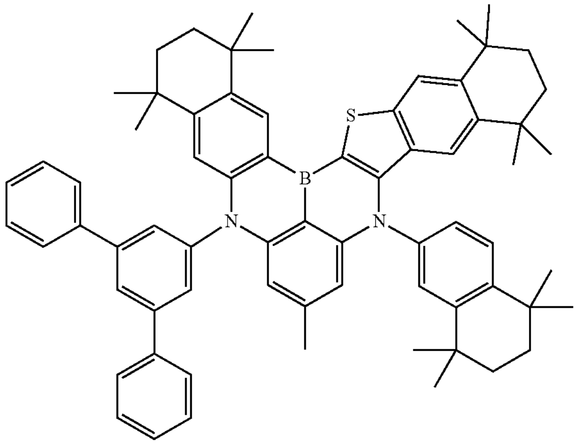
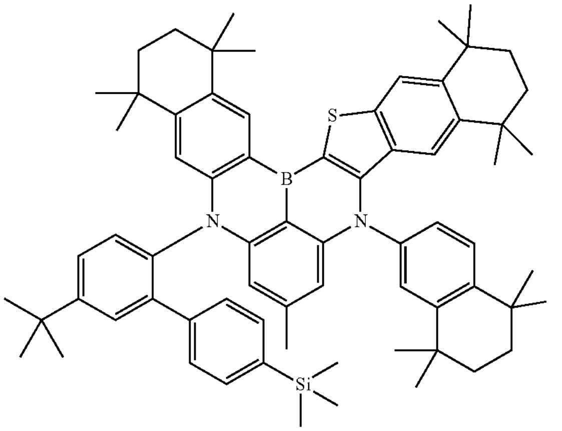
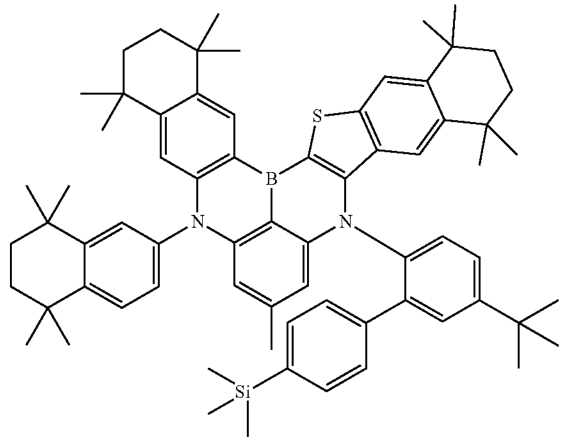

-continued
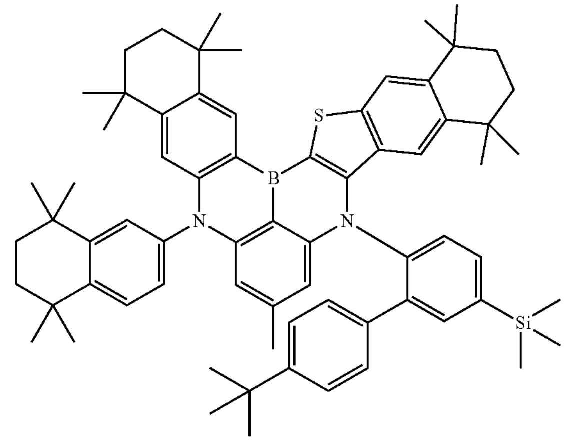
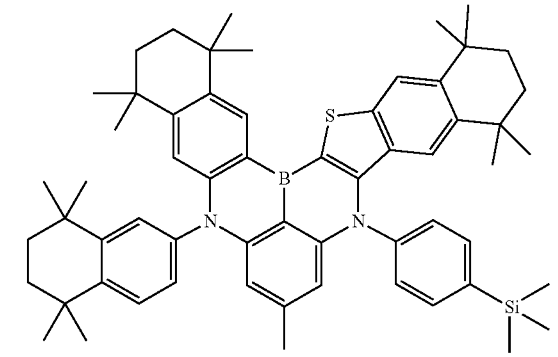
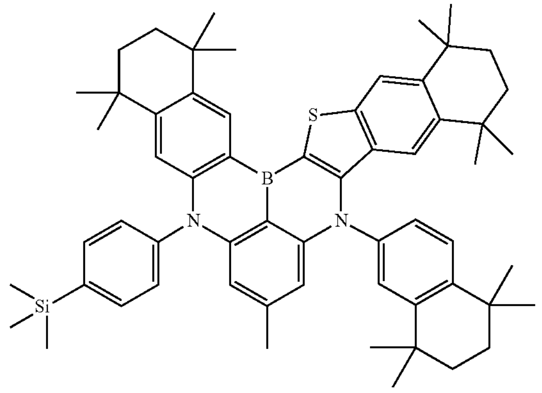
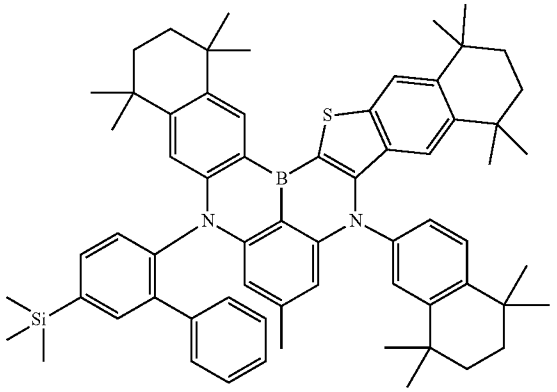
-continued
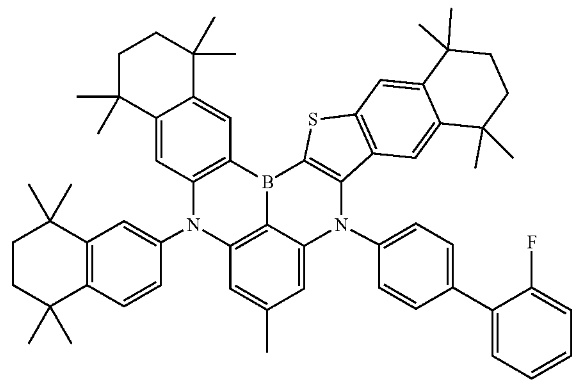
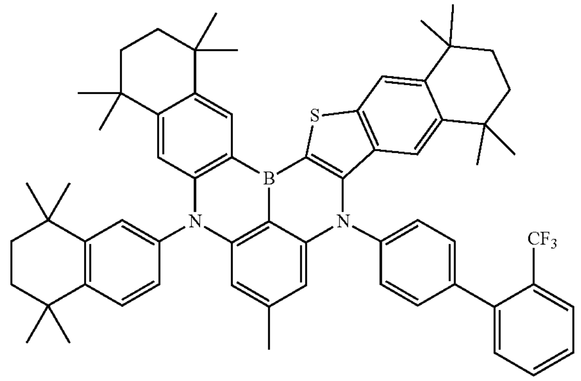
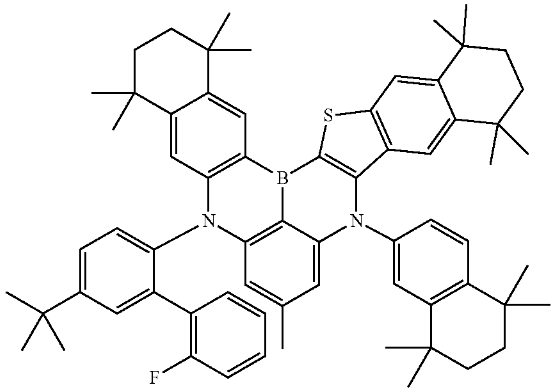
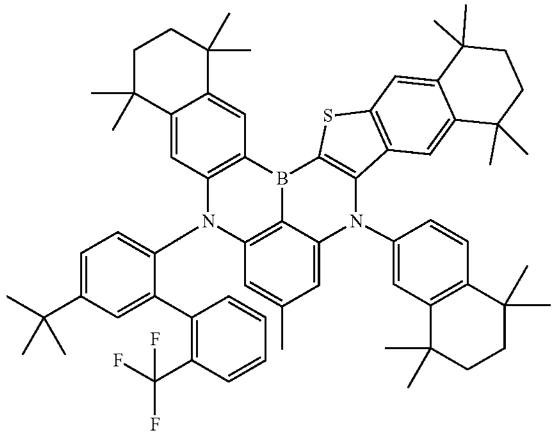

-continued
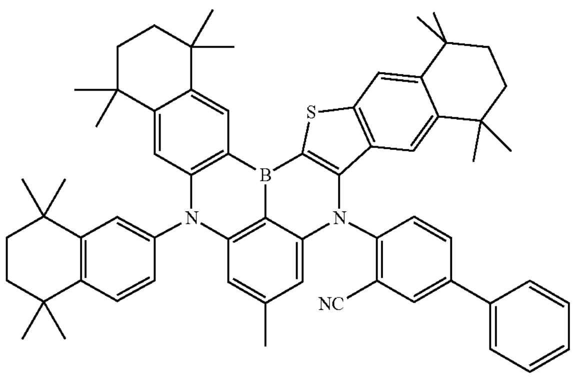
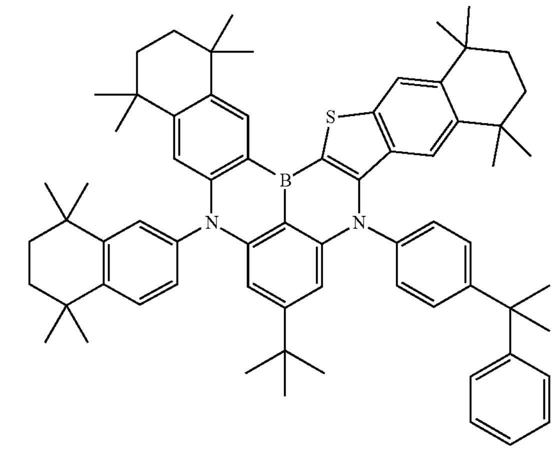
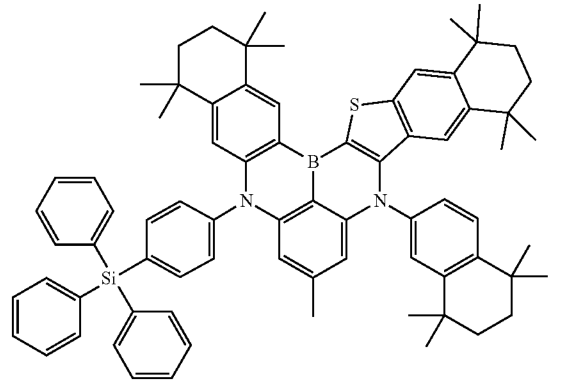
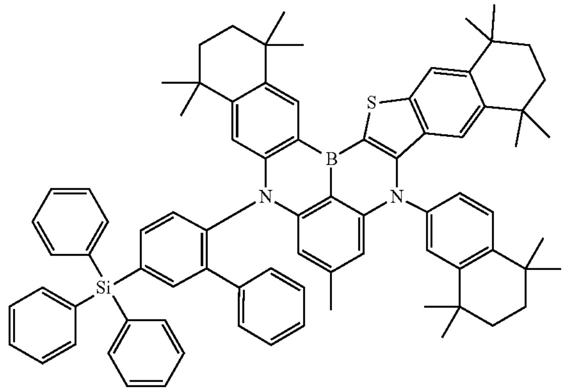
-continued
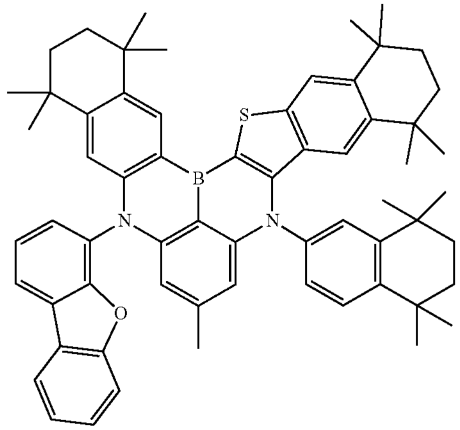
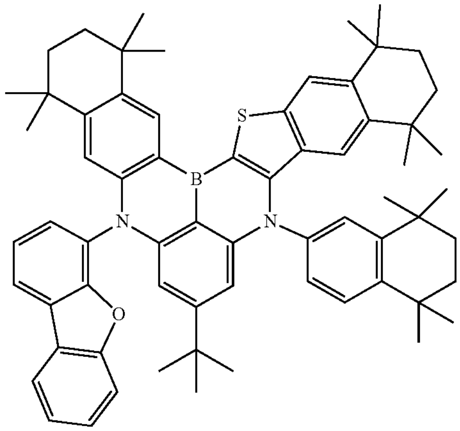
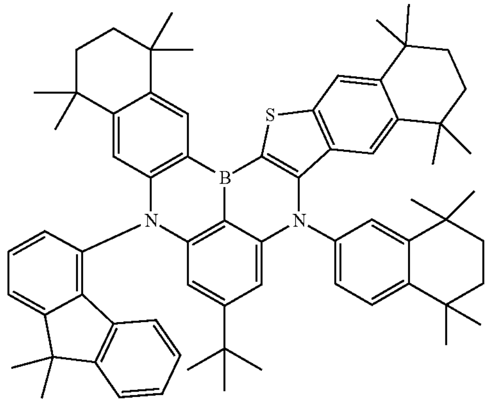
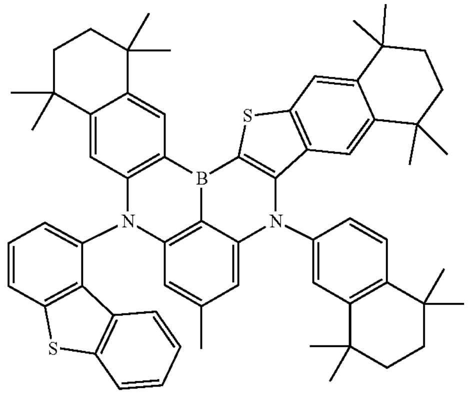

-continued
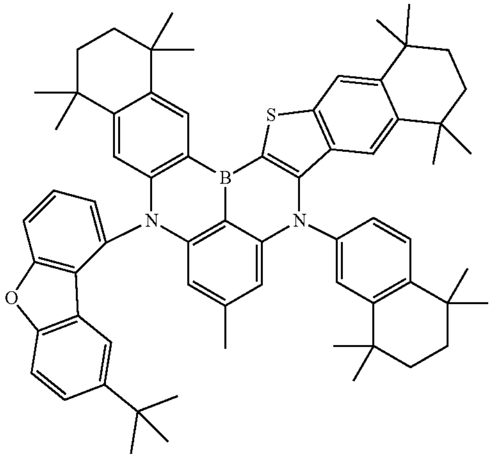
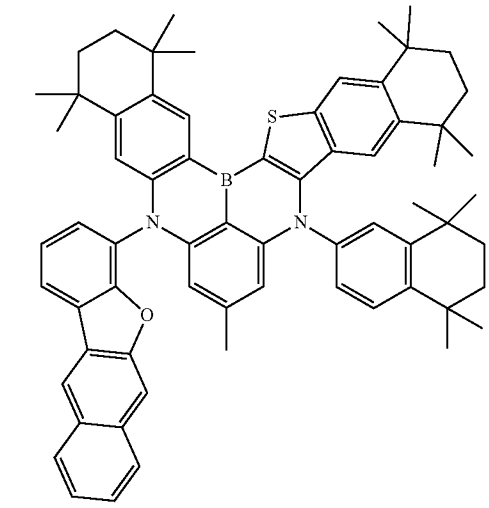
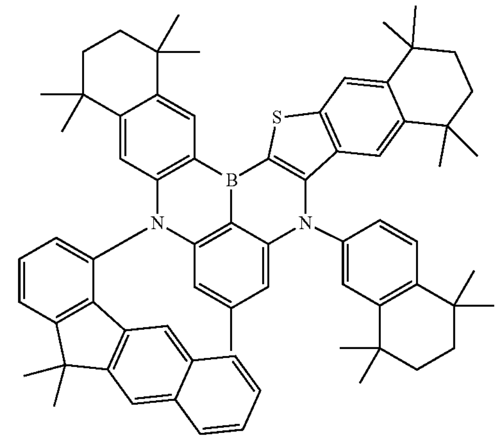
-continued
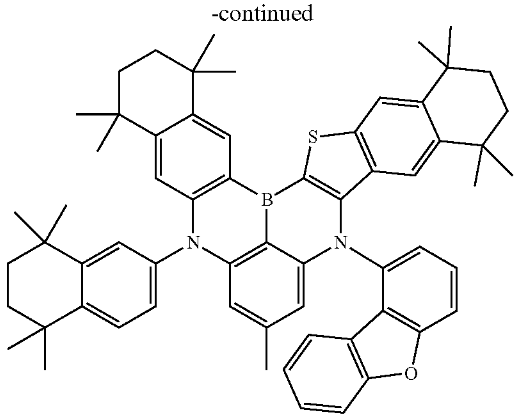
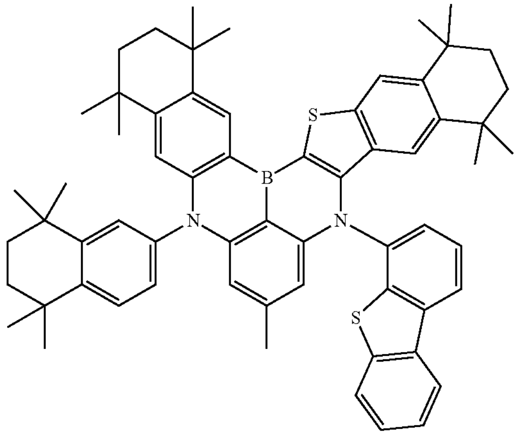
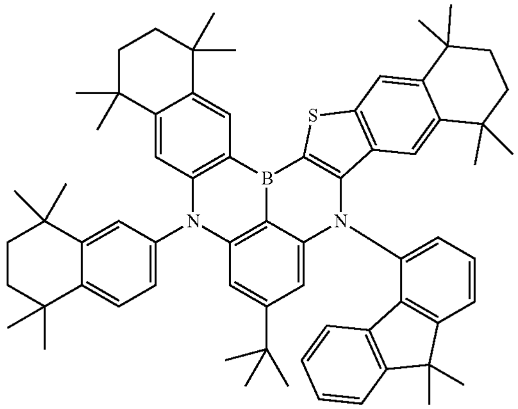
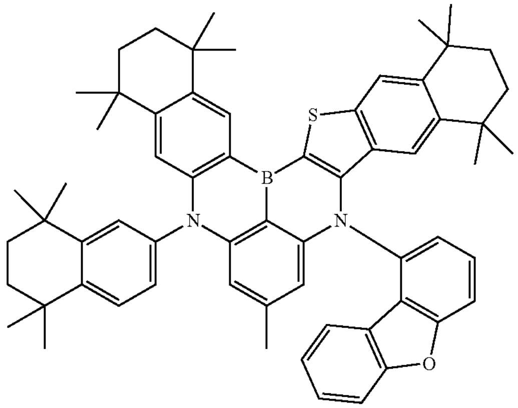

-continued
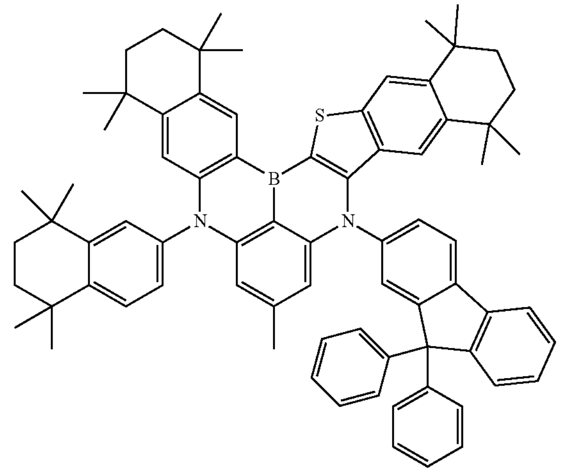
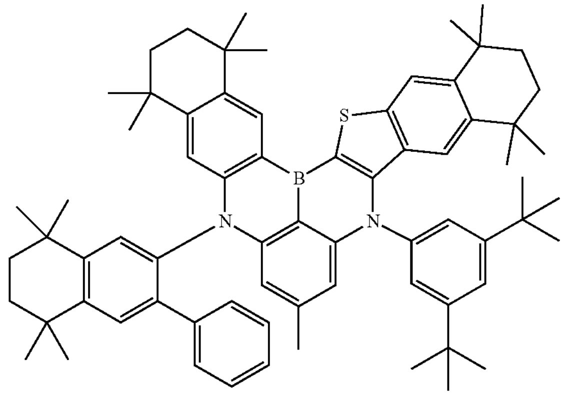
-continued
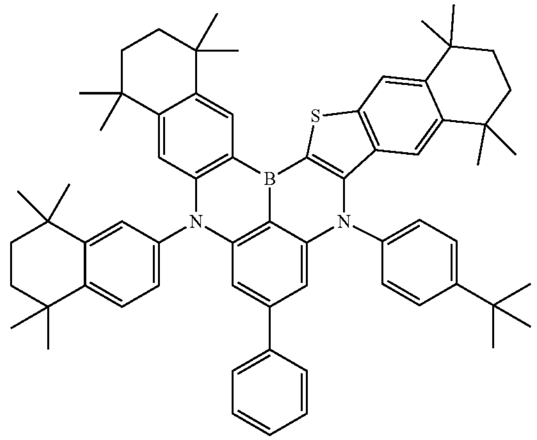
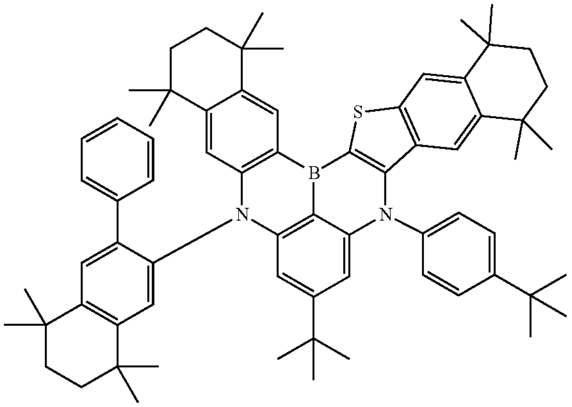
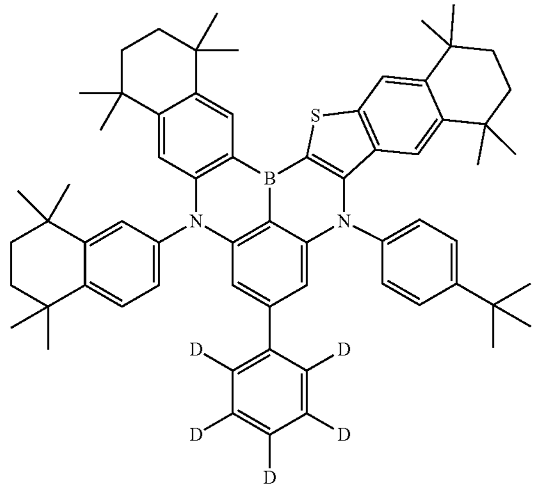
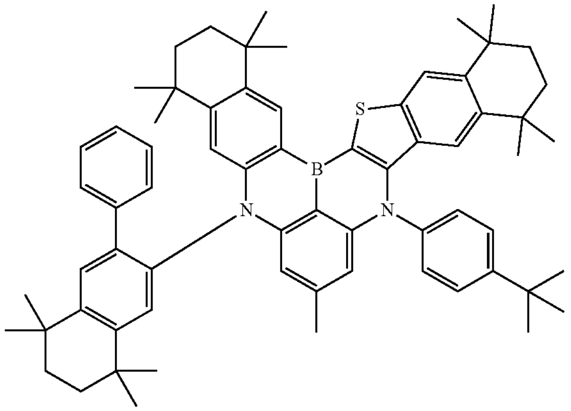

-continued
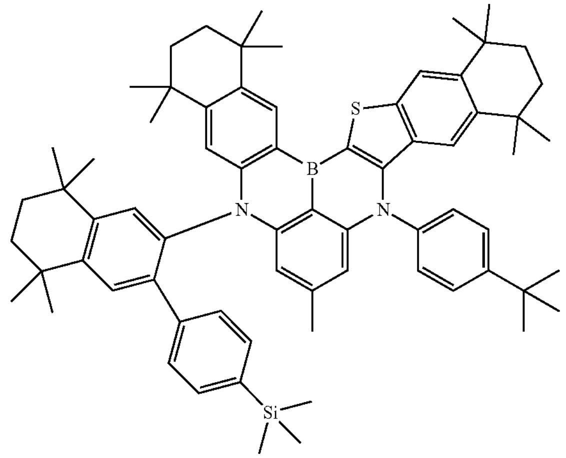
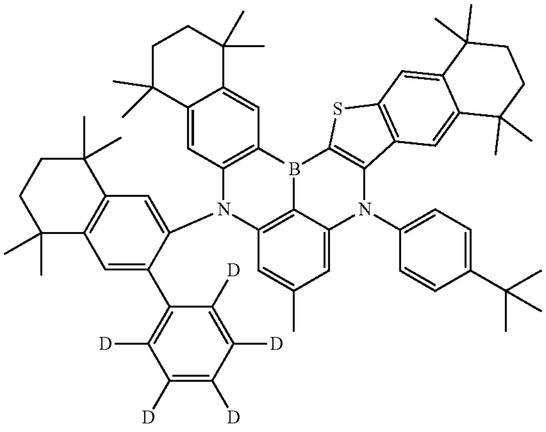
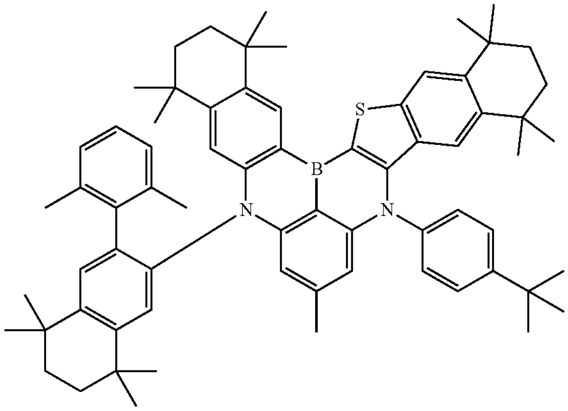
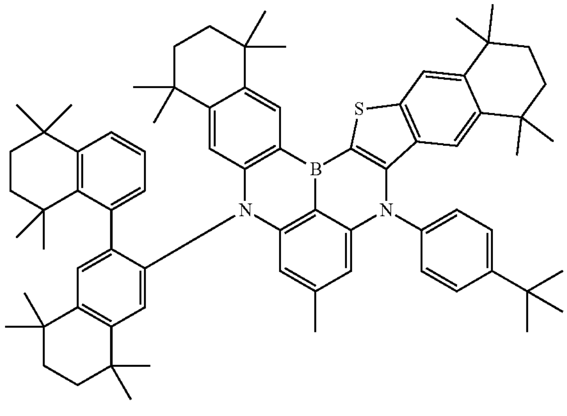
-continued
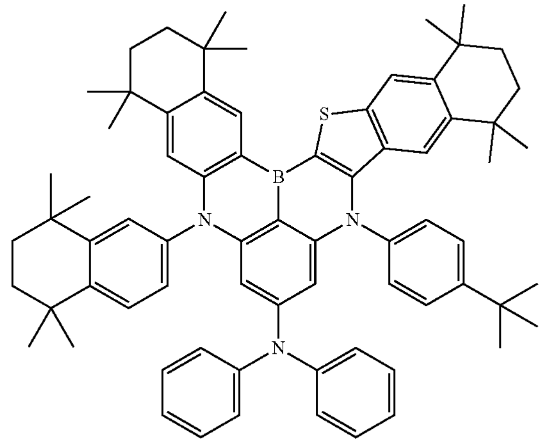
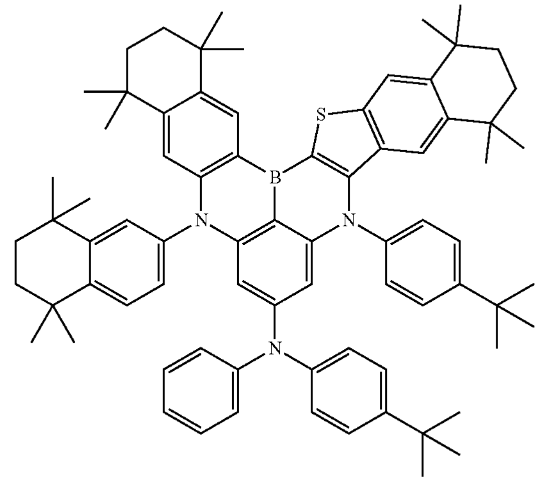
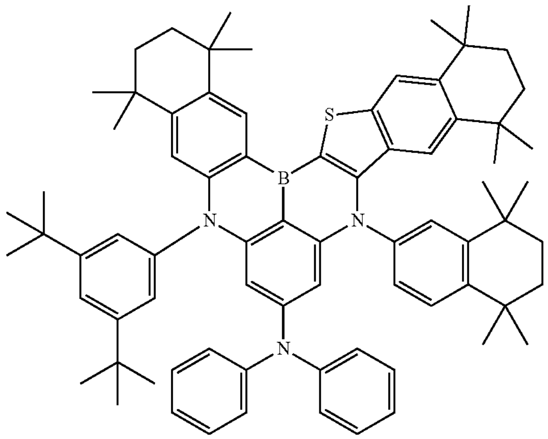

-continued
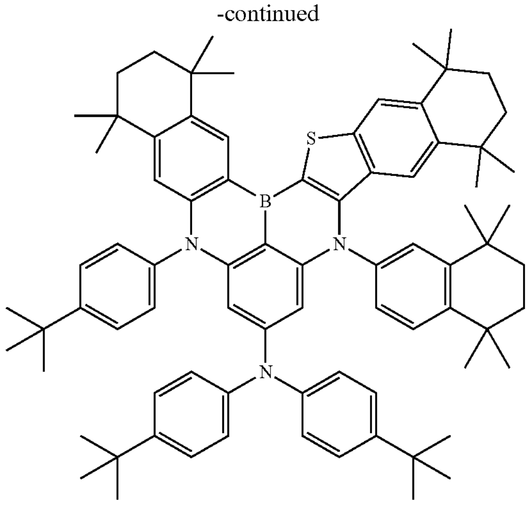
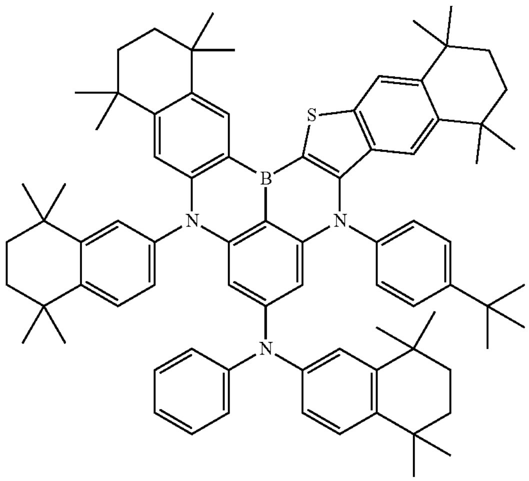
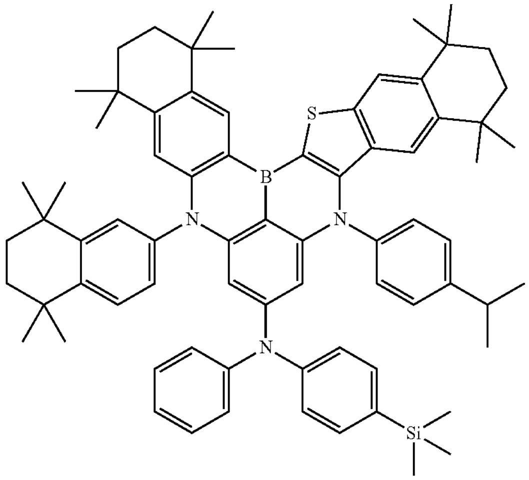
-continued
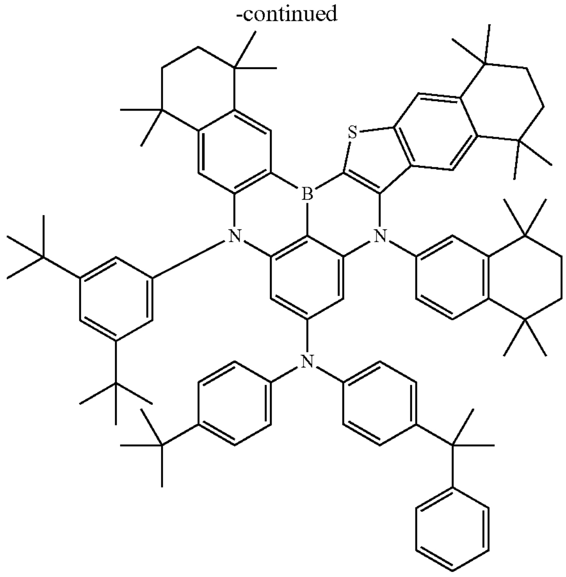
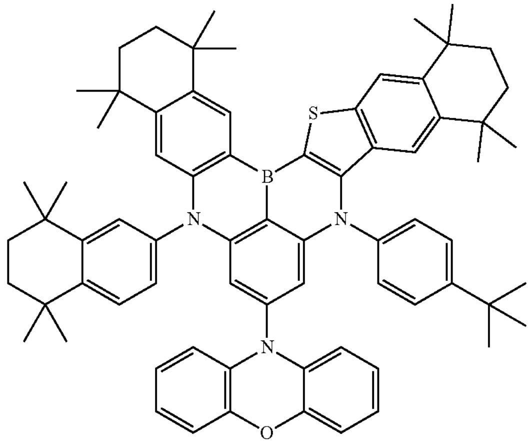
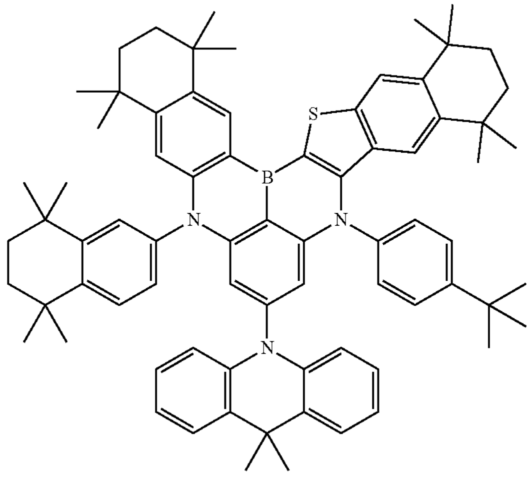

-continued
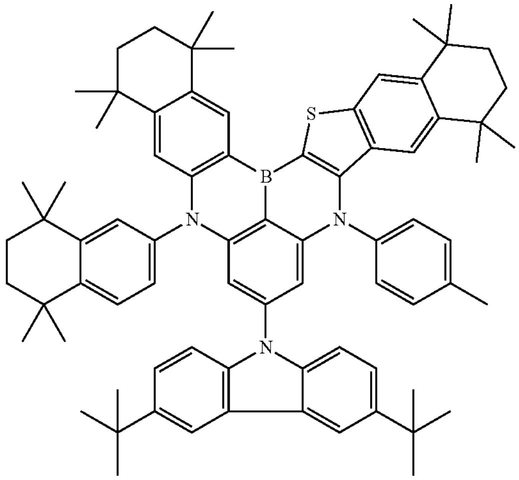
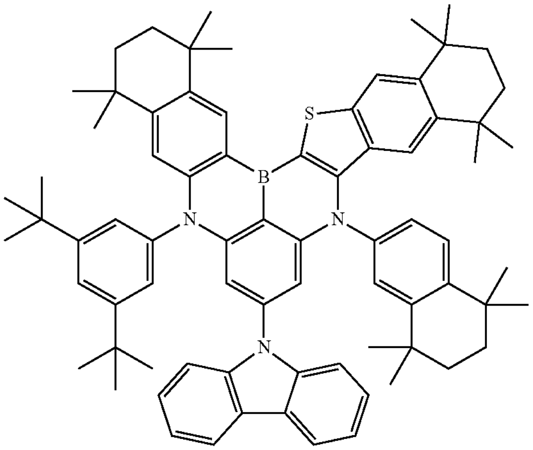
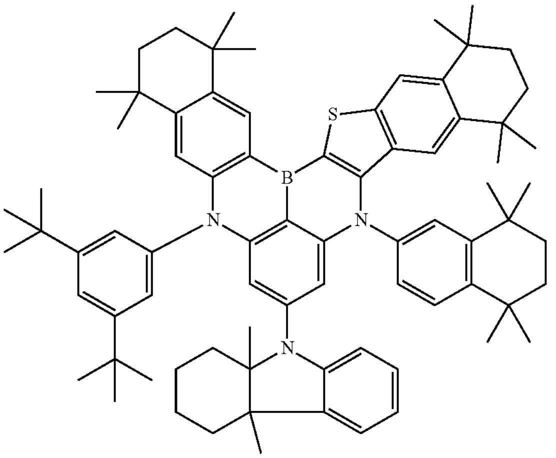
-continued
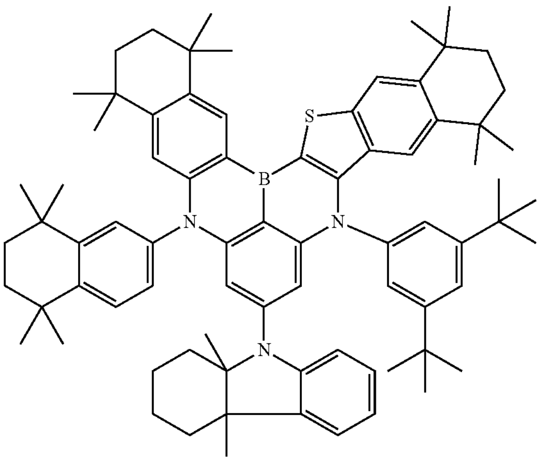
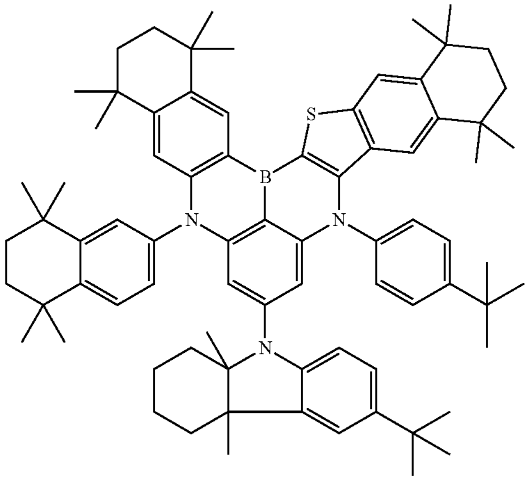
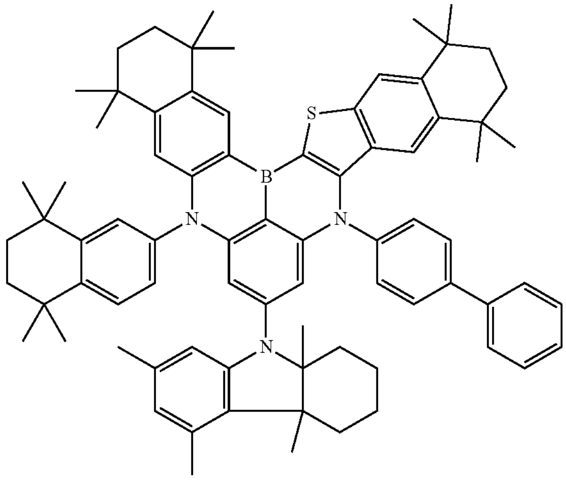

-continued
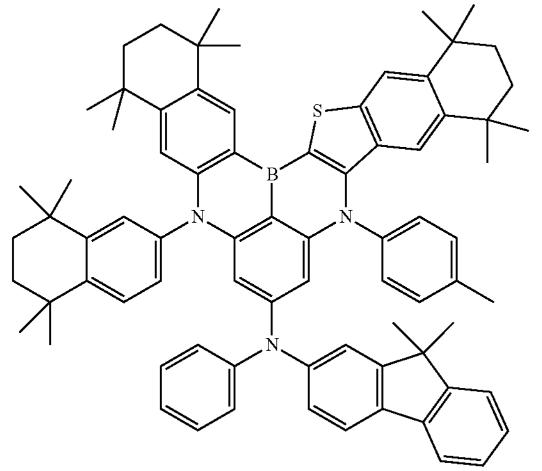
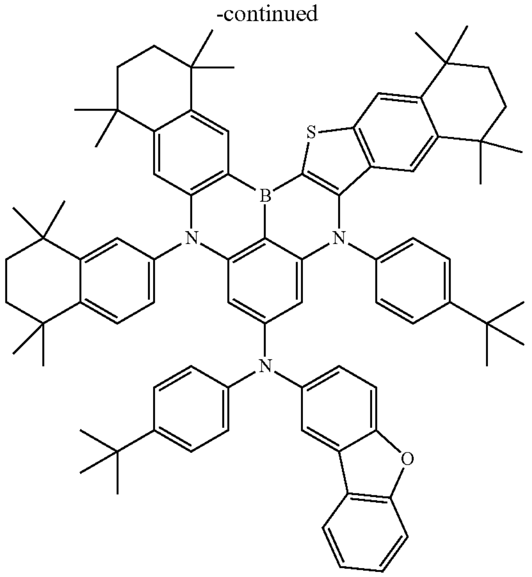
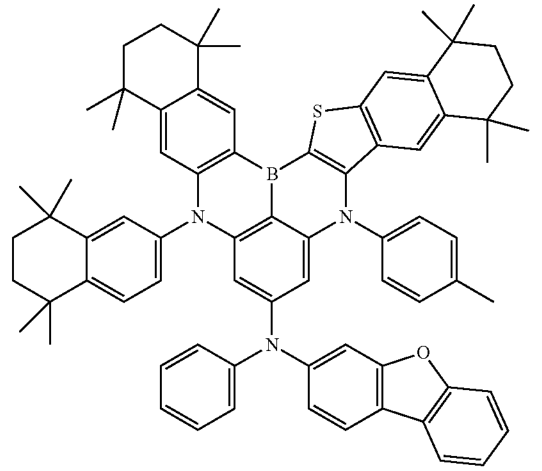
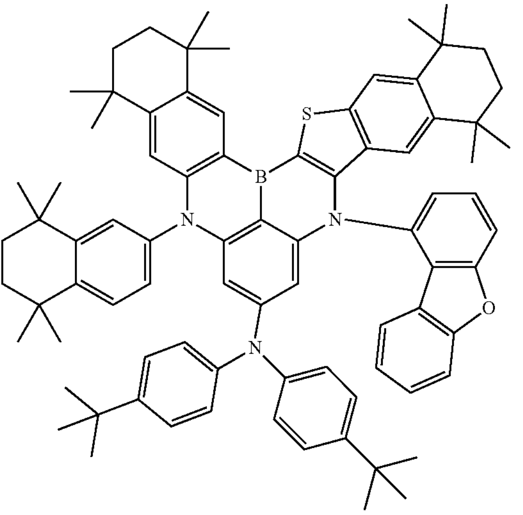
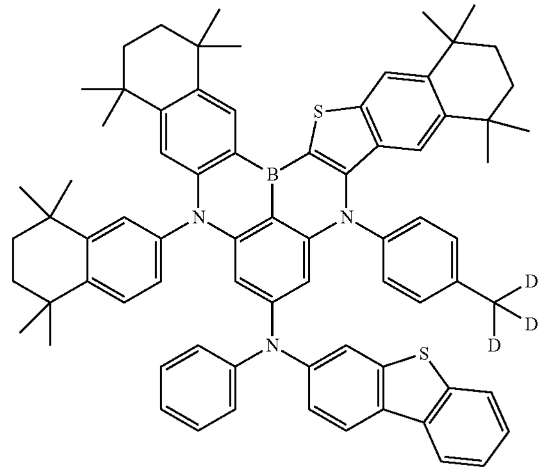
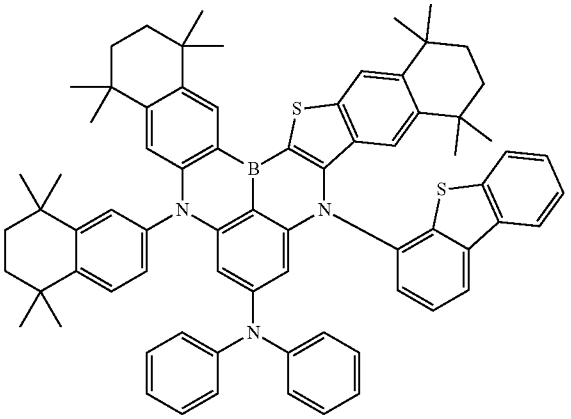
-continued -continued
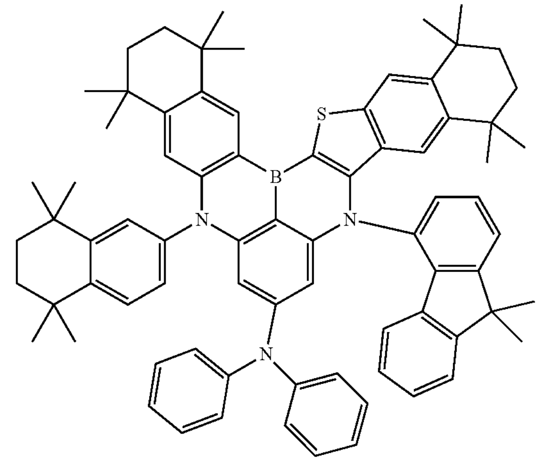
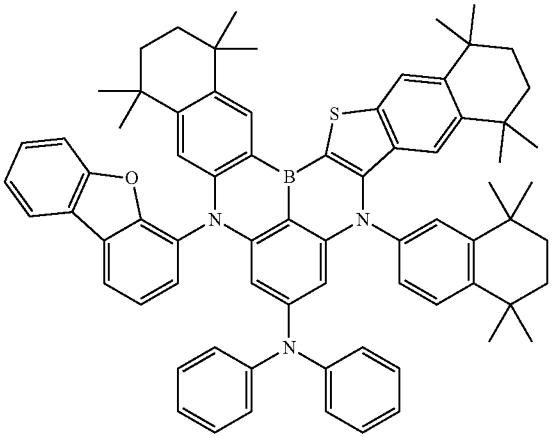
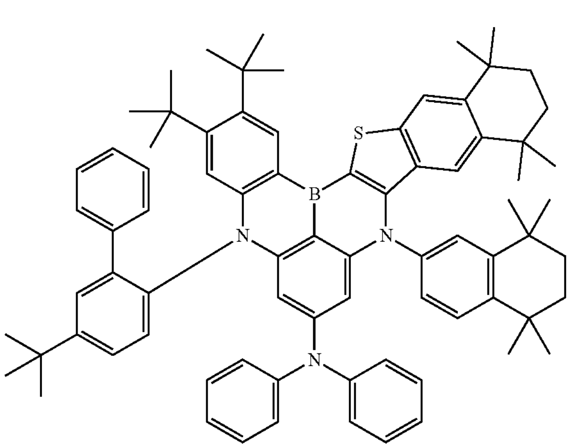
-continued
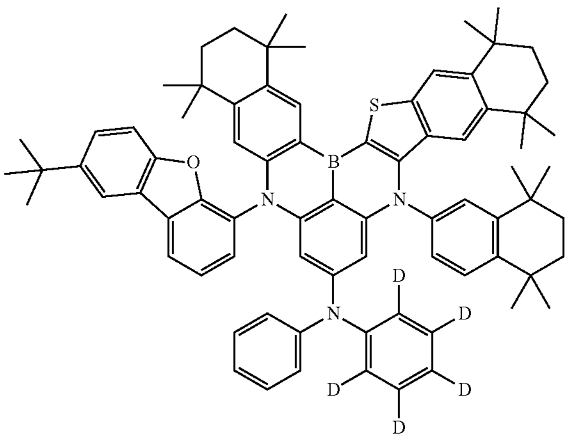
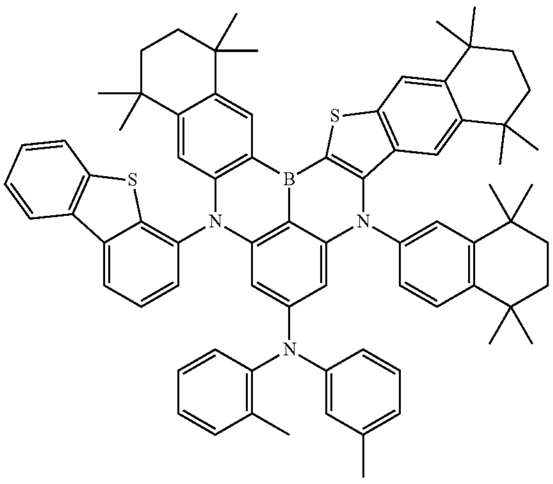
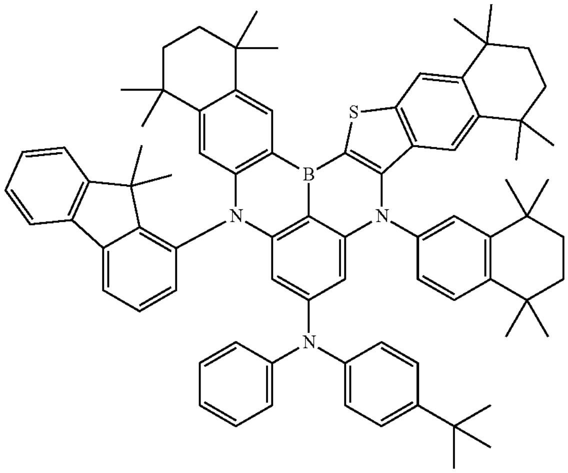

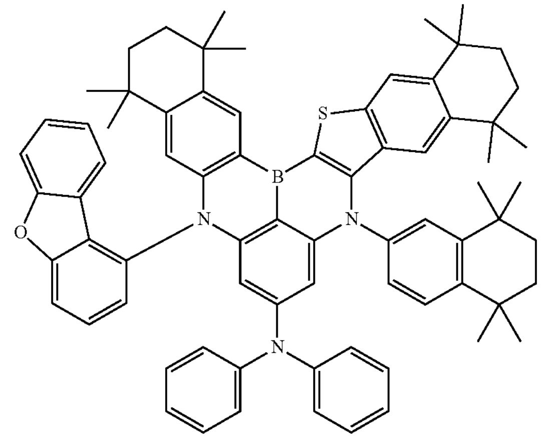
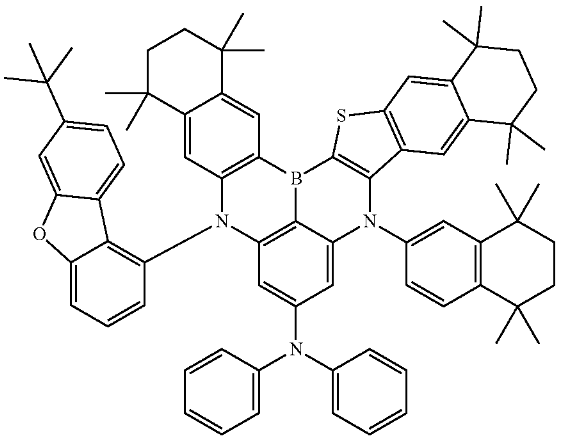
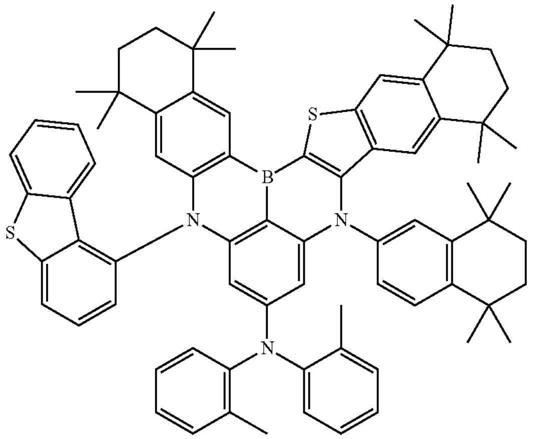
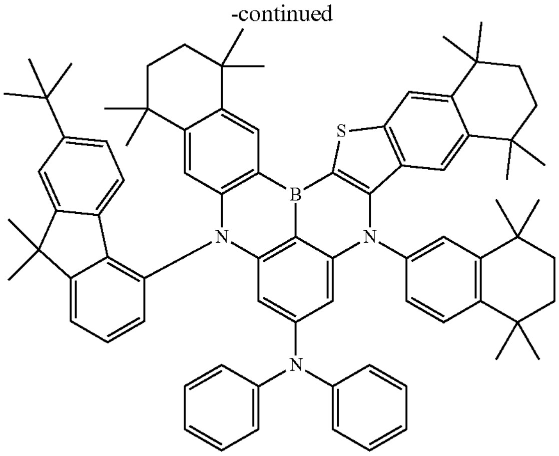
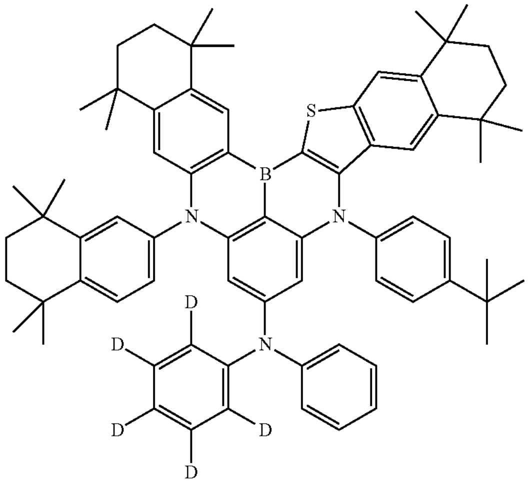
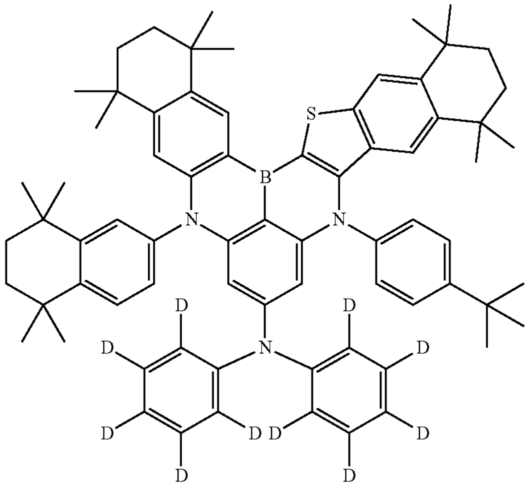

-continued
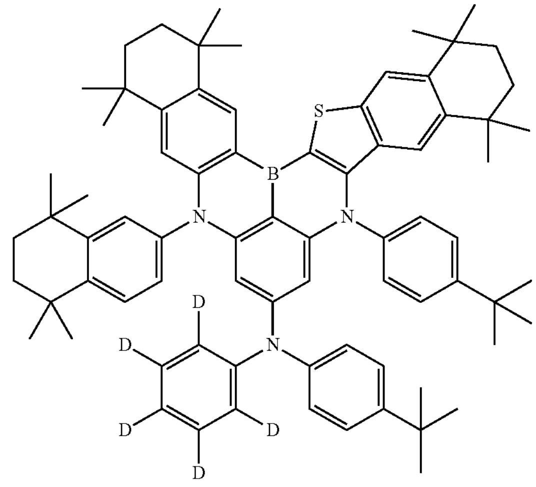
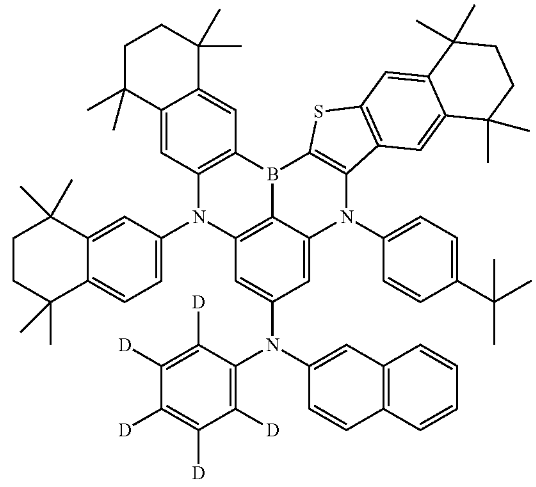
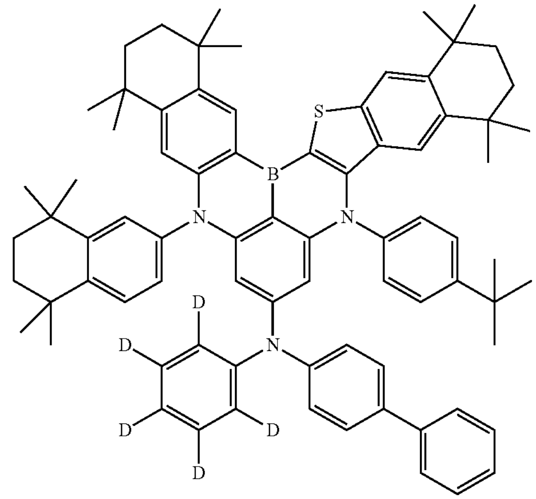
-continued
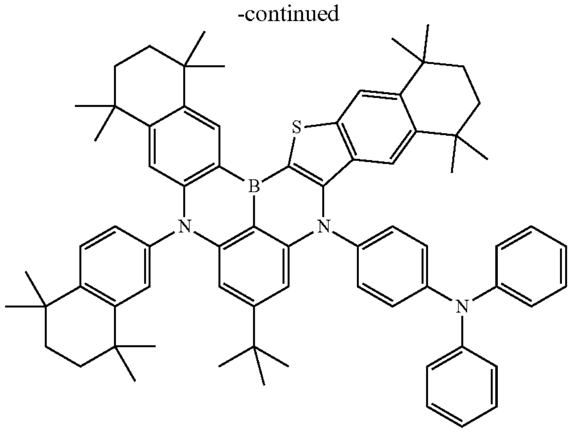
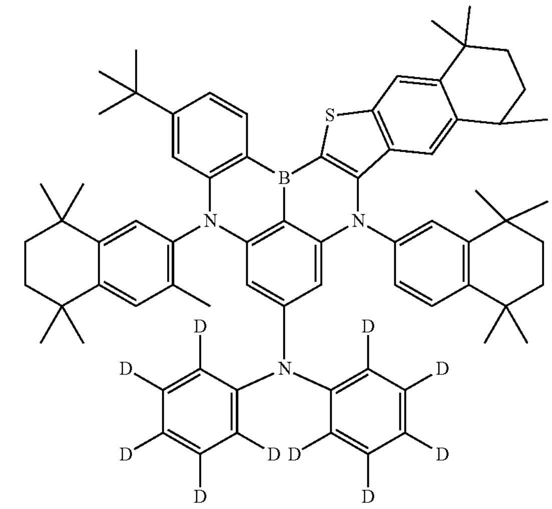
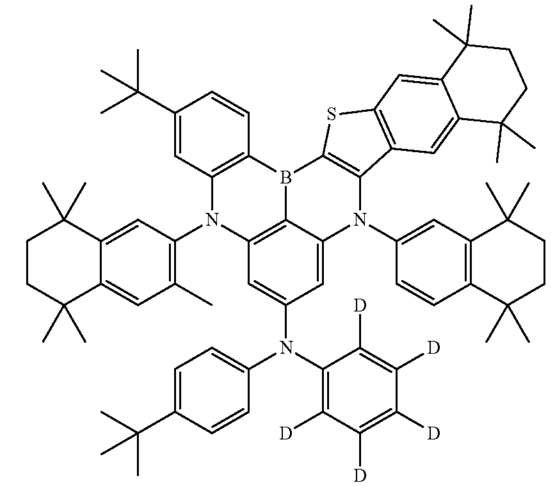

-continued
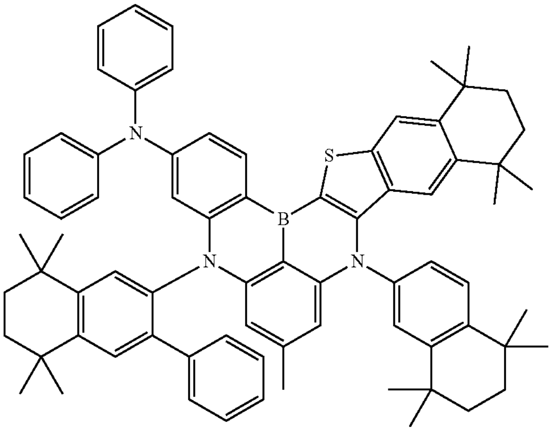
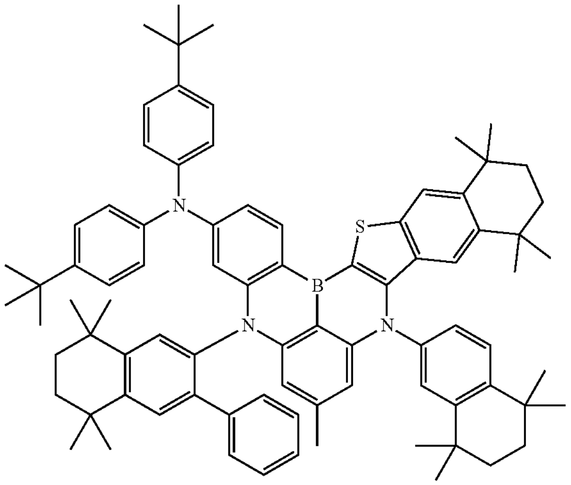
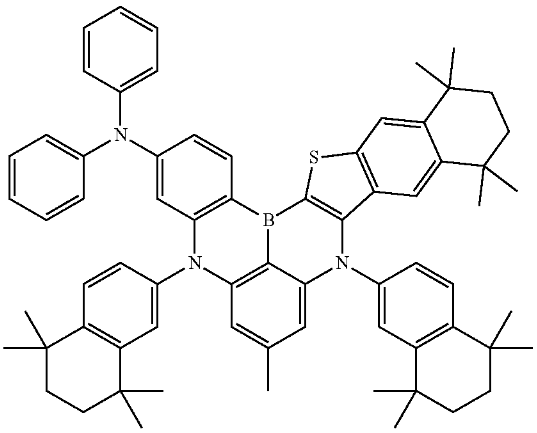
-continued
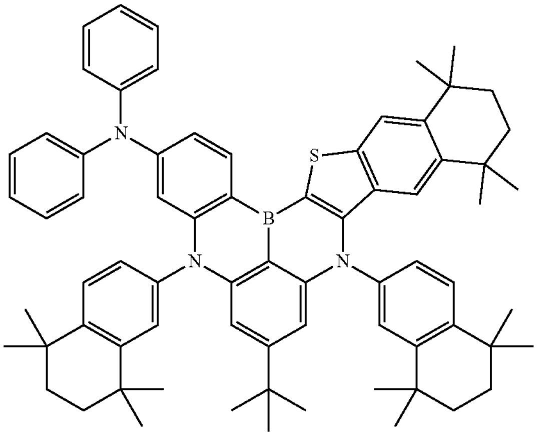
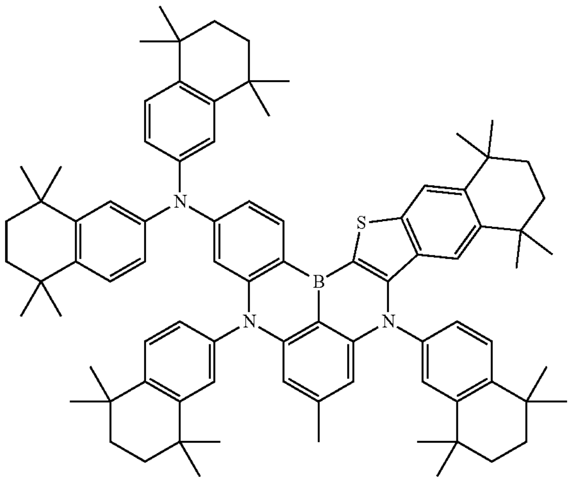
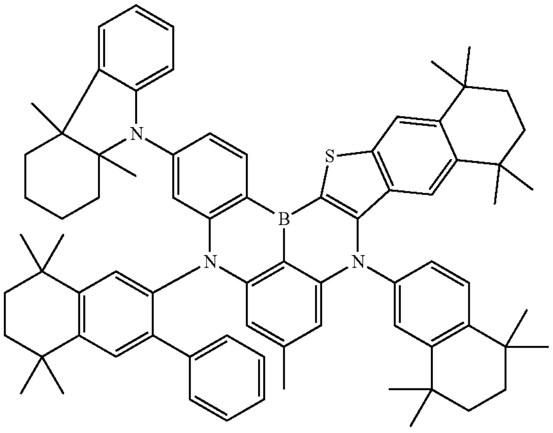

-continued
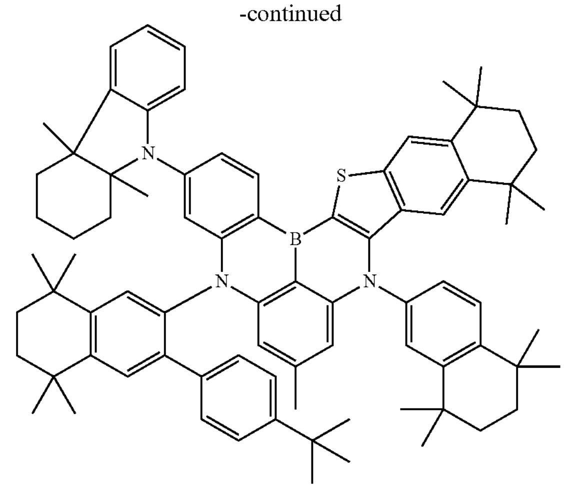
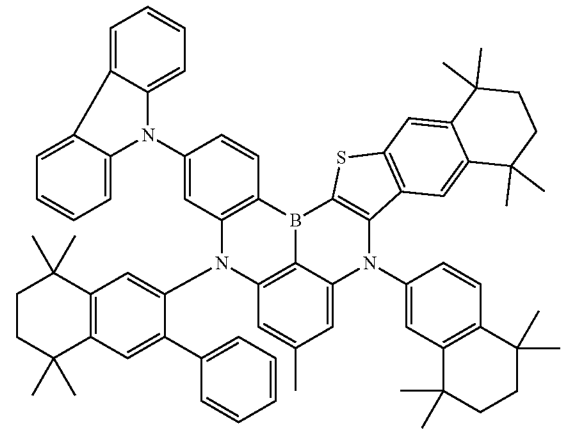
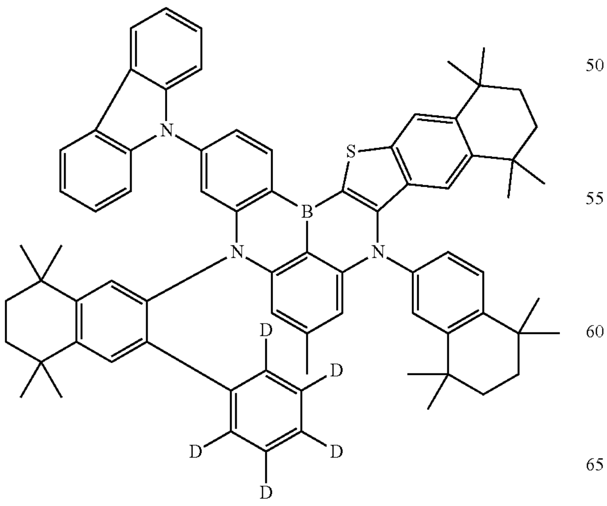
-continued
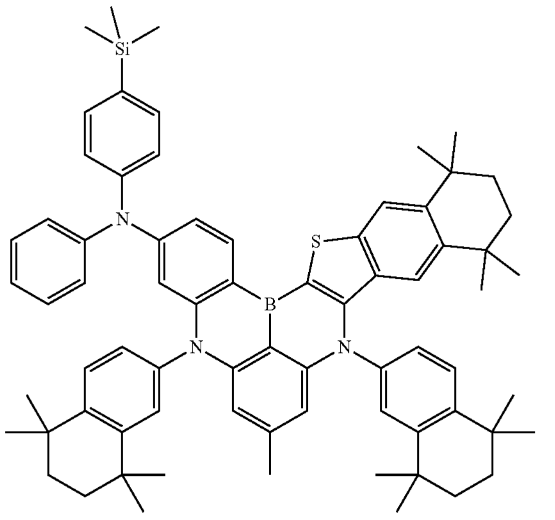
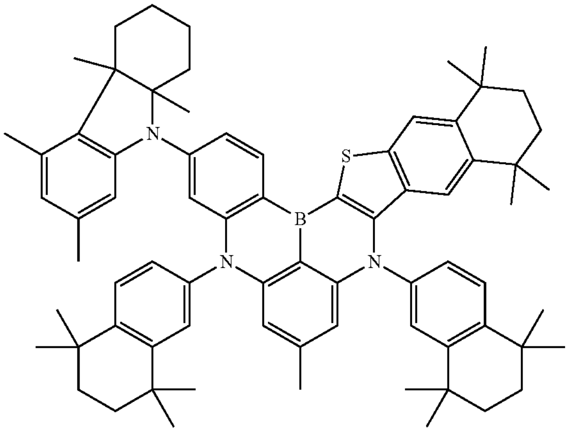
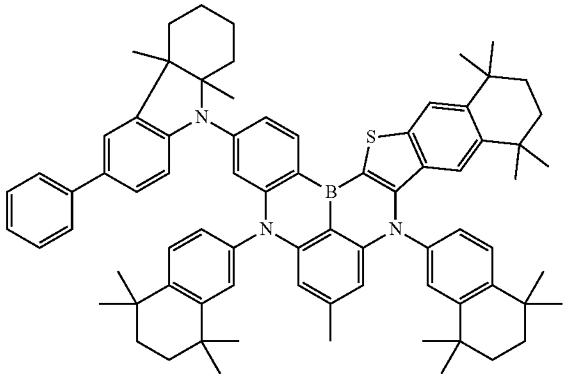
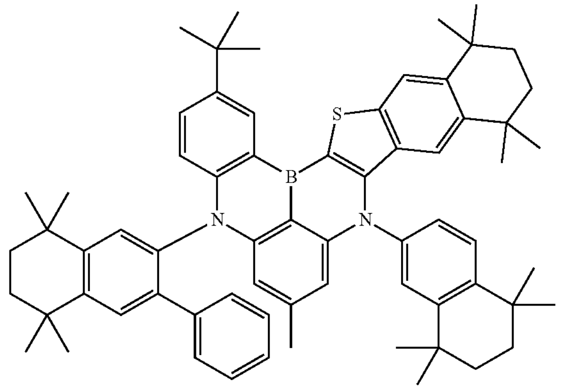

-continued
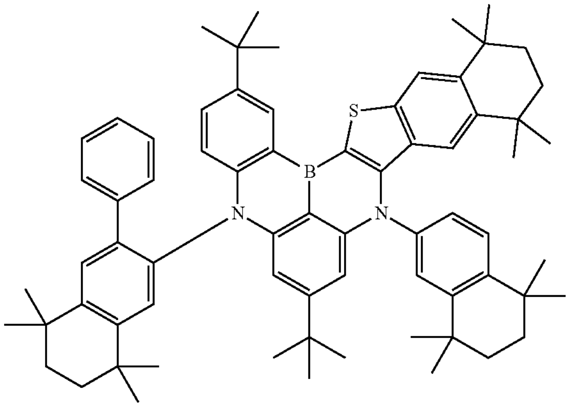
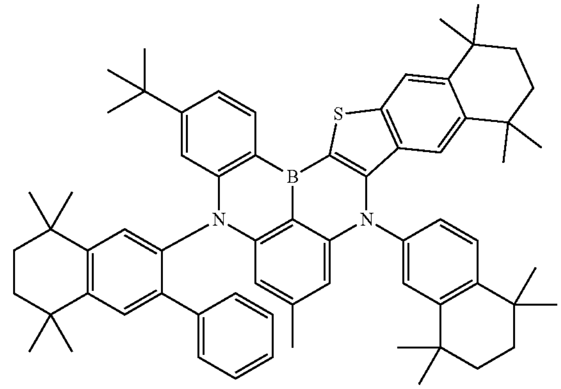
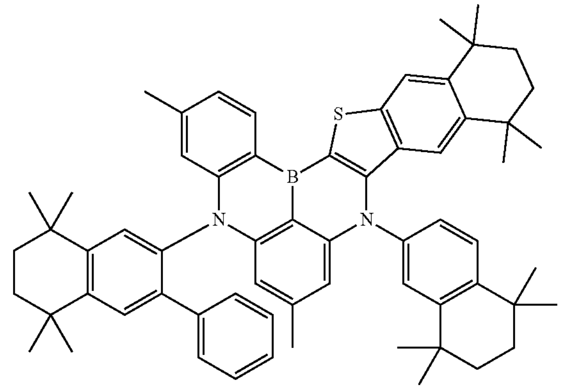
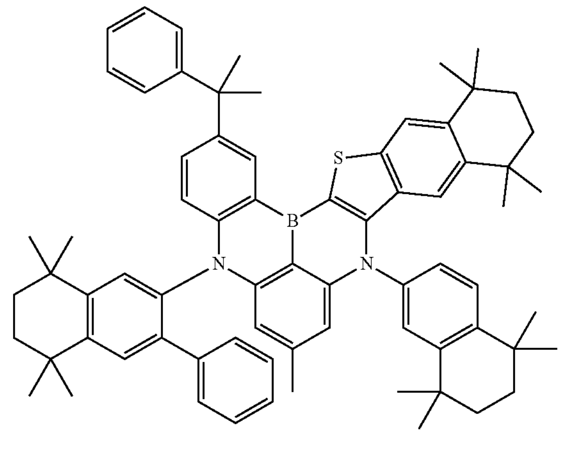
-continued
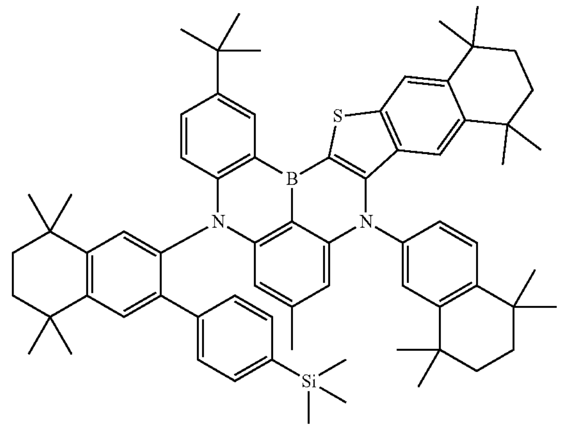
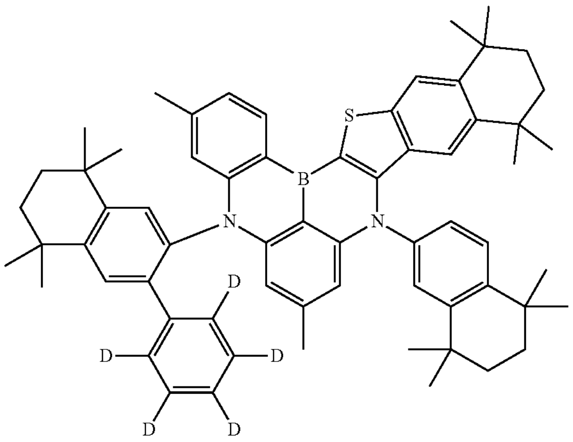
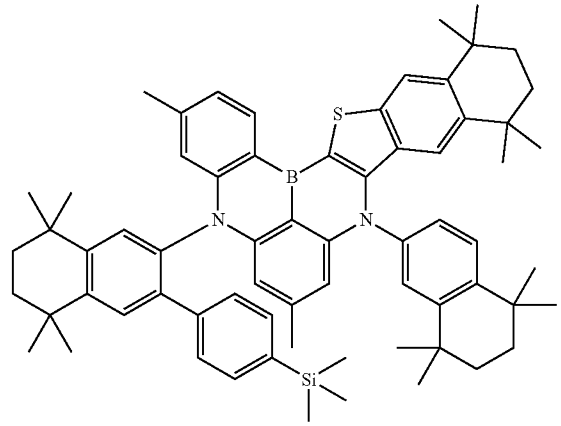
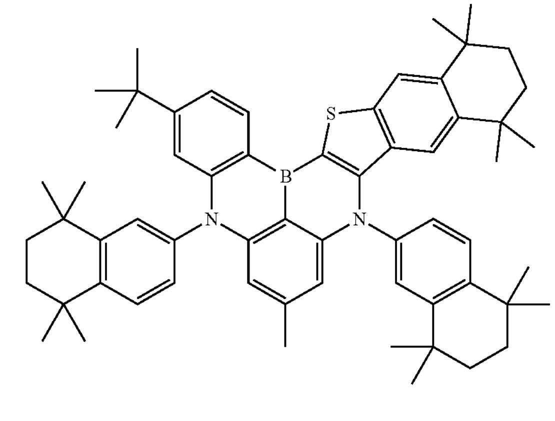

-continued
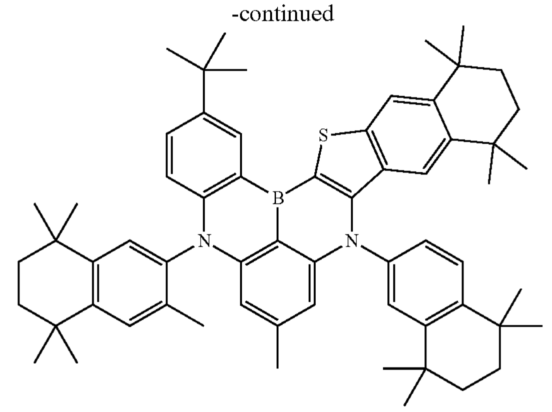
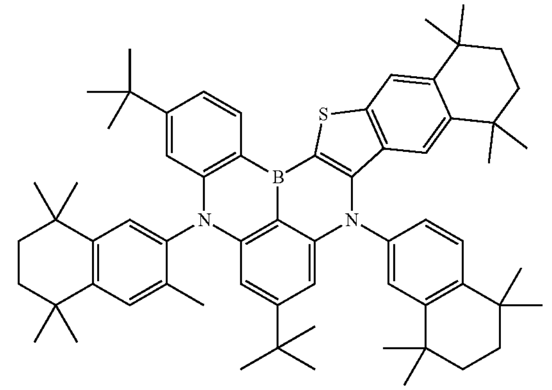
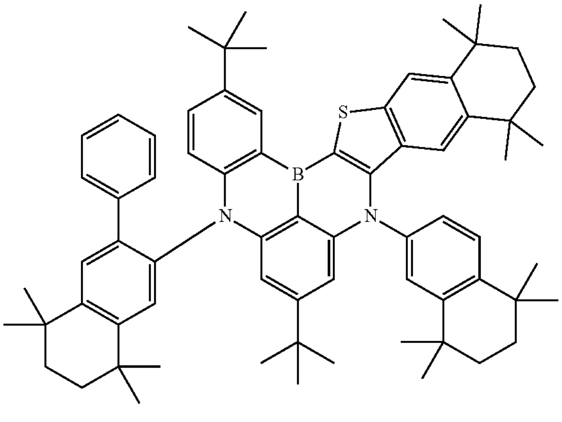
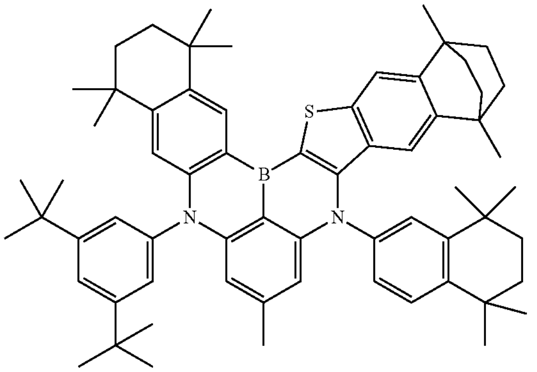
-continued
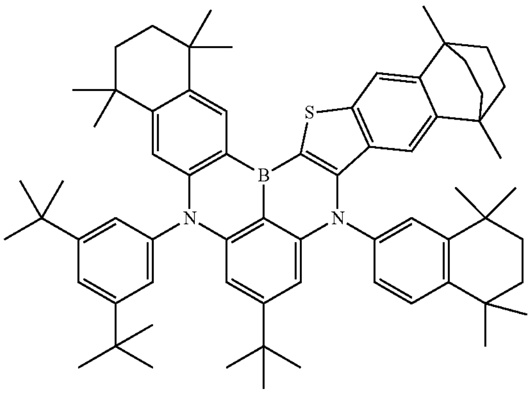
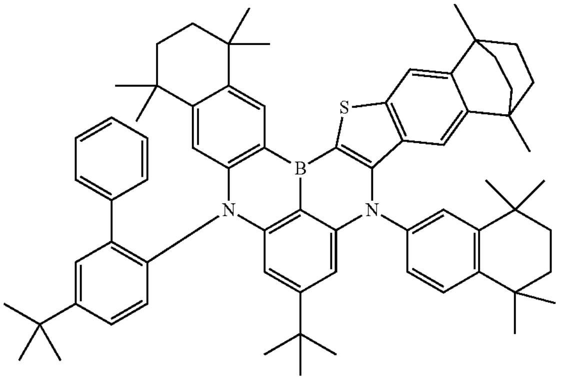
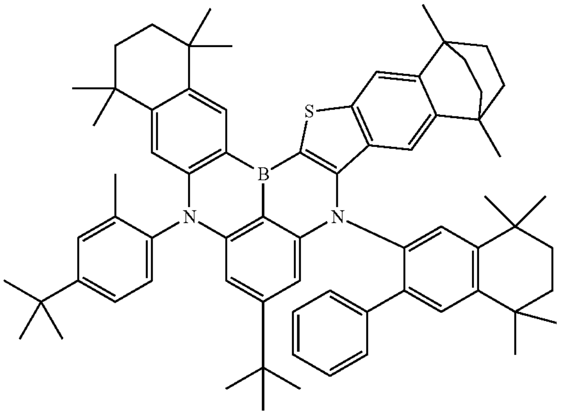
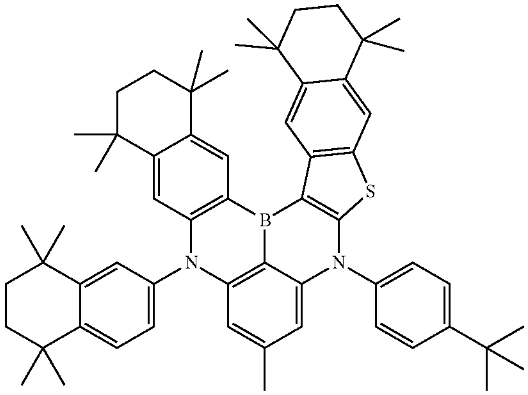

-continued
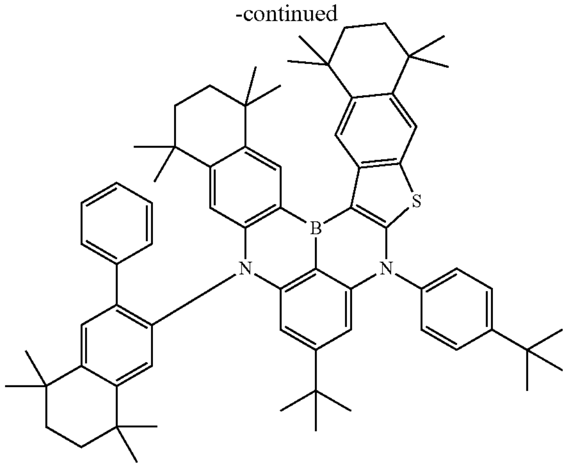
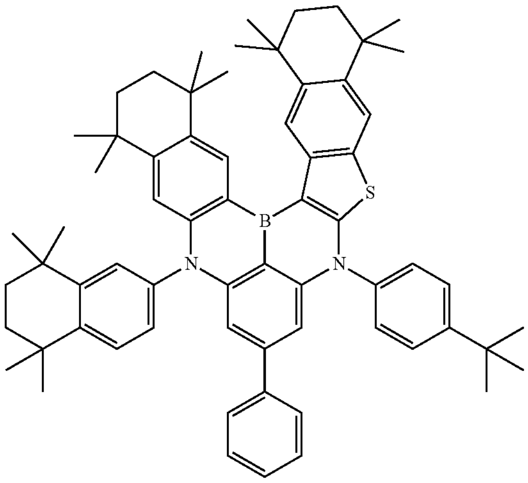
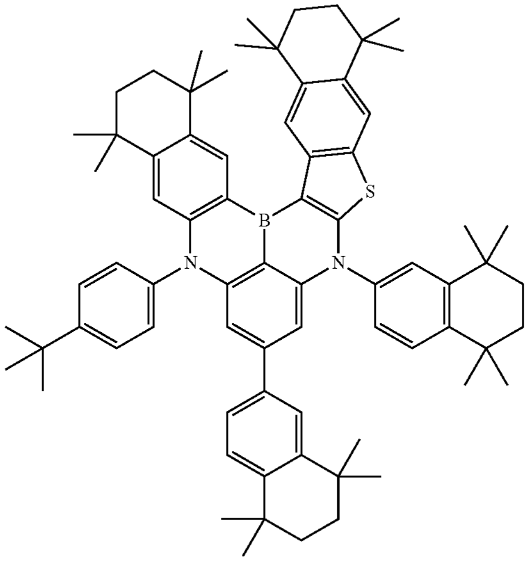
-continued
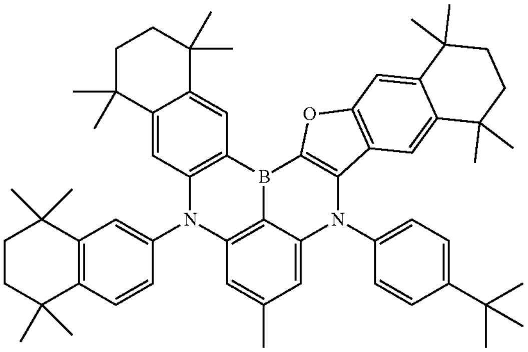
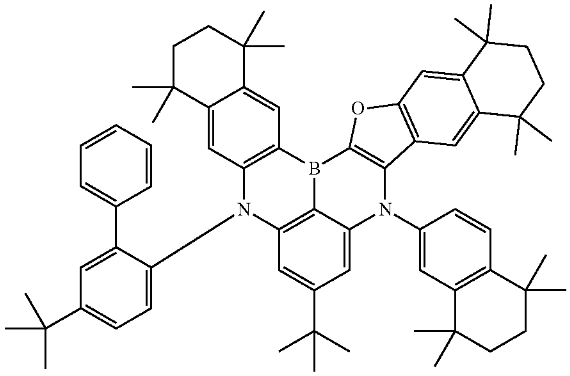
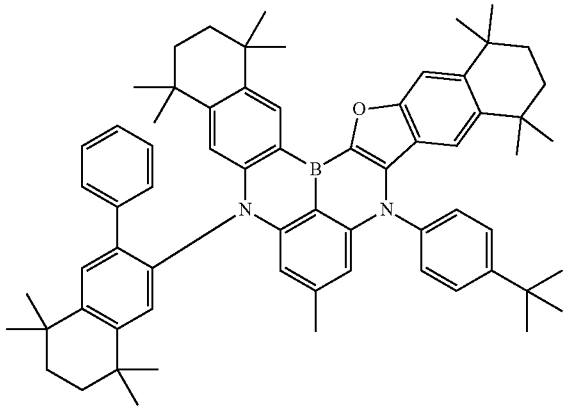
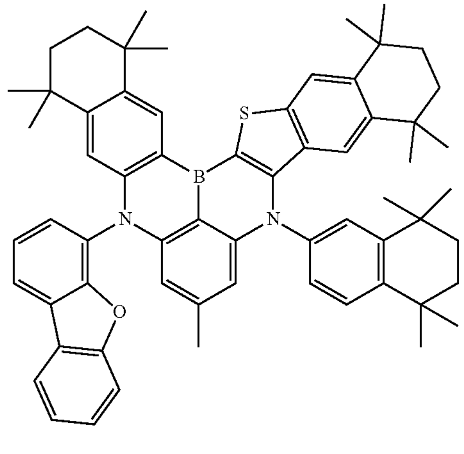

-continued
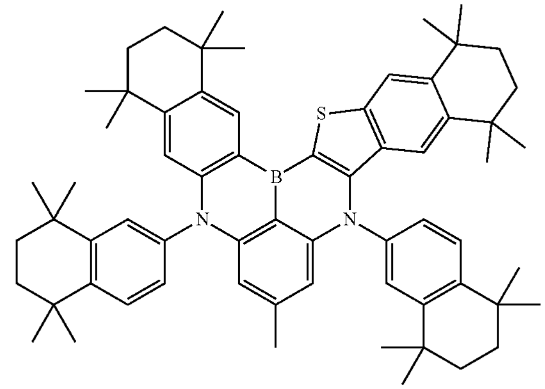
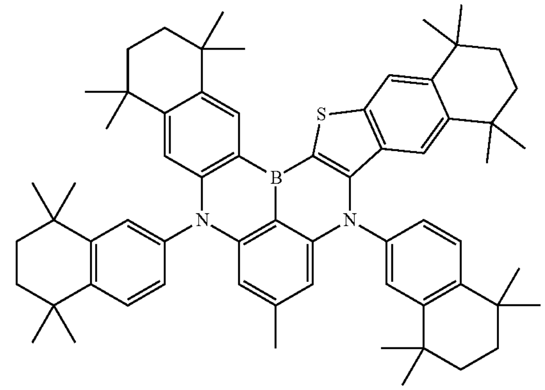
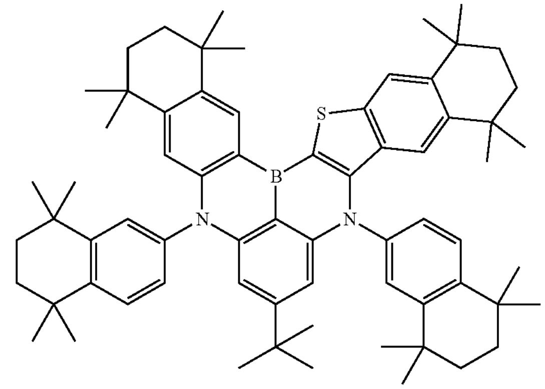
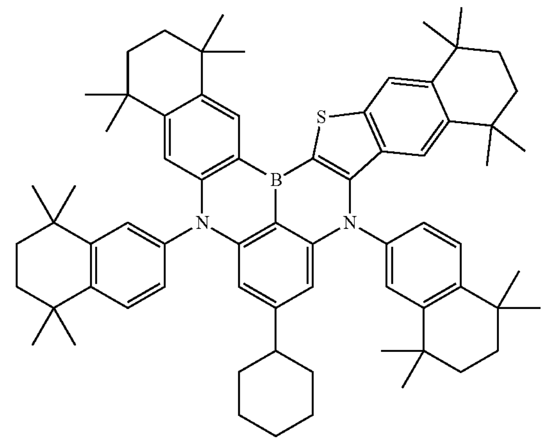
-continued
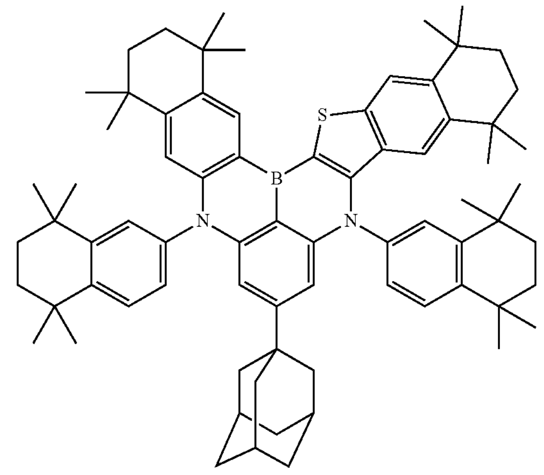
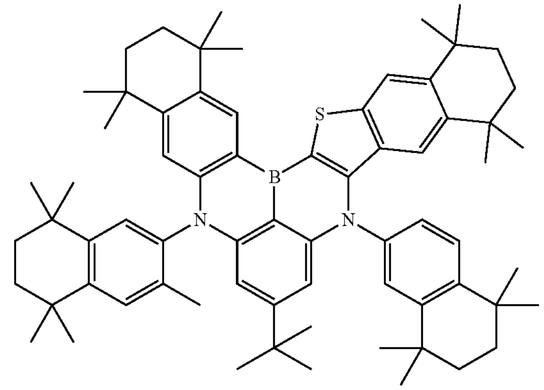
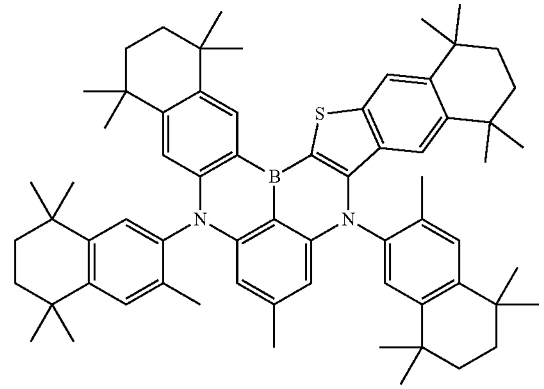
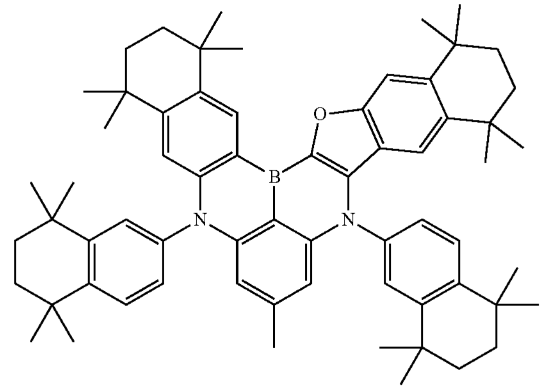

-continued
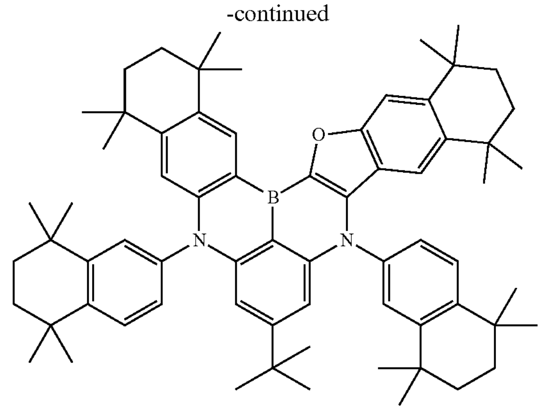
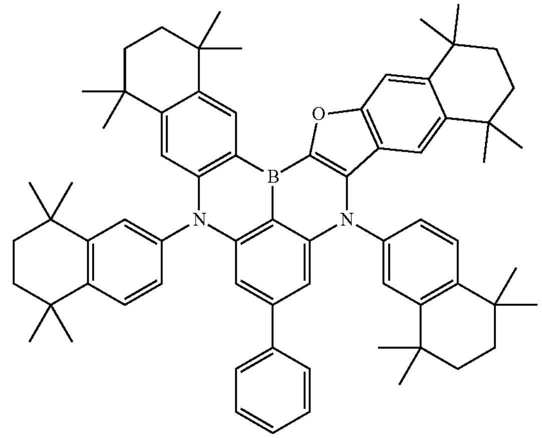
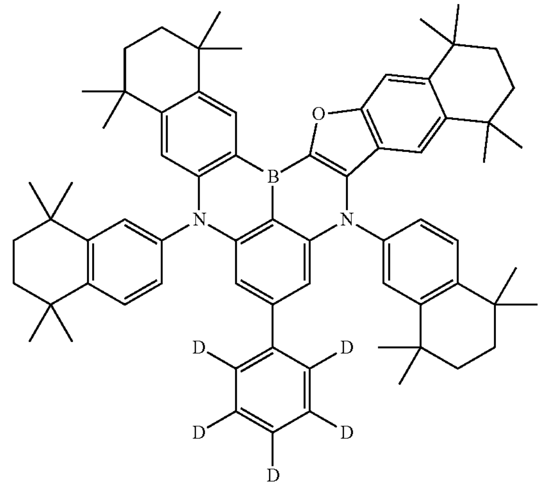
-continued
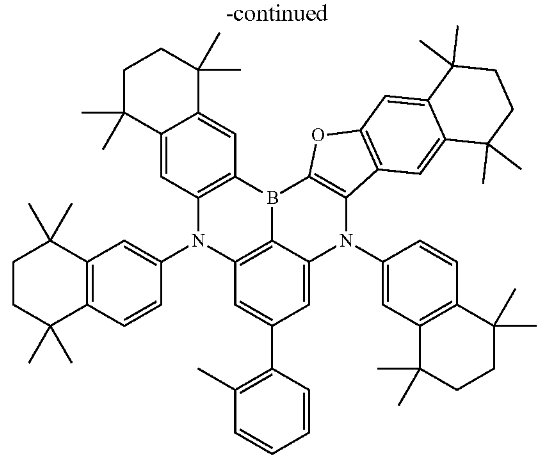
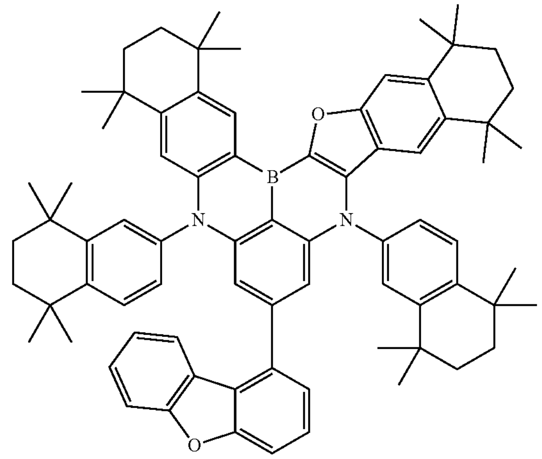
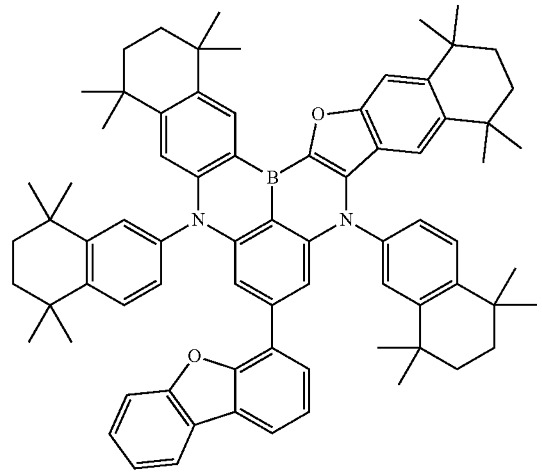

-continued
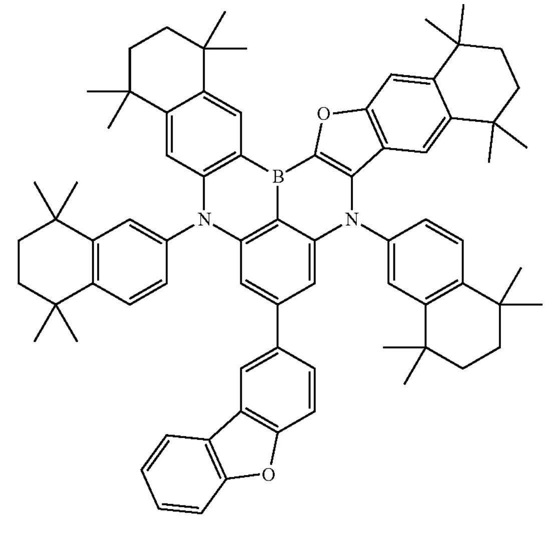
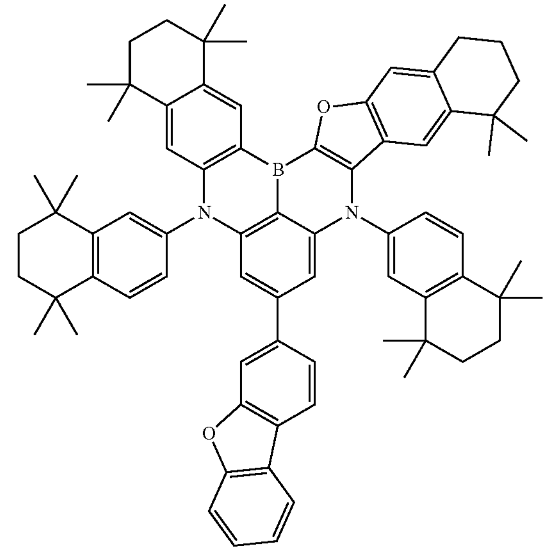
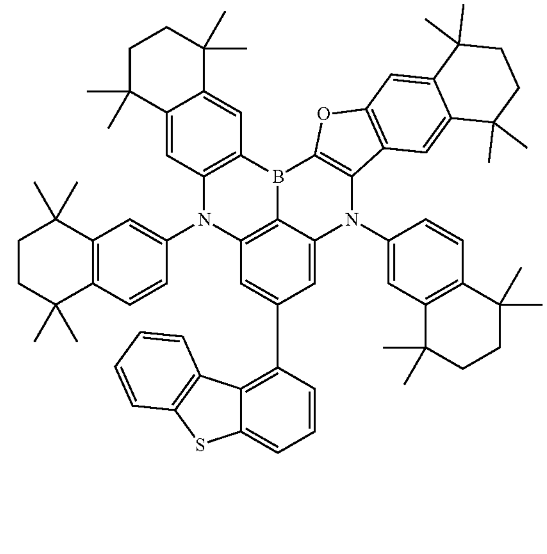
-continued
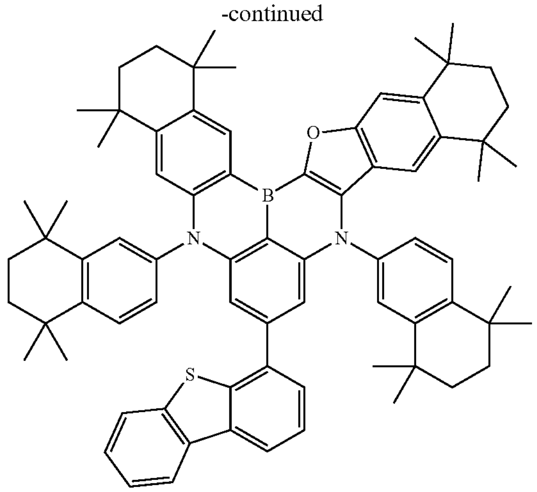
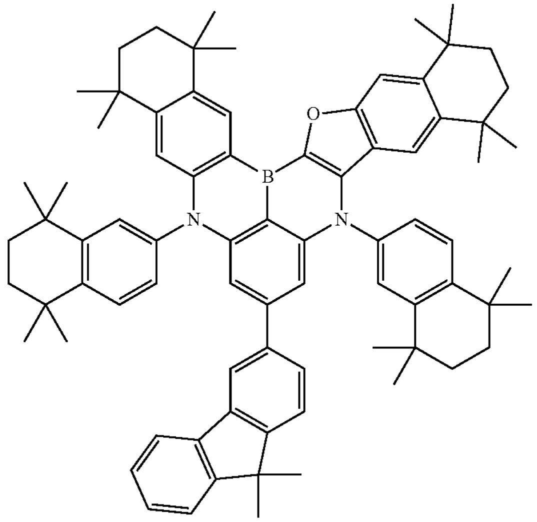
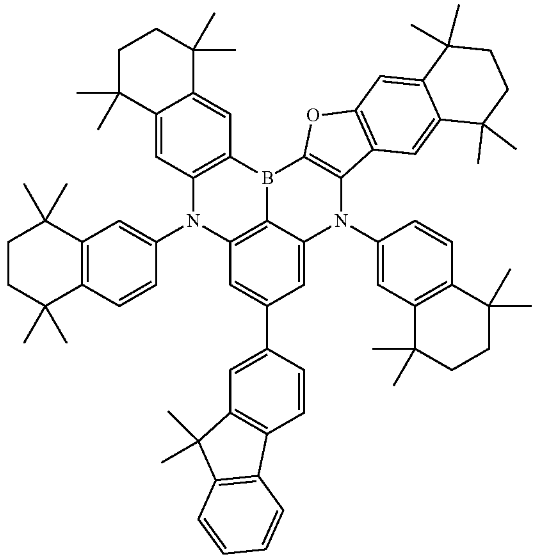

-continued
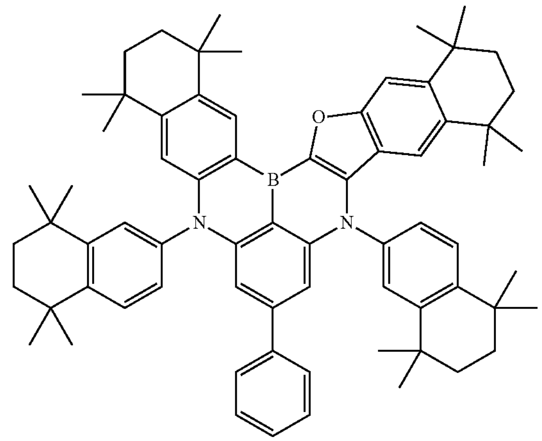
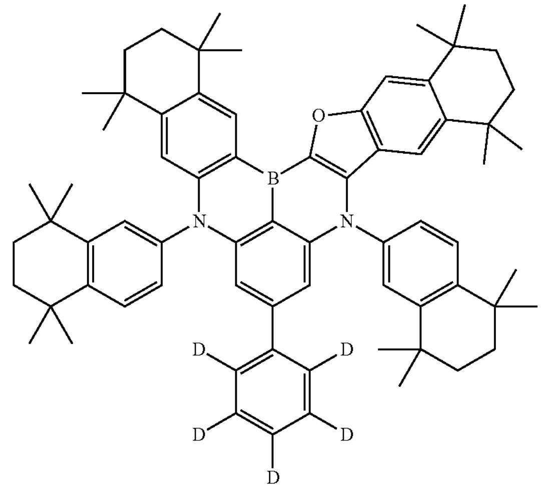
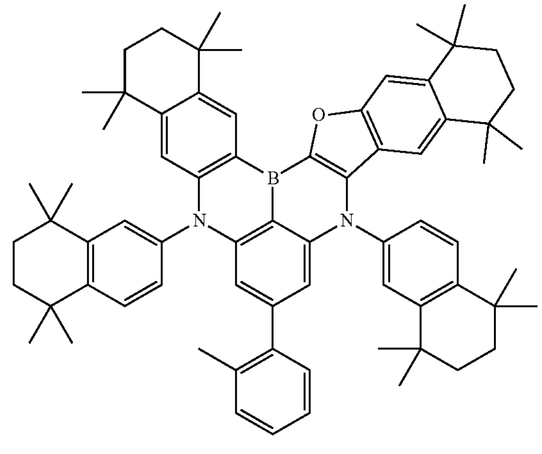
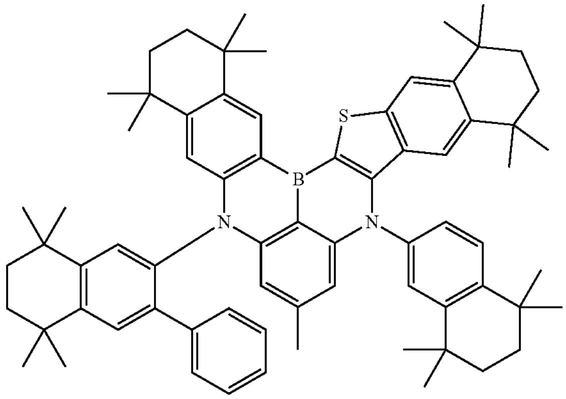
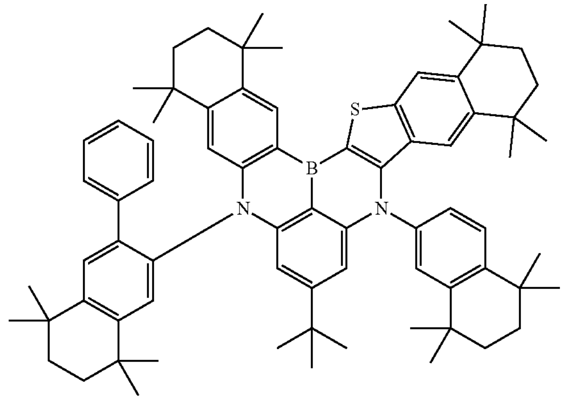
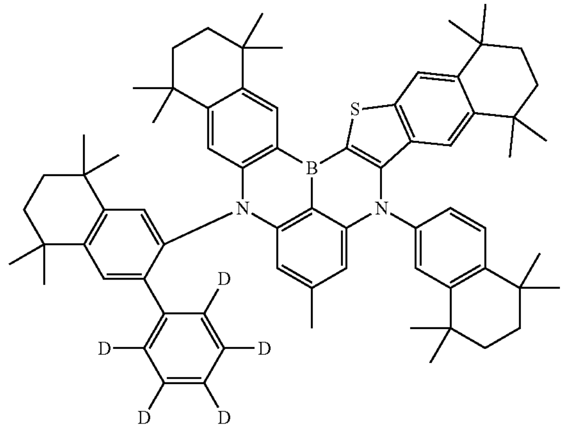
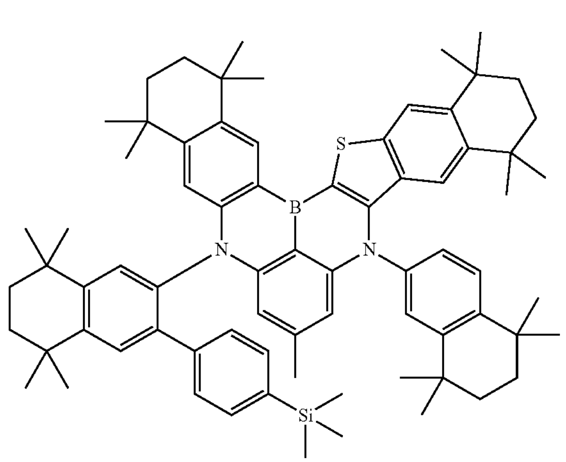

-continued
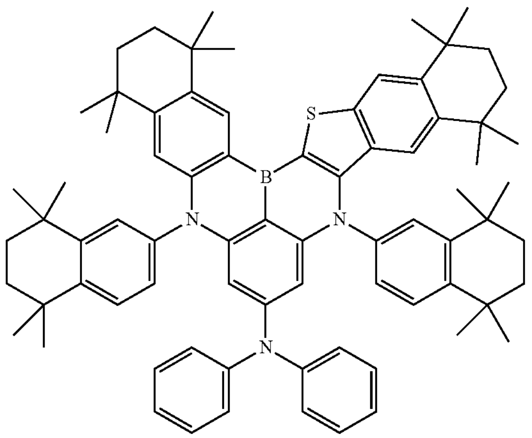
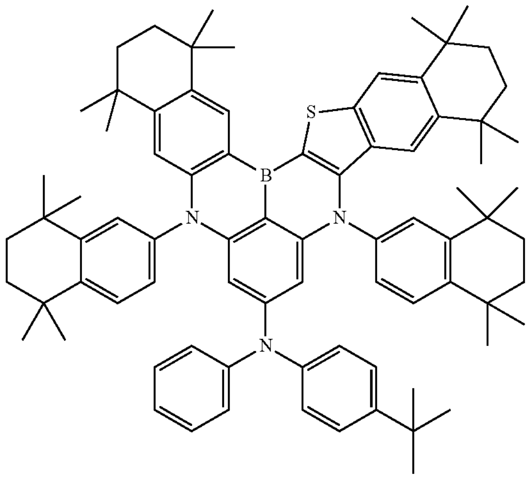
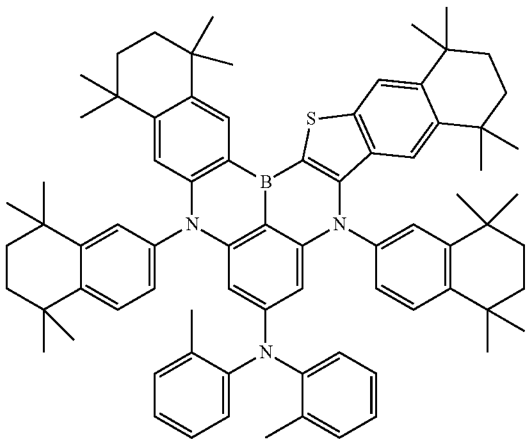
-continued
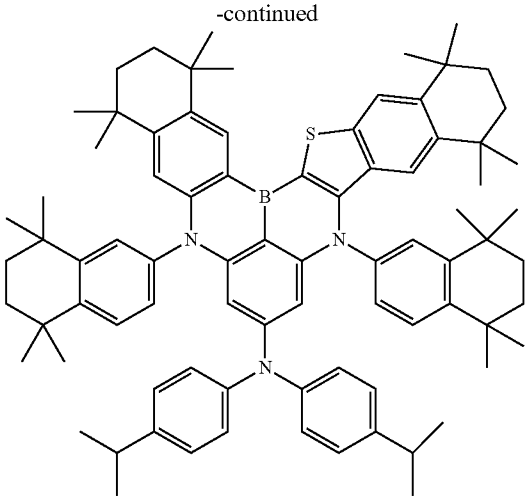
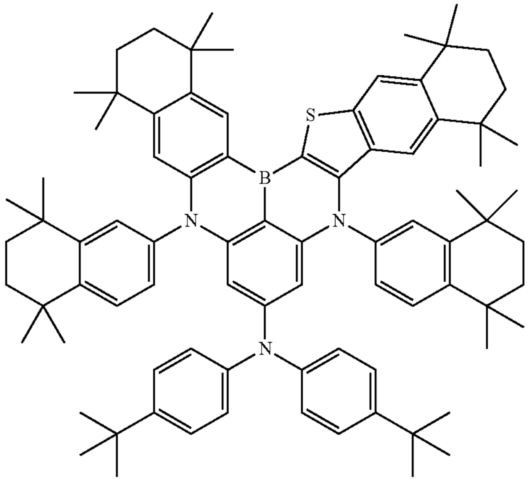
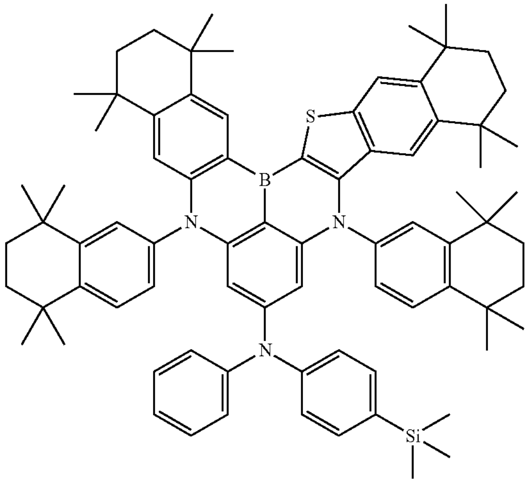

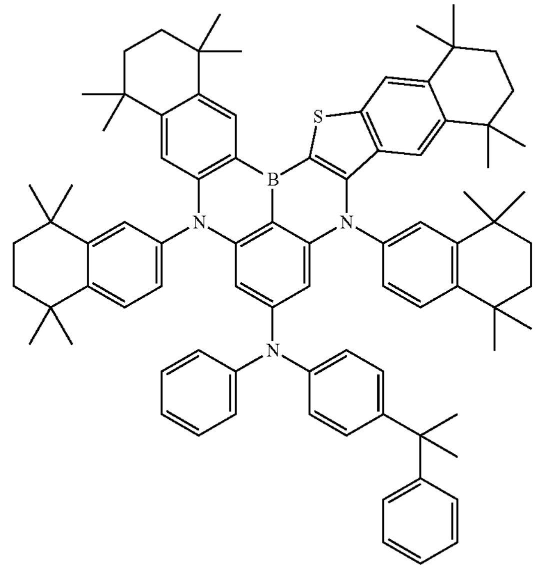
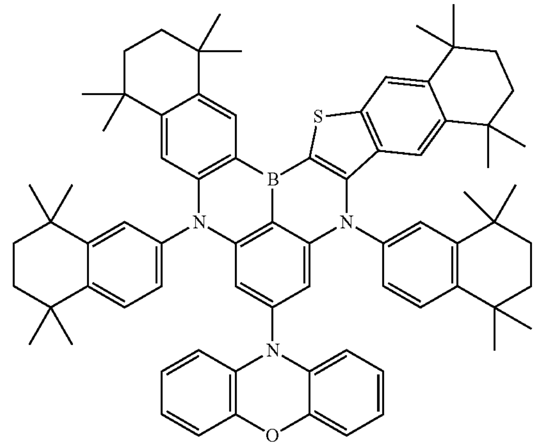
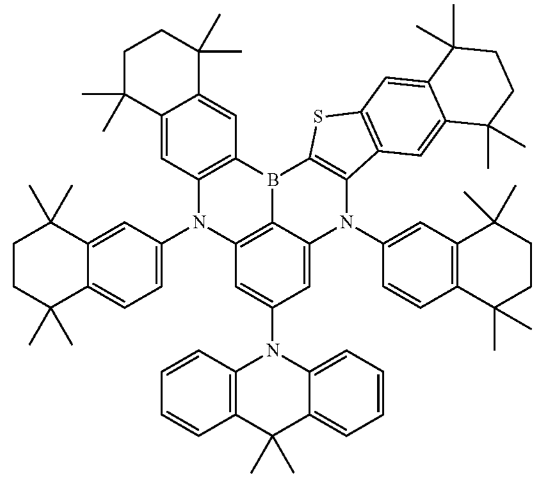
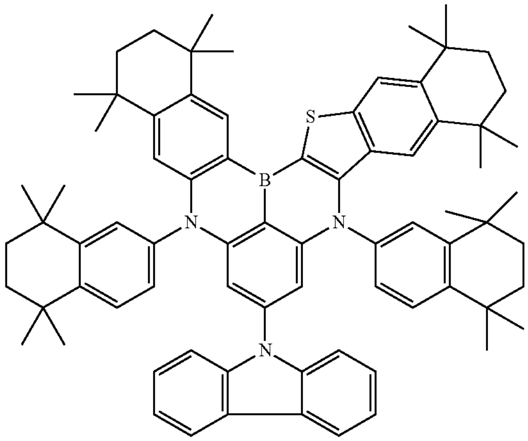
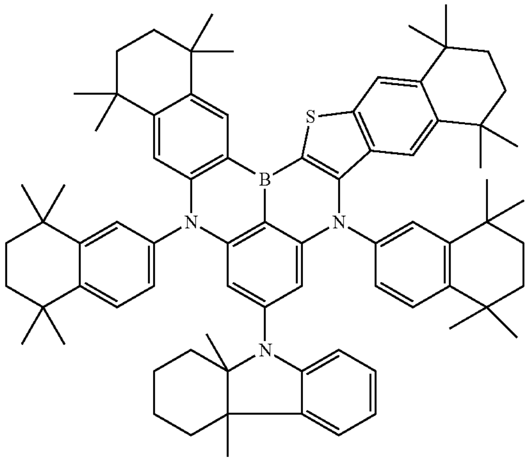
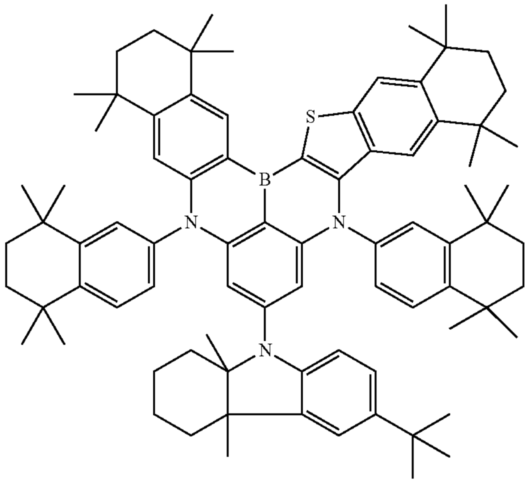

-continued
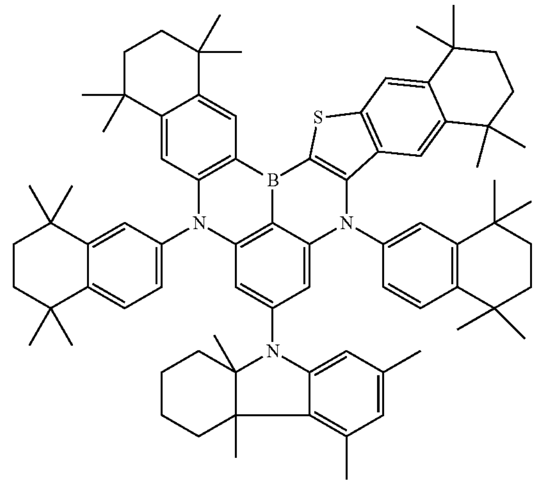
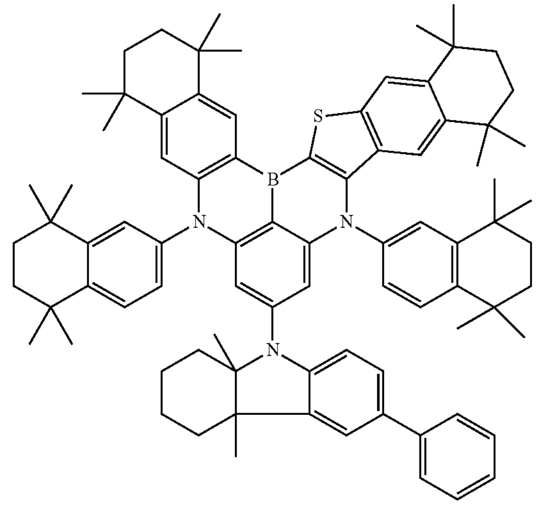
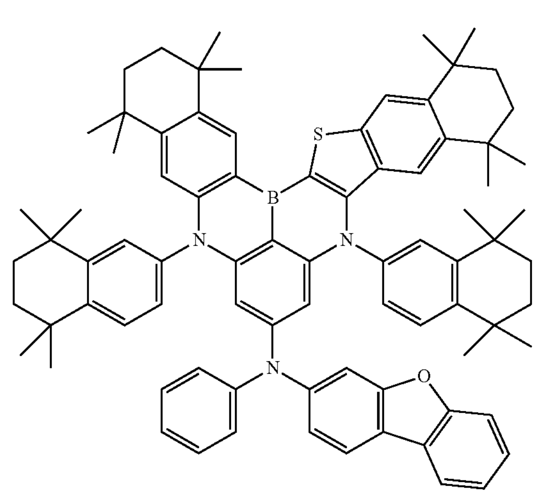
-continued
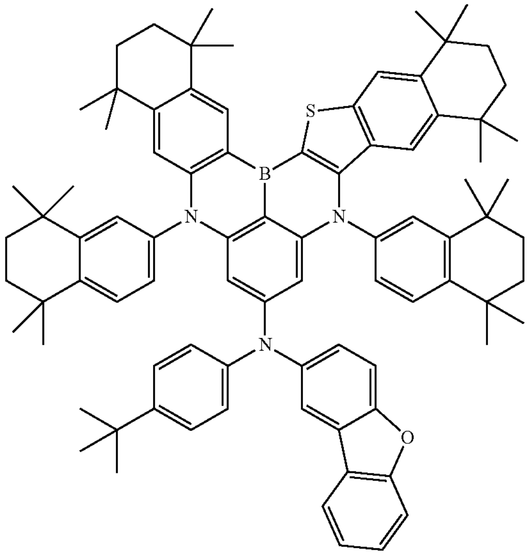
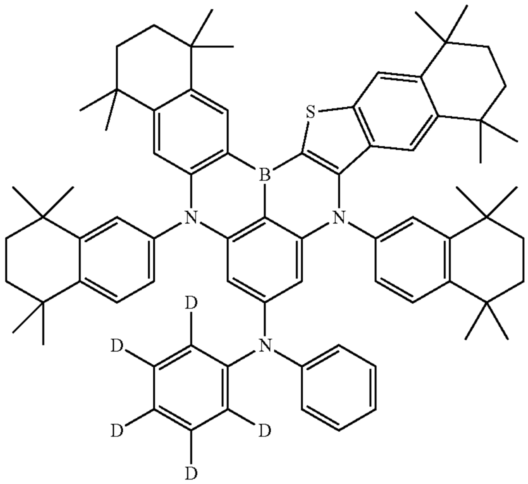
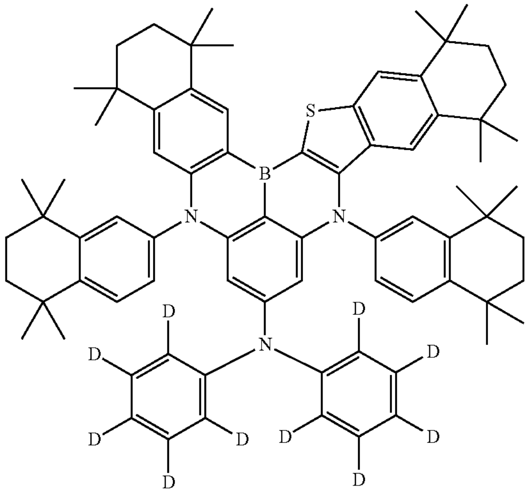

-continued
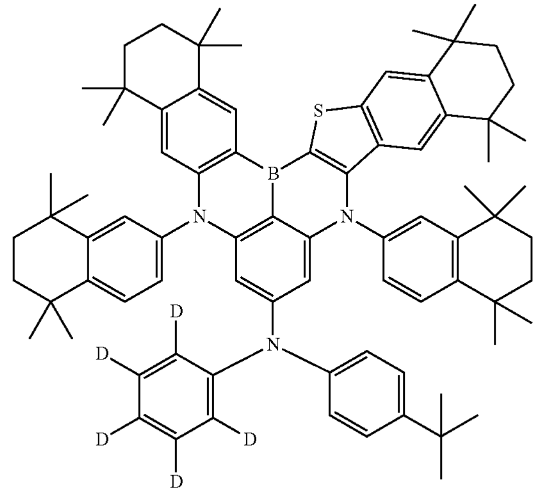
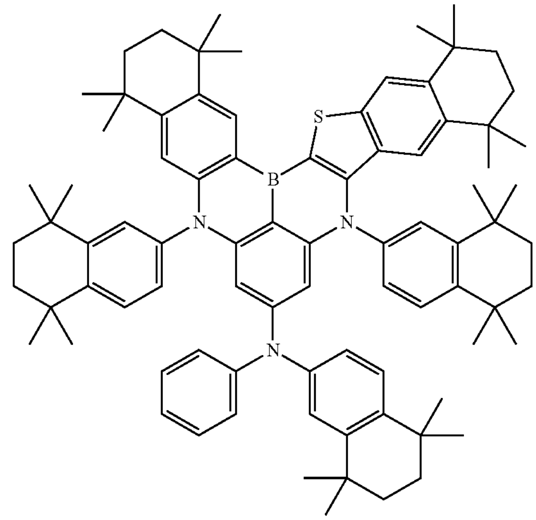
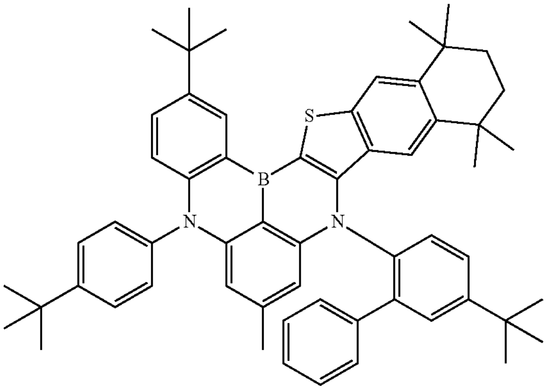
-continued
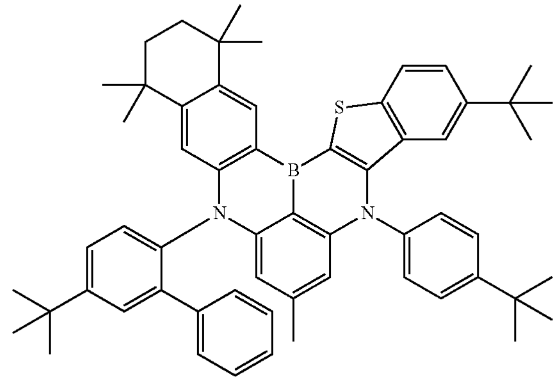
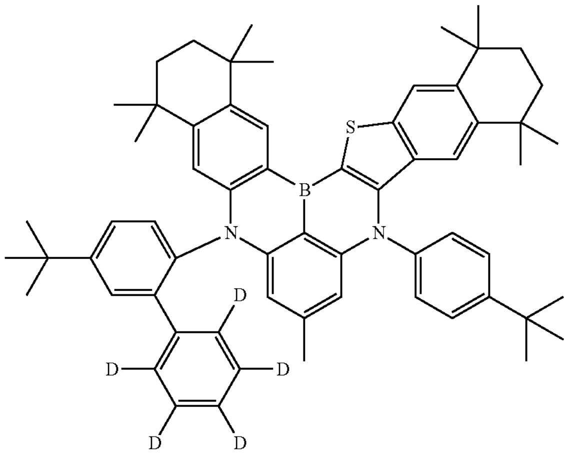
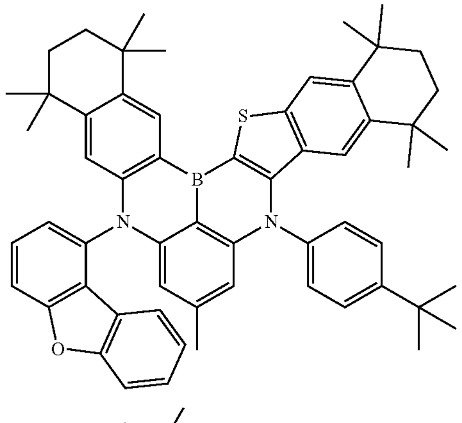
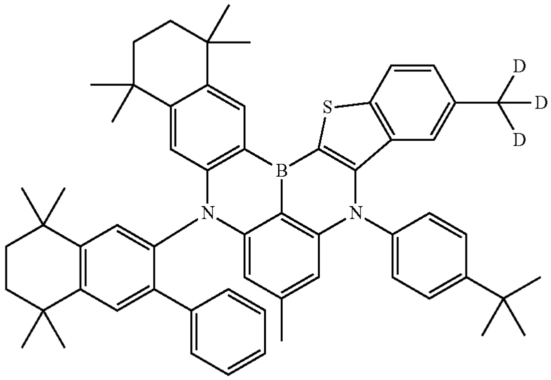

-continued
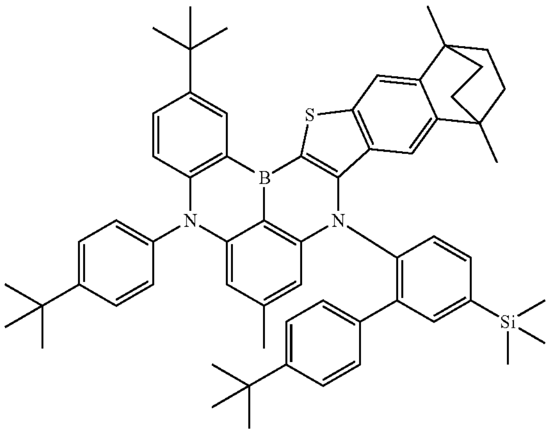
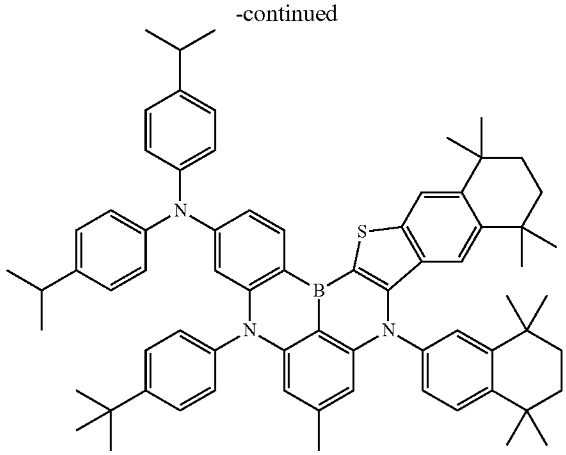
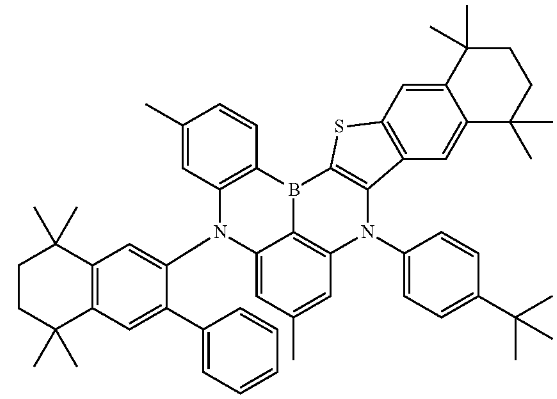
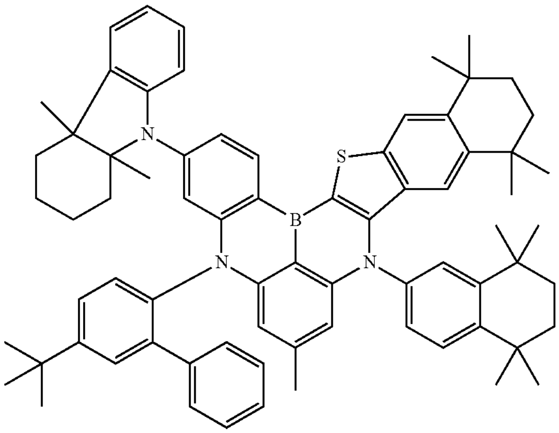
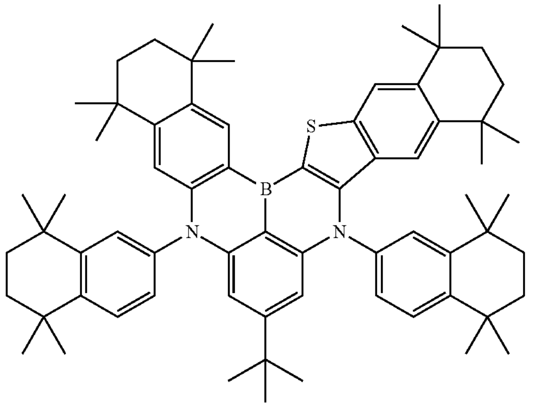
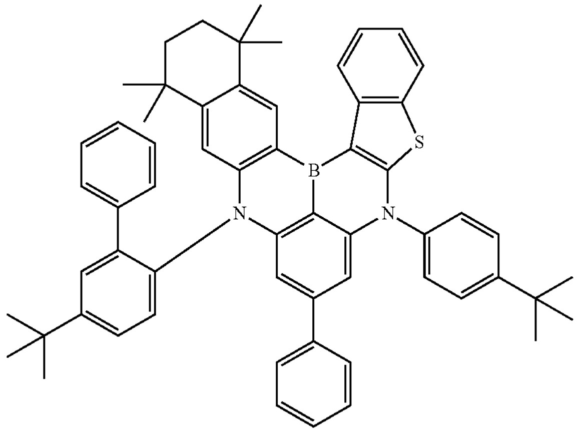
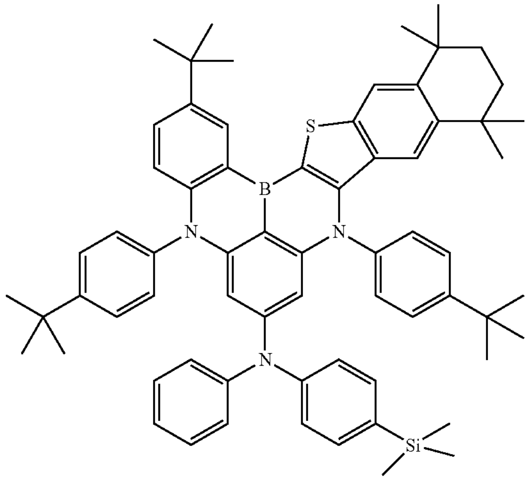
-continued -continued
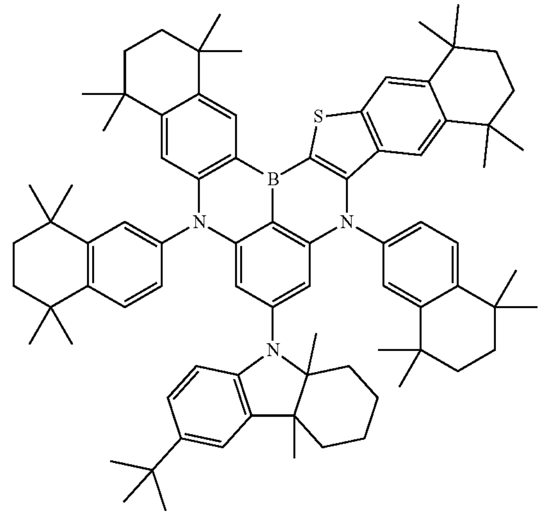
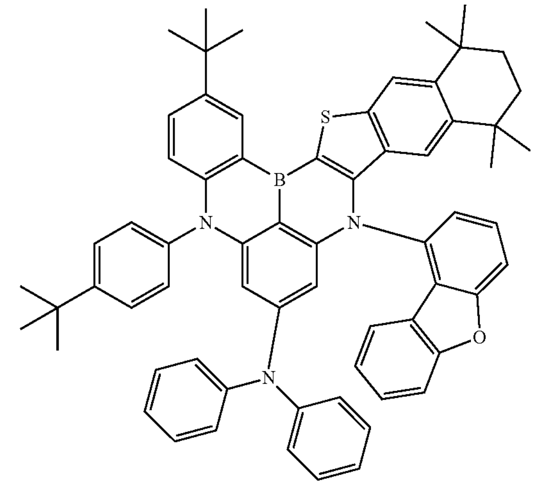
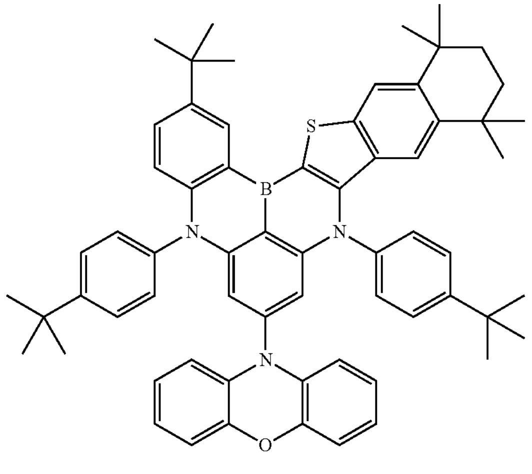
-continued
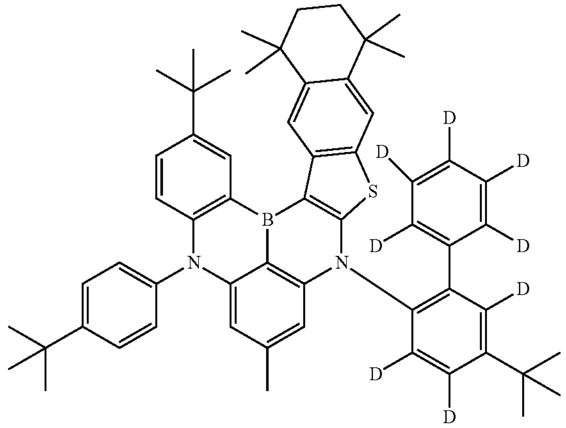
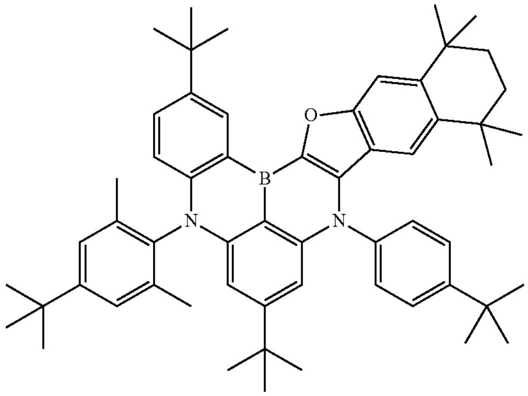
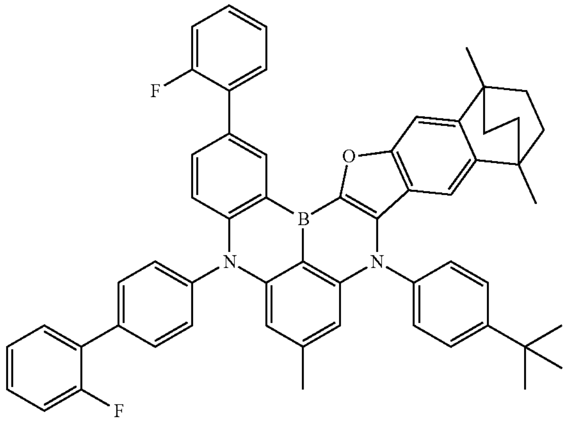
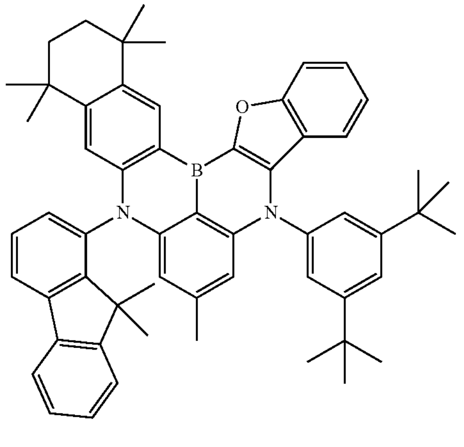

-continued
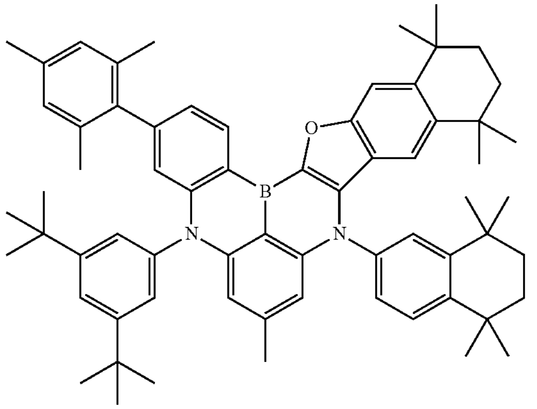
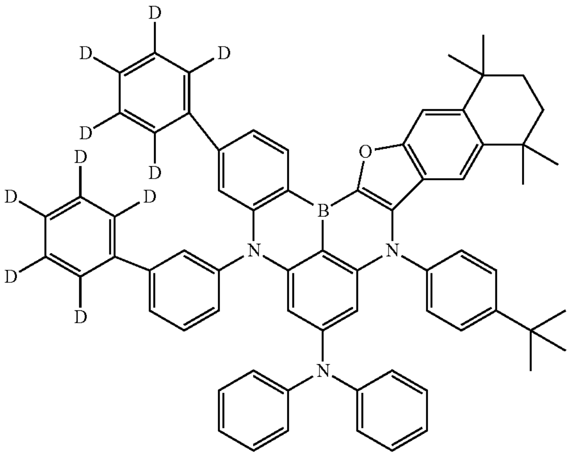
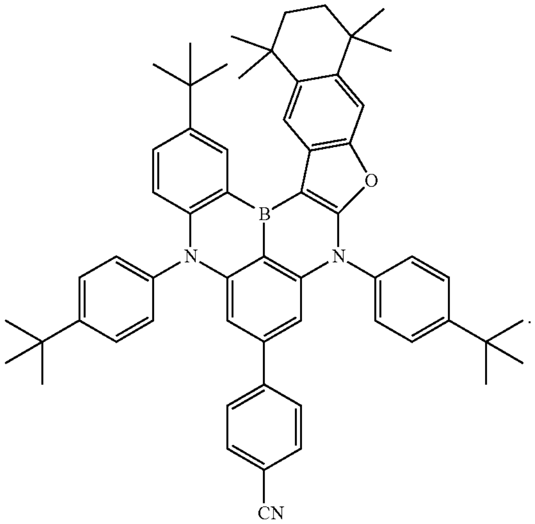
.
6. The organic light emitting device of claim 1, wherein the compound of Chemical Formula 2 is any one of the following compounds:
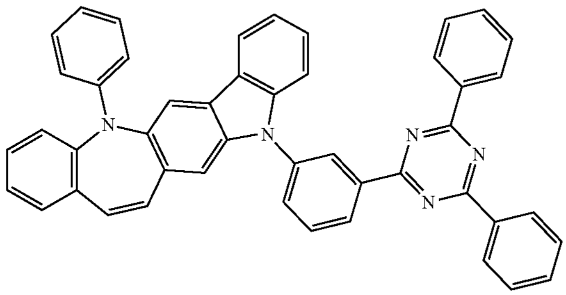
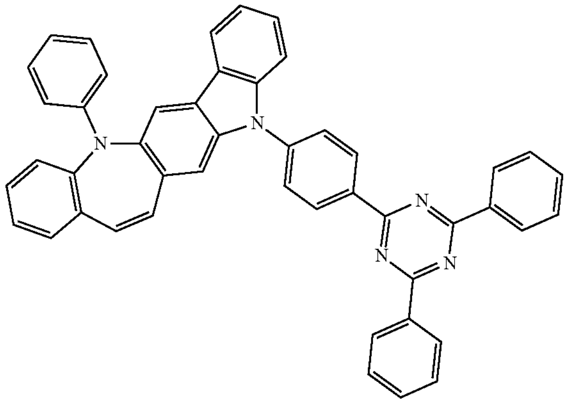
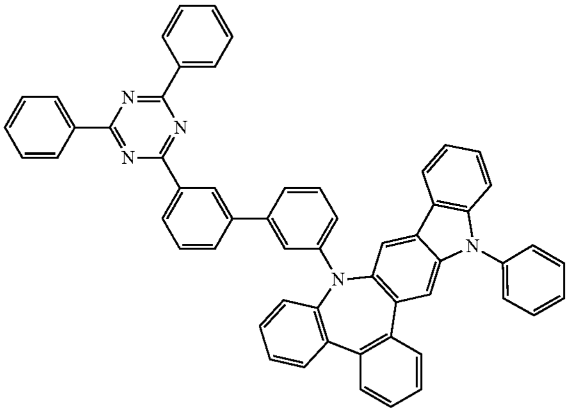

-continued

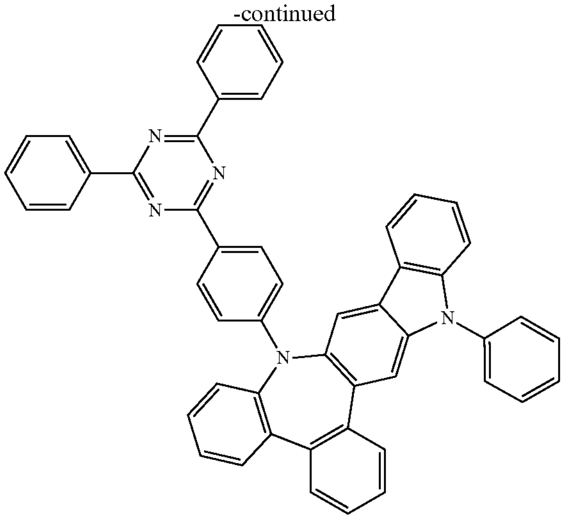

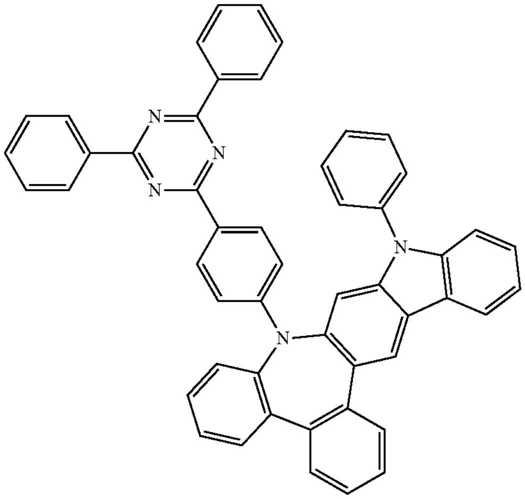

-continued

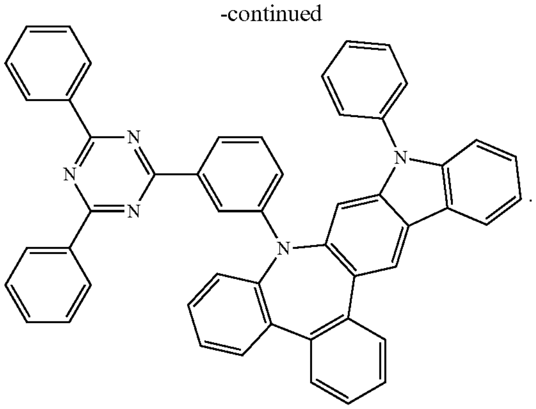

7. The organic light emitting device of claim 1, wherein the first organic material layer is in direct contact with the light emitting layer.

8. The organic light emitting device of claim 1, wherein the light emitting layer has a maximum emission peak at 400 nm to 500 nm.

9. The organic light emitting device of claim 1, wherein the light emitting layer includes the compound of Chemical Formula 1 as a dopant.

10. The organic light emitting device of claim 1, further comprising one or more organic material layers of a hole transfer layer, a hole injection layer, an electron blocking layer, an electron transfer and injection layer, an electron transfer layer, an electron injection layer, a hole blocking layer and a hole transfer and injection layer.

* * * * *